(12) United States Patent
Cummins et al.

(10) Patent No.: US 8,586,725 B2
(45) Date of Patent: Nov. 19, 2013

(54) MICRORNAOME

(75) Inventors: Jordan Cummins, Baltimore, MD (US);
Victor Velculescu, Dayton, MD (US);
Kenneth W. Kinzler, Bel Air, MD (US);
Bert Vogelstein, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 694 days.

(21) Appl. No.: 12/521,695

(22) PCT Filed: Feb. 16, 2007

(86) PCT No.: PCT/US2007/004518
§ 371 (c)(1),
(2), (4) Date: Jan. 15, 2010

(87) PCT Pub. No.: WO2008/103135
PCT Pub. Date: Aug. 28, 2008

(65) Prior Publication Data
US 2010/0137413 A1    Jun. 3, 2010

(51) Int. Cl.
*C07H 21/02* (2006.01)
*C07H 21/04* (2006.01)

(52) U.S. Cl.
USPC ...... 536/24.5; 536/23.1; 536/24.3; 536/24.33

(58) Field of Classification Search
USPC .............................................. 536/24.5, 23.1
See application file for complete search history.

(56) References Cited

U.S. PATENT DOCUMENTS

| 8,129,515 B2 * | 3/2012 | Esau et al. ................... 536/24.5 |
| 2005/0261218 A1 | 11/2005 | Esau et al. |

FOREIGN PATENT DOCUMENTS

WO    WO2005084712 A2 *    9/2005

OTHER PUBLICATIONS

International Search Report dated Oct. 20, 2008 cited in PCT/US07/04518.

* cited by examiner

*Primary Examiner* — Terra Cotta Gibbs
(74) *Attorney, Agent, or Firm* — Banner & Witcoff, Ltd

(57) ABSTRACT

MicroRNAs (miRNAs) are a class of small noncoding RNAs that have important regulatory roles in multicellular organisms. The public miRNA database contains 321 human miRNA sequences, 234 of which have been experimentally verified. To explore the possibility that additional miRNAs are present in the human genome, we have developed an experimental approach called miRNA serial analysis of gene expression (miRAGE) and used it to perform the largest experimental analysis of human miRNAs to date. Sequence analysis of 273,966 small RNA tags from human colorectal cells allowed us to identify 200 known mature miRNAs, 133 novel miRNA candidates, and 112 previously uncharacterized miRNA* forms. To aid in the evaluation of candidate miRNAs, we disrupted the Dicer locus in three human colorectal cancer cell lines and examined known and novel miRNAs in these cells. The miRNAs are useful to diagnose and treat cancers.

9 Claims, 57 Drawing Sheets

TABLE 1

EVALUATION OF DIFFERENTIALLY EXPRESSED CANDIDATE miRNAs BY miRAGE

| NAME | DICER WT | DICER $^{ex5}$ | P VALUE |
|---|---|---|---|
| miR-92b | 38 | 1 | 0 |
| miR-590 | 30 | 2 | 0 |
| miR-193b | 12 | 1 | 0.003415 |
| miR-340* | 11 | 2 | 0.022446 |
| miR-450 | 6 | 0 | 0.031242 |
| miR-618 | 5 | 0 | 0.031244 |

(Table 2.) miRAGE tags of known miRNAs observed in colorectal cells (SEQ ID NOS: 1-200, respectively)

| Sequence | miRNA Name | Evidence | 308N | 308T | 309N | 309T | CACO-2 | SW480 | HCT116 WT | HCT116 EX5 | SUM | seq id no: |
|---|---|---|---|---|---|---|---|---|---|---|---|---|
| UAGCUUAUCAGACUGAUGUUGA | HSA-MIR-21 | C | 1177 | 822 | 1306 | 428 | 2347 | 5906 | 7537 | 3908 | 23431 | 1 |
| UAACACUGUCUGGUAACGAUGU | HSA-MIR-200A | C | 1050 | 742 | 719 | 420 | 173 | 176 | 919 | 77 | 4276 | 2 |
| UAAUACUGCCGGGUAAUGAUGG | HSA-MIR-200C | C | 612 | 159 | 470 | 66 | 267 | 166 | 1330 | 779 | 3849 | 3 |
| UGAGAUGAAGCACUGUAGCUCA | HSA-MIR-143 | C | 724 | 125 | 1823 | 57 | 0 | 0 | 0 | 0 | 2729 | 4 |
| UAAUACUGCCUGGUAAUGAUGAC | HSA-MIR-200B | C | 582 | 226 | 329 | 150 | 144 | 208 | 432 | 375 | 2446 | 5 |
| UUCACAGUGGCUAAGUUCCGC | HSA-MIR-27A | C | 138 | 82 | 426 | 67 | 50 | 84 | 313 | 682 | 1842 | 6 |
| UGGCUCAGUUCAGCAGGAACAG | HSA-MIR-24 | C | 202 | 100 | 445 | 36 | 70 | 219 | 362 | 172 | 1606 | 7 |
| UUCAAGUAAUCCAGGAUAGGC | HSA-MIR-26A | C | 304 | 66 | 564 | 59 | 76 | 121 | 101 | 61 | 1352 | 8 |
| GUCCAGUUUUCCCAGGAAUCCCUU | HSA-MIR-145 | C | 367 | 30 | 878 | 27 | 0 | 0 | 5 | 4 | 1311 | 9 |
| UACAGUACUGUGAUAACUGAAG | HSA-MIR-101 | C | 179 | 37 | 289 | 34 | 24 | 61 | 229 | 220 | 1073 | 10 |
| UGUAACAGCAACUCCAUGUGGA | HSA-MIR-194 | C | 320 | 82 | 253 | 111 | 222 | 5 | 2 | 1 | 996 | 11 |
| CUGACCUAUGAAUUGACAGCC | HSA-MIR-192 | C | 296 | 102 | 205 | 148 | 154 | 1 | 1 | 2 | 909 | 12 |
| AAACCGUUACCAUUACUGAGUU | HSA-MIR-451 | C | 311 | 74 | 393 | 107 | 0 | 0 | 0 | 0 | 885 | 13 |
| AAGCUGCCAGUUGAAGAACUGU | HSA-MIR-22 | C | 128 | 54 | 178 | 44 | 165 | 71 | 74 | 142 | 856 | 14 |
| AGCAGCAUUGUACAGGGCUAUGA | HSA-MIR-103 | C | 44 | 2 | 58 | 4 | 238 | 113 | 285 | 31 | 775 | 15 |
| UAGCAGCACGUAAAUAUUGGCG | HSA-MIR-16 | C | 81 | 13 | 114 | 22 | 56 | 63 | 245 | 146 | 740 | 16 |
| CAUUGCACUUGUCUCGGUCUGA | HSA-MIR-25 | C | 9 | 10 | 13 | 6 | 103 | 159 | 281 | 156 | 737 | 17 |
| UAACACUGUCUGGUAAAGAUGG | HSA-MIR-141 | C | 69 | 23 | 59 | 20 | 99 | 44 | 228 | 176 | 718 | 18 |
| UAGCACCAUUUGAAAUCAGUGUU | HSA-MIR-29B | C | 66 | 14 | 101 | 10 | 17 | 39 | 280 | 174 | 701 | 19 |
| UGUAAACAUCCUUGACUGGA | HSA-MIR-30E-5P | C | 125 | 24 | 180 | 17 | 30 | 28 | 148 | 142 | 694 | 20 |
| UGUAGUGUUUCCUACUUUAUGGA | HSA-MIR-142-3P | C | 170 | 108 | 201 | 98 | 2 | 5 | 7 | 7 | 598 | 21 |
| CAACGGAAUCCCAAAGUCAGCU | HSA-MIR-191 | C | 47 | 76 | 73 | 21 | 37 | 42 | 181 | 109 | 586 | 22 |
| AACUGGCCUACAAAGUCCCAG | HSA-MIR-193A | H | 77 | 22 | 225 | 3 | 164 | 4 | 27 | 27 | 549 | 23 |
| UACAGUAUAGAUGAUGUACUAG | HSA-MIR-144 | H | 173 | 53 | 219 | 57 | 0 | 10 | 1 | 0 | 503 | 24 |
| AGCUACAUCUGGCUACUGGGUCUC | HSA-MIR-222 | C | 21 | 4 | 17 | 8 | 22 | 24 | 242 | 155 | 493 | 25 |
| UGUGCAAAUCCAUGCAAAACUGA | HSA-MIR-19B | C | 42 | 40 | 80 | 27 | 29 | 20 | 91 | 145 | 474 | 26 |
| UGUAAACAUCCCCGACUGGAAG | HSA-MIR-30D | H | 38 | 7 | 85 | 10 | 141 | 10 | 94 | 69 | 454 | 27 |
| GGCAAGAUGCUGGCAUAGCUG | HSA-MIR-31 | C | 0 | 0 | 0 | 0 | 5 | 1 | 214 | 230 | 450 | 28 |
| UGUAAACAUCCUCGACUGGAAG | HSA-MIR-30A-5P | C | 152 | 29 | 227 | 16 | 5 | 1 | 1 | 1 | 432 | 29 |
| AUCACAUUGCCAGGGAUUUCC | HSA-MIR-23A | C | 9 | 3 | 15 | 8 | 35 | 67 | 95 | 171 | 403 | 30 |

Fig. 9B

| Sequence | Name | Type | | | | | | | | | ID |
|---|---|---|---|---|---|---|---|---|---|---|---|
| UGAGGUAGUAGUUUGUACAGU | HSA-LET-7G | H | 82 | 15 | 102 | 15 | 9 | 23 | 66 | 81 | 393 | 31 |
| UAGCACCAUCUGAAAUCGGUU | HSA-MIR-29A | C | 44 | 33 | 64 | 23 | 3 | 42 | 88 | 89 | 386 | 32 |
| UUCACAGUGGCUAAGUUCUGC | HSA-MIR-27B | C | 66 | 21 | 153 | 24 | 21 | 63 | 10 | 21 | 379 | 33 |
| UGAGGUAGUAGAUUGUAUAGUU | HSA-LET-7F | C | 67 | 21 | 106 | 6 | 3 | 20 | 100 | 52 | 375 | 34 |
| UUAUAAUACAACCUGAUAAGUG | HSA-MIR-374 | C | 53 | 19 | 108 | 22 | 26 | 7 | 79 | 59 | 373 | 35 |
| UAAGGUGCAUCUAGUGCAGAUA | HSA-MIR-18A | C | 13 | 22 | 9 | 11 | 100 | 32 | 144 | 17 | 348 | 36 |
| UGAGGUAGUAGGUUGUAUAGUU | HSA-LET-7A | C | 43 | 8 | 95 | 9 | 3 | 16 | 92 | 77 | 343 | 37 |
| UCAAGAGCAAUAACGAAAAAUGU | HSA-MIR-335 | H | 80 | 36 | 43 | 11 | 40 | 42 | 40 | 29 | 321 | 38 |
| UAUUGCACUUGUCCCGGCCUG | HSA-MIR-92 | AC | 8 | 8 | 14 | 6 | 93 | 44 | 74 | 58 | 305 | 39 |
| UAAAGUGCUGACAGUGCAGAU | HSA-MIR-106B | C | 9 | 20 | 7 | 9 | 48 | 51 | 137 | 21 | 302 | 40 |
| UAGCAGCACAUAAUGGUUUGUG | HSA-MIR-15A | C | 42 | 8 | 51 | 10 | 61 | 73 | 45 | 0 | 290 | 41 |
| GUGCAUUGUAGUUGCAUUG | HSA-MIR-33 | C | 5 | 11 | 10 | 3 | 46 | 17 | 64 | 116 | 272 | 42 |
| AAAGUGCUGCGACAUUUGAGCGU | HSA-MIR-372 | C | 0 | 0 | 0 | 0 | 265 | 4 | 0 | 0 | 269 | 43 |
| AUCACAUUGCCAGGGAUUACC | HSA-MIR-23B | H | 29 | 6 | 74 | 4 | 41 | 73 | 30 | 5 | 262 | 44 |
| GAAGUGCUUCGAUUUUGGGGUGU | HSA-MIR-373 | C | 0 | 0 | 0 | 0 | 247 | 4 | 0 | 0 | 251 | 45 |
| UGUAAACAUCCUACACUCAGCU | HSA-MIR-30B | H | 22 | 7 | 43 | 4 | 83 | 5 | 23 | 45 | 232 | 46 |
| UCGUACCGUGAGUAAUAAUGC | HSA-MIR-126 | H | 61 | 31 | 82 | 23 | 3 | 4 | 18 | 0 | 222 | 47 |
| UGUGCAAAUCUAUGCAAAACUGA | HSA-MIR-19A | C | 11 | 13 | 25 | 6 | 19 | 8 | 79 | 60 | 221 | 48 |
| UGUAAACAUCCUACACUCUCAGC | HSA-MIR-30C | C | 43 | 2 | 64 | 3 | 14 | 6 | 42 | 31 | 205 | 49 |
| UUCAAGUAAUUCAGAUAGGUU | HSA-MIR-26B | C | 37 | 13 | 82 | 9 | 17 | 10 | 17 | 16 | 201 | 50 |
| UAUUGCACAUUACUAAGUUGC | HSA-MIR-32 | C | 14 | 9 | 9 | 6 | 32 | 8 | 88 | 33 | 199 | 51 |
| UCCCUGAGACCCUAACUUGUGA | HSA-MIR-125B | C | 33 | 0 | 65 | 2 | 0 | 0 | 47 | 48 | 195 | 52 |
| AGCUACAUUGUCUGCUGGGUUUC | HSA-MIR-221 | C | 10 | 4 | 9 | 1 | 10 | 22 | 71 | 63 | 190 | 53 |
| AGCAGCAUUGUACAGGGCUAUCA | HSA-MIR-107 | C | 17 | 0 | 22 | 1 | 40 | 17 | 68 | 18 | 183 | 54 |
| UAGCACCAUUUGAAAUCGGU | HSA-MIR-29C | C | 60 | 5 | 84 | 10 | 7 | 0 | 8 | 0 | 174 | 55 |
| UACCCUGUAGAUCCGAAUUUGUG | HSA-MIR-10A | H | 10 | 2 | 14 | 1 | 4 | 127 | 6 | 8 | 172 | 56 |
| AACAUUCAACGCUGUCGGUGAGU | HSA-MIR-181A | C | 26 | 5 | 36 | 0 | 16 | 34 | 22 | 22 | 161 | 57 |
| CAAAGUGCUUACAGUGCAGGUAGU | HSA-MIR-17-5P | C | 9 | 8 | 11 | 3 | 32 | 16 | 52 | 15 | 146 | 58 |
| UGAGGUAGUAGGUUGUGUGGUU | HSA-LET-7B | C | 32 | 3 | 59 | 4 | 0 | 1 | 10 | 27 | 136 | 59 |
| UAAAGUGCUUAUAGUGCAGGUAG | HSA-MIR-20A | C | 12 | 9 | 13 | 4 | 32 | 12 | 41 | 10 | 133 | 60 |
| ACUGCAGUGAAGGCACUUGU | HSA-MIR-17-3P | C | 7 | 5 | 11 | 4 | 34 | 20 | 32 | 20 | 133 | 61 |
| UAGCAGCACAGAAAUAUUGGC | HSA-MIR-195 | H | 31 | 2 | 87 | 10 | 0 | 0 | 0 | 0 | 130 | 62 |
| UGGAAUGUAAAGAAGUAUGUA | HSA-MIR-1 | H | 27 | 0 | 95 | 3 | 0 | 1 | 0 | 0 | 126 | 63 |
| CAGUGCAAUGAUGAAAGGGCAU | HSA-MIR-130B | C | 3 | 1 | 1 | 0 | 8 | 5 | 59 | 49 | 126 | 64 |
| UUGUGCUUGAUCUAACCAUGU | HSA-MIR-218 | H | 43 | 9 | 53 | 2 | 4 | 0 | 7 | 7 | 125 | 65 |
| CAGUGCAAUGUUAAAAGGGCAU | HSA-MIR-130A | C | 11 | 6 | 30 | 1 | 1 | 0 | 46 | 28 | 123 | 66 |

Fig. 9C

| Sequence | Name | | | | | | | | | | |
|---|---|---|---|---|---|---|---|---|---|---|---|
| AAAGUGCUGUUCGUGCAGGUAG | HSA-MIR-93 | C | 9 | 2 | 3 | 1 | 28 | 35 | 37 | 5 | 120 | 67 |
| UUUGGCAAUGGUAGAACUCACA | HSA-MIR-182 | H | 1 | 3 | 0 | 0 | 32 | 22 | 51 | 4 | 113 | 68 |
| CUGUGCGUGUGACAGCGGCUGA | HSA-MIR-210 | C | 9 | 1 | 5 | 1 | 1 | 2 | 25 | 67 | 111 | 69 |
| UCUCCCAACCCUUGUACCAGUG | HSA-MIR-150 | H | 41 | 4 | 26 | 24 | 0 | 1 | 0 | 0 | 96 | 70 |
| UAGCAGCACAUCAUGGUUUACA | HSA-MIR-15B | C | 9 | 1 | 11 | 3 | 14 | 28 | 15 | 11 | 92 | 71 |
| UGAGGUAGUAGGUUGUGUGGUU | HSA-LET-7I | H | 10 | 2 | 12 | 1 | 1 | 2 | 24 | 33 | 85 | 72 |
| AAAGCUGGGUUGAGAGGGCGAA | HSA-MIR-320 | C | 7 | 1 | 3 | 0 | 7 | 4 | 19 | 41 | 82 | 73 |
| CAGCAGCAAUUCAUGUUUUGAA | HSA-MIR-424 | C | 3 | 2 | 5 | 4 | 5 | 52 | 5 | 3 | 79 | 74 |
| CAGUGCAAUAGUAUUGUCAAAGC | HSA-MIR-301 | C | 5 | 4 | 3 | 0 | 18 | 4 | 33 | 2 | 69 | 75 |
| CAUAAAGUAGAAAGCACUAC | HSA-MIR-142-5P | C | 10 | 13 | 27 | 13 | 0 | 0 | 0 | 3 | 66 | 76 |
| UAAUACUGUCUGGUAAAACCGU | HSA-MIR-429 | C | 9 | 13 | 6 | 5 | 4 | 7 | 16 | 6 | 66 | 77 |
| UUUGGCACUAGCACAUUUUUGC | HSA-MIR-96 | C | 0 | 0 | 0 | 0 | 5 | 5 | 40 | 14 | 64 | 78 |
| ACUAGACUGAAGCUCCUUGAGG | HSA-MIR-151 | H | 0 | 2 | 2 | 0 | 9 | 1 | 22 | 25 | 61 | 79 |
| UUUGUUCGUUCGGCUCGCGUGA | HSA-MIR-375 | H | 16 | 1 | 29 | 2 | 2 | 2 | 6 | 2 | 60 | 80 |
| UCUUUGGUUAUCUAGCUGUAUGA | HSA-MIR-9 | H | 1 | 0 | 0 | 0 | 10 | 11 | 24 | 13 | 59 | 81 |
| GUGCCGCCAUCUUUUGAGUGU | HSA-MIR-371 | C | 0 | 0 | 0 | 0 | 58 | 1 | 0 | 0 | 59 | 82 |
| AUGACCUAUGAAUUGACAGAC | HSA-MIR-215 | H | 16 | 2 | 13 | 6 | 19 | 0 | 0 | 0 | 56 | 83 |
| AACCCGUAGAUCCGAACUUGUG | HSA-MIR-100 | C | 2 | 0 | 6 | 1 | 0 | 0 | 20 | 20 | 49 | 84 |
| UUGGUCCCCUUCAACCAGCUGU | HSA-MIR-133A | H | 14 | 0 | 34 | 0 | 0 | 0 | 0 | 0 | 48 | 85 |
| AAGGAGCUCACAGUCUAUUGAG | HSA-MIR-28 | C | 9 | 0 | 12 | 0 | 12 | 3 | 6 | 6 | 48 | 86 |
| CUUUCAGUCGGAUGUUUACAGC | HSA-MIR-30E-3P | C | 3 | 0 | 3 | 1 | 2 | 1 | 18 | 17 | 45 | 87 |
| GUGAAAUGUUUAGGACCACUAG | HSA-MIR-203 | H | 8 | 3 | 10 | 3 | 5 | 4 | 7 | 3 | 43 | 88 |
| AGAGGUAGUAGGUUGCAUAGU | HSA-LET-7D | C | 8 | 1 | 5 | 2 | 1 | 3 | 11 | 11 | 42 | 89 |
| UUCAACGGGUAUUUAUUGAGCA | HSA-MIR-95 | C | 2 | 2 | 5 | 2 | 0 | 8 | 8 | 12 | 39 | 90 |
| AGUGGUUUUACCCUAUGGUAG | HSA-MIR-140 | C | 12 | 2 | 8 | 3 | 0 | 3 | 8 | 2 | 38 | 91 |
| UAGGUAGUUUCCUGUUGUUGG | HSA-MIR-196B | H | 7 | 7 | 7 | 0 | 1 | 5 | 8 | 2 | 37 | 92 |
| UCCAGCAUCAGUGAUUUUGUUGA | HSA-MIR-338 | C | 3 | 0 | 8 | 0 | 20 | 1 | 0 | 0 | 32 | 93 |
| UAAUGCCCCUAAAAAUCCUUAU | HSA-MIR-365 | H | 6 | 0 | 16 | 1 | 1 | 1 | 4 | 3 | 32 | 94 |
| CAAAGAAUUCUCCUUUUGGGCUU | HSA-MIR-186 | C | 1 | 0 | 1 | 0 | 7 | 2 | 6 | 14 | 32 | 95 |
| UCUCACACAGAAAUCGCACCCGUC | HSA-MIR-342 | H | 11 | 0 | 14 | 0 | 2 | 0 | 4 | 0 | 31 | 96 |
| CCCAGUGUUCAGACUACCUGUUC | HSA-MIR-199A | C | 12 | 4 | 12 | 2 | 0 | 2 | 0 | 0 | 30 | 97 |
| AACAUUCACAUUGUGCUGUGGG | HSA-MIR-181B | C | 3 | 2 | 3 | 0 | 11 | 1 | 8 | 2 | 30 | 98 |
| ACAGCAGGCACAGACAGGCAG | HSA-MIR-214 | H | 9 | 7 | 11 | 2 | 0 | 0 | 0 | 0 | 29 | 99 |
| CACCCGUAGAACCGACCUUGCG | HSA-MIR-99B | H | 4 | 0 | 8 | 0 | 3 | 2 | 9 | 3 | 29 | 100 |
| UCAGUGCACUACAGAACUUUGU | HSA-MIR-148A | C | 2 | 3 | 8 | 5 | 4 | 4 | 1 | 2 | 29 | 101 |
| CAGCAGCACACUGUGGUUUGU | HSA-MIR-497 | AC | 10 | 1 | 15 | 1 | 0 | 0 | 0 | 0 | 27 | 102 |

Fig. 9D

| Sequence | Name | | | | | | | | |
|---|---|---|---|---|---|---|---|---|---|
| GCCCCUGGGCCUAUCCUAGAA | HSA-MIR-331 | H | 3 | 2 | 5 | 0 | 2 | 1 | 12 | 0 | 25 | 103 |
| UGGAAGACUAGUGAUUUUGUUG | HSA-MIR-7 | H | 0 | 0 | 1 | 0 | 1 | 5 | 12 | 6 | 25 | 104 |
| UGGCAGUGUCUUAGCUGGUUGUU | HSA-MIR-34A | C | 5 | 0 | 7 | 1 | 2 | 0 | 5 | 3 | 23 | 106 |
| UUAAUGCUAAUCGUGAUAGGGG | HSA-MIR-155 | C | 9 | 0 | 9 | 1 | 4 | 0 | 0 | 0 | 23 | 106 |
| UCACAGUGAACCGGUCUCUUUC | HSA-MIR-128B | H | 0 | 1 | 2 | 0 | 7 | 4 | 5 | 3 | 22 | 107 |
| UCACAGUGAACCGGUCUCUUUU | HSA-MIR-128A | C | 0 | 1 | 2 | 0 | 7 | 4 | 5 | 3 | 22 | 108 |
| UAUGGCUUUUCAUUCCUAUGUG | HSA-MIR-135B | H | 0 | 1 | 0 | 1 | 3 | 7 | 6 | 2 | 20 | 109 |
| UCAGUGCAUGACAGAACUGGG | HSA-MIR-152 | H | 7 | 3 | 3 | 2 | 0 | 2 | 0 | 2 | 19 | 110 |
| UGAGGUAGUAAGUUGUAUUGUU | HSA-MIR-98 | C | 2 | 1 | 1 | 0 | 0 | 1 | 5 | 9 | 19 | 111 |
| UUUUUGCGAUGUGUUCCUAAUA | HSA-MIR-450 | C | 1 | 2 | 0 | 5 | 0 | 6 | 4 | 0 | 18 | 112 |
| UCUGGCUCCGUGUCUUCACUCC | HSA-MIR-149 | H | 0 | 0 | 0 | 0 | 2 | 2 | 8 | 5 | 17 | 113 |
| GCAAAGCACACGGCCUGCAGAGA | HSA-MIR-330 | H | 0 | 0 | 2 | 2 | 0 | 1 | 6 | 6 | 17 | 114 |
| UGAGGUAGUAGGUUGUAUGGUU | HSA-LET-7C | C | 5 | 0 | 10 | 0 | 0 | 1 | 0 | 1 | 17 | 115 |
| AACUGGCCCUCAAAGUCCCGCUUU | HSA-MIR-193B | AC | 1 | 1 | 3 | 0 | 2 | 1 | 8 | 1 | 17 | 116 |
| UGUCAGUUUGUCAAAUACCCC | HSA-MIR-223 | H | 2 | 3 | 6 | 4 | 0 | 0 | 1 | 0 | 16 | 117 |
| UGAGGUAGGAGGUUGUAUAGU | HSA-LET-7E | C | 4 | 4 | 2 | 0 | 1 | 0 | 4 | 1 | 16 | 118 |
| UCCCUGAGACCCUUUAACCUGUG | HSA-MIR-125A | H | 3 | 0 | 7 | 0 | 1 | 0 | 2 | 1 | 14 | 119 |
| ACUCCAUUUGUUUUGAUGAUGGA | HSA-MIR-136 | C | 4 | 1 | 9 | 0 | 0 | 0 | 0 | 0 | 14 | 120 |
| UAUGGCACUGGUAGAAUUCACUG | HSA-MIR-183 | C | 0 | 0 | 0 | 0 | 2 | 2 | 6 | 4 | 14 | 121 |
| UCACCACCUUCUCCACCCAGC | HSA-MIR-197 | H | 1 | 1 | 4 | 0 | 1 | 0 | 4 | 3 | 14 | 122 |
| AUUGCACGGUAUCCAUCUGUAA | HSA-MIR-363 | AC | 5 | 0 | 9 | 0 | 0 | 0 | 0 | 0 | 14 | 123 |
| UCUACAGUGCACGUGUCU | HSA-MIR-139 | H | 4 | 0 | 2 | 0 | 1 | 0 | 5 | 1 | 13 | 124 |
| AAAAGUGCUUACAGUGCAGGUAGC | HSA-MIR-106A | C | 2 | 0 | 4 | 0 | 2 | 0 | 3 | 2 | 13 | 125 |
| UGGAGAGAAAGGCAGUUC | HSA-MIR-185 | C | 1 | 0 | 0 | 0 | 3 | 1 | 3 | 5 | 13 | 126 |
| AACAUUCAACCUGUCGGUGAGU | HSA-MIR-181C | H | 1 | 2 | 4 | 1 | 0 | 2 | 1 | 1 | 12 | 127 |
| CAUCCCUUGCAUGGUGGAGGGU | HSA-MIR-188 | H | 0 | 0 | 0 | 0 | 7 | 0 | 4 | 1 | 12 | 128 |
| UAAGGUGCAUCUAGUGCAGUUA | HSA-MIR-18B | H | 0 | 1 | 1 | 1 | 0 | 0 | 9 | 0 | 12 | 129 |
| UAAGUGCUUCCAUGUUUUAGUAG | HSA-MIR-302B | C | 0 | 0 | 0 | 0 | 0 | 12 | 0 | 0 | 12 | 130 |
| CCCAGUGUUUAGACUAUCUGUUC | HSA-MIR-199B | C | 3 | 1 | 5 | 2 | 0 | 0 | 0 | 1 | 12 | 131 |
| UUAAGACUUGCAGUGAUGUUUAA | HSA-MIR-499 | AC | 0 | 0 | 0 | 0 | 0 | 11 | 0 | 0 | 11 | 132 |
| CGAAUGUUGCUCGGUGAACCCCU | HSA-MIR-409-3P | C | 3 | 2 | 3 | 1 | 0 | 0 | 1 | 0 | 11 | 133 |
| AUCGGGAAUGUCGUGUCCGCC | HSA-MIR-425 | C | 0 | 0 | 0 | 0 | 5 | 1 | 2 | 2 | 10 | 134 |
| UUGCAUAGUCACAAAGUGA | HSA-MIR-153 | H | 1 | 0 | 1 | 0 | 0 | 0 | 3 | 3 | 9 | 135 |
| UCCUUCAUUCCACCGGAGUCUG | HSA-MIR-205 | H | 0 | 0 | 0 | 0 | 5 | 4 | 0 | 0 | 9 | 136 |
| UGAAUGUCCAAACGCAAUUCU | HSA-MIR-219 | H | 0 | 1 | 1 | 0 | 1 | 0 | 4 | 2 | 9 | 137 |
| CGCAUCCCCUAGGGCAUUGGUGU | HSA-MIR-324-5P | H | 0 | 0 | 6 | 0 | 0 | 0 | 3 | 0 | 9 | 138 |

Fig. 9E

| Sequence | Name | Type | | | | | | | | | ID |
|---|---|---|---|---|---|---|---|---|---|---|---|
| UCCCUGUCCUCCAGGAGCUCA | HSA-MIR-339 | C | 0 | 0 | 0 | 1 | 2 | 5 | 1 | 9 | 139 |
| AGCUGGUGUUGUGAAUC | HSA-MIR-138 | H | 2 | 0 | 0 | 2 | 3 | 0 | 0 | 8 | 140 |
| UGAGAACUGAAUUCCAUGGGUU | HSA-MIR-146A | C | 1 | 0 | 5 | 2 | 0 | 0 | 0 | 8 | 141 |
| AGCUCGGUCAGAGGCCCCUCAG | HSA-MIR-423 | C | 0 | 0 | 0 | 0 | 4 | 3 | 1 | 8 | 142 |
| GUCAACACUUGCUGGUUUCCUC | HSA-MIR-505 | AC | 0 | 0 | 0 | 4 | 0 | 2 | 3 | 8 | 143 |
| AACCCGUAGAUCCGAUCUUGUG | HSA-MIR-99A | C | 2 | 0 | 1 | 2 | 1 | 0 | 0 | 7 | 144 |
| AAUCCUUGGAACCUAGGUGUGAG | HSA-MIR-362 | AC | 0 | 0 | 4 | 0 | 2 | 1 | 3 | 6 | 145 |
| GCACAUUACACGGUCGACCUCU | HSA-MIR-323 | H | 1 | 0 | 0 | 2 | 0 | 0 | 0 | 5 | 146 |
| UUAUCAGAAUCUCCAGGGGUAC | HSA-MIR-361 | H | 0 | 0 | 4 | 0 | 1 | 0 | 0 | 5 | 147 |
| UACCCUGUAGAACCGAAUUUGU | HSA-MIR-10B | C | 4 | 0 | 2 | 0 | 0 | 0 | 2 | 5 | 148 |
| UAGGUUAUCCGUGUUGCCUUCG | HSA-MIR-154 | C | 1 | 0 | 3 | 1 | 0 | 0 | 1 | 5 | 149 |
| UAGGUAGUUUCAUGUUGUUGGG | HSA-MIR-196A | C | 1 | 0 | 1 | 0 | 1 | 2 | 0 | 5 | 150 |
| CCACUGCCCCAGGUGCUGCUGG | HSA-MIR-324-3P | C | 1 | 1 | 0 | 0 | 0 | 4 | 0 | 5 | 151 |
| AACAUUCAUUGUUGUCGGUGGGUU | HSA-MIR-181D | AC | 0 | 0 | 1 | 4 | 0 | 2 | 0 | 5 | 152 |
| AAUAUAACACAGAUGGCCUGUU | HSA-MIR-410 | AC | 2 | 0 | 0 | 1 | 1 | 0 | 0 | 5 | 153 |
| CUGGACUUGGAGUCAGAAGGCC | HSA-MIR-422B | C | 0 | 0 | 3 | 2 | 0 | 1 | 0 | 4 | 154 |
| UGAUAUGUUUGAUAUAUUAGGU | HSA-MIR-190 | H | 4 | 0 | 1 | 0 | 0 | 0 | 0 | 4 | 155 |
| CUCCUGACUCCAGGUCCUGUGU | HSA-MIR-378 | H | 0 | 0 | 0 | 0 | 0 | 0 | 0 | 4 | 156 |
| AAUUGCACUUUAGCAAUGGUGA | HSA-MIR-367 | C | 0 | 0 | 4 | 0 | 0 | 0 | 0 | 4 | 157 |
| UGAGAACUGAAUUCCAUAGGCU | HSA-MIR-146B | AC | 1 | 0 | 0 | 4 | 0 | 0 | 0 | 4 | 158 |
| UAACAGUCUACAGCCAUGGUCG | HSA-MIR-132 | H | 2 | 0 | 2 | 1 | 0 | 0 | 1 | 3 | 159 |
| AUCACACAAAGGCAACUUUUGU | HSA-MIR-377 | C | 1 | 1 | 0 | 0 | 0 | 0 | 0 | 3 | 160 |
| UUAAGGCACGCGGUGAAUGCCA | HSA-MIR-124A | C | 1 | 0 | 2 | 0 | 0 | 0 | 0 | 3 | 161 |
| UAUGUGGGAUGGUAAACCGCUU | HSA-MIR-299-3P | C | 0 | 0 | 2 | 0 | 0 | 0 | 1 | 3 | 162 |
| UGUUUGCAGAGGAAACUGAGAC | HSA-MIR-452 | C | 0 | 0 | 0 | 2 | 0 | 0 | 0 | 3 | 163 |
| AACCUUUGUCCUGGGUGAGA | HSA-MIR-501 | AC | 0 | 0 | 0 | 2 | 0 | 0 | 1 | 3 | 164 |
| AUUGACACUUCUGUGAGUAG | HSA-MIR-514 | AC | 0 | 0 | 0 | 0 | 3 | 0 | 0 | 3 | 165 |
| ACCAUCGACCGUUGAUUGUACC | HSA-MIR-213 | H | 0 | 0 | 1 | 1 | 0 | 1 | 0 | 2 | 166 |
| UGCUGACUCCUAGUCCAGGGC | HSA-MIR-345 | C | 0 | 0 | 0 | 0 | 0 | 1 | 0 | 2 | 167 |
| UAUACAAGGCAAGCUCUCUGU | HSA-MIR-381 | H | 2 | 0 | 1 | 0 | 0 | 0 | 1 | 2 | 168 |
| CAAGUCACUAGUGGUUCCGUUUA | HSA-MIR-224 | C | 0 | 0 | 1 | 0 | 0 | 1 | 0 | 2 | 169 |
| AGGGCCCCUCAAUCCUGU | HSA-MIR-296 | C | 0 | 0 | 2 | 0 | 0 | 0 | 0 | 2 | 170 |
| UAAGUGCUUCCAUGUUUUGGUGA | HSA-MIR-302A | C | 0 | 0 | 2 | 0 | 0 | 0 | 0 | 2 | 171 |
| UAAGUGCUUCCAUGUUUCAGUGG | HSA-MIR-302C | C | 0 | 0 | 2 | 0 | 0 | 0 | 0 | 2 | 172 |
| UAAGUGCUUCCAUGUUUGAGUGU | HSA-MIR-302D | C | 0 | 0 | 2 | 0 | 0 | 0 | 0 | 2 | 173 |
| UAUGGCUUUUUAUUCCUAUGUGA | HSA-MIR-135A | C | 1 | 0 | 0 | 0 | 0 | 1 | 0 | 2 | 174 |

Fig. 9F

| Sequence | Name | Evidence | | | | | | | # |
|---|---|---|---|---|---|---|---|---|---|
| CUUUCAGUCGGAUGUUUGCAGC | HSA-MIR-30A-3P | C | 0 | 0 | 1 | 0 | 0 | 2 | 175 |
| CAAAGUGCUCAUAGUGCAGGUAG | HSA-MIR-20B | AC | 0 | 0 | 2 | 0 | 0 | 2 | 176 |
| AAACAAACAUGGUGCACUUCUUU | HSA-MIR-495 | AC | 0 | 0 | 1 | 0 | 1 | 2 | 177 |
| UCAGUGCAUCACAGAACUUUGU | HSA-MIR-148B | H | 0 | 0 | 0 | 1 | 0 | 1 | 178 |
| UGGACGGAGAACUGAUAAGGGU | HSA-MIR-184 | H | 0 | 0 | 0 | 1 | 0 | 1 | 179 |
| UUCCCUUUGUCAUCCUAUGCCU | HSA-MIR-204 | H | 0 | 0 | 1 | 0 | 0 | 1 | 180 |
| UGGUUUACCGUCCCACAUACAU | HSA-MIR-299-5P | H | 0 | 0 | 1 | 0 | 0 | 1 | 181 |
| CCUCUGGGCCCUUCCUCCAG | HSA-MIR-326 | H | 0 | 0 | 0 | 0 | 1 | 1 | 182 |
| AGGCAGUGUAGUUAGCUGAUUGC | HSA-MIR-34C | H | 0 | 0 | 1 | 0 | 0 | 1 | 183 |
| UGGUAGACUAUGGAACGUA | HSA-MIR-379 | C | 0 | 0 | 0 | 1 | 0 | 1 | 184 |
| GAAGUUGUUCGUGGUGGAUUCG | HSA-MIR-382 | C | 0 | 1 | 0 | 0 | 0 | 1 | 185 |
| UGGCAGUGUAUUGUUAGCUGGU | HSA-MIR-449 | C | 0 | 0 | 0 | 0 | 1 | 1 | 186 |
| CACUCAGCCUUGAGGGCACUUUC | HSA-MIR-512-1 5P | AC | 0 | 0 | 0 | 1 | 0 | 1 | 187 |
| CACUCAGCCUUGAGGGCACUUUC | HSA-MIR-512-2 5P | AC | 0 | 0 | 0 | 1 | 0 | 1 | 188 |
| UGAAACAUACACGGAAACCUCUU | HSA-MIR-494 | AC | 0 | 0 | 1 | 1 | 0 | 1 | 189 |
| UUUCAAGCCAGGGGCGUUUUC | HSA-MIR-498 | AC | 0 | 0 | 0 | 0 | 1 | 1 | 190 |
| AUCCUUGCUAUCUGGGUGCUA | HSA-MIR-502 | AC | 0 | 0 | 1 | 1 | 0 | 1 | 191 |
| UUUUGCACCUUUUGGAGUGAA | HSA-MIR-507 | AC | 0 | 0 | 0 | 0 | 0 | 1 | 192 |
| AUCGUGCAUCCCUUUAGAGUGUU | HSA-MIR-517A | AC | 0 | 0 | 0 | 1 | 0 | 1 | 193 |
| AUCGUGCAUCCUUUUAGAGUGU | HSA-MIR-517C | AC | 0 | 0 | 0 | 1 | 0 | 1 | 194 |
| CAAAGCGCUCCCCUUUAGAGGU | HSA-MIR-518B | AC | 0 | 0 | 0 | 0 | 0 | 1 | 195 |
| AAAGUGCUUCUCUUUGGUGGGU | HSA-MIR-520D | AC | 0 | 0 | 0 | 1 | 0 | 1 | 196 |
| ACAAAGUGCUUCCCUUUAGAGUGU | HSA-MIR-520G | AC | 0 | 0 | 0 | 1 | 0 | 1 | 197 |
| ACAAAGUGCUUCCCUUUAGAGU | HSA-MIR-520H | AC | 0 | 0 | 0 | 0 | 0 | 1 | 198 |
| AACGCACUUCCCUUUAGAGUGU | HSA-MIR-521 | AC | 0 | 0 | 0 | 0 | 0 | 1 | 199 |
| CUCCAGAGGGAUGCACUUUCU | HSA-MIR-525 | AC | 0 | 0 | 0 | 0 | 0 | 1 | 200 |

Abbreviations for the Evidence column are as follows: H, evidence of homology to other species (not directly cloned prior to this study); C, evidence by direct cloning; AC, evidence by array cloning Fig. 10. (Table 3.) Differential expression of known miRNAs in tumor versus normal tissue

| Seq Id No: | Description | Tumor Sum | Normal Sum | Tumor Sum (Normalized) | Normal Sum (Normalized) | Normal / Tumor | Tumor / Normal | Fisher Exact P-Value |
|---|---|---|---|---|---|---|---|---|
| 1 | HSA-MIR-21 | 1250 | 2483 | 2043.5 | 1171.4 | 0.6 | 1.7 | 0 |
| 2 | HSA-MIR-200A | 1162 | 1769 | 1899.6 | 834.6 | 0.4 | 2.3 | 0 |
| 3 | HSA-MIR-200C | 225 | 1082 | 367.8 | 510.4 | 1.4 | 0.7 | 0.000003 |
| 4 | HSA-MIR-143 | 182 | 2547 | 297.5 | 1201.6 | 4.0 | 0.2 | 0 |
| 5 | HSA-MIR-200B | 376 | 911 | 614.7 | 429.8 | 0.7 | 1.4 | 0 |
| 7 | HSA-MIR-24 | 136 | 647 | 222.3 | 305.2 | 1.4 | 0.7 | 0.000495 |
| 8 | HSA-MIR-26A | 125 | 868 | 204.3 | 409.5 | 2.0 | 0.5 | 0 |
| 9 | HSA-MIR-145 | 57 | 1245 | 93.2 | 587.3 | 6.3 | 0.2 | 0 |
| 10 | HSA-MIR-101 | 71 | 468 | 116.1 | 220.8 | 1.9 | 0.5 | 0 |
| 12 | HSA-MIR-192 | 250 | 501 | 408.7 | 236.4 | 0.6 | 1.7 | 0 |
| 15 | HSA-MIR-103 | 6 | 102 | 9.8 | 48.1 | 4.9 | 0.2 | 0.000003 |
| 16 | HSA-MIR-16 | 35 | 195 | 57.2 | 91.1 | 1.6 | 0.6 | 0.008553 |
| 17 | HSA-MIR-25 | 16 | 22 | 26.2 | 10.4 | 0.4 | 2.5 | 0.00597 |
| 19 | HSA-MIR-29B | 24 | 167 | 39.2 | 78.8 | 2.0 | 0.5 | 0.000649 |
| 20 | HSA-MIR-30E-5P | 41 | 305 | 67 | 143.9 | 2.1 | 0.5 | 0 |
| 21 | HSA-MIR-142-3P | 206 | 371 | 336.8 | 175 | 0.5 | 1.9 | 0 |
| 22 | HSA-MIR-191 | 97 | 120 | 158.6 | 56.6 | 0.4 | 2.8 | 0 |
| 23 | HSA-MIR-193A | 25 | 302 | 40.9 | 142.5 | 3.5 | 0.3 | 0 |
| 26 | HSA-MIR-19B | 67 | 122 | 109.5 | 57.6 | 0.5 | 1.9 | 0.000048 |
| 27 | HSA-MIR-30D | 17 | 123 | 27.8 | 58 | 2.1 | 0.5 | 0.002996 |
| 29 | HSA-MIR-30A-5P | 45 | 379 | 73.6 | 178.8 | 2.4 | 0.4 | 0 |
| 31 | HSA-LET-7G | 30 | 184 | 49 | 86.8 | 1.8 | 0.6 | 0.002286 |
| 32 | HSA-MIR-29A | 56 | 108 | 91.5 | 50.1 | 0.5 | 1.8 | 0.000651 |
| 33 | HSA-MIR-27B 45 | 219 | 426 | 358 | 200.1 | 0.6 | 1.8 | 0 |
| 34 | HSA-LET-7F | 27 | 173 | 44.1 | 81.6 | 1.9 | 0.5 | 0.002066 |
| 36 | HSA-MIR-18A | 33 | 22 | 53.9 | 10.4 | 0.2 | 5.2 | 0 |
| 37 | HSA-LET-7A | 17 | 138 | 27.8 | 65.1 | 2.3 | 0.4 | 0.000318 |
| 39 | HSA-MIR-92 | 14 | 22 | 22.9 | 10.4 | 0.5 | 2.2 | 0.025867 |
| 40 | HSA-MIR-106B | 29 | 16 | 47.4 | 7.5 | 0.2 | 6.3 | 0 |
| 42 | HSA-MIR-33 | 14 | 15 | 22.9 | 7.1 | 0.3 | 3.2 | 0.002535 |
| 44 | HSA-MIR-23B | 10 | 103 | 16.3 | 48.6 | 3.0 | 0.3 | 0.000249 |
| 48 | HSA-MIR-19A | 19 | 36 | 31.1 | 16.1 | 0.5 | 1.9 | 0.035482 |
| 49 | HSA-MIR-30C | 5 | 107 | 8.2 | 50.5 | 6.2 | 0.2 | 0 |
| 51 | HSA-MIR-32 | 15 | 23 | 24.5 | 10.9 | 0.4 | 2.2 | 0.017873 |
| 52 | HSA-MIR-125B | 2 | 98 | 3.3 | 46.2 | 14.0 | 0.1 | 0 |
| 54 | HSA-MIR-107 | 1 | 39 | 1.6 | 18.4 | 11.5 | 0.1 | 0.000893 |
| 55 | HSA-MIR-29C | 15 | 144 | 24.5 | 67.9 | 2.8 | 0.4 | 0.000033 |
| 57 | HSA-MIR-181A | 5 | 62 | 8.2 | 29.2 | 3.6 | 0.3 | 0.001832 |
| 59 | HSA-LET-7B | 7 | 91 | 11.4 | 42.9 | 3.8 | 0.3 | 0.000082 |
| 62 | HSA-MIR-195 | 12 | 118 | 19.6 | 55.7 | 2.8 | 0.4 | 0.000124 |
| 63 | HSA-MIR-1 | 3 | 122 | 4.9 | 57.6 | 11.8 | 0.1 | 0 |
| 65 | HSA-MIR-218 | 11 | 96 | 17.1 | 45.3 | 2.6 | 0.4 | 0.001589 |
| 76 | HSA-MIR-142-5P | 26 | 37 | 42.5 | 17.5 | 0.4 | 2.4 | 0.000739 |
| 77 | HSA-MIR-429 | 18 | 15 | 29.4 | 7.1 | 0.2 | 4.1 | 0.000059 |
| 80 | HSA-MIR-375 | 3 | 45 | 4.9 | 21.2 | 4.3 | 0.2 | 0.004887 |
| 85 | HSA-MIR-133A | 0 | 48 | 0 | 22.6 | 22.6 | 0.0 | 0.000012 |
| 86 | HSA-MIR-28 | 0 | 21 | 0 | 9.9 | 9.9 | 0.0 | 0.007428 |
| 94 | HSA-MIR-365 | 1 | 22 | 1.6 | 10.4 | 6.5 | 0.2 | 0.042079 |
| 96 | HSA-MIR-342 | 0 | 25 | 0 | 11.8 | 11.8 | 0.0 | 0.002915 |
| 101 | HSA-MIR-148A | 8 | 10 | 13.1 | 4.7 | 0.4 | 2.8 | 0.041616 |
| 112 | HSA-MIR-450 | 7 | 1 | 11.4 | 0.5 | 0.0 | 22.8 | 0.000181 |
| 115 | HSA-LET-7C | 0 | 15 | 0 | 7.1 | 7.1 | 0.0 | 0.031018 |

Fig. 11 A (Table 4.) miRNA* forms in colorectal cells (SEQ ID NOS: 201-336, respectively)

| Classification | Sequence | miRNA* name/number | 308N | 308T | 309N | 309T | CACO-2 | SW480 | HCT WT | HCT Ex5 | SUM |
|---|---|---|---|---|---|---|---|---|---|---|---|
| Novel miRNA* of Novel Candidate | CAGUGCCUCGGCAGUGCAGCC | HSA-MIR-33B* | 0 | 0 | 0 | 0 | 0 | 0 | 0 | 2 | 2 |
| Novel miRNA* of Novel Candidate | AAAAGUAAUUGCGAGUUUUACC | HSA-MIR-548A-3* | 0 | 0 | 0 | 0 | 0 | 0 | 0 | 1 | 1 |
| Novel miRNA* of Novel Candidate | AUCAAGGAUCUUAAACUUUGC | HSA-MIR-561* | 0 | 0 | 0 | 0 | 0 | 0 | 1 | 1 | 2 |
| Novel miRNA* of Novel Candidate | AAGAUGUGGAAAAAUUGGAA | HSA-MIR-576* | 0 | 0 | 0 | 0 | 0 | 0 | 0 | 3 | 3 |
| Novel miRNA* of Novel Candidate | UAACUGGUUGAACAACUGAAC | HSA-MIR-582* | 0 | 0 | 2 | 0 | 0 | 1 | 0 | 0 | 3 |
| Novel miRNA* of Novel Candidate | UAAUUUUAUGUAUAAGCUAGUC | HSA-MIR-590* | 1 | 1 | 3 | 0 | 0 | 0 | 11 | 22 | 38 |
| Novel miRNA* of Novel Candidate | UUUGAUAAGCUGACAUGGGACA | HSA-MIR-599* | 0 | 0 | 0 | 0 | 0 | 16 | 0 | 0 | 16 |
| Novel miRNA* of Novel Candidate | CACAAGGUAUUGGUAUUACC | HSA-MIR-624* | 0 | 1 | 0 | 0 | 0 | 0 | 0 | 0 | 1 |
| Novel miRNA* of Novel Candidate | CUAUAGAACUUUCCCCCUC | HSA-MIR-625* | 0 | 0 | 0 | 0 | 0 | 1 | 0 | 2 | 3 |
| Novel miRNA* of Novel Candidate | UGGGUUUACGUUGGGAGAACU | HSA-MIR-629* | 0 | 0 | 0 | 0 | 2 | 2 | 0 | 1 | 5 |
| Novel miRNA* of Novel Candidate | AAAGGAAAGUGUAUCCUAAAAG | HSA-MIR-651* | 0 | 0 | 0 | 0 | 0 | 1 | 0 | 0 | 1 |
| Novel miRNA* of Novel Candidate | ACAACCUAGGAGAGGGUGCCA | HSA-MIR-652* | 0 | 0 | 0 | 0 | 0 | 0 | 1 | 0 | 1 |
| Novel miRNA* of Known miRNA | CUAUACAAUCUACUGUCUUUC | HSA-LET-7A-1* | 1 | 0 | 0 | 1 | 0 | 0 | 0 | 2 | 3 |
| Novel miRNA* of Known miRNA | CUGUACAGCCUCCUAGCUUUCC | HSA-LET-7A-2* | 0 | 0 | 0 | 0 | 0 | 0 | 2 | 2 | 4 |
| Novel miRNA* of Known miRNA | CUAUACGACCUGCUGCUUUCU | HSA-LET-7D* | 0 | 0 | 0 | 0 | 0 | 0 | 0 | 2 | 2 |
| Novel miRNA* of Known miRNA | CUAUACGGCCUCCUAGCUUUCC | HSA-LET-7E* | 0 | 0 | 0 | 0 | 0 | 0 | 1 | 1 | 2 |
| Novel miRNA* of Known miRNA | GAUAACUAUACAAUCUAUUGCCUUC | HSA-LET-7F-1* | 0 | 0 | 0 | 0 | 0 | 0 | 1 | 0 | 1 |
| Novel miRNA* of Known miRNA | CUAUACAGUCUACUGUCU | HSA-LET-7F-2* | 1 | 0 | 0 | 1 | 0 | 0 | 0 | 0 | 2 |
| Novel miRNA* of Known miRNA | CUGUACAGGCCACUGCCUUGC | HSA-LET-7G* | 2 | 0 | 1 | 0 | 0 | 1 | 4 | 2 | 10 |
| Novel miRNA* of Known miRNA | CUGCGCAAGCUACUGCCUU | HSA-LET-7I* | 3 | 2 | 0 | 0 | 0 | 1 | 11 | 5 | 22 |
| Novel miRNA* of Known miRNA | CAAGCUUGUAUCUAUAGGUAUG | HSA-MIR-100* | 0 | 0 | 1 | 0 | 0 | 0 | 13 | 12 | 26 |
| Novel miRNA* of Known miRNA | CAGUUAUCACAGUGCUGAUGC | HSA-MIR-101-1* | 0 | 0 | 0 | 0 | 0 | 1 | 0 | 2 | 3 |
| Novel miRNA* of Known miRNA | GGCUUCUUUACAGUGCUGCCUU | HSA-MIR-103-1* | 0 | 0 | 1 | 0 | 3 | 0 | 4 | 0 | 9 |
| Novel miRNA* of Known miRNA | AGCUUCUUUACAGUGCUGCCUUGU | HSA-MIR-103-2* | 0 | 0 | 1 | 0 | 0 | 1 | 3 | 0 | 5 |
| Novel miRNA* of Known miRNA | UACUGCAAUGUAAGCACUUCUU | HSA-MIR-106A* | 1 | 0 | 0 | 0 | 0 | 0 | 1 | 0 | 2 |
| Novel miRNA* of Known miRNA | CCGCACUGUGGGUACUUGCUG | HSA-MIR-106B* | 0 | 1 | 0 | 1 | 3 | 2 | 4 | 1 | 12 |
| Novel miRNA* of Known miRNA | CAAAUCGUAUCUAGGGGAAU | HSA-MIR-10A* | 0 | 0 | 0 | 1 | 1 | 5 | 2 | 1 | 10 |
| Novel miRNA* of Known miRNA | ACAGGUGAGGUUCUUGGGAGC | HSA-MIR-125A* | 1 | 0 | 0 | 0 | 0 | 1 | 2 | 2 | 6 |
| Novel miRNA* of Known miRNA | ACGGGUUAGGCUCUUGGGAG | HSA-MIR-125B-1* | 0 | 0 | 0 | 0 | 0 | 0 | 3 | 3 | 6 |
| Novel miRNA* of Known miRNA | AAGCCCUUACCCCAAAAAGCAU | HSA-MIR-129-2* | 0 | 0 | 0 | 0 | 0 | 0 | 0 | 0 | 1 |
| Novel miRNA* of Known miRNA | ACUCUUUCCCUGUUGCACUA | HSA-MIR-130B* | 0 | 0 | 0 | 0 | 0 | 0 | 1 | 0 | 2 |

Fig. 11B

| | Sequence | miRNA | | | | | | | | |
|---|---|---|---|---|---|---|---|---|---|---|
| Novel miRNA* of Known miRNA | ACCGUGGCUUUCGAUUGUUAC | HSA-MIR-132* | 1 | 0 | 0 | 0 | 0 | 0 | 2 | 3 |
| Novel miRNA* of Known miRNA | AGCUGGUAAAAUGGAACCAAAU | HSA-MIR-133A-1* | 3 | 0 | 0 | 0 | 0 | 0 | 0 | 11 |
| Novel miRNA* of Known miRNA | ACCACAGGUAGAACCACGGA | HSA-MIR-140* | 7 | 3 | 8 | 1 | 5 | 3 | 7 | 10 | 46 |
| Novel miRNA* of Known miRNA | CAUCUCCAGUACAGUGUUGGA | HSA-MIR-141* | 0 | 0 | 10 | 0 | 1 | 2 | 5 | 1 | 9 |
| Novel miRNA* of Known miRNA | GGUGCAGUGCUGCAUCUCUGG | HSA-MIR-143* | 4 | 1 | 20 | 0 | 0 | 0 | 0 | 0 | 25 |
| Novel miRNA* of Known miRNA | GGAUAUCAUCAUAUACUGUAAGU | HSA-MIR-144* | 1 | 0 | 1 | 1 | 0 | 0 | 0 | 0 | 3 |
| Novel miRNA* of Known miRNA | AUUCUGGAAAUACUGUUC | HSA-MIR-145* | 6 | 0 | 3 | 0 | 0 | 0 | 0 | 0 | 9 |
| Novel miRNA* of Known miRNA | AAAGUUCUGAGACACUCCGACU | HSA-MIR-148A* | 0 | 0 | 0 | 0 | 1 | 0 | 1 | 0 | 1 |
| Novel miRNA* of Known miRNA | GAAGUUCUGUUAUACACUCA | HSA-MIR-148B* | 1 | 0 | 0 | 1 | 0 | 0 | 0 | 0 | 2 |
| Novel miRNA* of Known miRNA | GUCAUUUUGUGAUGUUGCAG | HSA-MIR-153-2* | 0 | 0 | 0 | 0 | 0 | 0 | 1 | 6 | 8 |
| Novel miRNA* of Known miRNA | CAGGCCAUAUUGUGCUGCCUCA | HSA-MIR-15A* | 0 | 1 | 1 | 0 | 4 | 6 | 2 | 1 | 15 |
| Novel miRNA* of Known miRNA | CGAAUCAUUAUUGCUGUC | HSA-MIR-15B* | 0 | 0 | 0 | 0 | 0 | 0 | 3 | 1 | 4 |
| Novel miRNA* of Known miRNA | CCAGUAUUAACUGUGCUGCUGAA | HSA-MIR-16-1* | 0 | 0 | 1 | 0 | 1 | 1 | 0 | 1 | 2 |
| Novel miRNA* of Known miRNA | ACCAAUAUUACUGUGCUGCUUU | HSA-MIR-16-2* | 0 | 0 | 1 | 0 | 0 | 0 | 4 | 1 | 7 |
| Novel miRNA* of Known miRNA | ACCACUGACCGUUGACUGUAC | HSA-MIR-181A* | 0 | 1 | 1 | 0 | 1 | 1 | 0 | 0 | 3 |
| Novel miRNA* of Known miRNA | ACCAUCGACCGUUGAGUGGACC | HSA-MIR-181C* | 0 | 0 | 0 | 0 | 2 | 0 | 0 | 0 | 2 |
| Novel miRNA* of Known miRNA | UGAAUUACCGAAGGGCCAUAAA | HSA-MIR-183* | 0 | 0 | 0 | 0 | 1 | 0 | 1 | 0 | 2 |
| Novel miRNA* of Known miRNA | AGGGGCUGGCUUUCCUCUGG | HSA-MIR-185* | 0 | 0 | 0 | 0 | 0 | 0 | 0 | 1 | 1 |
| Novel miRNA* of Known miRNA | CCCAAAGGUGAAUUUUUGGGAA | HSA-MIR-186* | 1 | 0 | 2 | 0 | 4 | 4 | 7 | 6 | 24 |
| Novel miRNA* of Known miRNA | CUCCCACAUGCAGGGUUUGCA | HSA-MIR-188* | 0 | 1 | 0 | 0 | 0 | 0 | 1 | 0 | 2 |
| Novel miRNA* of Known miRNA | ACUGCCCUUAAGUGCUCCUCUGGC | HSA-MIR-18A* | 0 | 0 | 0 | 1 | 0 | 1 | 0 | 0 | 1 |
| Novel miRNA* of Known miRNA | CUGCCAAUUCCAUAGGUCACA | HSA-MIR-192* | 4 | 3 | 4 | 2 | 1 | 0 | 0 | 1 | 15 |
| Novel miRNA* of Known miRNA | UGGGUCUUUGCGGGCGAGA | HSA-MIR-193A* | 1 | 0 | 1 | 0 | 1 | 1 | 0 | 0 | 4 |
| Novel miRNA* of Known miRNA | CCAGUGGAGUGGCUGUAC | HSA-MIR-194-1* | 0 | 0 | 0 | 1 | 0 | 0 | 0 | 0 | 1 |
| Novel miRNA* of Known miRNA | ACAGUAGUCUGCACAUUGGUU | HSA-MIR-199B* | 23 | 15 | 55 | 12 | 0 | 0 | 0 | 0 | 105 |
| Novel miRNA* of Known miRNA | AGUUUUGCAUAGUUGCACUAC | HSA-MIR-19A* | 0 | 0 | 0 | 0 | 0 | 5 | 4 | 1 | 10 |
| Novel miRNA* of Known miRNA | AGUUUUGCAGGUUUGCAUCCAGC | HSA-MIR-19B-1* | 0 | 0 | 1 | 0 | 1 | 1 | 3 | 7 | 13 |
| Novel miRNA* of Known miRNA | CAUCUUACUGGGCAGCAUUGG | HSA-MIR-19B-2* | 2 | 0 | 0 | 0 | 0 | 0 | 0 | 0 | 3 |
| Novel miRNA* of Known miRNA | CGUCUUACCCAGCAGUGUUUG | HSA-MIR-200B* | 0 | 1 | 1 | 0 | 2 | 0 | 2 | 0 | 4 |
| Novel miRNA* of Known miRNA | AGUGGUUCUUAACAGUUCAACA | HSA-MIR-200C* | 0 | 0 | 0 | 0 | 0 | 0 | 0 | 1 | 1 |
| Novel miRNA* of Known miRNA | CUGCAUUAUGAGCACUUAAAGU | HSA-MIR-203* | 1 | 1 | 4 | 1 | 4 | 2 | 5 | 5 | 23 |
| Novel miRNA* of Known miRNA | CAACACCAGUCGAUGGGCUGUC | HSA-MIR-20A* | 15 | 2 | 8 | 2 | 6 | 10 | 13 | 20 | 76 |
| Novel miRNA* of Known miRNA | UGCCUGUCUACACUGUGC | HSA-MIR-214* | 2 | 0 | 3 | 0 | 0 | 0 | 0 | 0 | 5 |
| Novel miRNA* of Known miRNA | AGUCUUCAGUGGCAAGCUUU | HSA-MIR-22* | 0 | 1 | 1 | 0 | 2 | 2 | 0 | 3 | 8 |
| Novel miRNA* of Known miRNA | ACCUGGCAUACAAUGUAGAUUUCU | HSA-MIR-221* | 0 | 0 | 0 | 0 | 0 | 1 | 2 | 1 | 4 |

Fig. 11C

| | Sequence | miRNA | | | | | | | | | |
|---|---|---|---|---|---|---|---|---|---|---|---|
| Novel miRNA* of Known miRNA | GGCUCAGUAGCCAGUGUAGAUCC | HSA-MIR-222* | 0 | 0 | 1 | 0 | 0 | 3 | 2 | 2 | 8 |
| Novel miRNA* of Known miRNA | CGUGUAUUUGACAAGCUGAGUUG | HSA-MIR-223* | 0 | 0 | 1 | 0 | 0 | 0 | 0 | 0 | 1 |
| Novel miRNA* of Known miRNA | AGGGCUUAGCUGCUUGUGAG | HSA-MIR-27A* | 0 | 0 | 0 | 1 | 0 | 1 | 2 | 1 | 5 |
| Novel miRNA* of Known miRNA | CAGAGCUUAGCUGAUUGGUGAACA | HSA-MIR-27B* | 0 | 0 | 0 | 0 | 0 | 0 | 0 | 0 | 1 |
| Novel miRNA* of Known miRNA | CACUAGAUUGUGAGCUCCUGGA | HSA-MIR-28* | 3 | 0 | 1 | 3 | 0 | 1 | 7 | 9 | 33 |
| Novel miRNA* of Known miRNA | ACUGAUUUCUUUUGGUGUUCAG | HSA-MIR-29A* | 0 | 0 | 2 | 0 | 1 | 7 | 6 | 3 | 19 |
| Novel miRNA* of Known miRNA | GCUGGUUUCAUAUGGUGGUUUAGA | HSA-MIR-29B-1* | 2 | 0 | 0 | 0 | 0 | 2 | 7 | 1 | 12 |
| Novel miRNA* of Known miRNA | UGACCGAUUUCUCCUGGUGUU | HSA-MIR-29C* | 1 | 1 | 2 | 0 | 0 | 1 | 1 | 1 | 7 |
| Novel miRNA* of Known miRNA | GCUCUGACUUUAUUGCACUAC | HSA-MIR-301* | 0 | 0 | 0 | 0 | 1 | 0 | 1 | 0 | 1 |
| Novel miRNA* of Known miRNA | CUGGGAGGUGGAUGUUUACUUC | HSA-MIR-30B* | 1 | 0 | 0 | 0 | 0 | 0 | 0 | 0 | 1 |
| Novel miRNA* of Known miRNA | CUUUCAGUCAGAUGUUUGCUGC | HSA-MIR-30D* | 0 | 0 | 0 | 0 | 1 | 0 | 1 | 5 | 7 |
| Novel miRNA* of Known miRNA | UGCUAUGCCAACAUAUUGCCAUC | HSA-MIR-31* | 0 | 0 | 0 | 0 | 2 | 1 | 81 | ## | 258 |
| Novel miRNA* of Known miRNA | CAAUUUAGUGUGUGUGGAUAUU | HSA-MIR-32* | 0 | 0 | 0 | 0 | 0 | 0 | 1 | 0 | 1 |
| Novel miRNA* of Known miRNA | UGGAGGCAGGGCCUUUGUGAAG | HSA-MIR-326* | 0 | 0 | 0 | 1 | 0 | 0 | 0 | 0 | 1 |
| Novel miRNA* of Known miRNA | AUGCAAUGUUUCCACAGUGCAUC | HSA-MIR-33* | 0 | 0 | 1 | 1 | 0 | 1 | 2 | 1 | 6 |
| Novel miRNA* of Known miRNA | UCUCUGGGCCUGUGUCUUAG | HSA-MIR-330* | 0 | 0 | 0 | 0 | 0 | 0 | 1 | 0 | 1 |
| Novel miRNA* of Known miRNA | CUAGGUAUGGUCCCAGGGAUCC | HSA-MIR-331* | 0 | 0 | 0 | 2 | 0 | 0 | 0 | 0 | 2 |
| Novel miRNA* of Known miRNA | UUUUUCAUUAUUGCUCCUGAC | HSA-MIR-335* | 1 | 0 | 0 | 8 | 1 | 0 | 1 | 0 | 11 |
| Novel miRNA* of Known miRNA | GAACGGCUUCAUACAGAGUU | HSA-MIR-337* | 0 | 0 | 0 | 1 | 0 | 0 | 0 | 0 | 1 |
| Novel miRNA* of Known miRNA | AACAAUAUCCUGGUGCUGAGU | HSA-MIR-338* | 0 | 0 | 0 | 6 | 0 | 0 | 0 | 0 | 6 |
| Novel miRNA* of Known miRNA | UGAGCCCUCGACGACAGAGC | HSA-MIR-339* | 0 | 0 | 0 | 1 | 2 | 0 | 1 | 0 | 4 |
| Novel miRNA* of Known miRNA | UUAUAAAGCAAUGAGAGUGAU | HSA-MIR-340* | 1 | 1 | 2 | 1 | 2 | 5 | 7 | 2 | 21 |
| Novel miRNA* of Known miRNA | AAUCAGCAAGUAUACUGCCC | HSA-MIR-34A* | 0 | 0 | 1 | 0 | 0 | 0 | 0 | 0 | 1 |
| Novel miRNA* of Known miRNA | CCCCCAGGUGUGAUUCUGAUUUG | HSA-MIR-361* | 0 | 0 | 1 | 0 | 0 | 0 | 1 | 1 | 3 |
| Novel miRNA* of Known miRNA | AACACCUAUUCAAGGAUUC | HSA-MIR-362* | 0 | 0 | 3 | 2 | 0 | 0 | 1 | 0 | 6 |
| Novel miRNA* of Known miRNA | ACUCAAACUGUGGGGCAC | HSA-MIR-371* | 0 | 0 | 0 | 0 | 34 | 1 | 0 | 0 | 35 |
| Novel miRNA* of Known miRNA | CCUCAAAUGUGAGCACUAUUC | HSA-MIR-372* | 0 | 0 | 0 | 0 | 3 | 0 | 0 | 0 | 3 |
| Novel miRNA* of Known miRNA | CUUAUCAGAUUGUAUUGUAAU | HSA-MIR-374* | 1 | 1 | 0 | 0 | 0 | 0 | 1 | 5 | 8 |
| Novel miRNA* of Known miRNA | GUAGAUUCCUCUCUAUGAGU | HSA-MIR-376A* | 1 | 0 | 0 | 0 | 0 | 1 | 0 | 0 | 2 |
| Novel miRNA* of Known miRNA | AGCGAGGUUGCCCUUGUAUAU | HSA-MIR-381* | 1 | 0 | 0 | 0 | 0 | 0 | 0 | 0 | 1 |
| Novel miRNA* of Known miRNA | UGAGGGGCAGAGAGCGAGACUU | HSA-MIR-423* | 1 | 1 | 0 | 0 | 0 | 1 | 1 | 2 | 6 |
| Novel miRNA* of Known miRNA | AAUGACACGAUCACUCCCGUUGAGU | HSA-MIR-425* | 26 | 7 | 27 | 4 | 35 | 56 | 149 | 11 | 315 |
| Novel miRNA* of Known miRNA | CCAUGGAUCUCCAGGUGGG | HSA-MIR-490* | 0 | 0 | 0 | 1 | 0 | 0 | 0 | 0 | 1 |
| Novel miRNA* of Known miRNA | CUUAUGCAAGAUUCCCUUCUAC | HSA-MIR-491* | 0 | 0 | 0 | 0 | 0 | 0 | 2 | 1 | 3 |
| Novel miRNA* of Known miRNA | UGAAGGUCUACUGUGUGCCAGG | HSA-MIR-493* | 2 | 0 | 0 | 1 | 0 | 0 | 0 | 0 | 3 |

Fig. 11D

| | | | | | | | | | |
|---|---|---|---|---|---|---|---|---|---|
| Novel miRNA* of Known miRNA | CCAAACCACACUGUGGUGUUAG | HSA-MIR-497* | 0 | 0 | 0 | 1 | 0 | 0 | 1 |
| Novel miRNA* of Known miRNA | GAACAUCACAGCAAGUCUGUGC | HSA-MIR-499* | 0 | 0 | 0 | 0 | 6 | 0 | 6 |
| Novel miRNA* of Known miRNA | UAAUCCUUGCUACCUGGUGAGAG | HSA-MIR-500* | 3 | 1 | 0 | 0 | 3 | 0 | 7 |
| Novel miRNA* of Known miRNA | AAUGCACCCGGGCAAGGAUUC | HSA-MIR-501* | 0 | 0 | 0 | 0 | 0 | 1 | 1 |
| Novel miRNA* of Known miRNA | GGGUAUUGUUUCCGCUGCCAG | HSA-MIR-503* | 0 | 0 | 0 | 0 | 0 | 1 | 1 |
| Novel miRNA* of Known miRNA | AAUGUGUAGCAAAAGACAGAAU | HSA-MIR-511-1* | 2 | 0 | 0 | 2 | 0 | 0 | 4 |
| Novel miRNA* of Known miRNA | CAACAAAUCACAGUCUGCCAUA | HSA-MIR-7-1* | 0 | 0 | 0 | 2 | 0 | 4 | 3 | 9 |
| Novel miRNA* of Known miRNA | ACUGCUGAGCUAGCACUUCCCGA | HSA-MIR-93* | 0 | 0 | 0 | 0 | 1 | 0 | 1 | 0 | 2 |
| Novel miRNA* of Known miRNA | CAAUCAUGUGCAGUGCCAAUAU | HSA-MIR-96* | 0 | 0 | 0 | 0 | 0 | 2 | 0 | 0 | 2 |
| Novel miRNA* of Known miRNA | CAAGCUCGCUUCUAUGGGUCUG | HSA-MIR-99A* | 1 | 0 | 0 | 0 | 0 | 2 | 0 | 0 | 3 |
| Novel miRNA* of Known miRNA | CAAGCUCGUGUCUGUGGGUCC | HSA-MIR-99B* | 0 | 0 | 0 | 0 | 0 | 0 | 1 | 1 | 2 |
| Known miRNA* | CAUUAUUACUUUUGGUACGCG | HSA-MIR-126* | 15 | 5 | 10 | 3 | 3 | 6 | 5 | 47 |
| Known miRNA* | AAUCAUACACGGUUGACCUAUU | HSA-MIR-154* | 1 | 0 | 0 | 1 | 0 | 0 | 0 | 0 | 2 |
| Known miRNA* | UGGUUCUAGACUGUGCCAACUA | HSA-MIR-182* | 0 | 0 | 0 | 0 | 0 | 0 | 1 | 0 | 1 |
| Known miRNA* | GCUGGCGUUGGAUUUCGUCCCC | HSA-MIR-191* | 0 | 0 | 0 | 0 | 0 | 1 | 0 | 1 | 2 |
| Known miRNA* | UACAGUAGUCUGCACAUUGGUU | HSA-MIR-199A* | 18 | 13 | 43 | 10 | 0 | 0 | 0 | 0 | 84 |
| Known miRNA* | CAUCUUACCGGACAGUGCUGGA | HSA-MIR-200A* | 0 | 0 | 0 | 0 | 1 | 0 | 0 | 0 | 1 |
| Known miRNA* | UUUCCUAUGCAUAUACUUCUUU | HSA-MIR-202* | 0 | 0 | 0 | 0 | 0 | 0 | 0 | 0 | 0 |
| Known miRNA* | UAAACGUGGAUGUACUUGCUUU | HSA-MIR-302A* | 0 | 0 | 0 | 0 | 5 | 0 | 0 | 0 | 5 |
| Known miRNA* | ACUUUAACAUGGAAGUGCUUUCU | HSA-MIR-302B* | 0 | 0 | 0 | 0 | 0 | 0 | 0 | 0 | 0 |
| Known miRNA* | UUUAACAUGGGGGUACCUGCUG | HSA-MIR-302C* | 0 | 0 | 0 | 0 | 1 | 0 | 0 | 0 | 1 |
| Known miRNA* | ACUCAAAAUGGGGGCGCUUUCC | HSA-MIR-373* | 0 | 0 | 0 | 0 | 1 | 0 | 0 | 0 | 1 |
| Known miRNA* | CUGGAUGGCUCCUCCAUGUCU | HSA-MIR-432* | 0 | 0 | 0 | 0 | 0 | 0 | 0 | 0 | 0 |
| Known miRNA* | UCAGUCUCAUCUGCAAAGAAG | HSA-MIR-452* | 0 | 0 | 0 | 0 | 0 | 0 | 2 | 0 | 3 |
| Known miRNA* | CCUCUAGAGGGAAGCACUGUCU | HSA-MIR-517* | 0 | 0 | 0 | 0 | 0 | 0 | 0 | 0 | 0 |
| Known miRNA* | UCUGCAAAGGGAAGCCCUUU | HSA-MIR-518A-2* | 0 | 0 | 0 | 0 | 0 | 0 | 0 | 0 | 0 |
| Known miRNA* | UCUCUGGAGGGAAGCACUUUCUG | HSA-MIR-518C* | 0 | 0 | 0 | 0 | 0 | 0 | 0 | 0 | 0 |
| Known miRNA* | CUCUAGAGGGAAGCACUUUCUC | HSA-MIR-518F* | 0 | 0 | 0 | 0 | 0 | 0 | 0 | 0 | 0 |
| Known miRNA* | UUCUCCAAAAGGGAGCACUUUC | HSA-MIR-519E* | 0 | 0 | 0 | 0 | 0 | 0 | 0 | 0 | 0 |
| Known miRNA* | CUCCAGAGGGAAGUACUUUCU | HSA-MIR-520A* | 0 | 0 | 0 | 0 | 0 | 0 | 0 | 0 | 0 |
| Known miRNA* | UCUACAAAGGGAAGCCCUUUCUG | HSA-MIR-520D* | 0 | 0 | 0 | 0 | 0 | 0 | 0 | 0 | 0 |
| Known miRNA* | CUACAAAGGGAAGCACUUUCUC | HSA-MIR-524* | 0 | 0 | 0 | 0 | 0 | 0 | 0 | 0 | 0 |
| Known miRNA* | GAAGGCGCUUCCCUUUAGAGC | HSA-MIR-525* | 0 | 0 | 0 | 0 | 0 | 0 | 0 | 0 | 0 |
| Known miRNA* | AAAGUGCUUCCCUUUUAGAGGC | HSA-MIR-526B* | 0 | 0 | 0 | 0 | 0 | 0 | 0 | 0 | 0 |
| Known miRNA* | UAAAGCUAGAUAACCGAAAGU | HSA-MIR-9* | 2 | 0 | 7 | 0 | 2 | 7 | 76 | ## | 198 |

Fig. 11E

| | | | | | | | | | |
|---|---|---|---|---|---|---|---|---|---|
| Known miRNA* | UAAACGUGGAUGUACUUGCUUU | HSA-MIR-302A* | 0 | 0 | 0 | 5 | 0 | 0 | 5 |
| Known miRNA* | ACUUUAACAUGGAAGUGCUUUCU | HSA-MIR-302B* | 0 | 0 | 0 | 0 | 0 | 0 | 0 |
| Known miRNA* | UUUAACAUGGGGGUACCUGCUG | HSA-MIR-302C* | 0 | 0 | 0 | 1 | 0 | 0 | 1 |
| Known miRNA* | ACUCAAAAUGGGGGGCGCUUUCC | HSA-MIR-373* | 0 | 0 | 0 | 1 | 0 | 0 | 1 |
| Known miRNA* | CUGGAUGGCUCCUCCAUGUCU | HSA-MIR-432* | 0 | 0 | 0 | 0 | 0 | 0 | 0 |
| Known miRNA* | UCAGUCUCAUCUGCAAAGAAG | HSA-MIR-452* | 0 | 0 | 0 | 1 | 0 | 2 | 3 |
| Known miRNA* | CCUCUAGAUGGAAGCACUGUCU | HSA-MIR-517* | 0 | 0 | 0 | 0 | 0 | 0 | 0 |
| Known miRNA* | UCUGCAAAGGGAAGCCCUUU | HSA-MIR-518A-2* | 0 | 0 | 0 | 0 | 0 | 0 | 0 |
| Known miRNA* | UCUCUGGAGGGAAGCACUUUCUG | HSA-MIR-518C* | 0 | 0 | 0 | 0 | 0 | 0 | 0 |
| Known miRNA* | CUCUAGAGGGAAGCACUUUCUCU | HSA-MIR-518F* | 0 | 0 | 0 | 0 | 0 | 0 | 0 |
| Known miRNA* | UUCUCCAAAAGGGAGCACUUUC | HSA-MIR-519E* | 0 | 0 | 0 | 0 | 0 | 0 | 0 |
| Known miRNA* | CUCCAGAGGGAAGUACUUUCU | HSA-MIR-520A* | 0 | 0 | 0 | 0 | 0 | 0 | 0 |
| Known miRNA* | UCUACAAAGGGAAGCCCUUUCUG | HSA-MIR-520D* | 0 | 0 | 0 | 0 | 0 | 0 | 0 |
| Known miRNA* | CUACAAAGGGAAGCACUUUCUC | HSA-MIR-524* | 0 | 0 | 0 | 0 | 0 | 0 | 0 |
| Known miRNA* | GAAGGCGCUUCCCUUUAGAGC | HSA-MIR-525* | 0 | 0 | 0 | 0 | 0 | 0 | 0 |
| Known miRNA* | AAAGUGCUUCCCUUUUAGAGGG | HSA-MIR-526B* | 0 | 0 | 0 | 0 | 0 | 0 | 0 |
| Known miRNA* | UAAAGCUAGAUAACCGAAAGU | HSA-MIR-9* | 2 | 0 | 7 | 2 | 7 | 76 | 104 | 198 |

Fig. 12A (Table 5) Mature miRNAs (SEQ ID NOS: 337-469, respectively) and precursor miRNAs (SEQ ID NOS: 1386-1518, respectively)

Fig. 12B

| miRNA | Mature miRNA | Precursor miRNA | | | | | | | | | | | Location | S/AS |
|---|---|---|---|---|---|---|---|---|---|---|---|---|---|---|
| hsa-mir-548b | CAAGAACCUCAGUUGCUUUUGU | CAGACUAUAUU     U  G  UUUAU<br>        UUAGGUGGCGUGAAAGUAAUUG GGUUUU GCC   U<br>        AAUCCAACCGUGUUUUCGUUGAC CCAAGA CGG   U<br>UUCAU--------A                    C   A  UACAC | 6 | - | 119370803 | 119370824 | + | - | - | ++ | 0 | 0 | 1 | 1 | Intron of C6orf60 | S |
| hsa-mir-548c | CAAAAAUCUCAAUUACUUUUGC | CAUUGGCAUC|                      C         CAU UAC U<br>            UAUUAGGUGGUGCAAAAGUAAUUG GGUUUUGC   AUG \<br>            AUAAUUCAACACCGUUUUCAUUAAC CUAAAACG   UAC AC<br>UUC--------A                       | 12 | + | 63902616 | 63902637 | + | - | - | + | 0 | 0 | 0 | 1 | Intron of RASSF3 | S |
| hsa-mir-548d-1 | CAAAAACCACAGUUUCUUUUGC | AAACAAGUAA|                      U           UGUAA<br>            UAUUAG UUGGUGCAAAAG AAUGUGGUUUUGCC     A<br>            AUAAUC GACCAGGUUUUC UUGACCACCAAAAACGG     A<br>GAA--------A                    U           UAAUG | 8 | - | 124316877 | 124316898 | + | - | - | ++ | 0 | 0 | 1 | 1 | Intron of ATAD1 | S |
| hsa-mir-548d-2 | CAAAAACCACAGUUUCUUUUGC | GAGAGGAAGAU|                U                A<br>            UUAGGUGGUGCAAAAG AAUGUGGUUUUGCCAUUG  A<br>            AAUCCAACCGUUUUC UUGACCACCAAAAGGUAAU  A<br>AAAAU--------A             U                G | 17 | - | 66017721 | 66017742 | + | - | - | ++ | 0 | 0 | 1 | 1 | Intron of PITPN | S |
| hsa-mir-549 | UGACAACUAUGGAUGAGGUCU | AGCAUGCAACUCAAGA|                     UCU<br>                AUAUAUUGAGAGCUCAUCCAUAGUUGCACUG    C<br>                UAUAUAUUAA UCUCGAGUAGGUAACAACAGUGAC    A<br>CGGACCC--------                      UAA | 15 | + | 78850153 | 78850173 | + | - | + | ++ | 0 | 0 | 0 | 1 | Intron of KIAA1199 | AS |
| hsa-mir-549b | GACAACUAUGGAUGAGGUCUCA | CU----       A                       AUU<br>      GGGAUAUAUU AGAGCUCAUCCAUAGUUGCACUG      C<br>      UCUAUAUAUAA UCUCGAGUAGGUAACAACAGUGAC      G<br>UUGAGU       C                       AGA | 15 | + | 78850189 | 78850210 | + | - | - | ++ | 0 | 0 | 1 | 0 | Intron of KIAA1199 | S |
| hsa-mir-550 | UGUCUUACUCCCUCAGGCACAU | U   U|     C  CU   GCA                       G   C     GUU<br>  GA GCUU G UGG GGU    GUCCCUGAGGCAGUAAGA C CUGUU   G<br>  CU UGAA C ACC CUA    CACGGACUCCUCAUUCU G GAUAG   G<br>U   C     A  U-   ---                    -   U     AAU | 7 | + | 30071742 | 30071763 | + | - | + | ++ | 0 | 0 | 2 | 0 | Intron of ZNRF2 | S |
| hsa-mir-550-2 | UGUCUUACUCCCUCAGGCACAU | UGAUGCUUU|    A   G          UGCA                               GUU<br>         GCU GCUUGG       GUCCCUGAGGCAGUAAGA C CUGUU   G<br>         UGA CGACC       CACGGACUCCCUCAUUCU G GAUAG   ACU<br>UCUC--------A   G   UCUA                        | 7 | + | 32514871 | 32514892 | + | - | - | ++ | 0 | 1 | 0 | 2 | Extragenic | N/A |
| hsa-mir-551a | GCGACCCACUCUUGGUUUCCA | GGGGACUG| -   UG                C        GGG      -   UCUGA<br>      CC GGG   ACCCUGGAAAUC AGACUGGGU    GCC AG   C<br>      GG CCC   UGGGACCCUUUGG UCUCACCCA    CGG UC   G<br>AAA--------A   U         GU                G              E--   A   UUUGC | 1 | - | 3280267 | 3280277 | + | - | - | +++ | 0 | 1 | 0 | 2 | Extragenic | N/A |
| hsa-mir-551b | GCGACCCAUACUUGGUUUCAG | AGCAUGUGC|                      CA                    CG      -AGA-     U<br>       UCUC UGGCC   UCAAACAAG   UGGGU G    CCUG     C<br>       AGAG GUCGG   ACUUUGGUUC   ACCCA C    GGGA     AAG<br>AAUA--------A      U         AG               AU   G    GGAA | 3 | + | 169590615 | 169590635 | + | - | - | +++ | 0 | 0 | 0 | 4 | Extragenic | N/A |
| hsa-mir-552 | AACAGGUGACUGGUUAGACAA | AACCAUUCAA|                      UU  UG               A<br>         AUAUAACCAGUUGUUUAACC   U  CCUGUUG  GAAG U<br>         UAUAUGUGUCAACAACAGAUGG   A  GGACAAC  UUUC G<br>ACA--------A                        UC  GU               C | 1 | - | 34637654 | 34637674 | + | - | - | ++ | 1 | 3 | 0 | 4 | Extragenic | N/A |
| hsa-mir-553 | AAAACGUCAGAUUUUGUUUU | .-CUUCAA|                             G  UU<br>       UUUUA UUUAAAACGUGAGAUUUU UU   G<br>       GGAGU AGAUUUUCUCUCUAAAA AG   C<br>\--------U                             G  UC | 1 | + | 100209735 | 100209755 | + | - | - | + | 0 | 1 | 0 | 5 | Extragenic | N/A |
| hsa-mir-554 | GCUAGUCCCUGACUCAGCCAGU | A---             U  UAACCUU                                   A          G<br>    CC GAG     UGGCUAG      UCCUGACUCA GCCAGU CUG  U<br>    GG CUC     ACCGGU      GGGACUGGGU UCGGUCA GAC  C<br>UCUACGA   U  UCUCU-   UUAUUACUU                       AG          U | 1 | + | 148734869 | 148734889 | + | - | - | + | 1 | 0 | 0 | 1 | Intron of TUFT1 | S |
| hsa-mir-555 | AGGGUAAGCUGAACCUCUCAU |                GAAC      U  GG     AC     U  GA     U  GAC<br>            GGAGU UCAGA GU   AGC   UACCUU GU  GCAG GU   C<br>            UCUCA AGUCU CA   UCG   AUGGGA CA  CGUC CG   G<br>UAUCUAGA  AAAU      -  GG     A-     -  GG     -  GAA | 1 | - | 152532940 | 152532960 | + | - | - | +++ | 0 | 2 | 0 | 2 | Intron of ASH1L | S |

(Table 6) Mature miRNAs (SEQ ID NOS: 337-469, respectively) and precursor miRNAs (SEQ ID NOS: 1386-1518, respectively)

Fig. 12C

| | | | | | | | | | | | | | | | |
|---|---|---|---|---|---|---|---|---|---|---|---|---|---|---|---|
| hsa-mir-556 | GAUGAGCUCAUUGUAAUAUG | GA------¦ CUUCAU U UAGUAAUAAGAAAGAUGAGCU AU GUAAUAUGAG AUCAUAUAUUUUCUACUCGA UA CAUAUACUG U ACACUUCCA------¦ UACAUA | 1 | + | 194499728 | 194499747 | + | - | - | + | 0 | 0 | 1 | 0 | Intron of NOS1AP | S |
| hsa-mir-557 | GUUUGCACGGGUGCGGCCUUGUCU | AGAAUGGGCAAAUGAACAGUAAA¦ UG CU U GG UUU GAGGC GGGGCCC CCC UGC UGCU AA UUCUG UUCCCGG GGG ACG GUCA A AGGUGGAGCA--------¦ U C UUU AG | 1 | + | 165532199 | 165532221 | + | - | - | ++ | 1 | 0 | 0 | 0 | Extragenic | N/A |
| hsa-mir-558 | UGAGCUGCUGUACCAAAAU | GUGUGUGU¦ G G U UA CU U GU UGU UGUGUG AUUUUCGUAUAGUAGCUC GA CUA \ CG GCA ACACA UAAAACCACUGUCGAG CU GAU U GU------¦ ^ G A UC UU A | 2 | + | 32731815 | 32731833 | + | - | - | + | 0 | 1 | 0 | 0 | Intron of BIRC6 | S |
| hsa-mir-559 | UAAAGUAAAAUAUGCACCAAAA | ------¦ UU GCUCCAGUAAACAUCUUAAAGUAAAAUAUGCACCAAAAU UAC \ CGAGCUCAUGUAGAUUUCAUUUAUAUCGUGGUUUUUG AUC U ACCCUA------¦ ACAUAA GU | 2 | + | 47579363 | 47579383 | + | - | - | + | 0 | 0 | 0 | 1 | Intron of TACSTD1 (tumor-associated calcium signal transducer 1) | S |
| hsa-mir-560 | GCGUGCGCCGGCCGGCGC | U------¦ GAG A G U CCCCUC GCCGGCUC GC CC CGU CU UUU CCG G GGGGAG CCGGCCGAG CG GCC GA GG GUC G CUUGCCAUC^------¦ ^ G GUA C G A | 2 | + | 133226285 | 133226304 | + | - | - | + | 0 | 1 | 0 | 0 | Extragenic | N/A |
| hsa-mir-561 | CAAAGUUUAAGAUCGUUGAAGU | CUUCAUCCACCAG¦ A AGAGC UCCUCCAGGAAC UCAAGGAUCUUAAACUUUGCC \ AGGGGUCCCUUG AGUUCCUAGAAUUUGAAACGG U UACCA--------¦ A AAACA | 2 | + | 189364822 | 189364843 | + | + | - | +++ | 0 | 0 | 1 | 0 | Intron of GLIPR1 | S |
| hsa-mir-562 | AAAGUAGCUGUACCAUUUGC | AGUGAA¦ UA U UG AUUGCUA GGU CA AUGGU CAG CUACUUU GAG AAU G UAACGGU UCA GU UACCA GUC GAUGAAA CUU UUG C A ------¦ ^ GUCCC C U U U AA | 2 | + | 233239962 | 233239981 | + | - | - | ++ | 1 | 0 | 0 | 0 | Intron of MGC42174 | S |
| hsa-mir-563 | AGGUUGACAUACGUUUCCC | AGCAAAGAAG¦ U CUCUA G AGCAAGAAG UG GUUGCC GGAAAUGUGUUUG CUGAU \ AC CGAUGG CCUUUGCAUACAGU GAUUA U UC--------¦ ^ A | 3 | + | 15580333 | 15580351 | + | - | - | + | 0 | 1 | 0 | 0 | Extragenic | N/A |
| hsa-mir-564 | AGGCACGUGUCACAGGC | C------¦¦ICA- G CA A AACA G CCC GGGG UGC GGCCACGGGUGC GC AGGC UGGCC A CAGU ^AUG GCC GG CUGUGCCGCGG CG GGU GCCGG G CAGU ^AUG A C--------¦ GGGC GG--- A | 3 | + | 44863987 | 44864006 | + | + | - | ++ | 0 | 1 | 0 | 0 | 5'UTR of TMEM42 | S |
| hsa-mir-565 | GGCUGCGCUCCGCAUGUCGUUUU | CCA------¦ A U- GA A UGGCCG ANUGGAUA CGCG CU CUA CGGAUC AGA G CACCGG UUGCUCUGU GGCC GG GCUUCGG UCU A CCAGUCCAGUCA------¦ ¦ U UC UC CCUCA A U | 3 | + | 45691071 | 45691092 | + | - | - | ++ | 0 | 0 | 0 | 0 | Extragenic | N/A |
| hsa-mir-566 | GGGCGCCUGUGAUCCCAAC | -¦-AGG U CC U GA C--- .ACU GCU CC GGU CCCGCG CUCU UCCCA CU CGA GC CCA GUUCGC GGGAG GGGGU CU A--------¦ UAA AC C CAGG | 3 | + | 50189736 | 50189604 | + | - | - | + | 0 | 1 | 0 | 0 | Intron of SEMA3F | S |
| hsa-mir-567 | AGUAUGUCUUCCAGGACAGAAC | GGAUUCUUA¦ G UU UAC GUAUGUUUCUUCCAG ACAGAA CA \ AUC CGUACAAGAAGGUC UGUUUU GU C UCGAUUAUGGAAAAAAAAAAAAA^ AAAA A AUC UU | 3 | + | 113152564 | 113152586 | + | + | - | +++ | 0 | 0 | 0 | 2 | Intron of TTMP | S |
| hsa-mir-568 | AUGUAUAAAUGUAUAUACACAC | G------¦ U ACACUCC ^ AUAUACAC UAUAU AUGUAUAA UGUAUACAC UAUAUGU U UAUGUGUG AUAUG UACAUAUU AUAUAUGU C GUA----¦ ^ G A AUAU-- | 3 | - | 115566283 | 115566302 | + | - | - | ++ | 0 | 1 | 0 | 0 | Extragenic | N/A |

(Table 6) Mature miRNAs (SEQ ID NOS: 337-469, respectively) and precursor miRNAs (SEQ ID NOS: 1386-1518, respectively)

Fig. 12D (Table 5) Mature miRNAs (SEQ ID NOS: 337-469, respectively), and precursor miRNAs (SEQ ID NOS: 1386-1518, respectively)

| | | | | | | | | | | | | | | |
|---|---|---|---|---|---|---|---|---|---|---|---|---|---|---|
| hsa-mir-569 | AGUUAAUGAAUCCUGGAAAGU | ‎ ‎ ‎ ‎ ‎ UU ‎ ‎ GA ‎ ‎ ‎ ‎ ‎ ‎ G ‎ ‎ ‎ ‎ ‎ ‎ ‎ ‎ ‎ -- ‎ ‎ ‎ ‎ AAC ‎ ‎ AUCAGAA<br>‎ ‎ GGUA ‎ GUUA ‎ UUAAUUUU ‎ UGGGA ‎ CAUUAAC ‎ ‎ ‎ AGC ‎ ‎ ‎ ‎ ‎ ‎ G<br>‎ ‎ UUAU ‎ CAGU ‎ AAUUGAAA ‎ GUCCU ‎ GUAAUUG ‎ ‎ ‎ UCG ‎ ‎ GUAAAG<br>‎ ‎ ‎ ‎ A ‎ ‎ UU ‎ G- ‎ ‎ ‎ ‎ ‎ ‎ ‎ ‎ ‎ G ‎ ‎ ‎ ‎ ‎ ‎ ‎ ‎ ‎ AA ‎ ‎ ‎ ‎ ‎ ‎ AUU ‎ ‎ ACUACAA | 3 | - | 1721145361 | 1721145401 | + | - | - | ++ | 0 | 0 | 0 | 0 | 1 | Intron of TNIK | S |
| hsa-mir-570 | GAAAACAGCAAUUACCUUUGCA | CUAGAUAAG| ‎ ‎ ‎ ‎ ‎ ‎ A ‎ ‎ ‎ ‎ ‎ ‎ ‎ ‎ CCC ‎ ‎ ‎ ‎ ‎ ‎ ‎ ‎ ‎ ‎ ‎ ‎ ‎ ‎ ‎<br>‎ ‎ ‎ ‎ ‎ ‎ ‎ ‎ ‎ ‎ ‎ | ‎ UUAUUUAAGGU ‎ GGUGCAAGGUAAUUGC ‎ GUUUU ‎ ‎ AUUA ‎ ‎ \\<br>‎ ‎ ‎ ‎ ‎ ‎ ‎ ‎ ‎ ‎ ‎ | ‎ GGUAGUCCA ‎ CCACGUUCCAUUAACG ‎ CAAAAG ‎ ‎ UAAU ‎ ‎ U<br>UGA ‎ ‎ ‎ ‎ ‎ ‎ ‎ ‎ ‎ - ‎ ‎ ‎ ‎ ‎ A ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ CGU ‎ ‎ U | 3 | + | 196753636 | 196753657 | + | - | - | ++ | 0 | 0 | 1 | 0 | 3 | Extragenic | N/A |
| hsa-mir-571 | UGAGUUGGCCAUCUGUAGUGAG | CCUC---| ‎ ‎ ‎ AGA ‎ AA ‎ ‎ - ‎ ‎ U ‎ ‎ U ‎ ‎ CUU- ‎ ‎ ‎ ‎ ‎ ‎ ‎ ‎ ‎ ‎ ‎ ‎ ‎ CC<br>‎ ‎ ‎ ‎ ‎ ‎ AGUA ‎ ‎ ‎ CC ‎ GCUCAG ‎ UG ‎ GCCA ‎ UUC ‎ ‎ GUCUGUAG ‎ ‎ A<br>‎ ‎ ‎ ‎ ‎ ‎ UCCU ‎ ‎ ‎ GG ‎ UGAGUC ‎ AC ‎ CGGU ‎ GAG ‎ ‎ CGGGUAUC ‎ ‎ U<br>AUCUAUA ‎ ‎ CCG ‎ AG ‎ ‎ ‎ ‎ ‎ U ‎ ‎ ‎ ‎ U ‎ ‎ JUCU ‎ ‎ ‎ ‎ ‎ ‎ ‎ ‎ ‎ ‎ UG | 4 | + | 334008 | 334026 | + | - | - | ++ | 0 | 0 | 1 | 0 | 1 | Intron of ZNF-141 | S |
| hsa-mir-572 | GUCCGCUGCGGCGGUGGCCCA | GUCCAGG| ‎ ‎ ‎ ‎ CG ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ C<br>‎ ‎ ‎ ‎ ‎ ‎ CCGUG ‎ ‎ CC ‎ ‎ ‎ ‎ UGGU ‎ ‎ GGGCCGUCC ‎ GGGCGA ‎ ‎ GGGCG ‎ C<br>‎ ‎ ‎ ‎ ‎ ‎ GGCGCC ‎ ‎ GG ‎ ‎ ‎ ‎ ACCG ‎ ‎ CCCGUGCG ‎ CUCGCCU ‎ ‎ UUCGU ‎ U<br>AG------A ‎ ‎ ‎ C ‎ ‎ ‎ ‎ ‎ ‎ ‎ ‎ ‎ A- ‎ ‎ ‎ ‎ ‎ ‎ ‎ ‎ ‎ ‎ ‎ G ‎ ‎ ‎ ‎ ‎ ‎ ‎ ‎ ‎ GC ‎ ‎ ‎ G | 4 | + | 11121394 | 11121413 | + | - | - | ++ | 0 | 0 | 0 | 0 | 1 | Intron of RNPS1 | S |
| hsa-mir-573 | CUGAAGUAUGUGUAACUGAUCAG | UUU--| ‎ GG- ‎ ‎ ‎ ‎ U ‎ ‎ ‎ ‎ ‎ GU ‎ ‎ ‎ ‎ ‎ ‎ ‎ ‎ ‎ ‎ ‎ ‎ G- ‎ ‎ CU ‎ U<br>‎ ‎ ‎ ‎ AGC ‎ ‎ ‎ ‎ UUUUC ‎ CCCUGA ‎ ‎ AGUGAU ‎ ‎ GUAACU ‎ AUCAG ‎ GAU ‎ AC ‎ C<br>‎ ‎ ‎ ‎ UUG ‎ ‎ ‎ ‎ GGAG ‎ GGGACU ‎ ‎ UCGCUG ‎ ‎ UAUUGA ‎ UCGUU ‎ CUG ‎ UG ‎ A<br>GUUUA ‎ AGA ‎ ‎ ‎ ‎ ‎ U- ‎ ‎ ‎ ‎ ‎ ‎ ‎ G ‎ ‎ ‎ ‎ ‎ ‎ AA ‎ ‎ ‎ ‎ ‎ U ‎ ‎ ‎ ‎ C- ‎ ‎ U | 4 | - | 24272758 | 24272781 | + | - | - | ++ | 0 | 0 | 0 | 0 | 2 | Extragenic | N/A |
| hsa-mir-574 | CACGCUCAUGCACACACCCAC | GGGACCUGCG| ‎ ‎ ‎ ‎ C ‎ ‎ ‎ ‎ ‎ ‎ AGU ‎ ‎ ‎ ‎ ‎ ‎ ‎ ‎ ‎ ‎ ‎ UG ‎ GC<br>‎ ‎ ‎ ‎ ‎ ‎ ‎ ‎ ‎ ‎ ‎ UGGGUG ‎ GGGCGUGUG ‎ ‎ GUGUGUGUGAGUGUG ‎ UC ‎ U<br>‎ ‎ ‎ ‎ ‎ ‎ ‎ ‎ ‎ ‎ ‎ ACUCAC ‎ CCCGCACAC ‎ ‎ CACACACUACUCCGAC ‎ GG ‎ C<br>GG-------A ‎ ‎ ‎ ‎ C-- ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ CU ‎ GC | 4 | + | 38766893 | 38766913 | + | + | - | ++++ | 0 | 1 | 3 | 0 | 5 | Intron of LOC92689 | S |
| hsa-mir-575 | GAGCCAGUUGGACAGGAGC | AAUUCA--------| ‎ ‎ ‎ ‎ - ‎ ‎ ‎ ‎ ‎ - ‎ ‎ ‎ ‎ ‎ ‎ ‎ U ‎ ‎ ‎ - ‎ ‎ ‎ - ‎ ‎ ‎ C<br>‎ ‎ ‎ ‎ ‎ ‎ ‎ ‎ ‎ ‎ ‎ ‎ GC ‎ CCUG ‎ CCA ‎ CUGGCCUUAU ‎ GU ‎ CA ‎ GAC ‎ ‎ CUUGGG ‎ \\<br>‎ ‎ ‎ ‎ ‎ ‎ ‎ ‎ ‎ ‎ ‎ ‎ CG ‎ GGAC ‎ GGU ‎ GACCGGAGUA ‎ CA ‎ GU ‎ CUG ‎ ‎ GGACUC ‎ U<br>CUCACACACCCGUGA ‎ A ‎ ‎ ‎ ‎ ‎ ‎ ‎ ‎ ‎ ‎ ‎ ‎ ‎ ‎ ‎ ‎ ‎ ‎ ‎ ‎ ‎ A ‎ ‎ ‎ C ‎ ‎ ‎ -- ‎ ‎ ‎ UC ‎ ‎ ‎ A | 4 | - | 84132900 | 84132918 | + | - | - | ++ | 1 | 0 | 0 | 0 | 1 | Intron of SCD5 | AS |
| hsa-mir-576 | AUUCUAAUUUCUCCACGUCUUUG | UA--------| ‎ ‎ ‎ ‎ ‎ ‎ ‎ ‎ C ‎ ‎ ‎ ‎ ‎ ‎ ‎ ‎ ‎ ‎ ‎ ‎ ‎ ‎ ‎ ‎ ‎ ‎ ‎ ‎ ‎ ‎ C ‎ ‎ ‎ ‎ ‎ ‎ ‎ ‎ G ‎ UA<br>‎ ‎ ‎ ‎ ‎ ‎ ‎ ‎ CAUUC ‎ AA ‎ GAGGAUUCUAAAUUU ‎ UCCACGUCUUUG ‎ UAA ‎ \\<br>‎ ‎ ‎ ‎ ‎ ‎ ‎ ‎ GUUAG ‎ UU ‎ CUCCUAAGGUUAAA ‎ AGGUGUAGAAAC ‎ GUU ‎ U<br>ACCAAUAUUCA ‎ ‎ ‎ ‎ C ‎ ‎ ‎ A ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ A ‎ ‎ ‎ ‎ ‎ G | 4 | + | 110868669 | 110868711 | + | + | - | +++ | 0 | 0 | 0 | 1 | 2 | Intron of SEC24B | S |
| hsa-mir-577 | UAGAUAAAAAUAUUGGUACCUG | --------| ‎ ‎ ‎ ‎ ‎ ‎ ‎ ‎ ‎ ‎ A ‎ ‎ ‎ ‎ ‎ ‎ ‎ ‎ ‎ ‎ ‎ ‎ ‎ ‎ U ‎ ‎ ‎ ‎ AUUUG ‎ ACCUG ‎ ‎ ‎ ‎ ‎ AUGAU<br>‎ ‎ ‎ ‎ ‎ ‎ ‎ UGGGGAGUUGAACAGUUAGAAUAAA ‎ UAUUGG ‎ ACCUG ‎ ‎ ‎ ‎ ‎ \\<br>‎ ‎ ‎ ‎ ‎ ‎ ‎ ACCCUUUACUCUGUCUAUUU ‎ AUAACU ‎ UGGAC ‎ ‎ ‎ ‎ CGGAGU<br>CAUUCAUCUAUA ‎ ‎ ‎ ‎ ‎ ‎ ‎ ‎ ‎ ‎ ‎ A ‎ ‎ ‎ ‎ ‎ ‎ ‎ ‎ ‎ ‎ ‎ ‎ U ‎ ‎ ‎ ‎ ‎ ‎ ‎ ‎ ‎ ‎ C ‎ ‎ ‎ ‎ ‎ ‎ ‎ ‎ ‎ ‎ ‎ | 4 | + | 116036750 | 116036770 | + | - | - | ++ | 1 | 0 | 0 | 1 | 3 | Intron of UGT8 | S |
| hsa-mir-578 | CUUCUUGUGCUCUAGGAUUGU | AGAUAAAUC| ‎ ‎ ‎ ‎ ‎ ‎ ‎ ‎ CG ‎ CA ‎ ‎ ‎ ‎ ‎ ‎ ‎ ‎ ‎ ‎ CCU ‎ ‎ ‎ ‎ ‎ ‎ ‎ ‎ ‎ C<br>‎ ‎ ‎ ‎ ‎ ‎ ‎ ‎ UAUAGACAAAAUACAAUCC ‎ GA ‎ ACAAGAAGCU ‎ AUAG ‎ \\<br>‎ ‎ ‎ ‎ ‎ ‎ ‎ ‎ AUAUUGUUUUAUGUAGG ‎ CU ‎ UGUUCUUCGA ‎ ‎ UGUC ‎ U<br>UAU-------A ‎ ‎ ‎ ‎ ‎ ‎ ‎ ‎ ‎ ‎ ‎ ‎ AU ‎ CG ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ C | 4 | + | 166685081 | 166685101 | + | - | - | + | 0 | 0 | 0 | 0 | 1 | Intron of CPE | S |
| hsa-mir-579 | AUUCAUUUGGUAUAAACCGCGAU | CAUUAUUAG| ‎ ‎ ‎ ‎ A ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ CG ‎ ‎ ‎ ‎ ‎ ‎ AA<br>‎ ‎ ‎ ‎ ‎ ‎ ‎ ‎ ‎ GUU ‎ AUGCAAAGUAAUCCGCGGUAUAAACCGCGAU ‎ AUUUG ‎ U<br>‎ ‎ ‎ ‎ ‎ ‎ ‎ ‎ ‎ CAA ‎ UACGUUUUAUUAGGCGCCAAAUAUUGGCGUUU ‎ UAAAU ‎ AA<br>------A ‎ ‎ ‎ ‎ C ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ ‎ ACU ‎ ‎ ‎ ‎ ‎ ‎ ‎ ‎ AA | 5 | - | 32440000 | 32440022 | + | - | - | + | 0 | 1 | 0 | 0 | 1 | Intron of ZFR | S |
| hsa-mir-580 | UUUGAGAAUGAUGAAUCAUUAGG | AUAA| ‎ ‎ ‎ ‎ ‎ ‎ ‎ CA ‎ ‎ ‎ ‎ ‎ ‎ ‎ ‎ ‎ ‎ ‎ ‎ ‎ ‎ ‎ ‎ ‎ ‎ ‎ GA ‎ ‎ ‎ ‎ CUCAGAUAUU ‎ ‎ ‎ UAAG<br>‎ ‎ ‎ ‎ ‎ ‎ ‎ AAUUUC ‎ AUUGGAACCUAAUGAAUCAUCA ‎ ‎ ‎ ‎ ‎ ‎ ‎ ‎ ‎ ‎ ‎ ‎ \\<br>‎ ‎ ‎ ‎ ‎ ‎ ‎ UAAAAG ‎ UGGCCUUGGAUUACUAAGAUAGU ‎ GAGUUUAUAG ‎ U<br>----A ‎ ‎ ‎ ‎ ‎ AC ‎ ‎ ‎ ‎ ‎ ‎ ‎ ‎ ‎ ‎ ‎ ‎ ‎ ‎ ‎ ‎ ‎ ‎ ‎ AA ‎ ‎ ‎ ‎ ‎ ‎ ‎ ‎ ‎ ‎ ‎ ‎ ‎ ‎ CAAU | 5 | + | 36193510 | 36193531 | + | + | - | ++ | 0 | 0 | 1 | 0 | 2 | Intron of LMBRD2 | S |
| hsa-mir-581 | UCUUGUGUUCUCUAGAUCAGU | -----| ‎ ‎ A ‎ ‎ ‎ ‎ A ‎ ‎ ‎ ‎ ‎ - ‎ ‎ ‎ ‎ A ‎ ‎ ‎ ‎ ‎ ‎ ‎ ‎ ‎ C ‎ ‎ ‎ ‎ ‎ G ‎ ‎ ‎ ‎ UUUUAG<br>‎ ‎ ‎ ‎ GUU ‎ UGUG ‎ AGGUAUGUCU ‎ UCCAUAAGA ‎ GUGUCU ‎ UAGAUCA ‎ GUG ‎ \\<br>‎ ‎ ‎ ‎ CAA ‎ ACAC ‎ UCCAUAAGA ‎ CACAAGA ‎ AUCUAGU ‎ GUG ‎ ‎ ‎ ‎ ‎ ‎ ‎ U<br>CCUUCACA ‎ G ‎ ‎ ‎ ‎ A ‎ ‎ ‎ ‎ ‎ - ‎ ‎ ‎ ‎ A ‎ ‎ ‎ ‎ ‎ ‎ ‎ ‎ ‎ C ‎ ‎ ‎ ‎ ‎ G ‎ ‎ ‎ ‎ UUUAAA | 5 | - | 53263279 | 53263299 | + | + | - | ++ | 0 | 0 | 0 | 0 | 1 | Intron of ARFRP2 | S |
| hsa-mir-582 | UUACAGUGUGUUCAACCAGUUACU | AUC---| ‎ ‎ ‎ ‎ ‎ ‎ UG ‎ ‎ CUCUUUG ‎ ‎ ‎ ‎ ‎ AUUA ‎ ‎ ‎ ‎ ‎ ‎ ‎ ‎ ‎ ‎ ‎ UAAUCU<br>‎ ‎ ‎ ‎ ‎ ‎ ‎ ‎ ‎ ‎ ‎ ‎ ‎ AC ‎ ‎ GGGAAC ‎ GU ‎ ‎ ‎ CAGUGUCAACCAGUUAC ‎ ‎ ‎ ‎ ‎ A<br>‎ ‎ ‎ ‎ ‎ ‎ ‎ ‎ ‎ ‎ ‎ ‎ ‎ UG ‎ ‎ CUCUUUG ‎ ‎ ‎ ‎ ‎ GUCAACAAGUUGGUCAAUG ‎ ‎ A<br>UUACAAAGAUGAA ‎ GU ‎ ‎ ‎ ‎ ‎ ‎ ‎ ‎ ‎ ‎ CCAA ‎ ‎ ‎ ‎ ‎ ‎ ‎ ‎ ‎ ‎ ‎ ‎ ‎ ‎ ‎ ‎ ‎ ‎ ‎ UUAAUC | 5 | - | 59015377 | 59015399 | + | + | - | ++++ | 0 | 0 | 4 | 0 | 4 | Extragenic | N/A |

Fig. 12E

| | | | | | | | | | | | | | | | | |
|---|---|---|---|---|---|---|---|---|---|---|---|---|---|---|---|---|
| hsa-mir-563 | CAAAGAGGAAGGUCCCAUUAC | -AACUCACACAUUA\ACCAAACACG AGGUCCCA UACUCC - G<br>\ \ \<br>UGGUUUCUCC UCCAGGGU AUGACG UUC A<br>/ / /<br>UAGGG GACCAGGCA U A U | 5 | + | 95468930 | 95486950 | + | - | + | 0 | 0 | 0 | 0 | 1 | 0 | 1 | Extragenic | N/A |
| hsa-mir-564 | UUUAUGGUUUGCCUGGGACUGAG | UAGGG GACCAGGCA UGGGU GCCUGGACUGA AUUU G<br>GUCCC CUGGUUGGU ACCAA CGGACCUUGACU UAAG C<br>CAACGAAA U CCG C GUA G | 5 | - | 148470446 | 148470467 | + | - | ++ | 0 | 0 | 0 | 2 | 3 | 2 | 7 | Intron of SH3TC2 | S |
| hsa-mir-565 | UGGGCGUAUCUGUAUGCUA | UGGGGUCUCUC C AGAAAG<br>UG UAUGCAGCCCUAGCA ACAGAUACCCCAG C<br>AC AUGUCGCUGGGAUCGU UGUCUAUGCGGGU C<br>A-- A GCAAGU | 5 | - | 168671515 | 168671533 | + | - | + | 0 | 1 | 0 | 0 | 0 | 0 | 1 | Intron of SLIT3 | S |
| hsa-mir-566 | UAUGCAUUGUAUUUUAGGUCC | AU-- U AUA<br>GGGGU AAAACAUUAUGCAUUGUAUUUUAGG CCCA \<br>UCUCA UUUUGGUAAUACGUAACAUAAAAAAUCC GGGU C<br>UAUUUCUUCUAUU A CU C GUA | 5 | + | 45212326 | 45212347 | + | - | + | 0 | 0 | 0 | 0 | 1 | 0 | 1 | Intron of SUPT3H | S |
| hsa-mir-567 | UUUCCAUAGGUGAUGAGUCAC | CUCCU CACCCU- A UCA AA<br>UAUG CUUUCCAU GGUGAUGAGUCACAGG GC GGG U<br>AUAC GAAAGGUG CCACUACUCAGUGUCC CG UCU A<br>U-A CCUUACCC U A GU | 6 | + | 107277985 | 107277805 | + | - | + | 0 | 0 | 0 | 0 | 0 | 0 | 1 | Extragenic | N/A |
| hsa-mir-568 | UUGGCCACAAUGGGUUAGAAC | -AG CAA U UAUU<br>CUAGGU CCAAUUU GCCCA UGGGU AGAACAC \<br>GAUCCG GGUAAA CCGGU ACCCA UCUUGUG C<br>\ A AC U U UUAC | 6 | + | 126786362 | 126786382 | + | - | ++ | 0 | 0 | 0 | 0 | 0 | 0 | 2 | Extragenic | N/A |
| hsa-mir-569 | UCAGAACAAAUGCCGGUUCCCAGA | U-I C UGGCCA A- C C UA<br>CCAGC UG GCAGC CUG GAACC CGU UG UCUGAGC GGG \<br>GGUCG AC CGUCG GAC CUUGG GUA AC AGACUUG UCC C<br>CCA CA C CC A A A GU | 7 | - | 5279803 | 5279826 | + | - | +++ | 0 | 0 | 0 | 0 | 0 | 1 | 2 | Intron of FBXL18 | S |
| hsa-mir-570 | GAGCUUAUAUUCAUAAAGUGCAG | UAGC A C G UA UG<br>CAGUCAGA AU ACCUAUU CAUAAAA UGCAG UCG \<br>GUUAGUCU UG UCGAAUA GUAUUUU AUGUC ACU A<br>ACGAGUACAAA C A U A UA GA | 7 | + | 73017640 | 73017661 | + | + | ++++ | 3 | 0 | 4 | 6 | 2 | 4 | 20 | 41 | Intron of WBSCR1 | S |
| hsa-mir-571 | AGACCAUGGGUUCUCAUUGU | UCUUAUCAA-- GU - U GUG<br>UCAG AGA CCA GG GUUC CA UUG UAAUA U<br>ACUC UCU GGU CC CAGG GU AAU GUUGU A<br>CUUAGUCAUCUAAA UG C U U UG AAG | 7 | - | 95461063 | 95461082 | + | - | + | 1 | 0 | 0 | 0 | 0 | 0 | 1 | Intron of SLC25A13 | S |
| hsa-mir-572 | UUGUGUCAAUAUGGCGAUGAUGU | UA-- CA C A GU A<br>UUAUG CAUGA UUUGGUCA UAUG GAUGAUGU UGUG U<br>AAUGC GUACU AACGGACGU GUGC CUACUGG ACAC G<br>CAACUGCAGA AC AC C --- GUAG UG | 7 | + | 126252891 | 126252712 | + | - | +++ | 5 | 2 | 2 | 4 | 2 | 0 | 15 | Intron of GRM8 | S |
| hsa-mir-573 | AGGCACCAGCCAGGCAUUUGGCUCUCAGG | C-------- AAUUCUCU U UG AGCCC U<br>CCCCAG CAGG AC ACCC GGCAU CUC GUUUCCC C<br>GGGGUC GUCC UG UUGG UCGUG GAG CGAGGGG U<br>UCCUCUUUA U G U GAA- G | 7 | + | 127276408 | 127276432 | + | - | + | 0 | 0 | 0 | 0 | 1 | 0 | 1 | Intron of SND1 | S |
| hsa-mir-574 | CCCAUCUGGGUGGUGGCCUGUGACUU | CUAAU-- U A CCA G G<br>GGAUAAG G CAU GGCC CCU AG GGGAUU UG C<br>CCUGUUU C GUG CCGG GGG UC CCCUGA CA U<br>CCCCUUUU U A U U UA-- U | 7 | + | 138439905 | 138439929 | + | + | ++ | 0 | 1 | 0 | 0 | 0 | 0 | 1 | Extragenic | N/A |
| hsa-mir-575 | GAAGUGUCCGUGGUGUCU | AC-| AAG-- G C AUUA GUAG UCU<br>GG CCU CA GC ACACCA GCACGCU CAAU AGG \<br>CC GGA UG UG UGUGGU CGUUGCA GUUG ACA C<br>UGUA GCCAA U G C A GACA AA | 7 | - | 157742280 | 157742300 | + | - | ++ | 0 | 1 | 0 | 0 | 0 | 0 | 1 | Intron of PTPRN2 | S |
| hsa-mir-576 | AAGCCUGCCCGUGUCUCCUCGGG | -AGCA| CCU C- C U-- ACC<br>CGGGCC UCCGAAG CC CCGGCU CC CCGGA \<br>GCCCGG AGGCUUC GG GUCCGA GG GCCCU U<br>\-A GCCAA C-- C UAC CCG | 8 | + | 1752819 | 1752839 | + | - | + | 0 | 0 | 0 | 0 | 1 | 0 | 1 | Extragenic | N/A |

(Table 5) Mature miRNAs (SEQ ID NOS: 337-469, respectively) and precursor miRNAs (SEQ ID NOS: 1386-1518, respectively)

Fig. 12F (Table 5) Mature miRNAs (SEQ ID NOS: 337-469, respectively) and precursor miRNAs (SEQ ID NOS: 1386-1518, respectively)

| | | | | | | | | | | | | | |
|---|---|---|---|---|---|---|---|---|---|---|---|---|---|
| hsa-mir-597 | UGUGUCACUCGAUGACCACUGU | ```
          UACUU AC UACGU UG GUCAC   GA GACCACUCU       GAAG     GU
ALIGAG LIG  AUGCC AC CCGUG  CU UUGGUGACA        ACA  A
CUGGUCA   A  UA  A  U   CC       CU UUGGUGACA        UGU  A
                                                    ----- AA
``` | 8 | + | 9638607 | 9636628 | + | - | ++ | 0 | 0 | 2 | 1 | 6 Intron of TNKS | S |
| hsa-mir-598 | UACGUCAUCGUUGUCAUCGUCA | ```
G  -    UGCUGC     C     CC    GU  G   UCGAA
CUUC AUGA      UGAUC UGCCGUGAU CGAUG GU ACC    A
GAGC UACU      ACUAC ACUGCUACUG GCUAC CA UCG    U
-A    C        -----           UU   UG - UGGGG
``` | 8 | - | 109301141 | 109301162 | + | - | +++ | 0 | 1 | 1 | 0 | 2 Intron of XKR6 | S |
| hsa-mir-599 | CUUUGUGUCAGUUUAUCAAAC | ```
AAAGACAUGCU|      C         GG          UU
         GUCCA AGUGU  GUUUGAUAAAGCUGACAU  GACAG GGA \
         UAGGU UCAUA  CAAACUAUUGACUGUG    UUGCC CUU  C
CAG------         CC                          A   AU
``` | 8 | - | 100505462 | 100505481 | + | - | ++++ | 0 | 0 | 0 | 0 | Intron of 3 VPS13B | AS |
| hsa-mir-600 | ACUUACAGAACAAGAGCCUUGCUC | ```
AAGUCACGU| UGU   CCA  CAU  G              C  GCAGU
         GC  GGCU  GCU AG AAGGCUCUUGUCUGU AG       G
         CG  CCGA  CGA UC UUCCGAGAACAGACA UC       G
CC------          UC-   C--   G            U  AUUGA
``` | 9 | - | 121249885 | 121249907 | + | - | ++ | 0 | 0 | 1 | 0 | 5UTR of 1 C9orf45 | S |
| hsa-mir-601 | UGGUCUAGGAUUGUUGGAGGAG | ```
  -UGCAUGAG| GU   U-  U    G A  -            CAG
          UUC  CU  GG CU AGGAUU UUGG GG AGU
          AGG  GG  CC GA UCCUAG GACC CC UCA    A
\-------A UG   UUU  U  AG      G    -  A  AAA
``` | 9 | - | 121540891 | 121540912 | + | - | ++ | 0 | 1 | 1 | 0 | Intron of 1 DENND1A | S |
| hsa-mir-602 | GACACGGGCGACAGCUGCGGCCC | ```
UU-------    A  |CC       C C  A--  G    CCC    CU G
         CUC CCC   GCCUGAGA GGG GAC GCU CGGCCCG GU U
         GAG GGG   CGGAUCGU CCU CUG UGA GCCGGGC CA U
GUCCCCCGAGAC  A  A^A      -  --  -         CG       C
``` | 9 | + | 135951500 | 135951522 | + | - | ++ | 0 | 0 | 1 | 0 | 1 Extragenic | N/A |
| hsa-mir-603 | CACACACUGCAAUUAUCUUUGC | ```
GAUUGAUGC|    U         U              CUUC  UAA
         UGUGG UUGG GCAAAAGUAAUUGCAGU       CCAUU    \
         AUAAUU AACC CGUUUUCAUUAACGUCAC     GGUAA    A
UUC------     ^       ACAC                      UGA
``` | 10 | + | 24568680 | 24568701 | + | - | ++ | 0 | 0 | 1 | 0 | Intron of 1 KIAA1217 | S |
| hsa-mir-604 | AGGCUGCGGAAUUCAGGAC | ```
A-------|-     C    G   CC  A-   U  C  CACU      AG
         GA  GCAU  GU CUUGA  UUCC C GC CU GUGUC      AGC  G
         CU  CGUG  CA  GGACU  AAGG G CG GA CACAG     UUG  C
AGAGGUA^  A    A   -    C -  -   U  -         UCUU      GA
``` | 10 | + | 28937954 | 28937972 | + | - | + | 0 | 0 | 0 | 1 | 1 Intron of SVIL | S |
| hsa-mir-605 | UAAAUCCCAUGGUGCCUUCUCU | ```
 -GC|           C                CU  GGA
         CCUAGCUUGGUUCUAAAUC CAUGGUGCCUUCUC UG        \
         GGAUUGAAGCUAAGAAGUUAG GUAUACGGAAGAG AC        C
\--A                        A    --          AAA
``` | 10 | + | 52403851 | 52403973 | + | - | + | 0 | 0 | 1 | 0 | Intron of 1 PRKG1 | S |
| hsa-mir-606 | AAACUACUGAAAAUCAAAGAU | ```
 -------|          U                       A       UGC
           UGUAUC UUGGGUUUUAGUAGAU ACUAUGUG ACCCCCAG  \
           ACAUAG AACUAAAAGUCAUCAA UGAUACUAC CCAC    C
ACCAGUCGUGA^    A                           --       CUA
``` | 10 | + | 76656879 | 76656899 | + | - | + | 0 | 1 | 0 | 0 | 1 Extragenic | N/A |
| hsa-mir-607 | GUUCAAAUCCAGAUCUAUAAC | ```
UUG    |                 G           G   CC
       CCUAAAAGUCACACAGGUAAGUAUAGAUCUGGAUU GAACCCAGG AG     \
       GGGUUUCAGUGUGUUCCAAUAUUCUAGACCUAA   CUUGGGUCC UC     A
UUG-    A                      A              G      AG
``` | 10 | - | 98253028 | 98253048 | + | - | + | 0 | 0 | 0 | 1 | 1 Extragenic | N/A |
| hsa-mir-608 | AGGGGUGUUGGGACAGCUCCG | ```
GG-|   AAG - G              - UG G-  -    UG  CGUUUAAAAA
     GCC  G UG GCCAGG GG  GU  UUG   GGA AGCUC
     UGG  C AC UGGUUC CC  CG  AAC  CCU UCGAG        G
AGA^    ACA G   G     UA  UA    -   A           AACCUCUACG
``` | 10 | - | 102399344 | 102399368 | + | - | ++ | 0 | 0 | 1 | 0 | Intron of 1 SEMA4G | S |
| hsa-mir-609 | AGGGGUUUCUCUCAUCUCU | ```
UG---|    G                               AAUG
        CUC  GCUAGGUCCUAGGGUGU   CUCUCAUCUCUG   CUAU   G
        GAG  CGACAAGGAUCCUCACA   GGGAGUAGAGAU   GAUA   C
CCAAGA^   A       -----                       --       AAUU
``` | 10 | - | 106643194 | 106643213 | + | - | + | 0 | 0 | 0 | 1 | Intron of 1 C10orf79 | S |
| hsa-mir-610 | UGAGCUAAAAUGUGUGGGGA | ```
               G                                  CA    A
         UCUAUU UCUUA GUGAGCUAAAAUGUGUGGGACA     UUUG   \
         AGGUAAA AGAAU CACUCGAUUUACACACGACCCUGU   AAAC   G
UGAUCUCA^      A   A             -----                  C
``` | 11 | + | 26042686 | 26042706 | + | - | + | 0 | 0 | 0 | 1 | Intron of 1 KIF16A | S |

Fig. 12G (Table 5) Mature miRNAs (SEQ ID NOS: 337-469, respectively) and precursor miRNAs (SEQ ID NOS: 1386-1518, respectively)

| | | | | | | | | | | | | | | |
|---|---|---|---|---|---|---|---|---|---|---|---|---|---|---|
| hsa-mir-611 | GCGAGGACCCCUGGGGUCUGAC | AAAAU G G G AG - GAC<br>GGU AGA C UUGAGGGG UUC CA G<br>CCA UCU G GGCUCCCC GAG GU G<br>ACAC- G - G AG C AGA | 11 | - | 61335332 | 61335354 | + | - | + | 0 | 0 | 0 | 1 | 0 | S | Intron of 1 C11orf10 |
| hsa-mir-612 | GCUGGGCAGGGCUUCUGAGCUUCCU | ---------| CA- - CU C A- A<br>UCC UCUGG GGG ACGGCUUCUG AGCUCCUU GC C<br>AGG GGACC CCC UCCCGGGCAG UCGGGGAG CG U<br>ACUCUCA^ ACA GAC U CU C GA A | 11 | + | 64987304 | 64987328 | + | + | ++ | 0 | 0 | 2 | 0 | 0 | N/A | 2 Extragenic |
| hsa-mir-613 | AGGAAUGUUCCUUCUUUGCC | ---| A C UUC UGU CC UA CUUA<br>GGUG GUG GU CAAG GAAGGGAC UUCCUG GUGU U<br>CCAC UAC CA GUUU CUUCCCUUG AAGGAU CAUA A<br>AUUUA^ A U CC- - U- GA ACAU | 12 | + | 12808910 | 12808929 | + | - | + | 0 | 1 | 0 | 0 | 0 | N/A | 1 Extragenic |
| hsa-mir-614 | GAACGCCUGGUUCUGGCCAGGUGG | UCUAAGAAAC| GG AA ---- CCC<br>GCAGU UCU CUG CCCUG CAGGGGACAGGC CAG \<br>CGUCG GGA GAC UGGAC GUCUUGGUCCG GUC U<br>------------| UU A GG C CAA ACG | 12 | + | 12960083 | 12960105 | + | - | + | 0 | 0 | 0 | 0 | 0 | N/A | 1 Extragenic |
| hsa-mir-615 | UCCGAGCCUGGGUCUCCCUCU | CUC |AG C UC- U UC G UG<br>GGG GGG GGGAGGGGGG CCCGG GCUCGGAUC GA GG C<br>CCC CCC CCCUUCCCCC GGGUC CGAGCCUGG UU UU U<br>--- AAA - - UCU - C- G AU ACG | 12 | + | 527114061 | 527114081 | + | + | +++ | 0 | 0 | 0 | 0 | 3 | S | Intron of 3 HOXC4 |
| hsa-mir-616 | ACUCAAAAACCCUUCAGUGACUU | U------------| A CA U GAC<br>UAAGU AUUCCUC CUCAAA CCCUUCAGUGAACUUCC AU A<br>GUCCA UAAGGAG GAGUUU GGGAGGUUACUUGAAGG UA U<br>AAAAUUUUA^ G AC C - G AAG | 12 | - | 56199273 | 56199294 | + | + | ++ | 0 | 0 | 0 | 0 | 0 | S | Intron of 3 DDIT3 |
| hsa-mir-617 | AGAGUUCCCAUUUGAAGGUGG | C----------- A C CCAU U<br>AUCA AAGGACCCU GACUU CCAUUUGAAGGUGG U<br>UAGU UUCCUGGA CUGAA GGUAAACUUCCACC AUCC<br>CGAGGAGUAAAUACUA^ C C U A AAG | 12 | - | 79728840 | 79728861 | + | - | ++ | 0 | 1 | 0 | 0 | 0 | S | Intron of 1 LIN7A |
| hsa-mir-618 | AAACUCUACUUGUCCUUCUGAGU | CU--- | UG CC- U A C GUAAU - A<br>CU UUCACAG AAAC CU CUUGUC UUCUGAGU UAC GU C<br>GA AGGUGUC UUUG GA GAACAG AGGACUCG AUG CG A<br>AGUCUA GU CCA - C - A U | 12 | - | 79832043 | 79832065 | + | - | ++ | 0 | 0 | 0 | 1 | 3 | S | Intron of 4 LIN7A |
| hsa-mir-619 | GACCUGGACAUGUUUGUGCCAGUG | C-| CC CU- CCUCCCAAA AG CUGC GA.<br>GC AC CAG UCUGGG UACAGGCAUG CCA GGUC GGCAC C<br>CG UG GUC AGACCC GUGUUUGUAC GGU CCAG CCAG C<br>GA^ UU ACU A- ---- A- -- - - - UA | 12 | - | 107733185 | 107733188 | + | - | + | 1 | 0 | 0 | 3 | 0 | S | Intron of 1 SSH1 |
| hsa-mir-620 | AUGGAGAUAGAUAUAGAAAU | AUA-------------| A G AUAU AUA<br>UAU UCUAUAUCUA CUCCGUAUAUAU AUAU U<br>AUA AGAUAUAGAU GAGGUAUAUAUA UAUA A<br>AAGAAACGAACAAA^ A A CCUUC GAU | 12 | - | 114998333 | 114998352 | + | - | + | 0 | 1 | 0 | 0 | 0 | S | Intron of 1 THRAP2 |
| hsa-mir-621 | GGCUAGCAACAGCGCUUACCU | UAGAUUGA| --- U G C CUG AA<br>GGA AGGGGC GGA GGUAGGGCC UG UGCUG GCU AUG G<br>CCU UCUCUG UUU CCAUUCGG AC ACGAG CGG UAC A<br>--------^ GGG G A ------ UG-- CC | 13 | + | 39182962 | 39182982 | + | - | + | 0 | 0 | 1 | 0 | 0 | S | Intron of 1 SLC25A15 |
| hsa-mir-622 | ACAGCUCUGACUGAGGUUGAGC | AGACA--------| UGGACA A GG AG-- - G- A<br>AGC AGU CU UCUACCAGAUUG GA GA CAC A<br>UCG GG GGAGUCGUCUGAC CU CU GUG C<br>UCACAGUAGACA^ A UU ACA A G A | 13 | + | 88581497 | 88581517 | + | + | +++ | 1 | 0 | 0 | 0 | 0 | N/A | 1 Extragenic |
| hsa-mir-623 | AUCCCUUGCAGGGGCGUUGGGU | GUACACA-| AG CCU GC UU A UA U<br>GUAGA CAUC UGCAGGG UCUUGG CU UCC AGC \<br>CGUUU GUAG AUGUCG GUACCC CG AGG UCG U<br>GUCUCCAA^ CU AU UU U - U | 13 | + | 97706401 | 97706423 | + | - | ++ | 0 | 1 | 0 | 1 | 0 | S | Intron of 1 PHGDHL1 |
| hsa-mir-624 | UAGUACCAGUACCUUGUGUUCA | ----------| CAG--- G<br>AAUGCUGUUUCAAGGUAGUACCAGUACCUUGUGUU UG A<br>UUACGAGAGAUUCCAUAUGGUUAUGGGAACACAA AC C<br>GUGAAUCCACA^ AUGGA C | 14 | - | 29473951 | 29473972 | + | + | +++ | 1 | 0 | 0 | 3 | 1 | S | Intron of 6 STRN3 |

Fig. 12H (Table 5) Mature miRNAs (SEQ ID NOS: 337-469, respectively) and precursor miRNAs (SEQ ID NOS: 1386-1518, respectively)

| | | | | | | | | | | | | | | | |
|---|---|---|---|---|---|---|---|---|---|---|---|---|---|---|---|
| hsa-mir-625 | AGGGGGAAAGUUCUAUAGUCCU | A------\|<br>AGGGUAGAGGAGGAUGAGGGGAAAGUUCUAUAGUCCUG UAAUU<br>UCCCGGCUCCCUACUCCCCUUUCAAGAUAUCAGGAC A<br>UGUCAACCAUCA' UCUAG | 14 | - | 63927910 | 63927931 | + | - | + | +++ | - | 0 | 0 | 0 | 3 | 5 Intron of FUT8 | AS |
| hsa-mir-626 | AGCUCUCUGAAAAUCUCUU | ACUGAUAUAUU\| AUU GC G U AU AU<br>GUCUU UGAGA UAUUUUUA GCA CUCA G<br>CGGAA AUUUU ACUUCU GUAAAAGU UGU GACU A<br>UUU --- -A-- C C- CU | 15 | + | 39690899 | 39699917 | + | - | - | + | - | 1 | 0 | 0 | 0 | 1 Extragenic | N/A |
| hsa-mir-627 | GUGAGUCUCUAAGAAAAGAGGA | UA-- U UG U<br>CUAUUA UGGUAGUGAGUCUC AACAAAAGAGGAGG G U<br>GAUAAU ACCAUCACUCAGAG UGUUUUCUCCUCC UU G<br>AUCAUCAUAAA' A A AUAA | 15 | - | 40207864 | 40207905 | + | - | - | ++ | - | 0 | 0 | 0 | 3 | Intron of VPS39 | S |
| hsa-mir-628 | UCUAGUAGUGGCAGUCG | AUAGCUCU\| U A CA - A A AAAA<br>UG GUC CUUCCU UG GUC CAU UUUACUAGAGGU U<br>AC CGG GAAGGG GC GAC GUG GAAUGAUCUUCCA U<br>U------A\| U - AA U G A AUAA | 15 | - | 53381209 | 53381228 | + | - | - | +++ | - | 0 | 1 | 1 | 0 | 3 Intron of CCPG1 | S |
| hsa-mir-629 | GUUCUCCCAACGUAAGCCCAGC | UCCCUUUCCC\| AC U<br>AGGGGAGGGGCUGGUUACGUUGGAGAACUUUU GG G<br>UCCCCCUCCCGACCGAAUGCAACCCUUGGAGG CC A<br>UCCGUC------A\| A- A | 15 | - | 68087544 | 68087565 | + | - | - | +++ | - | 0 | 0 | 2 | 6 | 10 Intron of TLE3 | S |
| hsa-mir-630 | AGUAUUCUGUACCAGGGAAGGU | AACUUAACAUCAU\| - G<br>GCUACCU CUUUG UAU AUAUU GUUAUUCUG U<br>UGAUGGA GGGAC AUG UAUGA CAGUAAGAC C<br>UAUAUCAAUUCU--A\| --- C UCU AGGGAC A | 15 | + | 70595436 | 70595457 | + | - | - | ++ | - | 1 | 0 | 0 | 0 | 1 Extragenic | N/A |
| hsa-mir-631 | AGACCUGGCCAGAGACCUCAGC | .-GU\| C AC G<br>GGGGAG UGGGU CCUGGC CAG CC UCAGCU \<br>CCUCUC ACCGG GGACUG GUC GG AGUCGA A<br>\ -A AC --- - G --- A | 15 | - | 73361808 | 73361828 | + | - | - | + | - | 1 | 0 | 1 | 0 | 1 Intron of NEIL1 | AS |
| hsa-mir-632 | GUGUCUGCUUCCUGUGGGA | -\| C C A G UG G G CGA G<br>CG CU CUACCGC GU CU ACCGGAGGCGGA CG GGAA GGCC \<br>GC GA GGUGCUG CA GG UGUCCUUCGUCU GU UUUU CCGG U<br>UA C AC --- - G ----- A--- U | 17 | + | 30822738 | 30822756 | + | - | - | ++ | - | 0 | 1 | 0 | 0 | 5'UTR of ZNF207 | S |
| hsa-mir-633 | CUAAUAGUAUCUACCACAAUAAAA | AACCUCUCUUAG\| UCUUUC-- A AAAA<br>CCUC UUUAUUG GGUAGUAGUACUAUUA CCU<br>GGAG AAAUAAC CCAUCUAUGAUAAU GGA U<br>AUA------\| A C AGAG | 17 | + | 61495007 | 61495029 | + | - | - | + | - | 0 | 1 | 0 | 0 | 1 Extragenic | N/A |
| hsa-mir-634 | AACCAGCACCCCAACUUUGGAC | AACCCCACACC\| C UG CA G C- AUGC<br>ACUG AUUU GC UC AGGGUUGGG UUUGG GUC C<br>UGAU UAGG CG AG UUUCAACCCC GACCA UAG G<br>UC------A\| --- UA AC G AC A AACC | 17 | - | 65333361 | 65333372 | + | - | - | + | - | 1 | 0 | 0 | 0 | Intron of PRKCA | S |
| hsa-mir-635 | ACUUGGGGCACUGAAACAAUGUCC | CAGAGA\| U UCC CUUU AU<br>GGAGCU CA UGGGCAC GAAACAAUG AUUAGG GUU G<br>CUUCGA GU ACCCGUG UUUUGGUUAC UAGUCC CAA G<br>UAAC-----\| U- --- UCUU UCUU A | 17 | + | 67017775 | 67017797 | + | - | - | + | - | 0 | 0 | 0 | 0 | Intron of WIPI49 | S |
| hsa-mir-636 | UGUGCUUGCUCGUCCCCGCAGCAG | UG--\| G CGGGA GC CC - U CU AA<br>GC GCCUGGG GC GCCGGGGC GGC CGC GC GG U<br>CG CGGAUCC CG CGGCCCCG UCG GUG CG GCC U<br>\GCUA- G A- --- U UUC U CG AA | 17 | - | 75329670 | 75329693 | + | - | - | ++ | - | 0 | 0 | 1 | 0 | Intron of SFRS2 | S |
| hsa-mir-637 | ACUGGGGGCUUUCGGCGGCUCUGCGU | ------\| --- UA GU U-- U UCC<br>UG GC AG GU GGCUCG GGC CCCCA UGC AGU GC GCC \<br>AC CG UC CG UCGGGC ACG GGGGU ACG UCA UG GG A<br>CUUCAUAGA A --- UG UC --- C AG CGC A | 19 | - | 3912427 | 3912450 | + | - | - | - | - | 1 | 0 | 0 | 0 | Intron of DAPK3 | S |
| hsa-mir-638 | AGGGAUCGCGGGCGGGUGGCGGCC | GUGAGCC\| G GG G UA----- G- GG<br>GGCCGC GCAG A CGC GGCCUG CU GGCGG GCC \<br>UCGGCG CGUC U GCG CCGGGC CG CCGG GGG A<br>\ A G U C UG C UAAGGG AG GG | 19 | + | 10690095 | 10690119 | + | + | - | +++ | - | 1 | 0 | 0 | 0 | 1 Intron of DNM2 | S |

Fig. 12I (Table 5) Mature miRNAs (SEQ ID NOS: 337-469, respectively) and precursor miRNAs (SEQ ID NOS: 1386-1518, respectively)

| miRNA | Mature sequence | Precursor structure | Chr | Strand | Start | End | | | | | | | | Location | Type |
|---|---|---|---|---|---|---|---|---|---|---|---|---|---|---|---|
| hsa-mir-639 | AUCGCUGCGGUUGCAAGCGCUGU | (structure) | 19 | + | 145011415 | 145011437 | + | - | + | 1 | 0 | 0 | 1 | 5UTR of GPSN2 | S |
| hsa-mir-640 | AUGAUCCAGGAACCUGCCCUCU | (structure) | 19 | + | 19406932 | 19406952 | + | - | ++ | 0 | 1 | 0 | 1 | Extragenic | N/A |
| hsa-mir-641 | AAAGACAUAGGAUAGAGAGUCACCUC | (structure) | 19 | - | 45480350 | 45480373 | + | - | + | 0 | 1 | 0 | 1 | Intron of AKT2 | S |
| hsa-mir-642 | GUCCCUCUCCAAAUGUGUCUUG | (structure) | 19 | + | 50870041 | 50870062 | + | - | ++ | 0 | 0 | 0 | 1 | Intron of GIPR | AS |
| hsa-mir-643 | ACUUGUAUGCUAGCUUCAGGUAG | (structure) | 19 | + | 57476922 | 57476943 | + | - | + | 0 | 1 | 0 | 1 | Intron of LOC90321 | S |
| hsa-mir-644 | AGUGUGGCUUUCUUUAGAGC | (structure) | 19 | - | 33769866 | 33769884 | + | - | + | 1 | 0 | 0 | 1 | Intron of ITCH | S |
| hsa-mir-645 | UCUAGGCUGGUACUGCUGA | (structure) | 20 | + | 49867805 | 49867623 | + | - | + | 1 | 0 | 0 | 1 | Extragenic | N/A |
| hsa-mir-646 | AAGCAGCUGCCUCUGAGGC | (structure) | 20 | + | 59569902 | 59569920 | + | - | + | 1 | 0 | 0 | 1 | Extragenic | N/A |
| hsa-mir-647 | GUGGCUGCACUCUCAGGC | (structure) | 20 | - | 63300392 | 63300412 | + | - | ++ | 1 | 1 | 0 | 1 | Intron of UCKL1 | S |
| hsa-mir-648 | AAGUGUGCAGGGCACUGGU | (structure) | 22 | - | 16938248 | 16938266 | + | - | + | 0 | 1 | 0 | 1 | Extragenic | N/A |
| hsa-mir-649 | AAACCUGUGUUGUUCAAGAGUC | (structure) | 22 | - | 19713034 | 19713055 | + | - | ++ | 1 | 0 | 0 | 1 | Extragenic | N/A |
| hsa-mir-650 | AGGAGGCAGCGCUCUCAGGAC | (structure) | 22 | + | 21489639 | 21489659 | + | - | ++ | 0 | 0 | 0 | 1 | Extragenic | N/A |
| hsa-mir-651 | UUUUAGGAUAAGCUUGACUUUUG | (structure) | X | + | 7506526 | 7506547 | + | + | +++ | 0 | 2 | 1 | 3 | Extragenic | N/A |
| hsa-mir-652 | AAUGGCGCCACUAGGGUUGUCCA | (structure) | X | + | 108062588 | 108062610 | + | + | ++++ | 1 | 0 | 1 | 6 | Intron of RP13-360B22.2 | S |

Fig. 12J (Table 5) Mature miRNAs( SEQ ID NOS: 337-469, respectively) and precursor miRNAs (SEQ ID NOS: 1366-1518, respectively)

| | | Predicted precursor structure | | | | | | | | | | | | | |
|---|---|---|---|---|---|---|---|---|---|---|---|---|---|---|---|
| hsa-mir-653 | UUGAAACAAUCUCUACUGAAC | U————\|  CUU          C     CAGCUU<br>        UCAUUC  CAGUGUGAAACAA  CUCUA UGAAC       \<br>        AGUAAG  GUUAUAACUUUGUU  GAGGU ACUUG       AACAAA<br>CGAAGGUAGAAUA      AAC          U    C | 7 | - | + | | | | | | + | 0 | 0 | 0 | 0 | Intron of CALCR | S |
| hsa-mir-654 | UGGUGGGCCGCAGAACAUGUGC | \|         AAGUGG    A     GCC       A<br>        -GGGU     AAAG UCGUGG  GCaGA CAUGUG C UG  G<br>        CCCG     UUUC ACUACC  CGUCU GUAUAC G GC  U<br>\ A   AAGA——        C     AGU        —   C U  U | 14 | + | 99496612 | 99496633 | + | + | - | + | +++ | 0 | 0 | 2 | 0 | 0 | 2 Extragenic | N/A |
| hsa-mir-655 | AUAUAUACAUGGUUAACCUCUUU | AACUAUGCAAG\|       UG                UA    CUUCA<br>           GAUAUU  AGGAGAGGUUA  CCGUGU  UGUCG<br>           CUAUAA  UUUCUCCAAU  GGUACA  AUAAGU<br>CUCAGA————\ A       GU         U     UA    ACUAC | 14 | + | 99505980 | 99506009 | + | + | - | + | ++++ | 0 | 2 | 0 | 0 | 0 | 2 Extragenic | N/A |
| hsa-mir-656 | AAUAUUAUACAGUCAACCUCU | CU————\|     U     C        CUU  UA<br>         GAAA AGGUUG CUGUG  GUGUUCA   UC    \<br>         CUUU UCCAAC GACAU  CAUAAGU   AG    U<br>CUAAGCUAUAGC\     C      U    AU         —   UA | 14 | + | 99523144 | 99523164 | + | + | - | + | +++ | 0 | 1 | 0 | 1 | 0 | 1 Extragenic | N/A |
| hsa-mir-657 | GGCAGGUUCUCACCUCUCUAGG | GUGUACUAGAGCUA\|        —— A C        —— G U<br>              GGAGGAGA   GGG  CCUGGAGA G GUG GA CC G CCGGG \<br>              UCUCCUCU   CCC  GGAUCUCU C CAC CU GG C GGCCU UG<br>G—————————A          UA    C            C U U A— — C UG | 17 | - | 79799210 | 79799232 | + | + | - | + | ++ | 0 | 0 | 1 | 0 | 0 | 1 Extragenic | N/A |
| hsa-mir-658 | GGCGGAGGGAAGUAGGUCCGUUGGG | G\|      G   G     —— GC       AGC——      C A<br>    CUCG UU CCG UGG G CCGGCC   CU CCC    CCGCC    UCG UG C \<br>    GAGC AA GGC CCU U GCCUGG   GA GGG    GGCGG    AGC AC A<br>GGA\ — G UG  GG U  AU A    A—   GACUC  — G | 22 | - | 36483333 | 36483357 | + | + | - | + | +++++ | 0 | 0 | 0 | 0 | 0 | 1 5UTR of LOC129138 | S |
| hsa-mir-659 | CUUGGUUCAGGGAGGGUCCCCA | UACCGACCCUC\| UUG  CA<br>           GAU  GUU  GGACCUUCCCUGAACCAAGGAAGAG<br>           CUG  CAA  CCUGGGAGGGACUUGGUUCCUUCUC<br>GGUACUC————\ UAA   CC                  UGA | 22 | + | 36486739 | 36486760 | + | + | - | + | +++ | 0 | 0 | 0 | 1 | 0 | 1 Extragenic | N/A |
| hsa-mir-660 | UACCCAUUGCAUAUCGGAGUUG | CU————\|             CAUAC—    U    C   U  GAAUU<br>                GCUC  UUCUCC       CCAU GCAUAU GGAG UGU   \<br>                CGAG  GGGAGG       GGUA CGUGUG CCUC ACA   C<br>GUGUACUGUUC\ U    ACAUUA    —       J   C     —    AAACU | X | + | 48695204 | 48695225 | + | + | - | + | ++++ | 0 | 1 | 0 | 8 | 0 | 13 Extragenic | N/A |
| hsa-mir-661 | UGCCUGGGCUCUGGCCUGCGCGU | GGAGA    GU   G  GG   —G   —   U    U     UUC<br>       GGCU  GCU U  GG  CA CCCGCAGGCC GAC CCC GGU   G<br>       UCGG  UGG G  UC GU CGCGGUCCGG  CUC GGG CCG   G<br>————     —— A G    G UU A G     U      U   U UCG | 8 | - | 145125355 | 145125378 | + | + | - | - | ++ | 0 | 0 | 1 | 0 | 0 | 1 Intron of PLEC | S |
| hsa-mir-662 | UCCCACGUUUGUGGCCCAGCAG | \| UGU   A      CA    C    —   A   G——    C<br>    GC   UG GGCUGCCG GC GGCC UGACG UGGGG GGCU CGGG \<br>    CG   GC CUGACGCG CG CCGG GUUGC ACCCU CUGG GUCU U<br>A UU—  A          A     AC   U        AA    U | 16 | + | 760244 | 760264 | + | - | - | - | + | 1 | 0 | 0 | 0 | 1 | 1 Exon of MPFL | AS |
| hsa-mir-663 | AGGCGGGGCGCCGCGGGACCGC | CUU——\|      C— —    C— —       C             U    UG<br>C     CCGG GUC CCAGG  GG GCG CCCGGGGA   CCCGC UCG U   \<br>G     GGCC CGG CGGCC  UU UGC GCCGCCCU   GGGGG GGU C    GU<br>UACC        U   UU  G  C    UU            AG   C   AG | 20 | - | 26183679 | 26183900 | + | - | - | - | + | 1 | 0 | 0 | 0 | 0 | 1 Extragenic | N/A |

Explanations for selected columns are as follows: Predicted precursor structure (red sequences correspond to mature miRNA sequence within precursor structure; blue sequences correspond to experimentally derived miRNA* sequence, if applicable); Mature miRNA position (coordinates are with respect to Santa Cruz July 2003, build 34, HG16); Validation (+, fulfills criterion; -, does not fulfill criterion)

Fig. 13A (Table 6.) Microarray expression validation of selected miRNA candidates and known miRNAs

| miRNA Name | miRNA Status | miRNA Sequence | Probe Sequence | Placenta | Prostate | Testes | Brain | Placenta Detection | Prostate Detection | Testes Detection | Brain Detection | Detected in at least one tissue |
|---|---|---|---|---|---|---|---|---|---|---|---|---|
| hsa-mir-33b | Novel Candidate | GUGCAUUGCUGUUGCAUUGCA | TGCAATGCAACAGCAATGCAC | 168.3 | 64.2 | 183.7 | 40.0 | - | - | - | - | - |
| hsa-mir-92b | Novel Candidate | UAUUGCACUCGUCCCGGCCUC | GAGGCCGGGACGAGTGCAATA | 3447.6 | 3511.8 | 6629.4 | 6725.8 | + | + | + | + | + |
| hsa-mir-411 | Novel Candidate | UAGUAGACCGUAUAGCGUACG | CGTACGCTATACGGTCTACTA | 1956.2 | 325.8 | 660.3 | 2109.4 | + | + | + | + | + |
| hsa-mir-421-3p | Novel Candidate | AUCAACAGACAAUUAAUUGGGCGC | GCCGCCAATTAATGTCTGTTGAT | 753.1 | 1518.1 | 980.9 | 3992.1 | + | + | + | + | + |
| hsa-mir-449b | Novel Candidate | AGGCAGUGUAUUGUUAGCUGGU | GCCAGCTAACATACAACTGCCT | 157.5 | 58.4 | 3942.6 | 54.2 | - | - | + | - | + |
| hsa-mir-483* | Novel Candidate | AAGACGGGAGGAAAGAAGGGAG | CTCCCTTCTTTCCTCCCGTCT | 4887.4 | 4752.3 | 4772.6 | 473.3 | + | + | + | + | + |
| hsa-mir-542 | Novel Candidate | UCGGGGAUCAUCAUGUCACGAG | CTCGTGACATGATGATCCCCGA | 492.3 | 64.1 | 495.3 | 44.0 | - | - | - | - | - |
| hsa-mir-545 | Novel Candidate | UCAGCAAACAUUUAUUGUGUGC | GCACACAATAAATGTTTGCTGA | 177.5 | 55.9 | 196.6 | 36.0 | - | - | - | - | - |
| hsa-mir-548a-1 | Novel Candidate | CAAAACUGGCAAUUACUUUUGC | GCAAAAGTAATTGCCAGTTTG | 155.4 | 49.6 | 190.6 | 38.0 | - | - | - | - | - |
| hsa-mir-548b | Novel Candidate | CAAGAACCUCAGUUGCUUUUGU | ACAAAAGCAACTGAGGTTCTTG | 197.1 | 68.4 | 217.4 | 46.7 | - | - | - | - | - |
| hsa-mir-548c | Novel Candidate | CAAAAAUCUCAAUUACUUUUGC | GCAAAAGTAATTGAGATTTTTG | 150.2 | 48.0 | 189.1 | 32.6 | - | - | - | - | - |
| hsa-mir-549a | Novel Candidate | UGACAACUAUGGAUGAGCUCU | AGAGCTCATCCATAGTTGTCA | 181.7 | 81.0 | 205.7 | 47.2 | - | - | - | - | - |
| hsa-mir-549b | Novel Candidate | GACAACUAUGGAUGAGCUCUCA | TGAGAGCTCATCCATAGTTGTC | 174.9 | 66.6 | 184.7 | 35.7 | - | - | - | - | - |
| hsa-mir-550-1 | Novel Candidate | UGUCUUACUCCCUCAGGCACAU | ATGTGCCTGAGGGAGTAAGACA | 239.0 | 117.0 | 215.7 | 76.9 | - | - | - | - | - |
| hsa-mir-551a | Novel Candidate | GCGACCCACUCGUUGGUUUCCA | TGGAAACCAAGAGTGGGTCGC | 184.9 | 65.5 | 197.0 | 37.3 | - | - | - | - | - |
| hsa-mir-551b | Novel Candidate | GCGACCCAUACUUGGUUUCAG | CTGAAACCAAGTATGGGTCGC | 1099.7 | 133.0 | 236.0 | 152.6 | + | - | - | + | + |
| hsa-mir-552 | Novel Candidate | AACAGGUGACUGGUUAGACAA | TTGTCTAACCAGTCACCTGTT | 145.4 | 48.1 | 195.2 | 37.0 | - | - | - | - | - |
| hsa-mir-553 | Novel Candidate | AAAACGAAAAUCUCACCGUUUU | AAAACGAAAATCTCACCGTTTT | 147.4 | 39.5 | 189.0 | 35.5 | - | - | - | - | - |
| hsa-mir-554 | Novel Candidate | GCUAGUCCUGACACUCAGCCAGU | ACTGGCTGAGTCAGGACTAGC | 182.1 | 76.5 | 218.5 | 40.2 | - | - | - | - | - |
| hsa-mir-555 | Novel Candidate | AGGGUAAGCUGAACCUCUGAU | ATCAGAGGTTCAGCTTACCCT | 165.5 | 59.6 | 204.2 | 36.0 | - | - | - | - | - |
| hsa-mir-556 | Novel Candidate | GAUGAGCCAUUGUAAUAUG | CATATTACAATGAGCTCATC | 162.3 | 51.0 | 182.0 | 35.1 | - | - | - | - | - |
| hsa-mir-557 | Novel Candidate | GUUUGCACGGGGUGGGCCUUGUCU | AGACAAGGCCCACCCGTGCAAAC | 423.7 | 296.5 | 765.6 | 65.8 | + | + | + | - | + |
| hsa-mir-558 | Novel Candidate | UGAGCUGCUGUACCAAAAU | ATTTTGGTACAGCAGCTCA | 171.9 | 71.5 | 203.8 | 37.6 | - | - | - | - | - |
| hsa-mir-559 | Novel Candidate | UAAAGUAAAUAUGCACCAAAA | TTTTGGTGCATATTTACTTTA | 147.9 | 41.3 | 194.1 | 35.1 | - | - | - | - | - |
| hsa-mir-560 | Novel Candidate | GCGUGCCGCCACUCGGCCGCC | GGCGGCCGAGTGGCGGCACGC | 200.7 | 159.9 | 285.5 | 84.0 | - | + | - | - | - |
| hsa-mir-561 | Novel Candidate | CAAAGUUUAAGAUCCUUGAAGU | ACTTCAAGGATCTTAAACTTTG | 167.4 | 48.4 | 186.1 | 33.0 | - | - | - | - | - |
| hsa-mir-562 | Novel Candidate | AAAGUAGCUGUACCAUUUGC | GCAAATGGTACAGCTACTTT | 152.1 | 54.3 | 201.4 | 40.2 | - | - | - | - | - |
| hsa-mir-563 | Novel Candidate | AGGUAACGTATGTCAACCT | GGGAAACGTATGTCAACCT | 195.5 | 125.7 | 628.6 | 222.0 | - | + | + | + | + |
| hsa-mir-564 | Novel Candidate | AGGCACGGUGUCAGCAGGC | GCCTGCTGACACCGTGCCT | 359.4 | 181.0 | 250.3 | 50.2 | + | + | - | - | + |
| hsa-mir-565 | Novel Candidate | GGCUGGCUCGCGAUGUCUGUUU | AAACAGACATCGCGAGCCAGCC | 2128.7 | 2035.0 | 2065.9 | 1129.2 | + | + | + | + | + |
| hsa-mir-566 | Novel Candidate | GGGGCGGGGAUCGAUCCGGCCC | GTTGGGATCACAGGCGCCC | 185.5 | 94.3 | 213.1 | 42.2 | - | - | - | - | - |
| hsa-mir-567 | Novel Candidate | AGUAUGUUCUUCCAGGAACAGAAC | GTTCTGTCCTGGAAGAACATACT | 169.2 | 69.5 | 203.2 | 39.1 | - | - | - | - | - |
| hsa-mir-568 | Novel Candidate | AUGUAUAAAUGUAACACAC | GTGTGTATACATTTATACAT | 1895.5 | 1096.4 | 354.5 | 73.9 | + | + | + | - | + |
| hsa-mir-569 | Novel Candidate | AGUAAGGAAUCCUGGAAAGU | ACTTTCCAGGATTCATTAACT | 161.2 | 44.8 | 188.1 | 34.1 | - | - | - | - | - |
| hsa-mir-570 | Novel Candidate | GAAAACAGCAAUUACCUUUGCA | TGCAAAGGTAATTGCTGTTTTC | 157.7 | 57.6 | 197.2 | 41.1 | - | - | - | - | - |
| hsa-mir-571 | Novel Candidate | UGAGUUGGCCAUCUGAGUGAG | CTCACTCAGATGGCCAACTCA | 184.3 | 77.9 | 200.5 | 42.6 | - | - | - | - | - |
| hsa-mir-572 | Novel Candidate | GUCCGCUCGGCGGUGGCCCA | TGGGCCACCGCCGAGCGGAC | 3234.5 | 884.7 | 5679.6 | 1298.8 | + | + | + | + | + |
| hsa-mir-573 | Novel Candidate | CUGAAGUGAUGUGUAACGAUCAG | CTGATCAGTTACACATCACTTCAG | 159.6 | 55.3 | 203.1 | 36.1 | - | - | - | - | - |
| hsa-mir-574 | Novel Candidate | CACGCUCAUGCACACACCCAC | GTGGGTGTGTGCATGAGCGTG | 4213.9 | 4822.8 | 2110.0 | 2407.8 | + | + | + | + | + |
| hsa-mir-575 | Novel Candidate | GAGCCAGUUGGACAGGAGC | CTCCTGTCCAACTGGCTC | 910.3 | 728.2 | 1467.1 | 177.4 | + | + | + | + | + |
| hsa-mir-576 | Novel Candidate | AUUCUAAAUUCUCCACGGUCUUUG | CAAAGACGTGGAGAATTAGAAT | 242.4 | 96.4 | 206.9 | 54.2 | - | - | - | - | - |
| hsa-mir-577 | Novel Candidate | UAGAUAAAAUAUUGGUACCUG | CAGGTACCAATATTTATCTA | 161.4 | 44.7 | 192.9 | 674.8 | - | - | - | + | + |
| hsa-mir-578 | Novel Candidate | CUUCUUGUGCUCUAGGAUUGU | ACAATCCTAGAGCACAAGAAG | 152.9 | 63.7 | 193.3 | 35.1 | - | - | - | - | - |

Fig. 13B

| ID | Type | Sequence (RNA) | Sequence (DNA) | V1 | V2 | V3 | V4 | C1 | C2 | C3 | C4 | C5 | C6 |
|---|---|---|---|---|---|---|---|---|---|---|---|---|---|
| hsa-mir-579 | Novel Candidate | AUUCAUUUGGUAUAAACCGCGAU | ATCGCGGTTTATACCAAATGAAT | 153.1 | 49.7 | 197.1 | 38.0 | - | - | - | - | - | - |
| hsa-mir-580 | Novel Candidate | UUGAGAAUGAUGAAUCAUUAGG | CCTAATGATTCATCATTCTCAA | 171.5 | 57.7 | 187.4 | 37.6 | - | - | - | - | - | - |
| hsa-mir-581 | Novel Candidate | UCUUGUGUUCUCUAGAGAUCAGU | ACTGATCTAGAGAACACAAGA | 174.8 | 65.1 | 197.4 | 38.6 | - | - | - | - | - | - |
| hsa-mir-582 | Novel Candidate | UUACAGUUGUUCAACCAGUUACU | AGTAACTGGTTGAACAACTGTAA | 434.7 | 1974.5 | 470.7 | 2106.4 | - | + | - | - | - | + |
| hsa-mir-583 | Novel Candidate | CAAAGAGGAAGGUCCCAUUAC | GTAATGGGACCTTCCTCTTTG | 178.9 | 128.7 | 214.1 | 37.1 | - | - | - | - | - | - |
| hsa-mir-584 | Novel Candidate | UUAUGGUUUGCCUGGACUGAG | CTCAGTCCCAGGCAAACCATAA | 3358.4 | 188.5 | 541.1 | 5693.9 | + | - | + | - | + | + |
| hsa-mir-585 | Novel Candidate | UGGGCGUAUCGUAUGCUA | TAGCATACAGATACGCCCA | 192.3 | 105.3 | 189.3 | 41.9 | - | - | - | - | - | - |
| hsa-mir-586 | Novel Candidate | UAUGCAUUGUAUUUUAGGUCC | GGACCTAAAAATACAATGCATA | 168.8 | 56.4 | 202.1 | 42.2 | - | - | - | - | - | - |
| hsa-mir-587 | Novel Candidate | UGUGAUCUCAUCACCUAUCGAAA | GTGATCATCACCTATCGAAA | 186.6 | 77.0 | 195.7 | 41.1 | - | - | - | - | - | - |
| hsa-mir-588 | Novel Candidate | UUGGCCACAAUGGGUUAGAAC | GTTCTAACCCATTGTGGCCAA | 179.5 | 73.2 | 188.4 | 39.8 | - | - | - | - | - | - |
| hsa-mir-589 | Novel Candidate | UCAGAACAAAUGCCGGUUCCCAGA | TCTGGGAACCGGCATTTGTTCTGA | 194.6 | 77.1 | 211.5 | 90.9 | - | - | - | - | - | - |
| hsa-mir-590 | Novel Candidate | GAGCUUAUUCAUAAAAGUGCAG | CTGCACTTTTATGAATAAGCTC | 810.5 | 768.5 | 469.3 | 473.7 | + | + | + | - | + | + |
| hsa-mir-591 | Novel Candidate | ACAAUGAGAACCCAUUAGU | ACAATGAGGTTCCATTGTCT | 148.9 | 48.4 | 185.1 | 37.4 | - | - | - | - | - | - |
| hsa-mir-592 | Novel Candidate | UUGUGUCAAUAUGCCAUGAUGU | ACATCATCGCATATTGACACAA | 177.9 | 121.0 | 264.2 | 729.2 | - | - | - | + | - | + |
| hsa-mir-593 | Novel Candidate | AGGCACCAGCCAGGCAUUGCUCAGC | GCTGAGCAATGCCTGGCTGGTGCCT | 164.1 | 69.8 | 228.2 | 39.5 | - | - | - | - | - | - |
| hsa-mir-594 | Novel Candidate | CCCAUUCGGGCCUGAGCCUGUGACUUU | AAAGTCACAGGCCTCCCCAGATGGG | 5389.2 | 1021.7 | 4025.6 | 2776.1 | + | + | + | + | + | + |
| hsa-mir-595 | Novel Candidate | GAAGUGUCCGUGGUGUGUCU | AGACACACCACGGCACACTTC | 348.9 | 148.9 | 261.9 | 46.5 | - | - | - | - | - | - |
| hsa-mir-596 | Novel Candidate | AAGCCUGCCCGGCUCCUCGGG | CCCGAGGAGCCGGGCAGGCTT | 167.9 | 81.3 | 251.9 | 48.9 | - | - | - | - | - | - |
| hsa-mir-597 | Novel Candidate | UGUGUACUCAUCGAUGACCACUGU | ACAGTGGTCATCGAGTGACACA | 197.0 | 87.5 | 211.3 | 42.4 | - | - | - | - | - | - |
| hsa-mir-598 | Novel Candidate | UACGUCAUCGUUGUCAUCGUCA | TGACGATGACAACGATGACGTA | 150.3 | 319.4 | 415.2 | 5078.7 | - | - | - | + | - | + |
| hsa-mir-599 | Novel Candidate | GUUGUGUCAGUUUAUCAAAC | GTTTGATAAACTGACACAAC | 163.8 | 53.6 | 210.3 | 36.0 | - | - | - | - | - | - |
| hsa-mir-600 | Novel Candidate | ACUUACAGAACAAGAGCCUUGCUC | GAGCAAGGTCTTGTCTGTAAGT | 154.3 | 51.6 | 195.3 | 36.3 | - | - | - | - | - | - |
| hsa-mir-601 | Novel Candidate | UGGGUAGGAUUUGUUGGAGGAG | CTCCTCCAACAATCCTAGACCA | 564.1 | 329.7 | 688.5 | 165.3 | + | + | + | + | + | + |
| hsa-mir-602 | Novel Candidate | GACACGGGCCACAGUGCGGGCCC | GGGCCGCAGCTGTCGCCCGTGTC | 460.4 | 321.0 | 821.5 | 146.4 | + | + | + | - | + | + |
| hsa-mir-603 | Novel Candidate | CACACUCCAAUUACUUGUUGC | GCAAAGTAATTGCAGTGTGTG | 429.8 | 176.8 | 201.2 | 35.3 | + | - | - | - | - | - |
| hsa-mir-604 | Novel Candidate | AGGCUGCGAAUUCGCAGGAG | GTCCTGAATTCGCAGCCT | 166.7 | 97.9 | 197.1 | 38.7 | - | - | - | - | - | - |
| hsa-mir-605 | Novel Candidate | UAAAUCCCAUGGUGCCUUCUCCU | AGGAGAAGGCACCATGGGATTTA | 289.6 | 191.6 | 281.4 | 41.0 | + | - | - | - | - | - |
| hsa-mir-606 | Novel Candidate | AAACUACUGAAAAUCAAAGAU | ATCTTTGATTTTCAGTAGTTT | 162.7 | 59.2 | 233.0 | 49.7 | - | - | - | - | - | - |
| hsa-mir-607 | Novel Candidate | GUUCAAAUCCAGAAUCAUAAC | GTTATAGATCTGGATTTGAAC | 147.1 | 43.2 | 188.0 | 34.0 | - | - | - | - | - | - |
| hsa-mir-608 | Novel Candidate | AGGGGUGUUGGGGACAGCUCCGU | ACGGAGCTGTCCCAACACCACCCCT | 166.6 | 56.0 | 190.9 | 36.6 | - | - | - | - | - | - |
| hsa-mir-609 | Novel Candidate | AGGGGUGUUUCUCUCAUCUCU | AGAGATGAGAGAAACACCCT | 208.8 | 162.6 | 362.1 | 65.6 | - | + | + | + | + | + |
| hsa-mir-610 | Novel Candidate | UGAGCUAAAUGUGUGCUGGA | TCCAGCACACATTTAGCTCA | 175.0 | 60.1 | 204.4 | 38.9 | - | - | - | - | - | - |
| hsa-mir-611 | Novel Candidate | GCGAGGACCCCUCGGGGUCUGAC | GTCAGACCCCGAGGGGTCCTCGC | 194.3 | 107.8 | 215.8 | 40.7 | - | - | - | - | - | - |
| hsa-mir-612 | Novel Candidate | GCUGGGCAGGGCGGUUCUGAGCUCCUU | AAGGAGCTCAGAAGCCCCTGCCCAGC | 188.3 | 97.9 | 212.0 | 43.4 | - | - | - | - | - | - |
| hsa-mir-613 | Novel Candidate | AGGAAAUGUCCUUCUUUGCC | GGCAAAGAAGGACATTCCT | 289.6 | 191.6 | 281.4 | 41.0 | - | - | - | - | - | - |
| hsa-mir-614 | Novel Candidate | GAACGCCUGUUCUUGCCAGGUUG | CCACCTGGCAAGAACAGGCGTTC | 166.7 | 62.3 | 203.6 | 41.7 | - | - | - | - | - | - |
| hsa-mir-615 | Novel Candidate | UCCGAGCCUGGGGUCUCCCCUCU | AGAGGGAGACCCAGGCTCGGA | 161.0 | 76.9 | 206.0 | 38.0 | - | - | - | - | - | - |
| hsa-mir-616 | Novel Candidate | ACUCAAAACCCUUCAGUGACUU | AAGTCACTGAAGGGTTTTGAGT | 207.0 | 104.4 | 243.4 | 46.1 | - | - | - | - | - | - |
| hsa-mir-617 | Novel Candidate | AGACUACCCAAAUGCAAGGGU | ACCCTTGCATTTGGGTAGTCT | 181.9 | 63.1 | 209.7 | 47.9 | - | - | - | - | - | - |
| hsa-mir-618 | Novel Candidate | AAACUCUACUUGUCCUUCUGAGU | ACTCAGAAGGACAAGTAGAGTTT | 281.8 | 271.6 | 3270.3 | 731.6 | - | - | + | + | + | + |
| hsa-mir-619 | Novel Candidate | GACCUGGACAUGUUUGUGCCCAGU | ACTGGGCACAAACATGTCCAGGTC | 161.1 | 46.7 | 194.2 | 45.0 | - | - | - | - | - | - |
| hsa-mir-620 | Novel Candidate | AUGGAGAUAGAUAAAAAU | ATTTCTATATCTCCAT | 182.3 | 66.9 | 189.7 | 36.1 | - | - | - | - | - | - |
| hsa-mir-621 | Novel Candidate | GGCUAGCAACAGCGCUUACCU | AGGTAAGCGCTGTTGCTAGCC | 139.3 | 41.4 | 180.9 | 33.2 | - | - | - | - | - | - |
| hsa-mir-622 | Novel Candidate | ACAGUCUGCUGAGGUUGGAGC | GCTCCAACCTCAGCAGACTGT | 170.1 | 90.8 | 199.6 | 38.2 | - | - | - | - | - | - |
| hsa-mir-623 | Novel Candidate | AUCUCAAAACCCUUCAGUGACUU | AAGTCACTGAAGGGTTTTGAGAT | 195.6 | 124.4 | 231.3 | 41.0 | - | - | - | - | - | - |
| hsa-mir-624 | Novel Candidate | AGACUACCAGUUGUACCUUGGGU | ACCCAAGGTACAACTGGTACTA | 636.2 | 400.0 | 1121.3 | 89.2 | + | + | + | - | + | + |
| hsa-mir-625 | Novel Candidate | AGGGGAAAGUUCUAUAGUCCU | AGGACTATAGAACTTTCCCCCT | 340.8 | 103.5 | 331.4 | 98.1 | - | - | - | - | - | - |
| hsa-mir-626 | Novel Candidate | AGCUGUGUUCUGAAAUGUCUU | AAGACATTTCAGACAGCT | 1470.0 | 235.8 | 505.2 | 914.5 | + | + | + | + | + | + |
| hsa-mir-627 | Novel Candidate | GUGAGUCUUAAGAAAAGAGGA | TCCTCTTTTCTTAGAGACTAC | 153.6 | 46.3 | 191.8 | 33.5 | - | - | - | - | - | - |
| hsa-mir-628 | Novel Candidate | UCUAGUAAGAGUGGCAGUCG | CGACTGCCACTCTTACTAGA | 201.6 | 116.6 | 222.8 | 48.9 | - | - | - | - | - | - |
| hsa-mir-629 | Novel Candidate | GUUCUCCCAACGUAAGCCCAGC | GCTGGGCTTACGTTGGGAGAAC | 3054.0 | 2700.9 | 3520.2 | 2188.8 | + | + | + | + | + | + |
| hsa-mir-630 | Novel Candidate | | | 212.4 | 96.3 | 308.1 | 64.9 | - | - | - | - | - | - |

Fig. 13C

| ID | Type | Sequence (RNA) | Sequence (DNA) | V1 | V2 | V3 | V4 | I1 | I2 | I3 | I4 |
|---|---|---|---|---|---|---|---|---|---|---|---|
| hsa-mir-630 | Novel Candidate | AGUAUUCUGUACCAGGGAAGGU | ACCTTCCTGGTACAGAATACT | 252.8 | 305.3 | 290.7 | 44.3 | - | - | - | - |
| hsa-mir-631 | Novel Candidate | AGACCUGGCCCAGACCUCAGC | GCTGAGGTCTGGGCAGGTCT | 166.6 | 75.5 | 225.9 | 44.6 | - | - | - | - |
| hsa-mir-632 | Novel Candidate | GUGUCUGCUUCCUGUGGGA | TCCCACAGGAAGCAGACAC | 177.2 | 66.2 | 204.7 | 33.7 | - | - | - | - |
| hsa-mir-633 | Novel Candidate | CUAAUAGUAUCUACCACAAUAAA | TTTATTGTGGTAGATACTATTAG | 159.2 | 49.2 | 198.8 | 35.5 | - | - | - | - |
| hsa-mir-634 | Novel Candidate | AACCAGCACCCCAACUUUGAC | GTCAAAGTTGGGTGCTGTT | 183.3 | 70.1 | 210.7 | 43.6 | - | - | - | - |
| hsa-mir-635 | Novel Candidate | ACUUGGGCACUGAAACAAUUGAC | GGACATTGTTTCAGTGCCCAAGT | 161.4 | 65.5 | 207.5 | 37.7 | - | - | - | - |
| hsa-mir-636 | Novel Candidate | UGUGCUUGCUCGUCCCGCCCGAG | CTGCGGGCGGGACGAGCAAGCACA | 204.4 | 129.6 | 217.8 | 51.9 | - | - | - | - |
| hsa-mir-637 | Novel Candidate | ACUGGGGGCUUUCGGGCUCUGCGU | ACGCAGAGCCCGAAAGCCCCAGT | 196.7 | 130.8 | 283.1 | 45.9 | - | - | - | - |
| hsa-mir-638 | Novel Candidate | AGGGAUCGCGGGCGGGUCGGGGCCU | AGGCCGCCACCCGCCCGCGATCCCT | 13665.6 | 10952.2 | 24888.4 | 4061.4 | + | + | + | - |
| hsa-mir-639 | Novel Candidate | AUCGCUGCGGUUGCGAGCGCUGU | ACAGCGCTCGCAACGCAGCGAT | 157.7 | 69.0 | 206.7 | 43.3 | - | - | - | - |
| hsa-mir-640 | Novel Candidate | AUGAUCCAGGAACCUGCCCUCU | AGAGGCAGGTTCCTGGATCAT | 166.9 | 70.8 | 209.7 | 38.5 | - | - | - | - |
| hsa-mir-641 | Novel Candidate | AAAGACAUAGGAUAGAGUCACCUC | GAGGTGACTCTATCCTATGTCTTT | 178.8 | 80.9 | 276.9 | 105.0 | - | - | - | + |
| hsa-mir-642 | Novel Candidate | GUCCCCUGCCCCAAAUGUGUGG | CAAGACACATTTGGAGAGGGAC | 166.9 | 59.1 | 196.1 | 131.3 | - | - | - | - |
| hsa-mir-643 | Novel Candidate | ACUUGUAUGCUAGCUCAGGUAG | CTACCTGAGCTAGCATACAAGT | 168.9 | 54.4 | 195.4 | 40.3 | - | - | - | - |
| hsa-mir-644 | Novel Candidate | AGUGUGGCUUUCUUAGAGC | GCTCTAAGAAAGCCACACT | 167.6 | 62.2 | 196.6 | 35.9 | - | - | - | - |
| hsa-mir-645 | Novel Candidate | UCUAGGUACCUAGCCUAGA | TCAGAGGTACCTAGG | 177.8 | 77.2 | 194.2 | 39.1 | - | - | - | - |
| hsa-mir-646 | Novel Candidate | AAGCAGCUGCCUCUGAGGC | GCCTCAGAGGCAGCTGCTT | 153.6 | 72.0 | 209.6 | 47.8 | - | - | - | - |
| hsa-mir-647 | Novel Candidate | GUGGCUGCACUCACUUCCUUC | GAAGGAAGTGAGTGCAGCCAC | 202.2 | 133.5 | 402.3 | 102.5 | - | - | + | + |
| hsa-mir-648 | Novel Candidate | AAGUGUGCAGGGCACUGGU | ACCAGTGCCCTGCACACTT | 159.7 | 80.6 | 217.1 | 41.8 | - | - | - | - |
| hsa-mir-649 | Novel Candidate | AAACCUGUGUUGUUCAAGAGUC | GACTCTTGAACAACACAGGTTT | 150.1 | 49.0 | 203.7 | 42.8 | - | - | - | - |
| hsa-mir-650 | Novel Candidate | AGGAGGCAGCGCUCUCAGGAC | GTCCTGAGAGCGCTGCCTCCT | 329.8 | 1089.7 | 302.9 | 53.6 | - | - | - | + |
| hsa-mir-651 | Novel Candidate | UUUAGGAUAAGCUUGACUUUG | CAAAAGTCAAGCTTATCCTAAA | 210.5 | 129.6 | 280.6 | 68.0 | - | - | - | + |
| hsa-mir-652 | Novel Candidate | AAUGGCGCCACUAGGGUUGUGCA | TGCACAACCCTAGTGGCGCCATT | 572.8 | 456.1 | 327.6 | 634.0 | + | + | + | + |
| hsa-mir-653 | Novel Candidate | UUGAAACAAUCUACUGAAC | GTTCAGTAGAGATTGTTTCAA | 275.9 | 93.2 | 257.4 | 49.2 | - | - | - | + |
| hsa-mir-654 | Novel Candidate | UGGUGGGCCGCAGAACAUGUGC | GCACATGTTCTGCGGCCCACCA | 407.3 | 165.4 | 256.7 | 81.3 | - | - | + | + |
| hsa-mir-655 | Novel Candidate | AUAAUACGGGUUAACAUGUAUAU | AAAGAGGTTAACCATGTATTAT | 1273.0 | 260.5 | 313.9 | 697.9 | + | - | + | + |
| hsa-mir-656 | Novel Candidate | AAUAUUAUACAGUCAACCUCU | AGAGGTTGACTGTATATATT | 514.2 | 165.4 | 328.4 | 1133.3 | + | - | + | + |
| hsa-mir-657 | Novel Candidate | GGCAGGUUCUCACCCCUCUAGG | CCTAGAGGGGTGAGAACCTGCC | 176.4 | 64.3 | 203.4 | 37.8 | - | - | - | - |
| hsa-mir-658 | Novel Candidate | GGCGGUGGGCCGCAGAACAGGUCCUGGGU | ACCAACGGACCTACTTCCCTCCGCC | 438.7 | 592.3 | 483.1 | 66.8 | - | + | + | + |
| hsa-mir-659 | Novel Candidate | CUUGGUUCAGGGAGGGCCCCA | TGGGGACCCTCCCTGAACCAAG | 205.3 | 227.6 | 441.2 | 104.4 | - | + | + | + |
| hsa-mir-660 | Novel Candidate | UACCCAUUGCAUAUCGGAGUUG | CAACTCCGATATGCAATGGGTA | 1564.7 | 1099.5 | 1780.1 | 708.7 | + | + | + | + |
| hsa-let-7a | Known | UGAGGUAGUAGGUUGUAUAGUU | AACTATACAACCTACTACCTCA | 14012.3 | 62390.8 | 25134.7 | 34182.1 | + | + | + | + |
| hsa-let-7b | Known | UGAGGUAGUAGGUUGUGUGGUU | AACCACACAACCTACTACCTCA | 12921.7 | 59882.0 | 25354.3 | 32517.8 | + | + | + | + |
| hsa-let-7c | Known | UGAGGUAGUAGGUUGUAUGGUU | AACCATACAACCTACTACCTCA | 13627.9 | 61565.4 | 25836.3 | 33232.8 | + | + | + | + |
| hsa-let-7d | Known | AGAGGUAGUAGGUUGCAUAGU | ACTATGCAACCTACTACCTCT | 14793.6 | 59042.8 | 24513.8 | 34206.1 | + | + | + | + |
| hsa-let-7e | Known | UGAGGUAGGAGGUUGUAUAGU | ACTATACAACCTCCTACCTCA | 18839.9 | 49474.3 | 23654.3 | 33841.4 | + | + | + | + |
| hsa-let-7f | Known | UGAGGUAGUAGAUUGUAUAGUU | AACTATACAATCTACTACCTCA | 14198.4 | 60153.9 | 24705.4 | 34995.5 | + | + | + | + |
| hsa-let-7g | Known | UGAGGUAGUAGUUUGUACAGUU | ACTGTACAAACTACTACCTCA | 6922.8 | 43673.0 | 15881.0 | 28050.6 | + | + | + | + |
| hsa-let-7i | Known | UGAGGUAGUAGUUUGUGCUGU | ACAGCACAAACTACTACCTCA | 5688.0 | 31890.2 | 11227.8 | 22518.0 | + | + | + | + |
| hsa-miR-1 | Known | UGGAAUGUAAAGAAGUAUGUA | TACATACTTCTTTACATTCCA | 2403.4 | 41400.7 | 7949.7 | 5287.9 | + | + | + | + |
| hsa-miR-100 | Known | AACCCGUAGAUCCGAACUUGUG | CACAAGTTCGGATCTACGGGTT | 18168.7 | 31064.2 | 12825.6 | 22540.0 | + | + | + | + |
| hsa-miR-101 | Known | UACAGUACUGUGAUAACUGAAG | CTTCAGTTATCACAGTACTGTA | 4575.7 | 9896.2 | 3184.2 | 7543.9 | + | + | + | + |
| hsa-miR-103 | Known | AGCAGCAUUGUACAGGGCUAUGA | TCATAGCCCTGTACAATGCTGCT | 13794.7 | 9738.1 | 5925.3 | 18200.2 | + | + | + | + |
| hsa-miR-105 | Known | UCAAAUGCUCAGACUCCUGUGGU | ACAGGAGTCTGAGCATTTGA | 232.6 | 53.6 | 237.6 | 218.0 | - | - | - | - |
| hsa-miR-106a | Known | AAAAGUGCUUACAGUGCAGGUAGC | GCTACCTGCACTGTAAGCACTTTT | 8685.9 | 11815.4 | 9238.3 | 7997.8 | + | + | + | + |
| hsa-miR-106b | Known | UAAAGUGCUGACAGUGCAGAU | ATCTGCACTGTCAGCACTTTA | 5058.5 | 4823.7 | 2596.5 | 4248.1 | + | + | + | + |
| hsa-miR-107 | Known | AGCAGCAUUGUACAGGGCUAUCA | TGATAGCCCTGTACAATGCTGCT | 13159.7 | 9541.8 | 5614.8 | 17620.2 | + | + | + | + |
| hsa-miR-10a | Known | UACCCUGUAGAUCCGAAUUUGUG | CACAAATTCGGATCTACAGGGTA | 2347.8 | 11858.9 | 9813.8 | 286.5 | + | + | + | - |
| hsa-miR-10b | Known | UACCCUGUAGAACCGAAUUUGU | ACAAATTCGGTTCTACAGGGTA | 2438.6 | 18207.9 | 20544.1 | 133.8 | + | + | + | - |
| hsa-miR-122a | Known | UGGAGUGUGACAAUGGUGUUUGU | ACAAACACCATTGTCACACTCCA | 173.4 | 98.6 | 1782.6 | 95.7 | - | - | + | + |

Fig. 13D

| | | | | | | | | | |
|---|---|---|---|---|---|---|---|---|---|
| hsa-miR-124a | Known | UUAAGGCACGCGGUGAAUGCCA | TGGCATTCACCGCGTGCCTTAA | 175.6 | 98.2 | 256.3 | 26730.5 | - | + |
| hsa-miR-125a | Known | UCCCUGAGACCCUUUAACCUGUG | CACAGGTTAAAGGGTCTCAGGGA | 21235.4 | 23195.1 | 12062.1 | 31822.3 | + | + |
| hsa-miR-125b | Known | UCCCUGAGACCCUAACUUGUGA | TCACAAGTTAGGGTCTCAGGGA | 16054.3 | 34697.6 | 13461.6 | 43684.2 | + | + |
| hsa-miR-126 | Known | UCGUACCGUGAGUAAUAAUGC | GCATTATTACTCACGGTACGA | 27211.3 | 24288.8 | 14051.2 | 22681.3 | + | + |
| hsa-miR-126* | Known | CAUUAUUACUUUUGGUACGCG | CGCGTACCAAAAGTAATAATG | 5321.2 | 15422.4 | 3533.5 | 9356.8 | + | + |
| hsa-miR-127 | Known | UCGGAUCCGUCUGAGCUUGGCU | AGCCAAGCTCAGACGGATCCGA | 3036.6 | 749.4 | 1440.9 | 5469.8 | + | + |
| hsa-miR-128a | Known | UCACAGUGAACCGGUCUCUUUU | AAAAGAGACGGTTCACTGTGA | 826.9 | 1934.3 | 1041.4 | 41838.9 | + | + |
| hsa-miR-128b | Known | UCACAGUGAACCGGUCUCUUUC | GAAAGAGACCGGTTCACTGTGA | 787.7 | 1860.2 | 988.3 | 40455.6 | + | + |
| hsa-miR-129 | Known | CUUUUUGCGGUCUGGGCUUGC | GCAAGCCCAGACCGCAAAAAG | 234.8 | 299.4 | 1174.9 | 3155.2 | - | + |
| hsa-miR-130a | Known | CAGUGCAAUGUUAAAAGGGCAU | ATGCCCTTTAACATTGCACTG | 6032.5 | 9369.9 | 3166.7 | 2590.0 | + | + |
| hsa-miR-130b | Known | CAGUGCAAUGAUGAAAGGGCAU | ATGCCCTTTCATCATTGCACTG | 2374.7 | 1259.6 | 466.4 | 1275.0 | + | + |
| hsa-miR-132 | Known | UAACAGUCUACAGCCAUGGUCG | CGACCATGGCTGTAGACTGTTA | 656.7 | 3487.3 | 2229.7 | 16224.7 | + | + |
| hsa-miR-133a | Known | UUGGUCCCCUUCAACCAGCUGU | ACAGCTGGTTGAAGGGGACCAA | 647.2 | 7239.6 | 631.3 | 722.5 | + | + |
| hsa-miR-133b | Known | UUGGUCCCCUUCAACCAGCUA | TAGCTGGTTGAAGGGGACCAA | 589.9 | 6965.1 | 527.5 | 571.6 | + | + |
| hsa-miR-134 | Known | UGUGACUGGUUGACCAGAGGG | CCCTCTGGTCAACCAGTCACA | 530.2 | 330.9 | 576.8 | 724.8 | - | + |
| hsa-miR-135a | Known | UAUGGCUUUUUAUUCCUAUGUGA | TCACATAGGAATAAAAAGCCATA | 233.8 | 7784.2 | 3262.4 | 3207.5 | + | + |
| hsa-miR-135b | Known | UAUGGCUUUUCAUUCCUAUGUG | CACATAGGAATGAAAAGCCATA | 789.4 | 236.1 | 1887.6 | 89.1 | - | + |
| hsa-miR-136 | Known | ACUCCAUUUGUUUUGAUGAUGGA | TCCATCATCAAAACAAATGGAGT | 496.4 | 67.5 | 207.8 | 64.4 | + | + |
| hsa-miR-137 | Known | UAUUGCUUAAGAAUACGCGUAG | CTACGCGTATTCTTAAGCAATA | 806.6 | 158.4 | 294.3 | 12310.2 | - | + |
| hsa-miR-138 | Known | AGCUGGUGUUGUGAAUC | GATTCACAAACACCAGCT | 313.2 | 80.7 | 217.2 | 5785.1 | - | + |
| hsa-miR-139 | Known | UCUACAGUGCACGUGUCU | AGACACGTGCACTGTAGA | 888.5 | 1522.9 | 1423.8 | 18246.5 | + | + |
| hsa-miR-140 | Known | AGUGGUUUUACCCUAUGGUAG | CTACCATAGGGTAAAACCACT | 397.8 | 479.9 | 452.3 | 833.3 | + | + |
| hsa-miR-141 | Known | UAACACUGUCUGGUAAAGAUGG | CCATCTTTACCAGACAGTGTTA | 3474.9 | 3655.8 | 711.7 | 46.7 | + | + |
| hsa-miR-142-3p | Known | UGUAGUGUUUCCUACUUUAUGGA | TCCATAAAGTAGGAAACACTACA | 550.4 | 543.5 | 289.4 | 235.1 | + | + |
| hsa-miR-142-5p | Known | CAUAAAGUAGAAAGCACUAC | GTAGTGCTTTCTACTTTATG | 906.3 | 1613.9 | 314.0 | 285.2 | + | + |
| hsa-miR-143 | Known | UGAGAUGAAGCACUGUAGCUCA | TGAGCTACAGTGCTTCATCTCA | 8275.1 | 59357.4 | 18362.7 | 8761.3 | + | + |
| hsa-miR-144 | Known | UACAGUAUAGAUGAUGUACUAG | CTAGTACATCATCTATACTGTA | 983.3 | 245.2 | 261.8 | 107.7 | + | + |
| hsa-miR-145 | Known | GUCCAGUUUUCCCAGGAAUCCCUU | AAGGGATTCCTGGGAAAACTGGAC | 9574.3 | 58631.2 | 25808.5 | 8709.1 | + | + |
| hsa-miR-146a | Known | UGAGAACUGAAUUCCAUGGGUU | AACCCATGGAATTCAGTTCTCA | 2259.7 | 7328.4 | 3399.1 | 4540.8 | + | + |
| hsa-miR-146b | Known | UGAGAACUGAAUUCCAUAGGCU | AGCCTATGGAATTCAGTTCTCA | 2367.6 | 9479.1 | 4914.7 | 8467.2 | + | + |
| hsa-miR-147 | Known | GUGUGUGGAAAUGCUUCUGC | GCAGAAGCATTTCCACACAC | 179.1 | 64.7 | 195.5 | 44.4 | - | + |
| hsa-miR-148a | Known | UCAGUGCACUACAGAACUUUGU | ACAAAGTTCTGTAGTGCACTGA | 2137.8 | 11110.5 | 5902.3 | 1159.4 | + | + |
| hsa-miR-148b | Known | UCAGUGCAUCACAGAACUUUGU | ACAAAGTTCTGTGATGCACTGA | 3853.8 | 4725.0 | 1688.0 | 4054.0 | + | + |
| hsa-miR-149 | Known | UCUGGCUCCGUGUCUUCACUCC | GGAGTGAAGACACGGAGCCAGA | 2694.0 | 915.9 | 601.5 | 8095.5 | + | + |
| hsa-miR-150 | Known | UCUCCCAACCCUUGUACCAGUG | CACTGGTACAAGGGTTGGGAGA | 901.2 | 4383.8 | 1760.9 | 4118.5 | + | + |
| hsa-miR-151 | Known | ACUAGACUGAAGCUCCUUGAGG | CCTCAAGGAGCTTCAGTTCAGT | 1765.7 | 3200.9 | 1856.4 | 4695.9 | + | + |
| hsa-miR-152 | Known | UCAGUGCAUGACAGAACUUGG | CCAAGTTCTGTCATGCACTGA | 3653.2 | 11111.1 | 5839.3 | 4034.4 | + | + |
| hsa-miR-153 | Known | UUGCAUAGUCACAAAAGUGA | TCACTTTTGTGACTATGCAA | 160.2 | 59.1 | 238.8 | 922.0 | - | + |
| hsa-miR-154 | Known | UAGGUUAUCCGUGUUGCCUUCG | CGAAGGCAACACGGATAACCTA | 1893.8 | 383.1 | 501.4 | 1156.2 | + | + |
| hsa-miR-154* | Known | AAUCAUACAGGUGUGAUCUAUU | AATAGGTCAACGCTTGTATGATT | 1621.3 | 135.9 | 268.0 | 1522.4 | - | + |
| hsa-miR-155 | Known | UUAAUGCUAAUCGUGAUAGGGG | CCCCTATCACGATTAGCATTAA | 936.7 | 3319.4 | 3483.2 | 1895.8 | + | + |
| hsa-miR-15a | Known | UAGCAGCACAUAAUGGUUUGUG | CACAAACCATTATGTGCTGCTA | 7801.5 | 15807.0 | 6460.2 | 15482.6 | + | + |
| hsa-miR-15b | Known | UAGCAGCACAUCAUGGUUUACA | TGTAAACCATGATGTGCTGCTA | 12465.4 | 10319.9 | 13917.2 | 8670.8 | + | + |
| hsa-miR-16 | Known | UAGCAGCACGUAAAUAUUGGCG | CGCCAATATTTACGTGCTGCTA | 22202.1 | 24957.2 | 19133.3 | 26193.0 | + | + |
| hsa-miR-17-3p | Known | ACUGCAGUGAAGGCACUUGU | ACAAGTGCCTTCACTGCAGT | 309.5 | 197.6 | 387.9 | 140.6 | - | + |
| hsa-miR-17-5p | Known | CAAAGUGCUUACAGUGCAGGUAGU | ACTACCTGCACTGTAAGCACTTTG | 9966.4 | 11709.3 | 10499.1 | 9551.1 | + | + |
| hsa-miR-181a | Known | AACAUUCAACGCUGUCGGUGAGU | ACTCACCGACAGCGTTGAATGTT | 13715.6 | 3428.3 | 3055.2 | 26072.5 | + | + |
| hsa-miR-181b | Known | AACAUUCAUUGCUGUCGGUGGGU | CCCACCGACAGCAATGAATGTT | 4204.6 | 2288.3 | 1986.2 | 23560.1 | + | + |
| hsa-miR-181c | Known | AACAUUCAACCUGUCGGUGAGU | ACTCACCGACAGGTTGAATGTT | 8463.7 | 1519.9 | 1780.3 | 15009.9 | + | + |
| hsa-miR-181d | Known | AACAUUCAUUGUUGUCGGUGGGUU | AACCCACCGACAACAATGAATGTT | 3157.8 | 1692.3 | 1591.2 | 20627.5 | + | + |
| hsa-miR-182 | Known | UUUGGCAAUGGUAGAACUCACA | TGTGAGTTCTACCATTGCCAAA | 943.9 | 2963.3 | 1733.1 | 192.6 | + | - |

Fig. 13E

| | | | | | | | | |
|---|---|---|---|---|---|---|---|---|
| hsa-miR-182* | Known | UGGUUCUAGACUUGCCAACUA | TAGTTGGCAAGTCTAGAACCA | 169.2 | 56.6 | 201.8 | 38.3 | - | - | - |
| hsa-miR-183 | Known | UAUGGCACUGGUAGAAUUCACUG | CAGTGAATTCTACCAGTGCCATA | 483.1 | 1145.8 | 777.8 | 98.5 | + | + | + |
| hsa-miR-184 | Known | UGGACGGAGAACUGAUAAGGGU | ACCCTTATCAGTTCTCCGTCCA | 829.5 | 158.8 | 622.8 | 427.0 | - | + | + |
| hsa-miR-185 | Known | UGGAGAGAAAGGCAGUUC | GAACTGCCTTTCTCTCCA | 5395.5 | 2124.4 | 1437.9 | 7983.3 | + | + | + |
| hsa-miR-186 | Known | CAAAGAAUUCUCCUUUUGGGCUU | AAGCCCAAAAGGAGAATTCTTTG | 1952.8 | 3553.4 | 1902.1 | 3088.4 | + | + | + |
| hsa-miR-187 | Known | UCGUGUCUUGUGUUGCAGCCG | CGGCTGCAACACAAGACACGA | 184.4 | 2057.6 | 1914.6 | 353.7 | - | + | + |
| hsa-miR-188 | Known | CAUCCCUUGCAUGGUGGAGGGU | ACCCTCCACCATGCAAGGGATG | 591.5 | 576.7 | 1576.2 | 590.5 | + | + | + |
| hsa-miR-189 | Known | GUGCCUACUGAGCUGAUAUCAGU | ACTGATATCAGCTCAGTAGGCAC | 587.3 | 602.9 | 324.5 | 400.6 | + | + | + |
| hsa-miR-18a | Known | UAAGGUGCAUCUAGUGCAGAUA | TATCTGCACTAGATGCACCTTA | 311.3 | 141.0 | 399.4 | 206.2 | + | + | + |
| hsa-miR-18b | Known | UAAGGUGCAUCUAGUGCAGUUA | TAACTGCACTAGATGCACCTTA | 306.5 | 121.0 | 359.8 | 184.4 | + | - | - |
| hsa-miR-190 | Known | UGAUAUGUUUGAUAUAUUAGGU | ACCTAATATATCAAACATATCA | 158.7 | 69.4 | 198.3 | 191.6 | - | - | - |
| hsa-miR-191 | Known | CAACGGAAUCCCAAAAGCAGCU | AGCTGCTTTTGGGATTCCGTTG | 18043.9 | 12739.0 | 10770.3 | 20273.3 | + | + | + |
| hsa-miR-191* | Known | GCUGCGCUUGGAUUUCGUCCCC | GGGGACGAAATCCAAGCGCAGC | 229.8 | 229.3 | 799.0 | 307.3 | - | + | + |
| hsa-miR-192 | Known | CUGACCUAUGAAUUGACAGCC | GGCTGTCAATTCATAGGTCAG | 1397.5 | 1342.6 | 2690.6 | 1759.5 | + | + | + |
| hsa-miR-193a | Known | AACUGGCCUACAAAGUCCCAG | CTGGGACTTTGTAGGCCAGTT | 1004.3 | 410.0 | 284.5 | 73.4 | + | + | + |
| hsa-miR-193b | Known | AACUGGCCCUCAAAGUCCCGCUUU | AAAGCGGGACTTTGAGGGCCAGTT | 2413.0 | 757.6 | 594.5 | 261.8 | + | + | + |
| hsa-miR-194 | Known | UGUAACAGCAACUCCAUGUGGA | TCCACATGGAGTTGCTGTTACA | 1224.2 | 617.3 | 1383.6 | 1274.4 | + | + | + |
| hsa-miR-195 | Known | UAGCAGCACAGAAAUAUUGGC | GCCAATATTTCTGTGCTGCTA | 4634.2 | 32104.6 | 18202.2 | 13713.5 | + | + | + |
| hsa-miR-196a | Known | UAGGUAGUUUCAUGUUGUUGG | CCAACAACATGAAACTACCTA | 645.8 | 424.2 | 1695.9 | 44.0 | + | + | + |
| hsa-miR-196b | Known | UAGGUAGUUUCCUGUUGUUGG | CCAACAACAGGAAACTACCTA | 437.1 | 794.8 | 324.1 | 37.2 | + | + | + |
| hsa-miR-197 | Known | UUCACCACCUUCUCCACCCAGC | GCTGGGTGGAGAAGGTGGTGAA | 208.8 | 123.4 | 362.4 | 727.1 | + | + | + |
| hsa-miR-198 | Known | GGUCCAGAGGGGAGAUAGG | CCTATCTCCCCTCTGGACC | 234.8 | 555.8 | 742.1 | 92.7 | - | - | - |
| hsa-miR-199a | Known | CCCAGUGUUCAGACUACCUGUUC | GAACAGGTAGTCTGAACACTGGG | 8741.0 | 9010.5 | 5292.4 | 395.8 | + | + | + |
| hsa-miR-199a* | Known | UACAGUAGUCUGCACAUUGGUU | AACCAATGTGCAGACTACTGTA | 10970.5 | 31506.2 | 19451.2 | 2004.9 | + | + | + |
| hsa-miR-199b | Known | CCCAGUGUUUAGACUAUCUGUUC | GAACAGATAGTCTAAACACTGGG | 4672.9 | 6177.4 | 2010.2 | 157.5 | + | + | + |
| hsa-miR-19a | Known | UGUGCAAAUCUAUGCAAAACUGA | TCAGTTTTGCATAGATTTGCACA | 4782.6 | 6613.6 | 4423.5 | 2927.5 | + | + | + |
| hsa-miR-19b | Known | UGUGCAAAUCCAUGCAAAACUGA | TCAGTTTTGCATGGATTTGCACA | 7875.5 | 10711.2 | 8885.8 | 6718.0 | + | + | + |
| hsa-miR-200a | Known | UAACACUGUCUGGUAACGAUGU | ACATCGTTACCAGACAGTGTTA | 1280.0 | 5416.5 | 1664.8 | 122.7 | + | + | + |
| hsa-miR-200a* | Known | CAUCUUACCGGACAGUGCUGGA | TCCAGCACTGTCCGGTAAGATG | 171.9 | 98.9 | 223.4 | 42.8 | - | - | - |
| hsa-miR-200b | Known | UAAUACUGCCUGGUAAUGAUGAC | GTCATCATTACCAGGCAGTATTA | 10348.6 | 18180.2 | 5891.1 | 481.1 | + | + | + |
| hsa-miR-200c | Known | UAAUACUGCCGGGUAAUGAUGG | CCATCATTACCCGGCAGTATTA | 16793.6 | 16532.9 | 6165.3 | 138.0 | + | + | + |
| hsa-miR-202 | Known | AGAGGUAUAGGGCAUGGGAAAA | TTTTCCCATGCCCTATACCTCT | 175.8 | 195.4 | 147364 | 61.2 | - | - | - |
| hsa-miR-202* | Known | UUUCCUAUGCAUAUACUUCUUU | AAAGAAGTATATGCATAGGAAA | 165.9 | 57.5 | 29548.4 | 49.6 | - | - | - |
| hsa-miR-203 | Known | GUGAAAUGUUUAGGACCACUAG | CTAGTGGTCCTAAACATTTCAC | 2365.5 | 3424.5 | 1026.0 | 1729.7 | + | + | + |
| hsa-miR-204 | Known | UUCCCUUUGUCAUCCUAUGCCU | AGGCATAGGATGACAAAGGGAA | 776.9 | 2928.1 | 6855.4 | 9561.3 | + | + | + |
| hsa-miR-205 | Known | UCCUUCAUUCCACCGGAGUCUG | CAGACTCCGGTGGAATGAAGGA | 3290.2 | 10544.1 | 1957.3 | 46.8 | + | + | + |
| hsa-miR-206 | Known | UGGAAUGUAAGGAAGUGUGUGG | CCACACTTCCTTACATTCCA | 566.2 | 7890.6 | 889.6 | 63.2 | + | + | + |
| hsa-miR-208 | Known | AUAAGACGAGCAAAAAGCUUGU | ACAAGCTTTTTGCTCGTCTTAT | 160.7 | 69.6 | 191.5 | 38.2 | - | - | - |
| hsa-miR-20a | Known | UAAAGUGCUUAUAGUGCAGGUAG | CTACCTGCACTATAAGCACTTTA | 9061.9 | 10756.0 | 10057.9 | 7396.6 | + | + | + |
| hsa-miR-20b | Known | CAAAGUGCUCAUAGUGCAGGUAG | CTACCTGCACTATGAGCACTTTG | 9078.1 | 10513.9 | 9680.2 | 6960.6 | + | + | + |
| hsa-miR-21 | Known | UAGCUUAUCAGACUGAUGUUGA | TCAACATCAGTCTGATAAGCTA | 23153.7 | 38543.3 | 245018 | 10841.8 | + | + | + |
| hsa-miR-210 | Known | CUGUGCGUGUGACAGCGGCUGA | TCAGCCGCTGTCACACGCACAG | 2438.1 | 744.5 | 2457.0 | 399.6 | + | + | + |
| hsa-miR-211 | Known | UUCCCUUUGUCAUCCUUCGCCU | AGGCGAAGGATGACAAAGGGAA | 191.2 | 100.9 | 247.2 | 129.9 | - | + | + |
| hsa-miR-212 | Known | UAACAGUCUCCAGUCACGGCC | GGCCGTGACTGGAGACTGTTA | 201.5 | 253.4 | 334.1 | 1274.2 | - | - | + |
| hsa-miR-213 | Known | ACCAUCGACCGUUGAUUGUACC | GGTACAATCAACGGTCGATGGT | 495.9 | 135.8 | 299.9 | 962.5 | + | + | + |
| hsa-miR-214 | Known | ACAGCAGGCACAGACAGGCAG | CTGCCTGTCTGTGCCTGCTGT | 7258.4 | 17673.8 | 18880.2 | 649.9 | + | + | + |
| hsa-miR-215 | Known | AUGACCUAUGAAUUGACAGAC | GTCTGTCAATTCATAGGTCAT | 799.4 | 659.6 | 11195.6 | 455.1 | + | + | + |
| hsa-miR-216 | Known | UAAUCUCAGCUGGCAACUGUG | CACAGTTGCCAGCTGAGATTA | 192.7 | 98.4 | 222.6 | 47.6 | - | - | - |
| hsa-miR-217 | Known | UACUGCAUCAGGAACUGAUUGGAU | ATCCAATCAGTTCCTGATGCAGTA | 181.3 | 77.0 | 220.1 | 49.8 | - | - | - |
| hsa-miR-218 | Known | UUGUGCUUGAUCUAACCAUGU | ACATGGTTAGATCAAGCACAA | 2794.7 | 9493.0 | 1580.1 | 13922.8 | + | + | + |
| hsa-miR-219 | Known | UGAUUGUCCAAACGCAAUUCU | AGAATTGCGTTTGGACAATCA | 191.6 | 81.2 | 204.7 | 1589.2 | + | + | + |

Fig. 13F

| | | | | | | | | | |
|---|---|---|---|---|---|---|---|---|---|
| hsa-miR-22 | Known | AAGCUGCCAGUUGAAGAACUGU | ACAGTTCTTCAACTGGCAGCTT | 8846.1 | 9237.0 | 4235.5 | 5286.5 | + | + | + | + |
| hsa-miR-220 | Known | CCACACCGUAUCUGACACUUU | AAAGTGTCAGATACGGTGTGG | 172.3 | 59.4 | 194.5 | 35.0 | - | - | - | - |
| hsa-miR-221 | Known | AGCUACAUUGUCUGCUGGGUUUC | GAAACCCAGCAGACAATGTAGCT | 15379.5 | 20727.0 | 3721.5 | 12968.5 | + | + | + | + |
| hsa-miR-222 | Known | AGCUACAUCUGGCUACUGGGUCUC | GAGACCCAGTAGCCAGATGTAGCT | 8513.6 | 15001.0 | 2770.4 | 9131.5 | + | + | + | + |
| hsa-miR-223 | Known | UGUCAGUUUGUCAAAUACCCC | GGGGTATTTGACAAACTGACA | 8955.0 | 3853.1 | 2169.5 | 4778.6 | + | + | + | + |
| hsa-miR-224 | Known | CAAGUCACUAGUGGUUCCGUUUA | TAAACGGAACCACTAGTGACTTG | 14511.7 | 1958.8 | 2821.5 | 173.0 | + | + | + | + |
| hsa-miR-23a | Known | AUCACAUUGCCAGGGAUUUCC | GGAATCCCTGGCAATGTGAT | 25334.2 | 31745.6 | 16595.6 | 18706.2 | + | + | + | + |
| hsa-miR-23b | Known | AUCACAUUGCCAGGGAUUACC | GGTAATCCCTGGCAATGTGAT | 23062.8 | 35585.4 | 16259.2 | 22966.9 | + | + | + | + |
| hsa-miR-24 | Known | UGGCUCAGUUCAGCAGGAACAG | CTGTTCCTGCTGAACTGAGCCA | 27645.3 | 23525.4 | 9334.4 | 13711.7 | + | + | + | + |
| hsa-miR-25 | Known | CAUUGCACUUGUCUCGGUCUGA | TCAGACCGAGACAAGTGCAATG | 8624.8 | 8119.4 | 8317.9 | 7812.2 | + | + | + | + |
| hsa-miR-26a | Known | UUCAAGUAAUCCAGGAUAGGC | GCCTATCCTGGATTACTTGAA | 21800.0 | 53243.1 | 22237.5 | 35197.8 | + | + | + | + |
| hsa-miR-26b | Known | UUCAAGUAAUUCAGGAUAGGUU | AACCTATCCTGAATTACTTGAA | 26604.3 | 37793.9 | 18979.5 | 21136.9 | + | + | + | + |
| hsa-miR-27a | Known | UUCACAGUGGCUAAGUUCCGC | GCGGAACTTAGCCACTGTGAA | 25684.4 | 31627.2 | 11288.8 | 17621.2 | + | + | + | + |
| hsa-miR-27b | Known | UUCACAGUGGCUAAGUUCUGC | GCAGAACTTAGCCACTGTGAA | 20245.0 | 36613.9 | 11532.7 | 19520.3 | + | + | + | + |
| hsa-miR-28 | Known | AAGGAGCUCACAGUCUAUUGAG | CTCAATAGACTGTGAGCTCCTT | 6043.8 | 11700.1 | 4871.4 | 12477.3 | + | + | + | + |
| hsa-miR-296 | Known | AGGGCCCCCCUCAACUUUAG | ACAGAATTGAGGGGGGCCCT | 180.2 | 78.9 | 233.9 | 58.3 | - | - | - | - |
| hsa-miR-299-3p | Known | UAUGUGGGAUGGUAAACCGCUU | AAGCGGTTTACCATCCCACATA | 239.7 | 69.6 | 215.6 | 77.6 | - | - | - | - |
| hsa-miR-299-5p | Known | UGGUUUACCGUCCCACAUACAU | ATGTATGTGGGACGGTAAACCA | 1728.1 | 323.9 | 623.9 | 2368.5 | + | + | + | + |
| hsa-miR-29a | Known | UAGCACCAUCUGAAAUCGGUU | AACCGATTTCAGATGGTGCTA | 19284.4 | 30890.0 | 12407.1 | 24624.1 | + | + | + | + |
| hsa-miR-29b | Known | UAGCACCAUUUGAAAUCAGUGUU | AACACTGATTTCAAATGGTGCTA | 8617.6 | 21685.1 | 5828.2 | 19542.7 | + | + | + | + |
| hsa-miR-29c | Known | UAGCACCAUUUGAAAUCGGU | ACCGATTTCAAATGGTGCTA | 6936.5 | 22429.2 | 7942.3 | 13913.6 | + | + | + | + |
| hsa-miR-301 | Known | CAGUGCAAUAGUAUUGUCAAAGC | GCTTTGACAATACTATTGCACTG | 366.1 | 182.2 | 277.1 | 394.1 | + | + | + | + |
| hsa-miR-302a | Known | UAAGUGCUUCCAUGUUUUGGUGA | TCACCAAAACATGGAAGCACTTA | 173.1 | 52.3 | 187.3 | 40.4 | - | - | - | - |
| hsa-miR-302a* | Known | UAAACGUGGAUGUACUUGCUUU | AAAGCAAGTACATCCACGTTTA | 160.7 | 47.0 | 189.2 | 42.0 | - | - | - | - |
| hsa-miR-302b | Known | UAAGUGCUUCCAUGUUUUAGUAG | CTACTAAAACATGGAAGCACTTA | 163.3 | 49.8 | 194.2 | 41.9 | - | - | - | - |
| hsa-miR-302b* | Known | ACUUAACAUGGAAGUGCUUUCU | AGAAAGCACTTCCATGTTAAGT | 176.4 | 57.5 | 197.5 | 38.1 | - | - | - | - |
| hsa-miR-302c | Known | UAAGUGCUUCCAUGUUUCAGUGG | CCACTGAAACATGGAAGCACTTA | 172.6 | 58.9 | 194.4 | 38.7 | - | - | - | - |
| hsa-miR-302c* | Known | UUUAACAUGGGGGUACCUGCUG | CAGCAGGTACCCCCATGTTAAA | 181.8 | 84.8 | 230.0 | 55.4 | - | - | - | - |
| hsa-miR-302d | Known | UAAGUGCUUCCAUGUUUGAGUGU | ACACTCAAACATGGAAGCACTTA | 176.6 | 64.0 | 191.4 | 47.1 | - | - | - | - |
| hsa-miR-30a-3p | Known | CUUUCAGUCGGAUGUUUGCAGC | GCTGCAAACATCCGACTGAAAG | 3553.5 | 2918.0 | 1673.9 | 4891.0 | + | + | + | + |
| hsa-miR-30a-5p | Known | UGUAAACAUCCUCGACUGGAAG | CTTCCAGTCGAGGATGTTTACA | 24090.6 | 19719.2 | 7781.7 | 17862.9 | + | + | + | + |
| hsa-miR-30b | Known | UGUAAACAUCCUACACUCAGCU | AGCTGAGTGTAGGATGTTTACA | 33536.5 | 21371.3 | 10873.7 | 29584.7 | + | + | + | + |
| hsa-miR-30c | Known | UGUAAACAUCCUACACUCUCAGC | GCTGAGAGTGTAGGATGTTTACA | 30908.2 | 22761.4 | 10744.4 | 30505.8 | + | + | + | + |
| hsa-miR-30d | Known | UGUAAACAUCCCCGACUGGAAG | CTTCCAGTCGGGGATGTTTACA | 23149.2 | 17333.2 | 6932.6 | 15822.6 | + | + | + | + |
| hsa-miR-30e-3p | Known | CUUUCAGUCGGAUGUUUACAGC | GCTGTAAACATCCGACTGAAAG | 2479.9 | 4029.0 | 2674.7 | 5849.4 | + | + | + | + |
| hsa-miR-30e-5p | Known | UGUAAACAUCCUUGACUGGAAG | CTTCCAGTCAAGGATGTTTACA | 5206.3 | 7052.8 | 2459.7 | 5740.4 | + | + | + | + |
| hsa-miR-31 | Known | GGCAAGAUGCUGGCAUAGCUG | CAGCTATGCCAGCATCTTGCC | 768.5 | 1412.0 | 1639.1 | 1438.8 | + | + | + | + |
| hsa-miR-32 | Known | UAUUGCACAUUACUAAGUUGC | GCAACTTAGTAATGTGCAATA | 197.8 | 73.7 | 197.5 | 50.6 | - | - | - | - |
| hsa-miR-320 | Known | AAAAGCUGGGUUGAGAGGGCGAA | TTCGCCCTCTCAACCCAGCTTT | 13086.9 | 7765.4 | 3679.2 | 7492.6 | + | + | + | + |
| hsa-miR-323 | Known | GCACAUUACACGGUCGACCUCU | AGAGGTCGACCGTGTAATGTGC | 601.6 | 139.4 | 317.9 | 4901.5 | + | + | + | + |
| hsa-miR-324-3p | Known | CCACUGCCCCAGGUGCUGCUG | CCAGCAGCACCTGGGGCAGTGG | 752.4 | 866.8 | 505.7 | 795.7 | + | + | + | + |
| hsa-miR-324-5p | Known | CGCAUCCCCUAGGGCAUUGGUGU | ACACCAATGCCCTAGGGGATGCG | 1286.5 | 1042.8 | 542.1 | 1784.4 | + | + | + | + |
| hsa-miR-325 | Known | CCUAGUAGGUGUCCAGUAAGUGU | ACACTTACTGGACACCTACTAGG | 159.5 | 45.9 | 185.6 | 33.8 | - | - | - | - |
| hsa-miR-326 | Known | CCUCUGGGCCCUUCCUCCAG | CTGGAGGAAGGGCCCAGAGG | 167.6 | 66.3 | 204.9 | 59.2 | - | - | - | - |
| hsa-miR-328 | Known | CUGGCCCUCUCUGCCCUUCCGU | ACGGAAGGGCAGAGAGGGCCAG | 190.3 | 115.8 | 263.8 | 702.2 | + | + | + | + |
| hsa-miR-329 | Known | ACACACCUGGUUAACCUCU | AGAGGTTAACCAGGTGTGT | 1751.0 | 300.4 | 385.7 | 5042.4 | + | + | + | + |
| hsa-miR-33 | Known | GUGCAUUGUAGUUGCAUUG | CAATGCAACTACAATGCAC | 158.0 | 47.1 | 186.5 | 41.0 | - | - | - | - |
| hsa-miR-330 | Known | GCAAAGCACACGGCCUGCAGAGA | TCTCTGCAGGCCGTGTGCTTTGC | 453.5 | 199.7 | 215.0 | 1766.6 | + | + | + | + |
| hsa-miR-331 | Known | GCCCCUGGGCCUAUCCUAGAA | TTCTAGGATAGGCCCAGGGGC | 1191.2 | 749.0 | 553.5 | 1536.3 | + | + | + | + |
| hsa-miR-335 | Known | UCAAGAGCAAUAACGAAAAAUGU | ACATTTTCGTTATTGCTCTTGA | 30379.2 | 5638.0 | 6748.1 | 12336.9 | + | + | + | + |
| hsa-miR-337 | Known | UCCAGCUCCUAUAUGAUGCCUUU | AAAGGCATCATATAGGAGCTGGA | 461.6 | 85.4 | 196.2 | 44.5 | - | + | + | + |

Fig. 13G

| | | | | | | | | | |
|---|---|---|---|---|---|---|---|---|---|
| hsa-miR-338 | Known | UCCAGCAUCAGUGAUUUUGUUGA | TCAACAAATCACTGATGCTGGA | 237.7 | 1167.1 | 331.4 | 13934.5 | - | + | + |
| hsa-miR-339 | Known | UCCCUGUCCUCCAGGAGCUCA | TGAGCTCCTGGAGGACAGGGA | 367.1 | 189.1 | 251.2 | 117.4 | + | - | + |
| hsa-miR-340 | Known | UCCGUCUCAGUUACUUUAUAGCC | GGCTATAAAGTAACTGAGACGGA | 307.0 | 279.6 | 319.2 | 3138.6 | - | - | + |
| hsa-miR-342 | Known | UCUCACAGAGAAUCGCACCCGUC | GACGGGTGCGATTTCTGTGTGAGA | 2795.2 | 10088.6 | 2530.3 | 20703.5 | + | + | + |
| hsa-miR-345 | Known | UGCUGACUCCUAGUCCAGGGC | GCCCTGGACTAGGAGTCAGCA | 281.8 | 237.8 | 368.8 | 329.0 | - | + | + |
| hsa-miR-346 | Known | UGUCUGCCCGCAUGCCUGCCUCU | AGAGGCAGGCATGCGGGCAGACA | 192.7 | 93.0 | 226.0 | 1247.7 | - | - | + |
| hsa-miR-34a | Known | UGGCAGUGUCUUAGCUGGUUGU | AACAACCAGCTAAGACACTGCCA | 1075.0 | 2778.3 | 1321.3 | 2486.3 | + | + | + |
| hsa-miR-34b | Known | UAGGCAGUGUCAUUAGCUGAUUG | CAATCAGCTAATGACACTGCCTA | 459.3 | 868.6 | 984.0 | 501.8 | - | + | + |
| hsa-miR-34c | Known | AGGCAGUGUAGUUAGCUGAUUGC | GCAATCAGCTAACTACACTGCCT | 332.9 | 122.3 | 2227.3 | 166.0 | - | + | + |
| hsa-miR-361 | Known | UUAUCAGAAUCUCCAGGGGUAC | GTACCCCTGGAGATTCTGATAA | 5377.8 | 10129.6 | 5367.8 | 13406.4 | + | + | + |
| hsa-miR-362 | Known | AAUCCUUGGAACCUAGGUGUGAGU | ACTCACACCTAGGTTCCAAGGATT | 771.8 | 327.6 | 485.7 | 231.6 | - | + | + |
| hsa-miR-363 | Known | AAUUGCACGGUAUCCAUCUGUA | TACAGATGGATACCGTGCAATT | 1159.5 | 4824.1 | 543.7 | 2479.5 | + | + | + |
| hsa-miR-365 | Known | AUAAUGCCCCUAAAAAUCCUUA | TAAGGATTTTTAGGGGCATTAT | 4313.7 | 5834.6 | 1334.1 | 3323.3 | + | + | + |
| hsa-miR-368 | Known | AAUUGCACUUUAGCAAUGGUGA | TCACCATTGCTAAAGTGCAATT | 166.3 | 57.3 | 186.4 | 35.2 | - | - | + |
| hsa-miR-368 | Known | ACAUAGAGGAAAUUCCACGUUU | AAACGTGGAATTTCCTCTATGT | 15863.7 | 4044.1 | 2766.2 | 3874.9 | + | + | + |
| hsa-miR-369-3p | Known | AAUAAUACAUGGUUGAUCUUU | AAAGATCAACCATGTATTATT | 4141.2 | 242.1 | 203.6 | 468.5 | - | + | + |
| hsa-miR-369-5p | Known | AGAUCGACCGUGUUAUAUUCGC | GCGAATATAACACGGTCGATCT | 1294.4 | 351.8 | 443.3 | 911.4 | + | + | + |
| hsa-miR-370 | Known | GCCUGCUGGGGUGGAACCUGG | CCAGGTTCCACCCCAGCAGGC | 667.0 | 549.3 | 657.6 | 708.9 | + | + | + |
| hsa-miR-371 | Known | GUGCCGCCAUCUUUUGAGUGU | ACACTCAAAAGATGCGGGCAC | 342.1 | 55.6 | 222.5 | 38.4 | - | - | - |
| hsa-miR-372 | Known | AAAGUGCUGCGACAUUUGAGCGU | ACGCTCAAATGTCGCAGCACTTT | 696.1 | 69.5 | 252.8 | 37.9 | - | + | + |
| hsa-miR-373 | Known | GAAGUGCUUCGAUUUUGGGGUGU | ACACCCCAAAATCGAAGCACTTC | 614.8 | 60.8 | 354.6 | 39.0 | - | + | + |
| hsa-miR-373* | Known | ACUCAAAAUGGGGGCGCUUUCC | GGAAAGCGCCCCCATTTTGAGT | 303.0 | 196.1 | 550.2 | 87.2 | - | - | - |
| hsa-miR-374 | Known | UUAUAAUACAACCUGAUAAGUG | CACTTATCAGGTTGTATTATAA | 6736.3 | 10290.6 | 4553.7 | 8032.0 | + | + | + |
| hsa-miR-375 | Known | UUUGUUCGUUCGGCUCGCGUGA | TCACGCGAGCCGAACGAACAAA | 334.0 | 11168.2 | 1338.0 | 387.7 | - | + | + |
| hsa-miR-376a | Known | AUCAUAGAGGAAAAUCCACGU | ACGTGGATTTTCCTCTATGAT | 8744.6 | 2729.5 | 1425.4 | 2326.3 | + | + | + |
| hsa-miR-376b | Known | AUCAUAGAGGAAAAUCCAUGUU | AACATGGATTTTCCTCTATGAT | 1419.1 | 263.8 | 277.2 | 174.3 | + | + | + |
| hsa-miR-377 | Known | AUCACACAAAGGCAACUUUUGU | ACAAAAGTTGCCTTTGTGTGAT | 2375.3 | 313.6 | 360.5 | 363.3 | + | + | + |
| hsa-miR-378 | Known | CUCCUGACUCCAGGUCCUGUGU | ACACAGGACCTGGAGTCAGGAG | 274.7 | 180.4 | 219.3 | 63.0 | - | - | - |
| hsa-miR-379 | Known | UGGUAGACUAUGGAACGUA | TACGTTCCATAGTCTACCA | 2379.2 | 859.1 | 1365.3 | 6402.6 | + | + | + |
| hsa-miR-380-3p | Known | UAUGUAAAUAUGGUCCACAUCUU | AAGATGTGGACCATATTACACA | 556.1 | 111.3 | 295.8 | 1384.8 | - | + | + |
| hsa-miR-380-5p | Known | UGGUUGACCAUAGAACAUGCGC | GCGCATGTTCTATGGTCAACCA | 169.9 | 75.0 | 211.7 | 102.8 | + | + | + |
| hsa-miR-381 | Known | ACUACAAGGGCAAGCUCUCUGU | ACAGAGAGCTTGCCCTTGTATA | 1065.0 | 408.9 | 354.3 | 556.8 | + | + | + |
| hsa-miR-382 | Known | GAAGUUGUUCGUGGUGGAUUCG | CGAATCCACCACGAACAACTTC | 3391.1 | 598.7 | 1189.9 | 4616.0 | + | + | + |
| hsa-miR-383 | Known | AGAUCAAAGGUGAUUGUGGCU | AGCCACAATCACCTTCTGATCT | 164.4 | 107.1 | 240.9 | 1789.9 | - | + | + |
| hsa-miR-384 | Known | AUUCCUAGAAAUUGUUCAUA | TATGAACAATTTCTAGGAAT | 156.7 | 47.5 | 187.0 | 34.1 | - | - | - |
| hsa-miR-409-3p | Known | AGGUUGUCUGGUGAACCCCU | AGGGGTTCACCGAGCAACATT | 1201.8 | 280.0 | 613.8 | 1566.3 | - | + | + |
| hsa-miR-409-5p | Known | AGGUUACCCGAGCAACUUUGCA | TGCAAAGTTGCTCGGGTAACCT | 344.2 | 112.5 | 259.0 | 315.6 | - | + | + |
| hsa-miR-410 | Known | AAUAUAACACAGAUGGCCUGU | ACAGGCCATCTGTGTTATAT | 1562.4 | 146.7 | 264.0 | 1523.2 | + | + | + |
| hsa-miR-412 | Known | ACUUCACCUGGUCCACUAGCCGU | ACGGCTAGTGGACCAGGTGAAGT | 167.4 | 69.4 | 200.0 | 41.7 | - | - | + |
| hsa-miR-422a | Known | CUGGACUUGGAGGUCAGAAGGC | GCCTTCTGACCTCCAAGTCCAG | 1091.7 | 1974.9 | 533.5 | 403.4 | + | + | + |
| hsa-miR-422b | Known | CUGGACUUGGAGUCAGAAGGCC | GGCCTTCTGACTCCAAGTCCAG | 1158.0 | 2390.7 | 617.2 | 523.2 | + | + | + |
| hsa-miR-423 | Known | AGCUCGGUCUGAGGCCCCUCAG | CTGAGGGGCCTCAGACCGAGCT | 2942.3 | 905.6 | 1663.1 | 1096.9 | + | + | + |
| hsa-miR-424 | Known | CAGCAGCAAUUCAUGUUUUGAA | TTCAAAACATGAATTGCTGCTG | 41149.3 | 2840.3 | 19031.2 | 1365.3 | + | + | + |
| hsa-miR-425 | Known | AUCGGGAAUGUCGUGUCCGCCC | GGGCGGACACGACATTCCCGAT | 277.2 | 199.6 | 668.2 | 502.5 | - | - | + |
| hsa-miR-429 | Known | UAAUACUGUCUGGUAAAACCGU | ACGGTTTTACCAGACAGTATTA | 159.7 | 2823.5 | 734.2 | 108.8 | - | + | + |
| hsa-miR-431 | Known | UGUCUUGCAGGCCGUCAUGCA | TGCATGACGGCCTGCAAGACA | 613.9 | 64.1 | 209.8 | 60.3 | - | + | + |
| hsa-miR-432 | Known | UCUUGGAGUAGGUCAUUGGGUGG | CCACCCAATGACCTACTCCAAGA | 3584.2 | 316.3 | 725.2 | 3109.5 | + | + | + |
| hsa-miR-432* | Known | CUGGAUGGCUCCUCCAUGUCU | AGACATGGAGGAGCCATCCAG | 158.4 | 45.6 | 206.1 | 42.9 | - | - | - |
| hsa-miR-433 | Known | AUCAUGAUGGGCUCCUCGGUGU | ACACCGAGGAGCCCATCATGAT | 502.8 | 62.7 | 308.5 | 3374.6 | - | + | + |
| hsa-miR-448 | Known | UUGCAUAUGUAGGAUGUCCCAU | ATGGGACATCCTACATATGCAA | 137.5 | 38.7 | 193.1 | 51.9 | - | + | + |
| hsa-miR-449 | Known | UGGCAGUGUAUUGUUAGCUGGU | ACCAGCTAACAATACACTGCCA | 163.3 | 44.7 | 2987.5 | 46.3 | - | - | + |

Fig. 13H

| | | | | | | | | | |
|---|---|---|---|---|---|---|---|---|---|
| hsa-miR-450 | Known | UUUUGCGAUGUGUUCCUAAUAU | ATATTAGGAACACATCGCAAAA | 5831.7 | 424.5 | 5536.7 | 182.8 | + | + |
| hsa-miR-451 | Known | GGAAACCGUUACCAUUACUGAGU | ACTCAGTAATGGTAACGGTTTCC | 49055.2 | 13188.0 | 16684.6 | 16952.3 | + | + |
| hsa-miR-452 | Known | UGUUUGCAGAGGAAACUGAGAC | GTCTCAGTTTCCTCTGCAAACA | 1087.2 | 939.2 | 423.2 | 109.3 | + | + |
| hsa-miR-452* | Known | UCAGUCUCAUUCUGCAAAGAAG | CTTCTTTGCAGATGAGACTGA | 741.7 | 138.5 | 206.4 | 46.4 | + | + |
| hsa-miR-453 | Known | GAGGUUGUCCGUGGUGAGUUCG | CGAACTCACCACGGACAACCTC | 174.4 | 61.5 | 188.7 | 46.5 | + | - |
| hsa-miR-485-3p | Known | GUCAUACACGGCUCUCCUCUCU | AGAGAGGAGAGCCGTGTATGAC | 341.8 | 88.8 | 267.0 | 848.3 | + | + |
| hsa-miR-485-5p | Known | AGAGGCUGGCCGUGAUGAAUUC | GAATTCATCACGGCCAGCCTCT | 269.1 | 95.8 | 272.2 | 795.1 | + | + |
| hsa-miR-488 | Known | CCCAGAUAAUGGCACUCUCAA | TTGAGAGTGCCATTATCTGGG | 178.3 | 66.8 | 195.2 | 88.8 | + | - |
| hsa-miR-489 | Known | AGUGACAUACAUAUAUACGGCAGC | GCTGCCGTATATGTGATGTCACT | 1257.7 | 320.8 | 484.7 | 121.0 | + | - |
| hsa-miR-490 | Known | CAACCUGGAGGACUCCAUGCUG | CAGCATGGAGTCCTCCAGGTTG | 185.2 | 116.0 | 216.1 | 57.5 | - | - |
| hsa-miR-491 | Known | AGUGGGGAACCCUUCCAUGAGGA | TCCTCATGGAAGGGTTCCCCACT | 215.1 | 125.3 | 232.1 | 441.5 | - | + |
| hsa-miR-492 | Known | AGGACCUGCGGGACGAAGAUUCU | AAGAATCTTGTCCCGCAGGTCCT | 179.3 | 112.1 | 213.8 | 41.1 | - | + |
| hsa-miR-493 | Known | UUGUACAUGGUAGGCUUUCAU | AATGAAAGCCTACCATGTACAA | 9353.6 | 806.8 | 2314.7 | 160.8 | + | + |
| hsa-miR-494 | Known | UGAAACAUACACGGGAAACCUCUU | AAGAGGTTTCCCGTGTATGTTTCA | 10892.7 | 5221.4 | 1471.1 | 2539.9 | + | + |
| hsa-miR-495 | Known | AAACAAACAUGGUGCACUUCUUU | AAAGAAGTGCACCATGTTTGTTT | 5415.0 | 1547.9 | 686.9 | 8930.3 | + | + |
| hsa-miR-496 | Known | AUUACAUGGCCAAUCUC | GAGATTGGCCATGTAAT | 180.8 | 92.3 | 192.7 | 40.9 | - | - |
| hsa-miR-497 | Known | CAGCAGCACACUGUGGUUUGU | ACAAACCACAGTGTGCTGCTG | 1069.7 | 2563.4 | 1414.8 | 1110.1 | + | + |
| hsa-miR-498 | Known | UUUCAAGCCAGGGAGCGUUUUUC | GAAAAACGCCCCTGGCTTGAAA | 7096.0 | 389.3 | 1420.7 | 122.6 | - | + |
| hsa-miR-499 | Known | UUAAGACUUGCAGUGAUGUUUAA | TTAAACATCACTGCAAGTCTTAA | 213.2 | 1895.4 | 605.2 | 1122.4 | - | + |
| hsa-miR-500 | Known | AUGCACCUGGGCAAGGAUUCUG | CAGAATCCTTGCCCAGGTGCAT | 684.8 | 559.1 | 671.7 | 171.4 | + | + |
| hsa-miR-501 | Known | AAUCCUUUGUCCCUGGGUGAGA | TCTCACCCAGGGACAAAGGATT | 297.9 | 186.3 | 398.6 | 83.1 | - | + |
| hsa-miR-502 | Known | AUCCUUGCUAUCUGGGUGCUA | TAGCACCCAGATAGCAAGGAT | 288.5 | 143.6 | 265.0 | 64.6 | - | + |
| hsa-miR-503 | Known | UAGCAGCGGGAACAGUUCUGCAG | CTGCAGAACTGTTCCCGCTGCTA | 4118.8 | 254.6 | 1988.7 | 114.4 | + | + |
| hsa-miR-504 | Known | AGACCCUGGUCUGCACUCUAU | ATAGAGTGCAGACCAGGGTCT | 335.8 | 133.3 | 227.3 | 245.4 | - | + |
| hsa-miR-505 | Known | GUCAACACUUGCUGGUUUCCUC | GAGGAAACCAGCAAGTGTTGAC | 465.0 | 1444.1 | 660.5 | 743.5 | + | + |
| hsa-miR-506 | Known | UAAGGCACCCUUCUGAGUAGA | TCTACTCAGAAGGGTGCCTTA | 167.1 | 68.3 | 6867.7 | 46.6 | - | + |
| hsa-miR-507 | Known | UUUUGCACCUUUUGGAGUGAA | TTCACTCCAAAAGGTGCAAAA | 177.4 | 76.8 | 1085.5 | 37.1 | - | + |
| hsa-miR-508 | Known | UGAUUGUAGCCUUUUGGAGUGA | TCATCTCCAAAAGGCTACAATCA | 192.2 | 64.3 | 17655.4 | 61.4 | - | + |
| hsa-miR-509 | Known | UGAUUGGUAGCGUCUGGGUAGA | TCTACCCAGACGCTACCAATCA | 242.2 | 79.2 | 16214.6 | 58.4 | - | + |
| hsa-miR-510 | Known | UACUCAGGAGAGUGGCAAUCACA | TGTGATTGCCACTCTCCTGAGTA | 195.0 | 126.5 | 3878.3 | 44.3 | - | + |
| hsa-miR-511 | Known | GUGUCUUUUGCUCUGCAGUCA | TGACTGCAGAGCAAAAGACAC | 259.4 | 99.2 | 215.1 | 42.0 | - | + |
| hsa-miR-512-3p | Known | AAGUGCUGUCAUAGCUGAGGUC | GACCTCAGCTATGACAGGCACTC | 13851.9 | 98.0 | 319.6 | 38.9 | + | + |
| hsa-miR-512-5p | Known | CACUCAGCCUUGAGGGCACUUUC | GAAAGTGCCCTCAAGGCTGAGTG | 3798.6 | 100.4 | 207.1 | 38.2 | + | + |
| hsa-miR-513 | Known | UUCACAGGAGGUGUCAUUUAU | ATAAATGACACCTCCCTGTGAA | 209.4 | 413.8 | 16335.2 | 58.2 | - | + |
| hsa-miR-514 | Known | AUUGACACACUUCUGUGAGUAG | CTACTCACAGAAGTGTCAAT | 200.7 | 59.2 | 20386.7 | 55.8 | - | + |
| hsa-miR-515-3p | Known | GAGUGCCUUCUUUUGGAGCGU | ACGCTCCAAAAGAAGGCACTC | 2610.0 | 76.8 | 229.6 | 39.2 | + | + |
| hsa-miR-515-5p | Known | UUCUCCAAAAGAAAGCACUUUCUG | CAGAAAGTGCTTTCTTTTGGAGAA | 31193.3 | 84.3 | 491.4 | 41.3 | + | + |
| hsa-miR-516-3p | Known | UGCUUCCUUUCAGAGGGU | ACCCTCTGAAAGGAAGCA | 210.5 | 70.5 | 193.7 | 39.3 | - | + |
| hsa-miR-516-5p | Known | AUCUGGAGGUAAGAAGCACUUUG | CAGAAGTGCTTCTTACCTCCAGAT | 21668.4 | 95.7 | 325.4 | 45.1 | + | + |
| hsa-miR-516*-5p | Known | CAUCUGGAGGUAAGAAGCACACUG | ACAGTGTGCTTCTTACCTCCAGATG | 24282.0 | 111.2 | 387.5 | 40.9 | + | + |
| hsa-miR-517* | Known | CCUCUAGAUGGAAGCACUGUCU | AGACAGTGCTTCCATCTAGAGG | 2203.6 | 99.9 | 195.1 | 38.2 | - | + |
| hsa-miR-517a | Known | AUCGUGCAUCCUUUUAGAGUGU | AACACTCTAAAAGGATGCACGAT | 59595.0 | 84.9 | 1432.6 | 47.8 | + | + |
| hsa-miR-517b | Known | UCGUGCAUCCCUUUAGAGUGUU | AACACTCTAAAAGGGATGCACGA | 59075.5 | 88.6 | 1323.8 | 42.3 | + | + |
| hsa-miR-517c | Known | AUCGUGCAUCCUUUUAGAGUGU | ACACTCTAAAAGGATGCACGAT | 59698.1 | 81.6 | 1311.2 | 60.6 | + | + |
| hsa-miR-518a | Known | AAAGCGCUUCCCUUUAGAGCUGA | TCCAGGCTCTAAAGGGAAGCGCTTT | 2783.1 | 69.0 | 200.9 | 36.8 | - | + |
| hsa-miR-518a-2* | Known | UCUCAAAGGGAAGCCCUUU | AAAGGGCTTCCCTTTGAGA | 1779.6 | 75.5 | 199.1 | 38.5 | - | + |
| hsa-miR-518b | Known | CAAAGCGCUCCCCUUUAGAGGU | ACCTCTAAAGGGGAGCGCTTTG | 4948.1 | 65.4 | 205.5 | 36.0 | - | + |
| hsa-miR-518c | Known | CAAAGCGCUUCUCUUUAGAGUG | CACTCTAAAGAGAAGCGCTTTG | 9396.1 | 70.2 | 198.2 | 36.3 | - | + |
| hsa-miR-518c* | Known | UCUCUGGAGGGAAGCACUUUCUG | CAGAAAGTGCTTCCCTCCAGAGA | 14578.6 | 153.6 | 394.6 | 50.5 | + | + |
| hsa-miR-518d | Known | CAAAGCGCUUCCCUUUGGAGC | GCTCCAAAGGGAAGCGCTTTG | 459.0 | 58.4 | 194.7 | 39.0 | - | + |
| hsa-miR-518e | Known | AAAGCGCUUCCCUUCAGAGUGU | ACACTCTGAAGGGAAGCGCTTT | 13085.0 | 74.4 | 309.1 | 39.6 | - | + |

Fig. 13I

| | | | | | | | | |
|---|---|---|---|---|---|---|---|---|
| hsa-miR-518f | Known | AAAGCGCUUCUCUUUAGAGGA | TCCTCTAAAGAGAAGCGCTTT | 5399.8 | 59.8 | 195.8 | 36.5 | + | - | - | + |
| hsa-miR-518f* | Known | CUCUAGAGGGAAGCACUUUCU | AGAGAAAGTGCTTCCCTCTAGAG | 14332.9 | 84.2 | 417.1 | 42.9 | + | + | - | + |
| hsa-miR-519a | Known | AAAGUGCAUCCUUUUAGAGUGUUAC | GTAACACTCTAAAAGGATGCACTTT | 37906.3 | 79.4 | 570.3 | 58.2 | + | - | - | + |
| hsa-miR-519b | Known | AAAGUGCAUCCUUUUAGAGGAUU | AACCTCTAAAAGGATGCACTTT | 25612.5 | 81.8 | 427.5 | 41.2 | + | - | - | + |
| hsa-miR-519c | Known | AAAGUGCAUCUUUUAGAGGAU | ATCCTCTAAAAGATGCACTTT | 5986.0 | 59.6 | 299.4 | 36.0 | + | - | - | + |
| hsa-miR-519d | Known | CAAAGUGCCUCCCUUUAGAGUGU | ACACTCTAAAGGGAGGCACTTTG | 25904.5 | 78.9 | 442.6 | 38.3 | + | + | - | + |
| hsa-miR-519e | Known | AAAGUGCCUCCUUUUAGAGUGU | ACACTCTAAAAGGAGGCACTTT | 24461.8 | 92.4 | 273.2 | 40.5 | + | + | - | + |
| hsa-miR-519e* | Known | UUCUCCAAAGGGAGCACUUUC | GAAAGTGCTCCCTTTTGGAGAA | 2465.3 | 98.7 | 206.7 | 44.2 | + | - | - | + |
| hsa-miR-520a | Known | AAAGUGCUUCCCUUUGGACUGU | ACAGTCCAAAGGGAAGCACTTT | 775.2 | 60.1 | 219.3 | 39.3 | + | - | - | + |
| hsa-miR-520a* | Known | CUCCAGAGGGAAGUACUUUCU | AGAAAGTACTTCCCTCTGGAG | 7494.1 | 81.0 | 280.0 | 38.2 | + | - | - | + |
| hsa-miR-520b | Known | AAAGUGCUUCCUUUUAGAGGG | CCCTCTAAAAGGAAGCACTTT | 737.1 | 67.8 | 378.2 | 38.3 | + | - | - | + |
| hsa-miR-520c | Known | AAAGUGCUUCCUUUUAGAGGGUU | AACCCTCTAAAAGGAAGCACTTT | 831.3 | 62.3 | 380.7 | 33.5 | + | - | - | + |
| hsa-miR-520d | Known | AAAGUGCUUCUCUUUGGUGGGU | ACCCCACCAAAGAGAAGCACTTT | 6709.7 | 81.3 | 233.8 | 34.9 | + | - | - | + |
| hsa-miR-520d* | Known | UCUACAAAGGGAAGCCCUUUCUG | CAGAAAGGGCTTCCCTTTGTAGA | 6665.7 | 77.7 | 200.4 | 35.9 | + | - | - | + |
| hsa-miR-520e | Known | AAAGUGCUUCCUUUUAGAGGG | CCCTCAAAAGGAAGCACTTT | 351.2 | 83.0 | 229.6 | 39.2 | + | - | - | + |
| hsa-miR-520f | Known | AAGUGCUUCCUUUUAGAGGGUU | AACCCTCTAAAAGGAAGCACTTT | 779.8 | 60.2 | 380.8 | 33.2 | + | - | - | + |
| hsa-miR-520g | Known | ACAAAGUGCUUCCCUUUAGAGUGU | ACACTCTAAAGGGAAGCACTTTGT | 23414.6 | 82.0 | 540.5 | 34.4 | + | - | - | + |
| hsa-miR-520h | Known | ACAAAGUGCUUCCCUUUAGAGU | ACTCTAAAGGGAAGCACTTTGT | 14853.1 | 77.3 | 457.1 | 33.0 | + | - | - | + |
| hsa-miR-521 | Known | AACGCACUUCCCUUUAGAGUGU | ACACTCTAAAGGGAAGTGCGTT | 4533.5 | 51.1 | 183.4 | 34.5 | + | - | - | + |
| hsa-miR-522 | Known | AAAAGUGUUCCUUUUAGAGUGUU | AACACTCTAAAGGGAACCATTT | 23970.7 | 76.1 | 392.5 | 73.0 | + | - | - | + |
| hsa-miR-523 | Known | AACGCGUUCCUCCUUUAGAGGG | CCCTCTATAGGGGAAGCGCGTT | 1587.4 | 61.7 | 197.7 | 35.3 | + | - | - | + |
| hsa-miR-524 | Known | GAAGGCGCUUCCCUUUAGAGU | ACTCTAAAGGGAAGCGCCTTC | 1291.8 | 63.5 | 189.7 | 35.0 | + | - | - | + |
| hsa-miR-524* | Known | CUACAAAGGGAAGCACUUUCUC | GAGAAAGTGCTTCCCTTTGTAG | 13708.7 | 90.3 | 232.3 | 37.0 | + | - | - | + |
| hsa-miR-525 | Known | CUCCAGAGGGAUGCACUUUCU | AGAAAGTGCATCCCTCTGGAG | 6667.5 | 79.3 | 210.8 | 34.6 | + | + | - | + |
| hsa-miR-525* | Known | GAAGGCGCUUCCCUUUAGAGC | GCTCTAAAGGGAAGCGCCTTC | 2211.6 | 68.9 | 185.5 | 35.9 | + | - | - | + |
| hsa-miR-526a | Known | CUCUAGAGGGAAGCACUUUCU | AGAAAGTGCTTCCCTCTAGAG | 15437.6 | 109.6 | 465.9 | 43.2 | + | - | - | + |
| hsa-miR-526b | Known | CUCUUGAGGGAAGCACUUUCUGUU | AACAGAAAGTGCTTCCCTCAAGAG | 12967.7 | 88.6 | 303.4 | 38.4 | + | - | - | + |
| hsa-miR-526b* | Known | AAAGUGCUUCCUUUUAGAGGC | GCCTCTAAAAGGAAGCACTTT | 504.7 | 65.2 | 257.6 | 33.5 | + | - | - | + |
| hsa-miR-526c | Known | CUCUAGAGGGAAGCGCUUUCUGUU | AACAGAAAGCGCTTCCCTCTAGAG | 7310.0 | 79.7 | 277.2 | 36.3 | + | - | - | + |
| hsa-miR-527 | Known | CUGCAAAGGGAAGCCCUUUCU | AGAAAGGGCTTCCCTTTGCAG | 3041.5 | 81.1 | 187.1 | 35.3 | + | + | - | + |
| hsa-miR-7 | Known | UGGAAGACUAGUGAUUUUGUUGU | CAACAAAATCACTAGTCTTCCA | 994.7 | 874.5 | 1949.4 | 15337.0 | + | + | + | + |
| hsa-miR-9 | Known | UCUUUGGUUAUCUAGCUGUAUGA | TCATACAGCTAGATAACCAAAGA | 436.9 | 1705.4 | 383.1 | 58089.4 | - | + | + | + |
| hsa-miR-9* | Known | UAAAGCUAGAUAACCGAAAGU | ACTTTCGGTTATCTAGCTTTA | 302.2 | 855.8 | 387.7 | 34095.2 | - | + | + | + |
| hsa-miR-92 | Known | UAUUGCACUUGUCCCGGCCUG | CAGGCCGGGACAAGTGCAATA | 6873.8 | 7716.6 | 9541.4 | 10635.3 | + | + | + | + |
| hsa-miR-93 | Known | AAAGUGCUGUUCGUGCAGGUAG | CTACCTGCACGAACAGCACTTT | 5092.7 | 3878.2 | 1782.1 | 2649.3 | + | + | + | + |
| hsa-miR-95 | Known | UUCAACGGGUAUUUAUUGAGCA | TGCTCAATAAATACCCGTTGAA | 310.8 | 2055.1 | 746.0 | 8573.9 | + | + | - | + |
| hsa-miR-96 | Known | UUUGGCACUAGCACAUUUUUGC | GCAAAATGTGCTAGTGCCAAA | 565.1 | 667.1 | 395.7 | 53.4 | + | + | + | + |
| hsa-mir-96_rel | Known | ACGAGACUUCUGCAUGUCUAAC | GTTAGACATGCAGAAGTCTCGT | 33103.4 | 11930.9 | 12501.3 | 5531.2 | + | + | + | + |
| hsa-miR-98 | Known | UGAGGUAGUAAGUUGUAUUGUU | AACAATACAACTTACTACCTCA | 12240.9 | 315560.5 | 12307.3 | 24613.9 | + | + | + | + |
| hsa-miR-99a | Known | AACCCGUAGAUCCGAUCUUGUG | CACAAGATCGGATCTACGGGTT | 14896.3 | 29513.3 | 12757.8 | 21865.5 | + | + | + | + |
| hsa-miR-99b | Known | CACCCGUAGAACCGACCUUGCG | CGCAAGGTCGGTTCTACGGGTG | 7570.1 | 14798.1 | 4990.8 | 13918.8 | + | + | + | + |

Explanations for selected columns are as follows: Placenta (microarray signal intensity for each given candidate or known miRNA probe hybridized to placental total RNA); Placenta Detection (+, sequence passes threshold of detection in placenta total RNA; -, sequence does not pass threshold of detection in placenta total RNA)

Fig. 14A (Table 7.) qRT-PCR validation of selected miRNA candidates

| Tag Name | Tag | Colon Tissue (Normal) Ct | Colon Tissue (Tumor) Ct | Pooled Colon Cell Lines Ct | Pooled Extra-Colonic Tissue Ct | Observation |
|---|---|---|---|---|---|---|
| hsa-mir-92b | UAUUGCACUCGUCCCGGCCUC | 20.18 | 19.41 | 21.03 | 17.77 | abundant product present |
| hsa-mir-411 | UAGUAGACCGUAUAGCGUACG | 29.43 | 27.73 | 29.48 | 22.84 | product present |
| hsa-mir-449b | AGGCAGUGUAUUGUUAGCUGGC | 31.06 | 29.81 | 27.85 | 26.02 | product present with strong primer-dimer |
| hsa-mir-545 | UCAGCAAACAUUUAUUGUGUGC | 27.93 | 28.86 | 28.13 | 27.74 | product present |
| hsa-mir-548d-1 | CAAAAACCACAGUUUCUUUUGC | 24.62 | 26.97 | 29.58 | 27.08 | product present |
| hsa-mir-551b | GCGACCCAUACUUGGUUUCAG | 25.12 | 31.4 | 34.6 | 22.62 | product present |
| hsa-mir-558 | UGAGCUGCUGUACCAAAAU | 32.25 | 32.48 | 34.05 | 30.84 | product present with strong primer-dimer |
| hsa-mir-564 | AGGCACGGUCAGCAGGC | 29.51 | 29.21 | 28.87 | 26.44 | product present |
| hsa-mir-565 | GGCUGGCUCGCGAUGUCUGUUU | 16.76 | 18.2 | 17.71 | 16.24 | abundant product present |
| hsa-mir-571 | UGAGUUGGCCAUCUGAGUGAG | 30.09 | 28.63 | 31.02 | 27.6 | product present |
| hsa-mir-574 | CACGCUCAUGCACACACCCAC | 19.48 | 20.19 | 23.58 | 17.4 | abundant product present |
| hsa-mir-577 | UAGAUAAAAUAUUGGUACCUG | 29.01 | 30.34 | 30.76 | 26.06 | product present |
| hsa-mir-580 | UUGAGAAUGAUGAAUCAUUAGG | 32.15 | 35.03 | 34.29 | 30.64 | product present |
| hsa-mir-581 | UCUUGUGUUCUCUAGAUCAGU | 32.97 | 36.35 | 34.98 | 32.7 | product present |
| hsa-mir-582 | UUACAGUUGUUCAACCAGUUACU | 29.84 | 32.36 | 33.17 | 27.35 | product present |
| hsa-mir-584 | UUAUGGUUUGCCUGGGACUGAG | 30.59 | 26.63 | 34.29 | 23.82 | product present |
| hsa-mir-592 | UUGUGUCAAUAUGCGAUGAUGU | 31.78 | 30.85 | 35.88 | 27.71 | product present |
| hsa-mir-594 | CCCAUCUGGGGUGGCCUGUGACUUU | 20.62 | 20.72 | 22.5 | 20.62 | abundant product present |
| hsa-mir-595 | GAAGUGCCGUGGGUGUGUCU | 23.5 | 23.58 | 26.65 | 23.71 | product present |
| hsa-mir-600 | ACUUACAGACAAGAGCCUUGCUC | 32.5 | 35.65 | 34.01 | 33.94 | product present with strong primer-dimer |
| hsa-mir-601 | UGGUCUAGGAUUGUUGGAGAG | 30.05 | 32.46 | 32.68 | 32.26 | product present with strong primer-dimer |
| hsa-mir-612 | GCUGGGCAGGGCUUCUGAGCUCCUU | 27.01 | 28.43 | 30.28 | 28.27 | product present |
| hsa-mir-615 | UCCGAGCCUGGGUCUCCCUCU | 29.61 | 30.58 | 29.06 | 26.74 | product present |
| hsa-mir-618 | AAACUCUACUUGUCCUUCUGAGU | 30.08 | 29.43 | 31.61 | 27.39 | product present |
| hsa-mir-622 | ACAGUCUGCUGAGGUUGGAGC | 23.41 | 26.17 | 31.15 | 27.64 | product present |
| hsa-mir-625 | AGGGGAAAGUUCUAUAGUCCU | 24.84 | 26.17 | 26.21 | 23.29 | product present |
| hsa-mir-628 | UCUAGUAAGAGUGGCCAGUCG | 28.72 | 28.24 | 28.68 | 25.25 | product present with strong primer-dimer |
| hsa-mir-630 | AGUAUUCUGUACCAGGGAAGGU | 30.83 | 30.02 | 35.64 | 28.79 | product present |
| hsa-mir-640 | AUGAUCCAGGAACCUGCCUCU | 27.6 | 28.77 | 30.06 | 27.95 | product present with strong primer-dimer |
| hsa-mir-642 | GUCCCUCCAAAUGUGUCUUG | 28.29 | 28.75 | 29.67 | 28.35 | product present |
| hsa-mir-649 | AAACCUGUGUUGUUCAAGAGUC | 24.95 | 25.24 | 25.7 | 25.45 | product present with strong primer-dimer |

Fig. 14 B

| | | | | | |
|---|---|---|---|---|---|
| hsa-mir-650 | AGGAGGCAGGCGCUCUCAGGAC | 21.41 | 22.89 | 27.93 | 25.61 | product present |
| hsa-mir-651 | UUUAGGAUAAGCUUGACUUUUG | 28.67 | 30.43 | 29.32 | 26.28 | product present with strong primer-dimer |
| hsa-mir-655 | AUAAUACAUGGUUAACCUCUUU | 30.36 | 32.82 | 34.19 | 29 | product present |
| hsa-mir-656 | AAUAUUAUACAGUCAACCUCU | 37.13 | 37.22 | 35.27 | 32.43 | product present |
| hsa-mir-660 | UACCCAUUGCAUAUCGGAGUUG | 23.5 | 23.71 | 26.14 | 21.19 | product present |
| miR-16 | Control | 15.86 | 15.96 | 18.34 | 12.14 | abundant product present, positive control |
| miR-24 | Control | 16.67 | 17.21 | 20.16 | 14.17 | abundant product present, positive control |
| miR-143 | Control | 16.37 | 21.02 | 31.14 | 14.16 | abundant product present, positive control |
| 5s rRNA | Control | 17.16 | 16.28 | 15.37 | 13.8 | abundant product present, positive contrc |

Explanations for selected columns are as follows: Observation (product present indicates that a PCR product of the appropriate size was observed by gel electrophoresis); Ct (indicates real time PCR threshold cycle number)

Fig. 15. (Table 8.) Differential expression of known miRNAs in Dicer$^{Ex5}$ versus WT

| Description | Dicer WT Tag Counts | Dicer WT Tag Counts (normalized) | Dicer$^{Ex5}$ Tag Counts | Fisher Exact P-Value | WT/Ex5 |
|---|---|---|---|---|---|
| HSA-MIR-15A | 45 | 69.8 | 0 | 0 | 70.0 |
| HSA-MIR-126 | 18 | 27.9 | 0 | 0 | 28.0 |
| HSA-MIR-301 | 33 | 51.2 | 2 | 0 | 25.6 |
| HSA-MIR-182 | 51 | 79.1 | 4 | 0 | 19.8 |
| HSA-MIR-331 | 12 | 18.6 | 0 | 0.000013 | 19.0 |
| HSA-MIR-200A | 919 | 1424.5 | 77 | 0 | 18.5 |
| HSA-MIR-103 | 285 | 441.8 | 31 | 0 | 14.3 |
| HSA-MIR-18B | 9 | 14.0 | 1 | 0.001381 | 14.0 |
| HSA-MIR-18A | 144 | 223.2 | 17 | 0 | 13.1 |
| HSA-MIR-193B | 8 | 12.4 | 1 | 0.003201 | 12.4 |
| HSA-MIR-29C | 8 | 12.4 | 0 | 0.000545 | 12.0 |
| HSA-MIR-93 | 37 | 57.4 | 5 | 0 | 11.5 |
| HSA-MIR-106B | 137 | 212.4 | 21 | 0 | 10.1 |
| HSA-MIR-23B | 30 | 46.5 | 5 | 0 | 9.3 |
| HSA-MIR-139 | 5 | 7.8 | 1 | 0.036925 | 7.8 |
| HSA-MIR-339 | 5 | 7.8 | 1 | 0.036925 | 7.8 |
| HSA-MIR-20A | 41 | 63.6 | 10 | 0 | 6.4 |
| HSA-MIR-140 | 8 | 12.4 | 2 | 0.017506 | 6.2 |
| HSA-MIR-181B | 8 | 12.4 | 2 | 0.017506 | 6.2 |
| HSA-MIR-196B | 8 | 12.4 | 2 | 0.017506 | 6.2 |
| HSA-MIR-107 | 68 | 105.4 | 18 | 0 | 5.9 |
| HSA-MIR-99B | 9 | 14.0 | 3 | 0.015489 | 4.7 |
| HSA-MIR-96 | 40 | 62.0 | 14 | 0 | 4.4 |
| HSA-MIR-32 | 88 | 136.4 | 33 | 0 | 4.1 |
| HSA-MIR-429 | 16 | 24.8 | 6 | 0.001717 | 4.1 |
| HSA-MIR-24 | 362 | 561.1 | 172 | 0 | 3.3 |
| HSA-MIR-7 | 12 | 18.6 | 6 | 0.026666 | 3.1 |
| HSA-MIR-21 | 7537 | 11682.4 | 3908 | 0 | 3.0 |
| HSA-LET-7F | 100 | 155.0 | 52 | 0 | 3.0 |
| HSA-MIR-9 | 24 | 37.2 | 13 | 0.001998 | 2.9 |
| HSA-MIR-25 | 281 | 435.6 | 156 | 0 | 2.8 |
| HSA-MIR-200C | 1330 | 2061.5 | 779 | 0 | 2.6 |
| HSA-MIR-16 | 245 | 379.8 | 146 | 0 | 2.6 |
| HSA-MIR-191 | 181 | 280.6 | 109 | 0 | 2.6 |
| HSA-MIR-26A | 101 | 156.6 | 61 | 0 | 2.6 |
| HSA-MIR-130A | 46 | 71.3 | 28 | 0.000067 | 2.5 |
| HSA-MIR-29B | 280 | 434.0 | 174 | 0 | 2.5 |
| HSA-MIR-222 | 242 | 375.1 | 155 | 0 | 2.4 |
| HSA-MIR-335 | 40 | 62.0 | 29 | 0.001833 | 2.1 |
| HSA-MIR-30D | 94 | 145.7 | 69 | 0.000002 | 2.1 |
| HSA-MIR-30C | 42 | 65.1 | 31 | 0.001653 | 2.1 |
| HSA-MIR-374 | 79 | 122.5 | 59 | 0.000023 | 2.1 |
| HSA-MIR-19A | 79 | 122.5 | 60 | 0.000025 | 2.0 |
| HSA-MIR-141 | 228 | 353.4 | 176 | 0 | 2.0 |
| HSA-MIR-92 | 74 | 114.7 | 58 | 0.000107 | 2.0 |
| HSA-MIR-130B | 59 | 91.5 | 49 | 0.001465 | 1.9 |
| HSA-LET-7A | 92 | 142.6 | 77 | 0.00007 | 1.9 |
| HSA-MIR-200B | 432 | 669.6 | 375 | 0 | 1.8 |
| HSA-MIR-221 | 71 | 110.1 | 63 | 0.001335 | 1.7 |
| HSA-MIR-101 | 229 | 355.0 | 220 | 0 | 1.6 |
| HSA-MIR-29A | 88 | 136.4 | 89 | 0.004255 | 1.5 |
| HSA-MIR-125B | 47 | 72.9 | 48 | 0.045141 | 1.5 |
| HSA-MIR-31 | 214 | 331.7 | 230 | 0.000111 | 1.4 |
| HSA-MIR-27A | 313 | 485.2 | 682 | 0.000001 | 0.7 |
| HSA-MIR-210 | 25 | 38.8 | 67 | 0.018687 | 0.6 |

Fig. 16A (Table 9) miRNA sequences identified with binding sequence and target gene

| id | miRNA_Name | mir_seq | target_gene | Bs_ids | disease_ids |
|---|---|---|---|---|---|
| 1 | hsa-mir-33b | GTGCATTGCTGTTGCATTGCA | ABCA1 | 11, 132, 136, 155 | 37, 119 |
| 2 | hsa-mir-92b | TATTGCACTCGTCCCGGCCTC | LYST | 30 | 16 |
| 3 | hsa-mir-411 | TAGTAGACCGTATAGCGTACG | NTRK2 | 14 | 89 |
| 4 | hsa-mir-421-3p | ATCAACAGACATTAATTGGGCGC | NR3C1 | 68, 81 | 22 |
| 5 | hsa-mir-449b | AGGCAGTGTATTGTTAGCTGGC | SRC | 62, 142 | 20 |
| 6 | hsa-mir-483* | AAGACGGGAGGAAAGAAGGGAG | MECP2 | 74, 112 | 7, 73, 77, 100, 104, 105 |
| 7 | hsa-mir-542 | TCGGGGATCATCATGTCACGAG | PRX | 126 | 27 |
| 8 | hsa-mir-545 | TCAGCAAACATTTATTGTGTGC | SLC16A2 | 75 | 3 |
| 9 | hsa-mir-548a-1 | CAAAACTGGCAATTACTTTTGC | PPP2R1B | 138, 166 | 68 |
| 10 | hsa-mir-548a-2 | CAAAACTGGCAATTACTTTTGC | PPP2R1B | 138, 166 | 68 |
| 11 | hsa-mir-548a-3 | CAAAACTGGCAATTACTTTTGC | PPP2R1B | 138, 166 | 68 |
| 12 | hsa-mir-548b | CAAGAACCTCAGTTGCTTTTGT | NHS | 197 | 87 |
| 13 | hsa-mir-548c | CAAAAATCTCAATTACTTTTGC | RUNX1 | 6, 15, 96, 115 | 56, 98 |
| 14 | hsa-mir-548d-1 | CAAAAACCACAGTTTCTTTTGC | MECP2 | 140, 190, 207 | 7, 73, 77, 100, 104, 105 |
| 15 | hsa-mir-548d-2 | CAAAAACCACAGTTTCTTTTGC | MECP2 | 140, 190, 207 | 7, 73, 77, 100, 104, 105 |
| 16 | hsa-mir-549a | TGACAACTATGGATGAGCTCT | AFF2 | 8, 151 | 76 |
| 17 | hsa-mir-549b | GACAACTATGGATGAGCTCTCA | DEK | 17, 162 | 58 |
| 18 | hsa-mir-550-1 | TGTCTTACTCCCTCAGGCACAT | SLC35C1 | 199 | 21 |
| 19 | hsa-mir-550-2 | TGTCTTACTCCCTCAGGCACAT | SLC35C1 | 199 | 21 |
| 20 | hsa-mir-551a | GCGACCCACTCTTGGTTTCCA | SQSTM1 | 100 | 93 |
| 21 | hsa-mir-551b | GCGACCCATACTTGGTTTCAG | SDHC | 64 | 95 |
| 22 | hsa-mir-552 | AACAGGTGACTGGTTAGACAA | MS4A2 | 19 | 10 |
| 23 | hsa-mir-553 | AAAACGGTGAGATTTTGTTT | PPP2R2B | 73 | 114 |
| 24 | hsa-mir-554 | GCTAGTCCTGACTCAGCCAGT | RP1 | 217 | 103 |
| 25 | hsa-mir-555 | AGGGTAAGCTGAACCTCTGAT | FGFR1OP | 104 | 86 |
| 26 | hsa-mir-556 | GATGAGCTCATTGTAATATG | KCNJ1 | 184 | 12 |
| 27 | hsa-mir-557 | GTTTGCACGGGTGGGCCTTGTCT | SIM1 | 56, 203 | 90 |
| 28 | hsa-mir-558 | TGAGCTGCTGTACCAAAAT | EDARADD | 152, 161 | 28 |
| 29 | hsa-mir-559 | TAAAGTAAATATGCACCAAAA | MYCN | 51 | 33 |
| 30 | hsa-mir-560 | GCGTGCGCCGGCCGGCCGCC | CHST6 | 128 | 70 |
| 31 | hsa-mir-561 | CAAAGTTTAAGATCCTTGAAGT | IGF1 | 42, 164, 169 | 36 |
| 32 | hsa-mir-562 | AAAGTAGCTGTACCATTTGC | FRAS1 | 124 | 34 |
| 33 | hsa-mir-563 | AGGTTGACATACGTTTCCC | UBE3A | 157 | 7 |
| 34 | hsa-mir-564 | AGGCACGGTGTCAGCAGGC | TRIOBP | 148 | 26 |
| 35 | hsa-mir-565 | GGCTGGCTCGCGATGTCTGTT | COL18A1 | 76, 159 | 55 |
| 36 | hsa-mir-566 | GGGCGCCTGTGATCCCAAC | SH3BP2 | 69 | 17 |

Fig. 16 B (Table 9) miRNA sequences identified with binding sequence and target gene

| # | miRNA | Sequence | Target gene | Positions |
|---|---|---|---|---|
| 37 | hsa-mir-567 | AGTATGTTCTTCCAGGACAGAAC | CSF1R | 98, 85 |
| 38 | hsa-mir-568 | ATGTATAAATGTATACACAC | NOTCH1 | 85, 204, 61 |
| 39 | hsa-mir-569 | AGTTAATGAATCCTGGAAAGT | MALT1 | 89, 123, 71 |
| 40 | hsa-mir-570 | GAAAACAGCAATTACCTTTGCA | AFF2 | 32, 198, 76 |
| 41 | hsa-mir-571 | TGAGTTGGCCATCTGAGTGAG | MOCS1 | 33, 80 |
| 42 | hsa-mir-572 | GTCCGCTCGGCGGTGGCCCA | RERE | 133, 57 |
| 43 | hsa-mir-573 | CTGAAGTGATGTGTAACTGATCAG | FANCM | 117, 32 |
| 44 | hsa-mir-574 | CACGCTCATGCACACACCCAC | UBR1 | 118, 53 |
| 45 | hsa-mir-575 | GAGCCAGTTGGACAGGAGC | KCNE1 | 26, 110, 52, 67 |
| 46 | hsa-mir-576 | ATTCTAATTTCTCCACGTCTTTG | MIPOL1 | 94, 214, 219, 78 |
| 47 | hsa-mir-577 | TAGATAAAATATTGGTACCTG | LIG4 | 47, 150, 65 |
| 48 | hsa-mir-578 | CTTCTTGTCTCTAGGATTGT | MLLT10 | 27, 122, 56, 59 |
| 49 | hsa-mir-579 | ATTCATTGGTATAAACCGCGAT | AFF2 | 28, 72, 79, 170, 76 |
| 50 | hsa-mir-580 | TTGAGAATGATGAAATCATTAGG | SPG20 | 57, 67, 123 |
| 51 | hsa-mir-581 | TCTTGTGTTCTCTAGATCAGT | SPAST | 149, 176, 111 |
| 52 | hsa-mir-582 | TTACAGTTGTTCAACCAGTTACT | ACACA | 29, 192, 1 |
| 53 | hsa-mir-583 | CAAAGAGGAAGGTCCCATTAC | NTRK2 | 167, 173, 89 |
| 54 | hsa-mir-584 | TTATGGTTTGCCTGGGACTGAG | PRSS12 | 20, 72 |
| 55 | hsa-mir-585 | TGGGCGTATCTGTATGCTA | PKD2 | 1, 99 |
| 56 | hsa-mir-586 | TATGCATTGTATTTTTAGGTCC | THBD | 180, 205, 121 |
| 57 | hsa-mir-587 | TTTCCATAGGTGATGAGTCAC | UBR1 | 7, 49, 53 |
| 58 | hsa-mir-588 | TTGGCCACAATGGGTTAGAAC | NTRK2 | 139, 216, 89 |
| 59 | hsa-mir-589 | TCAGAACAAATGCCGGTTCCCAGA | ACOX1 | 37, 111, 2 |
| 60 | hsa-mir-590 | GAGCTTATTCATAAAAGTGCAG | TIMP3 | 61, 206, 110 |
| 61 | hsa-mir-591 | AGACCATGGGTTCTCATTGT | FANCC | 134, 185, 31 |
| 62 | hsa-mir-592 | TTGTGTCAATATGCGATGATGT | DEK | 50, 212, 58 |
| 63 | hsa-mir-593 | AGGCACCAGCAGCCAGGCATTGCTCAGC | MTHFR | |
| 64 | hsa-mir-594 | CCCATCTGGGGTGCCCTGTGACTTT | NTRK2 | 87, 160, 89 |
| 65 | hsa-mir-595 | GAAGTGTGCCGTGGTGTCT | FOXN1 | 36, 118 |
| 66 | hsa-mir-596 | AAGCCTGCCCGGCTCCTCGGG | TRIOBP | 200, 26 |
| 67 | hsa-mir-597 | TGTGTCACTCGATGACCACTGT | TLX1 | 65, 78, 62 |
| 68 | hsa-mir-598 | TACGTCATCGTTGTCATCGTCA | PINK1 | 208, 96 |
| 69 | hsa-mir-599 | GTTGTGTCAGTTTATCAAAC | IGF1 | 35, 77, 153, 36 |
| 70 | hsa-mir-600 | ACTTACAGACAAGAGCCTTGCTC | SLC6A2 | 34, 92 |
| 71 | hsa-mir-601 | TGGTCTAGGATTGTTGGAGAG | AFF2 | 130, 76 |
| 72 | hsa-mir-602 | GACACGGGCGACAGCTGCGGCCC | CACNA1C | 194, 122 |
| 73 | hsa-mir-603 | CACACACTGCAATTACTTTTGC | NHS | 2, 13, 45, 143, 87 |

Fig. 16 C (Table 9) miRNA sequences identified with binding sequence and target gene

| # | miRNA | Sequence | Target gene | | |
|---|---|---|---|---|---|
| 74 | hsa-mir-604 | AGGCTGCGGAATTCAGGAC | SEPN1 | 93 | 84 |
| 75 | hsa-mir-605 | TAAATCCCATGGTGCCTTCTCCT | MTRR | 92, 146 | 42 |
| 76 | hsa-mir-606 | AAACTACTGAAATCAAAGAT | PLOD2 | 60 | 13 |
| 77 | hsa-mir-607 | GTTCAAATCCAGATCTATAAC | BMPR2 | 43, 103, 158 | 101 |
| 78 | hsa-mir-608 | AGGGGTGGTGTTGGGACAGCTCCGT | RAI1 | 12, 21, 22, 82, 102 | 109 |
| 79 | hsa-mir-609 | AGGGTGTTTCTCTCATCTCT | PRKCA | 16, 38 | 97 |
| 80 | hsa-mir-610 | TGAGCTAAATGTGTGCTGGGA | TIMP3 | 147, 220 | 110 |
| 81 | hsa-mir-611 | GCGAGGACCCCTGGGGTCTGAC | NIPA1 | 135 | 112 |
| 82 | hsa-mir-612 | GCTGGGCAGGGCTTCTGAGCTCCTT | PRKCA | 46, 70 | 97 |
| 83 | hsa-mir-613 | AGGAATGTTCCTTCTTTGCC | TAL1 | 171 | 63 |
| 84 | hsa-mir-614 | GAACGCCTGTTCTTGCCAGGTGG | HD | 196 | 43 |
| 85 | hsa-mir-615 | TCCGAGCCTGGGTCTCCCTCT | COL18A1 | 80 | 55 |
| 86 | hsa-mir-616 | ACTCAAAACCCTTCAGTGACTT | H6PD | 10, 90, 181 | 23 |
| 87 | hsa-mir-617 | AGACTTCCCATTTGAAGGTGGC | ARHGAP26 | 213 | 60 |
| 88 | hsa-mir-618 | AAACTCTACTTGTCCTTCTGAGT | MYH11 | 25 | 8 |
| 89 | hsa-mir-619 | GACCTGGACATGTTTGTGCCCAGT | NCF2 | 188 | 18 |
| 90 | hsa-mir-620 | ATGGAGATAGATATAGAAAT | GRHL2 | 106 | 24 |
| 91 | hsa-mir-621 | GGCTAGCAACAGCGCTTACCT | SH3BP2 | 84, 211 | 17 |
| 92 | hsa-mir-622 | ACAGTCTGCTGAGGTTGGAGC | CASR | 3, 107 | 46, 47, 48, 49 |
| 93 | hsa-mir-623 | ATCCCTTGCAGGGGCTGTTGGGT | VAPB | 156, 182 | 6, 113 |
| 94 | hsa-mir-624 | TAGTACCAGTACCTTGTGTTCA | TBX5 | 145 | 40 |
| 95 | hsa-mir-625 | AGGGGGAAAGTTCTATAGTCCT | TFE3 | 105, 189 | 102 |
| 96 | hsa-mir-626 | AGCTGTCTGAAAATGTCTT | HD | 125, 179 | 43 |
| 97 | hsa-mir-627 | GTGAGTCTCTAAGAAAAGAGGA | FVT1 | 215 | 69 |
| 98 | hsa-mir-628 | TCTAGTAAGAGTGCAGTCG | ATRX | 53, 218 | 4, 5, 19, 54, 108, 117 |
| 99 | hsa-mir-629 | GTTCTCCCAACGTAAGCCCAGC | KCNMA1 | 44, 97, 121 | 35 |
| 100 | hsa-mir-630 | AGTATTCTGTACCAGGGAAGGT | ALDH5A1 | 83, 210 | 116 |
| 101 | hsa-mir-631 | AGACCTGGCCCAGACCTCAGC | TGFB3 | 18, 48 | 9 |
| 102 | hsa-mir-632 | GTGTCTGCTTCCTGTGGA | GNPTG | 127 | 82 |
| 103 | hsa-mir-633 | CTAATAGTATCTACCACAATAAA | SLC19A2 | 116, 154 | 120 |
| 104 | hsa-mir-634 | AACCAGCACCCCAACTTTGGAC | AFF2 | 9, 88, | 76 |
| 105 | hsa-mir-635 | ACTTGGGCACTGAAACAATGTCC | CD59 | 71, 177 | 15 |
| 106 | hsa-mir-636 | TGTGCTTGCTCGTCCCGCCCAG | SLC25A15 | 186 | 45 |
| 107 | hsa-mir-637 | ACTGGGGGCTTTCGGGCTCTGCGT | PRKCA | 193 | 97 |
| 108 | hsa-mir-638 | AGGGATCGCGGGCGGGGTGGCGGCCT | SUMF1 | 193 | 83 |
| 109 | hsa-mir-639 | ATCGCTGCGGTTGCGAGCGCTGT | ARHGAP26 | 191 | 60 |
| 110 | hsa-mir-640 | ATGATCCAGGAACCTGCCTCT | TK2 | 66 | 79 |

Fig. 16 D

(Table 9) miRNA sequences identified with binding sequence and target gene

| # | miRNA | Sequence | Target gene | Positions | |
|---|---|---|---|---|---|
| 111 | hsa-mir-641 | AAAGACATAGGATAGAGTCACCTC | TGFBR1 | 41, 131 | 66 |
| 112 | hsa-mir-642 | GTCCCTCTCCAAATGTGTCTTG | KIAA1202 | 23, 55, 221 | 115 |
| 113 | hsa-mir-643 | ACTTGTATGCTAGCTCAGGTAG | USP9Y | 222 | 11 |
| 114 | hsa-mir-644 | AGTGTGGCTTTCTTAGAGC | MYLK2 | 39, 187 | 14 |
| 115 | hsa-mir-645 | TCTAGGCTGGTACTGCTGA | ACVR1B | 40, 195 | 94 |
| 116 | hsa-mir-646 | AAGCAGCTGCCTCTGAGGC | NP | 59, 168 | 88 |
| 117 | hsa-mir-647 | GTGGCTGCACTCACTTCCTC | ICOS | 52, 86 | 51 |
| 118 | hsa-mir-648 | AAGTGTGCAGGGCACTGGT | MYO1A | 5 | 25 |
| 119 | hsa-mir-649 | AAACCTGTGTTGTTCAAGAGTC | OPA1 | 109, 175 | 91 |
| 120 | hsa-mir-650 | AGGAGGCAGCGCTCTCAGGAC | H6PD | 95, 137, 172 | 23 |
| 121 | hsa-mir-651 | TTTAGGATAAGCTTGACTTTG | BCL2 | 108, 119 | 64 |
| 122 | hsa-mir-652 | AATGGCGCCACTAGGGTTGTGCA | HLCS | 223 | 39 |
| 123 | hsa-mir-653 | TTGAAACAATCTCTACTGAAC | SS18 | 4, 144, 178 | 107 |
| 124 | hsa-mir-654 | TGGTGGGCCGCAGAACATGTGC | PAX8 | 54, 165 | 50 |
| 125 | hsa-mir-655 | ATAATACATGGTTAACCTCTTT | ACSL4 | 163, 174 | 74 |
| 126 | hsa-mir-656 | AATATTATACAGTCAACCTCT | ARHGEF6 | 58, 183 | 75 |
| 127 | hsa-mir-657 | GGCAGGTTCTCACCCTCTCTAGG | F8 | 99 | 38 |
| 128 | hsa-mir-658 | GGCGGAGGGAAGTAGGTCCGTTGGT | F7 | 63 | 30 |
| 129 | hsa-mir-659 | CTTGGTTCAGGAGGGTCCCCA | LDLRAP1 | 24, 113 | 44 |
| 130 | hsa-mir-660 | TACCCATTGCATATCGGAGTTG | BCL2 | 141 | 64 |
| 131 | hsa-mir-661 | TGCCTGGGTCTCTGGCCTGCGCGT | SGSH | 101, 114 | 106 |
| 132 | hsa-mir-662 | TCCCACGTTGTGGCCCAGCAG | MCFD2 | 201, 202 | 29 |
| 133 | hsa-mir-663 | AGGCGGGGCGCCGCGGGACCGC | CRTC1 | 91, 209 | 81 |

Fig. 17A (Table 10.) Binding sequences and identifiers

| Bs_id | Bs_seq |
|---|---|
| 1 | AAAAAAATCTTCATGATGTGTATTGAGCGGTACGCCCAGTTGCCACCATGACTGAGTC |
| 2 | AAAAAATGTATCAGAAAGTTGATTACCTAGAAAGTGTGTATAGAAACTGCAAATAAACGT |
| 3 | AAACTATGGCTTTAAACTACCCTCCAGAGTGTGCAGACTGATGGGACATCAAATTTGCCAC |
| 4 | AAACTGAATAGTTCAGGAGACTTTACAAACCTTTGTTCAACTTTCTTATCTGGAAATAAT |
| 5 | AAAGTAGCTTCCTCCAACCCGCAGCCTCTCTGCACACTAATAAAAACATGTGGCTTGGAA |
| 6 | AAATACCTGTTTCTTTGGGACATTCCGTCCTGATGATTTTTATTTTTGTTGGTTTTATTTT |
| 7 | AAATGACGACAGTAGTAAAGGCTGATTCAAAATTATGGAAAACTTTCTGAGGGCTGGGAAA |
| 8 | AAATTAATTCTGTGGGAAAAATTATTGAGCCAGTTGTCAGTGTTCTGTTACATGACTGG |
| 9 | AACACTATCCATGCATTACTTACTGGTAATTACCTGCTGGTATATAATTCCATGTAGCCTT |
| 10 | AACCCAGCCAGACAGAGACATCTCTTTTTTTTTTGAGACAGAGTCTCTGTCGCCCAGG |
| 11 | AAGAAGTAAACTGGATCTGTACTGATACTATTCAATGACATGCAATTCAATGCAATGAAA |
| 12 | AAGACGACGTCGCACACATTCCACGTGGGTCCGCCGCCACCCAGTCGGTCGTGCGTGCAGCT |
| 13 | AAGAGGAGGGAGAGTCAGAGAGAGTCAGAGAGTGTGTATGGGTGTGTGAGTGTGAGTGTGTACG |
| 14 | AAGAGTTTACTTTTGCAAGTCATTTGGTCTTCAGTCTACTACTGAGGAATAGAGAGGCACT |
| 15 | AAGTGAGTAGCTCACGCAGCAACGTGTTTTAATAGGATTTTTAGACACTGAGGGTCACTCCAA |
| 16 | AATCATGCCACTACTCACCAGTGTTGTTCCTGCTTTATAGTTGTATTTGTACATTTGGATTC |
| 17 | AATCTTGCATGGCATTAATTGTTCCTGCTTTATAGTTGTATTTGTACATTTGGATTTC |
| 18 | AATTAACATCGTGGGTCACTACAGGGAGAAAATCCAGGTCATGCAGTTCCTGGCCCATCAA |
| 19 | ACAAAAAAAAATTAGCTGGGTGTGGTGGCAGTCACCTGTAGTCCCAGCTACTTGGGAGGC |
| 20 | ACAAGTATCCTTGTTGAGTACCAAGTGCTACAGAAACCATAAGATAAAATACTTTCTACCT |
| 21 | ACACCCTTGGCCTCTGTTTGTCCCCTTTCCAGTCCTCCACCCAACCCCTGGAGCCCAGCCTGGG |
| 22 | ACATAAGAGAGGCTGCCGTAGTTAATCAACAGCCTCTAAAGGCTCAGAGGGAATCTGCCTTGCAGCTCTACTC |
| 23 | ACCCACCCATATCATCAACAGCCTCTAAAGGCTCAGAGGGAATCTGCCTTGCAGCTCTACTC |
| 24 | ACCTCCTTTTCTTCTTCTAGCTTTTGTTGTCCTCCCAGGAACCAAAAAACCCCAGCTATTTCTGA |
| 25 | ACCTCTTTTCGTTCCTTCTAGAAGGTCTGGAGGACGTAGAGTTATTGAAAATGCAGATGGTTCT |
| 26 | ACGCACTGACTTTGATATTCCAGGCACACGGACTGGCTATTTATCACCACTTCTTTTC |
| 27 | ACTATTACCTGGTATTTATCCACTAATGAGTCACAAGAAAAAGGAGTGGATTTGGTAAGAA |
| 28 | ACTTAAGGTCGGATGCCTTTTCCATGTAAGGAAATGAAAAGACCAAAATCTTCAGGCAA |
| 29 | AGAAAAGGGCTAGAGAGCTGCCTTTACAACTGTAACCACTGTAATGAGAAGGCACAGGAGACCC |
| 30 | AGAAAATATGCAGAATAACTGGTCTTGTAAGAGTGCAATATTATATTTTATGTAAAAAT |
| 31 | AGAATGGAGCAGCAGCAGGACAGACCCCCACGAGGCCCCCAGAGGAGGAAGATCCACGGA |
| 32 | AGACATCTTTCAGTTTCATGATTAAGGATTGTTGCTGTTTTATAGTTACTCTGTTCATCACA |
| 33 | AGAGACACTACACTTCCCGTGCAGACTCAGATGCCAACTCAAAGTGCCTTAGCCCAGGTTC |
| 34 | AGCCACATCTACTGAGGCCTCATGCTCTTGCTCTGTAAGACACGGAGCCCAGAAACCCAT |
| 35 | AGCTTTTAAAGTAAAAAAAAAGAGAGGACACAAAACCAAATGTTACTGCTCAAC |
| 36 | AGGAAATGCCCTGTCCCTAGCTCACACTCATCCACACTTAAGCCCTGCACACACA |

Fig. 17B    (Table 10.) Binding sequences and identifiers

37 AGGAAACTGATGACCTGAGACCAAGAGTCTTGTTGATGTTCTGACTTAGATAAAGGTTTTGATC
38 AGGCAGCAGGCTTAGGCCTTCCCTGCAACCCCAACACCCACAAGTTTGTTTCTCTAGGAA
39 AGGCCCTGGGCGCAGCTGAAGCCTGGACGCAGCCAGCACAGTGGCCGGGGCTGAAGCCAC
40 AGGTTTCATAATTGGTTCTACGACCCTTTGAGCCTAGAATTATTGTTCTTATATAAGA
41 AGTGGCCATTACACTGAATGAGTTGCATTCTGATAATGTCTTATCTCTTATACGTAGAATAAA
42 AGTGTGTACCTTTAAAATTATTCCCTCAACAAAACTTTATAGGCAGTCTTCTGCAGACT
43 AGTTTATGATTGAATTTTTAAGCAAATTACTGTATTTGAAACTACAACTGATTTGGTTT
44 AGTTTCACATTCAATATGGTAGGAGTTGAAACAAGGAGAGAAATGCTGTGGTTTGAAGTGGTT
45 ATAAGAGGAGGGAGAGTCAGAGAGAGTGTATGGGTGTGTGAGTGTGAGTGTGTGTA
46 ATAGAAAGAGCCTAGGAGACAAAAGGGCCAGTCCCCCTGCCCAGAATGGAGCAGCAGGACAG
47 ATATTCTAAAAGTCAAAAACGTTAACAATAGTTTTATCTAATAAAAGCACTGCAAGAAAA
48 ATATTTCCCCTGGACACTTGGTTAGACGCCTTCCAGGTCAGGATGCACATTTCTGGATTG
49 ATCTCTATGTGGACAGAGAGATGATTTCTGCCAATATGGAAAAGCTTTTTCTCACTGTAGG
50 ATCTGAATTTTAAAACATGCTGTTTATGACACAATTGTTGCACCAATTAAGTGT
51 ATGAAAATGAGTTGTGAAAGTTTGAGTAGATATTACTTTATCACTTTTGAACTAAGAAA
52 ATGCCAGGGTACTGAATCTGCAAAGCAAATGAGCAGCCAAGGACCAGCATCTGTCCGCAT
53 ATTAAATCAAATTAATTCATCCAATACCCCTTTACTGAAGTTTTACTAGAAAATGTAT
54 ATTATACAGTTCCCACATCAAGGCCGCCAACCTGCCACCGCCCCACTGCCACGCCTTTGACCAT
55 ATTATTTTTTCTTTTTAACTAATAAGGCGAGAAGAGAAGAGGAAGTTGGAGGGAAAAGTTAG
56 ATTCAAACCAATTCACCCAGAAAAAAGACCAATAGGTGCAAAAATAAAAGGAAAACCAGTGAA
57 ATTCTTGCATCTGGCCTTAGAAATGTGAAGTTATATTCTCAAGTTTATTTTTCCAAGTGT
58 ATTGAGGCCAAAGGGCTGATCAGAATTGCCTTTATAATATATTGATGGATGCCTATAAAT
59 ATTTGACTCGGGCCCTTAGAACTTTGCATAGCAGCTGCTACTAGCTCTTTGAGATAATAC
60 ATTTTCTGAACACCTATGCAGAGGGCGGTTTGAGCTTTCTATAAGCTATAGCTTTGTTTATTTCACCC
61 CAAAGCGATGTCAGAGGGCCCCCTCATCATAGCAATAAACATTCCCACTGCCAGGGTTCTTGAGCCAGCAG
62 CACCATGGCCCCCCTCAGCTTCACAATAAACGGCTGCGTCTCCTCCGCACACCTGTGGTGCCTGCCACC
63 CACCTGCTTCCCAGTTGTTGGCCAGCTACGATCAGGCACAGTCAGGGGTGCACAGACTCATCCTGAACAGCATG
64 CACTTCGAGTTGTTGGCCAGCTACGATCAGGCACAGTCAGGGGTGCACAGACTCATCCTGAACAGCATG
65 CACTTTGACTTTACGATCAGGCACAGTCAGGGGTGCACAGACTCATCCTGAACAGCATG
66 CAGCTGGACTGCATTGAAGGCGAGGCTGCCCCTTGGATCAAGCAGAAAACAAGAGAAAGAA
67 CAGTGTGTAAGCTAAACAAAACTAAAACTAAGAATTCTCAAAAAAACTTGTTCAAAACAGG
68 CATAGAGTTAACACAAGTCCTGTGAATTTCTTCACTGTTGAAAATTATTTAAACAAATAG
69 CATCCAGCAGGTTGGGTTCTAGGGCTGAACCAGGCGCCAGGCTCCAGAGGACGAAGGGA
70 CATCTTTGGCAGGAGGAGGATGCTTCCTGCCTCTGTGCCCAGACCGCCTGTCCCCAGGTCT
71 CATGTCTTATGTGTCCTGAAAAAATAAGAGCCTGCCCAAGACTTTGGGCCTCTTGACAGAA
72 CATGTTCATTGGGCCCTTTCACACCCCACAGTGATAAATGAAAAGGATAGAGGTAGTTTTTTC
73 CATTTGATTGAAAAAATCAACAAAATAAACACCGTTTACTCTTAGACAAGGACAAGTT

Fig. 17C (Table 10.) Binding sequences and identifiers

74 CCAAGTGGAGCCTGACAGCCAGAACTCTGTGTCCCCGTCTAACCACAGCTCCTTTTCCAGA
75 CCCAGGAGCCTAATAGGGTAGGCCCAAATCTCTGTTTGCTGAGGAGGTCATTGCCATCCATA
76 CCCCCATCTCATGCCCCTGGCTGGGACGTGGCTCAGCCAGCACTTGTCCAGCTGAGCGCCAG
77 CCCCCCAGTATGCCTTCCAAGAGGAACTTCAGACACAAAAGTCCACTGATGCAAATTGG
78 CCCTCCAGCACAAACACAAGGTCATGGCCACACTGTGACACTACACCACACACAACAGCC
79 CCCTGGTTACATTACTATATGAAGGCAGTGATTTGAAATGAAAATTCCTTTCCTCTTGGAAGC
80 CCGCCTGGATGCCGGATGGCCGGAGAGGACCGGCGGCTCGGAGGAAGCCCCCACCGTGGGCA
81 CCTATGTATGTGTTATCTGGCCATCCCAAACCCAAACTGTTGAAGTTTGTAGTAACTTCAGTGA
82 CCTGCTCCCGGAACGGACGGACACAGGGCGTTCTTGCCCACCCAGGGGCCAGGCTTGCGGAGGG
83 CCTGATGACAGAGCAGACTCCGCCTCAAAAAAGAATACAAATGCTCCAACATATTT
84 CCTGGTCCAGCCTGCCTCCCAGACTCTGCACCTGCTAGCACAGCTGTCCAGTCTGTGTG
85 CGACCAGGAGCCTTTTAAAACACATGTTTTATACAAATAAGAACGAGGATTTAA
86 CTACTTCCTGTCTGCATGCCCAAGGCTTCTGAAGCACCCAATGCTGCAACAACATTTG
87 CTCATGTTCTTACCTTCTATTAATAGAGTACTTGAGCCAGATGGACTAACTGGTCTCACATTTC
88 CTCATTTGGTCAGCCTAGCATGCAACCAGTGGTGTGCTGGTAAAATGTTTAACAACCAGCTC
89 CTCTACCTAAAAGTTGGTTAAAATATAAACTTTCTAGCGCATTTGAGAGAGGGCTTTCTGGGTGAGG
90 CTCTGGATCAGGCAGATATAAACTTTCTAGCGCATTTGAGAGAGGGCTTTCTGGGTGAGG
91 CTGAGCTTGCAATGCCGCCAAGCGCCCCGGCCCCGCCCCGGTTGTCCACCTCCCGCG
92 CTGATAAAAATATTTAGGATAATGCCTACAGAGGGATTATTTTATGATGCTGGAAATA
93 CTGGCAGAGGAAGAAGGACAGACATCTCCGCAGCCAGATCTCCGCAGCCAGCACCACTCCGGGCCTTTATGTGC
94 CTGTATCCATTAGCTGGAAATCATCAGGAACCAGCTGCCTCCATCTCTCGAGATGTGCTGGG
95 CTGTATTAGCTGGAAATCATCAGGAACCAGCTGCCTCCATCTCTCGAGATGTGCTGGG
96 CTGTTTCTTTGGGACATTCCGTCCTGATGAATTATTTTGTTGGTTTTATTTTGGGGG
97 CTTAGAAAGTGAAGGATCCTGGATGGGGCGACACGGGGAGAAACATACAAACTCTGCCTTCGGTCATTT
98 CTTCAAACTCCTCCATGGATGGGGCGACACGGGGAGAAACATACAAACTCTGCCTTCGGTCATTT
99 CTTCCAATATAACTAGGCAAAAGAAGTGAGGAGAAAACCTGCATGAAAGCATTCTTCCCTGAA
100 CTTCCCCAGTTATAAAGAGGTCACATAGTCGTGTGGGTCGAGGATTCTGTGCCTCCAGGAC
101 CTTCTTCTGTTTTGCCCCATGTCAAGTCCCTGTTCCCCAGGCAGGTTCAGTGATTGGCAGC
102 CTTGGCCTCTGTTTGTCCCCTTTCCAGTGCTCCAGTACGATACATTTGAAAGTACTTCAGAAGAATTTATG
103 GAAAACCTAGAAATTTATCTCATGCAGATACATTTGAAAGTACTTCAGAAGAATTTATG
104 GAAAACCTTGGCTTTAGCCTCTGGAATCAGAGCTTACCCACCATAGTATATTTGATATT
105 GAAAGGAGGACCAGTCAGGATGAGGCCCCGTTTCCCCACCCTCCCATGAGACTGCCCT
106 GAACTGAACAGAACAAGACTTTTCCTCATACATCTCCAAATTGTTTAAACTACTTTAT
107 GAATGTCACCAGTCCTGCCCAATGCCTTGACAACAGACTGAATTTTAAATGTTCACAACAT
108 GAATTGCAAATAGTCTCTATTTGTAATTGAACTTATCCTAAAACAAATAGTTTATAAATGTG
109 GACCTTACTGGGTACACCCCTCTAACCAGTGCTTACAGGTTAATGCATGTTAATGAATATTT
110 GACGAAGCCTTCCCCATGAAACCCCACCACCACTGGCTAAAACTGGACACATCCTGCCT

Fig. 17D (Table 10.) Binding sequences and identifiers

| # | Sequence |
|---|----------|
| 111 | GACGTAGCACAGAAAAACCCTTTGACACAAACCATGTGTTCTGATTTTTGGTTCAGAAAATATT |
| 112 | GAGAGGACACTCCCGTTTTCGGTGCCATCAGTGCCCCGTCAGTGCCCCGTCTACAGCTCCCCCAGCTCCCCCC |
| 113 | GAGATTTTCTTTTAAGCCCTGCTCTTCTCTGAGAACCAAAAGATGCCTTGAATATTTATT |
| 114 | GAGCTGTGACCCATCCCAGGAGGACCTCAGAACAGTGTTTGATTTTATTTATAAATTTAAGCATTC |
| 115 | GAGTATTTGAAAGCAGGACTTCAGAACAGTGTTTGATTTTATTTATAAATTTAAGCATTC |
| 116 | GATAAGAATAGGTCATTTTCTATTCACCATCCTTTACTATTAAGGAAAAGAACACTA |
| 117 | GATGGGGTTTTCAAAGACCTCTCACAATATTAAATGCACTTCAATAATCATTGCTGTTTTATGT |
| 118 | GATTGAGATTGATTCAGATTTTTGCACTGTAGATGAGCGTATGTCTCAGTGCTGCCCAAG |
| 119 | GCAAGGCTTTAAATGACTTTGGAGAGAGGGTCACAAATCCTAAAAGAAGCATTGAAGTGAGGTG |
| 120 | GCACACTGCCTGAGGGACAACAGACATCAGAACAAACCCCAGAGAGAAACAGTCAAAATCAGG |
| 121 | GCACTCATAAAATATTTGTACAAGGAGTGAGTGGGGGAGAAATGAGCACAATATGGTTCTG |
| 122 | GCAGTCCTTTACTACAGCTATGAAGAAACGCAACAAGAAACTCAATGCAACAAAGGAT |
| 123 | GCCAATATTCCTTATTAATACAAACACAAAATCATTAACAAAATATTAGCAAACTGAAT |
| 124 | GCCCAGAGTCTGAAACTCCTGACTGGTCAGTGCTACTTAAGACCAGCTTGGGCAATTCA |
| 125 | GCCTCCCCCGCAGGTTATGTCAGCAGCTCTGAGACAGTATCACAGGCCAGATGTTG |
| 126 | GGAAAAGGCTGAGTCCACCGCTGTGCTCTAAGATCCCGAGGTGGAGCTGGTCACGCTGG |
| 127 | GGACCAGCTGACCAGGCTTGTGCTCAGAAGCAGACAAAACAAAGATTCAAGGTTTA |
| 128 | GGAGGAGAGCTCCTCTGCATGGTGCAGAGGGGCTGGGGCGCAGGGCGTTGGTGCCACTTCTTAAAGGCTGGAACC |
| 129 | GGCAGCTCCTCTCTGCATGGTGCAGAGGGGCTGGGCTCCTGGCTGCCAGGGCGTTGGTGCCACTTCTTAAAGGCTGGAACC |
| 130 | GGCTTGACTTGTAAGTTCAACCTAAACACAATCCTAGACACATCATGGATTTAGGAGTAGAT |
| 131 | GGGCAAAGGAGTTGGATTGCTGAATTACAATGCAACAATGTCTTATTACTAAAGAAAGTGATTTA |
| 132 | GGGCAGCCTTTTTTTTTTTCAGGAGGCCAGGCCTTCGTCAGGGAAGAACGTATAAGGG |
| 133 | GGGGGCTGCTTCTCAGGAGGCCAGGCCTTCGTCTGAGCGGAACCGTCCTGGAGAGAGCCTGC |
| 134 | GGTCATTGCCTTCATATAACATGCTTCGTCGTCATGGTCATTGCCTTCATATAACATGCT |
| 135 | GGTTTCTGGCCGTACTGTCGATTGGATGTGAAGTAGAAGAGGTCCTCGATCATGGTGTTAGAATTGACT |
| 136 | GTAAACTGGATACTGTCAGCCTCACAGAAGCAGCTCTGCCTCCACTTACCAGCTACGTTTTA |
| 137 | GTAAGATATATGCAGCCTCACAGAAGCAGCTCTGCCTCCACTTACCAGCTACGTTTTA |
| 138 | GTACAGTAGCTTTCAAACTGCAGTTTATTGCTAAGTTTTAGTATGGGTGATACTGGAGT |
| 139 | GTATTACTGTGATTCTCTGTAAGCTCCCATGTGGCCAAGGACCCCCTCCTACCAGGG |
| 140 | GTCTTTCTGGGGTTTTCTGTTTGGGTTTGGTTTGGTTTTTTATTCTCCTTTGTCCAA |
| 141 | GTGCAATGGTATAAATTTCAAGCTGGATATGTCTAATGGGTATTTAAACAATAAATGTGCAG |
| 142 | GTGCCTAAGCGGGGGGGGTGAAAGAGGACGTGTTACCCACTGCCATGCCACCAGGACTGGCTGTGT |
| 143 | GTGGAGGGGTATAAGAGGAGGGAGAGTCAGAGAGTCAGAAGAGTGTGTATGGTGTGTGAGTGTGAG |
| 144 | GTGTGTATGAGAGAGAGAGTGTGTTTGTGTTTCAAGGTCAGAACAGGTTTTTG |
| 145 | GTTATGTAGGGTTCTTCAGATGTAATATTTACTGGTACTATTTATTTATAAATAGGAATT |
| 146 | GTCTAATATATTGTATTTTATTTGATAGCTTGGGATTTAAAACATCTCTGTTGAAGCT |
| 147 | GTTGGGGCCTTTCTTTAACTGCCTTCCTGCCTTAGCTGCAGATGGCAGATGAGAGTGTAG |

Fig. 17E (Table 10.) Binding sequences and identifiers

| | |
|---|---|
| 148 | TAAAAATGGCAAAGAAGAAAGAGCCAGGACCCCGTGCCATCAAATCCTCCGGCCTTGTG |
| 149 | TAAACCTGCAGAACATTTACTTAAAAGAGGAAACACAAGATCTTCAATGAACGTCATCGG |
| 150 | TAAATAGTATTCACAAAAAGATTTCCTAGATTTTATCTATTGAATAGGTGTCAATATGG |
| 151 | TAAATTGACTGAGACTTGCAAAATACCCCTGAGAGTTGTCAGGGGTGTCTTCTGCCTGGTC |
| 152 | TAATTAGACCCCTCCCCTTGTGTCAACTCCGGCAGCTCAAGACACCCCGAGCAACATTTG |
| 153 | TACCAAATATAAGTGGATGCATTTTATTTTAGACACAAGACTTTATTTTCCACATCAT |
| 154 | TACGCTTGCTTGTCTTTAAATCTTCAATATGAAGGACTATTAATTCCAAGATTAAAGTTCAT |
| 155 | TACTGTACTGATACTATTCAATGCAATGACATTCAATGCAATGAAAACAAAATTCCATTAC |
| 156 | TAGAAGCGAGGGCACCCAGCAGTTGTGGGTGGGGAGCAAGGGAAGAGAGAAACTCTTCAGCGAA |
| 157 | TAGTGTCCCAGTACAAAAAGGCTGTAAGATAGTCAACCACAGTAGTCACCTATGTCTGT |
| 158 | TAGTTTGATAGAATCGAGAGTTAAGATGTTTCTATTTGAAAGTGGATTCAACCATCAGACC |
| 159 | TCAAAGAGGCTGAGGCTGGCACAGGACATGCGGTAGCCAGCACACAGGGCAGTGAGGGAGGG |
| 160 | TCACCAAAGCATCAGTGATGTTCTAGAAGCATCCCAGCAGTGGAGGATCCTAATGTATTGTTC |
| 161 | TCACTGACCTGCATGTGGGGCTGGGACCTGGCGACCTGGGACTGGTGCCCCTTGCTGA |
| 162 | TCACTTTTTAAACTCACATAGGTAGGTATCTTTATAGTTGTAGACTATGAATGTCAGTGTT |
| 163 | TCAGAAGTTTAAATATTAAGCATGACAGAAAATATGTATTAACACTACTCAAAGCAAAAGTG |
| 164 | TCATAGAAAGGAGCAACCAAATGTCTTCCTGCAGCTCACGCCACCAGCTACTGAAGGGACCCAAGG |
| 165 | TCCTGCCAAGCCAAATGTGCTTCCTGCAGCTCACGCCACCAGCTACTGAAGGGACCCAAGG |
| 166 | TCCTTGCTGCATTGTACAGTAGCTTTCAAACTCCAGTGTCCTTTATTGCTAAGTTTTAGTATGG |
| 167 | TCGGCATAGTTCTTGGCGTTAACATCTCAGTGTCCTCTTTAGTTCTCTTTGAGGATTCATG |
| 168 | TCGTCTGGCATCTCCCACACAAAGTTATCTCTTAACAAACTTACTCTTATTCTTAGCTGTATA |
| 169 | TCTAATAAAAGTCACAAACACTTATGCATCCAAAACACTGCAACATTCCAAGAATAGCATCTGTACAAAG |
| 170 | TCTCAGCAACAACACACTTATGCATCCAAAACACTGCAACATTCCAAGAATAGCATCTGTACAAAG |
| 171 | TCTCCTTCCTTGTTACCCATGAAAAACTGGCAACATTCCAAGAATAGCATCTGTACAAAG |
| 172 | TCTGCACATCTAGCCTCTGGCCCCTCCCTCTTCACTGCCTCCACCTGCTCCCGCTTGCCATCC |
| 173 | TCTTGGCGTTAACATCTCAGTGTCCTCTTAGTTCTCTTTGAGGATTCATGTCATTGAGGG |
| 174 | TCTTTGATAACAGGGATTGATTTTAAAATGTACATGTATTAAAATTACATTTGTAATTTAAGG |
| 175 | TGAAAGAAAAATGGGTAACAGAAGAAACCCTTAAAACAGGTTAATTTGGATTGTAACGTTCAG |
| 176 | TGAAAGTATTCCAGGAACAGTGAATGGTAGAAGACACAAGAACATTTGTTGTTTGTCTTC |
| 177 | TGACAGTGCAGCCAGCCTTCAGTCTGTGCCAAGTCTGTGCCAAGAGCCCCTGGCAACCAACCCAC |
| 178 | TGACATAACCAATTTGTAATGATTTGGAACTGTGTTCAAATGGACTGTTACAGACTGAA |
| 179 | TGAGCCCCACGTGGACTCGGGACGTAGTAGACAGCAATAACTCGGTGTGTGGCCGC |
| 180 | TGAGGACTTGTGTCTCTGTCTTTAAATGCATAAATGCATTATAGGATCATTTGTTGGAAT |
| 181 | TGATGAGGCACATTCAGAACAAATGCTTTTTTTTGAGACAGAGTCTCGCTCTGACGCC |
| 182 | TGATTGAGGGGGAAAAGAATGATCTTTATTAATGACAAGGGAAACCATGAGTAATGCCACAAT |
| 183 | TGCAGAGTGGTAACCATGCTTACACACTAAACTATAATATAAAGGAAATGAAGCCATGTTA |
| 184 | TGCTCTCTTGAAATCTTAAATATGATTATTTGAGCTCATATAAGGTGGATTGGAGCAGAT |

Fig. 17F     (Table 10.) Binding sequences and identifiers

185 TGCTGGTAAAGTATTTTGGTGGCAGCTGCCATCATGGTCATTGCCTTCATATAACATGCT
186 TGGAAGCATACTGAAAGTGTCTTGGTGGGCCTGAGCCAAGCACAGGTGTTTGAGGACTACAGTT
187 TGGACGCAGCCACACAGTGGCCGGGGCTGAAGCCACACAGCCCAGAAGGCCAGAAAAGG
188 TGGATGGAAGTGTCTGGAAAGGGCACGAGAGAGTCTTCCAGGTACTGATCCTGTTTCTTGCTCT
189 TGGGACCTCCCCCAGACCCCAGAGAAAAACTGGAAGCCTTCCCCAGCCAAGGCAGAAGCTTGGAGG
190 TGGTGTAGGGGCTTAGAGGCATGGGCTTGCTGTGGTTTTTAATTGATCAGTTTCATGTGG
191 TGTAATTGTAGCATCAAAATGACAACAGCAGACAGAGCAGCGAATCTTGCACAGCCCACAGCA
192 TGTCTCTGGAGAAAAGGGCTAGAGCTGCCTTTACAACTGTAACCACTGTAATGAGAAGGCAC
193 TGTCTGACCTACATTGGGCTTTCTCAGAAACTTTGAACGATCCCATGCAAAGAATTCCCACCCTG
194 TGTGTGTGGGTTGTCTGTGTGTCATATGTCCTGCCCGTGTATATGCACCCACACCATGTGC
195 TGTTATTTAACCTGAGTATAGTATTTAACGAAGCCTAGAAGCACGGCTGTGGGTGGTGA
196 TGTTTATGCATTCACAAGGTGACTGGGATGTAGAGAGGCGTTAGTGGGCAGGTGGCCACAGCA
197 TTAAACTCCTTAAACAGTTTAGAAAATTAGCTCCAGGTTCTTAACTAACAAAATAAAACCT
198 TTAACATTTGTTTTTAGTTAAAAGTATCTACTTACTGTTTTAGCTCTGAACTCAAACCAGAA
199 TTACAGCTGGTTCTGAGCCGCTTGCCTTGTGATGGTAAGACACCAACCTTTACATTCTTCCC
200 TTAGTACAGACTGTGACGCCCCAGTGTGGCTTGCAGGTAGTGGCAGCGGAAGCATGTGG
201 TTCAATTACCTCCCCCTGGGTCTGGGTCTCTCCCACAACACGTGGGAATTCTGGAGATACAATTCA
202 TTCAATTACCTCCCCTTGGGTCTCTCCCACAACACGTGGGAATTCTGTAGATACAATTTC
203 TTCAGGCATAAATTAGAGAAATGGTTCTGGATATGGTCAAAATGAGTTTTCACCTGGTATC
204 TTCAGGTTCAGTATTATGTAGTTGTTCGTTGGTTATACAAGTTCTTGGTCCCTCCAGAAC
205 TTCATATATGAGGACTTGTGTCTCTGTGCTTTAAATGCATAAATGCATTATAGGATCATTT
206 TTGTATACACATTTGCATATACCCACATGGGGACATAAGCTAATTTTTACAGGACACAGA
207 TTGTCACTGAGAAGATGTTTATTTGGTCAGTTGGGTTTTATGTATTATACTAGTCAAAT
208 TTGTGAAATATTAAATGCAAATTTACAACTGCAGATGACGTATGTGCCTTGAACTGAATATT
209 TTGTGATTCTGAGCTTGCAATGCCGCCAAGCGCCCCAGCGCCCCGCCCCGGTTGTCCAC
210 TTGTGATTTAGATGTATCCATCCTTTTCTATTAAGAATACAAATGCTGGGCTGGGCACAGT
211 TGTTTCTAGTTGGGTAACTACACACAATGCTTATGACACAACAATGACACATTTGTTGCACCAA
212 TTATTAAATCTGAATTTAAAACATGCTTCAGAAAGGACAAGTCAGATAGAAATAGTCCCTGAGA
213 TTTCAACGCTGATTTTAAAACGCCCAACCTTCAGAAAGGACAAGTCAGATAGAAATAGTCCCTGAGA
214 TTTCCAAACAAATCTTTCTACGCTTAAATGATCAAATTAGAAAAACCAATTCCTATAATTAAT
215 TTTCCAGTAGGAAAAGCAATGCTTTCTTGTCTTTAGACTCAAATGCTTAGGGAACGTTTCAT
216 TTTCCATACTCCTGAGCTTTGGGAGGGAGACAGTGGCCAAGTAGCAGGCAGAATAAGATC
217 TTTCCCATGAGATGAAGCACATGTTTAAACCTGACGAATACGGACTAGATAACCTCTAAGAATTTCA
218 TTTCTACAAGTTCAGAATATTTAAACCTGATTTACTAGACCTGGGAATTTCAACATGG
219 TTTCTGTGCTTGCTTCGGCAGCATATTTCCAGAATAGTGTTTAGCTCACCTAGGGGGATATGTTTTTA
220 TTTGGGTAGAGGATACTATTTCCAGAATAGTGTTTAGCTCACCTAGGGGGATATGTTTGTA
221 TTTTAACTAATAAGGCGAGAAAGAGGGAAGTTGGAGAGGGAAAAGTTAGCCCAGAAGGAAAG

Fig. 17G (Table 10.) Binding sequences and identifiers

222 TTTTTTTCATTATTCTAAAACTCTTGTTGTTAGATACAAGATTTAATTAAGATCTAAGCTC
223 TTTTTTTTGACGTATTATTGACAAATGTATTCAGGCGCCATACACAAGAGAGAAATATTATTAC

Fig. 18A (Table 11) Disease identification and code.

disease_id  disease
1 Acetyl-CoA carboxylase deficiency
2 Adrenoleukodystrophy, pseudoneonatal
3 Allan-Herndon-Dudley syndrome
4 Alpha-thalassemia myelodysplasia syndrome, somatic
5 Alpha-thalassemia/mental retardation syndrome
6 Amyotrophic lateral sclerosis 8
7 Angelman syndrome
8 Aortic aneurysm, familial thoracic 4
9 Arrhythmogenic right ventricular dysplasia 1
10 Atopy
11 Azoospermia
12 Bartter syndrome, type 2
13 Bruck syndrome 2
14 Cardiomyopathy, hypertrophic, midventricular, digenic
15 CD59 deficiency
16 Chediak-Higashi syndrome
17 Cherubism
18 Chronic granulomatous disease due to deficiency of NCF-2
19 Chudley-Lowry syndrome
20 Colon cancer, advanced
21 Congenital disorder of glycosylation, type IIc
22 Cortisol resistance
23 Cortisone reductase deficiency
24 Deafness, autosomal dominant 28
25 Deafness, autosomal dominant nonsyndromic sensorineural
26 Deafness, autosomal recessive 28
27 Dejerine-Sottas neuropathy, autosomal recessive
28 Ectodermal dysplasia, anhidrotic
29 Factor V and factor VIII, combined deficiency of
30 Factor VII deficiency
31 Fanconi anemia, complementation group C
32 Fanconi anemia, complementation group M
33 Feingold syndrome
34 Fraser syndrome
35 Generalized epilepsy and paroxysmal dyskinesia
36 Growth retardation with deafness and mental retardation due to IGF1 deficiency
37 HDL deficiency, familial
38 Hemophilia A
39 Holocarboxylase synthetase deficiency
40 Holt-Oram syndrome
41 Homocystinuria due to MTHFR deficiency
42 Homocystinuria-megaloblastic anemia, cbl E type
43 Huntington disease
44 Hypercholesterolemia, familial, autosomal recessive
45 Hyperornithinemia-hyperammonemia-homocitrullinemia syndrome
46 Hyperparathyroidism, neonatal
47 Hypocalcemia, autosomal dominant
48 Hypocalcemia, autosomal dominant, with Bartter syndrome
49 Hypocalciuric hypercalcemia, type I Fig. 18B  (Table 11) Disease identification and code.

50 Hypothyroidism, congenital, due to thyroid dysgenesis or hypoplasia
51 ICOS deficiency
52 Jervell and Lange-Nielsen syndrome
53 Johanson-Blizzard syndrome
54 Juberg-Marsidi syndrome
55 Knobloch syndrome
56 Leukemia, acute myeloid
57 Leukemia, acute myeloid, with eosinophilia
58 Leukemia, acute nonlymphocytic
59 Leukemia, acute T-cell lymphoblastic
60 Leukemia, juvenile myelomonocytic
61 Leukemia, T-cell acute lymphoblastic
62 Leukemia, T-cell acute lymphocytic
63 Leukemia-1, T-cell acute lymphocytic
64 Leukemia/lymphoma, B-cell, 2
65 LIG4 syndrome
66 Loeys-Dietz syndrome
67 Long QT syndrome-5
68 Lung cancer
69 Lymphoma/leukemia, B-cell, variant
70 Macular corneal dystrophy
71 MALT lymphoma
72 Mental retardation, autosomal recessive 1
73 Mental retardation, X-linked
74 Mental retardation, X-linked nonspecific, 63
75 Mental retardation, X-linked nonspecific, type 46
76 Mental retardation, X-linked, FRAXE type
77 Mental retardation, X-linked, with progressive spasticity
78 Mirror-image polydactyly
79 Mitochondrial DNA depletion myopathy
80 Molybdenum cofactor deficiency, type A
81 Mucoepidermoid salivary gland carcinoma
82 Mucolipidosis IIIC
83 Multiple sulfatase deficiency
84 Muscular dystrophy, rigid spine, 1
85 Myeloid malignancy, predisposition to
86 Myeloproliferative disorder
87 Nance-Horan syndrome
88 Nucleoside phosphorylase deficiency, immunodeficiency due to
89 Obesity, hyperphagia, and developmental delay
90 Obesity, severe
91 Optic atrophy 1
92 Orthostatic intolerance
93 Paget disease of bone
94 Pancreatic cancer, somatic
95 Paragangliomas, familial nonchromaffin, 3
96 Parkinson disease, early onset
97 Pituitary tumor, invasive
98 Platelet disorder, familial, with associated myeloid malignancy
99 Polycystic kidney disease, adult, type II Fig. 18C                        (Table 11) Disease identification and code.

100 PPM-X syndrome
101 Pulmonary hypertension, familial primary
102 Renal cell carcinoma, papillary, 1
103 Retinitis pigmentosa-1
104 Rett syndrome
105 Rett syndrome, preserved speech variant
106 Sanfilippo syndrome, type A
107 Sarcoma, synovial
108 Smith-Fineman-Myers syndrome
109 Smith-Magenis syndrome
110 Sorsby fundus dystrophy
111 Spastic paraplegia-4
112 Spastic paraplegia-6
113 Spinal muscrular atrophy, late-onset, Finkel type
114 Spinocerebellar ataxia 12
115 Stocco dos Santos X-linked mental retardation syndrome
116 Succinic semialdehyde dehydrogenase deficiency
117 Sutherland-Haan syndrome-like
118 T-cell immunodeficiency, congenital alopecia, and nail dystrophy
119 Tangier disease
120 Thiamine-responsive megaloblastic anemia syndrome
121 Thrombophilia due to thrombomodulin defect
122 Timothy syndrome
123 Troyer syndrome ent.
MICRORNAOME This invention was made using funds from the U.S. National Institutes of Health under grant no. CA 43460. Under terms of the grant, the United States Government retains certain rights in the invention.

TECHNICAL FIELD OF THE INVENTION

This invention is related to the area of microRNAs. In particular, it relates to the use of microRNAs for the diagnosis and treatment of cancer.

BACKGROUND OF THE INVENTION

MicroRNAs (miRNAs) are ≈22-nt noncoding RNAs that are processed from larger (≈80-nt) precursor hairpins by the RNase III enzyme Dicer into miRNA:miRNA* duplexes (1-3). One strand of these duplexes associates with the RNA-induced silencing complex (RISC), whereas the other is generally degraded (1). The miRNA-RISC complex targets messenger RNAs for translational repression or mRNA cleavage. There has been considerable debate about the total number of miRNAs that are encoded in the human genome. Initial estimates, relying mostly on evolutionary conservation, suggested there were up to 255 human miRNAs (4). More recent analyses have demonstrated there are numerous nonconserved human miRNAs and suggest this number may be significantly larger (5).

Both cloning and bioinformatic approaches have been used to identify miRNAs. Direct miRNA cloning strategies identified many of the initial miRNAs and demonstrated that miRNAs are found in many species (6-16). However, the throughput of this approach is low, and cloning approaches have appeared to approach saturation (8). Bioinformatic strategies have recently been used to identify potential miRNAs predicted on the basis of various sequence and structural characteristics (4, 7). However, such gene predictions may not point to all legitimate miRNAs, especially those that are not phylogenetically conserved, and all in silico predictions require independent experimental validation.

There is a continuing need in the art to identify additional miRNAs and to exploit their regulatory functions for human health.

SUMMARY OF THE INVENTION

One aspect of the invention is a composition comprising an isolated DNA or RNA polynucleotide comprising a sequence of approximately 18-26 nucleotides having a sequence of a miRNA shown in Table 5 or the complement of a sequence shown in Table 5 or a sequence which is at least 80% identical to said miRNA or complement.

Another aspect of the invention is a pharmaceutical composition comprising an isolated DNA or RNA polynucleotide. The polynucleotide comprises a sequence of approximately 18-26 nucleotides of a miRNA shown in Table 3 or Table 5 or the complement of a sequence shown in Table 3 or Table 5. The isolated DNA or RNA polynucleotide is between 18 and 200 nucleotides inclusive. The polynucleotide may optionally be in a sterile and pyrogen-free vehicle suitable for injection into a human.

Yet another aspect of the invention is an isolated cell line comprising homozygous RNaseIII enzyme Dicer-deficient human cells. The cells display a hypomorphic phenotype. The helicase domain of RNaseIII enzyme Dicer is disrupted.

Still another embodiment of the invention is a pair of isogenic cells. The first cell of said pair of cells is a homozygous RNaseIII enzyme Dicer-deficient human cell which displays a hypomorphic phenotype. The helicase domain of RNaseIII enzyme Dicer of the first cell is disrupted. The second cell is homozygous RNaseIII enzyme Dicer-proficient.

Another embodiment of the invention provides a method of diagnosing a cancer in a patient. The presence of an miRNA or miRNA precursor is detected in a body fluid or tumor specimen from the patient. The miRNA or miRNA precursor is expressed in tumor tissue or cell lines but not in normal tissue, as shown in Table 5. A cancer is identified in the patient when the miRNA or miRNA precursor is detected in the body fluid or tumor specimen from the patient.

Another aspect of the invention is a method of diagnosing a cancer in a patient. Presence or absence of an miRNA or its precursor in a body fluid or tumor specimen from the patient is detected by assaying. The miRNA or its precursor is one which is expressed in normal tissue but not in tumor tissue or cell lines, as shown in Table 5. A cancer in the patient is identified when absence of the miRNA is detected in the body fluid or tumor specimen.

According to one embodiment of the invention a method of diagnosing a colorectal cancer is provided. A miRNA selected from those shown in Table 3 or Table 5 is detected in a test sample of a human and in a normal sample. The amount detected in the test sample is compared to that detected in the normal sample. A ratio of less than 0.7 or greater than 1.4 indicates a colorectal cancer in the human.

According to another embodiment of the invention a method is provided for treating a colorectal cancer in a human. (a) an miRNA selected from those shown in Table 3 with a tumor to normal ratio of less than 0.7; or (b) an miRNA* selected from those shown in Table 3 with a tumor to normal ratio of greater than 1.4 is delivered to the human. Growth of the tumor is thereby arrested, slowed, or reversed.

Still another aspect of the invention is a method of experimentally validating a candidate miRNA. Generation of the candidate miRNA is determined in an isogenic pair of cells which differ in the dicer locus, wherein a first of the pair of cells is hypomorphic for RNaseIII enzyme Dicer activity and a second of the pair of cells has wild-type RNaseIII enzyme Dicer activity. The determined generation of the candidate miRNA in the first of the pair of cells is compared to the determined generation of the candidate miRNA in the second of the pair of cells. A statistically significant reduction of generation of the candidate miRNA in the first relative to the second provides experimental validation that the candidate miRNA is a physiologically relevant miRNA.

Still another embodiment of the invention provides a method of screening for test agents which affect miRNA generation. A test agent is contacted with a cancer cell. Generation of an miRNA in the cancer cell contacted with the test agent is determined. The miRNA is one whose generation is increased or decreased in cancer cells relative to normal cells. The determined generation of the miRNA in the cells contacted with the test agent is compared to generation of the miRNA in cells not contacted with the test agent. A test agent is identified as a potential therapeutic agent if it increases the amount of an miRNA whose generation is decreased in cancer cells or if it decreases the amount of an miRNA whose generation is increased in cancer cells.

According to yet another aspect of the invention a method is provided for identifying candidate agents that target a biosynthetic pathway for generating miRNA molecules or that target generation of an miRNA molecule. A test agent is contacted with a pair of isogenic cells as described above. Generation of an miRNA in the first and second isogenic cells contacted with the test agent is compared to generation of the miRNA in the first and second cells not contacted with the test agent. A test agent is identified as a candidate for affecting the biosynthetic pathway for generating miRNA molecules or generation of the miRNA if the test agent significantly affects generation of the miRNA in the second cell but not in the first cell.

According to another embodiment a method is provided of inhibiting expression of a target gene in a cell. A nucleic acid as described above is introduced into the cell in an amount sufficient to inhibit expression of the target gene. The target gene comprises a binding site substantially identical to a binding site as shown in Table 10 and SEQ ID NOS: 1652-1874.

According to another embodiment, a method is provided of increasing expression of a target gene in a cell. A nucleic acid as described above is introduced into the cell in an amount sufficient to increase expression of the target gene. The target gene comprises a binding site substantially identical to a binding site as shown in Table 10 and SEQ ID NOS: 1652-1874.

Yet another embodiment of the invention provides a method of treating a patient with a disorder listed in Table 9. A composition comprising a nucleic acid as described above is administered to the patient. The symptoms of the disorder are thereby ameliorated.

These and other embodiments which will be apparent to those of skill in the art upon reading the specification provide the art with new tools for diagnosis and therapy of cancer.

BRIEF DESCRIPTION OF THE DRAWINGS

FIG. 8. (Table 1.) Evaluation of differentially expressed candidate miRNAs by miRAGE.

FIG. 9A to 9F. (Table 2.) miRAGE tags of known miRNAs observed in colorectal cells (SEQ ID NO: 1-200).

FIG. 10. (Table 3.) Differential expression of known miRNAs in tumor versus normal tissue.

FIG. 11A to 11E. (Table 4.) miRNA* forms in colorectal cells (SEQ ID NO: 201-336).

FIG. 12A to 12J. (Table 5.) One hundred thirty-three candidate novel miRNAs: structure, validation, expression, and genomic organization (SEQ ID NO: 337-469 for mature miRNAs and SEQ ID NO: 1386-1518 for precursor miRNAs).

FIG. 13A to 13I. (Table 6.) Microarray expression validation of selected miRNA candidates and known miRNAs (SEQ ID NO:470-909 for miRNAs and SEQ ID NO: 910-1349 for probes)

FIG. 14A to 14B. (Table 7.) qRT-PCR validation of selected miRNA candidates (SEQ ID NO: 1350-1385 for tags).

FIG. 15. (Table 8.) Differential expression of known miRNAs in DicerEx5 versus WT.

FIG. 16A to 16D. (Table 9.) Provides the corresponding DNA sequence for the 133 novel miRNAs, the name of the target gene that each regulates, the identifier code for the binding sequence within the target gene (the identifier code and the binding sequence are identified in Table 10), and the identifier code for the disease which is associated with misregulation of the target gene (the identifier code and the disease are identified in Table 11). The DNA sequences of the 133 novel miRNAs are shown in SEQ ID NO: 1519-1651.

FIG. 17A to 17G. (Table 10.) Identifies the binding sequence identifier code and the corresponding binding sequence. These are shown in SEQ ID NO: 1652-1874.

FIG. 18A to 18C. (Table 11.) Identifies the disease identifier code and the corresponding disease.

DETAILED DESCRIPTION OF THE INVENTION

Figure 1A:
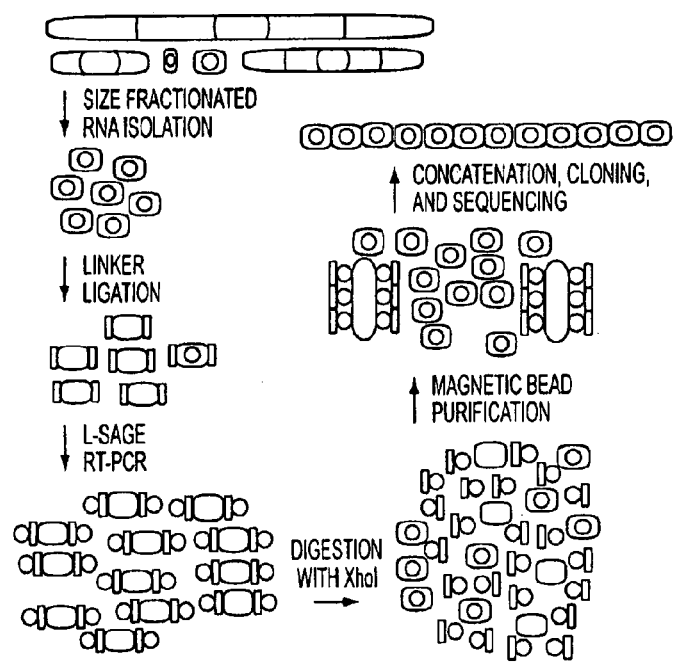
FIG. 1. miRAGE approach for isolation of miRNAs. (A) Schematic of miRAGE method. The approach involves isolation of small RNA species (red ovals), followed by ligation of specialized linkers (white rectangles) that enable robust RT-PCR with biotinylated primers (blue circles). Linkers are enzymatically cleaved and removed by binding to streptavidin-coated magnetic beads (yellow ovals). Released tags are concatenated, cloned, and sequenced. (B) Bioinformatic analyses of miRAGE tags. Tags were grouped together based on a 12-bp internal core sequence. The most highly represented tag in each group was then compared to various RNA databases. Tags not matching known RNA sequences were compared to the human genome and analyzed for precursors with thermodynamically stable hairpin structures.

To increase the efficiency of discovery of small RNA species, the inventors have developed an approach called miRNA serial analysis of gene expression (miRAGE). This approach combines aspects of direct miRNA cloning and SAGE (17). Similar to traditional cloning approaches, miRAGE starts with the isolation of 18- to 26-base RNA molecules to which specialized linkers are ligated, and which are reverse-transcribed into cDNA (FIG. 1A). However, subsequent steps, including amplification of the complex mixture of cDNAs using PCR, tag purification, concatenation, cloning, and sequencing, have been performed by using SAGE methodology optimized for small RNA species. This approach has the advantage of generating large concatemers that can be used to identify as many as 35 tags in a single sequencing reaction, whereas existing cloning protocols analyze on average approximately five miRNAs per reaction (8).

The inventors have found many new miRNA species and have found that many of these as well as many previously described miRNA species are differentially expressed between colorectal cancer cells and in normal cells. Thus these miRNA species can be used inter alia diagnostically to differentiate between cancer and normal cells. In order to identify clear and statistically significant differences, one can set limits on the ratio of expression of such species in cancer to normal. A ratio of less than 0.7 or greater than 1.4 of test sample to normal can be used. More stringent ratios which can be used are less than 0.6 or greater than 1.5, less than 0.5 or greater than 1.6, less than 0.4 or greater than 1.7. More lenient ratios which can be used include less than 0.8 or greater than 1.3, less than 0.9 or greater than 1.2. Moreover, if an miRNA species is not expressed in normal tissue or cells but is expressed in cancer cells or tissues, then its detection in test tissue or cells is indicative of cancer.

miRNAs can also be used to assess the effects of drugs and drug candidates on miRNA metabolism and generation pathways. Each can be used individually or cumulatively to confirm the effect of a drug or drug candidate on miRNA metabolism generally and on the extent of the effects of a drug or drug candidate. Some drugs or drug candidates may only affect a subset of miRNAs whereas some may affect such metabolism globally.

Test samples from patients having or suspected of having tumors, especially colorectal tumors, can be obtained from biopsies, body fluids (e.g., urine, blood, serum, plasma, tears, saliva) or stool. miRNA species can be detected using hybridization based techniques, such as microarrays, primer extension, PCR, and others.

The miRNAs and their complements (miRNA*s) which are identified herein as differentially expressed, see especially Table 3 and/or Table 5, can be used therapeutically. Either a miRNA or a miRNA precursor or a miRNA* can be delivered to a human with cancer, e.g., colorectal cancer. If the particular miRNA is overexpressed in cancer (relative to normal) then the complement or miRNA* can be administered. If the miRNA is underexpressed in cancer, then the miRNA or its precursor (hairpin loop structure) can be administered. Methods for delivering therapeutic RNA molecules are known in the art and any can be used. Optionally the mRNAs or miRNA*s, or precursors can be formulated in a sterile and pyrogen-free vehicle that is suitable for injection into a human. Such polynucleotides can between about 17 and 250 nucleotides and will contain the sequence of an miRNA or its complement, consisting of between about 17 and 26 nucleotides. The size of the polynucleotide can be at least 18, 19, 20, 21, 22, 23, 24, or 25 nucleotides. The size of the polynucleotide can be less than 225, 200, 175, 150, 125, 100, 75, 50, 40, or 30 nt, for example. The polynucleotide can also be used in a DNA form (having the same base sequence, substituting thymines for uracils).

The miRNAs and their complements (miRNA*s) which are identified herein as differentially expressed can also be used as probes or primers for detection and diagnosis. When used in a hybridization mode, probes or primers can be at least about 80, 82, 84, 86, 88, 90, 91, 92, 93, 94, 95, 96, 97, 98, or 99% identical to the miRNAs as disclosed here. A small amount of allelic variation is common among members of a species and a small amount of non-identical nucleotides in a probe or primer with typically not prevent hybridization. Probes and primers may be labeled, or may not be. They can be tethered to another substance or they may be tetherable to another substance for detection purposes. The arts of hybridization and amplification and detection are very well developed and many variations are known in how these are actually carried out.

The inventors have also developed hypomorphic mutant cell lines for the RNaseIII enzyme Dicer. These cell lines can be in any genetic background of a human cell, however, advantageously cancer cell lines, such as HCT116, DLD1, RKO, CACO-2, and SW480, can be used. Hypomorphic Dicer phenotype cell lines have disruptions in exon 5. Pairs of isogenic cell lines comprising such hypomorphic Dicer cell lines and their isogenic parents can also be used advantageously for substance screening. The isogenic cell lines can be packaged together in a common container, but will typically be kept in separate vessels so that they will not be mixed. As described in the experimental section below, the isogenic cell lines can also be used to confirm and validate the biological relevance of a candidate miRNA. If a miRNA species is dependent (totally or partially) on Dicer for its expression, then it is highly likely to be a physiological or biologically relevant miRNA.

MicroRNA.

A gene coding for a miRNA may be transcribed leading to production of an miRNA precursor known as the pri-miRNA. The pri-miRNA may be part of a polycistronic RNA comprising multiple pri-miRNAs. The pri-miRNA may form a hairpin with a stem and loop. The stem may comprise mismatched bases.

The hairpin structure of the pri-miRNA may be recognized by Drosha, which is an RNase III endonuclease. Drosha may recognize terminal loops in the pri-miRNA and cleave approximately two helical turns into the stem to produce a 60-70 nt precursor known as the pre-miRNA. Drosha may cleave the pri-miRNA with a staggered cut typical of RNase III endonucleases yielding a pre-miRNA stem loop with a 5' phosphate and ~2 nucleotide 3' overhang. Approximately one helical turn of stem (~10 nucleotides) extending beyond the Drosha cleavage site may be essential for efficient processing. The pre-miRNA may then be actively transported from the nucleus to the cytoplasm by Ran-GTP and the export receptor Ex-portin-5.

The pre-miRNA may be recognized by Dicer, which is also an RNase III endonuclease. Dicer may recognize the double-stranded stein of the pre-miRNA. Dicer may also recognize the 5' phosphate and 3' overhang at the base of the stem loop. Dicer may cleave off the terminal loop two helical turns away from the base of the stem loop leaving an additional 5' phosphate and ~2 nucleotide 3' overhang. The resulting siRNA-like duplex, which may comprise mismatches, comprises the mature miRNA and a similar-sized fragment known as the miRNA*.

The miRNA and miRNA* may be derived from opposing arms of the pri-miRNA and pre-miRNA. MiRNA* sequences may be found in libraries of cloned miRNAs but typically at lower frequency than the miRNAs.

Although initially present as a double-stranded species with miRNA*, the miRNA may eventually become incorporated as single-stranded RNAs into a ribonucleoprotein complex known as the RNA-induced silencing complex (RISC). Various proteins can form the RISC, which can lead to variability in specificity for miRNA/miRNA* duplexes, binding site of the target gene, activity of miRNA (repress or activate), which strand of the miRNA/miRNA* duplex is loaded in to the RISC.

When the miRNA strand of the miRNA:miRNA* duplex is loaded into the RISC, the miRNA* may be removed and degraded. The strand of the miRNA:miRNA* duplex that is loaded into the RISC may be the strand whose 5' end is less tightly paired. In cases where both ends of the miRNA: miRNA* have roughly equivalent 5' pairing, both miRNA and miRNA* may have gene silencing activity.

The RISC may identify target nucleic acids based on high levels of complementarity between the miRNA and the mRNA, especially by nucleotides 2-8 of the miRNA. Only one case has been reported in animals where the interaction between the miRNA and its target was along the entire length of the miRNA. This was shown for mir-196 and Hox B8 and it was further shown that mir-196 mediates the cleavage of the Hox B8 mRNA (Yekta et al 2004, Science 304-594). Otherwise, such interactions are known only in plants (Bartel & Bartel 2003, Plant Physiol 132-709).

A number of studies have looked at the base-pairing requirement between miRNA and its mRNA target for achieving efficient inhibition of translation (reviewed by Bartel, 2004, Cell 116-281). In mammalian cells, the first 8 nucleotides of the miRNA may be important (Doench & Sharp 2004 Genes Dev 2004-504). However, other parts of the microRNA may also participate in mRNA binding. Moreover, sufficient base pairing at the 3' can compensate for insufficient pairing at the 5' (Brennecke at al, 2005 PLoS 3-e85). Computation studies, analyzing miRNA binding on whole genomes have suggested a specific role for bases 2-7 at the 5' of the miRNA in target binding but the role of the first nucleotide, found usually to be "A" was also recognized (Lewis et at 2005 Cell 120-15). Similarly, nucleotides 1-7 or 2-8 were used to identify and validate targets by Krek et al (2005, Nat Genet 37-495).

The target sites in the mRNA may be in the 5' UTR, the 3' UTR or in the coding region. Interestingly, multiple miRNAs may regulate the same mRNA target by recognizing the same or multiple sites. The presence of multiple miRNA complementarity sites in most genetically identified targets may indicate that the cooperative action of multiple RISCs provides the most efficient translational inhibition.

MicroRNAs may direct the RISC to downregulate gene expression by either of two mechanisms: mRNA cleavage or translational repression. The miRNA may specify cleavage of the mRNA if the mRNA has a certain degree of complementarity to the miRNA. When a miRNA guides cleavage, the cut may be between the nucleotides pairing to residues 10 and 11 of the miRNA. Alternatively, the miRNA may repress translation if the miRNA does not have the requisite degree of complementarity to the miRNA.

There may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

Nucleic Acid.

A nucleic acid variant may be a complement of the referenced nucleotide sequence. The variant may also be a nucleotide sequence that is substantially identical to the referenced nucleotide sequence or the complement thereof. The variant may also be a nucleotide sequence which hybridizes under stringent conditions to the referenced nucleotide sequence, complements thereof, or nucleotide sequences substantially identical thereto. The nucleic acid may have a length of from 10 to 250 nucleotides. The nucleic acid may have a length of at least 10, 11, 12, 13, 14, 15, 16, 17, 18, 19, 20, 21, 22, 23, 24, 25, 26, 27, 28, 29, 30, 35, 40, 45, 50, 60, 70, 80 or 90 nucleotides and a length of less than 20, 21, 22, 23, 24, 25, 26, 27, 28, 29, 30, 35, 40, 45, 50, 60, 70, 80 or 90 nucleotides. The nucleic acid may be synthesized or expressed in a cell (in vitro or in vivo) using a synthetic gene described below. The nucleic acid may be synthesized as a single strand molecule and hybridized to a substantially complementary nucleic acid to form a duplex, which is also considered a nucleic acid of the invention. The nucleic acid may be introduced into a cell, tissue or organ in a single- or double-stranded form or capable of being expressed by a synthetic gene using methods well known to those skilled in the art, including as described in U.S. Pat. No. 6,506,559 which is incorporated by reference.

Pri-miRNA

The nucleic acid of the invention may comprise a sequence of a pri-miRNA or a variant thereof. The pri-miRNA sequence may comprise from 45-30,000 nucleotides, with examples of lengths of 45-250, 55-200, 70-150, 80-100, 45-90, 60-80, and 60-70 nucleotides. The sequence of the pri-miRNA may comprise a pre-miRNA, miRNA and miRNA* as set forth below. The pri-miRNA may also comprise a miRNA or miRNA* and the complement thereof, and variants thereof. The pri-miRNA may comprise at least 19% adenosine nucleotides, at least 16% cytosine nucleotides, at least 23% thymine nucleotides and at least 19% guanine nucleotides.

The pri-miRNA may form a hairpin structure. The hairpin may comprise a first and second nucleic acid sequence that are substantially complimentary. The first and second nucleic acid sequence may be from 30-200 nucleotides. The first and second nucleic acid sequence may be separated by a third sequence of from 8-12 nucleotides. The hairpin structure may have a free energy less than −25 Kcal/mole as calculated by the Vienna algorithm with default parameters, as described in Hofacker et al., Monatshefte f. Chemie 125: 167-188 (1994), the contents of which are incorporated herein. The hairpin may comprise a terminal loop of, for example, 4-20, 8-12 or 10 nucleotides.

MiRNA

The nucleic acid of the invention may also comprise a sequence of a miRNA, miRNA* or a variant thereof. The miRNA sequence may comprise from 13-33, 18-24 or 21-23 nucleotides. The sequence of the miRNA may be the first 13-33 nucleotides of the pre-miRNA. The sequence of the miRNA may be the last 13-33 nucleotides of the pre-miRNA.

Anti-miRNA

The nucleic acid of the invention may also comprise a sequence of an anti-miRNA that is capable of blocking the activity of a miRNA or miRNA*. The anti-miRNA may comprise a total of 5-100 or 10-60 nucleotides. The anti-miRNA may also comprise a total of at least 5, 6, 7, 8, 9, 10, 11, 12, 13, 14, 15, 16, 17, 18, 19, 20, 21, 22, 23, 24, 25 or 26 nucleotides. The sequence of the anti-miRNA may comprise (a) at least 5 nucleotides that are substantially identical to the 5' of a miRNA and at least 5-12 nucleotide that are substantially complimentary to the flanking regions of the target site from the 5' end of said miRNA, or (b) at least 5-12 nucleotides that are substantially identical to the 3' of a miRNA and at least 5 nucleotide that are substantially complimentary to the flanking region of the target site from the 3' end of the miRNA. The sequence of the anti-miRNA may comprise the compliment of a sequence of a miRNA disclosed herein or variants thereof.

Binding Site of Target

The nucleic acid of the invention may also comprise a sequence of a target miRNA binding site, or a variant thereof. The target site sequence may comprise a total of 5-100 or 10-60 nucleotides. The target site sequence may comprise at least 5 nucleotides of the sequence of a target gene binding site or variants thereof.

Synthetic Gene

The present invention also relates to a synthetic gene comprising a nucleic acid of the invention operably linked to transcriptional and/or translational regulatory sequences. The synthetic gene may be capable of modifying the expression of a target gene with a binding site for the nucleic acid of the invention. Expression of the target gene may be modified in a cell, tissue or organ. The synthetic gene may be synthesized or derived from naturally-occurring genes by standard recombinant techniques. The synthetic gene may also comprise terminators at the 3'-end of the transcriptional unit of the synthetic gene sequence. The synthetic gene may also comprise a selectable marker.

Vectors.

The present invention also relates to a vector comprising a synthetic gene of the invention. The vector may be an expression vector. An expression vector may comprise additional elements. For example, the expression vector may have two replication systems allowing it to be maintained in two organisms, e.g., in mammalian or insect cells for expression and in a prokaryotic host for cloning and amplification. For integrating expression vectors, the expression vector may contain at least one sequence homologous to the host cell genome, and preferably two homologous sequences which flank the expression construct. The integrating vector may be directed to a specific locus in the host cell by selecting the appropriate homologous sequence for inclusion in the vector. The vector may also comprise a selectable marker gene to allow the selection of transformed host cells. Host cells comprising a vector may be a bacterial, fungal, plant, insect or mammalian cell.

Probes.

Probes may be used for screening and diagnostic methods, as outlined below. The probe may be attached or immobilized to a solid substrate, such as a microarray. The probe may have a length of from 8 to 500, 10 to 100, or 20 to 60 nucleotides. The probe may also have a length of at least 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 220, 240, 260, 280 or 300 nucleotides and/or less than 20, 21, 22, 23, 24, 25, 26, 27, 28, 29, 30, 35, 40, 45, 50, 60, 70, 80, 90, 100, 120, 140, 160, 180, 200, 220, 240, 260, 280 or 300 nucleotides. The probe may further comprise a linker sequence of from 10-60 nucleotides.

Microarray

A microarray may comprise a solid substrate comprising an attached probe or plurality of probes of the invention. The probes may be capable of hybridizing to a target sequence under stringent hybridization conditions. The probes may be attached at spatially defined address on the substrate. More than one probe per target sequence may be used, with either overlapping probes or probes to different sections of a particular target sequence. The probes may be capable of hybridizing to target sequences associated with a single disorder. The probes may be attached to the microarray in a wide variety of ways, as will be appreciated by those in the art. The probes may either be synthesized first, with subsequent attachment to the microarray, or may be directly synthesized on the microarray.

The solid substrate may be a material that may be modified to contain discrete individual sites appropriate for the attachment or association of the probes and is amenable to at least one detection method. Representative examples of substrates include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. The substrates may allow optical detection without appreciably fluorescing. The substrate may be planar, although other configurations of substrates may be used as well. For example, probes may be placed on the inside surface of a tube, for flow-through sample analysis to minimize sample volume. Similarly, the substrate may be flexible, such as a flexible foam, including closed cell foams made of particular plastics.

The microarray and the probe may be derivatized with chemical functional groups for subsequent attachment of the two. For example, the microarray may be derivatized with a chemical functional group including, but not limited to, amino groups, carboxyl groups, oxo groups or thiol groups. Using these functional groups, the probes may be attached using functional groups on the probes either directly or indirectly using a linkers. The probes may be attached to the solid support by either the 5' terminus, 3' terminus, or via an internal nucleotide. The probe may also be attached to the solid support non-covalently. For example, biotinylated oligonucleotides can be made, which may bind to surfaces covalently coated with streptavidin, resulting in attachment. Alternatively, probes may be synthesized on the surface using techniques such as photopolymerization and photolithography.

miRNA Expression Analysis.

miRNAs that are associated with disease or a pathological condition can be identified. A biological sample can be contacted with a probe or microarray of the invention and the amount of hybridization determined. PCR may be used to amplify nucleic acids in the sample, which may provide higher sensitivity.

The ability to identify miRNAs that are overexpressed or underexpressed in pathological cells compared to a control can provide high-resolution, high-sensitivity datasets which may be used in the areas of diagnostics, therapeutics, drug development, pharmacogenetics, biosensor development, and other related areas. An expression profile may be a "fingerprint" of the state of the sample with respect to a number of miRNAs. While two states may have any particular miRNA similarly expressed, the evaluation of a number of miRNAs simultaneously allows the generation of a gene expression profile that is characteristic of the state of the cell. That is, normal tissue may be distinguished from diseased tissue. By comparing expression profiles of tissue in known different disease states, information regarding which miRNAs are associated with each of these states may be obtained. This provides a molecular diagnosis of related conditions.

Determining Expression Levels.

Expression level of a disease-associated miRNA can be determined. A biological sample can be contacted with a probe or microarray of the invention and the amount of hybridization determined. The expression level of a disease-associated miRNA can be used in a number of ways. For example, differential expression of a disease-associated miRNA compared to a control may be used as a diagnostic that a patient suffers from the disease. Expression levels of a disease-associated miRNA may also be used to monitor the treatment and disease state of a patient. Furthermore, expression levels of a disease-associated miRNA allows the screening of drug candidates for altering a particular expression profile or suppressing an expression profile associated with disease. Differential expression is determined if the differences are statistically significant.

A target nucleic acid may be detected by contacting a sample comprising the target nucleic acid with a microarray comprising an attached probe sufficiently complementary to the target nucleic acid and detecting hybridization to the probe above control levels. The target nucleic acid may also be detected by immobilizing the nucleic acid to be examined on a solid support such as nylon membranes and hybridizing a labelled probe with the sample. Similarly, the target nucleic may also be detected by immobilizing the labeled probe to the solid support and hybridizing a sample comprising a labeled target nucleic acid. Following washing to remove the non-specific hybridization, the label may be detected.

A target nucleic acid may also be detected in situ by contacting permeabilized cells or tissue samples with a labeled probe to allow hybridization with the target nucleic acid. Following washing to remove the non-specifically bound probe, the label may be detected. Such hybridization assays can be direct hybridization assays or can comprise sandwich assays, which include the use of multiple probes, as is generally outlined in U.S. Pat. Nos. 5,681,702; 5,597,909; 5,545,730; 5,594,117; 5,591,584; 5,571,670; 5,580,731; 5,571,670; 5,591,584; 5,624,802; 5,635,352; 5,594,118; 5,359,100; 5,124,246; and 5,681,697, each of which is hereby incorporated by reference.

A variety of hybridization conditions may be used, including high, moderate and low stringency conditions. The assays may be performed under stringency conditions which allow hybridization of the probe only to the target. Stringency can be controlled by altering a parameter that is a thermodynamic variable, including, but not limited to, temperature, formamide concentration, salt concentration, chaotropic salt concentration pH, or organic solvent concentration.

Hybridization reactions may be accomplished in a variety of ways. Components of the reaction may be added simultaneously, or sequentially, in different orders. In addition, the reaction may include a variety of other reagents. These include salts, buffers, neutral proteins, e.g., albumin, detergents, etc. which may be used to facilitate optimal hybridization and detection, and/or reduce non-specific or background interactions. Reagents that otherwise improve the efficiency of the assay, such as protease inhibitors, nuclease inhibitors and anti-microbial agents may also be used as appropriate, depending on the sample preparation methods and purity of the target.

Diagnostic Assays.

A differential expression level of a disease-associated miRNA in a biological sample can be determined. The sample may be derived from a patient, and may be a body fluid or a tissue sample. Diagnosis of a disease state in a patient allows for prognosis and selection of therapeutic strategy. Further, the developmental stage of cells may be classified by determining temporally expressed miRNA-molecules.

In situ hybridization of labeled probes to tissue arrays may be performed. When comparing the fingerprints between an individual and a standard, the skilled artisan can make a diagnosis, a prognosis, or a prediction based on the findings. It is further understood that the genes which indicate the diagnosis may be the same or differ from those which indicate the prognosis. Molecular profiling of the condition of the cells may lead to distinctions between responsive or refractory conditions or may be predictive of outcomes.

Drug Screening.

The present invention also relates to a method of screening therapeutics comprising contacting a pathological cell capable of expressing a disease related miRNA with a candidate therapeutic and evaluating the effect of a drug candidate on the expression profile of the disease associated miRNA. Having identified the differentially expressed miRNAs, a variety of assays may be executed. Test compounds may be screened for the ability to modulate gene expression of the disease associated miRNA. Modulation includes both an increase and a decrease in gene expression. Test can be conducted in any type of cell, including but not limited to human cells, human cell lines, mammalian cells and cell lines, mammalian cancer cells and cell lines.

The test compound or drug candidate may be any molecule, e.g., protein, oligopeptide, small organic molecule, polysaccharide, polynucleotide, etc., to be tested for the capacity to directly or indirectly alter the disease phenotype or the expression of the disease associated miRNA. Drug candidates encompass numerous chemical classes, such as small organic molecules having a molecular weight of more than 100 and less than about 500, 1,000, 1,500, 2,000, or 2,500 daltons. Candidate compounds may comprise functional groups necessary for structural interaction with proteins, particularly hydrogen bonding, and typically include at least an amine, carbonyl, hydroxyl or carboxyl group, preferably at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Combinatorial libraries of potential modulators may be screened for the ability to bind to the disease associated miRNA or to modulate the activity thereof. The combinatorial library may be a collection of diverse chemical compounds generated by either chemical synthesis or biological synthesis by combining a number of chemical building blocks such as reagents. Preparation and screening of combinatorial chemical libraries is well known to those of skill in the art. Such combinatorial chemical libraries include, but are not limited to, peptide libraries encoded peptides, benzodiazepines, diversomers such as hydantoins, benzodiazepines and dipeptide, vinylogous polypeptides, analogous organic syntheses of small compound libraries, oligocarbamates, and/or peptidyl phosphonates, nucleic acid libraries, peptide nucleic acid libraries, antibody libraries, carbohydrate libraries, and small organic molecule libraries.

Gene Silencing.

The present invention also relates to a method of using the nucleic acids of the invention to reduce expression of a target gene in a cell, tissue or organ. Expression of the target gene may be reduced by expressing a nucleic acid of the invention that comprises a sequence substantially complementary to one or more binding sites of the target mRNA. The nucleic acid may be a miRNA or a variant thereof. The nucleic acid may also be pri-miRNA, pre-miRNA, or a variant thereof, which may be processed to yield a miRNA. The expressed miRNA may hybridize to a substantially complementary binding site on the target mRNA, which may lead to activation of RISC-mediated gene silencing. An example for a study employing over-expression of miRNA is Yekta et al. 2004, *Science*, 304-594, which is incorporated herein by reference. One of ordinary skill in the art will recognize that the nucleic acids of the present invention may be used to inhibit expression of target genes using antisense methods well known in the art, as well as RNAi methods described in U.S. Pat. Nos. 6,506,559 and 6,573,099, which are incorporated by reference. The target of gene silencing may be a protein that causes the silencing of a second protein. By repressing expression of the target gene, expression of the second protein may be increased. Examples for efficient suppression of miRNA expression are the studies by Esau et al 2004 JBC 275-52361; and Cheng et al 2005 Nucleic Acids Res. 33-1290, which is incorporated herein by reference.

Gene Enhancement.

The present invention also relates to a method of using the nucleic acids of the invention to increase expression of a target gene in a cell, tissue or organ. Expression of the target gene may be increased by expressing a nucleic acid of the invention that comprises a sequence substantially complementary to a pri-miRNA, pre-miRNA, miRNA or a variant thereof. The nucleic acid may be an anti-miRNA. The anti-miRNA may hybridize with a pri-miRNA, pre-miRNA or miRNA, thereby reducing its gene repression activity. Expression of the target gene may also be increased by expressing a nucleic acid of the invention that is substantially complementary to a portion of the binding site in the target gene, such that binding of the nucleic acid to the binding site may prevent miRNA binding.

Therapeutic.

The present invention also relates to a method of using the nucleic acids of the invention as modulators or targets of disease or disorders associated with developmental dysfunctions, such as cancer. In general, the claimed nucleic acid molecules may be used as a modulator of the expression of genes which are at least partially complementary to said nucleic acid. Further, miRNA molecules may act as target for therapeutic screening procedures, e.g., inhibition or activation of miRNA molecules might modulate a cellular differentiation process, e.g. apoptosis.

Furthermore, existing miRNA molecules may be used as starting materials for the manufacture of sequence-modified miRNA molecules, in order to modify the target-specificity thereof, e.g., an oncogene, a multidrug-resistance gene or another therapeutic target gene. Further, miRNA molecules can be modified, in order that they are processed and then generated as double-stranded siRNAs which are again directed against therapeutically relevant targets. Furthermore, miRNA molecules may be used for tissue reprogramming procedures, e.g., a differentiated cell line might be transformed by expression of miRNA molecules into a different cell type or a stem cell.

Compositions.

The present invention also relates to a pharmaceutical composition comprising the nucleic acids of the invention and optionally a pharmaceutically acceptable carrier. The compositions may be used for diagnostic or therapeutic applications. The administration of the pharmaceutical composition may be carried out by known methods, wherein a nucleic acid is introduced into a desired target cell in vitro or in vivo. Commonly used gene transfer techniques include calcium phosphate, DEAE-dextran, electroporation, microinjection, viral methods and cationic liposomes.

Kits.

Kits may comprise a nucleic acid of the invention together with any or all of the following: assay reagents, buffers, probes and/or primers, and sterile saline or another pharmaceutically acceptable emulsion and suspension base. In addition, the kits may include instructional materials containing directions (e.g., protocols) for the practice of the methods of this invention.

Subjects.

Subjects can be mammals, such as humans, monkeys, rats, mice, dogs, cats, guinea pigs, pigs, etc. The humans can be those who are known to have cancer or are suspected of having cancer. The cancer may have been previously treated or not. The cancer may be colorectal, lung, breast, stomach, kidney, ovarian, bladder, head and neck, brain, bone, testicular, pancreatic, prostate, etc.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLE 1

Materials and Methods

Cell Culture and Colorectal Tissue.

Colorectal cancer cell lines HCT116, DLD1, RKO, CACO-2, SW480, and their derivatives were cultured in McCoy's 5A medium supplemented with 10% FCS and penicillin/streptomycin. Samples of colorectal cancer tissue and matched normal colonic epithelium were obtained from patients undergoing surgery and were frozen immediately (<10 min) after surgical resection. Acquisition of tissue specimens was performed in accordance with Health Insurance Portability and Accountability Act of 1996 (HIPAA) regulations.

RNA, DNA, and RNA/DNA Oligonucleotides.

RNA and RNA/DNA oligonucleotides were obtained from Dharmacon Research (Lafayette, Colo.). Deoxyribonucleotides are preceded by a "d." miRAGE 3' linker: 5'-phosphate-UCUCGAGGUACAUCGUUdAdGdAdAdGd-CdTdTdGdAdAdTdTdCdGdAdGdCd AdGdAdAdAN3-3' (SEQ ID NO: 1875); miRAGE 5' linker: 5'-dTdT-dTdGdGdAdTdTdTdGd-CdTdGdGdTdGdCdAdGdTdAdCdAdAdCdTdAdGdGd CdTdTdACUCGAGC(SEQ ID NO: 1876); 18-base RNA standard: 5'-phosphate-ACGUUGCACUCUGAUACC (SEQ ID NO: 1877); 26-base RNA standard: 5'-phosphate-CCGGUUCAUCACGUCUAAGAAUCAUG (SEQ ID NO: 1878). DNA oligonucleotides were obtained from Integrated DNA Technologies (San Jose, Calif.). miRAGE reverse transcription primer: 5'-TTTCTGCTCGAATTCAAGCTTCT (SEQ ID NO: 1879); LongSage PCR primer (forward): 5'-biotin-TTTTTTTTTGGATTTGCTGGTGCAGTACA-3' (SEQ ID NO: 1880); LongSage PCR primer (reverse): 5'-biotin-TTTTTTTTTCTGCTCGAATTCAAGCTTCT-3' (SEQ ID NO: 1881).

miRAGE Approach for miRNA Identification. Step 1: 18- to 26-bp RNA Isolation and Linker Ligation.

Total RNA was isolated from cell lines/tissue samples by using the RNagents kit (Promega) following the manufacturer's protocol, with the exception that no final 75% ethanol wash was performed. RNA of the 18- to 26-base size range was isolated by electrophoresing 1 mg of total RNA alongside 18- and 26-base RNA standards on two 15% polyacrylamide TBE/Urea Novex gels (Invitrogen) at 180 V for 70 min. The 18- and 26-base RNA standards were carried through all subsequent ligation steps to serve as size standards for gel purification. RNAs ranging from 18 to 26 bases in length were visualized with SYBR Gold Nucleic Acid Gel Stain (Molecular Probes), excised from the gel, pulverized by spinning at high speed through an 18-gauge needle-pierced centrifuge tube, and gel-extracted by incubating the gel slices in 0.3 M NaCl at 4° C. on a rotisserie-style rotator for 5 h. The contents were then transferred into a Costar Spin-X Centrifuge Tube Filter (VWR Scientific), spun into a fresh tube, EtOH-precipitated (by adding 3 volumes of 100% EtOH), and resuspended in water. Small RNAs were subsequently dephosphorylated with calf intestinal alkaline phosphatase (NEB, Beverly, Mass.) at 50° C. for 30 min, phenol/chloroform-extracted, re-EtOH precipitated, and ligated to the miRAGE 3' Linker with T4 RNA ligase (NEB) at 37° C. for 1 h. After gel purification of 58- to 66-base RNA products and EtOH precipitation (as described above), the samples were phosphorylated with T4 polynucleotide kinase (NEB) at 37° C. for 30 min, phenol/chloroform-extracted, EtOH-precipitated, and ligated (as above) to the miRAGE 5' Linker.

Step 2: Tag Amplification, Isolation, Concatenation, Cloning, and Sequencing.

After gel purification of RNA products ranging from 98 to 106 bases, reverse transcription of the ligation products was performed by using miRAGE reverse transcription primer and SuperScript II (Invitrogen) for 50 min at 45° C. Subsequently, the procedures for amplifying, isolating, purifying, concatenating, cloning, and sequencing tags are nearly identical to those performed in LongSAGE and Digital Karyotyping, except that miRAGE PCR products range in size from 110 to 118 bp, and miRAGE tags (not ditags) were released from linkers with XhoI endonuclease (NEB). The sequencing of concatemer clones was performed by contract sequencing at Agencourt (Beverly, Mass.). Resulting sequence files were trimmed by using PHRED sequence analysis software (CodonCode, Dedham, Mass.), and 18- to 26-bp tags were extracted by using the SAGE2000 software package, which identifies the fragmenting enzyme site between tags, extracts intervening tags, and records them in a database.

Bioinformatic Analyses of miRAGE Tags. Step 1: Grouping and Comparing miRAGE Tags to Known RNAs.

All tags sharing a common set of 11 of 12 core internal sequence elements were assembled into groups containing all related members. The tag with the most counts in each group was further analyzed. Grouping facilitated analysis by (i) eliminating rare sequencing errors and (ii) removing trivial miRNA variants, because miRNAs are known to display both 5' and 3' variation. The tags were subsequently compared to databases of known RNA sequences (miRNAs, mRNAs, rRNAs, etc.), using BLAST, and those tags matching known sequences were removed from further analysis. The tags obtained by miRAGE were compared with public databases on Sep. 1, 2005. Subsequent additions and changes to these databases are not reflected in the data analysis.

Step 2: Secondary Structure Analysis and Hairpin Stability Scoring of Candidate miRNAs.

To determine potential miRNA precursor structures, each tag was compared to the human genome sequence. For tags with perfect matches, a total of 75 bp (60+15 bp) of flanking genomic sequence around each tag was extracted. Because there are two possible precursors for each tag (i.e., the tag can be located on the 5' or 3' arm of a putative hairpin), pairs of theoretical precursors were extracted from the human genome at the position of each tag and were carried through the following analysis. Secondary structure and free energy of folding were determined for each pair of precursor structures by using MFOLD 3.2 (26, 27) and compared to values obtained for known miRNAs. The values used for thermodynamic evaluation were the free energy of folding of each precursor sequence ($\Delta G_{folding}$) and the difference of $\Delta G_{folding}$ between the two possible precursors ($\Delta\Delta G_{folding}$). Analysis of an arbitrary set of 126 known miRNAs using these thermodynamic analyses revealed that the highest $\Delta G_{folding}$ was −22.6, and there were no miRNAs with a $\Delta G_{folding}$>−29.0, which had a $\Delta\Delta G_{folding}$<5. Therefore, for a candidate miRNA precursor structure to be considered legitimate, it would have to have either (i) $\Delta G_{folding}$≤−29 or (ii) −29<$\Delta G_{folding}$≤−22 and $\Delta\Delta G_{folding}$>5. In cases where both precursors fulfilled these criteria, the member of each pair with the lowest $\Delta G_{folding}$ was further considered. Precursors that had not been excluded up to this point were subsequently analyzed to determine whether they conformed to generally acceptable miRNA base-pairing standards (base-pairing involving at least 16 of the first 22 nucleotides of the miRNA and the other arm of the hairpin) (18).

Step 3: Determination of Hairpin Conservation.

We classified all candidate miRNAs as either "conserved" or "nonconserved" by using the University of California at Santa Cruz phastCons database (28). This database has scores at each nucleotide in the human genome that correspond to the degree of conservation of that particular nucleotide in chimpanzee, mouse, rat, dog, chicken, pufferfish, and zebrafish. The algorithm is based on a phylogenetic hidden Markov model using best-in-genome pairwise alignment for each species (based on BLASTZ), followed by multialignment of the eight genomes. A hairpin was defined as conserved if the average phastCons conservation score over the seven species in any 15-nt sequence in the hairpin stem is at least 0.9 (5, 29).

Determination of Homology of Candidate miRNAs to Existing miRNAs.

One hundred random 22 mers were generated and compared to the miRBase database using the SSEARCH search algorithm, and expect values were obtained for each. E values for randomly generated sequences ranged from 0.07 to 23. All 133 miRNA candidates were subsequently analyzed, and tags with E values <0.05 were deemed to have homology to existing miRNAs.

miRNA Microarray Expression Analysis.

Five micrograms of total RNA from human placenta, prostate, testes, and brain (Ambion, Austin, Tex.) were size-fractionated (<200 nt) by using the mirVana kit (Ambion) and labeled with Cy3 (placenta and testes) and Cy5 (prostate and brain) fluorescent dyes. Pairs of labeled samples were hybridized to dual-channel microarrays. Microarray assays were performed on a µParaFlo microfluidics microarray with each of the detection probes containing a nucleotide sequence of coding segment complementary to a specific microRNA sequence and a long nonnucleotide molecule spacer that extended the detection probe away from the substrate. The melting temperature of the detection probes was balanced by incorporation of varying number of modified nucleotides with increased binding affinities. The maximal signal level of background probes was 180. A miRNA detection signal threshold was defined as twice the maximal background signal.

Quantitative RT-PCR (qRT-PCR) Expression Analysis.

qRT-PCRs were performed by using SuperTaq Polymerase (Ambion) and the mirVana qRT-PCR miRNA Detection Kit (Ambion) following the manufacturer's instructions. Reactions contained custom-designed oligonucleotide DNA primers (Integrated DNA Technologies) specific for 36 novel putative miRNAs or mirVana qRT-PCR Primer Sets specific for hsa-miR-16, hsa-miR-24, hsa-miR-143, or human 5S rRNA as positive controls. For each set of primers, 100 ng of FirstChoice human colon Tumor/Normal Adjacent Tissue RNA (Ambion); a pool containing 50 ng of HCT116, RKO, and DLD-1 cell lines total RNA; a pool containing 50 ng of FirstChoice Total RNA from human brain, cervix, thymus, and skeletal muscle (Ambion); and a no-template negative control were tested. All RNAs were treated with TURBO DNase. qRT-PCR was performed on an ABI7000 thermocycler (Applied Biosciences), and end-point reaction products were also analyzed on a 3.5% high-resolution agarose gel (Ambion) stained with ethidium bromide to discriminate between the correct amplification products (≈90 bp) and the potential primer dimers.

Targeted Disruption of the Human Dicer Locus.

The strategy for creating knockouts with AAV vectors was performed as described (30, 31). The targeting construct pAAV-Neo-Dicer was made by PCR, by using bacterial artificial chromosome clone CITB 2240H23 (Invitrogen) as the template for the homology arms. A targeted insertion was made in exon 5, which is part of the helicase domain. Details of the vector design and sequences of all PCR primers are available from the authors upon request. Stable G418-resistant clones were initially selected in the presence of Geneticin (Invitrogen), then routinely propagated in the absence of selective agents.

Determination of Differential Expression.

Tag numbers from the different libraries were normalized and compared by using a Fisher exact test (significance threshold P=0.05) with Bonferroni correction (32).

EXAMPLE 2

Genome-Wide miRNA Analysis with miRAGE.

Using miRAGE, we analyzed 273,966 cDNA tags obtained from four human colorectal cancers and two matching samples of normal colonic mucosae. Comparing these tags to the existing miRNA database identified 68,376 tags matching known miRNA sequences. These represent the largest collection of human miRNA sequences identified to date, because all previous human miRNA cloning analyses in aggregate have analyzed <2,000 miRNA molecules. The expression level of the miRNAs detected by miRAGE ranged over 4 orders of magnitude (from 23,431 observations for miR-21 to 20 miRNAs that were observed only once), suggesting this approach can detect miRNAs present at varied expression levels. The identified miRNA tags matched 200 of the mature miRNAs present in the public miRBase database (2) (Table 2, which is published as supporting information on the PNAS web site), and 52 of these were expressed at significantly different levels between tumor cells and normal colonic epithelium (P<0.05, Fisher exact test; Table 3, which is published as supporting information on the PNAS web site). Importantly, of the already catalogued miRNAs, these results provide novel experimental evidence for 62 miRNAs whose presence in this database was based solely on phylogenetic predictions.

In addition to detecting known or predicted miRNAs, 1,411 of the miRAGE tags represented 100 previously unrecognized miRNA* forms of known miRNAs (Table 4, which is published as supporting information on the PNAS web site). miRNA* molecules correspond to the short-lived complementary strand present in initial miRNA duplexes, and their biologic role, if any, has yet to be elucidated. Although miRNA* have been inferred to exist for all miRNAs, only 24 human miRNAs* have previously been reported in the public database. These analyses therefore provide substantially greater evidence for the presence of these molecules in human cells

EXAMPLE 3

Evaluation of Novel miRNAs.

Figure 1B:
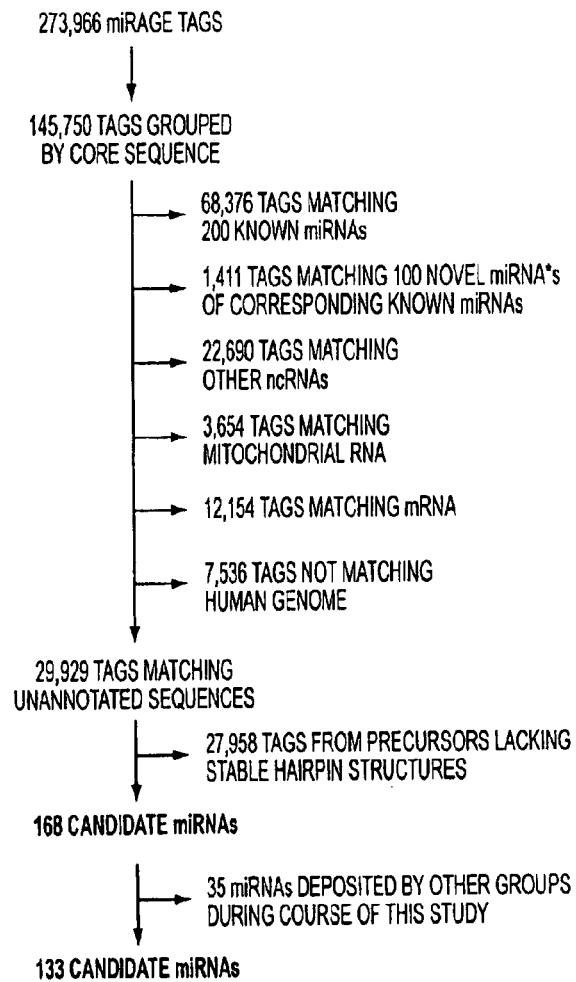

We next focused on evaluating whether the miRAGE tags not matching known miRNAs might represent novel miRNA species. As a first step, miRAGE tags were compared with existing gene databases to exclude sequences matching known RNAs, including noncoding RNAs, mRNAs, and RNAs derived from mitochondrial sequences (FIG. 1B). The remaining tags were then evaluated in silico for the ability of their putative precursor sequences to form hairpin structures that were thermodynamically stable. The miRAGE approach in combination with these steps were expected to fulfill both the "expression" and "biogenesis" criteria recently put forward by Ambros et al. (18) in an effort to maintain a uniform system for miRNA annotation. Using these criteria, a total of 168 tags were identified that corresponded to putative novel miRNAs.

EXAMPLE 4

Validation of Novel miRNAs.

Figure 2:
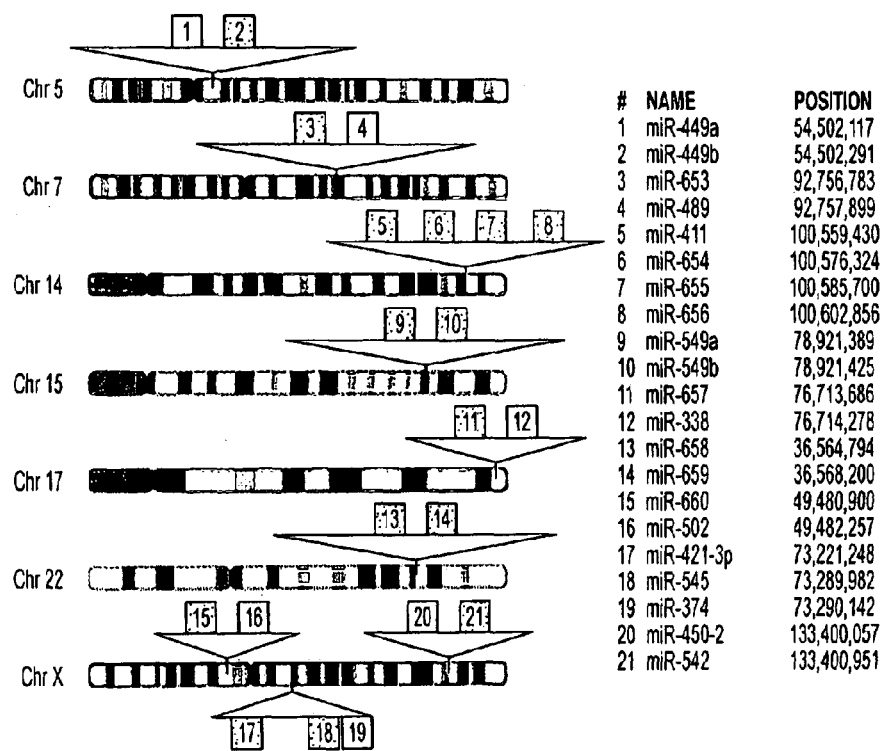
FIG. 2. Clustering of miRNAs in the human genome. Analysis of all 133 miRNAs identified 15 that were near other known or novel miRNAs. Yellow boxes represent candidate miRNAs, whereas white boxes represent known miRNAs. Position coordinates are based on National Center for Biotechnology Information Genome Build 35/University of California, Santa Cruz May 2004 assembly.
Figure 3:
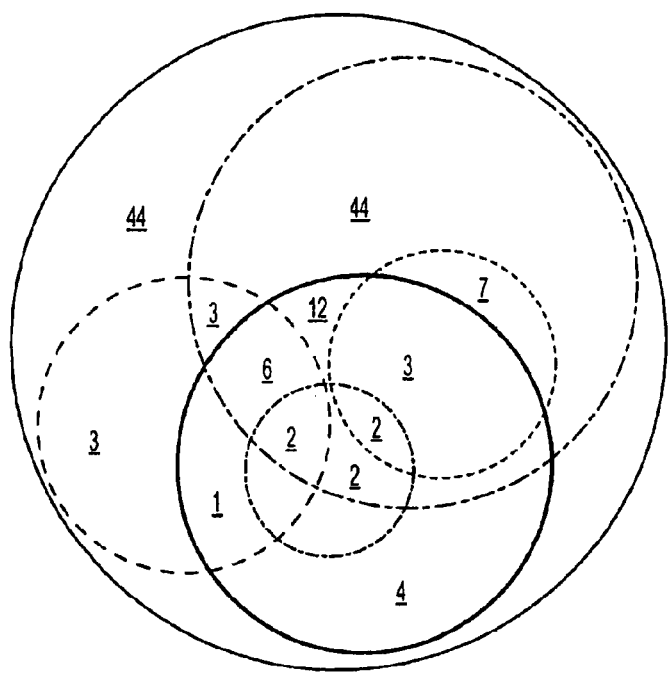
FIG. 3. Validation of 133 candidate human miRNAs. A total of 133 miRNA candidates fulfilled expression and biogenesis criteria (black circle). Additional levels of validation include phlyogenetically conserved precursor structures (blue circle), multiple observations of expression (red circle), genomic clustering (yellow circle), observation of corresponding miRNA* forms (green circle), and strong homology to known miRNAs (pink circle).
Figure 7:
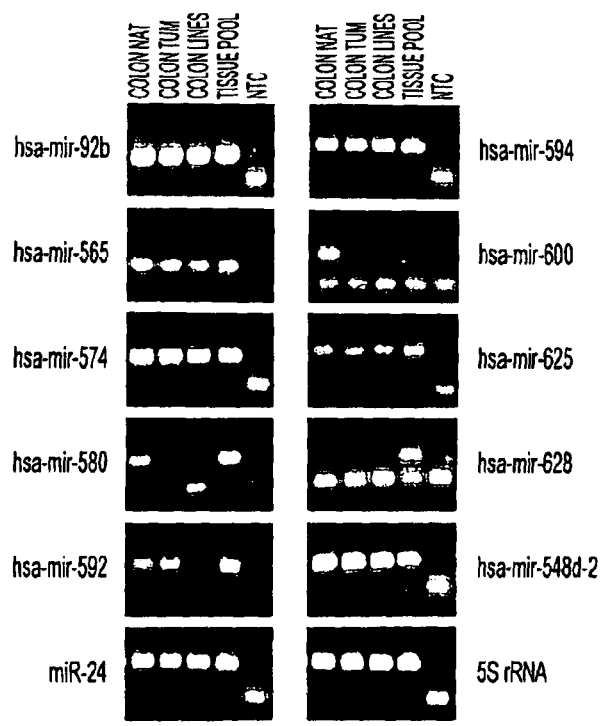
FIG. 7. qRT-PCR expression validation of miRNA candidates. Expression of miRNAs was analyzed in total RNA derived from colon tumor tissue (TUM); adjacent normal colonic epithelial tissue (NAT); pooled colorectal tumor cell lines HCT116, DLD-1, and RKO (Colon lines); pooled extracolonic tissue from brain, cervix, thymus, and skeletal muscle (Tissue pool); and a no template control (NTC). The lower band present in all NTC lanes represents primer dimers.

During the course of our study, 35 of these 168 miRAGE tags were independently identified by using a combination of bioinformatic and expression analyses (5). These findings provide a separate measure of validation of the miRAGE approach for miRNA identification. Several lines of evidence suggested that most of remaining 133 miRAGE tags also corresponded to previously uncharacterized miRNAs (Table 5, which is published as supporting information on the PNAS web site). First, phylogenetic conservation was determined for each tag precursor structure with respect to chimpanzee, mouse, rat, dog, chicken, pufferfish, and zebrafish genomes. A total of 32 of the 133 candidate miRNAs had conserved precursor structures. Furthermore, six of the miRNA candidates showed significant homology to the mature miRNA sequence of known miRNAs. Although these observations provide support for evolutionarily conserved novel miRNAs, they should not be used to exclude the remaining tags as legitimate miRNAs, because a significant number of recently reported human miRNAs lack homology to species other than primates (5). Second, 81 of the novel candidate miRNAs were represented by more than one miRAGE tag or were independently detected in additional samples by using either miRNA microarrays (5, 19) (Table 6, which is published as supporting information on the PNAS web site) or quantitative real-time PCR (Table 7 and FIG. 7, which are published as supporting information on the PNAS web site). Third, 15 of the candidate miRNAs were localized to genomic clusters of two or more miRNAs separated by an average distance of 10 kb (FIG. 2). This physical proximity is consistent with recent reports of miRNAs clustering within the human genome (20). Fourth, identification of a corresponding miRNA* sequence (with characteristic 3' overhangs) to a particular miRNA is a strong indicator that the small RNA species in question was processed by an RNase III enzyme such as Dicer. miRNA* tags were observed for 12 of the candidate miRNA sequences. In total, 89 of the 133 novel candidate miRNAs had at least one independent piece of supporting evidence buttressing their legitimacy (FIG. 3).

Figure 4A:
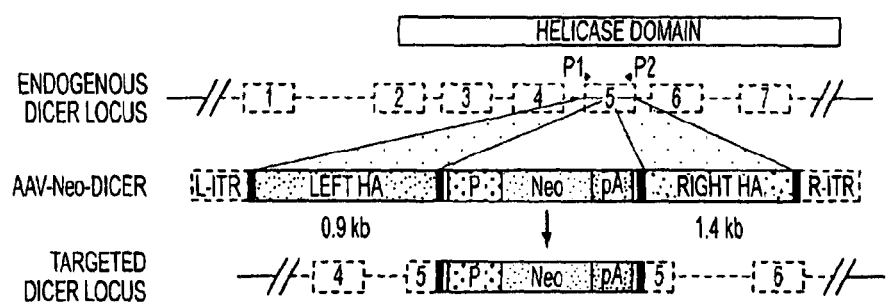
FIG. 4. Disruption of human DICER1 helicase domain in colorectal cancer cells. (A) The endogenous locus is shown together with an AAV-Neo targeting construct for insertion into exon 5 of DICER1. HA, homology arm; P, SV40 promoter; Neo, geneticin-resistance gene; R-ITR and L-ITR are right and left inverted terminal repeats; triangles, loxP sites. (B) PCR analysis of parental (+/+), heterozygous (+/Ex5), and homozygous (Ex5/Ex5) clones from DLD1, HCT116, and RKO colorectal cancer cell lines. Primers used for PCR analysis (P1 and P2) are indicated above the endogenous locus in A.
Figure 4B:
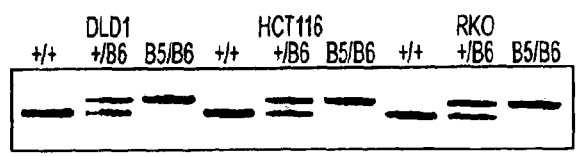

As a separate experimental approach to validate candidate miRNAs, we examined whether the generation of these small RNAs depended on Dicer processing. The rationale for this analysis was based on the fact that Dicer-depleted cells contain reduced amounts of mature miRNAs (18). However, because Dicer−/−vertebrate cells have been shown to be inviable (21), we sought to generate a Dicer mutant line displaying a hypomorphic phenotype. Such a mutant has been reported in mouse studies targeting the N terminus of Dicer (22). Accordingly, we disrupted exon 5 of the human Dicer gene by using an AAV targeting construct, thereby interrupting a well conserved segment of the N-terminal helicase domain while sparing the RNase III domains. The helicase domain was successfully disrupted by this approach in three different colorectal cancer cell lines (FIG. 4).

Figure 5A:
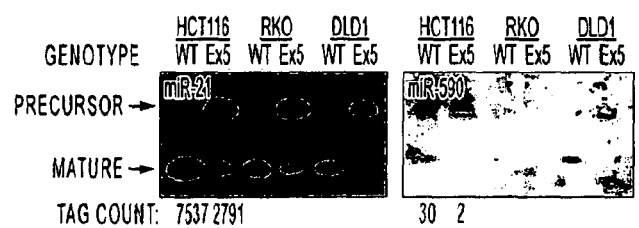
FIG. 5. miRNA expression in colorectal cancer cells with Dicer disruption. (A) Northern blot analyses show decreased mature miRNAs and increased levels of miRNA precursors in $Dicer^{ex5}$ (Ex5) compared with Dicer wild-type (WT) cells using probes for miR-21 and miR-590. (B) Expression levels of known miRNAs as determined by primer-extension quantitative PCR (PE-qPCR), as described (33). For each graph, pairwise comparisons are displayed showing the ratio of expression in $Dicer^{ex5}$ to WT clones of each cell type.
Figure 5B:
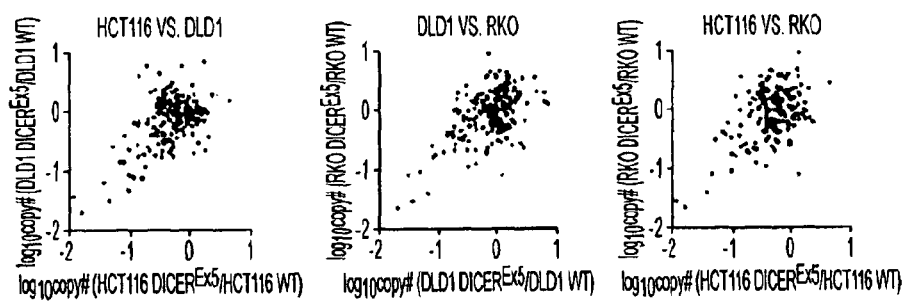

Analysis of selected miRNA genes from all three Dicer exon 5-disrupted lines (hereafter referred to as Dicer$^{ex5}$) revealed reduced amounts of mature miRNAs and accumulation of miRNA precursors, when compared to their corresponding parental lines (FIGS. 5A and B). miRAGE was then performed on both HCT116 wild type and HCT-Dicer$^{ex5}$ cells to quantify differences of known and novel miRNA levels. Of 97 known miRNAs detected in these two cell lines, 55 were differentially expressed, and for 53 of these 55, there was an average 7-fold reduction of miRNA levels in Dicer$^{ex5}$ cells compared with wild-type cells (Table 8, which is published as supporting information on the PNAS web site). Examination of the 168 candidate miRNAs similarly revealed that among the six candidates that were differentially expressed, there was an average 14-fold reduction of miRNA levels in Dicer$^{ex5}$ cells (Table 1). These observations are consistent with the conclusion that Dicer is required for the biogenesis of a subset of known and novel miRNAs.

EXAMPLE 5

Target Genes.

The miRNAs were used to predict target genes and their binding. Table 9 (FIG. 16) lists the predicted target gene for each miRNA. The names of the target genes were taken from NCBI Reference Sequence release 9 (http://www.ncbi.nlm.nih.gov; Pruitt et al., Nucleic Acids Res, 33(1):D501-D504, 2005; Pruitt et al., Trends Genet., 16(1):44-47, 2000; and Tatusova et al., Bioinformatics, 15(7-8):536-43, 1999). Target genes were identified by having a perfect complimentary match of a 7 nucleotide miRNA seed (positions 2-8) that have an "A" in the UTR opposite to position 1 of the miRNA, except in one case, hsa-mir-560, for which the binding site does not have an "A" in that position. For a discussion on identifying target genes, see Lewis et al., Cell, 120: 15-20, (2005). For a discussion of the seed being sufficient for binding of a miRNA to a UTR, see Lim et al., (Nature, 2005, 433:769-773) and Brenneck et al, (PLoS Biol, 2005, (3): e85).

Binding sites were predicted on genes whose UTR is of at least 30 nucleotides. In addition, the binding site screen only considered the first 8000 nucleotides per UTR and considered the longest transcript when there were several transcripts per gene. A total of 14,236 transcripts were included in the dataset. Table 9 [FIG. 16] lists the predicted binding sites for each target gene as predicted from each miRNA. The sequence of the binding site includes the 20 nucleotides 5' and 3' away from the binding site as they are located on the spliced mRNA.

EXAMPLE 6

Concluding Remarks.

Figure 6:
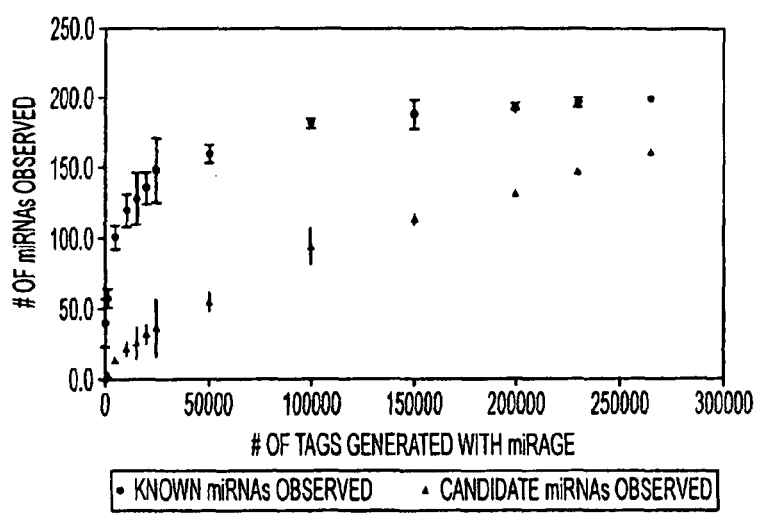
FIG. 6. Discovery of known and novel miRNAs using miRAGE. Each point represents the average number of known or novel miRNAs (y axis) that were identified by analysis of three simulated subsets comprising the number of miRAGE tags indicated (x axis).

Our studies have provided experimental evidence that the human genome contains a much larger number of miRNAs than previously appreciated (4). To determine the rate at which uncharacterized miRNAs are likely to be discovered by using miRAGE, we simulated the number of miRNAs species that would have been detected by using subsets of the tags analyzed (FIG. 6). Although the number of known miRNAs clearly plateaus after analysis of ≈50,000 tags, the number of novel miRNAs appears to increase linearly even at ≈270,000 tags. These observations suggest many novel miRNAs remain to be identified.

The tools we have developed, miRAGE and the Dicer$^{ex5}$ cells with defective miRNA processing, should provide a facile way to identify and validate novel miRNAs. As new lower-cost sequencing methods continue to be developed (23-25), this approach will become progressively more useful for the discovery of the compendium of miRNAs present in humans and other organisms.

REFERENCES

The disclosure of each reference cited is expressly incorporated herein.
1. Bartel, D. P. (2004) Cell 116, 281-297.
2. Griffiths-Jones, S. (2004) Nucleic Acids Res 32, D109-111.
3. Bernstein, F., Caudy, A. A., Hammond, S. M. & Hannon, G. J. (2001) Nature 409, 363-366.
4. Lim, L. P., Glasner, M. E., Yekta, S., Burge, C. B. & Bartel, D. P. (2003) Science 299, 1540.
5. Bentwich, I., Avniel, A., Karov, Y., Aharonov, R., Gilad, S., Barad, O., Barzilai, A., Einat, P., Einav, U. & Meiri, E., et al. (2005) Nat. Genet 37, 766-770.
6. Michael, M. Z., SM, O. C., van Holst Pellekaan, N. G., Young, G. P. & James, R. J. (2003) Mol. Cancer Res 1, 882-891.
7. Lagos-Quintana, M., Rauhut, R., Meyer, J., Borkhardt, A. & Tuschl, T. (2003) RNA 9, 175-179.
8. Lagos-Quintana, M., Rauhut, R., Lendeckel, W. & Tuschl, T. (2001) Science 294, 853-858.
9. Lau, N. C., Lim, L. P., Weinstein, E. G., & Bartel, D. P. (2001) Science 294, 858-862.
10. Lee, R. C. & Ambros, V. (2001) Science 294, 862-864.
11. Mourelatos, Z., Dostie, J., Paushkin, S., Sharma, A., Charroux, B., Abel, L., Rappsilber, J., Mann, M. & Dreyfuss, G. (2002) Genes Dev 16, 720-728.
12. Dostie, J., Mourelatos, Z., Yang, M., Sharma, A. & Dreyfuss, G. (2003) RNA 9, 180-186.
13. Houbaviy, H. B., Murray, M. F. & Sharp, P. A. (2003) Dev. Cell 5, 351-358.
14. Kim, J., Krichevsky, A., Grad, Y., Hayes, G. D., Kosik, K. S., Church, G. M. & Ruvkun, G. (2004) Proc. Natl. Acad. Sci. USA 101, 360-365.
15. Kasashima, K., Nakamura, Y. & Kozu, T. (2004) Biochem. Biophys. Res. Commun 322, 403-410.
16. Suh, M. R., Lee, Y., Kim, J. Y., Kim, S. K., Moon, S. H., Lee, J. Y., Cha, K. Y., Chung, H. M., Yoon, H. S. & Moon, S. Y., et al. (2004) Dev. Biol 270, 488-498.
17. Velculescu, V. E., Zhang, L., Vogelstein, B. & Kinzler, K. W. (1995) Science 270, 484-487.
18. Ambros, V., Bartel, B., Bartel, D. P., Burge, C. B., Carrington, J. C., Chen, X., Dreyfuss, G., Eddy, S. R., Griffiths-Jones, S. & Marshall, M., et al. (2003) RNA 9, 277-279.
19. Barad, O., Meiri, E., Avniel, A., Aharonov, R., Barzilai, A., Bentwich, I., Einav, U., Gilad, S., Hurban, P. & Karov, Y., et al. (2004) Genome Res 14, 2486-2494.
20. Altuvia, Y., L& graf, P., Lithwick, G., Elefant, N., Pfeffer, S., Aravin, A., Brownstein, M. J., Tuschl, T., Margalit, H. (2005) Nucleic Acids Res 33, 2697-2706.
21. Fukagawa, T., Nogami, M., Yoshikawa, M., Ikeno, M., Okazaki, T., Takami, Y., Nakayama, T. & Oshimura, M. (2004) Nat. Cell Biol 6, 784-791.
22. Yang, W. J., Yang, D. D., Na, S., Sandusky, G. E., Zhang, Q., Zhao, G. (2005) J. Biol. Chem 280, 9330-9335.

23. Margulies, M., Egholm, M., Altman, W. E., Attiya, S., Bader, J. S., Bemben, L. A., Berka, J., Braverman, M. S., Chen, Y. J. & Chen, Z., et al. (2005) *Nature* 437, 376-380.
24. Leamon, J. H., Lee, W. L., Tartaro, K. R., Lanza, J. R., Sarkis, G. J., deWinter, A. D., Berka, J., Weiner, M., Rothberg, J. M. & Lohman, K. L. (2003) *Electrophoresis* 24, 3769-3777.
25. Shendure, J., Mitra, R. D., Varma, C. & Church, G. M. (2004) *Nat. Rev. Genet* 5, 335-344.
26. Zuker, M. (2003) *Nucleic Acids Res* 31, 3406-3415.
27. Mathews, D. H., Sabina, J., Zuker, M. & Turner, D. H. (1999) *J. Mol. Biol* 288, 911-940.
28. Siepel, A., Bejerano, G., Pedersen, J. S., Hinrichs, A. S., Hou, M., Rosenbloom, K., Clawson, H., Spieth, J., Hillier, L. W. & Richards, S., et al. (2005) *Genome Res* 15, 1034-1050.
29. Berezikov, E., Guryev, V., van de Belt, J., Wienholds, E., Plasterk, R. H. & Cuppen, E. (2005) *Cell* 120, 21-24.
30. Hirata, R., Chamberlain, J., Dong, R. & Russell, D. W. (2002) *Nat. Biotechnol* 20, 735-738.
31. Kohli, M., Rago, C., Lengauer, C., Kinzler, K. W. & Vogelstein, B. (2004) *Nucleic Acids Res* 32, e3.
32. Romualdi, C., Bortoluzzi, S., D'Alessi, F. & Danieli, G. A. (2003) *Physiol. Genomics* 12, 159-162.
33. Raymond, C. K., Roberts, B. S., Garrett-Engele, P., Lim, L. P. & Johnson, J. M. (2005) *RNA* 11, 1737-1744.

The invention claimed is:

1. An isolated polynucleotide of approximately 17-250 nucleotides comprising a sequence selected from the group consisting of: (a) SEQ ID NO: 469 and (b) a sequence which is at least 84% identical to (a).

2. The polynucleotide of claim 1 wherein the polynucleotide is from 18-25 nucleotides in length.

3. The polynucleotide of claim 1 wherein the polynucleotide is from 19-24 nucleotides in length.

4. The polynucleotide of claim 1 wherein the polynucleotide is from 21-23 nucleotides in length.

5. The polynucleotide of claim 1 wherein the polynucleotide is DNA.

6. The polynucleotide of claim 1 wherein the polynucleotide is RNA.

7. The polynucleotide of claim 1 wherein the polynucleotide is labeled with a detectable label.

8. The polynucleotide of claim 1 wherein the polynucleotide is attached to a solid support.

9. The polynucleotide of claim 1 wherein the polynucleotide is attached to a solid support at a defined location.

* * * * *

UNITED STATES PATENT AND TRADEMARK OFFICE
CERTIFICATE OF CORRECTION

PATENT NO. : 8,586,725 B2
APPLICATION NO. : 12/521695
DATED : November 19, 2013
INVENTOR(S) : Cummins et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 876 days.

Signed and Sealed this
Twenty-second Day of September, 2015

Michelle K. Lee
*Director of the United States Patent and Trademark Office*

SEQUENCE LISTING

```
<160> NUMBER OF SEQ ID NOS: 1881

<210> SEQ ID NO 1
<211> LENGTH: 22
<212> TYPE: RNA
<213> ORGANISM: Homo sapiens

<400> SEQUENCE: 1
uagcuuauca gacugauguu ga                                              22

<210> SEQ ID NO 2
<211> LENGTH: 22
<212> TYPE: RNA
<213> ORGANISM: Homo sapiens

<400> SEQUENCE: 2
uaacacuguc ugguaacgau gu                                              22

<210> SEQ ID NO 3
<211> LENGTH: 22
<212> TYPE: RNA
<213> ORGANISM: Homo sapiens

<400> SEQUENCE: 3
uaauacugcc ggguaaugau gg                                              22

<210> SEQ ID NO 4
<211> LENGTH: 22
<212> TYPE: RNA
<213> ORGANISM: Homo sapiens

<400> SEQUENCE: 4
ugagaugaag cacuguagcu ca                                              22

<210> SEQ ID NO 5
<211> LENGTH: 23
<212> TYPE: RNA
<213> ORGANISM: Homo sapiens

<400> SEQUENCE: 5
uaauacugcc ugguaaugau gac                                             23

<210> SEQ ID NO 6
<211> LENGTH: 21
<212> TYPE: RNA
<213> ORGANISM: Homo sapiens

<400> SEQUENCE: 6
```

| | |
|---|---|
| uucacagugg cuaaguuccg c | 21 |

<210> SEQ ID NO 7
<211> LENGTH: 22
<212> TYPE: RNA
<213> ORGANISM: Homo sapiens

<400> SEQUENCE: 7

| | |
|---|---|
| uggcucaguu cagcaggaac ag | 22 |

<210> SEQ ID NO 8
<211> LENGTH: 21
<212> TYPE: RNA
<213> ORGANISM: Homo sapiens

<400> SEQUENCE: 8

| | |
|---|---|
| uucaaguaau ccaggauagg c | 21 |

<210> SEQ ID NO 9
<211> LENGTH: 24
<212> TYPE: RNA
<213> ORGANISM: Homo sapiens

<400> SEQUENCE: 9

| | |
|---|---|
| guccaguuuu cccaggaauc ccuu | 24 |

<210> SEQ ID NO 10
<211> LENGTH: 22
<212> TYPE: RNA
<213> ORGANISM: Homo sapiens

<400> SEQUENCE: 10

| | |
|---|---|
| uacaguacug ugauaacuga ag | 22 |

<210> SEQ ID NO 11
<211> LENGTH: 22
<212> TYPE: RNA
<213> ORGANISM: Homo sapiens

<400> SEQUENCE: 11

| | |
|---|---|
| uguaacagca acuccaugug ga | 22 |

<210> SEQ ID NO 12
<211> LENGTH: 21
<212> TYPE: RNA
<213> ORGANISM: Homo sapiens

<400> SEQUENCE: 12

| | |
|---|---|
| cugaccuaug aauugacagc c | 21 |

<210> SEQ ID NO 13
<211> LENGTH: 23
<212> TYPE: RNA
<213> ORGANISM: Homo sapiens

<400> SEQUENCE: 13

| | |
|---|---|
| aaaccguuac cauuacugag uuu | 23 |

<210> SEQ ID NO 14
<211> LENGTH: 22
<212> TYPE: RNA
<213> ORGANISM: Homo sapiens

<400> SEQUENCE: 14

```
aagcugccag uugaagaacu gu                                          22

<210> SEQ ID NO 15
<211> LENGTH: 23
<212> TYPE: RNA
<213> ORGANISM: Homo sapiens

<400> SEQUENCE: 15
agcagcauug uacagggcua uga                                         23

<210> SEQ ID NO 16
<211> LENGTH: 22
<212> TYPE: RNA
<213> ORGANISM: Homo sapiens

<400> SEQUENCE: 16
uagcagcacg uaaauauugg cg                                          22

<210> SEQ ID NO 17
<211> LENGTH: 22
<212> TYPE: RNA
<213> ORGANISM: Homo sapiens

<400> SEQUENCE: 17
cauugcacuu gucucggucu ga                                          22

<210> SEQ ID NO 18
<211> LENGTH: 22
<212> TYPE: RNA
<213> ORGANISM: Homo sapiens

<400> SEQUENCE: 18
uaacacuguc ugguaaagau gg                                          22

<210> SEQ ID NO 19
<211> LENGTH: 23
<212> TYPE: RNA
<213> ORGANISM: Homo sapiens

<400> SEQUENCE: 19
uagcaccauu ugaaaucagu guu                                         23

<210> SEQ ID NO 20
<211> LENGTH: 20
<212> TYPE: RNA
<213> ORGANISM: Homo sapiens

<400> SEQUENCE: 20
uguaaacauc cuugacugga                                             20

<210> SEQ ID NO 21
<211> LENGTH: 23
<212> TYPE: RNA
<213> ORGANISM: Homo sapiens

<400> SEQUENCE: 21
uguaguguuu ccuacuuuau gga                                         23

<210> SEQ ID NO 22
<211> LENGTH: 22
<212> TYPE: RNA
<213> ORGANISM: Homo sapiens

<400> SEQUENCE: 22
```

-continued

```
caacggaauc ccaaaagcag cu                                              22

<210> SEQ ID NO 23
<211> LENGTH: 21
<212> TYPE: RNA
<213> ORGANISM: Homo sapiens

<400> SEQUENCE: 23
aacuggccua caaaguccca g                                               21

<210> SEQ ID NO 24
<211> LENGTH: 22
<212> TYPE: RNA
<213> ORGANISM: Homo sapiens

<400> SEQUENCE: 24
uacaguauag augauguacu ag                                              22

<210> SEQ ID NO 25
<211> LENGTH: 24
<212> TYPE: RNA
<213> ORGANISM: Homo sapiens

<400> SEQUENCE: 25
agcuacaucu ggcuacuggg ucuc                                            24

<210> SEQ ID NO 26
<211> LENGTH: 23
<212> TYPE: RNA
<213> ORGANISM: Homo sapiens

<400> SEQUENCE: 26
ugugcaaauc caugcaaaac uga                                             23

<210> SEQ ID NO 27
<211> LENGTH: 22
<212> TYPE: RNA
<213> ORGANISM: Homo sapiens

<400> SEQUENCE: 27
uguaaacauc cccgacugga ag                                              22

<210> SEQ ID NO 28
<211> LENGTH: 21
<212> TYPE: RNA
<213> ORGANISM: Homo sapiens

<400> SEQUENCE: 28
ggcaagaugc uggcauagcu g                                               21

<210> SEQ ID NO 29
<211> LENGTH: 22
<212> TYPE: RNA
<213> ORGANISM: Homo sapiens

<400> SEQUENCE: 29
uguaaacauc cucgacugga ag                                              22

<210> SEQ ID NO 30
<211> LENGTH: 21
<212> TYPE: RNA
<213> ORGANISM: Homo sapiens

<400> SEQUENCE: 30
```

```
aucacauugc cagggauuuc c                                          21

<210> SEQ ID NO 31
<211> LENGTH: 21
<212> TYPE: RNA
<213> ORGANISM: Homo sapiens

<400> SEQUENCE: 31
ugagguagua guuuguacag u                                          21

<210> SEQ ID NO 32
<211> LENGTH: 21
<212> TYPE: RNA
<213> ORGANISM: Homo sapiens

<400> SEQUENCE: 32
uagcaccauc ugaaaucggu u                                          21

<210> SEQ ID NO 33
<211> LENGTH: 21
<212> TYPE: RNA
<213> ORGANISM: Homo sapiens

<400> SEQUENCE: 33
uucacagugg cuaaguucug c                                          21

<210> SEQ ID NO 34
<211> LENGTH: 22
<212> TYPE: RNA
<213> ORGANISM: Homo sapiens

<400> SEQUENCE: 34
ugagguagua gauuguauag uu                                         22

<210> SEQ ID NO 35
<211> LENGTH: 22
<212> TYPE: RNA
<213> ORGANISM: Homo sapiens

<400> SEQUENCE: 35
uuauaauaca accugauaag ug                                         22

<210> SEQ ID NO 36
<211> LENGTH: 22
<212> TYPE: RNA
<213> ORGANISM: Homo sapiens

<400> SEQUENCE: 36
uaaggugcau cuagugcaga ua                                         22

<210> SEQ ID NO 37
<211> LENGTH: 22
<212> TYPE: RNA
<213> ORGANISM: Homo sapiens

<400> SEQUENCE: 37
ugagguagua gguuguauag uu                                         22

<210> SEQ ID NO 38
<211> LENGTH: 23
<212> TYPE: RNA
<213> ORGANISM: Homo sapiens

<400> SEQUENCE: 38
```

```
ucaagagcaa uaacgaaaaa ugu                                              23

<210> SEQ ID NO 39
<211> LENGTH: 21
<212> TYPE: RNA
<213> ORGANISM: Homo sapiens

<400> SEQUENCE: 39
uauugcacuu gucccggccu g                                                21

<210> SEQ ID NO 40
<211> LENGTH: 21
<212> TYPE: RNA
<213> ORGANISM: Homo sapiens

<400> SEQUENCE: 40
uaaagugcug acagugcaga u                                                21

<210> SEQ ID NO 41
<211> LENGTH: 22
<212> TYPE: RNA
<213> ORGANISM: Homo sapiens

<400> SEQUENCE: 41
uagcagcaca uaaugguuug ug                                               22

<210> SEQ ID NO 42
<211> LENGTH: 19
<212> TYPE: RNA
<213> ORGANISM: Homo sapiens

<400> SEQUENCE: 42
gugcauugua guugcauug                                                   19

<210> SEQ ID NO 43
<211> LENGTH: 23
<212> TYPE: RNA
<213> ORGANISM: Homo sapiens

<400> SEQUENCE: 43
aaagugcugc gacauuugag cgu                                              23

<210> SEQ ID NO 44
<211> LENGTH: 21
<212> TYPE: RNA
<213> ORGANISM: Homo sapiens

<400> SEQUENCE: 44
aucacauugc cagggauuac c                                                21

<210> SEQ ID NO 45
<211> LENGTH: 23
<212> TYPE: RNA
<213> ORGANISM: Homo sapiens

<400> SEQUENCE: 45
gaagugcuuc gauuuugggg ugu                                              23

<210> SEQ ID NO 46
<211> LENGTH: 22
<212> TYPE: RNA
<213> ORGANISM: Homo sapiens

<400> SEQUENCE: 46
```

```
uguaaacauc cuacacucag cu                                        22
```

<210> SEQ ID NO 47
<211> LENGTH: 21
<212> TYPE: RNA
<213> ORGANISM: Homo sapiens

<400> SEQUENCE: 47

```
ucguaccgug aguaauaaug c                                         21
```

<210> SEQ ID NO 48
<211> LENGTH: 23
<212> TYPE: RNA
<213> ORGANISM: Homo sapiens

<400> SEQUENCE: 48

```
ugugcaaauc uaugcaaaac uga                                       23
```

<210> SEQ ID NO 49
<211> LENGTH: 23
<212> TYPE: RNA
<213> ORGANISM: Homo sapiens

<400> SEQUENCE: 49

```
uguaaacauc cuacacucuc agc                                       23
```

<210> SEQ ID NO 50
<211> LENGTH: 22
<212> TYPE: RNA
<213> ORGANISM: Homo sapiens

<400> SEQUENCE: 50

```
uucaaguaau ucaggauagg uu                                        22
```

<210> SEQ ID NO 51
<211> LENGTH: 21
<212> TYPE: RNA
<213> ORGANISM: Homo sapiens

<400> SEQUENCE: 51

```
uauugcacau uacuaaguug c                                         21
```

<210> SEQ ID NO 52
<211> LENGTH: 22
<212> TYPE: RNA
<213> ORGANISM: Homo sapiens

<400> SEQUENCE: 52

```
ucccugagac ccuaacuugu ga                                        22
```

<210> SEQ ID NO 53
<211> LENGTH: 23
<212> TYPE: RNA
<213> ORGANISM: Homo sapiens

<400> SEQUENCE: 53

```
agcuacauug ucugcugggu uuc                                       23
```

<210> SEQ ID NO 54
<211> LENGTH: 23
<212> TYPE: RNA
<213> ORGANISM: Homo sapiens

<400> SEQUENCE: 54

-continued agcagcauug uacagggcua uca                    23

<210> SEQ ID NO 55
<211> LENGTH: 20
<212> TYPE: RNA
<213> ORGANISM: Homo sapiens

<400> SEQUENCE: 55
uagcaccauu ugaaaucggu                        20

<210> SEQ ID NO 56
<211> LENGTH: 23
<212> TYPE: RNA
<213> ORGANISM: Homo sapiens

<400> SEQUENCE: 56
uacccuguag auccgaauuu gug                    23

<210> SEQ ID NO 57
<211> LENGTH: 23
<212> TYPE: RNA
<213> ORGANISM: Homo sapiens

<400> SEQUENCE: 57
aacauucaac gcugucggug agu                    23

<210> SEQ ID NO 58
<211> LENGTH: 24
<212> TYPE: RNA
<213> ORGANISM: Homo sapiens

<400> SEQUENCE: 58
caaagugcuu acagugcagg uagu                   24

<210> SEQ ID NO 59
<211> LENGTH: 22
<212> TYPE: RNA
<213> ORGANISM: Homo sapiens

<400> SEQUENCE: 59
ugagguagua gguugugugg uu                     22

<210> SEQ ID NO 60
<211> LENGTH: 23
<212> TYPE: RNA
<213> ORGANISM: Homo sapiens

<400> SEQUENCE: 60
uaaagugcuu auagugcagg uag                    23

<210> SEQ ID NO 61
<211> LENGTH: 20
<212> TYPE: RNA
<213> ORGANISM: Homo sapiens

<400> SEQUENCE: 61
acugcaguga aggcacuugu                        20

<210> SEQ ID NO 62
<211> LENGTH: 21
<212> TYPE: RNA
<213> ORGANISM: Homo sapiens

<400> SEQUENCE: 62
uagcagcaca gaaauauugg c                                          21

<210> SEQ ID NO 63
<211> LENGTH: 21
<212> TYPE: RNA
<213> ORGANISM: Homo sapiens

<400> SEQUENCE: 63
uggaauguaa agaaguaugu a                                          21

<210> SEQ ID NO 64
<211> LENGTH: 22
<212> TYPE: RNA
<213> ORGANISM: Homo sapiens

<400> SEQUENCE: 64
cagugcaaug augaaagggc au                                         22

<210> SEQ ID NO 65
<211> LENGTH: 21
<212> TYPE: RNA
<213> ORGANISM: Homo sapiens

<400> SEQUENCE: 65
uugugcuuga ucuaaccaug u                                          21

<210> SEQ ID NO 66
<211> LENGTH: 22
<212> TYPE: RNA
<213> ORGANISM: Homo sapiens

<400> SEQUENCE: 66
cagugcaaug uuaaaagggc au                                         22

<210> SEQ ID NO 67
<211> LENGTH: 22
<212> TYPE: RNA
<213> ORGANISM: Homo sapiens

<400> SEQUENCE: 67
aaagugcugu ucgugcaggu ag                                         22

<210> SEQ ID NO 68
<211> LENGTH: 22
<212> TYPE: RNA
<213> ORGANISM: Homo sapiens

<400> SEQUENCE: 68
uuuggcaaug guagaacuca ca                                         22

<210> SEQ ID NO 69
<211> LENGTH: 22
<212> TYPE: RNA
<213> ORGANISM: Homo sapiens

<400> SEQUENCE: 69
cugugcgugu gacagcggcu ga                                         22

<210> SEQ ID NO 70
<211> LENGTH: 22
<212> TYPE: RNA
<213> ORGANISM: Homo sapiens

<400> SEQUENCE: 70

```
ucucccaacc cuuguaccag ug                                              22

<210> SEQ ID NO 71
<211> LENGTH: 22
<212> TYPE: RNA
<213> ORGANISM: Homo sapiens

<400> SEQUENCE: 71
uagcagcaca ucaugguuua ca                                              22

<210> SEQ ID NO 72
<211> LENGTH: 21
<212> TYPE: RNA
<213> ORGANISM: Homo sapiens

<400> SEQUENCE: 72
ugagguagua guuugugcug u                                               21

<210> SEQ ID NO 73
<211> LENGTH: 23
<212> TYPE: RNA
<213> ORGANISM: Homo sapiens

<400> SEQUENCE: 73
aaaagcuggg uugagagggc gaa                                             23

<210> SEQ ID NO 74
<211> LENGTH: 22
<212> TYPE: RNA
<213> ORGANISM: Homo sapiens

<400> SEQUENCE: 74
cagcagcaau ucauguuuug aa                                              22

<210> SEQ ID NO 75
<211> LENGTH: 23
<212> TYPE: RNA
<213> ORGANISM: Homo sapiens

<400> SEQUENCE: 75
cagugcaaua guauugucaa agc                                             23

<210> SEQ ID NO 76
<211> LENGTH: 20
<212> TYPE: RNA
<213> ORGANISM: Homo sapiens

<400> SEQUENCE: 76
cauaaaguag aaagcacuac                                                 20

<210> SEQ ID NO 77
<211> LENGTH: 22
<212> TYPE: RNA
<213> ORGANISM: Homo sapiens

<400> SEQUENCE: 77
uaauacuguc ugguaaaacc gu                                              22

<210> SEQ ID NO 78
<211> LENGTH: 22
<212> TYPE: RNA
<213> ORGANISM: Homo sapiens

<400> SEQUENCE: 78
```
uuuggcacua gcacauuuuu gc					22

<210> SEQ ID NO 79
<211> LENGTH: 22
<212> TYPE: RNA
<213> ORGANISM: Homo sapiens

<400> SEQUENCE: 79
acuagacuga agcuccuuga gg					22

<210> SEQ ID NO 80
<211> LENGTH: 22
<212> TYPE: RNA
<213> ORGANISM: Homo sapiens

<400> SEQUENCE: 80
uuuguucguu cggcucgcgu ga					22

<210> SEQ ID NO 81
<211> LENGTH: 23
<212> TYPE: RNA
<213> ORGANISM: Homo sapiens

<400> SEQUENCE: 81
ucuuugguua ucuagcugua uga					23

<210> SEQ ID NO 82
<211> LENGTH: 21
<212> TYPE: RNA
<213> ORGANISM: Homo sapiens

<400> SEQUENCE: 82
gugccgccau cuuuugagug u					21

<210> SEQ ID NO 83
<211> LENGTH: 21
<212> TYPE: RNA
<213> ORGANISM: Homo sapiens

<400> SEQUENCE: 83
augaccuaug aauugacaga c					21

<210> SEQ ID NO 84
<211> LENGTH: 22
<212> TYPE: RNA
<213> ORGANISM: Homo sapiens

<400> SEQUENCE: 84
aacccguaga uccgaacuug ug					22

<210> SEQ ID NO 85
<211> LENGTH: 22
<212> TYPE: RNA
<213> ORGANISM: Homo sapiens

<400> SEQUENCE: 85
uugguccccu ucaaccagcu gu					22

<210> SEQ ID NO 86
<211> LENGTH: 22
<212> TYPE: RNA
<213> ORGANISM: Homo sapiens

<400> SEQUENCE: 86
aaggagcuca cagucuauug ag                                              22

<210> SEQ ID NO 87
<211> LENGTH: 22
<212> TYPE: RNA
<213> ORGANISM: Homo sapiens

<400> SEQUENCE: 87
cuuucagucg gauguuuaca gc                                              22

<210> SEQ ID NO 88
<211> LENGTH: 22
<212> TYPE: RNA
<213> ORGANISM: Homo sapiens

<400> SEQUENCE: 88
gugaaauguu uaggaccacu ag                                              22

<210> SEQ ID NO 89
<211> LENGTH: 21
<212> TYPE: RNA
<213> ORGANISM: Homo sapiens

<400> SEQUENCE: 89
agagguagua gguugcauag u                                               21

<210> SEQ ID NO 90
<211> LENGTH: 22
<212> TYPE: RNA
<213> ORGANISM: Homo sapiens

<400> SEQUENCE: 90
uucaacgggu auuuauugag ca                                              22

<210> SEQ ID NO 91
<211> LENGTH: 21
<212> TYPE: RNA
<213> ORGANISM: Homo sapiens

<400> SEQUENCE: 91
agugguuuua cccuauggua g                                               21

<210> SEQ ID NO 92
<211> LENGTH: 21
<212> TYPE: RNA
<213> ORGANISM: Homo sapiens

<400> SEQUENCE: 92
uagguaguuu ccuguuguug g                                               21

<210> SEQ ID NO 93
<211> LENGTH: 23
<212> TYPE: RNA
<213> ORGANISM: Homo sapiens

<400> SEQUENCE: 93
uccagcauca gugauuuugu uga                                             23

<210> SEQ ID NO 94
<211> LENGTH: 22
<212> TYPE: RNA
<213> ORGANISM: Homo sapiens

<400> SEQUENCE: 94
uaaugccccu aaaaauccuu au                                              22

<210> SEQ ID NO 95
<211> LENGTH: 23
<212> TYPE: RNA
<213> ORGANISM: Homo sapiens

<400> SEQUENCE: 95
caaagaauuc uccuuuggg cuu                                              23

<210> SEQ ID NO 96
<211> LENGTH: 24
<212> TYPE: RNA
<213> ORGANISM: Homo sapiens

<400> SEQUENCE: 96
ucucacacag aaaucgcacc cguc                                            24

<210> SEQ ID NO 97
<211> LENGTH: 23
<212> TYPE: RNA
<213> ORGANISM: Homo sapiens

<400> SEQUENCE: 97
cccaguguuc agacuaccug uuc                                             23

<210> SEQ ID NO 98
<211> LENGTH: 22
<212> TYPE: RNA
<213> ORGANISM: Homo sapiens

<400> SEQUENCE: 98
aacauucauu gcugucggug gg                                              22

<210> SEQ ID NO 99
<211> LENGTH: 21
<212> TYPE: RNA
<213> ORGANISM: Homo sapiens

<400> SEQUENCE: 99
acagcaggca cagacaggca g                                               21

<210> SEQ ID NO 100
<211> LENGTH: 22
<212> TYPE: RNA
<213> ORGANISM: Homo sapiens

<400> SEQUENCE: 100
cacccguaga accgaccuug cg                                              22

<210> SEQ ID NO 101
<211> LENGTH: 22
<212> TYPE: RNA
<213> ORGANISM: Homo sapiens

<400> SEQUENCE: 101
ucagugcacu acagaacuuu gu                                              22

<210> SEQ ID NO 102
<211> LENGTH: 21
<212> TYPE: RNA
<213> ORGANISM: Homo sapiens

<400> SEQUENCE: 102

```
cagcagcaca cugugguuug u                                          21

<210> SEQ ID NO 103
<211> LENGTH: 21
<212> TYPE: RNA
<213> ORGANISM: Homo sapiens

<400> SEQUENCE: 103
gccccugggc cuauccuaga a                                          21

<210> SEQ ID NO 104
<211> LENGTH: 22
<212> TYPE: RNA
<213> ORGANISM: Homo sapiens

<400> SEQUENCE: 104
uggaagacua gugauuuugu ug                                         22

<210> SEQ ID NO 105
<211> LENGTH: 23
<212> TYPE: RNA
<213> ORGANISM: Homo sapiens

<400> SEQUENCE: 105
uggcaguguc uuagcugguu guu                                        23

<210> SEQ ID NO 106
<211> LENGTH: 22
<212> TYPE: RNA
<213> ORGANISM: Homo sapiens

<400> SEQUENCE: 106
uuaaugcuaa ucgugauagg gg                                         22

<210> SEQ ID NO 107
<211> LENGTH: 22
<212> TYPE: RNA
<213> ORGANISM: Homo sapiens

<400> SEQUENCE: 107
ucacagugaa ccggucucuu uc                                         22

<210> SEQ ID NO 108
<211> LENGTH: 22
<212> TYPE: RNA
<213> ORGANISM: Homo sapiens

<400> SEQUENCE: 108
ucacagugaa ccggucucuu uu                                         22

<210> SEQ ID NO 109
<211> LENGTH: 22
<212> TYPE: RNA
<213> ORGANISM: Homo sapiens

<400> SEQUENCE: 109
uauggcuuuu cauuccuaug ug                                         22

<210> SEQ ID NO 110
<211> LENGTH: 22
<212> TYPE: RNA
<213> ORGANISM: Homo sapiens

<400> SEQUENCE: 110
```

```
ucagugcaug acagaacuug gg                                                  22

<210> SEQ ID NO 111
<211> LENGTH: 22
<212> TYPE: RNA
<213> ORGANISM: Homo sapiens

<400> SEQUENCE: 111
ugagguagua aguuguauug uu                                                  22

<210> SEQ ID NO 112
<211> LENGTH: 22
<212> TYPE: RNA
<213> ORGANISM: Homo sapiens

<400> SEQUENCE: 112
uuuuugcgau guguuccuaa ua                                                  22

<210> SEQ ID NO 113
<211> LENGTH: 22
<212> TYPE: RNA
<213> ORGANISM: Homo sapiens

<400> SEQUENCE: 113
ucuggcuccg ugcuucacu cc                                                   22

<210> SEQ ID NO 114
<211> LENGTH: 23
<212> TYPE: RNA
<213> ORGANISM: Homo sapiens

<400> SEQUENCE: 114
gcaaagcaca cggccugcag aga                                                 23

<210> SEQ ID NO 115
<211> LENGTH: 22
<212> TYPE: RNA
<213> ORGANISM: Homo sapiens

<400> SEQUENCE: 115
ugagguagua gguuguaugg uu                                                  22

<210> SEQ ID NO 116
<211> LENGTH: 24
<212> TYPE: RNA
<213> ORGANISM: Homo sapiens

<400> SEQUENCE: 116
aacuggcccu caaagucccg cuuu                                                24

<210> SEQ ID NO 117
<211> LENGTH: 21
<212> TYPE: RNA
<213> ORGANISM: Homo sapiens

<400> SEQUENCE: 117
ugucaguuug ucaaauaccc c                                                   21

<210> SEQ ID NO 118
<211> LENGTH: 21
<212> TYPE: RNA
<213> ORGANISM: Homo sapiens

<400> SEQUENCE: 118
```
ugagguagga gguuguauag u                                              21

<210> SEQ ID NO 119
<211> LENGTH: 23
<212> TYPE: RNA
<213> ORGANISM: Homo sapiens

<400> SEQUENCE: 119
ucccugagac ccuuuaaccu gug                                            23

<210> SEQ ID NO 120
<211> LENGTH: 23
<212> TYPE: RNA
<213> ORGANISM: Homo sapiens

<400> SEQUENCE: 120
acuccauuug uuuugaugau gga                                            23

<210> SEQ ID NO 121
<211> LENGTH: 23
<212> TYPE: RNA
<213> ORGANISM: Homo sapiens

<400> SEQUENCE: 121
uauggcacug guagaauuca cug                                            23

<210> SEQ ID NO 122
<211> LENGTH: 22
<212> TYPE: RNA
<213> ORGANISM: Homo sapiens

<400> SEQUENCE: 122
uucaccaccu ucuccaccca gc                                             22

<210> SEQ ID NO 123
<211> LENGTH: 22
<212> TYPE: RNA
<213> ORGANISM: Homo sapiens

<400> SEQUENCE: 123
auugcacggu auccaucugu aa                                             22

<210> SEQ ID NO 124
<211> LENGTH: 18
<212> TYPE: RNA
<213> ORGANISM: Homo sapiens

<400> SEQUENCE: 124
ucuacagugc acgugucu                                                  18

<210> SEQ ID NO 125
<211> LENGTH: 24
<212> TYPE: RNA
<213> ORGANISM: Homo sapiens

<400> SEQUENCE: 125
aaaagugcuu acagugcagg uagc                                           24

<210> SEQ ID NO 126
<211> LENGTH: 18
<212> TYPE: RNA
<213> ORGANISM: Homo sapiens

<400> SEQUENCE: 126
uggagagaaa ggcaguuc                                                     18

<210> SEQ ID NO 127
<211> LENGTH: 22
<212> TYPE: RNA
<213> ORGANISM: Homo sapiens

<400> SEQUENCE: 127
aacauucaac cugucgguga gu                                                22

<210> SEQ ID NO 128
<211> LENGTH: 22
<212> TYPE: RNA
<213> ORGANISM: Homo sapiens

<400> SEQUENCE: 128
caucccuugc augguggagg gu                                                22

<210> SEQ ID NO 129
<211> LENGTH: 22
<212> TYPE: RNA
<213> ORGANISM: Homo sapiens

<400> SEQUENCE: 129
uaaggugcau cuagugcagu ua                                                22

<210> SEQ ID NO 130
<211> LENGTH: 23
<212> TYPE: RNA
<213> ORGANISM: Homo sapiens

<400> SEQUENCE: 130
uaagugcuuc cauguuuuag uag                                               23

<210> SEQ ID NO 131
<211> LENGTH: 23
<212> TYPE: RNA
<213> ORGANISM: Homo sapiens

<400> SEQUENCE: 131
cccaguguuu agacuaucug uuc                                               23

<210> SEQ ID NO 132
<211> LENGTH: 23
<212> TYPE: RNA
<213> ORGANISM: Homo sapiens

<400> SEQUENCE: 132
uuaagacuug cagugauguu uaa                                               23

<210> SEQ ID NO 133
<211> LENGTH: 23
<212> TYPE: RNA
<213> ORGANISM: Homo sapiens

<400> SEQUENCE: 133
cgaauguugc ucggugaacc ccu                                               23

<210> SEQ ID NO 134
<211> LENGTH: 21
<212> TYPE: RNA
<213> ORGANISM: Homo sapiens

<400> SEQUENCE: 134
aucgggaaug ucguguccgc c                                              21

<210> SEQ ID NO 135
<211> LENGTH: 20
<212> TYPE: RNA
<213> ORGANISM: Homo sapiens

<400> SEQUENCE: 135
uugcauaguc acaaaaguga                                                20

<210> SEQ ID NO 136
<211> LENGTH: 22
<212> TYPE: RNA
<213> ORGANISM: Homo sapiens

<400> SEQUENCE: 136
uccuucauuc caccggaguc ug                                             22

<210> SEQ ID NO 137
<211> LENGTH: 21
<212> TYPE: RNA
<213> ORGANISM: Homo sapiens

<400> SEQUENCE: 137
ugauugucca aacgcaauuc u                                              21

<210> SEQ ID NO 138
<211> LENGTH: 23
<212> TYPE: RNA
<213> ORGANISM: Homo sapiens

<400> SEQUENCE: 138 cgcaucccu agggcauugg ugu                                             23

<210> SEQ ID NO 139
<211> LENGTH: 21
<212> TYPE: RNA
<213> ORGANISM: Homo sapiens

<400> SEQUENCE: 139
ucccuguccu ccaggagcuc a                                              21

<210> SEQ ID NO 140
<211> LENGTH: 17
<212> TYPE: RNA
<213> ORGANISM: Homo sapiens

<400> SEQUENCE: 140 agcuggguu gugaauc                                                    17

<210> SEQ ID NO 141
<211> LENGTH: 22
<212> TYPE: RNA
<213> ORGANISM: Homo sapiens

<400> SEQUENCE: 141
ugagaacuga auuccauggg uu                                             22

<210> SEQ ID NO 142
<211> LENGTH: 22
<212> TYPE: RNA
<213> ORGANISM: Homo sapiens

<400> SEQUENCE: 142

| | | |
|---|---|---|
| agcucggucu gaggccccuc ag | | 22 |

<210> SEQ ID NO 143
<211> LENGTH: 22
<212> TYPE: RNA
<213> ORGANISM: Homo sapiens

<400> SEQUENCE: 143

| | | |
|---|---|---|
| gucaacacuu gcugguuucc uc | | 22 |

<210> SEQ ID NO 144
<211> LENGTH: 22
<212> TYPE: RNA
<213> ORGANISM: Homo sapiens

<400> SEQUENCE: 144

| | | |
|---|---|---|
| aacccguaga uccgaucuug ug | | 22 |

<210> SEQ ID NO 145
<211> LENGTH: 23
<212> TYPE: RNA
<213> ORGANISM: Homo sapiens

<400> SEQUENCE: 145

| | | |
|---|---|---|
| aauccuugga accuaggugu gag | | 23 |

<210> SEQ ID NO 146
<211> LENGTH: 22
<212> TYPE: RNA
<213> ORGANISM: Homo sapiens

<400> SEQUENCE: 146

| | | |
|---|---|---|
| gcacauuaca cggucgaccu cu | | 22 |

<210> SEQ ID NO 147
<211> LENGTH: 22
<212> TYPE: RNA
<213> ORGANISM: Homo sapiens

<400> SEQUENCE: 147

| | | |
|---|---|---|
| uuaucagaau cuccaggggu ac | | 22 |

<210> SEQ ID NO 148
<211> LENGTH: 22
<212> TYPE: RNA
<213> ORGANISM: Homo sapiens

<400> SEQUENCE: 148

| | | |
|---|---|---|
| uacccuguag aaccgaauuu gu | | 22 |

<210> SEQ ID NO 149
<211> LENGTH: 22
<212> TYPE: RNA
<213> ORGANISM: Homo sapiens

<400> SEQUENCE: 149

| | | |
|---|---|---|
| uagguuaucc guguugccuu cg | | 22 |

<210> SEQ ID NO 150
<211> LENGTH: 21
<212> TYPE: RNA
<213> ORGANISM: Homo sapiens

<400> SEQUENCE: 150
uagguaguuu cauguuguug g                                           21

<210> SEQ ID NO 151
<211> LENGTH: 22
<212> TYPE: RNA
<213> ORGANISM: Homo sapiens

<400> SEQUENCE: 151
ccacugcccc aggugcugcu gg                                          22

<210> SEQ ID NO 152
<211> LENGTH: 24
<212> TYPE: RNA
<213> ORGANISM: Homo sapiens

<400> SEQUENCE: 152
aacauucauu guugucggug gguu                                        24

<210> SEQ ID NO 153
<211> LENGTH: 22
<212> TYPE: RNA
<213> ORGANISM: Homo sapiens

<400> SEQUENCE: 153
aauauaacac agauggccug uu                                          22

<210> SEQ ID NO 154
<211> LENGTH: 22
<212> TYPE: RNA
<213> ORGANISM: Homo sapiens

<400> SEQUENCE: 154
cuggacuugg agucagaagg cc                                          22

<210> SEQ ID NO 155
<211> LENGTH: 22
<212> TYPE: RNA
<213> ORGANISM: Homo sapiens

<400> SEQUENCE: 155
ugauauguuu gauauauuag gu                                          22

<210> SEQ ID NO 156
<211> LENGTH: 22
<212> TYPE: RNA
<213> ORGANISM: Homo sapiens

<400> SEQUENCE: 156
cuccugacuc cagguccugu gu                                          22

<210> SEQ ID NO 157
<211> LENGTH: 22
<212> TYPE: RNA
<213> ORGANISM: Homo sapiens

<400> SEQUENCE: 157
aauugcacuu uagcaauggu ga                                          22

<210> SEQ ID NO 158
<211> LENGTH: 22
<212> TYPE: RNA
<213> ORGANISM: Homo sapiens

<400> SEQUENCE: 158

```
ugagaacuga auuccauagg cu                                           22

<210> SEQ ID NO 159
<211> LENGTH: 22
<212> TYPE: RNA
<213> ORGANISM: Homo sapiens

<400> SEQUENCE: 159
uaacagucua cagccauggu cg                                           22

<210> SEQ ID NO 160
<211> LENGTH: 22
<212> TYPE: RNA
<213> ORGANISM: Homo sapiens

<400> SEQUENCE: 160
aucacacaaa ggcaacuuuu gu                                           22

<210> SEQ ID NO 161
<211> LENGTH: 22
<212> TYPE: RNA
<213> ORGANISM: Homo sapiens

<400> SEQUENCE: 161
uuaaggcacg cggugaaugc ca                                           22

<210> SEQ ID NO 162
<211> LENGTH: 22
<212> TYPE: RNA
<213> ORGANISM: Homo sapiens

<400> SEQUENCE: 162
uaugugggau gguaaaccgc uu                                           22

<210> SEQ ID NO 163
<211> LENGTH: 22
<212> TYPE: RNA
<213> ORGANISM: Homo sapiens

<400> SEQUENCE: 163
uguuugcaga ggaaacugag ac                                           22

<210> SEQ ID NO 164
<211> LENGTH: 22
<212> TYPE: RNA
<213> ORGANISM: Homo sapiens

<400> SEQUENCE: 164
aauccuuugu cccuggguga ga                                           22

<210> SEQ ID NO 165
<211> LENGTH: 20
<212> TYPE: RNA
<213> ORGANISM: Homo sapiens

<400> SEQUENCE: 165
auugacacuu cugugaguag                                              20

<210> SEQ ID NO 166
<211> LENGTH: 22
<212> TYPE: RNA
<213> ORGANISM: Homo sapiens

<400> SEQUENCE: 166
```

```
accaucgacc guugauugua cc                                              22

<210> SEQ ID NO 167
<211> LENGTH: 21
<212> TYPE: RNA
<213> ORGANISM: Homo sapiens

<400> SEQUENCE: 167
ugcugacucc uaguccaggg c                                               21

<210> SEQ ID NO 168
<211> LENGTH: 22
<212> TYPE: RNA
<213> ORGANISM: Homo sapiens

<400> SEQUENCE: 168
uauacaaggg caagcucucu gu                                              22

<210> SEQ ID NO 169
<211> LENGTH: 23
<212> TYPE: RNA
<213> ORGANISM: Homo sapiens

<400> SEQUENCE: 169
caagucacua gugguuccgu uua                                             23

<210> SEQ ID NO 170
<211> LENGTH: 21
<212> TYPE: RNA
<213> ORGANISM: Homo sapiens

<400> SEQUENCE: 170 agggccccccc cucaauccug u                                              21

<210> SEQ ID NO 171
<211> LENGTH: 23
<212> TYPE: RNA
<213> ORGANISM: Homo sapiens

<400> SEQUENCE: 171
uaagugcuuc cauguuuggg uga                                             23

<210> SEQ ID NO 172
<211> LENGTH: 23
<212> TYPE: RNA
<213> ORGANISM: Homo sapiens

<400> SEQUENCE: 172
uaagugcuuc cauguuucag ugg                                             23

<210> SEQ ID NO 173
<211> LENGTH: 23
<212> TYPE: RNA
<213> ORGANISM: Homo sapiens

<400> SEQUENCE: 173
uaagugcuuc cauguuugag ugu                                             23

<210> SEQ ID NO 174
<211> LENGTH: 23
<212> TYPE: RNA
<213> ORGANISM: Homo sapiens

<400> SEQUENCE: 174
```
uauggcuuuu uauuccuaug uga                                              23

<210> SEQ ID NO 175
<211> LENGTH: 22
<212> TYPE: RNA
<213> ORGANISM: Homo sapiens

<400> SEQUENCE: 175
cuuucagucg gauguuugca gc                                               22

<210> SEQ ID NO 176
<211> LENGTH: 23
<212> TYPE: RNA
<213> ORGANISM: Homo sapiens

<400> SEQUENCE: 176
caaagugcuc auagugcagg uag                                              23

<210> SEQ ID NO 177
<211> LENGTH: 23
<212> TYPE: RNA
<213> ORGANISM: Homo sapiens

<400> SEQUENCE: 177
aaacaaacau ggugcacuuc uuu                                              23

<210> SEQ ID NO 178
<211> LENGTH: 22
<212> TYPE: RNA
<213> ORGANISM: Homo sapiens

<400> SEQUENCE: 178
ucagugcauc acagaacuuu gu                                               22

<210> SEQ ID NO 179
<211> LENGTH: 22
<212> TYPE: RNA
<213> ORGANISM: Homo sapiens

<400> SEQUENCE: 179
uggacggaga acugauaagg gu                                               22

<210> SEQ ID NO 180
<211> LENGTH: 22
<212> TYPE: RNA
<213> ORGANISM: Homo sapiens

<400> SEQUENCE: 180
uucccuuugu cauccuaugc cu                                               22

<210> SEQ ID NO 181
<211> LENGTH: 22
<212> TYPE: RNA
<213> ORGANISM: Homo sapiens

<400> SEQUENCE: 181
ugguuuaccg ucccacauac au                                               22

<210> SEQ ID NO 182
<211> LENGTH: 20
<212> TYPE: RNA
<213> ORGANISM: Homo sapiens

<400> SEQUENCE: 182

-continued ccucuggpcc cuuccuccag                                      20

<210> SEQ ID NO 183
<211> LENGTH: 23
<212> TYPE: RNA
<213> ORGANISM: Homo sapiens

<400> SEQUENCE: 183
aggcagugua guuagcugau ugc                                  23

<210> SEQ ID NO 184
<211> LENGTH: 19
<212> TYPE: RNA
<213> ORGANISM: Homo sapiens

<400> SEQUENCE: 184
ugguagacua uggaacgua                                       19

<210> SEQ ID NO 185
<211> LENGTH: 22
<212> TYPE: RNA
<213> ORGANISM: Homo sapiens

<400> SEQUENCE: 185
gaaguuguuc gugguggauu cg                                   22

<210> SEQ ID NO 186
<211> LENGTH: 22
<212> TYPE: RNA
<213> ORGANISM: Homo sapiens

<400> SEQUENCE: 186
uggcagugua uuguuagcug gu                                   22

<210> SEQ ID NO 187
<211> LENGTH: 23
<212> TYPE: RNA
<213> ORGANISM: Homo sapiens

<400> SEQUENCE: 187
cacucagccu ugagggcacu uuc                                  23

<210> SEQ ID NO 188
<211> LENGTH: 23
<212> TYPE: RNA
<213> ORGANISM: Homo sapiens

<400> SEQUENCE: 188
cacucagccu ugagggcacu uuc                                  23

<210> SEQ ID NO 189
<211> LENGTH: 24
<212> TYPE: RNA
<213> ORGANISM: Homo sapiens

<400> SEQUENCE: 189
ugaaacauac acgggaaacc ucuu                                 24

<210> SEQ ID NO 190
<211> LENGTH: 23
<212> TYPE: RNA
<213> ORGANISM: Homo sapiens

<400> SEQUENCE: 190
uuucaagcca gggggcguuu uuc                                              23

<210> SEQ ID NO 191
<211> LENGTH: 21
<212> TYPE: RNA
<213> ORGANISM: Homo sapiens

<400> SEQUENCE: 191
auccuugcua ucugggugcu a                                                21

<210> SEQ ID NO 192
<211> LENGTH: 21
<212> TYPE: RNA
<213> ORGANISM: Homo sapiens

<400> SEQUENCE: 192
uuuugcaccu uuuggaguga a                                                21

<210> SEQ ID NO 193
<211> LENGTH: 23
<212> TYPE: RNA
<213> ORGANISM: Homo sapiens

<400> SEQUENCE: 193
aucgugcauc ccuuuagagu guu                                              23

<210> SEQ ID NO 194
<211> LENGTH: 22
<212> TYPE: RNA
<213> ORGANISM: Homo sapiens

<400> SEQUENCE: 194
aucgugcauc cuuuuagagu gu                                               22

<210> SEQ ID NO 195
<211> LENGTH: 22
<212> TYPE: RNA
<213> ORGANISM: Homo sapiens

<400> SEQUENCE: 195
caaagcgcuc cccuuuagag gu                                               22

<210> SEQ ID NO 196
<211> LENGTH: 23
<212> TYPE: RNA
<213> ORGANISM: Homo sapiens

<400> SEQUENCE: 196
aaagugcuuc ucuuuggugg guu                                              23

<210> SEQ ID NO 197
<211> LENGTH: 24
<212> TYPE: RNA
<213> ORGANISM: Homo sapiens

<400> SEQUENCE: 197
acaaagugcu ucccuuuaga gugu                                             24

<210> SEQ ID NO 198
<211> LENGTH: 22
<212> TYPE: RNA
<213> ORGANISM: Homo sapiens

<400> SEQUENCE: 198

```
acaaagugcu ucccuuuaga gu                                              22

<210> SEQ ID NO 199
<211> LENGTH: 22
<212> TYPE: RNA
<213> ORGANISM: Homo sapiens

<400> SEQUENCE: 199
aacgcacuuc ccuuuagagu gu                                              22

<210> SEQ ID NO 200
<211> LENGTH: 21
<212> TYPE: RNA
<213> ORGANISM: Homo sapiens

<400> SEQUENCE: 200
cuccagaggg augcacuuuc u                                               21

<210> SEQ ID NO 201
<211> LENGTH: 21
<212> TYPE: RNA
<213> ORGANISM: Homo sapiens

<400> SEQUENCE: 201
cagugccucg gcagugcagc c                                               21

<210> SEQ ID NO 202
<211> LENGTH: 22
<212> TYPE: RNA
<213> ORGANISM: Homo sapiens

<400> SEQUENCE: 202
aaaaguaauu gcgaguuuua cc                                              22

<210> SEQ ID NO 203
<211> LENGTH: 21
<212> TYPE: RNA
<213> ORGANISM: Homo sapiens

<400> SEQUENCE: 203
aucaaggauc uuaaacuuug c                                               21

<210> SEQ ID NO 204
<211> LENGTH: 20
<212> TYPE: RNA
<213> ORGANISM: Homo sapiens

<400> SEQUENCE: 204
aagaugugga aaaauuggaa                                                 20

<210> SEQ ID NO 205
<211> LENGTH: 21
<212> TYPE: RNA
<213> ORGANISM: Homo sapiens

<400> SEQUENCE: 205
uaacugguug aacaacugaa c                                               21

<210> SEQ ID NO 206
<211> LENGTH: 22
<212> TYPE: RNA
<213> ORGANISM: Homo sapiens

<400> SEQUENCE: 206
```

-continued uaauuuuaug uauaagcuag uc                                        22

<210> SEQ ID NO 207
<211> LENGTH: 22
<212> TYPE: RNA
<213> ORGANISM: Homo sapiens

<400> SEQUENCE: 207
uuugauaagc ugacauggga ca                                        22

<210> SEQ ID NO 208
<211> LENGTH: 20
<212> TYPE: RNA
<213> ORGANISM: Homo sapiens

<400> SEQUENCE: 208
cacaagguau ugguauuacc                                           20

<210> SEQ ID NO 209
<211> LENGTH: 19
<212> TYPE: RNA
<213> ORGANISM: Homo sapiens

<400> SEQUENCE: 209
cuauagaacu uuccccuc                                             19

<210> SEQ ID NO 210
<211> LENGTH: 21
<212> TYPE: RNA
<213> ORGANISM: Homo sapiens

<400> SEQUENCE: 210
uggguuuacg uugggagaac u                                         21

<210> SEQ ID NO 211
<211> LENGTH: 22
<212> TYPE: RNA
<213> ORGANISM: Homo sapiens

<400> SEQUENCE: 211
aaaggaaagu guauccuaaa ag                                        22

<210> SEQ ID NO 212
<211> LENGTH: 22
<212> TYPE: RNA
<213> ORGANISM: Homo sapiens

<400> SEQUENCE: 212
acaacccuag gagagggugc ca                                        22

<210> SEQ ID NO 213
<211> LENGTH: 21
<212> TYPE: RNA
<213> ORGANISM: Homo sapiens

<400> SEQUENCE: 213
cuauacaauc uacugucuuu c                                         21

<210> SEQ ID NO 214
<211> LENGTH: 22
<212> TYPE: RNA
<213> ORGANISM: Homo sapiens

<400> SEQUENCE: 214
cuguacagcc uccuagcuuu cc                                           22

<210> SEQ ID NO 215
<211> LENGTH: 22
<212> TYPE: RNA
<213> ORGANISM: Homo sapiens

<400> SEQUENCE: 215
cuauacgacc ugcugccuuu cu                                           22

<210> SEQ ID NO 216
<211> LENGTH: 22
<212> TYPE: RNA
<213> ORGANISM: Homo sapiens

<400> SEQUENCE: 216
cuauacggcc uccuagcuuu cc                                           22

<210> SEQ ID NO 217
<211> LENGTH: 25
<212> TYPE: RNA
<213> ORGANISM: Homo sapiens

<400> SEQUENCE: 217
gauaacuaua caaucuauug ccuuc                                        25

<210> SEQ ID NO 218
<211> LENGTH: 18
<212> TYPE: RNA
<213> ORGANISM: Homo sapiens

<400> SEQUENCE: 218
cuauacaguc uacugucu                                                18

<210> SEQ ID NO 219
<211> LENGTH: 21
<212> TYPE: RNA
<213> ORGANISM: Homo sapiens

<400> SEQUENCE: 219
cuguacaggc cacugccuug c                                            21

<210> SEQ ID NO 220
<211> LENGTH: 19
<212> TYPE: RNA
<213> ORGANISM: Homo sapiens

<400> SEQUENCE: 220
cugcgcaagc uacugccuu                                               19

<210> SEQ ID NO 221
<211> LENGTH: 22
<212> TYPE: RNA
<213> ORGANISM: Homo sapiens

<400> SEQUENCE: 221
caagcuugua ucuauaggua ug                                           22

<210> SEQ ID NO 222
<211> LENGTH: 21
<212> TYPE: RNA
<213> ORGANISM: Homo sapiens

<400> SEQUENCE: 222
caguuaucac agugcugaug c                                            21

<210> SEQ ID NO 223
<211> LENGTH: 22
<212> TYPE: RNA
<213> ORGANISM: Homo sapiens

<400> SEQUENCE: 223
ggcuucuuua cagugcugcc uu                                           22

<210> SEQ ID NO 224
<211> LENGTH: 24
<212> TYPE: RNA
<213> ORGANISM: Homo sapiens

<400> SEQUENCE: 224
agcuucuuua cagugcugcc uugu                                         24

<210> SEQ ID NO 225
<211> LENGTH: 22
<212> TYPE: RNA
<213> ORGANISM: Homo sapiens

<400> SEQUENCE: 225
uacugcaaug uaagcacuuc uu                                           22

<210> SEQ ID NO 226
<211> LENGTH: 21
<212> TYPE: RNA
<213> ORGANISM: Homo sapiens

<400> SEQUENCE: 226
ccgcacugug gguacuugcu g                                            21

<210> SEQ ID NO 227
<211> LENGTH: 21
<212> TYPE: RNA
<213> ORGANISM: Homo sapiens

<400> SEQUENCE: 227
caaauucgua ucuaggggaa u                                            21

<210> SEQ ID NO 228
<211> LENGTH: 21
<212> TYPE: RNA
<213> ORGANISM: Homo sapiens

<400> SEQUENCE: 228
acaggugagg uucuugggag c                                            21

<210> SEQ ID NO 229
<211> LENGTH: 20
<212> TYPE: RNA
<213> ORGANISM: Homo sapiens

<400> SEQUENCE: 229
acggguuagg cucuugggag                                              20

<210> SEQ ID NO 230
<211> LENGTH: 22
<212> TYPE: RNA
<213> ORGANISM: Homo sapiens

<400> SEQUENCE: 230

```
aagcccuuac cccaaaaagc au                                                22

<210> SEQ ID NO 231
<211> LENGTH: 20
<212> TYPE: RNA
<213> ORGANISM: Homo sapiens

<400> SEQUENCE: 231 acucuuccc uguugcacua                                                    20

<210> SEQ ID NO 232
<211> LENGTH: 21
<212> TYPE: RNA
<213> ORGANISM: Homo sapiens

<400> SEQUENCE: 232
accguggcuu ucgauuguua c                                                 21

<210> SEQ ID NO 233
<211> LENGTH: 22
<212> TYPE: RNA
<213> ORGANISM: Homo sapiens

<400> SEQUENCE: 233
agcugguaaa auggaaccaa au                                                22

<210> SEQ ID NO 234
<211> LENGTH: 21
<212> TYPE: RNA
<213> ORGANISM: Homo sapiens

<400> SEQUENCE: 234
accacagggu agaaccacgg a                                                 21

<210> SEQ ID NO 235
<211> LENGTH: 22
<212> TYPE: RNA
<213> ORGANISM: Homo sapiens

<400> SEQUENCE: 235
caucuuccag uacaguguug ga                                                22

<210> SEQ ID NO 236
<211> LENGTH: 21
<212> TYPE: RNA
<213> ORGANISM: Homo sapiens

<400> SEQUENCE: 236
ggugcagugc ugcaucucug g                                                 21

<210> SEQ ID NO 237
<211> LENGTH: 23
<212> TYPE: RNA
<213> ORGANISM: Homo sapiens

<400> SEQUENCE: 237
ggauaucauc auauacugua agu                                               23

<210> SEQ ID NO 238
<211> LENGTH: 19
<212> TYPE: RNA
<213> ORGANISM: Homo sapiens

<400> SEQUENCE: 238
``` auccuggaa auacguuc 19

<210> SEQ ID NO 239
<211> LENGTH: 22
<212> TYPE: RNA
<213> ORGANISM: Homo sapiens

<400> SEQUENCE: 239
aaaguucuga gacacuccga cu 22

<210> SEQ ID NO 240
<211> LENGTH: 20
<212> TYPE: RNA
<213> ORGANISM: Homo sapiens

<400> SEQUENCE: 240
gaaguucugu uauacacuca 20

<210> SEQ ID NO 241
<211> LENGTH: 21
<212> TYPE: RNA
<213> ORGANISM: Homo sapiens

<400> SEQUENCE: 241
gucauuuuug ugauguugca g 21

<210> SEQ ID NO 242
<211> LENGTH: 22
<212> TYPE: RNA
<213> ORGANISM: Homo sapiens

<400> SEQUENCE: 242
caggccauau ugugcugccu ca 22

<210> SEQ ID NO 243
<211> LENGTH: 20
<212> TYPE: RNA
<213> ORGANISM: Homo sapiens

<400> SEQUENCE: 243
cgaaucauua uuugcugcuc 20

<210> SEQ ID NO 244
<211> LENGTH: 23
<212> TYPE: RNA
<213> ORGANISM: Homo sapiens

<400> SEQUENCE: 244
ccaguauuaa cugugcugcu gaa 23

<210> SEQ ID NO 245
<211> LENGTH: 21
<212> TYPE: RNA
<213> ORGANISM: Homo sapiens

<400> SEQUENCE: 245
accaauauua cugugcugcu u 21

<210> SEQ ID NO 246
<211> LENGTH: 21
<212> TYPE: RNA
<213> ORGANISM: Homo sapiens

<400> SEQUENCE: 246

-continued accacugacc guugacugua c                                          21

<210> SEQ ID NO 247
<211> LENGTH: 22
<212> TYPE: RNA
<213> ORGANISM: Homo sapiens

<400> SEQUENCE: 247
accaucgacc guugagugga cc                                         22

<210> SEQ ID NO 248
<211> LENGTH: 22
<212> TYPE: RNA
<213> ORGANISM: Homo sapiens

<400> SEQUENCE: 248
ugaauuaccg aagggccaua aa                                         22

<210> SEQ ID NO 249
<211> LENGTH: 20
<212> TYPE: RNA
<213> ORGANISM: Homo sapiens

<400> SEQUENCE: 249
aggggcuggc uuccucugg                                             20

<210> SEQ ID NO 250
<211> LENGTH: 23
<212> TYPE: RNA
<213> ORGANISM: Homo sapiens

<400> SEQUENCE: 250
cccaaaggug aauuuuuugg gaa                                        23

<210> SEQ ID NO 251
<211> LENGTH: 21
<212> TYPE: RNA
<213> ORGANISM: Homo sapiens

<400> SEQUENCE: 251
cucccacaug caggguuugc a                                          21

<210> SEQ ID NO 252
<211> LENGTH: 24
<212> TYPE: RNA
<213> ORGANISM: Homo sapiens

<400> SEQUENCE: 252
acugcccuaa gugcuccuuc uggc                                       24

<210> SEQ ID NO 253
<211> LENGTH: 21
<212> TYPE: RNA
<213> ORGANISM: Homo sapiens

<400> SEQUENCE: 253
cugccaauuc cauaggucac a                                          21

<210> SEQ ID NO 254
<211> LENGTH: 19
<212> TYPE: RNA
<213> ORGANISM: Homo sapiens

<400> SEQUENCE: 254

-continued

| | |
|---|---|
| ugggucuuug cgggcgaga | 19 |

<210> SEQ ID NO 255
<211> LENGTH: 19
<212> TYPE: RNA
<213> ORGANISM: Homo sapiens

<400> SEQUENCE: 255

| | |
|---|---|
| ccaguggaga ugcuguuac | 19 |

<210> SEQ ID NO 256
<211> LENGTH: 21
<212> TYPE: RNA
<213> ORGANISM: Homo sapiens

<400> SEQUENCE: 256

| | |
|---|---|
| acaguagucu gcacauuggu u | 21 |

<210> SEQ ID NO 257
<211> LENGTH: 21
<212> TYPE: RNA
<213> ORGANISM: Homo sapiens

<400> SEQUENCE: 257

| | |
|---|---|
| aguuuugcau aguugcacua c | 21 |

<210> SEQ ID NO 258
<211> LENGTH: 23
<212> TYPE: RNA
<213> ORGANISM: Homo sapiens

<400> SEQUENCE: 258

| | |
|---|---|
| aguuuugcag guuugcaucc agc | 23 |

<210> SEQ ID NO 259
<211> LENGTH: 21
<212> TYPE: RNA
<213> ORGANISM: Homo sapiens

<400> SEQUENCE: 259

| | |
|---|---|
| caucuuacug ggcagcauug g | 21 |

<210> SEQ ID NO 260
<211> LENGTH: 22
<212> TYPE: RNA
<213> ORGANISM: Homo sapiens

<400> SEQUENCE: 260

| | |
|---|---|
| cgucuuaccc agcaguguuu gg | 22 |

<210> SEQ ID NO 261
<211> LENGTH: 22
<212> TYPE: RNA
<213> ORGANISM: Homo sapiens

<400> SEQUENCE: 261

| | |
|---|---|
| agugguucuu aacaguucaa ca | 22 |

<210> SEQ ID NO 262
<211> LENGTH: 22
<212> TYPE: RNA
<213> ORGANISM: Homo sapiens

<400> SEQUENCE: 262
cugcauuaug agcacuuaaa gu                                                   22

<210> SEQ ID NO 263
<211> LENGTH: 22
<212> TYPE: RNA
<213> ORGANISM: Homo sapiens

<400> SEQUENCE: 263
caacaccagu cgaugggcug uc                                                   22

<210> SEQ ID NO 264
<211> LENGTH: 22
<212> TYPE: RNA
<213> ORGANISM: Homo sapiens

<400> SEQUENCE: 264
ugccugucua cacuugcugu gc                                                   22

<210> SEQ ID NO 265
<211> LENGTH: 21
<212> TYPE: RNA
<213> ORGANISM: Homo sapiens

<400> SEQUENCE: 265
aguucuucag uggcaagcuu u                                                    21

<210> SEQ ID NO 266
<211> LENGTH: 24
<212> TYPE: RNA
<213> ORGANISM: Homo sapiens

<400> SEQUENCE: 266
accuggcaua caauguagau uucu                                                 24

<210> SEQ ID NO 267
<211> LENGTH: 23
<212> TYPE: RNA
<213> ORGANISM: Homo sapiens

<400> SEQUENCE: 267
ggcucaguag ccaguguaga ucc                                                  23

<210> SEQ ID NO 268
<211> LENGTH: 23
<212> TYPE: RNA
<213> ORGANISM: Homo sapiens

<400> SEQUENCE: 268
cguguauuug acaagcugag uug                                                  23

<210> SEQ ID NO 269
<211> LENGTH: 20
<212> TYPE: RNA
<213> ORGANISM: Homo sapiens

<400> SEQUENCE: 269
agggcuuagc ugcuugugag                                                      20

<210> SEQ ID NO 270
<211> LENGTH: 24
<212> TYPE: RNA
<213> ORGANISM: Homo sapiens

<400> SEQUENCE: 270

| | |
|---|---|
| cagagcuuag cugauuggug aaca | 24 |

<210> SEQ ID NO 271
<211> LENGTH: 22
<212> TYPE: RNA
<213> ORGANISM: Homo sapiens

<400> SEQUENCE: 271

| | |
|---|---|
| cacuagauug ugagcuccug ga | 22 |

<210> SEQ ID NO 272
<211> LENGTH: 22
<212> TYPE: RNA
<213> ORGANISM: Homo sapiens

<400> SEQUENCE: 272

| | |
|---|---|
| acugauuucu uuugguguuc ag | 22 |

<210> SEQ ID NO 273
<211> LENGTH: 24
<212> TYPE: RNA
<213> ORGANISM: Homo sapiens

<400> SEQUENCE: 273

| | |
|---|---|
| gcugguuuca uauggugguu uaga | 24 |

<210> SEQ ID NO 274
<211> LENGTH: 21
<212> TYPE: RNA
<213> ORGANISM: Homo sapiens

<400> SEQUENCE: 274

| | |
|---|---|
| ugaccgauuu cuccuggugu u | 21 |

<210> SEQ ID NO 275
<211> LENGTH: 21
<212> TYPE: RNA
<213> ORGANISM: Homo sapiens

<400> SEQUENCE: 275

| | |
|---|---|
| gcucugacuu uauugcacua c | 21 |

<210> SEQ ID NO 276
<211> LENGTH: 22
<212> TYPE: RNA
<213> ORGANISM: Homo sapiens

<400> SEQUENCE: 276

| | |
|---|---|
| cugggaggug gauguuuacu uc | 22 |

<210> SEQ ID NO 277
<211> LENGTH: 22
<212> TYPE: RNA
<213> ORGANISM: Homo sapiens

<400> SEQUENCE: 277

| | |
|---|---|
| cuuucaguca gauguuugcu gc | 22 |

<210> SEQ ID NO 278
<211> LENGTH: 23
<212> TYPE: RNA
<213> ORGANISM: Homo sapiens

<400> SEQUENCE: 278
ugcuaugcca acauauugcc auc                                          23

<210> SEQ ID NO 279
<211> LENGTH: 21
<212> TYPE: RNA
<213> ORGANISM: Homo sapiens

<400> SEQUENCE: 279
caauuuagug ugugugauau u                                            21

<210> SEQ ID NO 280
<211> LENGTH: 22
<212> TYPE: RNA
<213> ORGANISM: Homo sapiens

<400> SEQUENCE: 280
uggaggcagg gccuuuguga ag                                           22

<210> SEQ ID NO 281
<211> LENGTH: 23
<212> TYPE: RNA
<213> ORGANISM: Homo sapiens

<400> SEQUENCE: 281
augcaauguu uccacagugc auc                                          23

<210> SEQ ID NO 282
<211> LENGTH: 20
<212> TYPE: RNA
<213> ORGANISM: Homo sapiens

<400> SEQUENCE: 282
ucucugggcc ugugucuuag                                              20

<210> SEQ ID NO 283
<211> LENGTH: 22
<212> TYPE: RNA
<213> ORGANISM: Homo sapiens

<400> SEQUENCE: 283
cuagguaugg ucccagggau cc                                           22

<210> SEQ ID NO 284
<211> LENGTH: 21
<212> TYPE: RNA
<213> ORGANISM: Homo sapiens

<400> SEQUENCE: 284
uuuuucauua uugcuccuga c                                            21

<210> SEQ ID NO 285
<211> LENGTH: 21
<212> TYPE: RNA
<213> ORGANISM: Homo sapiens

<400> SEQUENCE: 285
gaacggcuuc auacaggagu u                                            21

<210> SEQ ID NO 286
<211> LENGTH: 21
<212> TYPE: RNA
<213> ORGANISM: Homo sapiens

<400> SEQUENCE: 286
aacaauaucc uggugcugag u                                               21

<210> SEQ ID NO 287
<211> LENGTH: 21
<212> TYPE: RNA
<213> ORGANISM: Homo sapiens

<400> SEQUENCE: 287
ugagcgccuc gacgacagag c                                               21

<210> SEQ ID NO 288
<211> LENGTH: 21
<212> TYPE: RNA
<213> ORGANISM: Homo sapiens

<400> SEQUENCE: 288
uuauaaagca augagacuga u                                               21

<210> SEQ ID NO 289
<211> LENGTH: 20
<212> TYPE: RNA
<213> ORGANISM: Homo sapiens

<400> SEQUENCE: 289
aaucagcaag uauacugccc                                                 20

<210> SEQ ID NO 290
<211> LENGTH: 23
<212> TYPE: RNA
<213> ORGANISM: Homo sapiens

<400> SEQUENCE: 290
cccccaggug ugauucugau uug                                             23

<210> SEQ ID NO 291
<211> LENGTH: 21
<212> TYPE: RNA
<213> ORGANISM: Homo sapiens

<400> SEQUENCE: 291
aacacaccua uucaaggauu c                                               21

<210> SEQ ID NO 292
<211> LENGTH: 19
<212> TYPE: RNA
<213> ORGANISM: Homo sapiens

<400> SEQUENCE: 292
acucaaacug uggggcac                                                   19

<210> SEQ ID NO 293
<211> LENGTH: 22
<212> TYPE: RNA
<213> ORGANISM: Homo sapiens

<400> SEQUENCE: 293
ccucaaaugu ggagcacuau uc                                              22

<210> SEQ ID NO 294
<211> LENGTH: 22
<212> TYPE: RNA
<213> ORGANISM: Homo sapiens

<400> SEQUENCE: 294

| | |
|---|---|
| cuuaucagau uguauuguaa uu | 22 |

<210> SEQ ID NO 295
<211> LENGTH: 21
<212> TYPE: RNA
<213> ORGANISM: Homo sapiens

<400> SEQUENCE: 295

| | |
|---|---|
| guagauucuc cuucuaugag u | 21 |

<210> SEQ ID NO 296
<211> LENGTH: 22
<212> TYPE: RNA
<213> ORGANISM: Homo sapiens

<400> SEQUENCE: 296

| | |
|---|---|
| agcgagguug cccuuuguau au | 22 |

<210> SEQ ID NO 297
<211> LENGTH: 22
<212> TYPE: RNA
<213> ORGANISM: Homo sapiens

<400> SEQUENCE: 297

| | |
|---|---|
| ugaggggcag agagcgagac uu | 22 |

<210> SEQ ID NO 298
<211> LENGTH: 25
<212> TYPE: RNA
<213> ORGANISM: Homo sapiens

<400> SEQUENCE: 298

| | |
|---|---|
| aaugacacga ucacucccgu ugagu | 25 |

<210> SEQ ID NO 299
<211> LENGTH: 20
<212> TYPE: RNA
<213> ORGANISM: Homo sapiens

<400> SEQUENCE: 299

| | |
|---|---|
| ccauggaucu ccaggugggu | 20 |

<210> SEQ ID NO 300
<211> LENGTH: 22
<212> TYPE: RNA
<213> ORGANISM: Homo sapiens

<400> SEQUENCE: 300

| | |
|---|---|
| cuuaugcaag auucccuucu ac | 22 |

<210> SEQ ID NO 301
<211> LENGTH: 22
<212> TYPE: RNA
<213> ORGANISM: Homo sapiens

<400> SEQUENCE: 301

| | |
|---|---|
| ugaaggucua cugugugcca gg | 22 |

<210> SEQ ID NO 302
<211> LENGTH: 22
<212> TYPE: RNA
<213> ORGANISM: Homo sapiens

<400> SEQUENCE: 302

```
ccaaaccaca cuguggucuu ag                                            22

<210> SEQ ID NO 303
<211> LENGTH: 22
<212> TYPE: RNA
<213> ORGANISM: Homo sapiens

<400> SEQUENCE: 303
gaacaucaca gcaagucugu gc                                            22

<210> SEQ ID NO 304
<211> LENGTH: 24
<212> TYPE: RNA
<213> ORGANISM: Homo sapiens

<400> SEQUENCE: 304
uaauccuugc uaccugggug agag                                          24

<210> SEQ ID NO 305
<211> LENGTH: 21
<212> TYPE: RNA
<213> ORGANISM: Homo sapiens

<400> SEQUENCE: 305
aaugcacccg ggcaaggauu c                                             21

<210> SEQ ID NO 306
<211> LENGTH: 21
<212> TYPE: RNA
<213> ORGANISM: Homo sapiens

<400> SEQUENCE: 306
ggguauuguu uccgcugcca g                                             21

<210> SEQ ID NO 307
<211> LENGTH: 22
<212> TYPE: RNA
<213> ORGANISM: Homo sapiens

<400> SEQUENCE: 307
aauguguagc aaaagacaga au                                            22

<210> SEQ ID NO 308
<211> LENGTH: 22
<212> TYPE: RNA
<213> ORGANISM: Homo sapiens

<400> SEQUENCE: 308
caacaaauca cagucugcca ua                                            22

<210> SEQ ID NO 309
<211> LENGTH: 23
<212> TYPE: RNA
<213> ORGANISM: Homo sapiens

<400> SEQUENCE: 309
acugcugagc uagcacuucc cga                                           23

<210> SEQ ID NO 310
<211> LENGTH: 22
<212> TYPE: RNA
<213> ORGANISM: Homo sapiens

<400> SEQUENCE: 310
```
caaucaugug cagugccaau au                                        22

<210> SEQ ID NO 311
<211> LENGTH: 22
<212> TYPE: RNA
<213> ORGANISM: Homo sapiens

<400> SEQUENCE: 311
caagcucgcu ucuaugguc ug                                         22

<210> SEQ ID NO 312
<211> LENGTH: 21
<212> TYPE: RNA
<213> ORGANISM: Homo sapiens

<400> SEQUENCE: 312
caagcucgug ucugugguc c                                          21

<210> SEQ ID NO 313
<211> LENGTH: 21
<212> TYPE: RNA
<213> ORGANISM: Homo sapiens

<400> SEQUENCE: 313
cauuauuacu uuugguacgc g                                         21

<210> SEQ ID NO 314
<211> LENGTH: 22
<212> TYPE: RNA
<213> ORGANISM: Homo sapiens

<400> SEQUENCE: 314
aaucauacac gguugaccua uu                                        22

<210> SEQ ID NO 315
<211> LENGTH: 21
<212> TYPE: RNA
<213> ORGANISM: Homo sapiens

<400> SEQUENCE: 315
ugguucuaga cuugccaacu a                                         21

<210> SEQ ID NO 316
<211> LENGTH: 22
<212> TYPE: RNA
<213> ORGANISM: Homo sapiens

<400> SEQUENCE: 316
gcugcgcuug gauuucgucc cc                                        22

<210> SEQ ID NO 317
<211> LENGTH: 22
<212> TYPE: RNA
<213> ORGANISM: Homo sapiens

<400> SEQUENCE: 317
uacaguaguc ugcacauugg uu                                        22

<210> SEQ ID NO 318
<211> LENGTH: 22
<212> TYPE: RNA
<213> ORGANISM: Homo sapiens

<400> SEQUENCE: 318
caucuuaccg dacagugcug ga                                         22

<210> SEQ ID NO 319
<211> LENGTH: 22
<212> TYPE: RNA
<213> ORGANISM: Homo sapiens

<400> SEQUENCE: 319
uuuccuaugc auauacuucu uu                                         22

<210> SEQ ID NO 320
<211> LENGTH: 22
<212> TYPE: RNA
<213> ORGANISM: Homo sapiens

<400> SEQUENCE: 320
uaaacgugga uguacuugcu uu                                         22

<210> SEQ ID NO 321
<211> LENGTH: 23
<212> TYPE: RNA
<213> ORGANISM: Homo sapiens

<400> SEQUENCE: 321
acuuuaacau ggaagugcuu ucu                                        23

<210> SEQ ID NO 322
<211> LENGTH: 22
<212> TYPE: RNA
<213> ORGANISM: Homo sapiens

<400> SEQUENCE: 322
uuuaacaugg ggguaccugc ug                                         22

<210> SEQ ID NO 323
<211> LENGTH: 22
<212> TYPE: RNA
<213> ORGANISM: Homo sapiens

<400> SEQUENCE: 323
acucaaaaug ggggcgcuuu cc                                         22

<210> SEQ ID NO 324
<211> LENGTH: 21
<212> TYPE: RNA
<213> ORGANISM: Homo sapiens

<400> SEQUENCE: 324
cuggauggcu ccuccauguc u                                          21

<210> SEQ ID NO 325
<211> LENGTH: 21
<212> TYPE: RNA
<213> ORGANISM: Homo sapiens

<400> SEQUENCE: 325
ucagucucau cugcaaagaa g                                          21

<210> SEQ ID NO 326
<211> LENGTH: 22
<212> TYPE: RNA
<213> ORGANISM: Homo sapiens

<400> SEQUENCE: 326

```
ccucuagaug gaagcacugu cu                                          22

<210> SEQ ID NO 327
<211> LENGTH: 20
<212> TYPE: RNA
<213> ORGANISM: Homo sapiens

<400> SEQUENCE: 327
ucugcaaagg gaagcccuuu                                             20

<210> SEQ ID NO 328
<211> LENGTH: 23
<212> TYPE: RNA
<213> ORGANISM: Homo sapiens

<400> SEQUENCE: 328
ucucuggagg gaagcacuuu cug                                         23

<210> SEQ ID NO 329
<211> LENGTH: 23
<212> TYPE: RNA
<213> ORGANISM: Homo sapiens

<400> SEQUENCE: 329
cucuagaggg aagcacuuuc ucu                                         23

<210> SEQ ID NO 330
<211> LENGTH: 22
<212> TYPE: RNA
<213> ORGANISM: Homo sapiens

<400> SEQUENCE: 330
uucuccaaaa gggagcacuu uc                                          22

<210> SEQ ID NO 331
<211> LENGTH: 21
<212> TYPE: RNA
<213> ORGANISM: Homo sapiens

<400> SEQUENCE: 331
cuccagaggg aaguacuuuc u                                           21

<210> SEQ ID NO 332
<211> LENGTH: 23
<212> TYPE: RNA
<213> ORGANISM: Homo sapiens

<400> SEQUENCE: 332
ucuacaaagg gaagcccuuu cug                                         23

<210> SEQ ID NO 333
<211> LENGTH: 22
<212> TYPE: RNA
<213> ORGANISM: Homo sapiens

<400> SEQUENCE: 333
cuacaaaggg aagcacuuuc uc                                          22

<210> SEQ ID NO 334
<211> LENGTH: 21
<212> TYPE: RNA
<213> ORGANISM: Homo sapiens

<400> SEQUENCE: 334
```

```
gaaggcgcuu cccuuuagag c                                          21

<210> SEQ ID NO 335
<211> LENGTH: 21
<212> TYPE: RNA
<213> ORGANISM: Homo sapiens

<400> SEQUENCE: 335
aaagugcuuc cuuuuagagg c                                          21

<210> SEQ ID NO 336
<211> LENGTH: 21
<212> TYPE: RNA
<213> ORGANISM: Homo sapiens

<400> SEQUENCE: 336
uaaagcuaga uaaccgaaag u                                          21

<210> SEQ ID NO 337
<211> LENGTH: 21
<212> TYPE: RNA
<213> ORGANISM: Homo sapiens

<400> SEQUENCE: 337
gugcauugcu guugcauugc a                                          21

<210> SEQ ID NO 338
<211> LENGTH: 21
<212> TYPE: RNA
<213> ORGANISM: Homo sapiens

<400> SEQUENCE: 338
uauugcacuc gucccggccu c                                          21

<210> SEQ ID NO 339
<211> LENGTH: 21
<212> TYPE: RNA
<213> ORGANISM: Homo sapiens

<400> SEQUENCE: 339
uaguagaccg uauagcguac g                                          21

<210> SEQ ID NO 340
<211> LENGTH: 23
<212> TYPE: RNA
<213> ORGANISM: Homo sapiens

<400> SEQUENCE: 340
aucaacagac auuaauuggg cgc                                        23

<210> SEQ ID NO 341
<211> LENGTH: 22
<212> TYPE: RNA
<213> ORGANISM: Homo sapiens

<400> SEQUENCE: 341
aggcagugua uuguuagcug gc                                         22

<210> SEQ ID NO 342
<211> LENGTH: 22
<212> TYPE: RNA
<213> ORGANISM: Homo sapiens

<400> SEQUENCE: 342
```
aagacgggag gaaagaaggg ag                                                22

<210> SEQ ID NO 343
<211> LENGTH: 22
<212> TYPE: RNA
<213> ORGANISM: Homo sapiens

<400> SEQUENCE: 343
ucggggauca ucaugucacg ag                                                22

<210> SEQ ID NO 344
<211> LENGTH: 22
<212> TYPE: RNA
<213> ORGANISM: Homo sapiens

<400> SEQUENCE: 344
ucagcaaaca uuuauugugu gc                                                22

<210> SEQ ID NO 345
<211> LENGTH: 22
<212> TYPE: RNA
<213> ORGANISM: Homo sapiens

<400> SEQUENCE: 345
caaaacuggc aauuacuuuu gc                                                22

<210> SEQ ID NO 346
<211> LENGTH: 22
<212> TYPE: RNA
<213> ORGANISM: Homo sapiens

<400> SEQUENCE: 346
caaaacuggc aauuacuuuu gc                                                22

<210> SEQ ID NO 347
<211> LENGTH: 22
<212> TYPE: RNA
<213> ORGANISM: Homo sapiens

<400> SEQUENCE: 347
caaaacuggc aauuacuuuu gc                                                22

<210> SEQ ID NO 348
<211> LENGTH: 22
<212> TYPE: RNA
<213> ORGANISM: Homo sapiens

<400> SEQUENCE: 348
caagaaccuc aguugcuuuu gu                                                22

<210> SEQ ID NO 349
<211> LENGTH: 22
<212> TYPE: RNA
<213> ORGANISM: Homo sapiens

<400> SEQUENCE: 349
caaaaaucuc aauuacuuuu gc                                                22

<210> SEQ ID NO 350
<211> LENGTH: 22
<212> TYPE: RNA
<213> ORGANISM: Homo sapiens

<400> SEQUENCE: 350
caaaaaccac aguuucuuuu gc                                              22

<210> SEQ ID NO 351
<211> LENGTH: 22
<212> TYPE: RNA
<213> ORGANISM: Homo sapiens

<400> SEQUENCE: 351
caaaaaccac aguuucuuuu gc                                              22

<210> SEQ ID NO 352
<211> LENGTH: 21
<212> TYPE: RNA
<213> ORGANISM: Homo sapiens

<400> SEQUENCE: 352
ugacaacuau ggaugagcuc u                                               21

<210> SEQ ID NO 353
<211> LENGTH: 22
<212> TYPE: RNA
<213> ORGANISM: Homo sapiens

<400> SEQUENCE: 353
gacaacuaug gaugagcucu ca                                              22

<210> SEQ ID NO 354
<211> LENGTH: 22
<212> TYPE: RNA
<213> ORGANISM: Homo sapiens

<400> SEQUENCE: 354
ugucuuacuc ccucaggcac au                                              22

<210> SEQ ID NO 355
<211> LENGTH: 22
<212> TYPE: RNA
<213> ORGANISM: Homo sapiens

<400> SEQUENCE: 355
ugucuuacuc ccucaggcac au                                              22

<210> SEQ ID NO 356
<211> LENGTH: 21
<212> TYPE: RNA
<213> ORGANISM: Homo sapiens

<400> SEQUENCE: 356
gcgacccacu cuugguuucc a                                               21

<210> SEQ ID NO 357
<211> LENGTH: 21
<212> TYPE: RNA
<213> ORGANISM: Homo sapiens

<400> SEQUENCE: 357
gcgacccaua cuugguuuca g                                               21

<210> SEQ ID NO 358
<211> LENGTH: 21
<212> TYPE: RNA
<213> ORGANISM: Homo sapiens

<400> SEQUENCE: 358
aacaggugac ugguuagaca a    21

<210> SEQ ID NO 359
<211> LENGTH: 21
<212> TYPE: RNA
<213> ORGANISM: Homo sapiens

<400> SEQUENCE: 359
aaaacgguga gauuuuguuu u    21

<210> SEQ ID NO 360
<211> LENGTH: 21
<212> TYPE: RNA
<213> ORGANISM: Homo sapiens

<400> SEQUENCE: 360
gcuaguccug acucagccag u    21

<210> SEQ ID NO 361
<211> LENGTH: 21
<212> TYPE: RNA
<213> ORGANISM: Homo sapiens

<400> SEQUENCE: 361
aggguaagcu gaaccucuga u    21

<210> SEQ ID NO 362
<211> LENGTH: 20
<212> TYPE: RNA
<213> ORGANISM: Homo sapiens

<400> SEQUENCE: 362
gaugagcuca uuguaauaug    20

<210> SEQ ID NO 363
<211> LENGTH: 23
<212> TYPE: RNA
<213> ORGANISM: Homo sapiens

<400> SEQUENCE: 363
guuugcacgg gugggccuug ucu    23

<210> SEQ ID NO 364
<211> LENGTH: 19
<212> TYPE: RNA
<213> ORGANISM: Homo sapiens

<400> SEQUENCE: 364
ugagcugcug uaccaaaau    19

<210> SEQ ID NO 365
<211> LENGTH: 21
<212> TYPE: RNA
<213> ORGANISM: Homo sapiens

<400> SEQUENCE: 365
uaaaguaaau augcaccaaa a    21

<210> SEQ ID NO 366
<211> LENGTH: 20
<212> TYPE: RNA
<213> ORGANISM: Homo sapiens

<400> SEQUENCE: 366
gcgugcgccg gccggccgcc                                                    20

<210> SEQ ID NO 367
<211> LENGTH: 22
<212> TYPE: RNA
<213> ORGANISM: Homo sapiens

<400> SEQUENCE: 367
caaaguuuaa gauccuugaa gu                                                 22

<210> SEQ ID NO 368
<211> LENGTH: 20
<212> TYPE: RNA
<213> ORGANISM: Homo sapiens

<400> SEQUENCE: 368
aaaguagcug uaccauuugc                                                    20

<210> SEQ ID NO 369
<211> LENGTH: 19
<212> TYPE: RNA
<213> ORGANISM: Homo sapiens

<400> SEQUENCE: 369
agguugacau acguuuccc                                                     19

<210> SEQ ID NO 370
<211> LENGTH: 19
<212> TYPE: RNA
<213> ORGANISM: Homo sapiens

<400> SEQUENCE: 370
aggcacggug ucagcaggc                                                     19

<210> SEQ ID NO 371
<211> LENGTH: 22
<212> TYPE: RNA
<213> ORGANISM: Homo sapiens

<400> SEQUENCE: 371
ggcuggcucg cgaugucugu uu                                                 22

<210> SEQ ID NO 372
<211> LENGTH: 19
<212> TYPE: RNA
<213> ORGANISM: Homo sapiens

<400> SEQUENCE: 372
gggcgccugu gaucccaac                                                     19

<210> SEQ ID NO 373
<211> LENGTH: 23
<212> TYPE: RNA
<213> ORGANISM: Homo sapiens

<400> SEQUENCE: 373
aguauguucu uccaggacag aac                                                23

<210> SEQ ID NO 374
<211> LENGTH: 20
<212> TYPE: RNA
<213> ORGANISM: Homo sapiens

<400> SEQUENCE: 374
auguauaaau guauacacac    20

<210> SEQ ID NO 375
<211> LENGTH: 21
<212> TYPE: RNA
<213> ORGANISM: Homo sapiens

<400> SEQUENCE: 375
aguuaaugaa uccuggaaag u    21

<210> SEQ ID NO 376
<211> LENGTH: 22
<212> TYPE: RNA
<213> ORGANISM: Homo sapiens

<400> SEQUENCE: 376
gaaaacagca auuaccuuug ca    22

<210> SEQ ID NO 377
<211> LENGTH: 21
<212> TYPE: RNA
<213> ORGANISM: Homo sapiens

<400> SEQUENCE: 377
ugaguuggcc aucugaguga g    21

<210> SEQ ID NO 378
<211> LENGTH: 20
<212> TYPE: RNA
<213> ORGANISM: Homo sapiens

<400> SEQUENCE: 378
guccgcucgg cgguggccca    20

<210> SEQ ID NO 379
<211> LENGTH: 24
<212> TYPE: RNA
<213> ORGANISM: Homo sapiens

<400> SEQUENCE: 379
cugaagugau guguaacuga ucag    24

<210> SEQ ID NO 380
<211> LENGTH: 21
<212> TYPE: RNA
<213> ORGANISM: Homo sapiens

<400> SEQUENCE: 380
cacgcucaug cacacaccca c    21

<210> SEQ ID NO 381
<211> LENGTH: 19
<212> TYPE: RNA
<213> ORGANISM: Homo sapiens

<400> SEQUENCE: 381
gagccaguug gacaggagc    19

<210> SEQ ID NO 382
<211> LENGTH: 23
<212> TYPE: RNA
<213> ORGANISM: Homo sapiens

<400> SEQUENCE: 382
auucuaauuu cuccacgucu uug                                           23

<210> SEQ ID NO 383
<211> LENGTH: 21
<212> TYPE: RNA
<213> ORGANISM: Homo sapiens

<400> SEQUENCE: 383
uagauaaaau auugguaccu g                                             21

<210> SEQ ID NO 384
<211> LENGTH: 21
<212> TYPE: RNA
<213> ORGANISM: Homo sapiens

<400> SEQUENCE: 384
cuucuugugc ucuaggauug u                                             21

<210> SEQ ID NO 385
<211> LENGTH: 23
<212> TYPE: RNA
<213> ORGANISM: Homo sapiens

<400> SEQUENCE: 385
auucauuugg uauaaaccgc gau                                           23

<210> SEQ ID NO 386
<211> LENGTH: 22
<212> TYPE: RNA
<213> ORGANISM: Homo sapiens

<400> SEQUENCE: 386
uugagaauga ugaaucauua gg                                            22

<210> SEQ ID NO 387
<211> LENGTH: 21
<212> TYPE: RNA
<213> ORGANISM: Homo sapiens

<400> SEQUENCE: 387
ucuuguguuc ucuagaucag u                                             21

<210> SEQ ID NO 388
<211> LENGTH: 23
<212> TYPE: RNA
<213> ORGANISM: Homo sapiens

<400> SEQUENCE: 388
uuacaguugu ucaaccaguu acu                                           23

<210> SEQ ID NO 389
<211> LENGTH: 21
<212> TYPE: RNA
<213> ORGANISM: Homo sapiens

<400> SEQUENCE: 389
caaagaggaa ggucccauua c                                             21

<210> SEQ ID NO 390
<211> LENGTH: 22
<212> TYPE: RNA
<213> ORGANISM: Homo sapiens

<400> SEQUENCE: 390
uuaugguuug ccugggacug ag         22

<210> SEQ ID NO 391
<211> LENGTH: 19
<212> TYPE: RNA
<213> ORGANISM: Homo sapiens

<400> SEQUENCE: 391
ugggcguauc uguaugcua             19

<210> SEQ ID NO 392
<211> LENGTH: 22
<212> TYPE: RNA
<213> ORGANISM: Homo sapiens

<400> SEQUENCE: 392
uaugcauugu auuuuaggu cc          22

<210> SEQ ID NO 393
<211> LENGTH: 21
<212> TYPE: RNA
<213> ORGANISM: Homo sapiens

<400> SEQUENCE: 393
uuuccauagg ugaugaguca c          21

<210> SEQ ID NO 394
<211> LENGTH: 21
<212> TYPE: RNA
<213> ORGANISM: Homo sapiens

<400> SEQUENCE: 394
uuggccacaa uggguuagaa c          21

<210> SEQ ID NO 395
<211> LENGTH: 24
<212> TYPE: RNA
<213> ORGANISM: Homo sapiens

<400> SEQUENCE: 395
ucagaacaaa ugccgguucc caga       24

<210> SEQ ID NO 396
<211> LENGTH: 22
<212> TYPE: RNA
<213> ORGANISM: Homo sapiens

<400> SEQUENCE: 396
gagcuuauuc auaaaagugc ag         22

<210> SEQ ID NO 397
<211> LENGTH: 20
<212> TYPE: RNA
<213> ORGANISM: Homo sapiens

<400> SEQUENCE: 397
agaccauggg uucucauugu            20

<210> SEQ ID NO 398
<211> LENGTH: 22
<212> TYPE: RNA
<213> ORGANISM: Homo sapiens

<400> SEQUENCE: 398

```
uugugucaau augcgaugau gu                                          22

<210> SEQ ID NO 399
<211> LENGTH: 25
<212> TYPE: RNA
<213> ORGANISM: Homo sapiens

<400> SEQUENCE: 399
aggcaccagc caggcauugc ucagc                                       25

<210> SEQ ID NO 400
<211> LENGTH: 25
<212> TYPE: RNA
<213> ORGANISM: Homo sapiens

<400> SEQUENCE: 400
cccaucuggg guggccugug acuuu                                       25

<210> SEQ ID NO 401
<211> LENGTH: 21
<212> TYPE: RNA
<213> ORGANISM: Homo sapiens

<400> SEQUENCE: 401
gaagugugcc gugguguguc u                                           21

<210> SEQ ID NO 402
<211> LENGTH: 21
<212> TYPE: RNA
<213> ORGANISM: Homo sapiens

<400> SEQUENCE: 402
aagccugccc ggcuccucgg g                                           21

<210> SEQ ID NO 403
<211> LENGTH: 22
<212> TYPE: RNA
<213> ORGANISM: Homo sapiens

<400> SEQUENCE: 403
ugugucacuc gaugaccacu gu                                          22

<210> SEQ ID NO 404
<211> LENGTH: 22
<212> TYPE: RNA
<213> ORGANISM: Homo sapiens

<400> SEQUENCE: 404
uacgucaucg uugucaucgu ca                                          22

<210> SEQ ID NO 405
<211> LENGTH: 20
<212> TYPE: RNA
<213> ORGANISM: Homo sapiens

<400> SEQUENCE: 405
guugugucag uuuaucaaac                                             20

<210> SEQ ID NO 406
<211> LENGTH: 23
<212> TYPE: RNA
<213> ORGANISM: Homo sapiens

<400> SEQUENCE: 406
```
acuuacagac aagagccuug cuc 23

<210> SEQ ID NO 407
<211> LENGTH: 22
<212> TYPE: RNA
<213> ORGANISM: Homo sapiens

<400> SEQUENCE: 407
uggucuagga uuguuggagg ag 22

<210> SEQ ID NO 408
<211> LENGTH: 23
<212> TYPE: RNA
<213> ORGANISM: Homo sapiens

<400> SEQUENCE: 408
gacacgggcg acagcugcgg ccc 23

<210> SEQ ID NO 409
<211> LENGTH: 22
<212> TYPE: RNA
<213> ORGANISM: Homo sapiens

<400> SEQUENCE: 409
cacacacugc aauuacuuuu gc 22

<210> SEQ ID NO 410
<211> LENGTH: 19
<212> TYPE: RNA
<213> ORGANISM: Homo sapiens

<400> SEQUENCE: 410
aggcugcgga auucaggac 19

<210> SEQ ID NO 411
<211> LENGTH: 23
<212> TYPE: RNA
<213> ORGANISM: Homo sapiens

<400> SEQUENCE: 411
uaaaucccau ggugccuucu ccu 23

<210> SEQ ID NO 412
<211> LENGTH: 21
<212> TYPE: RNA
<213> ORGANISM: Homo sapiens

<400> SEQUENCE: 412
aaacuacuga aaaucaaaga u 21

<210> SEQ ID NO 413
<211> LENGTH: 21
<212> TYPE: RNA
<213> ORGANISM: Homo sapiens

<400> SEQUENCE: 413
guucaaaucc agaucuauaa c 21

<210> SEQ ID NO 414
<211> LENGTH: 25
<212> TYPE: RNA
<213> ORGANISM: Homo sapiens

<400> SEQUENCE: 414

```
aggggguggug uugggacagc uccgu                                      25

<210> SEQ ID NO 415
<211> LENGTH: 20
<212> TYPE: RNA
<213> ORGANISM: Homo sapiens

<400> SEQUENCE: 415
aggguguuuc ucucaucucu                                             20

<210> SEQ ID NO 416
<211> LENGTH: 21
<212> TYPE: RNA
<213> ORGANISM: Homo sapiens

<400> SEQUENCE: 416
ugagcuaaau gugugcuggg a                                           21

<210> SEQ ID NO 417
<211> LENGTH: 23
<212> TYPE: RNA
<213> ORGANISM: Homo sapiens

<400> SEQUENCE: 417
gcgaggaccc cucggggucu gac                                         23

<210> SEQ ID NO 418
<211> LENGTH: 25
<212> TYPE: RNA
<213> ORGANISM: Homo sapiens

<400> SEQUENCE: 418
gcugggcagg gcuucugagc uccuu                                       25

<210> SEQ ID NO 419
<211> LENGTH: 20
<212> TYPE: RNA
<213> ORGANISM: Homo sapiens

<400> SEQUENCE: 419
aggaauguuc cuucuuugcc                                             20

<210> SEQ ID NO 420
<211> LENGTH: 23
<212> TYPE: RNA
<213> ORGANISM: Homo sapiens

<400> SEQUENCE: 420
gaacgccugu ucuugccagg ugg                                         23

<210> SEQ ID NO 421
<211> LENGTH: 21
<212> TYPE: RNA
<213> ORGANISM: Homo sapiens

<400> SEQUENCE: 421
uccgagccug ggucucccuc u                                           21

<210> SEQ ID NO 422
<211> LENGTH: 22
<212> TYPE: RNA
<213> ORGANISM: Homo sapiens

<400> SEQUENCE: 422
```

-continued

```
acucaaaacc cuucagugac uu                                              22

<210> SEQ ID NO 423
<211> LENGTH: 22
<212> TYPE: RNA
<213> ORGANISM: Homo sapiens

<400> SEQUENCE: 423
agacuuccca uuugaaggug gc                                              22

<210> SEQ ID NO 424
<211> LENGTH: 23
<212> TYPE: RNA
<213> ORGANISM: Homo sapiens

<400> SEQUENCE: 424
aaacucuacu uguccuucug agu                                             23

<210> SEQ ID NO 425
<211> LENGTH: 24
<212> TYPE: RNA
<213> ORGANISM: Homo sapiens

<400> SEQUENCE: 425
gaccuggaca uguuugugcc cagu                                            24

<210> SEQ ID NO 426
<211> LENGTH: 20
<212> TYPE: RNA
<213> ORGANISM: Homo sapiens

<400> SEQUENCE: 426
auggagauag auauagaaau                                                 20

<210> SEQ ID NO 427
<211> LENGTH: 21
<212> TYPE: RNA
<213> ORGANISM: Homo sapiens

<400> SEQUENCE: 427
ggcuagcaac agcgcuuacc u                                               21

<210> SEQ ID NO 428
<211> LENGTH: 21
<212> TYPE: RNA
<213> ORGANISM: Homo sapiens

<400> SEQUENCE: 428
acagucugcu gagguuggag c                                               21

<210> SEQ ID NO 429
<211> LENGTH: 23
<212> TYPE: RNA
<213> ORGANISM: Homo sapiens

<400> SEQUENCE: 429
aucccuugca ggggcuguug ggu                                             23

<210> SEQ ID NO 430
<211> LENGTH: 22
<212> TYPE: RNA
<213> ORGANISM: Homo sapiens

<400> SEQUENCE: 430
```
uaguaccagu accuuguguu ca                                    22

<210> SEQ ID NO 431
<211> LENGTH: 22
<212> TYPE: RNA
<213> ORGANISM: Homo sapiens

<400> SEQUENCE: 431 aggggggaaag uucuauaguc cu                                   22

<210> SEQ ID NO 432
<211> LENGTH: 19
<212> TYPE: RNA
<213> ORGANISM: Homo sapiens

<400> SEQUENCE: 432
agcugucuga aaaugucuu                                        19

<210> SEQ ID NO 433
<211> LENGTH: 22
<212> TYPE: RNA
<213> ORGANISM: Homo sapiens

<400> SEQUENCE: 433
gugagucucu aagaaaagag ga                                    22

<210> SEQ ID NO 434
<211> LENGTH: 20
<212> TYPE: RNA
<213> ORGANISM: Homo sapiens

<400> SEQUENCE: 434
ucuaguaaga guggcagucg                                       20

<210> SEQ ID NO 435
<211> LENGTH: 22
<212> TYPE: RNA
<213> ORGANISM: Homo sapiens

<400> SEQUENCE: 435
guucucccaa cguaagccca gc                                    22

<210> SEQ ID NO 436
<211> LENGTH: 22
<212> TYPE: RNA
<213> ORGANISM: Homo sapiens

<400> SEQUENCE: 436
aguauucugu accagggaag gu                                    22

<210> SEQ ID NO 437
<211> LENGTH: 21
<212> TYPE: RNA
<213> ORGANISM: Homo sapiens

<400> SEQUENCE: 437
agaccuggcc cagaccucag c                                     21

<210> SEQ ID NO 438
<211> LENGTH: 19
<212> TYPE: RNA
<213> ORGANISM: Homo sapiens

<400> SEQUENCE: 438

-continued

```
gugucugcuu ccuguggga                                            19

<210> SEQ ID NO 439
<211> LENGTH: 23
<212> TYPE: RNA
<213> ORGANISM: Homo sapiens

<400> SEQUENCE: 439
cuaauaguau cuaccacaau aaa                                       23

<210> SEQ ID NO 440
<211> LENGTH: 22
<212> TYPE: RNA
<213> ORGANISM: Homo sapiens

<400> SEQUENCE: 440
aaccagcacc ccaacuuugg ac                                        22

<210> SEQ ID NO 441
<211> LENGTH: 23
<212> TYPE: RNA
<213> ORGANISM: Homo sapiens

<400> SEQUENCE: 441
acuugggcac ugaaacaaug ucc                                       23

<210> SEQ ID NO 442
<211> LENGTH: 24
<212> TYPE: RNA
<213> ORGANISM: Homo sapiens

<400> SEQUENCE: 442
ugugcuugcu cgucccgccc gcag                                      24

<210> SEQ ID NO 443
<211> LENGTH: 24
<212> TYPE: RNA
<213> ORGANISM: Homo sapiens

<400> SEQUENCE: 443 acuggggcu uucgggcucu gcgu                                       24

<210> SEQ ID NO 444
<211> LENGTH: 25
<212> TYPE: RNA
<213> ORGANISM: Homo sapiens

<400> SEQUENCE: 444
agggaucgcg ggcgguggc ggccu                                      25

<210> SEQ ID NO 445
<211> LENGTH: 23
<212> TYPE: RNA
<213> ORGANISM: Homo sapiens

<400> SEQUENCE: 445
aucgcugcgg uugcgagcgc ugu                                       23

<210> SEQ ID NO 446
<211> LENGTH: 21
<212> TYPE: RNA
<213> ORGANISM: Homo sapiens

<400> SEQUENCE: 446
```
augauccagg aaccugccuc u                                              21

<210> SEQ ID NO 447
<211> LENGTH: 24
<212> TYPE: RNA
<213> ORGANISM: Homo sapiens

<400> SEQUENCE: 447
aaagacauag gauagaguca ccuc                                           24

<210> SEQ ID NO 448
<211> LENGTH: 22
<212> TYPE: RNA
<213> ORGANISM: Homo sapiens

<400> SEQUENCE: 448
gucccucucc aaaugugucu ug                                             22

<210> SEQ ID NO 449
<211> LENGTH: 22
<212> TYPE: RNA
<213> ORGANISM: Homo sapiens

<400> SEQUENCE: 449
acuuguaugc uagcucaggu ag                                             22

<210> SEQ ID NO 450
<211> LENGTH: 19
<212> TYPE: RNA
<213> ORGANISM: Homo sapiens

<400> SEQUENCE: 450
aguguggcuu ucuuagagc                                                 19

<210> SEQ ID NO 451
<211> LENGTH: 19
<212> TYPE: RNA
<213> ORGANISM: Homo sapiens

<400> SEQUENCE: 451
ucuaggcugg uacugcuga                                                 19

<210> SEQ ID NO 452
<211> LENGTH: 19
<212> TYPE: RNA
<213> ORGANISM: Homo sapiens

<400> SEQUENCE: 452
aagcagcugc cucugaggc                                                 19

<210> SEQ ID NO 453
<211> LENGTH: 21
<212> TYPE: RNA
<213> ORGANISM: Homo sapiens

<400> SEQUENCE: 453
guggcugcac ucacuuccuu c                                              21

<210> SEQ ID NO 454
<211> LENGTH: 19
<212> TYPE: RNA
<213> ORGANISM: Homo sapiens

<400> SEQUENCE: 454
aagugugcag ggcacuggu                                    19

<210> SEQ ID NO 455
<211> LENGTH: 22
<212> TYPE: RNA
<213> ORGANISM: Homo sapiens

<400> SEQUENCE: 455
aaaccugugu uguucaagag uc                                22

<210> SEQ ID NO 456
<211> LENGTH: 21
<212> TYPE: RNA
<213> ORGANISM: Homo sapiens

<400> SEQUENCE: 456
aggaggcagc gcucucagga c                                 21

<210> SEQ ID NO 457
<211> LENGTH: 22
<212> TYPE: RNA
<213> ORGANISM: Homo sapiens

<400> SEQUENCE: 457
uuuaggauaa gcuugacuuu ug                                22

<210> SEQ ID NO 458
<211> LENGTH: 23
<212> TYPE: RNA
<213> ORGANISM: Homo sapiens

<400> SEQUENCE: 458
aauggcgcca cuaggguugu gca                               23

<210> SEQ ID NO 459
<211> LENGTH: 21
<212> TYPE: RNA
<213> ORGANISM: Homo sapiens

<400> SEQUENCE: 459
uugaaacaau cucuacugaa c                                 21

<210> SEQ ID NO 460
<211> LENGTH: 22
<212> TYPE: RNA
<213> ORGANISM: Homo sapiens

<400> SEQUENCE: 460
uggugggccg cagaacaugu gc                                22

<210> SEQ ID NO 461
<211> LENGTH: 22
<212> TYPE: RNA
<213> ORGANISM: Homo sapiens

<400> SEQUENCE: 461
auaauacaug guuaaccucu uu                                22

<210> SEQ ID NO 462
<211> LENGTH: 21
<212> TYPE: RNA
<213> ORGANISM: Homo sapiens

<400> SEQUENCE: 462

```
aauauuauac agucaaccuc u                                           21

<210> SEQ ID NO 463
<211> LENGTH: 23
<212> TYPE: RNA
<213> ORGANISM: Homo sapiens

<400> SEQUENCE: 463
ggcagguucu cacccucucu agg                                         23

<210> SEQ ID NO 464
<211> LENGTH: 25
<212> TYPE: RNA
<213> ORGANISM: Homo sapiens

<400> SEQUENCE: 464
ggcggaggga aguagguccg uuggu                                       25

<210> SEQ ID NO 465
<211> LENGTH: 22
<212> TYPE: RNA
<213> ORGANISM: Homo sapiens

<400> SEQUENCE: 465
cuugguucag ggaggguccc ca                                          22

<210> SEQ ID NO 466
<211> LENGTH: 22
<212> TYPE: RNA
<213> ORGANISM: Homo sapiens

<400> SEQUENCE: 466
uacccauugc auaucggagu ug                                          22

<210> SEQ ID NO 467
<211> LENGTH: 24
<212> TYPE: RNA
<213> ORGANISM: Homo sapiens

<400> SEQUENCE: 467
ugccuggguc ucuggccugc gcgu                                        24

<210> SEQ ID NO 468
<211> LENGTH: 21
<212> TYPE: RNA
<213> ORGANISM: Homo sapiens

<400> SEQUENCE: 468
ucccacguug uggcccagca g                                           21

<210> SEQ ID NO 469
<211> LENGTH: 22
<212> TYPE: RNA
<213> ORGANISM: Homo sapiens

<400> SEQUENCE: 469
aggcggggcg ccgcgggacc gc                                          22

<210> SEQ ID NO 470
<211> LENGTH: 21
<212> TYPE: RNA
<213> ORGANISM: Homo sapiens

<400> SEQUENCE: 470
```

| | |
|---|---|
| gugcauugcu guugcauugc a | 21 |

<210> SEQ ID NO 471
<211> LENGTH: 21
<212> TYPE: RNA
<213> ORGANISM: Homo sapiens

<400> SEQUENCE: 471

| | |
|---|---|
| uauugcacuc gucccggccu c | 21 |

<210> SEQ ID NO 472
<211> LENGTH: 21
<212> TYPE: RNA
<213> ORGANISM: Homo sapiens

<400> SEQUENCE: 472

| | |
|---|---|
| uaguagaccg uauagcguac g | 21 |

<210> SEQ ID NO 473
<211> LENGTH: 23
<212> TYPE: RNA
<213> ORGANISM: Homo sapiens

<400> SEQUENCE: 473

| | |
|---|---|
| aucaacagac auuaauuggg cgc | 23 |

<210> SEQ ID NO 474
<211> LENGTH: 22
<212> TYPE: RNA
<213> ORGANISM: Homo sapiens

<400> SEQUENCE: 474

| | |
|---|---|
| aggcagugua uuguuagcug gc | 22 |

<210> SEQ ID NO 475
<211> LENGTH: 22
<212> TYPE: RNA
<213> ORGANISM: Homo sapiens

<400> SEQUENCE: 475

| | |
|---|---|
| aagacgggag gaaagaaggg ag | 22 |

<210> SEQ ID NO 476
<211> LENGTH: 22
<212> TYPE: RNA
<213> ORGANISM: Homo sapiens

<400> SEQUENCE: 476

| | |
|---|---|
| ucggggauca ucaugucacg ag | 22 |

<210> SEQ ID NO 477
<211> LENGTH: 22
<212> TYPE: RNA
<213> ORGANISM: Homo sapiens

<400> SEQUENCE: 477

| | |
|---|---|
| ucagcaaaca uuuauugugu gc | 22 |

<210> SEQ ID NO 478
<211> LENGTH: 22
<212> TYPE: RNA
<213> ORGANISM: Homo sapiens

<400> SEQUENCE: 478

```
caaaacuggc aauuacuuuu gc                                             22

<210> SEQ ID NO 479
<211> LENGTH: 22
<212> TYPE: RNA
<213> ORGANISM: Homo sapiens

<400> SEQUENCE: 479
caagaaccuc aguugcuuuu gu                                             22

<210> SEQ ID NO 480
<211> LENGTH: 22
<212> TYPE: RNA
<213> ORGANISM: Homo sapiens

<400> SEQUENCE: 480
caaaaaucuc aauuacuuuu gc                                             22

<210> SEQ ID NO 481
<211> LENGTH: 21
<212> TYPE: RNA
<213> ORGANISM: Homo sapiens

<400> SEQUENCE: 481
ugacaacuau ggaugagcuc u                                              21

<210> SEQ ID NO 482
<211> LENGTH: 22
<212> TYPE: RNA
<213> ORGANISM: Homo sapiens

<400> SEQUENCE: 482
gacaacuaug gaugagcucu ca                                             22

<210> SEQ ID NO 483
<211> LENGTH: 22
<212> TYPE: RNA
<213> ORGANISM: Homo sapiens

<400> SEQUENCE: 483
ugucuuacuc ccucaggcac au                                             22

<210> SEQ ID NO 484
<211> LENGTH: 21
<212> TYPE: RNA
<213> ORGANISM: Homo sapiens

<400> SEQUENCE: 484
gcgacccacu cuugguuucc a                                              21

<210> SEQ ID NO 485
<211> LENGTH: 21
<212> TYPE: RNA
<213> ORGANISM: Homo sapiens

<400> SEQUENCE: 485
gcgacccaua cuugguuuca g                                              21

<210> SEQ ID NO 486
<211> LENGTH: 21
<212> TYPE: RNA
<213> ORGANISM: Homo sapiens

<400> SEQUENCE: 486
```
aacaggugac ugguuagaca a                                              21

<210> SEQ ID NO 487
<211> LENGTH: 21
<212> TYPE: RNA
<213> ORGANISM: Homo sapiens

<400> SEQUENCE: 487
aaaacgguga gauuuuguuu u                                              21

<210> SEQ ID NO 488
<211> LENGTH: 21
<212> TYPE: RNA
<213> ORGANISM: Homo sapiens

<400> SEQUENCE: 488
gcuaguccug acucagccag u                                              21

<210> SEQ ID NO 489
<211> LENGTH: 21
<212> TYPE: RNA
<213> ORGANISM: Homo sapiens

<400> SEQUENCE: 489
aggguaagcu gaaccucuga u                                              21

<210> SEQ ID NO 490
<211> LENGTH: 20
<212> TYPE: RNA
<213> ORGANISM: Homo sapiens

<400> SEQUENCE: 490
gaugagcuca uuguaauaug                                                20

<210> SEQ ID NO 491
<211> LENGTH: 23
<212> TYPE: RNA
<213> ORGANISM: Homo sapiens

<400> SEQUENCE: 491
guuugcacgg gugggccuug ucu                                            23

<210> SEQ ID NO 492
<211> LENGTH: 19
<212> TYPE: RNA
<213> ORGANISM: Homo sapiens

<400> SEQUENCE: 492
ugagcugcug uaccaaaau                                                 19

<210> SEQ ID NO 493
<211> LENGTH: 21
<212> TYPE: RNA
<213> ORGANISM: Homo sapiens

<400> SEQUENCE: 493
uaaaguaaau augcaccaaa a                                              21

<210> SEQ ID NO 494
<211> LENGTH: 20
<212> TYPE: RNA
<213> ORGANISM: Homo sapiens

<400> SEQUENCE: 494

```
gcgugcgccg gccggccgcc                                            20

<210> SEQ ID NO 495
<211> LENGTH: 22
<212> TYPE: RNA
<213> ORGANISM: Homo sapiens

<400> SEQUENCE: 495
caaaguuuaa gauccuugaa gu                                         22

<210> SEQ ID NO 496
<211> LENGTH: 20
<212> TYPE: RNA
<213> ORGANISM: Homo sapiens

<400> SEQUENCE: 496
aaaguagcug uaccauuugc                                            20

<210> SEQ ID NO 497
<211> LENGTH: 19
<212> TYPE: RNA
<213> ORGANISM: Homo sapiens

<400> SEQUENCE: 497
agguugacau acguuuccc                                             19

<210> SEQ ID NO 498
<211> LENGTH: 19
<212> TYPE: RNA
<213> ORGANISM: Homo sapiens

<400> SEQUENCE: 498
aggcacggug ucagcaggc                                             19

<210> SEQ ID NO 499
<211> LENGTH: 22
<212> TYPE: RNA
<213> ORGANISM: Homo sapiens

<400> SEQUENCE: 499
ggcuggcucg cgaugucugu uu                                         22

<210> SEQ ID NO 500
<211> LENGTH: 19
<212> TYPE: RNA
<213> ORGANISM: Homo sapiens

<400> SEQUENCE: 500
gggcgccugu gaucccaac                                             19

<210> SEQ ID NO 501
<211> LENGTH: 23
<212> TYPE: RNA
<213> ORGANISM: Homo sapiens

<400> SEQUENCE: 501
aguauguucu uccaggacag aac                                        23

<210> SEQ ID NO 502
<211> LENGTH: 20
<212> TYPE: RNA
<213> ORGANISM: Homo sapiens

<400> SEQUENCE: 502
```
auguauaaau guauacacac                                              20

<210> SEQ ID NO 503
<211> LENGTH: 21
<212> TYPE: RNA
<213> ORGANISM: Homo sapiens

<400> SEQUENCE: 503
aguuaaugaa uccuggaaag u                                            21

<210> SEQ ID NO 504
<211> LENGTH: 22
<212> TYPE: RNA
<213> ORGANISM: Homo sapiens

<400> SEQUENCE: 504
gaaaacagca auuaccuuug ca                                           22

<210> SEQ ID NO 505
<211> LENGTH: 21
<212> TYPE: RNA
<213> ORGANISM: Homo sapiens

<400> SEQUENCE: 505
ugaguuggcc aucugaguga g                                            21

<210> SEQ ID NO 506
<211> LENGTH: 20
<212> TYPE: RNA
<213> ORGANISM: Homo sapiens

<400> SEQUENCE: 506
guccgcucgg cgguggccca                                              20

<210> SEQ ID NO 507
<211> LENGTH: 24
<212> TYPE: RNA
<213> ORGANISM: Homo sapiens

<400> SEQUENCE: 507
cugaagugau guguaacuga ucag                                         24

<210> SEQ ID NO 508
<211> LENGTH: 21
<212> TYPE: RNA
<213> ORGANISM: Homo sapiens

<400> SEQUENCE: 508
cacgcucaug cacacaccca c                                            21

<210> SEQ ID NO 509
<211> LENGTH: 19
<212> TYPE: RNA
<213> ORGANISM: Homo sapiens

<400> SEQUENCE: 509
gagccaguug gacaggagc                                               19

<210> SEQ ID NO 510
<211> LENGTH: 23
<212> TYPE: RNA
<213> ORGANISM: Homo sapiens

<400> SEQUENCE: 510
auucuaauuu cuccacgucu uug                                    23

<210> SEQ ID NO 511
<211> LENGTH: 21
<212> TYPE: RNA
<213> ORGANISM: Homo sapiens

<400> SEQUENCE: 511
uagauaaaau auugguaccu g                                      21

<210> SEQ ID NO 512
<211> LENGTH: 21
<212> TYPE: RNA
<213> ORGANISM: Homo sapiens

<400> SEQUENCE: 512
cuucuugugc ucuaggauug u                                      21

<210> SEQ ID NO 513
<211> LENGTH: 23
<212> TYPE: RNA
<213> ORGANISM: Homo sapiens

<400> SEQUENCE: 513
auucauuugg uauaaaccgc gau                                    23

<210> SEQ ID NO 514
<211> LENGTH: 22
<212> TYPE: RNA
<213> ORGANISM: Homo sapiens

<400> SEQUENCE: 514
uugagaauga ugaaucauua gg                                     22

<210> SEQ ID NO 515
<211> LENGTH: 21
<212> TYPE: RNA
<213> ORGANISM: Homo sapiens

<400> SEQUENCE: 515
ucuuguguuc ucuagaucag u                                      21

<210> SEQ ID NO 516
<211> LENGTH: 23
<212> TYPE: RNA
<213> ORGANISM: Homo sapiens

<400> SEQUENCE: 516
uuacaguugu ucaaccaguu acu                                    23

<210> SEQ ID NO 517
<211> LENGTH: 21
<212> TYPE: RNA
<213> ORGANISM: Homo sapiens

<400> SEQUENCE: 517
caaagaggaa ggucccauua c                                      21

<210> SEQ ID NO 518
<211> LENGTH: 22
<212> TYPE: RNA
<213> ORGANISM: Homo sapiens

<400> SEQUENCE: 518
uuaugguuug ccugggacug ag                                              22

<210> SEQ ID NO 519
<211> LENGTH: 19
<212> TYPE: RNA
<213> ORGANISM: Homo sapiens

<400> SEQUENCE: 519
ugggcguauc uguaugcua                                                  19

<210> SEQ ID NO 520
<211> LENGTH: 22
<212> TYPE: RNA
<213> ORGANISM: Homo sapiens

<400> SEQUENCE: 520
uaugcauugu auuuuaggu cc                                               22

<210> SEQ ID NO 521
<211> LENGTH: 21
<212> TYPE: RNA
<213> ORGANISM: Homo sapiens

<400> SEQUENCE: 521
uuuccauagg ugaugaguca c                                               21

<210> SEQ ID NO 522
<211> LENGTH: 21
<212> TYPE: RNA
<213> ORGANISM: Homo sapiens

<400> SEQUENCE: 522
uuggccacaa uggguuagaa c                                               21

<210> SEQ ID NO 523
<211> LENGTH: 24
<212> TYPE: RNA
<213> ORGANISM: Homo sapiens

<400> SEQUENCE: 523
ucagaacaaa ugccgguucc caga                                            24

<210> SEQ ID NO 524
<211> LENGTH: 22
<212> TYPE: RNA
<213> ORGANISM: Homo sapiens

<400> SEQUENCE: 524
gagcuuauuc auaaaagugc ag                                              22

<210> SEQ ID NO 525
<211> LENGTH: 20
<212> TYPE: RNA
<213> ORGANISM: Homo sapiens

<400> SEQUENCE: 525
agaccauggg uucucauugu                                                 20

<210> SEQ ID NO 526
<211> LENGTH: 22
<212> TYPE: RNA
<213> ORGANISM: Homo sapiens

<400> SEQUENCE: 526

| | |
|---|---|
| uugugucaau augcgaugau gu | 22 |

<210> SEQ ID NO 527
<211> LENGTH: 25
<212> TYPE: RNA
<213> ORGANISM: Homo sapiens

<400> SEQUENCE: 527

| | |
|---|---|
| aggcaccagc caggcauugc ucagc | 25 |

<210> SEQ ID NO 528
<211> LENGTH: 25
<212> TYPE: RNA
<213> ORGANISM: Homo sapiens

<400> SEQUENCE: 528

| | |
|---|---|
| cccaucuggg guggccugug acuuu | 25 |

<210> SEQ ID NO 529
<211> LENGTH: 21
<212> TYPE: RNA
<213> ORGANISM: Homo sapiens

<400> SEQUENCE: 529

| | |
|---|---|
| gaagugugcc guggugoguc u | 21 |

<210> SEQ ID NO 530
<211> LENGTH: 21
<212> TYPE: RNA
<213> ORGANISM: Homo sapiens

<400> SEQUENCE: 530

| | |
|---|---|
| aagccugccc ggcuccucgg g | 21 |

<210> SEQ ID NO 531
<211> LENGTH: 22
<212> TYPE: RNA
<213> ORGANISM: Homo sapiens

<400> SEQUENCE: 531

| | |
|---|---|
| ugugucacuc gaugaccacu gu | 22 |

<210> SEQ ID NO 532
<211> LENGTH: 22
<212> TYPE: RNA
<213> ORGANISM: Homo sapiens

<400> SEQUENCE: 532

| | |
|---|---|
| uacgucaucg uugucaucgu ca | 22 |

<210> SEQ ID NO 533
<211> LENGTH: 20
<212> TYPE: RNA
<213> ORGANISM: Homo sapiens

<400> SEQUENCE: 533

| | |
|---|---|
| guugugucag uuuaucaaac | 20 |

<210> SEQ ID NO 534
<211> LENGTH: 23
<212> TYPE: RNA
<213> ORGANISM: Homo sapiens

<400> SEQUENCE: 534

```
acuuacagac aagagccuug cuc                                              23

<210> SEQ ID NO 535
<211> LENGTH: 22
<212> TYPE: RNA
<213> ORGANISM: Homo sapiens

<400> SEQUENCE: 535
uggucuagga uuguuggagg ag                                               22

<210> SEQ ID NO 536
<211> LENGTH: 23
<212> TYPE: RNA
<213> ORGANISM: Homo sapiens

<400> SEQUENCE: 536
gacacgggcg acagcugcgg ccc                                              23

<210> SEQ ID NO 537
<211> LENGTH: 22
<212> TYPE: RNA
<213> ORGANISM: Homo sapiens

<400> SEQUENCE: 537
cacacacugc aauuacuuuu gc                                               22

<210> SEQ ID NO 538
<211> LENGTH: 19
<212> TYPE: RNA
<213> ORGANISM: Homo sapiens

<400> SEQUENCE: 538
aggcugcgga auucaggac                                                   19

<210> SEQ ID NO 539
<211> LENGTH: 23
<212> TYPE: RNA
<213> ORGANISM: Homo sapiens

<400> SEQUENCE: 539
uaaaucccau ggugccuucu ccu                                              23

<210> SEQ ID NO 540
<211> LENGTH: 21
<212> TYPE: RNA
<213> ORGANISM: Homo sapiens

<400> SEQUENCE: 540
aaacuacuga aaaucaaaga u                                                21

<210> SEQ ID NO 541
<211> LENGTH: 21
<212> TYPE: RNA
<213> ORGANISM: Homo sapiens

<400> SEQUENCE: 541
guucaaaucc agaucuauaa c                                                21

<210> SEQ ID NO 542
<211> LENGTH: 25
<212> TYPE: RNA
<213> ORGANISM: Homo sapiens

<400> SEQUENCE: 542
```

```
aggggugug uugggacagc uccgu                                            25

<210> SEQ ID NO 543
<211> LENGTH: 20
<212> TYPE: RNA
<213> ORGANISM: Homo sapiens

<400> SEQUENCE: 543
aggguguuuc ucucaucucu                                                 20

<210> SEQ ID NO 544
<211> LENGTH: 21
<212> TYPE: RNA
<213> ORGANISM: Homo sapiens

<400> SEQUENCE: 544
ugagcuaaau gugugcuggg a                                               21

<210> SEQ ID NO 545
<211> LENGTH: 23
<212> TYPE: RNA
<213> ORGANISM: Homo sapiens

<400> SEQUENCE: 545
gcgaggaccc cucggggucu gac                                             23

<210> SEQ ID NO 546
<211> LENGTH: 25
<212> TYPE: RNA
<213> ORGANISM: Homo sapiens

<400> SEQUENCE: 546
gcugggcagg gcuucugagc uccuu                                           25

<210> SEQ ID NO 547
<211> LENGTH: 20
<212> TYPE: RNA
<213> ORGANISM: Homo sapiens

<400> SEQUENCE: 547
aggaauguuc cuucuuugcc                                                 20

<210> SEQ ID NO 548
<211> LENGTH: 23
<212> TYPE: RNA
<213> ORGANISM: Homo sapiens

<400> SEQUENCE: 548
gaacgccugu ucuugccagg ugg                                             23

<210> SEQ ID NO 549
<211> LENGTH: 21
<212> TYPE: RNA
<213> ORGANISM: Homo sapiens

<400> SEQUENCE: 549
uccgagccug ggucucccuc u                                               21

<210> SEQ ID NO 550
<211> LENGTH: 22
<212> TYPE: RNA
<213> ORGANISM: Homo sapiens

<400> SEQUENCE: 550
```

-continued

| | |
|---|---|
| acucaaaacc cuucagugac uu | 22 |

<210> SEQ ID NO 551
<211> LENGTH: 22
<212> TYPE: RNA
<213> ORGANISM: Homo sapiens

<400> SEQUENCE: 551

| | |
|---|---|
| agacuuccca uuugaaggug gc | 22 |

<210> SEQ ID NO 552
<211> LENGTH: 23
<212> TYPE: RNA
<213> ORGANISM: Homo sapiens

<400> SEQUENCE: 552

| | |
|---|---|
| aaacucuacu uguccuucug agu | 23 |

<210> SEQ ID NO 553
<211> LENGTH: 24
<212> TYPE: RNA
<213> ORGANISM: Homo sapiens

<400> SEQUENCE: 553

| | |
|---|---|
| gaccuggaca uguuugugcc cagu | 24 |

<210> SEQ ID NO 554
<211> LENGTH: 20
<212> TYPE: RNA
<213> ORGANISM: Homo sapiens

<400> SEQUENCE: 554

| | |
|---|---|
| auggagauag auauagaaau | 20 |

<210> SEQ ID NO 555
<211> LENGTH: 21
<212> TYPE: RNA
<213> ORGANISM: Homo sapiens

<400> SEQUENCE: 555

| | |
|---|---|
| ggcuagcaac agcgcuuacc u | 21 |

<210> SEQ ID NO 556
<211> LENGTH: 21
<212> TYPE: RNA
<213> ORGANISM: Homo sapiens

<400> SEQUENCE: 556

| | |
|---|---|
| acagucugcu gagguuggag c | 21 |

<210> SEQ ID NO 557
<211> LENGTH: 23
<212> TYPE: RNA
<213> ORGANISM: Homo sapiens

<400> SEQUENCE: 557

| | |
|---|---|
| aucccuugca ggggcuguug ggu | 23 |

<210> SEQ ID NO 558
<211> LENGTH: 22
<212> TYPE: RNA
<213> ORGANISM: Homo sapiens

<400> SEQUENCE: 558

```
uaguaccagu accugaguu ca                                    22

<210> SEQ ID NO 559
<211> LENGTH: 22
<212> TYPE: RNA
<213> ORGANISM: Homo sapiens

<400> SEQUENCE: 559 aggggggaaag uucuauaguc cu                                  22

<210> SEQ ID NO 560
<211> LENGTH: 19
<212> TYPE: RNA
<213> ORGANISM: Homo sapiens

<400> SEQUENCE: 560
agcugucuga aaaugucuu                                       19

<210> SEQ ID NO 561
<211> LENGTH: 22
<212> TYPE: RNA
<213> ORGANISM: Homo sapiens

<400> SEQUENCE: 561
gugagucucu aagaaaagag ga                                   22

<210> SEQ ID NO 562
<211> LENGTH: 20
<212> TYPE: RNA
<213> ORGANISM: Homo sapiens

<400> SEQUENCE: 562
ucuaguaaga guggcagucg                                      20

<210> SEQ ID NO 563
<211> LENGTH: 22
<212> TYPE: RNA
<213> ORGANISM: Homo sapiens

<400> SEQUENCE: 563
guucucccaa cguaagccca gc                                   22

<210> SEQ ID NO 564
<211> LENGTH: 22
<212> TYPE: RNA
<213> ORGANISM: Homo sapiens

<400> SEQUENCE: 564
aguauucugu accagggaag gu                                   22

<210> SEQ ID NO 565
<211> LENGTH: 21
<212> TYPE: RNA
<213> ORGANISM: Homo sapiens

<400> SEQUENCE: 565
agaccuggcc cagaccucag c                                    21

<210> SEQ ID NO 566
<211> LENGTH: 19
<212> TYPE: RNA
<213> ORGANISM: Homo sapiens

<400> SEQUENCE: 566
```

-continued

| | |
|---|---|
| gugucugcuu ccuguggga | 19 |

<210> SEQ ID NO 567
<211> LENGTH: 23
<212> TYPE: RNA
<213> ORGANISM: Homo sapiens

<400> SEQUENCE: 567

| | |
|---|---|
| cuaauaguau cuaccacaau aaa | 23 |

<210> SEQ ID NO 568
<211> LENGTH: 22
<212> TYPE: RNA
<213> ORGANISM: Homo sapiens

<400> SEQUENCE: 568

| | |
|---|---|
| aaccagcacc ccaacuuugg ac | 22 |

<210> SEQ ID NO 569
<211> LENGTH: 23
<212> TYPE: RNA
<213> ORGANISM: Homo sapiens

<400> SEQUENCE: 569

| | |
|---|---|
| acuugggcac ugaaacaaug ucc | 23 |

<210> SEQ ID NO 570
<211> LENGTH: 24
<212> TYPE: RNA
<213> ORGANISM: Homo sapiens

<400> SEQUENCE: 570

| | |
|---|---|
| ugugcuugcu cgucccgccc gcag | 24 |

<210> SEQ ID NO 571
<211> LENGTH: 24
<212> TYPE: RNA
<213> ORGANISM: Homo sapiens

<400> SEQUENCE: 571

| | |
|---|---|
| acuggggcu uucgggcucu gcgu | 24 |

<210> SEQ ID NO 572
<211> LENGTH: 25
<212> TYPE: RNA
<213> ORGANISM: Homo sapiens

<400> SEQUENCE: 572

| | |
|---|---|
| agggaucgcg ggcggguggc ggccu | 25 |

<210> SEQ ID NO 573
<211> LENGTH: 23
<212> TYPE: RNA
<213> ORGANISM: Homo sapiens

<400> SEQUENCE: 573

| | |
|---|---|
| aucgcugcgg uugcgagcgc ugu | 23 |

<210> SEQ ID NO 574
<211> LENGTH: 21
<212> TYPE: RNA
<213> ORGANISM: Homo sapiens

<400> SEQUENCE: 574
augauccagg aaccugccuc u                                        21

<210> SEQ ID NO 575
<211> LENGTH: 24
<212> TYPE: RNA
<213> ORGANISM: Homo sapiens

<400> SEQUENCE: 575
aaagacauag gauagaguca ccuc                                     24

<210> SEQ ID NO 576
<211> LENGTH: 22
<212> TYPE: RNA
<213> ORGANISM: Homo sapiens

<400> SEQUENCE: 576
gucccucucc aaaugugucu ug                                       22

<210> SEQ ID NO 577
<211> LENGTH: 22
<212> TYPE: RNA
<213> ORGANISM: Homo sapiens

<400> SEQUENCE: 577
acuuguaugc uagcucaggu ag                                       22

<210> SEQ ID NO 578
<211> LENGTH: 19
<212> TYPE: RNA
<213> ORGANISM: Homo sapiens

<400> SEQUENCE: 578
aguguggcuu ucuuagagc                                           19

<210> SEQ ID NO 579
<211> LENGTH: 19
<212> TYPE: RNA
<213> ORGANISM: Homo sapiens

<400> SEQUENCE: 579
ucuaggcugg uacugcuga                                           19

<210> SEQ ID NO 580
<211> LENGTH: 19
<212> TYPE: RNA
<213> ORGANISM: Homo sapiens

<400> SEQUENCE: 580
aagcagcugc cucugaggc                                           19

<210> SEQ ID NO 581
<211> LENGTH: 21
<212> TYPE: RNA
<213> ORGANISM: Homo sapiens

<400> SEQUENCE: 581
guggcugcac ucacuuccuu c                                        21

<210> SEQ ID NO 582
<211> LENGTH: 19
<212> TYPE: RNA
<213> ORGANISM: Homo sapiens

<400> SEQUENCE: 582

```
aagugugcag ggcacuggu                                                  19

<210> SEQ ID NO 583
<211> LENGTH: 22
<212> TYPE: RNA
<213> ORGANISM: Homo sapiens

<400> SEQUENCE: 583
aaaccugugu uguucaagag uc                                              22

<210> SEQ ID NO 584
<211> LENGTH: 21
<212> TYPE: RNA
<213> ORGANISM: Homo sapiens

<400> SEQUENCE: 584
aggaggcagc gcucucagga c                                               21

<210> SEQ ID NO 585
<211> LENGTH: 22
<212> TYPE: RNA
<213> ORGANISM: Homo sapiens

<400> SEQUENCE: 585
uuuaggauaa gcuugacuuu ug                                              22

<210> SEQ ID NO 586
<211> LENGTH: 23
<212> TYPE: RNA
<213> ORGANISM: Homo sapiens

<400> SEQUENCE: 586
aauggcgcca cuaggguugu gca                                             23

<210> SEQ ID NO 587
<211> LENGTH: 21
<212> TYPE: RNA
<213> ORGANISM: Homo sapiens

<400> SEQUENCE: 587
uugaaacaau cucuacugaa c                                               21

<210> SEQ ID NO 588
<211> LENGTH: 22
<212> TYPE: RNA
<213> ORGANISM: Homo sapiens

<400> SEQUENCE: 588 ugguggccg cagaacaugu gc                                               22

<210> SEQ ID NO 589
<211> LENGTH: 22
<212> TYPE: RNA
<213> ORGANISM: Homo sapiens

<400> SEQUENCE: 589
auaauacaug guuaaccucu uu                                              22

<210> SEQ ID NO 590
<211> LENGTH: 21
<212> TYPE: RNA
<213> ORGANISM: Homo sapiens

<400> SEQUENCE: 590
```

-continued aauauuauac agucaaccuc u          21

<210> SEQ ID NO 591
<211> LENGTH: 23
<212> TYPE: RNA
<213> ORGANISM: Homo sapiens

<400> SEQUENCE: 591
ggcagguucu cacccucucu agg          23

<210> SEQ ID NO 592
<211> LENGTH: 25
<212> TYPE: RNA
<213> ORGANISM: Homo sapiens

<400> SEQUENCE: 592
ggcggaggga aguagguccg uuggu          25

<210> SEQ ID NO 593
<211> LENGTH: 22
<212> TYPE: RNA
<213> ORGANISM: Homo sapiens

<400> SEQUENCE: 593
cuugguucag ggaggguccc ca          22

<210> SEQ ID NO 594
<211> LENGTH: 22
<212> TYPE: RNA
<213> ORGANISM: Homo sapiens

<400> SEQUENCE: 594
uacccauugc auaucggagu ug          22

<210> SEQ ID NO 595
<211> LENGTH: 22
<212> TYPE: RNA
<213> ORGANISM: Homo sapiens

<400> SEQUENCE: 595
ugagguagua gguuguauag uu          22

<210> SEQ ID NO 596
<211> LENGTH: 22
<212> TYPE: RNA
<213> ORGANISM: Homo sapiens

<400> SEQUENCE: 596
ugagguagua gguugugugg uu          22

<210> SEQ ID NO 597
<211> LENGTH: 22
<212> TYPE: RNA
<213> ORGANISM: Homo sapiens

<400> SEQUENCE: 597
ugagguagua gguuguaugg uu          22

<210> SEQ ID NO 598
<211> LENGTH: 21
<212> TYPE: RNA
<213> ORGANISM: Homo sapiens

<400> SEQUENCE: 598
agagguagua gguugcauag u                                      21

<210> SEQ ID NO 599
<211> LENGTH: 21
<212> TYPE: RNA
<213> ORGANISM: Homo sapiens

<400> SEQUENCE: 599
ugagguagga gguuguauag u                                      21

<210> SEQ ID NO 600
<211> LENGTH: 22
<212> TYPE: RNA
<213> ORGANISM: Homo sapiens

<400> SEQUENCE: 600
ugagguagua gauuguauag uu                                     22

<210> SEQ ID NO 601
<211> LENGTH: 21
<212> TYPE: RNA
<213> ORGANISM: Homo sapiens

<400> SEQUENCE: 601
ugagguagua guuuguacag u                                      21

<210> SEQ ID NO 602
<211> LENGTH: 21
<212> TYPE: RNA
<213> ORGANISM: Homo sapiens

<400> SEQUENCE: 602
ugagguagua guuugugcug u                                      21

<210> SEQ ID NO 603
<211> LENGTH: 21
<212> TYPE: RNA
<213> ORGANISM: Homo sapiens

<400> SEQUENCE: 603
uggaauguaa agaaguaugu a                                      21

<210> SEQ ID NO 604
<211> LENGTH: 22
<212> TYPE: RNA
<213> ORGANISM: Homo sapiens

<400> SEQUENCE: 604
aacccguaga uccgaacuug ug                                     22

<210> SEQ ID NO 605
<211> LENGTH: 22
<212> TYPE: RNA
<213> ORGANISM: Homo sapiens

<400> SEQUENCE: 605
uacaguacug ugauaacuga ag                                     22

<210> SEQ ID NO 606
<211> LENGTH: 23
<212> TYPE: RNA
<213> ORGANISM: Homo sapiens

<400> SEQUENCE: 606

-continued agcagcauug uacagggcua uga                                        23

<210> SEQ ID NO 607
<211> LENGTH: 20
<212> TYPE: RNA
<213> ORGANISM: Homo sapiens

<400> SEQUENCE: 607
ucaaaugcuc agacuccugu                                            20

<210> SEQ ID NO 608
<211> LENGTH: 24
<212> TYPE: RNA
<213> ORGANISM: Homo sapiens

<400> SEQUENCE: 608
aaaagugcuu acagugcagg uagc                                       24

<210> SEQ ID NO 609
<211> LENGTH: 21
<212> TYPE: RNA
<213> ORGANISM: Homo sapiens

<400> SEQUENCE: 609
uaaagugcug acagugcaga u                                          21

<210> SEQ ID NO 610
<211> LENGTH: 23
<212> TYPE: RNA
<213> ORGANISM: Homo sapiens

<400> SEQUENCE: 610
agcagcauug uacagggcua uca                                        23

<210> SEQ ID NO 611
<211> LENGTH: 23
<212> TYPE: RNA
<213> ORGANISM: Homo sapiens

<400> SEQUENCE: 611
uacccuguag auccgaauuu gug                                        23

<210> SEQ ID NO 612
<211> LENGTH: 22
<212> TYPE: RNA
<213> ORGANISM: Homo sapiens

<400> SEQUENCE: 612
uacccuguag aaccgaauuu gu                                         22

<210> SEQ ID NO 613
<211> LENGTH: 23
<212> TYPE: RNA
<213> ORGANISM: Homo sapiens

<400> SEQUENCE: 613
uggaguguga caaugguguu ugu                                        23

<210> SEQ ID NO 614
<211> LENGTH: 22
<212> TYPE: RNA
<213> ORGANISM: Homo sapiens

<400> SEQUENCE: 614
uuaaggcacg cggugaaugc ca                                              22

<210> SEQ ID NO 615
<211> LENGTH: 23
<212> TYPE: RNA
<213> ORGANISM: Homo sapiens

<400> SEQUENCE: 615
ucccugagac ccuuuaaccu gug                                             23

<210> SEQ ID NO 616
<211> LENGTH: 22
<212> TYPE: RNA
<213> ORGANISM: Homo sapiens

<400> SEQUENCE: 616
ucccugagac ccuaacuugu ga                                              22

<210> SEQ ID NO 617
<211> LENGTH: 21
<212> TYPE: RNA
<213> ORGANISM: Homo sapiens

<400> SEQUENCE: 617
ucguaccgug aguaauaaug c                                               21

<210> SEQ ID NO 618
<211> LENGTH: 21
<212> TYPE: RNA
<213> ORGANISM: Homo sapiens

<400> SEQUENCE: 618
cauuauuacu uuugguacgc g                                               21

<210> SEQ ID NO 619
<211> LENGTH: 22
<212> TYPE: RNA
<213> ORGANISM: Homo sapiens

<400> SEQUENCE: 619
ucggauccgu cugagcuugg cu                                              22

<210> SEQ ID NO 620
<211> LENGTH: 22
<212> TYPE: RNA
<213> ORGANISM: Homo sapiens

<400> SEQUENCE: 620
ucacagugaa ccggucucuu uu                                              22

<210> SEQ ID NO 621
<211> LENGTH: 22
<212> TYPE: RNA
<213> ORGANISM: Homo sapiens

<400> SEQUENCE: 621
ucacagugaa ccggucucuu uc                                              22

<210> SEQ ID NO 622
<211> LENGTH: 21
<212> TYPE: RNA
<213> ORGANISM: Homo sapiens

<400> SEQUENCE: 622

```
cuuuuugcgg ucugggcuug c                                           21

<210> SEQ ID NO 623
<211> LENGTH: 22
<212> TYPE: RNA
<213> ORGANISM: Homo sapiens

<400> SEQUENCE: 623
cagugcaaug uuaaaagggc au                                          22

<210> SEQ ID NO 624
<211> LENGTH: 22
<212> TYPE: RNA
<213> ORGANISM: Homo sapiens

<400> SEQUENCE: 624
cagugcaaug augaaagggc au                                          22

<210> SEQ ID NO 625
<211> LENGTH: 22
<212> TYPE: RNA
<213> ORGANISM: Homo sapiens

<400> SEQUENCE: 625
uaacagucua cagccauggu cg                                          22

<210> SEQ ID NO 626
<211> LENGTH: 22
<212> TYPE: RNA
<213> ORGANISM: Homo sapiens

<400> SEQUENCE: 626
uugguccccu ucaaccagcu gu                                          22

<210> SEQ ID NO 627
<211> LENGTH: 21
<212> TYPE: RNA
<213> ORGANISM: Homo sapiens

<400> SEQUENCE: 627
uugguccccu ucaaccagcu a                                           21

<210> SEQ ID NO 628
<211> LENGTH: 21
<212> TYPE: RNA
<213> ORGANISM: Homo sapiens

<400> SEQUENCE: 628
ugugacuggu ugaccagagg g                                           21

<210> SEQ ID NO 629
<211> LENGTH: 23
<212> TYPE: RNA
<213> ORGANISM: Homo sapiens

<400> SEQUENCE: 629
uauggcuuuu uauuccuaug uga                                         23

<210> SEQ ID NO 630
<211> LENGTH: 22
<212> TYPE: RNA
<213> ORGANISM: Homo sapiens

<400> SEQUENCE: 630
```

```
uauggcuuuu cauuccuaug ug                                        22

<210> SEQ ID NO 631
<211> LENGTH: 23
<212> TYPE: RNA
<213> ORGANISM: Homo sapiens

<400> SEQUENCE: 631
acuccauuug uuuugaugau gga                                       23

<210> SEQ ID NO 632
<211> LENGTH: 22
<212> TYPE: RNA
<213> ORGANISM: Homo sapiens

<400> SEQUENCE: 632
uauugcuuaa gaauacgcgu ag                                        22

<210> SEQ ID NO 633
<211> LENGTH: 17
<212> TYPE: RNA
<213> ORGANISM: Homo sapiens

<400> SEQUENCE: 633
agcugguguu gugaauc                                              17

<210> SEQ ID NO 634
<211> LENGTH: 18
<212> TYPE: RNA
<213> ORGANISM: Homo sapiens

<400> SEQUENCE: 634
ucuacagugc acgugucu                                             18

<210> SEQ ID NO 635
<211> LENGTH: 21
<212> TYPE: RNA
<213> ORGANISM: Homo sapiens

<400> SEQUENCE: 635
agugguuuua cccuauggua g                                         21

<210> SEQ ID NO 636
<211> LENGTH: 22
<212> TYPE: RNA
<213> ORGANISM: Homo sapiens

<400> SEQUENCE: 636
uaacacuguc ugguaaagau gg                                        22

<210> SEQ ID NO 637
<211> LENGTH: 23
<212> TYPE: RNA
<213> ORGANISM: Homo sapiens

<400> SEQUENCE: 637
uguaguguuu ccuacuuuau gga                                       23

<210> SEQ ID NO 638
<211> LENGTH: 20
<212> TYPE: RNA
<213> ORGANISM: Homo sapiens

<400> SEQUENCE: 638
```

-continued

```
cauaaaguag aaagcacuac                                              20

<210> SEQ ID NO 639
<211> LENGTH: 22
<212> TYPE: RNA
<213> ORGANISM: Homo sapiens

<400> SEQUENCE: 639
ugagaugaag cacuguagcu ca                                           22

<210> SEQ ID NO 640
<211> LENGTH: 22
<212> TYPE: RNA
<213> ORGANISM: Homo sapiens

<400> SEQUENCE: 640
uacaguauag augauguacu ag                                           22

<210> SEQ ID NO 641
<211> LENGTH: 24
<212> TYPE: RNA
<213> ORGANISM: Homo sapiens

<400> SEQUENCE: 641
guccaguuuu cccaggaauc ccuu                                         24

<210> SEQ ID NO 642
<211> LENGTH: 22
<212> TYPE: RNA
<213> ORGANISM: Homo sapiens

<400> SEQUENCE: 642
ugagaacuga auuccauggg uu                                           22

<210> SEQ ID NO 643
<211> LENGTH: 22
<212> TYPE: RNA
<213> ORGANISM: Homo sapiens

<400> SEQUENCE: 643
ugagaacuga auuccauagg cu                                           22

<210> SEQ ID NO 644
<211> LENGTH: 20
<212> TYPE: RNA
<213> ORGANISM: Homo sapiens

<400> SEQUENCE: 644
guguguggaa augcuucugc                                              20

<210> SEQ ID NO 645
<211> LENGTH: 22
<212> TYPE: RNA
<213> ORGANISM: Homo sapiens

<400> SEQUENCE: 645
ucagugcacu acagaacuuu gu                                           22

<210> SEQ ID NO 646
<211> LENGTH: 22
<212> TYPE: RNA
<213> ORGANISM: Homo sapiens

<400> SEQUENCE: 646
```

-continued ucagugcauc acagaacuuu gu                                              22

<210> SEQ ID NO 647
<211> LENGTH: 22
<212> TYPE: RNA
<213> ORGANISM: Homo sapiens

<400> SEQUENCE: 647
ucuggcuccg ugucuucacu cc                                              22

<210> SEQ ID NO 648
<211> LENGTH: 22
<212> TYPE: RNA
<213> ORGANISM: Homo sapiens

<400> SEQUENCE: 648
ucucccaacc cuuguaccag ug                                              22

<210> SEQ ID NO 649
<211> LENGTH: 22
<212> TYPE: RNA
<213> ORGANISM: Homo sapiens

<400> SEQUENCE: 649
acuagacuga agcuccuuga gg                                              22

<210> SEQ ID NO 650
<211> LENGTH: 22
<212> TYPE: RNA
<213> ORGANISM: Homo sapiens

<400> SEQUENCE: 650
ucagugcaug acagaacuug gg                                              22

<210> SEQ ID NO 651
<211> LENGTH: 20
<212> TYPE: RNA
<213> ORGANISM: Homo sapiens

<400> SEQUENCE: 651
uugcauaguc acaaaaguga                                                 20

<210> SEQ ID NO 652
<211> LENGTH: 22
<212> TYPE: RNA
<213> ORGANISM: Homo sapiens

<400> SEQUENCE: 652
uagguuaucc guguugccuu cg                                              22

<210> SEQ ID NO 653
<211> LENGTH: 22
<212> TYPE: RNA
<213> ORGANISM: Homo sapiens

<400> SEQUENCE: 653
aaucauacac gguugaccua uu                                              22

<210> SEQ ID NO 654
<211> LENGTH: 22
<212> TYPE: RNA
<213> ORGANISM: Homo sapiens

<400> SEQUENCE: 654
uuaaugcuaa ucgugauagg gg                                    22

<210> SEQ ID NO 655
<211> LENGTH: 22
<212> TYPE: RNA
<213> ORGANISM: Homo sapiens

<400> SEQUENCE: 655
uagcagcaca uaaugguuug ug                                    22

<210> SEQ ID NO 656
<211> LENGTH: 22
<212> TYPE: RNA
<213> ORGANISM: Homo sapiens

<400> SEQUENCE: 656
uagcagcaca ucaugguuua ca                                    22

<210> SEQ ID NO 657
<211> LENGTH: 22
<212> TYPE: RNA
<213> ORGANISM: Homo sapiens

<400> SEQUENCE: 657
uagcagcacg uaaauauugg cg                                    22

<210> SEQ ID NO 658
<211> LENGTH: 20
<212> TYPE: RNA
<213> ORGANISM: Homo sapiens

<400> SEQUENCE: 658
acugcaguga aggcacuugu                                       20

<210> SEQ ID NO 659
<211> LENGTH: 24
<212> TYPE: RNA
<213> ORGANISM: Homo sapiens

<400> SEQUENCE: 659
caaagugcuu acagugcagg uagu                                  24

<210> SEQ ID NO 660
<211> LENGTH: 23
<212> TYPE: RNA
<213> ORGANISM: Homo sapiens

<400> SEQUENCE: 660
aacauucaac gcugucggug agu                                   23

<210> SEQ ID NO 661
<211> LENGTH: 22
<212> TYPE: RNA
<213> ORGANISM: Homo sapiens

<400> SEQUENCE: 661
aacauucauu gcugucggug gg                                    22

<210> SEQ ID NO 662
<211> LENGTH: 22
<212> TYPE: RNA
<213> ORGANISM: Homo sapiens

<400> SEQUENCE: 662

```
aacauucaac cugucgguga gu                                              22

<210> SEQ ID NO 663
<211> LENGTH: 24
<212> TYPE: RNA
<213> ORGANISM: Homo sapiens

<400> SEQUENCE: 663
aacauucauu guugucggug gguu                                            24

<210> SEQ ID NO 664
<211> LENGTH: 22
<212> TYPE: RNA
<213> ORGANISM: Homo sapiens

<400> SEQUENCE: 664
uuuggcaaug guagaacuca ca                                              22

<210> SEQ ID NO 665
<211> LENGTH: 21
<212> TYPE: RNA
<213> ORGANISM: Homo sapiens

<400> SEQUENCE: 665
ugguucuaga cuugccaacu a                                               21

<210> SEQ ID NO 666
<211> LENGTH: 23
<212> TYPE: RNA
<213> ORGANISM: Homo sapiens

<400> SEQUENCE: 666
uauggcacug guagaauuca cug                                             23

<210> SEQ ID NO 667
<211> LENGTH: 22
<212> TYPE: RNA
<213> ORGANISM: Homo sapiens

<400> SEQUENCE: 667
uggacggaga acugauaagg gu                                              22

<210> SEQ ID NO 668
<211> LENGTH: 18
<212> TYPE: RNA
<213> ORGANISM: Homo sapiens

<400> SEQUENCE: 668
uggagagaaa ggcaguuc                                                   18

<210> SEQ ID NO 669
<211> LENGTH: 23
<212> TYPE: RNA
<213> ORGANISM: Homo sapiens

<400> SEQUENCE: 669
caaagaauuc uccuuuuggg cuu                                             23

<210> SEQ ID NO 670
<211> LENGTH: 21
<212> TYPE: RNA
<213> ORGANISM: Homo sapiens

<400> SEQUENCE: 670
```
ucgugucuug uguugcagcc g                                          21

<210> SEQ ID NO 671
<211> LENGTH: 22
<212> TYPE: RNA
<213> ORGANISM: Homo sapiens

<400> SEQUENCE: 671
caucccuugc augguggagg gu                                         22

<210> SEQ ID NO 672
<211> LENGTH: 23
<212> TYPE: RNA
<213> ORGANISM: Homo sapiens

<400> SEQUENCE: 672
gugccuacug agcugauauc agu                                        23

<210> SEQ ID NO 673
<211> LENGTH: 22
<212> TYPE: RNA
<213> ORGANISM: Homo sapiens

<400> SEQUENCE: 673
uaaggugcau cuagugcaga ua                                         22

<210> SEQ ID NO 674
<211> LENGTH: 22
<212> TYPE: RNA
<213> ORGANISM: Homo sapiens

<400> SEQUENCE: 674
uaaggugcau cuagugcagu ua                                         22

<210> SEQ ID NO 675
<211> LENGTH: 22
<212> TYPE: RNA
<213> ORGANISM: Homo sapiens

<400> SEQUENCE: 675
ugauauguuu gauauauuag gu                                         22

<210> SEQ ID NO 676
<211> LENGTH: 22
<212> TYPE: RNA
<213> ORGANISM: Homo sapiens

<400> SEQUENCE: 676
caacggaauc ccaaaagcag cu                                         22

<210> SEQ ID NO 677
<211> LENGTH: 22
<212> TYPE: RNA
<213> ORGANISM: Homo sapiens

<400> SEQUENCE: 677
gcugcgcuug gauuucgucc cc                                         22

<210> SEQ ID NO 678
<211> LENGTH: 21
<212> TYPE: RNA
<213> ORGANISM: Homo sapiens

<400> SEQUENCE: 678

-continued

```
cugaccuaug aauugacagc c                                        21

<210> SEQ ID NO 679
<211> LENGTH: 21
<212> TYPE: RNA
<213> ORGANISM: Homo sapiens

<400> SEQUENCE: 679
aacuggccua caaaguccca g                                        21

<210> SEQ ID NO 680
<211> LENGTH: 24
<212> TYPE: RNA
<213> ORGANISM: Homo sapiens

<400> SEQUENCE: 680
aacuggcccu caaagucccg cuuu                                     24

<210> SEQ ID NO 681
<211> LENGTH: 22
<212> TYPE: RNA
<213> ORGANISM: Homo sapiens

<400> SEQUENCE: 681
uguaacagca acuccaugug ga                                       22

<210> SEQ ID NO 682
<211> LENGTH: 21
<212> TYPE: RNA
<213> ORGANISM: Homo sapiens

<400> SEQUENCE: 682
uagcagcaca gaaauauugg c                                        21

<210> SEQ ID NO 683
<211> LENGTH: 21
<212> TYPE: RNA
<213> ORGANISM: Homo sapiens

<400> SEQUENCE: 683
uagguaguuu cauguuguug g                                        21

<210> SEQ ID NO 684
<211> LENGTH: 21
<212> TYPE: RNA
<213> ORGANISM: Homo sapiens

<400> SEQUENCE: 684
uagguaguuu ccuguuguug g                                        21

<210> SEQ ID NO 685
<211> LENGTH: 22
<212> TYPE: RNA
<213> ORGANISM: Homo sapiens

<400> SEQUENCE: 685
uucaccaccu ucuccaccca gc                                       22

<210> SEQ ID NO 686
<211> LENGTH: 19
<212> TYPE: RNA
<213> ORGANISM: Homo sapiens

<400> SEQUENCE: 686
```

-continued

```
gguccagagg ggagauagg                                                    19

<210> SEQ ID NO 687
<211> LENGTH: 23
<212> TYPE: RNA
<213> ORGANISM: Homo sapiens

<400> SEQUENCE: 687
cccaguguuc agacuaccug uuc                                               23

<210> SEQ ID NO 688
<211> LENGTH: 22
<212> TYPE: RNA
<213> ORGANISM: Homo sapiens

<400> SEQUENCE: 688
uacaguaguc ugcacauugg uu                                                22

<210> SEQ ID NO 689
<211> LENGTH: 23
<212> TYPE: RNA
<213> ORGANISM: Homo sapiens

<400> SEQUENCE: 689
cccaguguuu agacuaucug uuc                                               23

<210> SEQ ID NO 690
<211> LENGTH: 23
<212> TYPE: RNA
<213> ORGANISM: Homo sapiens

<400> SEQUENCE: 690
ugugcaaauc uaugcaaaac uga                                               23

<210> SEQ ID NO 691
<211> LENGTH: 23
<212> TYPE: RNA
<213> ORGANISM: Homo sapiens

<400> SEQUENCE: 691
ugugcaaauc caugcaaaac uga                                               23

<210> SEQ ID NO 692
<211> LENGTH: 22
<212> TYPE: RNA
<213> ORGANISM: Homo sapiens

<400> SEQUENCE: 692
uaacacuguc ugguaacgau gu                                                22

<210> SEQ ID NO 693
<211> LENGTH: 22
<212> TYPE: RNA
<213> ORGANISM: Homo sapiens

<400> SEQUENCE: 693
caucuuaccg gacagugcug ga                                                22

<210> SEQ ID NO 694
<211> LENGTH: 23
<212> TYPE: RNA
<213> ORGANISM: Homo sapiens

<400> SEQUENCE: 694
```

```
uaauacugcc ugguaaugau gac                                          23

<210> SEQ ID NO 695
<211> LENGTH: 22
<212> TYPE: RNA
<213> ORGANISM: Homo sapiens

<400> SEQUENCE: 695
uaauacugcc ggguaaugau gg                                           22

<210> SEQ ID NO 696
<211> LENGTH: 22
<212> TYPE: RNA
<213> ORGANISM: Homo sapiens

<400> SEQUENCE: 696
agagguauag ggcaugggaa aa                                           22

<210> SEQ ID NO 697
<211> LENGTH: 22
<212> TYPE: RNA
<213> ORGANISM: Homo sapiens

<400> SEQUENCE: 697
uuuccuaugc auauacuucu uu                                           22

<210> SEQ ID NO 698
<211> LENGTH: 22
<212> TYPE: RNA
<213> ORGANISM: Homo sapiens

<400> SEQUENCE: 698
gugaaauguu uaggaccacu ag                                           22

<210> SEQ ID NO 699
<211> LENGTH: 22
<212> TYPE: RNA
<213> ORGANISM: Homo sapiens

<400> SEQUENCE: 699
uucccuuugu cauccuaugc cu                                           22

<210> SEQ ID NO 700
<211> LENGTH: 22
<212> TYPE: RNA
<213> ORGANISM: Homo sapiens

<400> SEQUENCE: 700
uccuucauuc caccggaguc ug                                           22

<210> SEQ ID NO 701
<211> LENGTH: 22
<212> TYPE: RNA
<213> ORGANISM: Homo sapiens

<400> SEQUENCE: 701
uggaauguaa ggaagugugu gg                                           22

<210> SEQ ID NO 702
<211> LENGTH: 22
<212> TYPE: RNA
<213> ORGANISM: Homo sapiens

<400> SEQUENCE: 702
```
auaagacgag caaaaagcuu gu                                              22

<210> SEQ ID NO 703
<211> LENGTH: 23
<212> TYPE: RNA
<213> ORGANISM: Homo sapiens

<400> SEQUENCE: 703
uaaagugcuu auagugcagg uag                                             23

<210> SEQ ID NO 704
<211> LENGTH: 23
<212> TYPE: RNA
<213> ORGANISM: Homo sapiens

<400> SEQUENCE: 704
caaagugcuc auagugcagg uag                                             23

<210> SEQ ID NO 705
<211> LENGTH: 22
<212> TYPE: RNA
<213> ORGANISM: Homo sapiens

<400> SEQUENCE: 705
uagcuuauca gacugauguu ga                                              22

<210> SEQ ID NO 706
<211> LENGTH: 22
<212> TYPE: RNA
<213> ORGANISM: Homo sapiens

<400> SEQUENCE: 706
cugugcgugu gacagcggcu ga                                              22

<210> SEQ ID NO 707
<211> LENGTH: 22
<212> TYPE: RNA
<213> ORGANISM: Homo sapiens

<400> SEQUENCE: 707 uuccccuuugu cauccuucgc cu                                             22

<210> SEQ ID NO 708
<211> LENGTH: 21
<212> TYPE: RNA
<213> ORGANISM: Homo sapiens

<400> SEQUENCE: 708
uaacagucuc cagucacggc c                                               21

<210> SEQ ID NO 709
<211> LENGTH: 22
<212> TYPE: RNA
<213> ORGANISM: Homo sapiens

<400> SEQUENCE: 709
accaucgacc guugauugua cc                                              22

<210> SEQ ID NO 710
<211> LENGTH: 21
<212> TYPE: RNA
<213> ORGANISM: Homo sapiens

<400> SEQUENCE: 710

| | |
|---|---|
| acagcaggca cagacaggca g | 21 |

<210> SEQ ID NO 711
<211> LENGTH: 21
<212> TYPE: RNA
<213> ORGANISM: Homo sapiens

<400> SEQUENCE: 711

| | |
|---|---|
| augaccuaug aauugacaga c | 21 |

<210> SEQ ID NO 712
<211> LENGTH: 21
<212> TYPE: RNA
<213> ORGANISM: Homo sapiens

<400> SEQUENCE: 712

| | |
|---|---|
| uaaucucagc uggcaacugu g | 21 |

<210> SEQ ID NO 713
<211> LENGTH: 24
<212> TYPE: RNA
<213> ORGANISM: Homo sapiens

<400> SEQUENCE: 713

| | |
|---|---|
| uacugcauca ggaacugauu ggau | 24 |

<210> SEQ ID NO 714
<211> LENGTH: 21
<212> TYPE: RNA
<213> ORGANISM: Homo sapiens

<400> SEQUENCE: 714

| | |
|---|---|
| uugugcuuga ucuaaccaug u | 21 |

<210> SEQ ID NO 715
<211> LENGTH: 21
<212> TYPE: RNA
<213> ORGANISM: Homo sapiens

<400> SEQUENCE: 715

| | |
|---|---|
| ugauugucca aacgcaauuc u | 21 |

<210> SEQ ID NO 716
<211> LENGTH: 22
<212> TYPE: RNA
<213> ORGANISM: Homo sapiens

<400> SEQUENCE: 716

| | |
|---|---|
| aagcugccag uugaagaacu gu | 22 |

<210> SEQ ID NO 717
<211> LENGTH: 21
<212> TYPE: RNA
<213> ORGANISM: Homo sapiens

<400> SEQUENCE: 717

| | |
|---|---|
| ccacaccgua ucugacacuu u | 21 |

<210> SEQ ID NO 718
<211> LENGTH: 23
<212> TYPE: RNA
<213> ORGANISM: Homo sapiens

<400> SEQUENCE: 718
agcuacauug ucugcuggguu uuc                23

<210> SEQ ID NO 719
<211> LENGTH: 24
<212> TYPE: RNA
<213> ORGANISM: Homo sapiens

<400> SEQUENCE: 719
agcuacaucu ggcuacuggg ucuc                24

<210> SEQ ID NO 720
<211> LENGTH: 21
<212> TYPE: RNA
<213> ORGANISM: Homo sapiens

<400> SEQUENCE: 720
ugucaguuug ucaaauaccc c                   21

<210> SEQ ID NO 721
<211> LENGTH: 23
<212> TYPE: RNA
<213> ORGANISM: Homo sapiens

<400> SEQUENCE: 721
caagucacua gugguuccgu uua                 23

<210> SEQ ID NO 722
<211> LENGTH: 21
<212> TYPE: RNA
<213> ORGANISM: Homo sapiens

<400> SEQUENCE: 722
aucacauugc cagggauuuc c                   21

<210> SEQ ID NO 723
<211> LENGTH: 21
<212> TYPE: RNA
<213> ORGANISM: Homo sapiens

<400> SEQUENCE: 723
aucacauugc cagggauuac c                   21

<210> SEQ ID NO 724
<211> LENGTH: 22
<212> TYPE: RNA
<213> ORGANISM: Homo sapiens

<400> SEQUENCE: 724
uggcucaguu cagcaggaac ag                  22

<210> SEQ ID NO 725
<211> LENGTH: 22
<212> TYPE: RNA
<213> ORGANISM: Homo sapiens

<400> SEQUENCE: 725
cauugcacuu gucucggucu ga                  22

<210> SEQ ID NO 726
<211> LENGTH: 21
<212> TYPE: RNA
<213> ORGANISM: Homo sapiens

<400> SEQUENCE: 726
uucaaguaau ccaggauagg c        21

<210> SEQ ID NO 727
<211> LENGTH: 22
<212> TYPE: RNA
<213> ORGANISM: Homo sapiens

<400> SEQUENCE: 727
uucaaguaau ucaggauagg uu       22

<210> SEQ ID NO 728
<211> LENGTH: 21
<212> TYPE: RNA
<213> ORGANISM: Homo sapiens

<400> SEQUENCE: 728
uucacagugg cuaaguuccg c        21

<210> SEQ ID NO 729
<211> LENGTH: 21
<212> TYPE: RNA
<213> ORGANISM: Homo sapiens

<400> SEQUENCE: 729
uucacagugg cuaaguucug c        21

<210> SEQ ID NO 730
<211> LENGTH: 22
<212> TYPE: RNA
<213> ORGANISM: Homo sapiens

<400> SEQUENCE: 730
aaggagcuca cagucuauug ag       22

<210> SEQ ID NO 731
<211> LENGTH: 21
<212> TYPE: RNA
<213> ORGANISM: Homo sapiens

<400> SEQUENCE: 731 agggccccccc cucaauccug u       21

<210> SEQ ID NO 732
<211> LENGTH: 22
<212> TYPE: RNA
<213> ORGANISM: Homo sapiens

<400> SEQUENCE: 732
uaugugggau gguaaaccgc uu       22

<210> SEQ ID NO 733
<211> LENGTH: 22
<212> TYPE: RNA
<213> ORGANISM: Homo sapiens

<400> SEQUENCE: 733
ugguuuaccg ucccacauac au       22

<210> SEQ ID NO 734
<211> LENGTH: 21
<212> TYPE: RNA
<213> ORGANISM: Homo sapiens

<400> SEQUENCE: 734
uagcaccauc ugaaaucggu u                                          21

<210> SEQ ID NO 735
<211> LENGTH: 23
<212> TYPE: RNA
<213> ORGANISM: Homo sapiens

<400> SEQUENCE: 735
uagcaccauu ugaaaucagu guu                                        23

<210> SEQ ID NO 736
<211> LENGTH: 20
<212> TYPE: RNA
<213> ORGANISM: Homo sapiens

<400> SEQUENCE: 736
uagcaccauu ugaaaucggu                                            20

<210> SEQ ID NO 737
<211> LENGTH: 23
<212> TYPE: RNA
<213> ORGANISM: Homo sapiens

<400> SEQUENCE: 737
cagugcaaua guauugucaa agc                                        23

<210> SEQ ID NO 738
<211> LENGTH: 23
<212> TYPE: RNA
<213> ORGANISM: Homo sapiens

<400> SEQUENCE: 738
uaagugcuuc cauguuuugg uga                                        23

<210> SEQ ID NO 739
<211> LENGTH: 22
<212> TYPE: RNA
<213> ORGANISM: Homo sapiens

<400> SEQUENCE: 739
uaaacgugga uguacuugcu uu                                         22

<210> SEQ ID NO 740
<211> LENGTH: 23
<212> TYPE: RNA
<213> ORGANISM: Homo sapiens

<400> SEQUENCE: 740
uaagugcuuc cauguuuuag uag                                        23

<210> SEQ ID NO 741
<211> LENGTH: 23
<212> TYPE: RNA
<213> ORGANISM: Homo sapiens

<400> SEQUENCE: 741
acuuuaacau ggaagugcuu ucu                                        23

<210> SEQ ID NO 742
<211> LENGTH: 23
<212> TYPE: RNA
<213> ORGANISM: Homo sapiens

<400> SEQUENCE: 742
uaagugcuuc cauguuucag ugg    23

<210> SEQ ID NO 743
<211> LENGTH: 22
<212> TYPE: RNA
<213> ORGANISM: Homo sapiens

<400> SEQUENCE: 743
uuuaacaugg ggguaccugc ug    22

<210> SEQ ID NO 744
<211> LENGTH: 23
<212> TYPE: RNA
<213> ORGANISM: Homo sapiens

<400> SEQUENCE: 744
uaagugcuuc cauguuugag ugu    23

<210> SEQ ID NO 745
<211> LENGTH: 22
<212> TYPE: RNA
<213> ORGANISM: Homo sapiens

<400> SEQUENCE: 745
cuuucagucg gauguuugca gc    22

<210> SEQ ID NO 746
<211> LENGTH: 22
<212> TYPE: RNA
<213> ORGANISM: Homo sapiens

<400> SEQUENCE: 746
uguaaacauc cucgacugga ag    22

<210> SEQ ID NO 747
<211> LENGTH: 22
<212> TYPE: RNA
<213> ORGANISM: Homo sapiens

<400> SEQUENCE: 747
uguaaacauc cuacacucag cu    22

<210> SEQ ID NO 748
<211> LENGTH: 23
<212> TYPE: RNA
<213> ORGANISM: Homo sapiens

<400> SEQUENCE: 748
uguaaacauc cuacacucuc agc    23

<210> SEQ ID NO 749
<211> LENGTH: 22
<212> TYPE: RNA
<213> ORGANISM: Homo sapiens

<400> SEQUENCE: 749
uguaaacauc cccgacugga ag    22

<210> SEQ ID NO 750
<211> LENGTH: 22
<212> TYPE: RNA
<213> ORGANISM: Homo sapiens

<400> SEQUENCE: 750
cuuucagucg gauguuuaca gc                                          22

<210> SEQ ID NO 751
<211> LENGTH: 20
<212> TYPE: RNA
<213> ORGANISM: Homo sapiens

<400> SEQUENCE: 751
uguaaacauc cuugacugga                                             20

<210> SEQ ID NO 752
<211> LENGTH: 21
<212> TYPE: RNA
<213> ORGANISM: Homo sapiens

<400> SEQUENCE: 752
ggcaagaugc uggcauagcu g                                           21

<210> SEQ ID NO 753
<211> LENGTH: 21
<212> TYPE: RNA
<213> ORGANISM: Homo sapiens

<400> SEQUENCE: 753
uauugcacau uacuaaguug c                                           21

<210> SEQ ID NO 754
<211> LENGTH: 23
<212> TYPE: RNA
<213> ORGANISM: Homo sapiens

<400> SEQUENCE: 754
aaaagcuggg uugagagggc gaa                                         23

<210> SEQ ID NO 755
<211> LENGTH: 22
<212> TYPE: RNA
<213> ORGANISM: Homo sapiens

<400> SEQUENCE: 755
gcacauuaca cggucgaccu cu                                          22

<210> SEQ ID NO 756
<211> LENGTH: 22
<212> TYPE: RNA
<213> ORGANISM: Homo sapiens

<400> SEQUENCE: 756
ccacugcccc aggugcugcu gg                                          22

<210> SEQ ID NO 757
<211> LENGTH: 23
<212> TYPE: RNA
<213> ORGANISM: Homo sapiens

<400> SEQUENCE: 757
cgcauccccu agggcauugg ugu                                         23

<210> SEQ ID NO 758
<211> LENGTH: 23
<212> TYPE: RNA
<213> ORGANISM: Homo sapiens

<400> SEQUENCE: 758

```
ccuaguaggu guccaguaag ugu                                         23

<210> SEQ ID NO 759
<211> LENGTH: 20
<212> TYPE: RNA
<213> ORGANISM: Homo sapiens

<400> SEQUENCE: 759
ccucugggcc cuuccuccag                                             20

<210> SEQ ID NO 760
<211> LENGTH: 22
<212> TYPE: RNA
<213> ORGANISM: Homo sapiens

<400> SEQUENCE: 760
cuggcccucu cugcccuucc gu                                          22

<210> SEQ ID NO 761
<211> LENGTH: 19
<212> TYPE: RNA
<213> ORGANISM: Homo sapiens

<400> SEQUENCE: 761
acacaccugg uuaaccucu                                              19

<210> SEQ ID NO 762
<211> LENGTH: 19
<212> TYPE: RNA
<213> ORGANISM: Homo sapiens

<400> SEQUENCE: 762
gugcauugua guugcauug                                              19

<210> SEQ ID NO 763
<211> LENGTH: 23
<212> TYPE: RNA
<213> ORGANISM: Homo sapiens

<400> SEQUENCE: 763
gcaaagcaca cggccugcag aga                                         23

<210> SEQ ID NO 764
<211> LENGTH: 21
<212> TYPE: RNA
<213> ORGANISM: Homo sapiens

<400> SEQUENCE: 764
gccccugggc cuauccuaga a                                           21

<210> SEQ ID NO 765
<211> LENGTH: 23
<212> TYPE: RNA
<213> ORGANISM: Homo sapiens

<400> SEQUENCE: 765
ucaagagcaa uaacgaaaaa ugu                                         23

<210> SEQ ID NO 766
<211> LENGTH: 23
<212> TYPE: RNA
<213> ORGANISM: Homo sapiens

<400> SEQUENCE: 766
```
uccagcuccu auaugaugcc uuu                                                     23

<210> SEQ ID NO 767
<211> LENGTH: 23
<212> TYPE: RNA
<213> ORGANISM: Homo sapiens

<400> SEQUENCE: 767
uccagcauca gugauuuugu uga                                                     23

<210> SEQ ID NO 768
<211> LENGTH: 21
<212> TYPE: RNA
<213> ORGANISM: Homo sapiens

<400> SEQUENCE: 768
ucccuguccu ccaggagcuc a                                                       21

<210> SEQ ID NO 769
<211> LENGTH: 23
<212> TYPE: RNA
<213> ORGANISM: Homo sapiens

<400> SEQUENCE: 769
uccgucucag uuacuuuaua gcc                                                     23

<210> SEQ ID NO 770
<211> LENGTH: 24
<212> TYPE: RNA
<213> ORGANISM: Homo sapiens

<400> SEQUENCE: 770
ucucacacag aaaucgcacc cguc                                                    24

<210> SEQ ID NO 771
<211> LENGTH: 21
<212> TYPE: RNA
<213> ORGANISM: Homo sapiens

<400> SEQUENCE: 771
ugcugacucc uaguccaggg c                                                       21

<210> SEQ ID NO 772
<211> LENGTH: 23
<212> TYPE: RNA
<213> ORGANISM: Homo sapiens

<400> SEQUENCE: 772
ugucugcccg caugccugcc ucu                                                     23

<210> SEQ ID NO 773
<211> LENGTH: 23
<212> TYPE: RNA
<213> ORGANISM: Homo sapiens

<400> SEQUENCE: 773
uggcaguguc uuagcugguu guu                                                     23

<210> SEQ ID NO 774
<211> LENGTH: 23
<212> TYPE: RNA
<213> ORGANISM: Homo sapiens

<400> SEQUENCE: 774

-continued

| uaggcagugu cauuagcuga uug | 23 |

<210> SEQ ID NO 775
<211> LENGTH: 23
<212> TYPE: RNA
<213> ORGANISM: Homo sapiens

<400> SEQUENCE: 775

| aggcagugua guuagcugau ugc | 23 |

<210> SEQ ID NO 776
<211> LENGTH: 22
<212> TYPE: RNA
<213> ORGANISM: Homo sapiens

<400> SEQUENCE: 776

| uuaucagaau cuccaggggu ac | 22 |

<210> SEQ ID NO 777
<211> LENGTH: 24
<212> TYPE: RNA
<213> ORGANISM: Homo sapiens

<400> SEQUENCE: 777

| aauccuugga accuaggugu gagu | 24 |

<210> SEQ ID NO 778
<211> LENGTH: 22
<212> TYPE: RNA
<213> ORGANISM: Homo sapiens

<400> SEQUENCE: 778

| aauugcacgg uauccaucug ua | 22 |

<210> SEQ ID NO 779
<211> LENGTH: 22
<212> TYPE: RNA
<213> ORGANISM: Homo sapiens

<400> SEQUENCE: 779

| auaaugcccc uaaaaauccu ua | 22 |

<210> SEQ ID NO 780
<211> LENGTH: 22
<212> TYPE: RNA
<213> ORGANISM: Homo sapiens

<400> SEQUENCE: 780

| aauugcacuu uagcaauggu ga | 22 |

<210> SEQ ID NO 781
<211> LENGTH: 22
<212> TYPE: RNA
<213> ORGANISM: Homo sapiens

<400> SEQUENCE: 781

| acauagagga aauuccacgu uu | 22 |

<210> SEQ ID NO 782
<211> LENGTH: 21
<212> TYPE: RNA
<213> ORGANISM: Homo sapiens

<400> SEQUENCE: 782
aauaauacau gguugaucuu u                                              21

<210> SEQ ID NO 783
<211> LENGTH: 22
<212> TYPE: RNA
<213> ORGANISM: Homo sapiens

<400> SEQUENCE: 783
agaucgaccg uguuauauuc gc                                             22

<210> SEQ ID NO 784
<211> LENGTH: 21
<212> TYPE: RNA
<213> ORGANISM: Homo sapiens

<400> SEQUENCE: 784
gccugcuggg guggaaccug g                                              21

<210> SEQ ID NO 785
<211> LENGTH: 21
<212> TYPE: RNA
<213> ORGANISM: Homo sapiens

<400> SEQUENCE: 785
gugccgccau cuuuugagug u                                              21

<210> SEQ ID NO 786
<211> LENGTH: 23
<212> TYPE: RNA
<213> ORGANISM: Homo sapiens

<400> SEQUENCE: 786
aaagugcugc gacauuugag cgu                                            23

<210> SEQ ID NO 787
<211> LENGTH: 23
<212> TYPE: RNA
<213> ORGANISM: Homo sapiens

<400> SEQUENCE: 787
gaagugcuuc gauuuugggg ugu                                            23

<210> SEQ ID NO 788
<211> LENGTH: 22
<212> TYPE: RNA
<213> ORGANISM: Homo sapiens

<400> SEQUENCE: 788
acucaaaaug ggggcgcuuu cc                                             22

<210> SEQ ID NO 789
<211> LENGTH: 22
<212> TYPE: RNA
<213> ORGANISM: Homo sapiens

<400> SEQUENCE: 789
uuauaauaca accugauaag ug                                             22

<210> SEQ ID NO 790
<211> LENGTH: 22
<212> TYPE: RNA
<213> ORGANISM: Homo sapiens

<400> SEQUENCE: 790
uuuguucguu cggcucgcgu ga                           22

<210> SEQ ID NO 791
<211> LENGTH: 21
<212> TYPE: RNA
<213> ORGANISM: Homo sapiens

<400> SEQUENCE: 791
aucauagagg aaaauccacg u                            21

<210> SEQ ID NO 792
<211> LENGTH: 22
<212> TYPE: RNA
<213> ORGANISM: Homo sapiens

<400> SEQUENCE: 792
aucauagagg aaaauccaug uu                           22

<210> SEQ ID NO 793
<211> LENGTH: 22
<212> TYPE: RNA
<213> ORGANISM: Homo sapiens

<400> SEQUENCE: 793
aucacacaaa ggcaacuuuu gu                           22

<210> SEQ ID NO 794
<211> LENGTH: 22
<212> TYPE: RNA
<213> ORGANISM: Homo sapiens

<400> SEQUENCE: 794
cuccugacuc cagguccugu gu                           22

<210> SEQ ID NO 795
<211> LENGTH: 19
<212> TYPE: RNA
<213> ORGANISM: Homo sapiens

<400> SEQUENCE: 795
ugguagacua uggaacgua                               19

<210> SEQ ID NO 796
<211> LENGTH: 22
<212> TYPE: RNA
<213> ORGANISM: Homo sapiens

<400> SEQUENCE: 796
uauguaauau gguccacauc uu                           22

<210> SEQ ID NO 797
<211> LENGTH: 22
<212> TYPE: RNA
<213> ORGANISM: Homo sapiens

<400> SEQUENCE: 797
ugguugacca uagaacaugc gc                           22

<210> SEQ ID NO 798
<211> LENGTH: 22
<212> TYPE: RNA
<213> ORGANISM: Homo sapiens

<400> SEQUENCE: 798
uauacaaggg caagcucucu gu 22

<210> SEQ ID NO 799
<211> LENGTH: 22
<212> TYPE: RNA
<213> ORGANISM: Homo sapiens

<400> SEQUENCE: 799
gaaguuguuc gugguggauu cg 22

<210> SEQ ID NO 800
<211> LENGTH: 22
<212> TYPE: RNA
<213> ORGANISM: Homo sapiens

<400> SEQUENCE: 800
agaucagaag gugauugugg cu 22

<210> SEQ ID NO 801
<211> LENGTH: 20
<212> TYPE: RNA
<213> ORGANISM: Homo sapiens

<400> SEQUENCE: 801
auuccuagaa auuguucaua 20

<210> SEQ ID NO 802
<211> LENGTH: 21
<212> TYPE: RNA
<213> ORGANISM: Homo sapiens

<400> SEQUENCE: 802
aauguugcuc ggugaacccc u 21

<210> SEQ ID NO 803
<211> LENGTH: 22
<212> TYPE: RNA
<213> ORGANISM: Homo sapiens

<400> SEQUENCE: 803
agguuacccg agcaacuuug ca 22

<210> SEQ ID NO 804
<211> LENGTH: 21
<212> TYPE: RNA
<213> ORGANISM: Homo sapiens

<400> SEQUENCE: 804
aauauaacac agauggccug u 21

<210> SEQ ID NO 805
<211> LENGTH: 23
<212> TYPE: RNA
<213> ORGANISM: Homo sapiens

<400> SEQUENCE: 805
acuucaccug guccacuagc cgu 23

<210> SEQ ID NO 806
<211> LENGTH: 22
<212> TYPE: RNA
<213> ORGANISM: Homo sapiens

<400> SEQUENCE: 806

-continued cuggacuuag ggucagaagg cc                                22

<210> SEQ ID NO 807
<211> LENGTH: 22
<212> TYPE: RNA
<213> ORGANISM: Homo sapiens

<400> SEQUENCE: 807
cuggacuugg agucagaagg cc                                22

<210> SEQ ID NO 808
<211> LENGTH: 22
<212> TYPE: RNA
<213> ORGANISM: Homo sapiens

<400> SEQUENCE: 808
agcucggucu gaggccccuc ag                                22

<210> SEQ ID NO 809
<211> LENGTH: 22
<212> TYPE: RNA
<213> ORGANISM: Homo sapiens

<400> SEQUENCE: 809
cagcagcaau ucauguuuug aa                                22

<210> SEQ ID NO 810
<211> LENGTH: 21
<212> TYPE: RNA
<213> ORGANISM: Homo sapiens

<400> SEQUENCE: 810
aucgggaaug ucguguccgc c                                 21

<210> SEQ ID NO 811
<211> LENGTH: 22
<212> TYPE: RNA
<213> ORGANISM: Homo sapiens

<400> SEQUENCE: 811
uaauacuguc ugguaaaacc gu                                22

<210> SEQ ID NO 812
<211> LENGTH: 21
<212> TYPE: RNA
<213> ORGANISM: Homo sapiens

<400> SEQUENCE: 812
ugucuugcag gccgucaugc a                                 21

<210> SEQ ID NO 813
<211> LENGTH: 23
<212> TYPE: RNA
<213> ORGANISM: Homo sapiens

<400> SEQUENCE: 813
ucuuggagua ggucauuggg ugg                               23

<210> SEQ ID NO 814
<211> LENGTH: 21
<212> TYPE: RNA
<213> ORGANISM: Homo sapiens

<400> SEQUENCE: 814
cuggauggcu ccuccauguc u                                                      21

<210> SEQ ID NO 815
<211> LENGTH: 22
<212> TYPE: RNA
<213> ORGANISM: Homo sapiens

<400> SEQUENCE: 815
aucaugaugg gcuccucggu gu                                                     22

<210> SEQ ID NO 816
<211> LENGTH: 22
<212> TYPE: RNA
<213> ORGANISM: Homo sapiens

<400> SEQUENCE: 816
uugcauaugu aggaugcccc au                                                     22

<210> SEQ ID NO 817
<211> LENGTH: 22
<212> TYPE: RNA
<213> ORGANISM: Homo sapiens

<400> SEQUENCE: 817
uggcagugua uuguuagcug gu                                                     22

<210> SEQ ID NO 818
<211> LENGTH: 22
<212> TYPE: RNA
<213> ORGANISM: Homo sapiens

<400> SEQUENCE: 818
uuuugcgaug uguuccuaau au                                                     22

<210> SEQ ID NO 819
<211> LENGTH: 23
<212> TYPE: RNA
<213> ORGANISM: Homo sapiens

<400> SEQUENCE: 819
ggaaaccguu accauuacug agu                                                    23

<210> SEQ ID NO 820
<211> LENGTH: 22
<212> TYPE: RNA
<213> ORGANISM: Homo sapiens

<400> SEQUENCE: 820
uguuugcaga ggaaacugag ac                                                     22

<210> SEQ ID NO 821
<211> LENGTH: 21
<212> TYPE: RNA
<213> ORGANISM: Homo sapiens

<400> SEQUENCE: 821
ucagucucau cugcaaagaa g                                                      21

<210> SEQ ID NO 822
<211> LENGTH: 22
<212> TYPE: RNA
<213> ORGANISM: Homo sapiens

<400> SEQUENCE: 822

```
gagguugucc guggugaguu cg                                              22

<210> SEQ ID NO 823
<211> LENGTH: 22
<212> TYPE: RNA
<213> ORGANISM: Homo sapiens

<400> SEQUENCE: 823
gucauacacg gcucuccucu cu                                              22

<210> SEQ ID NO 824
<211> LENGTH: 22
<212> TYPE: RNA
<213> ORGANISM: Homo sapiens

<400> SEQUENCE: 824
agaggcuggc cgugaugaau uc                                              22

<210> SEQ ID NO 825
<211> LENGTH: 21
<212> TYPE: RNA
<213> ORGANISM: Homo sapiens

<400> SEQUENCE: 825
cccagauaau ggcacucuca a                                               21

<210> SEQ ID NO 826
<211> LENGTH: 23
<212> TYPE: RNA
<213> ORGANISM: Homo sapiens

<400> SEQUENCE: 826
agugacauca cauauacggc agc                                             23

<210> SEQ ID NO 827
<211> LENGTH: 22
<212> TYPE: RNA
<213> ORGANISM: Homo sapiens

<400> SEQUENCE: 827
caaccuggag gacuccaugc ug                                              22

<210> SEQ ID NO 828
<211> LENGTH: 23
<212> TYPE: RNA
<213> ORGANISM: Homo sapiens

<400> SEQUENCE: 828 agugggaac ccuuccauga gga                                              23

<210> SEQ ID NO 829
<211> LENGTH: 23
<212> TYPE: RNA
<213> ORGANISM: Homo sapiens

<400> SEQUENCE: 829
aggaccugcg ggacaagauu cuu                                             23

<210> SEQ ID NO 830
<211> LENGTH: 22
<212> TYPE: RNA
<213> ORGANISM: Homo sapiens

<400> SEQUENCE: 830
```
uuguacaugg uaggcuuuca uu                                    22

<210> SEQ ID NO 831
<211> LENGTH: 24
<212> TYPE: RNA
<213> ORGANISM: Homo sapiens

<400> SEQUENCE: 831
ugaaacauac acgggaaacc ucuu                                  24

<210> SEQ ID NO 832
<211> LENGTH: 23
<212> TYPE: RNA
<213> ORGANISM: Homo sapiens

<400> SEQUENCE: 832
aaacaaacau ggugcacuuc uuu                                   23

<210> SEQ ID NO 833
<211> LENGTH: 17
<212> TYPE: RNA
<213> ORGANISM: Homo sapiens

<400> SEQUENCE: 833
auuacauggc caaucuc                                          17

<210> SEQ ID NO 834
<211> LENGTH: 21
<212> TYPE: RNA
<213> ORGANISM: Homo sapiens

<400> SEQUENCE: 834
cagcagcaca cugugguuug u                                     21

<210> SEQ ID NO 835
<211> LENGTH: 23
<212> TYPE: RNA
<213> ORGANISM: Homo sapiens

<400> SEQUENCE: 835
uuucaagcca gggggcguuu uuc                                   23

<210> SEQ ID NO 836
<211> LENGTH: 23
<212> TYPE: RNA
<213> ORGANISM: Homo sapiens

<400> SEQUENCE: 836
uuaagacuug cagugauguu uaa                                   23

<210> SEQ ID NO 837
<211> LENGTH: 22
<212> TYPE: RNA
<213> ORGANISM: Homo sapiens

<400> SEQUENCE: 837
augcaccugg gcaaggauuc ug                                    22

<210> SEQ ID NO 838
<211> LENGTH: 22
<212> TYPE: RNA
<213> ORGANISM: Homo sapiens

<400> SEQUENCE: 838

```
aauccuuugu cccuggguga ga                                              22

<210> SEQ ID NO 839
<211> LENGTH: 21
<212> TYPE: RNA
<213> ORGANISM: Homo sapiens

<400> SEQUENCE: 839
auccuugcua ucugggugcu a                                               21

<210> SEQ ID NO 840
<211> LENGTH: 23
<212> TYPE: RNA
<213> ORGANISM: Homo sapiens

<400> SEQUENCE: 840
uagcagcggg aacaguucug cag                                             23

<210> SEQ ID NO 841
<211> LENGTH: 21
<212> TYPE: RNA
<213> ORGANISM: Homo sapiens

<400> SEQUENCE: 841
agacccuggu cugcacucua u                                               21

<210> SEQ ID NO 842
<211> LENGTH: 22
<212> TYPE: RNA
<213> ORGANISM: Homo sapiens

<400> SEQUENCE: 842
gucaacacuu gcugguuucc uc                                              22

<210> SEQ ID NO 843
<211> LENGTH: 21
<212> TYPE: RNA
<213> ORGANISM: Homo sapiens

<400> SEQUENCE: 843
uaaggcaccc uucugaguag a                                               21

<210> SEQ ID NO 844
<211> LENGTH: 21
<212> TYPE: RNA
<213> ORGANISM: Homo sapiens

<400> SEQUENCE: 844
uuuugcaccu uuuggaguga a                                               21

<210> SEQ ID NO 845
<211> LENGTH: 23
<212> TYPE: RNA
<213> ORGANISM: Homo sapiens

<400> SEQUENCE: 845
ugauuguagc cuuuuggagu aga                                             23

<210> SEQ ID NO 846
<211> LENGTH: 23
<212> TYPE: RNA
<213> ORGANISM: Homo sapiens

<400> SEQUENCE: 846
```
ugauuggyac gucugugggu aga                                    23

<210> SEQ ID NO 847
<211> LENGTH: 23
<212> TYPE: RNA
<213> ORGANISM: Homo sapiens

<400> SEQUENCE: 847
uacucaggag aguggcaauc aca                                    23

<210> SEQ ID NO 848
<211> LENGTH: 21
<212> TYPE: RNA
<213> ORGANISM: Homo sapiens

<400> SEQUENCE: 848
gugucuuuug cucugcaguc a                                      21

<210> SEQ ID NO 849
<211> LENGTH: 22
<212> TYPE: RNA
<213> ORGANISM: Homo sapiens

<400> SEQUENCE: 849
aagugcuguc auagcugagg uc                                     22

<210> SEQ ID NO 850
<211> LENGTH: 23
<212> TYPE: RNA
<213> ORGANISM: Homo sapiens

<400> SEQUENCE: 850
cacucagccu ugagggcacu uuc                                    23

<210> SEQ ID NO 851
<211> LENGTH: 22
<212> TYPE: RNA
<213> ORGANISM: Homo sapiens

<400> SEQUENCE: 851
uucacaggga ggugucauuu au                                     22

<210> SEQ ID NO 852
<211> LENGTH: 20
<212> TYPE: RNA
<213> ORGANISM: Homo sapiens

<400> SEQUENCE: 852
auugacacuu cugugaguag                                        20

<210> SEQ ID NO 853
<211> LENGTH: 21
<212> TYPE: RNA
<213> ORGANISM: Homo sapiens

<400> SEQUENCE: 853
gagugccuuc uuuuggagcg u                                      21

<210> SEQ ID NO 854
<211> LENGTH: 24
<212> TYPE: RNA
<213> ORGANISM: Homo sapiens

<400> SEQUENCE: 854

| | | |
|---|---|---|
| uucuccaaaa gaaagcacuu ucug | | 24 |

<210> SEQ ID NO 855
<211> LENGTH: 18
<212> TYPE: RNA
<213> ORGANISM: Homo sapiens

<400> SEQUENCE: 855

| | | |
|---|---|---|
| ugcuuccuuu cagagggu | | 18 |

<210> SEQ ID NO 856
<211> LENGTH: 25
<212> TYPE: RNA
<213> ORGANISM: Homo sapiens

<400> SEQUENCE: 856

| | | |
|---|---|---|
| aucuggaggu aagaagcacu uucug | | 25 |

<210> SEQ ID NO 857
<211> LENGTH: 23
<212> TYPE: RNA
<213> ORGANISM: Homo sapiens

<400> SEQUENCE: 857

| | | |
|---|---|---|
| caucuggagg uaagaagcac uuu | | 23 |

<210> SEQ ID NO 858
<211> LENGTH: 22
<212> TYPE: RNA
<213> ORGANISM: Homo sapiens

<400> SEQUENCE: 858

| | | |
|---|---|---|
| ccucuagaug gaagcacugu cu | | 22 |

<210> SEQ ID NO 859
<211> LENGTH: 23
<212> TYPE: RNA
<213> ORGANISM: Homo sapiens

<400> SEQUENCE: 859

| | | |
|---|---|---|
| aucgugcauc ccuuuagagu guu | | 23 |

<210> SEQ ID NO 860
<211> LENGTH: 22
<212> TYPE: RNA
<213> ORGANISM: Homo sapiens

<400> SEQUENCE: 860

| | | |
|---|---|---|
| ucgugcaucc cuuuagagug uu | | 22 |

<210> SEQ ID NO 861
<211> LENGTH: 22
<212> TYPE: RNA
<213> ORGANISM: Homo sapiens

<400> SEQUENCE: 861

| | | |
|---|---|---|
| aucgugcauc cuuuuagagu gu | | 22 |

<210> SEQ ID NO 862
<211> LENGTH: 21
<212> TYPE: RNA
<213> ORGANISM: Homo sapiens

<400> SEQUENCE: 862
aaagcgcuuc ccuuugcugg a                                            21

<210> SEQ ID NO 863
<211> LENGTH: 20
<212> TYPE: RNA
<213> ORGANISM: Homo sapiens

<400> SEQUENCE: 863
ucugcaaagg gaagcccuuu                                              20

<210> SEQ ID NO 864
<211> LENGTH: 22
<212> TYPE: RNA
<213> ORGANISM: Homo sapiens

<400> SEQUENCE: 864
caaagcgcuc cccuuuagag gu                                           22

<210> SEQ ID NO 865
<211> LENGTH: 22
<212> TYPE: RNA
<213> ORGANISM: Homo sapiens

<400> SEQUENCE: 865
caaagcgcuu cucuuuagag ug                                           22

<210> SEQ ID NO 866
<211> LENGTH: 23
<212> TYPE: RNA
<213> ORGANISM: Homo sapiens

<400> SEQUENCE: 866
ucucuggagg gaagcacuuu cug                                          23

<210> SEQ ID NO 867
<211> LENGTH: 21
<212> TYPE: RNA
<213> ORGANISM: Homo sapiens

<400> SEQUENCE: 867
caaagcgcuu cccuuuggag c                                            21

<210> SEQ ID NO 868
<211> LENGTH: 22
<212> TYPE: RNA
<213> ORGANISM: Homo sapiens

<400> SEQUENCE: 868
aaagcgcuuc ccuucagagu gu                                           22

<210> SEQ ID NO 869
<211> LENGTH: 21
<212> TYPE: RNA
<213> ORGANISM: Homo sapiens

<400> SEQUENCE: 869
aaagcgcuuc ucuuuagagg a                                            21

<210> SEQ ID NO 870
<211> LENGTH: 23
<212> TYPE: RNA
<213> ORGANISM: Homo sapiens

<400> SEQUENCE: 870

```
cucuagaggg aagcacuuuc ucu                                              23

<210> SEQ ID NO 871
<211> LENGTH: 25
<212> TYPE: RNA
<213> ORGANISM: Homo sapiens

<400> SEQUENCE: 871
aaagugcauc cuuuuagagu guuac                                            25

<210> SEQ ID NO 872
<211> LENGTH: 23
<212> TYPE: RNA
<213> ORGANISM: Homo sapiens

<400> SEQUENCE: 872
aaagugcauc cuuuuagagg uuu                                              23

<210> SEQ ID NO 873
<211> LENGTH: 22
<212> TYPE: RNA
<213> ORGANISM: Homo sapiens

<400> SEQUENCE: 873
aaagugcauc uuuuuagagg au                                               22

<210> SEQ ID NO 874
<211> LENGTH: 23
<212> TYPE: RNA
<213> ORGANISM: Homo sapiens

<400> SEQUENCE: 874
caaagugccu cccuuuagag ugu                                              23

<210> SEQ ID NO 875
<211> LENGTH: 22
<212> TYPE: RNA
<213> ORGANISM: Homo sapiens

<400> SEQUENCE: 875
aaagugccuc cuuuuagagu gu                                               22

<210> SEQ ID NO 876
<211> LENGTH: 22
<212> TYPE: RNA
<213> ORGANISM: Homo sapiens

<400> SEQUENCE: 876
uucuccaaaa gggagcacuu uc                                               22

<210> SEQ ID NO 877
<211> LENGTH: 22
<212> TYPE: RNA
<213> ORGANISM: Homo sapiens

<400> SEQUENCE: 877
aaagugcuuc ccuuuggacu gu                                               22

<210> SEQ ID NO 878
<211> LENGTH: 21
<212> TYPE: RNA
<213> ORGANISM: Homo sapiens

<400> SEQUENCE: 878
```
cuccagaggg aaguacuuuc u                                          21

<210> SEQ ID NO 879
<211> LENGTH: 21
<212> TYPE: RNA
<213> ORGANISM: Homo sapiens

<400> SEQUENCE: 879
aaagugcuuc cuuuuagagg g                                          21

<210> SEQ ID NO 880
<211> LENGTH: 23
<212> TYPE: RNA
<213> ORGANISM: Homo sapiens

<400> SEQUENCE: 880
aaagugcuuc cuuuuagagg guu                                        23

<210> SEQ ID NO 881
<211> LENGTH: 23
<212> TYPE: RNA
<213> ORGANISM: Homo sapiens

<400> SEQUENCE: 881
aaagugcuuc ucuuuggugg guu                                        23

<210> SEQ ID NO 882
<211> LENGTH: 23
<212> TYPE: RNA
<213> ORGANISM: Homo sapiens

<400> SEQUENCE: 882
ucuacaaagg gaagcccuuu cug                                        23

<210> SEQ ID NO 883
<211> LENGTH: 21
<212> TYPE: RNA
<213> ORGANISM: Homo sapiens

<400> SEQUENCE: 883
aaagugcuuc cuuuuugagg g                                          21

<210> SEQ ID NO 884
<211> LENGTH: 22
<212> TYPE: RNA
<213> ORGANISM: Homo sapiens

<400> SEQUENCE: 884
aagugcuucc uuuuagaggg uu                                         22

<210> SEQ ID NO 885
<211> LENGTH: 24
<212> TYPE: RNA
<213> ORGANISM: Homo sapiens

<400> SEQUENCE: 885
acaaagugcu ucccuuuaga gugu                                       24

<210> SEQ ID NO 886
<211> LENGTH: 22
<212> TYPE: RNA
<213> ORGANISM: Homo sapiens

<400> SEQUENCE: 886

| | |
|---|---|
| acaaagugcu ucccuuuaga gu | 22 |

<210> SEQ ID NO 887
<211> LENGTH: 22
<212> TYPE: RNA
<213> ORGANISM: Homo sapiens

<400> SEQUENCE: 887

| | |
|---|---|
| aacgcacuuc ccuuuagagu gu | 22 |

<210> SEQ ID NO 888
<211> LENGTH: 23
<212> TYPE: RNA
<213> ORGANISM: Homo sapiens

<400> SEQUENCE: 888

| | |
|---|---|
| aaaaugguuc ccuuuagagu guu | 23 |

<210> SEQ ID NO 889
<211> LENGTH: 21
<212> TYPE: RNA
<213> ORGANISM: Homo sapiens

<400> SEQUENCE: 889

| | |
|---|---|
| aacgcgcuuc ccauagagg g | 21 |

<210> SEQ ID NO 890
<211> LENGTH: 21
<212> TYPE: RNA
<213> ORGANISM: Homo sapiens

<400> SEQUENCE: 890

| | |
|---|---|
| gaaggcgcuu cccuuuggag u | 21 |

<210> SEQ ID NO 891
<211> LENGTH: 22
<212> TYPE: RNA
<213> ORGANISM: Homo sapiens

<400> SEQUENCE: 891

| | |
|---|---|
| cuacaaaggg aagcacuuuc uc | 22 |

<210> SEQ ID NO 892
<211> LENGTH: 21
<212> TYPE: RNA
<213> ORGANISM: Homo sapiens

<400> SEQUENCE: 892

| | |
|---|---|
| cuccagaggg augcacuuuc u | 21 |

<210> SEQ ID NO 893
<211> LENGTH: 21
<212> TYPE: RNA
<213> ORGANISM: Homo sapiens

<400> SEQUENCE: 893

| | |
|---|---|
| gaaggcgcuu cccuuuagag c | 21 |

<210> SEQ ID NO 894
<211> LENGTH: 21
<212> TYPE: RNA
<213> ORGANISM: Homo sapiens

<400> SEQUENCE: 894

```
cucuagaggg aagcacuuuc u                                              21

<210> SEQ ID NO 895
<211> LENGTH: 24
<212> TYPE: RNA
<213> ORGANISM: Homo sapiens

<400> SEQUENCE: 895
cucuugaggg aagcacuuuc uguu                                           24

<210> SEQ ID NO 896
<211> LENGTH: 21
<212> TYPE: RNA
<213> ORGANISM: Homo sapiens

<400> SEQUENCE: 896
aaagugcuuc cuuuuagagg c                                              21

<210> SEQ ID NO 897
<211> LENGTH: 24
<212> TYPE: RNA
<213> ORGANISM: Homo sapiens

<400> SEQUENCE: 897
cucuagaggg aagcgcuuuc uguu                                           24

<210> SEQ ID NO 898
<211> LENGTH: 21
<212> TYPE: RNA
<213> ORGANISM: Homo sapiens

<400> SEQUENCE: 898
cugcaaaggg aagcccuuuc u                                              21

<210> SEQ ID NO 899
<211> LENGTH: 22
<212> TYPE: RNA
<213> ORGANISM: Homo sapiens

<400> SEQUENCE: 899
uggaagacua gugauuuugu ug                                             22

<210> SEQ ID NO 900
<211> LENGTH: 23
<212> TYPE: RNA
<213> ORGANISM: Homo sapiens

<400> SEQUENCE: 900
ucuuugguua ucuagcugua uga                                            23

<210> SEQ ID NO 901
<211> LENGTH: 21
<212> TYPE: RNA
<213> ORGANISM: Homo sapiens

<400> SEQUENCE: 901
uaaagcuaga uaaccgaaag u                                              21

<210> SEQ ID NO 902
<211> LENGTH: 21
<212> TYPE: RNA
<213> ORGANISM: Homo sapiens

<400> SEQUENCE: 902
```
uauugcacuu gucccggccu g                    21

<210> SEQ ID NO 903
<211> LENGTH: 22
<212> TYPE: RNA
<213> ORGANISM: Homo sapiens

<400> SEQUENCE: 903
aaagugcugu ucgugcaggu ag                   22

<210> SEQ ID NO 904
<211> LENGTH: 22
<212> TYPE: RNA
<213> ORGANISM: Homo sapiens

<400> SEQUENCE: 904
uucaacgggu auuuauugag ca                   22

<210> SEQ ID NO 905
<211> LENGTH: 22
<212> TYPE: RNA
<213> ORGANISM: Homo sapiens

<400> SEQUENCE: 905
uuuggcacua gcacauuuuu gc                   22

<210> SEQ ID NO 906
<211> LENGTH: 21
<212> TYPE: RNA
<213> ORGANISM: Homo sapiens

<400> SEQUENCE: 906
acgagacucu ggcaugcuaa c                    21

<210> SEQ ID NO 907
<211> LENGTH: 22
<212> TYPE: RNA
<213> ORGANISM: Homo sapiens

<400> SEQUENCE: 907
ugagguagua aguuguauug uu                   22

<210> SEQ ID NO 908
<211> LENGTH: 22
<212> TYPE: RNA
<213> ORGANISM: Homo sapiens

<400> SEQUENCE: 908
aacccguaga uccgaucuug ug                   22

<210> SEQ ID NO 909
<211> LENGTH: 22
<212> TYPE: RNA
<213> ORGANISM: Homo sapiens

<400> SEQUENCE: 909
cacccguaga accgaccuug cg                   22

<210> SEQ ID NO 910
<211> LENGTH: 21
<212> TYPE: DNA
<213> ORGANISM: Homo sapiens

<400> SEQUENCE: 910

```
tgcaatgcaa cagcaatgca c                                              21

<210> SEQ ID NO 911
<211> LENGTH: 21
<212> TYPE: DNA
<213> ORGANISM: Homo sapiens

<400> SEQUENCE: 911
gaggccggga cgagtgcaat a                                              21

<210> SEQ ID NO 912
<211> LENGTH: 21
<212> TYPE: DNA
<213> ORGANISM: Homo sapiens

<400> SEQUENCE: 912
cgtacgctat acggtctact a                                              21

<210> SEQ ID NO 913
<211> LENGTH: 23
<212> TYPE: DNA
<213> ORGANISM: Homo sapiens

<400> SEQUENCE: 913
gcgcccaatt aatgtctgtt gat                                            23

<210> SEQ ID NO 914
<211> LENGTH: 22
<212> TYPE: DNA
<213> ORGANISM: Homo sapiens

<400> SEQUENCE: 914
gccagctaac aatacactgc ct                                             22

<210> SEQ ID NO 915
<211> LENGTH: 22
<212> TYPE: DNA
<213> ORGANISM: Homo sapiens

<400> SEQUENCE: 915
ctcccttctt tcctcccgtc tt                                             22

<210> SEQ ID NO 916
<211> LENGTH: 22
<212> TYPE: DNA
<213> ORGANISM: Homo sapiens

<400> SEQUENCE: 916
ctcgtgacat gatgatcccc ga                                             22

<210> SEQ ID NO 917
<211> LENGTH: 22
<212> TYPE: DNA
<213> ORGANISM: Homo sapiens

<400> SEQUENCE: 917
gcacacaata aatgtttgct ga                                             22

<210> SEQ ID NO 918
<211> LENGTH: 22
<212> TYPE: DNA
<213> ORGANISM: Homo sapiens

<400> SEQUENCE: 918
```
gcaaaagtaa ttgccagttt tg                                      22

<210> SEQ ID NO 919
<211> LENGTH: 22
<212> TYPE: DNA
<213> ORGANISM: Homo sapiens

<400> SEQUENCE: 919
acaaaagcaa ctgaggttct tg                                      22

<210> SEQ ID NO 920
<211> LENGTH: 22
<212> TYPE: DNA
<213> ORGANISM: Homo sapiens

<400> SEQUENCE: 920
gcaaaagtaa ttgagatttt tg                                      22

<210> SEQ ID NO 921
<211> LENGTH: 21
<212> TYPE: DNA
<213> ORGANISM: Homo sapiens

<400> SEQUENCE: 921
agagctcatc catagttgtc a                                       21

<210> SEQ ID NO 922
<211> LENGTH: 22
<212> TYPE: DNA
<213> ORGANISM: Homo sapiens

<400> SEQUENCE: 922
tgagagctca tccatagttg tc                                      22

<210> SEQ ID NO 923
<211> LENGTH: 22
<212> TYPE: DNA
<213> ORGANISM: Homo sapiens

<400> SEQUENCE: 923
atgtgcctga gggagtaaga ca                                      22

<210> SEQ ID NO 924
<211> LENGTH: 21
<212> TYPE: DNA
<213> ORGANISM: Homo sapiens

<400> SEQUENCE: 924
tggaaaccaa gagtgggtcg c                                       21

<210> SEQ ID NO 925
<211> LENGTH: 21
<212> TYPE: DNA
<213> ORGANISM: Homo sapiens

<400> SEQUENCE: 925
ctgaaaccaa gtatgggtcg c                                       21

<210> SEQ ID NO 926
<211> LENGTH: 21
<212> TYPE: DNA
<213> ORGANISM: Homo sapiens

<400> SEQUENCE: 926

```
ttgtctaacc agtcacctgt t                                              21

<210> SEQ ID NO 927
<211> LENGTH: 21
<212> TYPE: DNA
<213> ORGANISM: Homo sapiens

<400> SEQUENCE: 927
aaaacaaaat ctcaccgttt t                                              21

<210> SEQ ID NO 928
<211> LENGTH: 21
<212> TYPE: DNA
<213> ORGANISM: Homo sapiens

<400> SEQUENCE: 928
actggctgag tcaggactag c                                              21

<210> SEQ ID NO 929
<211> LENGTH: 21
<212> TYPE: DNA
<213> ORGANISM: Homo sapiens

<400> SEQUENCE: 929
atcagaggtt cagcttaccc t                                              21

<210> SEQ ID NO 930
<211> LENGTH: 20
<212> TYPE: DNA
<213> ORGANISM: Homo sapiens

<400> SEQUENCE: 930
catattacaa tgagctcatc                                                20

<210> SEQ ID NO 931
<211> LENGTH: 23
<212> TYPE: DNA
<213> ORGANISM: Homo sapiens

<400> SEQUENCE: 931
agacaaggcc cacccgtgca aac                                            23

<210> SEQ ID NO 932
<211> LENGTH: 19
<212> TYPE: DNA
<213> ORGANISM: Homo sapiens

<400> SEQUENCE: 932
attttggtac agcagctca                                                 19

<210> SEQ ID NO 933
<211> LENGTH: 21
<212> TYPE: DNA
<213> ORGANISM: Homo sapiens

<400> SEQUENCE: 933
ttttggtgca tatttacttt a                                              21

<210> SEQ ID NO 934
<211> LENGTH: 20
<212> TYPE: DNA
<213> ORGANISM: Homo sapiens

<400> SEQUENCE: 934
```
ggcggccggc cggcgcacgc                                               20

<210> SEQ ID NO 935
<211> LENGTH: 22
<212> TYPE: DNA
<213> ORGANISM: Homo sapiens

<400> SEQUENCE: 935
acttcaagga tcttaaactt tg                                            22

<210> SEQ ID NO 936
<211> LENGTH: 20
<212> TYPE: DNA
<213> ORGANISM: Homo sapiens

<400> SEQUENCE: 936
gcaaatggta cagctacttt                                               20

<210> SEQ ID NO 937
<211> LENGTH: 19
<212> TYPE: DNA
<213> ORGANISM: Homo sapiens

<400> SEQUENCE: 937
gggaaacgta tgtcaacct                                                19

<210> SEQ ID NO 938
<211> LENGTH: 19
<212> TYPE: DNA
<213> ORGANISM: Homo sapiens

<400> SEQUENCE: 938
gcctgctgac accgtgcct                                                19

<210> SEQ ID NO 939
<211> LENGTH: 22
<212> TYPE: DNA
<213> ORGANISM: Homo sapiens

<400> SEQUENCE: 939
aaacagacat cgcgagccag cc                                            22

<210> SEQ ID NO 940
<211> LENGTH: 19
<212> TYPE: DNA
<213> ORGANISM: Homo sapiens

<400> SEQUENCE: 940
gttgggatca caggcgccc                                                19

<210> SEQ ID NO 941
<211> LENGTH: 23
<212> TYPE: DNA
<213> ORGANISM: Homo sapiens

<400> SEQUENCE: 941
gttctgtcct ggaagaacat act                                           23

<210> SEQ ID NO 942
<211> LENGTH: 20
<212> TYPE: DNA
<213> ORGANISM: Homo sapiens

<400> SEQUENCE: 942
gtgtgtatac atttatacat                                              20

<210> SEQ ID NO 943
<211> LENGTH: 21
<212> TYPE: DNA
<213> ORGANISM: Homo sapiens

<400> SEQUENCE: 943
actttccagg attcattaac t                                            21

<210> SEQ ID NO 944
<211> LENGTH: 22
<212> TYPE: DNA
<213> ORGANISM: Homo sapiens

<400> SEQUENCE: 944
tgcaaaggta attgctgttt tc                                           22

<210> SEQ ID NO 945
<211> LENGTH: 21
<212> TYPE: DNA
<213> ORGANISM: Homo sapiens

<400> SEQUENCE: 945
ctcactcaga tggccaactc a                                            21

<210> SEQ ID NO 946
<211> LENGTH: 20
<212> TYPE: DNA
<213> ORGANISM: Homo sapiens

<400> SEQUENCE: 946
tgggccaccg ccgagcggac                                              20

<210> SEQ ID NO 947
<211> LENGTH: 24
<212> TYPE: DNA
<213> ORGANISM: Homo sapiens

<400> SEQUENCE: 947
ctgatcagtt acacatcact tcag                                         24

<210> SEQ ID NO 948
<211> LENGTH: 21
<212> TYPE: DNA
<213> ORGANISM: Homo sapiens

<400> SEQUENCE: 948
gtgggtgtgt gcatgagcgt g                                            21

<210> SEQ ID NO 949
<211> LENGTH: 19
<212> TYPE: DNA
<213> ORGANISM: Homo sapiens

<400> SEQUENCE: 949
gctcctgtcc aactggctc                                               19

<210> SEQ ID NO 950
<211> LENGTH: 23
<212> TYPE: DNA
<213> ORGANISM: Homo sapiens

<400> SEQUENCE: 950

```
caaagacgtg gagaaattag aat                                      23

<210> SEQ ID NO 951
<211> LENGTH: 21
<212> TYPE: DNA
<213> ORGANISM: Homo sapiens

<400> SEQUENCE: 951
caggtaccaa tattttatct a                                        21

<210> SEQ ID NO 952
<211> LENGTH: 21
<212> TYPE: DNA
<213> ORGANISM: Homo sapiens

<400> SEQUENCE: 952
acaatcctag agcacaagaa g                                        21

<210> SEQ ID NO 953
<211> LENGTH: 23
<212> TYPE: DNA
<213> ORGANISM: Homo sapiens

<400> SEQUENCE: 953
atcgcggttt ataccaaatg aat                                      23

<210> SEQ ID NO 954
<211> LENGTH: 22
<212> TYPE: DNA
<213> ORGANISM: Homo sapiens

<400> SEQUENCE: 954
cctaatgatt catcattctc aa                                       22

<210> SEQ ID NO 955
<211> LENGTH: 21
<212> TYPE: DNA
<213> ORGANISM: Homo sapiens

<400> SEQUENCE: 955
actgatctag agaacacaag a                                        21

<210> SEQ ID NO 956
<211> LENGTH: 23
<212> TYPE: DNA
<213> ORGANISM: Homo sapiens

<400> SEQUENCE: 956
agtaactggt tgaacaactg taa                                      23

<210> SEQ ID NO 957
<211> LENGTH: 21
<212> TYPE: DNA
<213> ORGANISM: Homo sapiens

<400> SEQUENCE: 957
gtaatgggac cttcctctttt g                                       21

<210> SEQ ID NO 958
<211> LENGTH: 22
<212> TYPE: DNA
<213> ORGANISM: Homo sapiens

<400> SEQUENCE: 958
```

```
ctcagtccca ggcaaaccat aa                                              22

<210> SEQ ID NO 959
<211> LENGTH: 19
<212> TYPE: DNA
<213> ORGANISM: Homo sapiens

<400> SEQUENCE: 959
tagcatacag atacgccca                                                  19

<210> SEQ ID NO 960
<211> LENGTH: 22
<212> TYPE: DNA
<213> ORGANISM: Homo sapiens

<400> SEQUENCE: 960
ggacctaaaa atacaatgca ta                                              22

<210> SEQ ID NO 961
<211> LENGTH: 21
<212> TYPE: DNA
<213> ORGANISM: Homo sapiens

<400> SEQUENCE: 961
gtgactcatc acctatggaa a                                               21

<210> SEQ ID NO 962
<211> LENGTH: 21
<212> TYPE: DNA
<213> ORGANISM: Homo sapiens

<400> SEQUENCE: 962
gttctaaccc attgtggcca a                                               21

<210> SEQ ID NO 963
<211> LENGTH: 24
<212> TYPE: DNA
<213> ORGANISM: Homo sapiens

<400> SEQUENCE: 963
tctgggaacc ggcatttgtt ctga                                            24

<210> SEQ ID NO 964
<211> LENGTH: 22
<212> TYPE: DNA
<213> ORGANISM: Homo sapiens

<400> SEQUENCE: 964
ctgcactttt atgaataagc tc                                              22

<210> SEQ ID NO 965
<211> LENGTH: 20
<212> TYPE: DNA
<213> ORGANISM: Homo sapiens

<400> SEQUENCE: 965
acaatgagaa cccatggtct                                                 20

<210> SEQ ID NO 966
<211> LENGTH: 22
<212> TYPE: DNA
<213> ORGANISM: Homo sapiens

<400> SEQUENCE: 966
```

```
acatcatcgc atattgacac aa                                              22

<210> SEQ ID NO 967
<211> LENGTH: 25
<212> TYPE: DNA
<213> ORGANISM: Homo sapiens

<400> SEQUENCE: 967
gctgagcaat gcctggctgg tgcct                                           25

<210> SEQ ID NO 968
<211> LENGTH: 25
<212> TYPE: DNA
<213> ORGANISM: Homo sapiens

<400> SEQUENCE: 968
aaagtcacag gccaccccag atggg                                           25

<210> SEQ ID NO 969
<211> LENGTH: 21
<212> TYPE: DNA
<213> ORGANISM: Homo sapiens

<400> SEQUENCE: 969
agacacacca cggcacactt c                                               21

<210> SEQ ID NO 970
<211> LENGTH: 21
<212> TYPE: DNA
<213> ORGANISM: Homo sapiens

<400> SEQUENCE: 970
cccgaggagc cgggcaggct t                                               21

<210> SEQ ID NO 971
<211> LENGTH: 22
<212> TYPE: DNA
<213> ORGANISM: Homo sapiens

<400> SEQUENCE: 971
acagtggtca tcgagtgaca ca                                              22

<210> SEQ ID NO 972
<211> LENGTH: 22
<212> TYPE: DNA
<213> ORGANISM: Homo sapiens

<400> SEQUENCE: 972
tgacgatgac aacgatgacg ta                                              22

<210> SEQ ID NO 973
<211> LENGTH: 20
<212> TYPE: DNA
<213> ORGANISM: Homo sapiens

<400> SEQUENCE: 973
gtttgataaa ctgacacaac                                                 20

<210> SEQ ID NO 974
<211> LENGTH: 23
<212> TYPE: DNA
<213> ORGANISM: Homo sapiens

<400> SEQUENCE: 974
```

```
gagcaaggct cttgtctgta agt                                          23
```

<210> SEQ ID NO 975
<211> LENGTH: 22
<212> TYPE: DNA
<213> ORGANISM: Homo sapiens

<400> SEQUENCE: 975

```
ctcctccaac aatcctagac ca                                           22
```

<210> SEQ ID NO 976
<211> LENGTH: 23
<212> TYPE: DNA
<213> ORGANISM: Homo sapiens

<400> SEQUENCE: 976

```
gggccgcagc tgtcgcccgt gtc                                          23
```

<210> SEQ ID NO 977
<211> LENGTH: 22
<212> TYPE: DNA
<213> ORGANISM: Homo sapiens

<400> SEQUENCE: 977

```
gcaaaagtaa ttgcagtgtg tg                                           22
```

<210> SEQ ID NO 978
<211> LENGTH: 19
<212> TYPE: DNA
<213> ORGANISM: Homo sapiens

<400> SEQUENCE: 978

```
gtcctgaatt ccgcagcct                                               19
```

<210> SEQ ID NO 979
<211> LENGTH: 23
<212> TYPE: DNA
<213> ORGANISM: Homo sapiens

<400> SEQUENCE: 979

```
aggagaaggc accatgggat tta                                          23
```

<210> SEQ ID NO 980
<211> LENGTH: 21
<212> TYPE: DNA
<213> ORGANISM: Homo sapiens

<400> SEQUENCE: 980

```
atctttgatt ttcagtagtt t                                            21
```

<210> SEQ ID NO 981
<211> LENGTH: 21
<212> TYPE: DNA
<213> ORGANISM: Homo sapiens

<400> SEQUENCE: 981

```
gttatagatc tggatttgaa c                                            21
```

<210> SEQ ID NO 982
<211> LENGTH: 25
<212> TYPE: DNA
<213> ORGANISM: Homo sapiens

<400> SEQUENCE: 982
acggagctgt cccaacacca ccect                                     25

<210> SEQ ID NO 983
<211> LENGTH: 20
<212> TYPE: DNA
<213> ORGANISM: Homo sapiens

<400> SEQUENCE: 983
agagatgaga gaaacaccct                                           20

<210> SEQ ID NO 984
<211> LENGTH: 21
<212> TYPE: DNA
<213> ORGANISM: Homo sapiens

<400> SEQUENCE: 984
tcccagcaca catttagctc a                                         21

<210> SEQ ID NO 985
<211> LENGTH: 23
<212> TYPE: DNA
<213> ORGANISM: Homo sapiens

<400> SEQUENCE: 985
gtcagacccc gagggggtcct cgc                                      23

<210> SEQ ID NO 986
<211> LENGTH: 25
<212> TYPE: DNA
<213> ORGANISM: Homo sapiens

<400> SEQUENCE: 986
aaggagctca gaagccctgc ccagc                                     25

<210> SEQ ID NO 987
<211> LENGTH: 20
<212> TYPE: DNA
<213> ORGANISM: Homo sapiens

<400> SEQUENCE: 987
ggcaaagaag gaacattcct                                           20

<210> SEQ ID NO 988
<211> LENGTH: 23
<212> TYPE: DNA
<213> ORGANISM: Homo sapiens

<400> SEQUENCE: 988
ccacctggca agaacaggcg ttc                                       23

<210> SEQ ID NO 989
<211> LENGTH: 21
<212> TYPE: DNA
<213> ORGANISM: Homo sapiens

<400> SEQUENCE: 989
agagggagac ccaggctcgg a                                         21

<210> SEQ ID NO 990
<211> LENGTH: 22
<212> TYPE: DNA
<213> ORGANISM: Homo sapiens

<400> SEQUENCE: 990
aagtcactga agggttttga gt                                              22

<210> SEQ ID NO 991
<211> LENGTH: 22
<212> TYPE: DNA
<213> ORGANISM: Homo sapiens

<400> SEQUENCE: 991
gccaccttca aatgggaagt ct                                              22

<210> SEQ ID NO 992
<211> LENGTH: 23
<212> TYPE: DNA
<213> ORGANISM: Homo sapiens

<400> SEQUENCE: 992
actcagaagg acaagtagag ttt                                             23

<210> SEQ ID NO 993
<211> LENGTH: 24
<212> TYPE: DNA
<213> ORGANISM: Homo sapiens

<400> SEQUENCE: 993
actgggcaca aacatgtcca ggtc                                            24

<210> SEQ ID NO 994
<211> LENGTH: 20
<212> TYPE: DNA
<213> ORGANISM: Homo sapiens

<400> SEQUENCE: 994
atttctatat ctatctccat                                                 20

<210> SEQ ID NO 995
<211> LENGTH: 21
<212> TYPE: DNA
<213> ORGANISM: Homo sapiens

<400> SEQUENCE: 995
aggtaagcgc tgttgctagc c                                               21

<210> SEQ ID NO 996
<211> LENGTH: 21
<212> TYPE: DNA
<213> ORGANISM: Homo sapiens

<400> SEQUENCE: 996
gctccaacct cagcagactg t                                               21

<210> SEQ ID NO 997
<211> LENGTH: 23
<212> TYPE: DNA
<213> ORGANISM: Homo sapiens

<400> SEQUENCE: 997
acccaacagc ccctgcaagg gat                                             23

<210> SEQ ID NO 998
<211> LENGTH: 22
<212> TYPE: DNA
<213> ORGANISM: Homo sapiens

<400> SEQUENCE: 998
tgaacacaag gtactggtac ta                                              22

<210> SEQ ID NO 999
<211> LENGTH: 22
<212> TYPE: DNA
<213> ORGANISM: Homo sapiens

<400> SEQUENCE: 999
aggactatag aactttcccc ct                                              22

<210> SEQ ID NO 1000
<211> LENGTH: 19
<212> TYPE: DNA
<213> ORGANISM: Homo sapiens

<400> SEQUENCE: 1000
aagacatttt cagacagct                                                  19

<210> SEQ ID NO 1001
<211> LENGTH: 22
<212> TYPE: DNA
<213> ORGANISM: Homo sapiens

<400> SEQUENCE: 1001
tcctcttttc ttagagactc ac                                              22

<210> SEQ ID NO 1002
<211> LENGTH: 20
<212> TYPE: DNA
<213> ORGANISM: Homo sapiens

<400> SEQUENCE: 1002
cgactgccac tcttactaga                                                 20

<210> SEQ ID NO 1003
<211> LENGTH: 22
<212> TYPE: DNA
<213> ORGANISM: Homo sapiens

<400> SEQUENCE: 1003
gctgggctta cgttgggaga ac                                              22

<210> SEQ ID NO 1004
<211> LENGTH: 22
<212> TYPE: DNA
<213> ORGANISM: Homo sapiens

<400> SEQUENCE: 1004
accttccctg gtacagaata ct                                              22

<210> SEQ ID NO 1005
<211> LENGTH: 21
<212> TYPE: DNA
<213> ORGANISM: Homo sapiens

<400> SEQUENCE: 1005
gctgaggtct gggccaggtc t                                               21

<210> SEQ ID NO 1006
<211> LENGTH: 19
<212> TYPE: DNA
<213> ORGANISM: Homo sapiens

<400> SEQUENCE: 1006

```
tcccacagga agcagacac                                          19

<210> SEQ ID NO 1007
<211> LENGTH: 23
<212> TYPE: DNA
<213> ORGANISM: Homo sapiens

<400> SEQUENCE: 1007
tttattgtgg tagatactat tag                                     23

<210> SEQ ID NO 1008
<211> LENGTH: 22
<212> TYPE: DNA
<213> ORGANISM: Homo sapiens

<400> SEQUENCE: 1008
gtccaaagtt ggggtgctgg tt                                      22

<210> SEQ ID NO 1009
<211> LENGTH: 23
<212> TYPE: DNA
<213> ORGANISM: Homo sapiens

<400> SEQUENCE: 1009
ggacattgtt tcagtgccca agt                                     23

<210> SEQ ID NO 1010
<211> LENGTH: 24
<212> TYPE: DNA
<213> ORGANISM: Homo sapiens

<400> SEQUENCE: 1010
ctgcgggcgg gacgagcaag caca                                    24

<210> SEQ ID NO 1011
<211> LENGTH: 24
<212> TYPE: DNA
<213> ORGANISM: Homo sapiens

<400> SEQUENCE: 1011
acgcagagcc cgaaagcccc cagt                                    24

<210> SEQ ID NO 1012
<211> LENGTH: 25
<212> TYPE: DNA
<213> ORGANISM: Homo sapiens

<400> SEQUENCE: 1012
aggccgccac ccgcccgcga tccct                                   25

<210> SEQ ID NO 1013
<211> LENGTH: 23
<212> TYPE: DNA
<213> ORGANISM: Homo sapiens

<400> SEQUENCE: 1013
acagcgctcg caaccgcagc gat                                     23

<210> SEQ ID NO 1014
<211> LENGTH: 21
<212> TYPE: DNA
<213> ORGANISM: Homo sapiens

<400> SEQUENCE: 1014
```
agaggcaggt tcctggatca t                                         21

<210> SEQ ID NO 1015
<211> LENGTH: 24
<212> TYPE: DNA
<213> ORGANISM: Homo sapiens

<400> SEQUENCE: 1015
gaggtgactc tatcctatgt cttt                                      24

<210> SEQ ID NO 1016
<211> LENGTH: 22
<212> TYPE: DNA
<213> ORGANISM: Homo sapiens

<400> SEQUENCE: 1016
caagacacat ttggagaggg ac                                        22

<210> SEQ ID NO 1017
<211> LENGTH: 22
<212> TYPE: DNA
<213> ORGANISM: Homo sapiens

<400> SEQUENCE: 1017
ctacctgagc tagcatacaa gt                                        22

<210> SEQ ID NO 1018
<211> LENGTH: 19
<212> TYPE: DNA
<213> ORGANISM: Homo sapiens

<400> SEQUENCE: 1018
gctctaagaa agccacact                                            19

<210> SEQ ID NO 1019
<211> LENGTH: 19
<212> TYPE: DNA
<213> ORGANISM: Homo sapiens

<400> SEQUENCE: 1019
tcagcagtac cagcctaga                                            19

<210> SEQ ID NO 1020
<211> LENGTH: 19
<212> TYPE: DNA
<213> ORGANISM: Homo sapiens

<400> SEQUENCE: 1020
gcctcagagg cagctgctt                                            19

<210> SEQ ID NO 1021
<211> LENGTH: 21
<212> TYPE: DNA
<213> ORGANISM: Homo sapiens

<400> SEQUENCE: 1021
gaaggaagtg agtgcagcca c                                         21

<210> SEQ ID NO 1022
<211> LENGTH: 19
<212> TYPE: DNA
<213> ORGANISM: Homo sapiens

<400> SEQUENCE: 1022
accagtgccc tgcacactt                                              19

<210> SEQ ID NO 1023
<211> LENGTH: 22
<212> TYPE: DNA
<213> ORGANISM: Homo sapiens

<400> SEQUENCE: 1023
gactcttgaa caacacaggt tt                                          22

<210> SEQ ID NO 1024
<211> LENGTH: 21
<212> TYPE: DNA
<213> ORGANISM: Homo sapiens

<400> SEQUENCE: 1024
gtcctgagag cgctgcctcc t                                           21

<210> SEQ ID NO 1025
<211> LENGTH: 22
<212> TYPE: DNA
<213> ORGANISM: Homo sapiens

<400> SEQUENCE: 1025
caaaagtcaa gcttatccta aa                                          22

<210> SEQ ID NO 1026
<211> LENGTH: 23
<212> TYPE: DNA
<213> ORGANISM: Homo sapiens

<400> SEQUENCE: 1026
tgcacaaccc tagtggcgcc att                                         23

<210> SEQ ID NO 1027
<211> LENGTH: 21
<212> TYPE: DNA
<213> ORGANISM: Homo sapiens

<400> SEQUENCE: 1027
gttcagtaga gattgtttca a                                           21

<210> SEQ ID NO 1028
<211> LENGTH: 22
<212> TYPE: DNA
<213> ORGANISM: Homo sapiens

<400> SEQUENCE: 1028
gcacatgttc tgcggcccac ca                                          22

<210> SEQ ID NO 1029
<211> LENGTH: 22
<212> TYPE: DNA
<213> ORGANISM: Homo sapiens

<400> SEQUENCE: 1029
aaagaggtta accatgtatt at                                          22

<210> SEQ ID NO 1030
<211> LENGTH: 21
<212> TYPE: DNA
<213> ORGANISM: Homo sapiens

<400> SEQUENCE: 1030
agaggttgac tgtataatat t					21

<210> SEQ ID NO 1031
<211> LENGTH: 23
<212> TYPE: DNA
<213> ORGANISM: Homo sapiens

<400> SEQUENCE: 1031
cctagagagg gtgagaacct gcc				23

<210> SEQ ID NO 1032
<211> LENGTH: 25
<212> TYPE: DNA
<213> ORGANISM: Homo sapiens

<400> SEQUENCE: 1032
accaacggac ctacttccct ccgcc				25

<210> SEQ ID NO 1033
<211> LENGTH: 22
<212> TYPE: DNA
<213> ORGANISM: Homo sapiens

<400> SEQUENCE: 1033
tggggaccct ccctgaacca ag				22

<210> SEQ ID NO 1034
<211> LENGTH: 22
<212> TYPE: DNA
<213> ORGANISM: Homo sapiens

<400> SEQUENCE: 1034
caactccgat atgcaatggg ta				22

<210> SEQ ID NO 1035
<211> LENGTH: 22
<212> TYPE: DNA
<213> ORGANISM: Homo sapiens

<400> SEQUENCE: 1035
aactatacaa cctactacct ca				22

<210> SEQ ID NO 1036
<211> LENGTH: 22
<212> TYPE: DNA
<213> ORGANISM: Homo sapiens

<400> SEQUENCE: 1036
aaccacacaa cctactacct ca				22

<210> SEQ ID NO 1037
<211> LENGTH: 22
<212> TYPE: DNA
<213> ORGANISM: Homo sapiens

<400> SEQUENCE: 1037
aaccatacaa cctactacct ca				22

<210> SEQ ID NO 1038
<211> LENGTH: 21
<212> TYPE: DNA
<213> ORGANISM: Homo sapiens

<400> SEQUENCE: 1038
actatgcaac ctactacctc t                                      21

<210> SEQ ID NO 1039
<211> LENGTH: 21
<212> TYPE: DNA
<213> ORGANISM: Homo sapiens

<400> SEQUENCE: 1039
actatacaac ctcctacctc a                                      21

<210> SEQ ID NO 1040
<211> LENGTH: 22
<212> TYPE: DNA
<213> ORGANISM: Homo sapiens

<400> SEQUENCE: 1040
aactatacaa tctactacct ca                                     22

<210> SEQ ID NO 1041
<211> LENGTH: 21
<212> TYPE: DNA
<213> ORGANISM: Homo sapiens

<400> SEQUENCE: 1041
actgtacaaa ctactacctc a                                      21

<210> SEQ ID NO 1042
<211> LENGTH: 21
<212> TYPE: DNA
<213> ORGANISM: Homo sapiens

<400> SEQUENCE: 1042
acagcacaaa ctactacctc a                                      21

<210> SEQ ID NO 1043
<211> LENGTH: 21
<212> TYPE: DNA
<213> ORGANISM: Homo sapiens

<400> SEQUENCE: 1043
tacatacttc tttacattcc a                                      21

<210> SEQ ID NO 1044
<211> LENGTH: 22
<212> TYPE: DNA
<213> ORGANISM: Homo sapiens

<400> SEQUENCE: 1044
cacaagttcg gatctacggg tt                                     22

<210> SEQ ID NO 1045
<211> LENGTH: 22
<212> TYPE: DNA
<213> ORGANISM: Homo sapiens

<400> SEQUENCE: 1045
cttcagttat cacagtactg ta                                     22

<210> SEQ ID NO 1046
<211> LENGTH: 23
<212> TYPE: DNA
<213> ORGANISM: Homo sapiens

<400> SEQUENCE: 1046

```
tcatagccct gtacaatgct gct                                    23

<210> SEQ ID NO 1047
<211> LENGTH: 20
<212> TYPE: DNA
<213> ORGANISM: Homo sapiens

<400> SEQUENCE: 1047
acaggagtct gagcatttga                                        20

<210> SEQ ID NO 1048
<211> LENGTH: 24
<212> TYPE: DNA
<213> ORGANISM: Homo sapiens

<400> SEQUENCE: 1048
gctacctgca ctgtaagcac tttt                                   24

<210> SEQ ID NO 1049
<211> LENGTH: 21
<212> TYPE: DNA
<213> ORGANISM: Homo sapiens

<400> SEQUENCE: 1049
atctgcactg tcagcacttt a                                      21

<210> SEQ ID NO 1050
<211> LENGTH: 23
<212> TYPE: DNA
<213> ORGANISM: Homo sapiens

<400> SEQUENCE: 1050
tgatagccct gtacaatgct gct                                    23

<210> SEQ ID NO 1051
<211> LENGTH: 23
<212> TYPE: DNA
<213> ORGANISM: Homo sapiens

<400> SEQUENCE: 1051
cacaaattcg gatctacagg gta                                    23

<210> SEQ ID NO 1052
<211> LENGTH: 22
<212> TYPE: DNA
<213> ORGANISM: Homo sapiens

<400> SEQUENCE: 1052
acaaattcgg ttctacaggg ta                                     22

<210> SEQ ID NO 1053
<211> LENGTH: 23
<212> TYPE: DNA
<213> ORGANISM: Homo sapiens

<400> SEQUENCE: 1053
acaaacacca ttgtcacact cca                                    23

<210> SEQ ID NO 1054
<211> LENGTH: 22
<212> TYPE: DNA
<213> ORGANISM: Homo sapiens

<400> SEQUENCE: 1054
```

```
tggcattcac cgcgtgcctt aa                                               22

<210> SEQ ID NO 1055
<211> LENGTH: 23
<212> TYPE: DNA
<213> ORGANISM: Homo sapiens

<400> SEQUENCE: 1055
cacaggttaa agggtctcag gga                                              23

<210> SEQ ID NO 1056
<211> LENGTH: 22
<212> TYPE: DNA
<213> ORGANISM: Homo sapiens

<400> SEQUENCE: 1056
tcacaagtta gggtctcagg ga                                               22

<210> SEQ ID NO 1057
<211> LENGTH: 21
<212> TYPE: DNA
<213> ORGANISM: Homo sapiens

<400> SEQUENCE: 1057
gcattattac tcacggtacg a                                                21

<210> SEQ ID NO 1058
<211> LENGTH: 21
<212> TYPE: DNA
<213> ORGANISM: Homo sapiens

<400> SEQUENCE: 1058
cgcgtaccaa aagtaataat g                                                21

<210> SEQ ID NO 1059
<211> LENGTH: 22
<212> TYPE: DNA
<213> ORGANISM: Homo sapiens

<400> SEQUENCE: 1059
agccaagctc agacggatcc ga                                               22

<210> SEQ ID NO 1060
<211> LENGTH: 22
<212> TYPE: DNA
<213> ORGANISM: Homo sapiens

<400> SEQUENCE: 1060
aaaagagacc ggttcactgt ga                                               22

<210> SEQ ID NO 1061
<211> LENGTH: 22
<212> TYPE: DNA
<213> ORGANISM: Homo sapiens

<400> SEQUENCE: 1061
gaaagagacc ggttcactgt ga                                               22

<210> SEQ ID NO 1062
<211> LENGTH: 21
<212> TYPE: DNA
<213> ORGANISM: Homo sapiens

<400> SEQUENCE: 1062
```
gcaagcccag accgcaaaaa g                                          21

<210> SEQ ID NO 1063
<211> LENGTH: 22
<212> TYPE: DNA
<213> ORGANISM: Homo sapiens

<400> SEQUENCE: 1063
atgccctttt aacattgcac tg                                         22

<210> SEQ ID NO 1064
<211> LENGTH: 22
<212> TYPE: DNA
<213> ORGANISM: Homo sapiens

<400> SEQUENCE: 1064
atgccctttc atcattgcac tg                                         22

<210> SEQ ID NO 1065
<211> LENGTH: 22
<212> TYPE: DNA
<213> ORGANISM: Homo sapiens

<400> SEQUENCE: 1065
cgaccatggc tgtagactgt ta                                         22

<210> SEQ ID NO 1066
<211> LENGTH: 22
<212> TYPE: DNA
<213> ORGANISM: Homo sapiens

<400> SEQUENCE: 1066
acagctggtt gaaggggacc aa                                         22

<210> SEQ ID NO 1067
<211> LENGTH: 21
<212> TYPE: DNA
<213> ORGANISM: Homo sapiens

<400> SEQUENCE: 1067
tagctggttg aaggggacca a                                          21

<210> SEQ ID NO 1068
<211> LENGTH: 21
<212> TYPE: DNA
<213> ORGANISM: Homo sapiens

<400> SEQUENCE: 1068
ccctctggtc aaccagtcac a                                          21

<210> SEQ ID NO 1069
<211> LENGTH: 23
<212> TYPE: DNA
<213> ORGANISM: Homo sapiens

<400> SEQUENCE: 1069
tcacatagga ataaaaagcc ata                                        23

<210> SEQ ID NO 1070
<211> LENGTH: 22
<212> TYPE: DNA
<213> ORGANISM: Homo sapiens

<400> SEQUENCE: 1070

```
cacataggaa tgaaaagcca ta                                                22

<210> SEQ ID NO 1071
<211> LENGTH: 23
<212> TYPE: DNA
<213> ORGANISM: Homo sapiens

<400> SEQUENCE: 1071
tccatcatca aaacaaatgg agt                                               23

<210> SEQ ID NO 1072
<211> LENGTH: 22
<212> TYPE: DNA
<213> ORGANISM: Homo sapiens

<400> SEQUENCE: 1072
ctacgcgtat tcttaagcaa ta                                                22

<210> SEQ ID NO 1073
<211> LENGTH: 17
<212> TYPE: DNA
<213> ORGANISM: Homo sapiens

<400> SEQUENCE: 1073
gattcacaac accagct                                                      17

<210> SEQ ID NO 1074
<211> LENGTH: 18
<212> TYPE: DNA
<213> ORGANISM: Homo sapiens

<400> SEQUENCE: 1074
agacacgtgc actgtaga                                                     18

<210> SEQ ID NO 1075
<211> LENGTH: 21
<212> TYPE: DNA
<213> ORGANISM: Homo sapiens

<400> SEQUENCE: 1075
ctaccatagg gtaaaaccac t                                                 21

<210> SEQ ID NO 1076
<211> LENGTH: 22
<212> TYPE: DNA
<213> ORGANISM: Homo sapiens

<400> SEQUENCE: 1076
ccatctttac cagacagtgt ta                                                22

<210> SEQ ID NO 1077
<211> LENGTH: 23
<212> TYPE: DNA
<213> ORGANISM: Homo sapiens

<400> SEQUENCE: 1077
tccataaagt aggaaacact aca                                               23

<210> SEQ ID NO 1078
<211> LENGTH: 20
<212> TYPE: DNA
<213> ORGANISM: Homo sapiens

<400> SEQUENCE: 1078
``` gtagtgctttt ctactttatg                              20

<210> SEQ ID NO 1079
<211> LENGTH: 22
<212> TYPE: DNA
<213> ORGANISM: Homo sapiens

<400> SEQUENCE: 1079
tgagctacag tgcttcatct ca                            22

<210> SEQ ID NO 1080
<211> LENGTH: 22
<212> TYPE: DNA
<213> ORGANISM: Homo sapiens

<400> SEQUENCE: 1080
ctagtacatc atctatactg ta                            22

<210> SEQ ID NO 1081
<211> LENGTH: 24
<212> TYPE: DNA
<213> ORGANISM: Homo sapiens

<400> SEQUENCE: 1081
aagggattcc tgggaaaact ggac                          24

<210> SEQ ID NO 1082
<211> LENGTH: 22
<212> TYPE: DNA
<213> ORGANISM: Homo sapiens

<400> SEQUENCE: 1082
aacccatgga attcagttct ca                            22

<210> SEQ ID NO 1083
<211> LENGTH: 22
<212> TYPE: DNA
<213> ORGANISM: Homo sapiens

<400> SEQUENCE: 1083
agcctatgga attcagttct ca                            22

<210> SEQ ID NO 1084
<211> LENGTH: 20
<212> TYPE: DNA
<213> ORGANISM: Homo sapiens

<400> SEQUENCE: 1084
gcagaagcat ttccacacac                               20

<210> SEQ ID NO 1085
<211> LENGTH: 22
<212> TYPE: DNA
<213> ORGANISM: Homo sapiens

<400> SEQUENCE: 1085
acaaagttct gtagtgcact ga                            22

<210> SEQ ID NO 1086
<211> LENGTH: 22
<212> TYPE: DNA
<213> ORGANISM: Homo sapiens

<400> SEQUENCE: 1086
acaaagttct gtgatgcact ga    22

<210> SEQ ID NO 1087
<211> LENGTH: 22
<212> TYPE: DNA
<213> ORGANISM: Homo sapiens

<400> SEQUENCE: 1087
ggagtgaaga cacggagcca ga    22

<210> SEQ ID NO 1088
<211> LENGTH: 22
<212> TYPE: DNA
<213> ORGANISM: Homo sapiens

<400> SEQUENCE: 1088
cactggtaca agggttggga ga    22

<210> SEQ ID NO 1089
<211> LENGTH: 22
<212> TYPE: DNA
<213> ORGANISM: Homo sapiens

<400> SEQUENCE: 1089
cctcaaggag cttcagtcta gt    22

<210> SEQ ID NO 1090
<211> LENGTH: 22
<212> TYPE: DNA
<213> ORGANISM: Homo sapiens

<400> SEQUENCE: 1090
cccaagttct gtcatgcact ga    22

<210> SEQ ID NO 1091
<211> LENGTH: 20
<212> TYPE: DNA
<213> ORGANISM: Homo sapiens

<400> SEQUENCE: 1091
tcacttttgt gactatgcaa    20

<210> SEQ ID NO 1092
<211> LENGTH: 22
<212> TYPE: DNA
<213> ORGANISM: Homo sapiens

<400> SEQUENCE: 1092
cgaaggcaac acggataacc ta    22

<210> SEQ ID NO 1093
<211> LENGTH: 22
<212> TYPE: DNA
<213> ORGANISM: Homo sapiens

<400> SEQUENCE: 1093
aataggtcaa ccgtgtatga tt    22

<210> SEQ ID NO 1094
<211> LENGTH: 22
<212> TYPE: DNA
<213> ORGANISM: Homo sapiens

<400> SEQUENCE: 1094

| | |
|---|---|
| cccctatcac gattagcatt aa | 22 |

<210> SEQ ID NO 1095
<211> LENGTH: 22
<212> TYPE: DNA
<213> ORGANISM: Homo sapiens

<400> SEQUENCE: 1095

| | |
|---|---|
| cacaaaccat tatgtgctgc ta | 22 |

<210> SEQ ID NO 1096
<211> LENGTH: 22
<212> TYPE: DNA
<213> ORGANISM: Homo sapiens

<400> SEQUENCE: 1096

| | |
|---|---|
| tgtaaaccat gatgtgctgc ta | 22 |

<210> SEQ ID NO 1097
<211> LENGTH: 22
<212> TYPE: DNA
<213> ORGANISM: Homo sapiens

<400> SEQUENCE: 1097

| | |
|---|---|
| cgccaatatt tacgtgctgc ta | 22 |

<210> SEQ ID NO 1098
<211> LENGTH: 20
<212> TYPE: DNA
<213> ORGANISM: Homo sapiens

<400> SEQUENCE: 1098

| | |
|---|---|
| acaagtgcct tcactgcagt | 20 |

<210> SEQ ID NO 1099
<211> LENGTH: 24
<212> TYPE: DNA
<213> ORGANISM: Homo sapiens

<400> SEQUENCE: 1099

| | |
|---|---|
| actacctgca ctgtaagcac tttg | 24 |

<210> SEQ ID NO 1100
<211> LENGTH: 23
<212> TYPE: DNA
<213> ORGANISM: Homo sapiens

<400> SEQUENCE: 1100

| | |
|---|---|
| actcaccgac agcgttgaat gtt | 23 |

<210> SEQ ID NO 1101
<211> LENGTH: 22
<212> TYPE: DNA
<213> ORGANISM: Homo sapiens

<400> SEQUENCE: 1101

| | |
|---|---|
| cccaccgaca gcaatgaatg tt | 22 |

<210> SEQ ID NO 1102
<211> LENGTH: 22
<212> TYPE: DNA
<213> ORGANISM: Homo sapiens

<400> SEQUENCE: 1102
actcaccgac aggttgaatg tt                                          22

<210> SEQ ID NO 1103
<211> LENGTH: 24
<212> TYPE: DNA
<213> ORGANISM: Homo sapiens

<400> SEQUENCE: 1103
aacccaccga caacaatgaa tgtt                                        24

<210> SEQ ID NO 1104
<211> LENGTH: 22
<212> TYPE: DNA
<213> ORGANISM: Homo sapiens

<400> SEQUENCE: 1104
tgtgagttct accattgcca aa                                          22

<210> SEQ ID NO 1105
<211> LENGTH: 21
<212> TYPE: DNA
<213> ORGANISM: Homo sapiens

<400> SEQUENCE: 1105
tagttggcaa gtctagaacc a                                           21

<210> SEQ ID NO 1106
<211> LENGTH: 23
<212> TYPE: DNA
<213> ORGANISM: Homo sapiens

<400> SEQUENCE: 1106
cagtgaattc taccagtgcc ata                                         23

<210> SEQ ID NO 1107
<211> LENGTH: 22
<212> TYPE: DNA
<213> ORGANISM: Homo sapiens

<400> SEQUENCE: 1107
acccttatca gttctccgtc ca                                          22

<210> SEQ ID NO 1108
<211> LENGTH: 18
<212> TYPE: DNA
<213> ORGANISM: Homo sapiens

<400> SEQUENCE: 1108
gaactgcctt tctctcca                                               18

<210> SEQ ID NO 1109
<211> LENGTH: 23
<212> TYPE: DNA
<213> ORGANISM: Homo sapiens

<400> SEQUENCE: 1109
aagcccaaaa ggagaattct ttg                                         23

<210> SEQ ID NO 1110
<211> LENGTH: 21
<212> TYPE: DNA
<213> ORGANISM: Homo sapiens

<400> SEQUENCE: 1110
cggctgcaac acaagacacg a       21

<210> SEQ ID NO 1111
<211> LENGTH: 22
<212> TYPE: DNA
<213> ORGANISM: Homo sapiens

<400> SEQUENCE: 1111
accctccacc atgcaaggga tg       22

<210> SEQ ID NO 1112
<211> LENGTH: 23
<212> TYPE: DNA
<213> ORGANISM: Homo sapiens

<400> SEQUENCE: 1112
actgatatca gctcagtagg cac       23

<210> SEQ ID NO 1113
<211> LENGTH: 22
<212> TYPE: DNA
<213> ORGANISM: Homo sapiens

<400> SEQUENCE: 1113
tatctgcact agatgcacct ta       22

<210> SEQ ID NO 1114
<211> LENGTH: 22
<212> TYPE: DNA
<213> ORGANISM: Homo sapiens

<400> SEQUENCE: 1114
taactgcact agatgcacct ta       22

<210> SEQ ID NO 1115
<211> LENGTH: 22
<212> TYPE: DNA
<213> ORGANISM: Homo sapiens

<400> SEQUENCE: 1115
acctaatata tcaaacatat ca       22

<210> SEQ ID NO 1116
<211> LENGTH: 22
<212> TYPE: DNA
<213> ORGANISM: Homo sapiens

<400> SEQUENCE: 1116
agctgctttt gggattccgt tg       22

<210> SEQ ID NO 1117
<211> LENGTH: 22
<212> TYPE: DNA
<213> ORGANISM: Homo sapiens

<400> SEQUENCE: 1117
ggggacgaaa tccaagcgca gc       22

<210> SEQ ID NO 1118
<211> LENGTH: 21
<212> TYPE: DNA
<213> ORGANISM: Homo sapiens

<400> SEQUENCE: 1118
ggctgtcaat tcataggtca g                                             21

<210> SEQ ID NO 1119
<211> LENGTH: 21
<212> TYPE: DNA
<213> ORGANISM: Homo sapiens

<400> SEQUENCE: 1119
ctgggacttt gtaggccagt t                                             21

<210> SEQ ID NO 1120
<211> LENGTH: 24
<212> TYPE: DNA
<213> ORGANISM: Homo sapiens

<400> SEQUENCE: 1120
aaagcgggac tttgagggcc agtt                                          24

<210> SEQ ID NO 1121
<211> LENGTH: 22
<212> TYPE: DNA
<213> ORGANISM: Homo sapiens

<400> SEQUENCE: 1121
tccacatgga gttgctgtta ca                                            22

<210> SEQ ID NO 1122
<211> LENGTH: 21
<212> TYPE: DNA
<213> ORGANISM: Homo sapiens

<400> SEQUENCE: 1122
gccaatattt ctgtgctgct a                                             21

<210> SEQ ID NO 1123
<211> LENGTH: 21
<212> TYPE: DNA
<213> ORGANISM: Homo sapiens

<400> SEQUENCE: 1123
ccaacaacat gaaactacct a                                             21

<210> SEQ ID NO 1124
<211> LENGTH: 21
<212> TYPE: DNA
<213> ORGANISM: Homo sapiens

<400> SEQUENCE: 1124
ccaacaacag gaaactacct a                                             21

<210> SEQ ID NO 1125
<211> LENGTH: 22
<212> TYPE: DNA
<213> ORGANISM: Homo sapiens

<400> SEQUENCE: 1125
gctgggtgga gaaggtggtg aa                                            22

<210> SEQ ID NO 1126
<211> LENGTH: 19
<212> TYPE: DNA
<213> ORGANISM: Homo sapiens

<400> SEQUENCE: 1126

```
cctatctccc ctctggacc                                                19

<210> SEQ ID NO 1127
<211> LENGTH: 23
<212> TYPE: DNA
<213> ORGANISM: Homo sapiens

<400> SEQUENCE: 1127
gaacaggtag tctgaacact ggg                                           23

<210> SEQ ID NO 1128
<211> LENGTH: 22
<212> TYPE: DNA
<213> ORGANISM: Homo sapiens

<400> SEQUENCE: 1128
aaccaatgtg cagactactg ta                                            22

<210> SEQ ID NO 1129
<211> LENGTH: 23
<212> TYPE: DNA
<213> ORGANISM: Homo sapiens

<400> SEQUENCE: 1129
gaacagatag tctaaacact ggg                                           23

<210> SEQ ID NO 1130
<211> LENGTH: 23
<212> TYPE: DNA
<213> ORGANISM: Homo sapiens

<400> SEQUENCE: 1130
tcagttttgc atagatttgc aca                                           23

<210> SEQ ID NO 1131
<211> LENGTH: 23
<212> TYPE: DNA
<213> ORGANISM: Homo sapiens

<400> SEQUENCE: 1131
tcagttttgc atggatttgc aca                                           23

<210> SEQ ID NO 1132
<211> LENGTH: 22
<212> TYPE: DNA
<213> ORGANISM: Homo sapiens

<400> SEQUENCE: 1132
acatcgttac cagacagtgt ta                                            22

<210> SEQ ID NO 1133
<211> LENGTH: 22
<212> TYPE: DNA
<213> ORGANISM: Homo sapiens

<400> SEQUENCE: 1133
tccagcactg tccggtaaga tg                                            22

<210> SEQ ID NO 1134
<211> LENGTH: 23
<212> TYPE: DNA
<213> ORGANISM: Homo sapiens

<400> SEQUENCE: 1134
```

-continued gtcatcatta ccaggcagta tta                                    23

<210> SEQ ID NO 1135
<211> LENGTH: 22
<212> TYPE: DNA
<213> ORGANISM: Homo sapiens

<400> SEQUENCE: 1135
ccatcattac ccggcagtat ta                                     22

<210> SEQ ID NO 1136
<211> LENGTH: 22
<212> TYPE: DNA
<213> ORGANISM: Homo sapiens

<400> SEQUENCE: 1136
ttttcccatg ccctatacct ct                                     22

<210> SEQ ID NO 1137
<211> LENGTH: 22
<212> TYPE: DNA
<213> ORGANISM: Homo sapiens

<400> SEQUENCE: 1137
aaagaagtat atgcatagga aa                                     22

<210> SEQ ID NO 1138
<211> LENGTH: 22
<212> TYPE: DNA
<213> ORGANISM: Homo sapiens

<400> SEQUENCE: 1138
ctagtggtcc taaacatttc ac                                     22

<210> SEQ ID NO 1139
<211> LENGTH: 22
<212> TYPE: DNA
<213> ORGANISM: Homo sapiens

<400> SEQUENCE: 1139
aggcatagga tgacaaaggg aa                                     22

<210> SEQ ID NO 1140
<211> LENGTH: 22
<212> TYPE: DNA
<213> ORGANISM: Homo sapiens

<400> SEQUENCE: 1140
cagactccgg tggaatgaag ga                                     22

<210> SEQ ID NO 1141
<211> LENGTH: 22
<212> TYPE: DNA
<213> ORGANISM: Homo sapiens

<400> SEQUENCE: 1141
ccacacactt ccttacattc ca                                     22

<210> SEQ ID NO 1142
<211> LENGTH: 22
<212> TYPE: DNA
<213> ORGANISM: Homo sapiens

<400> SEQUENCE: 1142

```
acaagctttt tgctcgtctt at                                      22

<210> SEQ ID NO 1143
<211> LENGTH: 23
<212> TYPE: DNA
<213> ORGANISM: Homo sapiens

<400> SEQUENCE: 1143
ctacctgcac tataagcact tta                                     23

<210> SEQ ID NO 1144
<211> LENGTH: 23
<212> TYPE: DNA
<213> ORGANISM: Homo sapiens

<400> SEQUENCE: 1144
ctacctgcac tatgagcact ttg                                     23

<210> SEQ ID NO 1145
<211> LENGTH: 22
<212> TYPE: DNA
<213> ORGANISM: Homo sapiens

<400> SEQUENCE: 1145
tcaacatcag tctgataagc ta                                      22

<210> SEQ ID NO 1146
<211> LENGTH: 22
<212> TYPE: DNA
<213> ORGANISM: Homo sapiens

<400> SEQUENCE: 1146
tcagccgctg tcacacgcac ag                                      22

<210> SEQ ID NO 1147
<211> LENGTH: 22
<212> TYPE: DNA
<213> ORGANISM: Homo sapiens

<400> SEQUENCE: 1147
aggcgaagga tgacaaaggg aa                                      22

<210> SEQ ID NO 1148
<211> LENGTH: 21
<212> TYPE: DNA
<213> ORGANISM: Homo sapiens

<400> SEQUENCE: 1148
ggccgtgact ggagactgtt a                                       21

<210> SEQ ID NO 1149
<211> LENGTH: 22
<212> TYPE: DNA
<213> ORGANISM: Homo sapiens

<400> SEQUENCE: 1149
ggtacaatca acggtcgatg gt                                      22

<210> SEQ ID NO 1150
<211> LENGTH: 21
<212> TYPE: DNA
<213> ORGANISM: Homo sapiens

<400> SEQUENCE: 1150
```
ctgcctgtct gtgcctgctg t                                       21

<210> SEQ ID NO 1151
<211> LENGTH: 21
<212> TYPE: DNA
<213> ORGANISM: Homo sapiens

<400> SEQUENCE: 1151
gtctgtcaat tcataggtca t                                       21

<210> SEQ ID NO 1152
<211> LENGTH: 21
<212> TYPE: DNA
<213> ORGANISM: Homo sapiens

<400> SEQUENCE: 1152
cacagttgcc agctgagatt a                                       21

<210> SEQ ID NO 1153
<211> LENGTH: 24
<212> TYPE: DNA
<213> ORGANISM: Homo sapiens

<400> SEQUENCE: 1153
atccaatcag ttcctgatgc agta                                    24

<210> SEQ ID NO 1154
<211> LENGTH: 21
<212> TYPE: DNA
<213> ORGANISM: Homo sapiens

<400> SEQUENCE: 1154
acatggttag atcaagcaca a                                       21

<210> SEQ ID NO 1155
<211> LENGTH: 21
<212> TYPE: DNA
<213> ORGANISM: Homo sapiens

<400> SEQUENCE: 1155
agaattgcgt ttggacaatc a                                       21

<210> SEQ ID NO 1156
<211> LENGTH: 22
<212> TYPE: DNA
<213> ORGANISM: Homo sapiens

<400> SEQUENCE: 1156
acagttcttc aactggcagc tt                                      22

<210> SEQ ID NO 1157
<211> LENGTH: 21
<212> TYPE: DNA
<213> ORGANISM: Homo sapiens

<400> SEQUENCE: 1157
aaagtgtcag atacggtgtg g                                       21

<210> SEQ ID NO 1158
<211> LENGTH: 23
<212> TYPE: DNA
<213> ORGANISM: Homo sapiens

<400> SEQUENCE: 1158

```
gaaacccagc agacaatgta gct                                         23

<210> SEQ ID NO 1159
<211> LENGTH: 24
<212> TYPE: DNA
<213> ORGANISM: Homo sapiens

<400> SEQUENCE: 1159
gagacccagt agccagatgt agct                                        24

<210> SEQ ID NO 1160
<211> LENGTH: 21
<212> TYPE: DNA
<213> ORGANISM: Homo sapiens

<400> SEQUENCE: 1160
ggggtatttg acaaactgac a                                           21

<210> SEQ ID NO 1161
<211> LENGTH: 23
<212> TYPE: DNA
<213> ORGANISM: Homo sapiens

<400> SEQUENCE: 1161
taaacggaac cactagtgac ttg                                         23

<210> SEQ ID NO 1162
<211> LENGTH: 21
<212> TYPE: DNA
<213> ORGANISM: Homo sapiens

<400> SEQUENCE: 1162
ggaaatccct ggcaatgtga t                                           21

<210> SEQ ID NO 1163
<211> LENGTH: 21
<212> TYPE: DNA
<213> ORGANISM: Homo sapiens

<400> SEQUENCE: 1163
ggtaatccct ggcaatgtga t                                           21

<210> SEQ ID NO 1164
<211> LENGTH: 22
<212> TYPE: DNA
<213> ORGANISM: Homo sapiens

<400> SEQUENCE: 1164
ctgttcctgc tgaactgagc ca                                          22

<210> SEQ ID NO 1165
<211> LENGTH: 22
<212> TYPE: DNA
<213> ORGANISM: Homo sapiens

<400> SEQUENCE: 1165
tcagaccgag acaagtgcaa tg                                          22

<210> SEQ ID NO 1166
<211> LENGTH: 21
<212> TYPE: DNA
<213> ORGANISM: Homo sapiens

<400> SEQUENCE: 1166
```

-continued gcctatcctg gattacttga a                                    21

<210> SEQ ID NO 1167
<211> LENGTH: 22
<212> TYPE: DNA
<213> ORGANISM: Homo sapiens

<400> SEQUENCE: 1167
aacctatcct gaattacttg aa                                   22

<210> SEQ ID NO 1168
<211> LENGTH: 21
<212> TYPE: DNA
<213> ORGANISM: Homo sapiens

<400> SEQUENCE: 1168
gcggaactta gccactgtga a                                    21

<210> SEQ ID NO 1169
<211> LENGTH: 21
<212> TYPE: DNA
<213> ORGANISM: Homo sapiens

<400> SEQUENCE: 1169
gcagaactta gccactgtga a                                    21

<210> SEQ ID NO 1170
<211> LENGTH: 22
<212> TYPE: DNA
<213> ORGANISM: Homo sapiens

<400> SEQUENCE: 1170
ctcaatagac tgtgagctcc tt                                   22

<210> SEQ ID NO 1171
<211> LENGTH: 21
<212> TYPE: DNA
<213> ORGANISM: Homo sapiens

<400> SEQUENCE: 1171
acaggattga gggggggccc t                                    21

<210> SEQ ID NO 1172
<211> LENGTH: 22
<212> TYPE: DNA
<213> ORGANISM: Homo sapiens

<400> SEQUENCE: 1172
aagcggttta ccatcccaca ta                                   22

<210> SEQ ID NO 1173
<211> LENGTH: 22
<212> TYPE: DNA
<213> ORGANISM: Homo sapiens

<400> SEQUENCE: 1173
atgtatgtgg gacggtaaac ca                                   22

<210> SEQ ID NO 1174
<211> LENGTH: 21
<212> TYPE: DNA
<213> ORGANISM: Homo sapiens

<400> SEQUENCE: 1174

```
aaccgatttc agatggtgct a                                          21

<210> SEQ ID NO 1175
<211> LENGTH: 23
<212> TYPE: DNA
<213> ORGANISM: Homo sapiens

<400> SEQUENCE: 1175
aacactgatt tcaaatggtg cta                                        23

<210> SEQ ID NO 1176
<211> LENGTH: 20
<212> TYPE: DNA
<213> ORGANISM: Homo sapiens

<400> SEQUENCE: 1176
accgatttca aatggtgcta                                            20

<210> SEQ ID NO 1177
<211> LENGTH: 23
<212> TYPE: DNA
<213> ORGANISM: Homo sapiens

<400> SEQUENCE: 1177
gctttgacaa tactattgca ctg                                        23

<210> SEQ ID NO 1178
<211> LENGTH: 23
<212> TYPE: DNA
<213> ORGANISM: Homo sapiens

<400> SEQUENCE: 1178
tcaccaaaac atggaagcac tta                                        23

<210> SEQ ID NO 1179
<211> LENGTH: 22
<212> TYPE: DNA
<213> ORGANISM: Homo sapiens

<400> SEQUENCE: 1179
aaagcaagta catccacgtt ta                                         22

<210> SEQ ID NO 1180
<211> LENGTH: 23
<212> TYPE: DNA
<213> ORGANISM: Homo sapiens

<400> SEQUENCE: 1180
ctactaaaac atggaagcac tta                                        23

<210> SEQ ID NO 1181
<211> LENGTH: 23
<212> TYPE: DNA
<213> ORGANISM: Homo sapiens

<400> SEQUENCE: 1181
agaaagcact tccatgttaa agt                                        23

<210> SEQ ID NO 1182
<211> LENGTH: 23
<212> TYPE: DNA
<213> ORGANISM: Homo sapiens

<400> SEQUENCE: 1182
```

| | |
|---|---|
| ccactgaaac atggaagcac tta | 23 |

\<210\> SEQ ID NO 1183
\<211\> LENGTH: 22
\<212\> TYPE: DNA
\<213\> ORGANISM: Homo sapiens

\<400\> SEQUENCE: 1183

| | |
|---|---|
| cagcaggtac ccccatgtta aa | 22 |

\<210\> SEQ ID NO 1184
\<211\> LENGTH: 23
\<212\> TYPE: DNA
\<213\> ORGANISM: Homo sapiens

\<400\> SEQUENCE: 1184

| | |
|---|---|
| acactcaaac atggaagcac tta | 23 |

\<210\> SEQ ID NO 1185
\<211\> LENGTH: 22
\<212\> TYPE: DNA
\<213\> ORGANISM: Homo sapiens

\<400\> SEQUENCE: 1185

| | |
|---|---|
| gctgcaaaca tccgactgaa ag | 22 |

\<210\> SEQ ID NO 1186
\<211\> LENGTH: 22
\<212\> TYPE: DNA
\<213\> ORGANISM: Homo sapiens

\<400\> SEQUENCE: 1186

| | |
|---|---|
| cttccagtcg aggatgttta ca | 22 |

\<210\> SEQ ID NO 1187
\<211\> LENGTH: 22
\<212\> TYPE: DNA
\<213\> ORGANISM: Homo sapiens

\<400\> SEQUENCE: 1187

| | |
|---|---|
| agctgagtgt aggatgttta ca | 22 |

\<210\> SEQ ID NO 1188
\<211\> LENGTH: 23
\<212\> TYPE: DNA
\<213\> ORGANISM: Homo sapiens

\<400\> SEQUENCE: 1188

| | |
|---|---|
| gctgagagtg taggatgttt aca | 23 |

\<210\> SEQ ID NO 1189
\<211\> LENGTH: 22
\<212\> TYPE: DNA
\<213\> ORGANISM: Homo sapiens

\<400\> SEQUENCE: 1189

| | |
|---|---|
| cttccagtcg gggatgttta ca | 22 |

\<210\> SEQ ID NO 1190
\<211\> LENGTH: 22
\<212\> TYPE: DNA
\<213\> ORGANISM: Homo sapiens

\<400\> SEQUENCE: 1190

| | |
|---|---|
| gctgtaaaca tccgactgaa ag | 22 |

<210> SEQ ID NO 1191
<211> LENGTH: 20
<212> TYPE: DNA
<213> ORGANISM: Homo sapiens

<400> SEQUENCE: 1191

| | |
|---|---|
| tccagtcaag gatgtttaca | 20 |

<210> SEQ ID NO 1192
<211> LENGTH: 21
<212> TYPE: DNA
<213> ORGANISM: Homo sapiens

<400> SEQUENCE: 1192

| | |
|---|---|
| cagctatgcc agcatcttgc c | 21 |

<210> SEQ ID NO 1193
<211> LENGTH: 21
<212> TYPE: DNA
<213> ORGANISM: Homo sapiens

<400> SEQUENCE: 1193

| | |
|---|---|
| gcaacttagt aatgtgcaat a | 21 |

<210> SEQ ID NO 1194
<211> LENGTH: 23
<212> TYPE: DNA
<213> ORGANISM: Homo sapiens

<400> SEQUENCE: 1194

| | |
|---|---|
| ttcgccctct caacccagct ttt | 23 |

<210> SEQ ID NO 1195
<211> LENGTH: 22
<212> TYPE: DNA
<213> ORGANISM: Homo sapiens

<400> SEQUENCE: 1195

| | |
|---|---|
| agaggtcgac cgtgtaatgt gc | 22 |

<210> SEQ ID NO 1196
<211> LENGTH: 22
<212> TYPE: DNA
<213> ORGANISM: Homo sapiens

<400> SEQUENCE: 1196

| | |
|---|---|
| ccagcagcac ctggggcagt gg | 22 |

<210> SEQ ID NO 1197
<211> LENGTH: 23
<212> TYPE: DNA
<213> ORGANISM: Homo sapiens

<400> SEQUENCE: 1197

| | |
|---|---|
| acaccaatgc cctagggggat gcg | 23 |

<210> SEQ ID NO 1198
<211> LENGTH: 23
<212> TYPE: DNA
<213> ORGANISM: Homo sapiens

<400> SEQUENCE: 1198
acacttactg gacacctact agg 23

<210> SEQ ID NO 1199
<211> LENGTH: 20
<212> TYPE: DNA
<213> ORGANISM: Homo sapiens

<400> SEQUENCE: 1199
ctggaggaag ggcccagagg 20

<210> SEQ ID NO 1200
<211> LENGTH: 22
<212> TYPE: DNA
<213> ORGANISM: Homo sapiens

<400> SEQUENCE: 1200
acggaagggc agagagggcc ag 22

<210> SEQ ID NO 1201
<211> LENGTH: 19
<212> TYPE: DNA
<213> ORGANISM: Homo sapiens

<400> SEQUENCE: 1201
agaggttaac caggtgtgt 19

<210> SEQ ID NO 1202
<211> LENGTH: 19
<212> TYPE: DNA
<213> ORGANISM: Homo sapiens

<400> SEQUENCE: 1202
caatgcaact acaatgcac 19

<210> SEQ ID NO 1203
<211> LENGTH: 23
<212> TYPE: DNA
<213> ORGANISM: Homo sapiens

<400> SEQUENCE: 1203
tctctgcagg ccgtgtgctt tgc 23

<210> SEQ ID NO 1204
<211> LENGTH: 21
<212> TYPE: DNA
<213> ORGANISM: Homo sapiens

<400> SEQUENCE: 1204
ttctaggata ggcccagggg c 21

<210> SEQ ID NO 1205
<211> LENGTH: 23
<212> TYPE: DNA
<213> ORGANISM: Homo sapiens

<400> SEQUENCE: 1205
acatttttcg ttattgctct tga 23

<210> SEQ ID NO 1206
<211> LENGTH: 23
<212> TYPE: DNA
<213> ORGANISM: Homo sapiens

<400> SEQUENCE: 1206
aaaggcatca tataggagct gga 23

<210> SEQ ID NO 1207
<211> LENGTH: 23
<212> TYPE: DNA
<213> ORGANISM: Homo sapiens

<400> SEQUENCE: 1207
tcaacaaaat cactgatgct gga 23

<210> SEQ ID NO 1208
<211> LENGTH: 21
<212> TYPE: DNA
<213> ORGANISM: Homo sapiens

<400> SEQUENCE: 1208
tgagctcctg gaggacaggg a 21

<210> SEQ ID NO 1209
<211> LENGTH: 23
<212> TYPE: DNA
<213> ORGANISM: Homo sapiens

<400> SEQUENCE: 1209
ggctataaag taactgagac gga 23

<210> SEQ ID NO 1210
<211> LENGTH: 24
<212> TYPE: DNA
<213> ORGANISM: Homo sapiens

<400> SEQUENCE: 1210
gacgggtgcg atttctgtgt gaga 24

<210> SEQ ID NO 1211
<211> LENGTH: 21
<212> TYPE: DNA
<213> ORGANISM: Homo sapiens

<400> SEQUENCE: 1211
gccctggact aggagtcagc a 21

<210> SEQ ID NO 1212
<211> LENGTH: 23
<212> TYPE: DNA
<213> ORGANISM: Homo sapiens

<400> SEQUENCE: 1212
agaggcaggc atgcgggcag aca 23

<210> SEQ ID NO 1213
<211> LENGTH: 23
<212> TYPE: DNA
<213> ORGANISM: Homo sapiens

<400> SEQUENCE: 1213
aacaaccagc taagacactg cca 23

<210> SEQ ID NO 1214
<211> LENGTH: 23
<212> TYPE: DNA
<213> ORGANISM: Homo sapiens

<400> SEQUENCE: 1214

```
caatcagcta atgacactgc cta                                              23

<210> SEQ ID NO 1215
<211> LENGTH: 23
<212> TYPE: DNA
<213> ORGANISM: Homo sapiens

<400> SEQUENCE: 1215
gcaatcagct aactacactg cct                                              23

<210> SEQ ID NO 1216
<211> LENGTH: 22
<212> TYPE: DNA
<213> ORGANISM: Homo sapiens

<400> SEQUENCE: 1216
gtacccctgg agattctgat aa                                               22

<210> SEQ ID NO 1217
<211> LENGTH: 24
<212> TYPE: DNA
<213> ORGANISM: Homo sapiens

<400> SEQUENCE: 1217
actcacacct aggttccaag gatt                                             24

<210> SEQ ID NO 1218
<211> LENGTH: 22
<212> TYPE: DNA
<213> ORGANISM: Homo sapiens

<400> SEQUENCE: 1218
tacagatgga taccgtgcaa tt                                               22

<210> SEQ ID NO 1219
<211> LENGTH: 22
<212> TYPE: DNA
<213> ORGANISM: Homo sapiens

<400> SEQUENCE: 1219
taaggatttt tagggcatt at                                                22

<210> SEQ ID NO 1220
<211> LENGTH: 22
<212> TYPE: DNA
<213> ORGANISM: Homo sapiens

<400> SEQUENCE: 1220
tcaccattgc taaagtgcaa tt                                               22

<210> SEQ ID NO 1221
<211> LENGTH: 22
<212> TYPE: DNA
<213> ORGANISM: Homo sapiens

<400> SEQUENCE: 1221
aaacgtggaa tttcctctat gt                                               22

<210> SEQ ID NO 1222
<211> LENGTH: 21
<212> TYPE: DNA
<213> ORGANISM: Homo sapiens

<400> SEQUENCE: 1222
```
aaagatcaac catgtattat t                                          21

<210> SEQ ID NO 1223
<211> LENGTH: 22
<212> TYPE: DNA
<213> ORGANISM: Homo sapiens

<400> SEQUENCE: 1223
gcgaatataa cacggtcgat ct                                         22

<210> SEQ ID NO 1224
<211> LENGTH: 21
<212> TYPE: DNA
<213> ORGANISM: Homo sapiens

<400> SEQUENCE: 1224
ccaggttcca ccccagcagg c                                          21

<210> SEQ ID NO 1225
<211> LENGTH: 21
<212> TYPE: DNA
<213> ORGANISM: Homo sapiens

<400> SEQUENCE: 1225
acactcaaaa gatggcggca c                                          21

<210> SEQ ID NO 1226
<211> LENGTH: 23
<212> TYPE: DNA
<213> ORGANISM: Homo sapiens

<400> SEQUENCE: 1226
acgctcaaat gtcgcagcac ttt                                        23

<210> SEQ ID NO 1227
<211> LENGTH: 23
<212> TYPE: DNA
<213> ORGANISM: Homo sapiens

<400> SEQUENCE: 1227
acaccccaaa atcgaagcac ttc                                        23

<210> SEQ ID NO 1228
<211> LENGTH: 22
<212> TYPE: DNA
<213> ORGANISM: Homo sapiens

<400> SEQUENCE: 1228
ggaaagcgcc cccattttga gt                                         22

<210> SEQ ID NO 1229
<211> LENGTH: 22
<212> TYPE: DNA
<213> ORGANISM: Homo sapiens

<400> SEQUENCE: 1229
cacttatcag gttgtattat aa                                         22

<210> SEQ ID NO 1230
<211> LENGTH: 22
<212> TYPE: DNA
<213> ORGANISM: Homo sapiens

<400> SEQUENCE: 1230
tcacgcgagc cgaacgaaca aa                                    22

<210> SEQ ID NO 1231
<211> LENGTH: 21
<212> TYPE: DNA
<213> ORGANISM: Homo sapiens

<400> SEQUENCE: 1231
acgtggattt tcctctatga t                                     21

<210> SEQ ID NO 1232
<211> LENGTH: 22
<212> TYPE: DNA
<213> ORGANISM: Homo sapiens

<400> SEQUENCE: 1232
aacatggatt ttcctctatg at                                    22

<210> SEQ ID NO 1233
<211> LENGTH: 22
<212> TYPE: DNA
<213> ORGANISM: Homo sapiens

<400> SEQUENCE: 1233
acaaaagttg cctttgtgtg at                                    22

<210> SEQ ID NO 1234
<211> LENGTH: 22
<212> TYPE: DNA
<213> ORGANISM: Homo sapiens

<400> SEQUENCE: 1234
acacaggacc tggagtcagg ag                                    22

<210> SEQ ID NO 1235
<211> LENGTH: 19
<212> TYPE: DNA
<213> ORGANISM: Homo sapiens

<400> SEQUENCE: 1235
tacgttccat agtctacca                                        19

<210> SEQ ID NO 1236
<211> LENGTH: 22
<212> TYPE: DNA
<213> ORGANISM: Homo sapiens

<400> SEQUENCE: 1236
aagatgtgga ccatattaca ta                                    22

<210> SEQ ID NO 1237
<211> LENGTH: 22
<212> TYPE: DNA
<213> ORGANISM: Homo sapiens

<400> SEQUENCE: 1237
gcgcatgttc tatggtcaac ca                                    22

<210> SEQ ID NO 1238
<211> LENGTH: 22
<212> TYPE: DNA
<213> ORGANISM: Homo sapiens

<400> SEQUENCE: 1238
acagagagct tgcccttgta ta					22

<210> SEQ ID NO 1239
<211> LENGTH: 22
<212> TYPE: DNA
<213> ORGANISM: Homo sapiens

<400> SEQUENCE: 1239
cgaatccacc acgaacaact tc					22

<210> SEQ ID NO 1240
<211> LENGTH: 22
<212> TYPE: DNA
<213> ORGANISM: Homo sapiens

<400> SEQUENCE: 1240
agccacaatc accttctgat ct					22

<210> SEQ ID NO 1241
<211> LENGTH: 20
<212> TYPE: DNA
<213> ORGANISM: Homo sapiens

<400> SEQUENCE: 1241
tatgaacaat ttctaggaat					20

<210> SEQ ID NO 1242
<211> LENGTH: 21
<212> TYPE: DNA
<213> ORGANISM: Homo sapiens

<400> SEQUENCE: 1242
aggggttcac cgagcaacat t					21

<210> SEQ ID NO 1243
<211> LENGTH: 22
<212> TYPE: DNA
<213> ORGANISM: Homo sapiens

<400> SEQUENCE: 1243
tgcaaagttg ctcgggtaac ct					22

<210> SEQ ID NO 1244
<211> LENGTH: 21
<212> TYPE: DNA
<213> ORGANISM: Homo sapiens

<400> SEQUENCE: 1244
acaggccatc tgtgttatat t					21

<210> SEQ ID NO 1245
<211> LENGTH: 23
<212> TYPE: DNA
<213> ORGANISM: Homo sapiens

<400> SEQUENCE: 1245
acggctagtg gaccaggtga agt					23

<210> SEQ ID NO 1246
<211> LENGTH: 22
<212> TYPE: DNA
<213> ORGANISM: Homo sapiens

<400> SEQUENCE: 1246
ggccttctga ccctaagtcc ag                                              22

<210> SEQ ID NO 1247
<211> LENGTH: 22
<212> TYPE: DNA
<213> ORGANISM: Homo sapiens

<400> SEQUENCE: 1247
ggccttctga ctccaagtcc ag                                              22

<210> SEQ ID NO 1248
<211> LENGTH: 22
<212> TYPE: DNA
<213> ORGANISM: Homo sapiens

<400> SEQUENCE: 1248 ctgagggggcc tcagaccgag ct                                             22

<210> SEQ ID NO 1249
<211> LENGTH: 22
<212> TYPE: DNA
<213> ORGANISM: Homo sapiens

<400> SEQUENCE: 1249
ttcaaaacat gaattgctgc tg                                              22

<210> SEQ ID NO 1250
<211> LENGTH: 21
<212> TYPE: DNA
<213> ORGANISM: Homo sapiens

<400> SEQUENCE: 1250
ggcggacacg acattcccga t                                               21

<210> SEQ ID NO 1251
<211> LENGTH: 22
<212> TYPE: DNA
<213> ORGANISM: Homo sapiens

<400> SEQUENCE: 1251
acggttttac cagacagtat ta                                              22

<210> SEQ ID NO 1252
<211> LENGTH: 21
<212> TYPE: DNA
<213> ORGANISM: Homo sapiens

<400> SEQUENCE: 1252
tgcatgacgg cctgcaagac a                                               21

<210> SEQ ID NO 1253
<211> LENGTH: 23
<212> TYPE: DNA
<213> ORGANISM: Homo sapiens

<400> SEQUENCE: 1253
ccacccaatg acctactcca aga                                             23

<210> SEQ ID NO 1254
<211> LENGTH: 21
<212> TYPE: DNA
<213> ORGANISM: Homo sapiens

<400> SEQUENCE: 1254

-continued agacatggag gagccatcca g  21

<210> SEQ ID NO 1255
<211> LENGTH: 22
<212> TYPE: DNA
<213> ORGANISM: Homo sapiens

<400> SEQUENCE: 1255
acaccgagga gcccatcatg at  22

<210> SEQ ID NO 1256
<211> LENGTH: 22
<212> TYPE: DNA
<213> ORGANISM: Homo sapiens

<400> SEQUENCE: 1256
atgggacatc ctacatatgc aa  22

<210> SEQ ID NO 1257
<211> LENGTH: 22
<212> TYPE: DNA
<213> ORGANISM: Homo sapiens

<400> SEQUENCE: 1257
accagctaac aatacactgc ca  22

<210> SEQ ID NO 1258
<211> LENGTH: 22
<212> TYPE: DNA
<213> ORGANISM: Homo sapiens

<400> SEQUENCE: 1258
atattaggaa cacatcgcaa aa  22

<210> SEQ ID NO 1259
<211> LENGTH: 23
<212> TYPE: DNA
<213> ORGANISM: Homo sapiens

<400> SEQUENCE: 1259
actcagtaat ggtaacggtt tcc  23

<210> SEQ ID NO 1260
<211> LENGTH: 22
<212> TYPE: DNA
<213> ORGANISM: Homo sapiens

<400> SEQUENCE: 1260
gtctcagttt cctctgcaaa ca  22

<210> SEQ ID NO 1261
<211> LENGTH: 21
<212> TYPE: DNA
<213> ORGANISM: Homo sapiens

<400> SEQUENCE: 1261
cttctttgca gatgagactg a  21

<210> SEQ ID NO 1262
<211> LENGTH: 22
<212> TYPE: DNA
<213> ORGANISM: Homo sapiens

<400> SEQUENCE: 1262
cgaactcacc acggacaacc tc                                              22

<210> SEQ ID NO 1263
<211> LENGTH: 22
<212> TYPE: DNA
<213> ORGANISM: Homo sapiens

<400> SEQUENCE: 1263
agagaggaga gccgtgtatg ac                                              22

<210> SEQ ID NO 1264
<211> LENGTH: 22
<212> TYPE: DNA
<213> ORGANISM: Homo sapiens

<400> SEQUENCE: 1264
gaattcatca cggccagcct ct                                              22

<210> SEQ ID NO 1265
<211> LENGTH: 21
<212> TYPE: DNA
<213> ORGANISM: Homo sapiens

<400> SEQUENCE: 1265
ttgagagtgc cattatctgg g                                               21

<210> SEQ ID NO 1266
<211> LENGTH: 23
<212> TYPE: DNA
<213> ORGANISM: Homo sapiens

<400> SEQUENCE: 1266
gctgccgtat atgtgatgtc act                                             23

<210> SEQ ID NO 1267
<211> LENGTH: 22
<212> TYPE: DNA
<213> ORGANISM: Homo sapiens

<400> SEQUENCE: 1267
cagcatggag tcctccaggt tg                                              22

<210> SEQ ID NO 1268
<211> LENGTH: 23
<212> TYPE: DNA
<213> ORGANISM: Homo sapiens

<400> SEQUENCE: 1268
tcctcatgga agggttcccc act                                             23

<210> SEQ ID NO 1269
<211> LENGTH: 23
<212> TYPE: DNA
<213> ORGANISM: Homo sapiens

<400> SEQUENCE: 1269
aagaatcttg tcccgcaggt cct                                             23

<210> SEQ ID NO 1270
<211> LENGTH: 22
<212> TYPE: DNA
<213> ORGANISM: Homo sapiens

<400> SEQUENCE: 1270
aatgaaagcc taccatgtac aa    22

<210> SEQ ID NO 1271
<211> LENGTH: 24
<212> TYPE: DNA
<213> ORGANISM: Homo sapiens

<400> SEQUENCE: 1271
aagaggtttc ccgtgtatgt ttca    24

<210> SEQ ID NO 1272
<211> LENGTH: 23
<212> TYPE: DNA
<213> ORGANISM: Homo sapiens

<400> SEQUENCE: 1272
aaagaagtgc accatgtttg ttt    23

<210> SEQ ID NO 1273
<211> LENGTH: 17
<212> TYPE: DNA
<213> ORGANISM: Homo sapiens

<400> SEQUENCE: 1273
gagattggcc atgtaat    17

<210> SEQ ID NO 1274
<211> LENGTH: 21
<212> TYPE: DNA
<213> ORGANISM: Homo sapiens

<400> SEQUENCE: 1274
acaaaccaca gtgtgctgct g    21

<210> SEQ ID NO 1275
<211> LENGTH: 23
<212> TYPE: DNA
<213> ORGANISM: Homo sapiens

<400> SEQUENCE: 1275
gaaaaacgcc ccctggcttg aaa    23

<210> SEQ ID NO 1276
<211> LENGTH: 23
<212> TYPE: DNA
<213> ORGANISM: Homo sapiens

<400> SEQUENCE: 1276
ttaaacatca ctgcaagtct taa    23

<210> SEQ ID NO 1277
<211> LENGTH: 22
<212> TYPE: DNA
<213> ORGANISM: Homo sapiens

<400> SEQUENCE: 1277
cagaatcctt gcccaggtgc at    22

<210> SEQ ID NO 1278
<211> LENGTH: 22
<212> TYPE: DNA
<213> ORGANISM: Homo sapiens

<400> SEQUENCE: 1278
tctcacccag ggacaaagga tt                                          22

<210> SEQ ID NO 1279
<211> LENGTH: 21
<212> TYPE: DNA
<213> ORGANISM: Homo sapiens

<400> SEQUENCE: 1279
tagcacccag atagcaagga t                                           21

<210> SEQ ID NO 1280
<211> LENGTH: 23
<212> TYPE: DNA
<213> ORGANISM: Homo sapiens

<400> SEQUENCE: 1280
ctgcagaact gttcccgctg cta                                         23

<210> SEQ ID NO 1281
<211> LENGTH: 21
<212> TYPE: DNA
<213> ORGANISM: Homo sapiens

<400> SEQUENCE: 1281
atagagtgca gaccagggtc t                                           21

<210> SEQ ID NO 1282
<211> LENGTH: 22
<212> TYPE: DNA
<213> ORGANISM: Homo sapiens

<400> SEQUENCE: 1282
gaggaaacca gcaagtgttg ac                                          22

<210> SEQ ID NO 1283
<211> LENGTH: 21
<212> TYPE: DNA
<213> ORGANISM: Homo sapiens

<400> SEQUENCE: 1283
tctactcaga agggtgcctt a                                           21

<210> SEQ ID NO 1284
<211> LENGTH: 21
<212> TYPE: DNA
<213> ORGANISM: Homo sapiens

<400> SEQUENCE: 1284
ttcactccaa aaggtgcaaa a                                           21

<210> SEQ ID NO 1285
<211> LENGTH: 23
<212> TYPE: DNA
<213> ORGANISM: Homo sapiens

<400> SEQUENCE: 1285
tctactccaa aaggctacaa tca                                         23

<210> SEQ ID NO 1286
<211> LENGTH: 23
<212> TYPE: DNA
<213> ORGANISM: Homo sapiens

<400> SEQUENCE: 1286
tctacccaca gacgtaccaa tca                                              23

<210> SEQ ID NO 1287
<211> LENGTH: 23
<212> TYPE: DNA
<213> ORGANISM: Homo sapiens

<400> SEQUENCE: 1287
tgtgattgcc actctcctga gta                                              23

<210> SEQ ID NO 1288
<211> LENGTH: 21
<212> TYPE: DNA
<213> ORGANISM: Homo sapiens

<400> SEQUENCE: 1288
tgactgcaga gcaaaagaca c                                                21

<210> SEQ ID NO 1289
<211> LENGTH: 22
<212> TYPE: DNA
<213> ORGANISM: Homo sapiens

<400> SEQUENCE: 1289
gacctcagct atgacagcac tt                                               22

<210> SEQ ID NO 1290
<211> LENGTH: 23
<212> TYPE: DNA
<213> ORGANISM: Homo sapiens

<400> SEQUENCE: 1290
gaaagtgccc tcaaggctga gtg                                              23

<210> SEQ ID NO 1291
<211> LENGTH: 22
<212> TYPE: DNA
<213> ORGANISM: Homo sapiens

<400> SEQUENCE: 1291
ataaatgaca cctccctgtg aa                                               22

<210> SEQ ID NO 1292
<211> LENGTH: 20
<212> TYPE: DNA
<213> ORGANISM: Homo sapiens

<400> SEQUENCE: 1292
ctactcacag aagtgtcaat                                                  20

<210> SEQ ID NO 1293
<211> LENGTH: 21
<212> TYPE: DNA
<213> ORGANISM: Homo sapiens

<400> SEQUENCE: 1293
acgctccaaa agaaggcact c                                                21

<210> SEQ ID NO 1294
<211> LENGTH: 24
<212> TYPE: DNA
<213> ORGANISM: Homo sapiens

<400> SEQUENCE: 1294

-continued cagaaagtgc tttctttggg agaa                                    24

<210> SEQ ID NO 1295
<211> LENGTH: 18
<212> TYPE: DNA
<213> ORGANISM: Homo sapiens

<400> SEQUENCE: 1295
accctctgaa aggaagca                                           18

<210> SEQ ID NO 1296
<211> LENGTH: 25
<212> TYPE: DNA
<213> ORGANISM: Homo sapiens

<400> SEQUENCE: 1296
cagaaagtgc ttcttacctc cagat                                   25

<210> SEQ ID NO 1297
<211> LENGTH: 23
<212> TYPE: DNA
<213> ORGANISM: Homo sapiens

<400> SEQUENCE: 1297
aaagtgcttc ttacctccag atg                                     23

<210> SEQ ID NO 1298
<211> LENGTH: 22
<212> TYPE: DNA
<213> ORGANISM: Homo sapiens

<400> SEQUENCE: 1298
agacagtgct tccatctaga gg                                      22

<210> SEQ ID NO 1299
<211> LENGTH: 23
<212> TYPE: DNA
<213> ORGANISM: Homo sapiens

<400> SEQUENCE: 1299
aacactctaa agggatgcac gat                                     23

<210> SEQ ID NO 1300
<211> LENGTH: 22
<212> TYPE: DNA
<213> ORGANISM: Homo sapiens

<400> SEQUENCE: 1300
aacactctaa agggatgcac ga                                      22

<210> SEQ ID NO 1301
<211> LENGTH: 22
<212> TYPE: DNA
<213> ORGANISM: Homo sapiens

<400> SEQUENCE: 1301
acactctaaa aggatgcacg at                                      22

<210> SEQ ID NO 1302
<211> LENGTH: 21
<212> TYPE: DNA
<213> ORGANISM: Homo sapiens

<400> SEQUENCE: 1302
tccagcaaag ggaagcgctt t                                        21

<210> SEQ ID NO 1303
<211> LENGTH: 20
<212> TYPE: DNA
<213> ORGANISM: Homo sapiens

<400> SEQUENCE: 1303
aaagggcttc cctttgcaga                                          20

<210> SEQ ID NO 1304
<211> LENGTH: 22
<212> TYPE: DNA
<213> ORGANISM: Homo sapiens

<400> SEQUENCE: 1304
acctctaaag gggagcgctt tg                                       22

<210> SEQ ID NO 1305
<211> LENGTH: 22
<212> TYPE: DNA
<213> ORGANISM: Homo sapiens

<400> SEQUENCE: 1305
cactctaaag agaagcgctt tg                                       22

<210> SEQ ID NO 1306
<211> LENGTH: 23
<212> TYPE: DNA
<213> ORGANISM: Homo sapiens

<400> SEQUENCE: 1306
cagaaagtgc ttccctccag aga                                      23

<210> SEQ ID NO 1307
<211> LENGTH: 21
<212> TYPE: DNA
<213> ORGANISM: Homo sapiens

<400> SEQUENCE: 1307
gctccaaagg gaagcgcttt g                                        21

<210> SEQ ID NO 1308
<211> LENGTH: 22
<212> TYPE: DNA
<213> ORGANISM: Homo sapiens

<400> SEQUENCE: 1308
acactctgaa gggaagcgct tt                                       22

<210> SEQ ID NO 1309
<211> LENGTH: 21
<212> TYPE: DNA
<213> ORGANISM: Homo sapiens

<400> SEQUENCE: 1309
tcctctaaag agaagcgctt t                                        21

<210> SEQ ID NO 1310
<211> LENGTH: 23
<212> TYPE: DNA
<213> ORGANISM: Homo sapiens

<400> SEQUENCE: 1310

| | |
|---|---|
| agagaaagtg cttccctcta gag | 23 |

<210> SEQ ID NO 1311
<211> LENGTH: 25
<212> TYPE: DNA
<213> ORGANISM: Homo sapiens

<400> SEQUENCE: 1311

| | |
|---|---|
| gtaacactct aaaaggatgc acttt | 25 |

<210> SEQ ID NO 1312
<211> LENGTH: 23
<212> TYPE: DNA
<213> ORGANISM: Homo sapiens

<400> SEQUENCE: 1312

| | |
|---|---|
| aaacctctaa aaggatgcac ttt | 23 |

<210> SEQ ID NO 1313
<211> LENGTH: 22
<212> TYPE: DNA
<213> ORGANISM: Homo sapiens

<400> SEQUENCE: 1313

| | |
|---|---|
| atcctctaaa aagatgcact tt | 22 |

<210> SEQ ID NO 1314
<211> LENGTH: 23
<212> TYPE: DNA
<213> ORGANISM: Homo sapiens

<400> SEQUENCE: 1314

| | |
|---|---|
| acactctaaa gggaggcact ttg | 23 |

<210> SEQ ID NO 1315
<211> LENGTH: 22
<212> TYPE: DNA
<213> ORGANISM: Homo sapiens

<400> SEQUENCE: 1315

| | |
|---|---|
| acactctaaa aggaggcact tt | 22 |

<210> SEQ ID NO 1316
<211> LENGTH: 22
<212> TYPE: DNA
<213> ORGANISM: Homo sapiens

<400> SEQUENCE: 1316

| | |
|---|---|
| gaaagtgctc cctttggag aa | 22 |

<210> SEQ ID NO 1317
<211> LENGTH: 22
<212> TYPE: DNA
<213> ORGANISM: Homo sapiens

<400> SEQUENCE: 1317

| | |
|---|---|
| acagtccaaa gggaagcact tt | 22 |

<210> SEQ ID NO 1318
<211> LENGTH: 21
<212> TYPE: DNA
<213> ORGANISM: Homo sapiens

<400> SEQUENCE: 1318
agaaagtact tccctctgga g    21

<210> SEQ ID NO 1319
<211> LENGTH: 21
<212> TYPE: DNA
<213> ORGANISM: Homo sapiens

<400> SEQUENCE: 1319
ccctctaaaa ggaagcactt t    21

<210> SEQ ID NO 1320
<211> LENGTH: 23
<212> TYPE: DNA
<213> ORGANISM: Homo sapiens

<400> SEQUENCE: 1320
aaccctctaa aaggaagcac ttt    23

<210> SEQ ID NO 1321
<211> LENGTH: 23
<212> TYPE: DNA
<213> ORGANISM: Homo sapiens

<400> SEQUENCE: 1321
aacccaccaa agagaagcac ttt    23

<210> SEQ ID NO 1322
<211> LENGTH: 23
<212> TYPE: DNA
<213> ORGANISM: Homo sapiens

<400> SEQUENCE: 1322
cagaaagggc ttccctttgt aga    23

<210> SEQ ID NO 1323
<211> LENGTH: 21
<212> TYPE: DNA
<213> ORGANISM: Homo sapiens

<400> SEQUENCE: 1323
ccctcaaaaa ggaagcactt t    21

<210> SEQ ID NO 1324
<211> LENGTH: 22
<212> TYPE: DNA
<213> ORGANISM: Homo sapiens

<400> SEQUENCE: 1324
aaccctctaa aaggaagcac tt    22

<210> SEQ ID NO 1325
<211> LENGTH: 24
<212> TYPE: DNA
<213> ORGANISM: Homo sapiens

<400> SEQUENCE: 1325
acactctaaa gggaagcact ttgt    24

<210> SEQ ID NO 1326
<211> LENGTH: 22
<212> TYPE: DNA
<213> ORGANISM: Homo sapiens

<400> SEQUENCE: 1326
actctaaagg gaagcacttt gt                                        22

<210> SEQ ID NO 1327
<211> LENGTH: 22
<212> TYPE: DNA
<213> ORGANISM: Homo sapiens

<400> SEQUENCE: 1327
acactctaaa gggaagtgcg tt                                        22

<210> SEQ ID NO 1328
<211> LENGTH: 23
<212> TYPE: DNA
<213> ORGANISM: Homo sapiens

<400> SEQUENCE: 1328
aacactctaa agggaaccat ttt                                       23

<210> SEQ ID NO 1329
<211> LENGTH: 21
<212> TYPE: DNA
<213> ORGANISM: Homo sapiens

<400> SEQUENCE: 1329
ccctctatag ggaagcgcgt t                                         21

<210> SEQ ID NO 1330
<211> LENGTH: 21
<212> TYPE: DNA
<213> ORGANISM: Homo sapiens

<400> SEQUENCE: 1330
actccaaagg gaagcgcctt c                                         21

<210> SEQ ID NO 1331
<211> LENGTH: 22
<212> TYPE: DNA
<213> ORGANISM: Homo sapiens

<400> SEQUENCE: 1331
gagaaagtgc ttccctttgt ag                                        22

<210> SEQ ID NO 1332
<211> LENGTH: 21
<212> TYPE: DNA
<213> ORGANISM: Homo sapiens

<400> SEQUENCE: 1332
agaaagtgca tccctctgga g                                         21

<210> SEQ ID NO 1333
<211> LENGTH: 21
<212> TYPE: DNA
<213> ORGANISM: Homo sapiens

<400> SEQUENCE: 1333
gctctaaagg gaagcgcctt c                                         21

<210> SEQ ID NO 1334
<211> LENGTH: 21
<212> TYPE: DNA
<213> ORGANISM: Homo sapiens

<400> SEQUENCE: 1334
agaaagtgct tccctctaga g                                              21

<210> SEQ ID NO 1335
<211> LENGTH: 24
<212> TYPE: DNA
<213> ORGANISM: Homo sapiens

<400> SEQUENCE: 1335
aacagaaagt gcttccctca agag                                           24

<210> SEQ ID NO 1336
<211> LENGTH: 21
<212> TYPE: DNA
<213> ORGANISM: Homo sapiens

<400> SEQUENCE: 1336
gcctctaaaa ggaagcactt t                                              21

<210> SEQ ID NO 1337
<211> LENGTH: 24
<212> TYPE: DNA
<213> ORGANISM: Homo sapiens

<400> SEQUENCE: 1337
aacagaaagc gcttccctct agag                                           24

<210> SEQ ID NO 1338
<211> LENGTH: 21
<212> TYPE: DNA
<213> ORGANISM: Homo sapiens

<400> SEQUENCE: 1338
agaaagggct tccctttgca g                                              21

<210> SEQ ID NO 1339
<211> LENGTH: 22
<212> TYPE: DNA
<213> ORGANISM: Homo sapiens

<400> SEQUENCE: 1339
caacaaaatc actagtcttc ca                                             22

<210> SEQ ID NO 1340
<211> LENGTH: 23
<212> TYPE: DNA
<213> ORGANISM: Homo sapiens

<400> SEQUENCE: 1340
tcatacagct agataaccaa aga                                            23

<210> SEQ ID NO 1341
<211> LENGTH: 21
<212> TYPE: DNA
<213> ORGANISM: Homo sapiens

<400> SEQUENCE: 1341
actttcggtt atctagcttt a                                              21

<210> SEQ ID NO 1342
<211> LENGTH: 21
<212> TYPE: DNA
<213> ORGANISM: Homo sapiens

<400> SEQUENCE: 1342

| caggccggga caagtgcaat a | 21 |

<210> SEQ ID NO 1343
<211> LENGTH: 22
<212> TYPE: DNA
<213> ORGANISM: Homo sapiens

<400> SEQUENCE: 1343

| ctacctgcac gaacagcact tt | 22 |

<210> SEQ ID NO 1344
<211> LENGTH: 22
<212> TYPE: DNA
<213> ORGANISM: Homo sapiens

<400> SEQUENCE: 1344

| tgctcaataa atacccgttg aa | 22 |

<210> SEQ ID NO 1345
<211> LENGTH: 22
<212> TYPE: DNA
<213> ORGANISM: Homo sapiens

<400> SEQUENCE: 1345

| gcaaaaatgt gctagtgcca aa | 22 |

<210> SEQ ID NO 1346
<211> LENGTH: 21
<212> TYPE: DNA
<213> ORGANISM: Homo sapiens

<400> SEQUENCE: 1346

| gttagcatgc cagagtctcg t | 21 |

<210> SEQ ID NO 1347
<211> LENGTH: 22
<212> TYPE: DNA
<213> ORGANISM: Homo sapiens

<400> SEQUENCE: 1347

| aacaatacaa cttactacct ca | 22 |

<210> SEQ ID NO 1348
<211> LENGTH: 22
<212> TYPE: DNA
<213> ORGANISM: Homo sapiens

<400> SEQUENCE: 1348

| cacaagatcg gatctacggg tt | 22 |

<210> SEQ ID NO 1349
<211> LENGTH: 22
<212> TYPE: DNA
<213> ORGANISM: Homo sapiens

<400> SEQUENCE: 1349

| cgcaaggtcg gttctacggg tg | 22 |

<210> SEQ ID NO 1350
<211> LENGTH: 21
<212> TYPE: RNA
<213> ORGANISM: Homo sapiens

<400> SEQUENCE: 1350

-continued uauugcacuc gucccggccu c    21

<210> SEQ ID NO 1351
<211> LENGTH: 21
<212> TYPE: RNA
<213> ORGANISM: Homo sapiens

<400> SEQUENCE: 1351
uaguagaccg uauagcguac g    21

<210> SEQ ID NO 1352
<211> LENGTH: 22
<212> TYPE: RNA
<213> ORGANISM: Homo sapiens

<400> SEQUENCE: 1352
aggcagugua uuguuagcug gc    22

<210> SEQ ID NO 1353
<211> LENGTH: 22
<212> TYPE: RNA
<213> ORGANISM: Homo sapiens

<400> SEQUENCE: 1353
ucagcaaaca uuuauugugu gc    22

<210> SEQ ID NO 1354
<211> LENGTH: 22
<212> TYPE: RNA
<213> ORGANISM: Homo sapiens

<400> SEQUENCE: 1354
caaaaaccac aguuucuuuu gc    22

<210> SEQ ID NO 1355
<211> LENGTH: 21
<212> TYPE: RNA
<213> ORGANISM: Homo sapiens

<400> SEQUENCE: 1355
gcgacccaua cuugguuuca g    21

<210> SEQ ID NO 1356
<211> LENGTH: 19
<212> TYPE: RNA
<213> ORGANISM: Homo sapiens

<400> SEQUENCE: 1356
ugagcugcug uaccaaaau    19

<210> SEQ ID NO 1357
<211> LENGTH: 19
<212> TYPE: RNA
<213> ORGANISM: Homo sapiens

<400> SEQUENCE: 1357
aggcacggug ucagcaggc    19

<210> SEQ ID NO 1358
<211> LENGTH: 22
<212> TYPE: RNA
<213> ORGANISM: Homo sapiens

<400> SEQUENCE: 1358

```
ggcuggcucg cgaugucugu uu                                              22

<210> SEQ ID NO 1359
<211> LENGTH: 21
<212> TYPE: RNA
<213> ORGANISM: Homo sapiens

<400> SEQUENCE: 1359
ugaguuggcc aucugaguga g                                               21

<210> SEQ ID NO 1360
<211> LENGTH: 21
<212> TYPE: RNA
<213> ORGANISM: Homo sapiens

<400> SEQUENCE: 1360
cacgcucaug cacacaccca c                                               21

<210> SEQ ID NO 1361
<211> LENGTH: 21
<212> TYPE: RNA
<213> ORGANISM: Homo sapiens

<400> SEQUENCE: 1361
uagauaaaau auugguaccu g                                               21

<210> SEQ ID NO 1362
<211> LENGTH: 22
<212> TYPE: RNA
<213> ORGANISM: Homo sapiens

<400> SEQUENCE: 1362
uugagaauga ugaaucauua gg                                              22

<210> SEQ ID NO 1363
<211> LENGTH: 21
<212> TYPE: RNA
<213> ORGANISM: Homo sapiens

<400> SEQUENCE: 1363
ucuuguguuc ucuagaucag u                                               21

<210> SEQ ID NO 1364
<211> LENGTH: 23
<212> TYPE: RNA
<213> ORGANISM: Homo sapiens

<400> SEQUENCE: 1364
uuacaguugu ucaaccaguu acu                                             23

<210> SEQ ID NO 1365
<211> LENGTH: 22
<212> TYPE: RNA
<213> ORGANISM: Homo sapiens

<400> SEQUENCE: 1365
uuaugguuug ccugggacug ag                                              22

<210> SEQ ID NO 1366
<211> LENGTH: 22
<212> TYPE: RNA
<213> ORGANISM: Homo sapiens

<400> SEQUENCE: 1366
```
uugugucaau augcgaugau gu                                           22

<210> SEQ ID NO 1367
<211> LENGTH: 25
<212> TYPE: RNA
<213> ORGANISM: Homo sapiens

<400> SEQUENCE: 1367
cccaucuggg guggccugug acuuu                                        25

<210> SEQ ID NO 1368
<211> LENGTH: 21
<212> TYPE: RNA
<213> ORGANISM: Homo sapiens

<400> SEQUENCE: 1368
gaagugugcc guggugguguc u                                           21

<210> SEQ ID NO 1369
<211> LENGTH: 23
<212> TYPE: RNA
<213> ORGANISM: Homo sapiens

<400> SEQUENCE: 1369
acuuacagac aagagccuug cuc                                          23

<210> SEQ ID NO 1370
<211> LENGTH: 22
<212> TYPE: RNA
<213> ORGANISM: Homo sapiens

<400> SEQUENCE: 1370
uggucuagga uuguuggagg ag                                           22

<210> SEQ ID NO 1371
<211> LENGTH: 25
<212> TYPE: RNA
<213> ORGANISM: Homo sapiens

<400> SEQUENCE: 1371
gcugggcagg gcuucugagc uccuu                                        25

<210> SEQ ID NO 1372
<211> LENGTH: 21
<212> TYPE: RNA
<213> ORGANISM: Homo sapiens

<400> SEQUENCE: 1372
uccgagccug ggucucccuc u                                            21

<210> SEQ ID NO 1373
<211> LENGTH: 23
<212> TYPE: RNA
<213> ORGANISM: Homo sapiens

<400> SEQUENCE: 1373
aaacucuacu uguccuucug agu                                          23

<210> SEQ ID NO 1374
<211> LENGTH: 21
<212> TYPE: RNA
<213> ORGANISM: Homo sapiens

<400> SEQUENCE: 1374

-continued acagucugcu gagguuggag c                                    21

<210> SEQ ID NO 1375
<211> LENGTH: 22
<212> TYPE: RNA
<213> ORGANISM: Homo sapiens

<400> SEQUENCE: 1375 aggggggaaag uucuauaguc cu                                  22

<210> SEQ ID NO 1376
<211> LENGTH: 20
<212> TYPE: RNA
<213> ORGANISM: Homo sapiens

<400> SEQUENCE: 1376
ucuaguaaga guggcagucg                                      20

<210> SEQ ID NO 1377
<211> LENGTH: 22
<212> TYPE: RNA
<213> ORGANISM: Homo sapiens

<400> SEQUENCE: 1377
aguauucugu accagggaag gu                                   22

<210> SEQ ID NO 1378
<211> LENGTH: 21
<212> TYPE: RNA
<213> ORGANISM: Homo sapiens

<400> SEQUENCE: 1378
augauccagg aaccugccuc u                                    21

<210> SEQ ID NO 1379
<211> LENGTH: 22
<212> TYPE: RNA
<213> ORGANISM: Homo sapiens

<400> SEQUENCE: 1379
gucccucucc aaaugugucu ug                                   22

<210> SEQ ID NO 1380
<211> LENGTH: 22
<212> TYPE: RNA
<213> ORGANISM: Homo sapiens

<400> SEQUENCE: 1380
aaaccugugu uguucaagag uc                                   22

<210> SEQ ID NO 1381
<211> LENGTH: 21
<212> TYPE: RNA
<213> ORGANISM: Homo sapiens

<400> SEQUENCE: 1381
aggaggcagc gcucucagga c                                    21

<210> SEQ ID NO 1382
<211> LENGTH: 22
<212> TYPE: RNA
<213> ORGANISM: Homo sapiens

<400> SEQUENCE: 1382

-continued

```
uuuaggauaa gcuugacuuu ug                                              22

<210> SEQ ID NO 1383
<211> LENGTH: 22
<212> TYPE: RNA
<213> ORGANISM: Homo sapiens

<400> SEQUENCE: 1383
auaauacaug guuaaccucu uu                                              22

<210> SEQ ID NO 1384
<211> LENGTH: 21
<212> TYPE: RNA
<213> ORGANISM: Homo sapiens

<400> SEQUENCE: 1384
aauauuauac agucaaccuc u                                               21

<210> SEQ ID NO 1385
<211> LENGTH: 22
<212> TYPE: RNA
<213> ORGANISM: Homo sapiens

<400> SEQUENCE: 1385
uacccauugc auaucggagu ug                                              22

<210> SEQ ID NO 1386
<211> LENGTH: 96
<212> TYPE: RNA
<213> ORGANISM: Homo sapiens

<400> SEQUENCE: 1386
gcgggcggcc ccgcggugca uugcuguugc auugcacgug ugugaggcgg gugcagugcc     60
ucggcagugc agcccggagc cggcccugg caccac                                96

<210> SEQ ID NO 1387
<211> LENGTH: 96
<212> TYPE: RNA
<213> ORGANISM: Homo sapiens

<400> SEQUENCE: 1387
cgggccccgg gcgggcggga gggacgggac gcggugcagu guuguuuuu ccccgccaa       60 uauugcacuc guccggccu ccggcccccc cggccc                                96

<210> SEQ ID NO 1388
<211> LENGTH: 96
<212> TYPE: RNA
<213> ORGANISM: Homo sapiens

<400> SEQUENCE: 1388
ugguacuugg agagauagua gaccguauag cguacgcuuu aucugugacg uauguaacac     60
gguccacuaa cccucaguau caaauccauc cccgag                               96

<210> SEQ ID NO 1389
<211> LENGTH: 85
<212> TYPE: RNA
<213> ORGANISM: Homo sapiens

<400> SEQUENCE: 1389
gcacauugua ggcccauuua aauguuuguu gaaugaaaaa augaaucauc aacagacauu     60
aauugggcgc cugcucugug aucuc                                           85
```

-continued

```
<210> SEQ ID NO 1390
<211> LENGTH: 97
<212> TYPE: RNA
<213> ORGANISM: Homo sapiens

<400> SEQUENCE: 1390
ugaccugaau cagguaggca guguauuguu agcuggcugc uugggucaag ucagcagcca      60
caacuacccu gccacuugcu ucuggauaaa uucuucu                              97

<210> SEQ ID NO 1391
<211> LENGTH: 97
<212> TYPE: RNA
<213> ORGANISM: Homo sapiens

<400> SEQUENCE: 1391 guggggaga gggggaagac gggaggaaag aagggagugg uuccaucacg ccuccucacu       60
ccucuccucc cgucuucucc ucccugccc uugucuc                               97

<210> SEQ ID NO 1392
<211> LENGTH: 97
<212> TYPE: RNA
<213> ORGANISM: Homo sapiens

<400> SEQUENCE: 1392
cagaucucag acaucucggg gaucaucaug ucacgagaua ccagugugca cuugugacag      60
auugauaacu gaaaggucug ggagccacuc aucuuca                              97

<210> SEQ ID NO 1393
<211> LENGTH: 106
<212> TYPE: RNA
<213> ORGANISM: Homo sapiens

<400> SEQUENCE: 1393
cccagccugg cacauuagua ggccucagua aauguuuauu agaugaauaa augaaugacu      60
caucagcaaa cauuuauugu gugccugcua aagugagcuc cacagg                    106

<210> SEQ ID NO 1394
<211> LENGTH: 97
<212> TYPE: RNA
<213> ORGANISM: Homo sapiens

<400> SEQUENCE: 1394
ugcagggagg uauuaaguug gugcaaaagu aauugugauu uuugccauua aaaguaacga      60
caaaacuggc aauuacuuuu gcaccaaacc ugguauu                              97

<210> SEQ ID NO 1395
<211> LENGTH: 97
<212> TYPE: RNA
<213> ORGANISM: Homo sapiens

<400> SEQUENCE: 1395
ugugaugugu auuagguuug ugcaaaagua auuggguuu uuugccguua aaaguaaugg       60
caaaacuggc aauuacuuuu gcaccaaacu aauauaa                              97

<210> SEQ ID NO 1396
<211> LENGTH: 97
<212> TYPE: RNA
<213> ORGANISM: Homo sapiens

<400> SEQUENCE: 1396
```

```
ccuagaaugu uauuaggucg gugcaaaagu aauugcgagu uuuaccauua cuuucaaugg    60
caaaacuggc aauuacuuuu gcaccaacgu aauacuu                             97

<210> SEQ ID NO 1397
<211> LENGTH: 97
<212> TYPE: RNA
<213> ORGANISM: Homo sapiens

<400> SEQUENCE: 1397
cagacuauau auuuagguug gcgcaaaagu aauugugguu uuggccuuua uuuucaaugg    60
caagaaccuc aguugcuuuu gugccaaccu aauacuu                             97

<210> SEQ ID NO 1398
<211> LENGTH: 97
<212> TYPE: RNA
<213> ORGANISM: Homo sapiens

<400> SEQUENCE: 1398
cauuggcauc uauuagguug gugcaaaagu aauugcgguu uuugccauua cuuucaguag    60
caaaaaucuc aauuacuuuu gcaccaacuu aauacuu                             97

<210> SEQ ID NO 1399
<211> LENGTH: 97
<212> TYPE: RNA
<213> ORGANISM: Homo sapiens

<400> SEQUENCE: 1399
aaacaaguua uauuagguug gugcaaaagu aauugugguu uuugccugua aaaguaaugg    60
caaaaaccac aguucuuuuu gcaccagacu aauaaag                             97

<210> SEQ ID NO 1400
<211> LENGTH: 97
<212> TYPE: RNA
<213> ORGANISM: Homo sapiens

<400> SEQUENCE: 1400
gagagggaag auuuagguug gugcaaaagu aauugugguu uuugccauug aaaguaaugg    60
caaaaaccac aguucuuuuu gcaccaaccu aauaaaa                             97

<210> SEQ ID NO 1401
<211> LENGTH: 96
<212> TYPE: RNA
<213> ORGANISM: Homo sapiens

<400> SEQUENCE: 1401
agacaugcaa cucaagaaua uauugagagc ucauccauag uugucacugu cucaaaucag    60
ugacaacuau ggaugagcuc uuaauauauc ccaggc                              96

<210> SEQ ID NO 1402
<211> LENGTH: 86
<212> TYPE: RNA
<213> ORGANISM: Homo sapiens

<400> SEQUENCE: 1402
cugggauaua uuaagagcuc auccauaguu gucacugauu ugagacagug acaacuaugg    60
augagcucuc aauauauucu ugaguu                                         86

<210> SEQ ID NO 1403
<211> LENGTH: 97
<212> TYPE: RNA
```

```
<213> ORGANISM: Homo sapiens

<400> SEQUENCE: 1403
ugaugcuuug cuggcuggug cagugccuga gggaguaaga gcccuguugu uguaagauag    60
ugucuuacuc ccucaggcac aucuccaaca agucucu                             97

<210> SEQ ID NO 1404
<211> LENGTH: 97
<212> TYPE: RNA
<213> ORGANISM: Homo sapiens

<400> SEQUENCE: 1404
ugaugcuuug cuggcuggug cagugccuga gggaguaaga gcccuguugu ugucagauag    60
ugucuuacuc ccucaggcac aucuccagcg agucucu                             97

<210> SEQ ID NO 1405
<211> LENGTH: 96
<212> TYPE: RNA
<213> ORGANISM: Homo sapiens

<400> SEQUENCE: 1405
ggggacugcc gggugacccu ggaaauccag aguggguggg gccagucuga ccguuucuag    60
gcgacccacu cuugguuucc aggguugccc uggaaa                              96

<210> SEQ ID NO 1406
<211> LENGTH: 96
<212> TYPE: RNA
<213> ORGANISM: Homo sapiens

<400> SEQUENCE: 1406
agaugugcuc uccuggccca ugaaaucaag cgugggugag accuggugca gaacgggaag    60
gcgacccaua cuugguuuca gaggcuguga gaauaa                              96

<210> SEQ ID NO 1407
<211> LENGTH: 96
<212> TYPE: RNA
<213> ORGANISM: Homo sapiens

<400> SEQUENCE: 1407
aaccauucaa auauaccaca guuuguuuaa ccuuuugccu guugguugaa gaugccuuuc    60
aacaggugac ugguuagaca aacugggua uauaca                               96

<210> SEQ ID NO 1408
<211> LENGTH: 68
<212> TYPE: RNA
<213> ORGANISM: Homo sapiens

<400> SEQUENCE: 1408
cuucaauuuu auuuuaaaac ggugagauuu uguuuugucu gagaaaaucu cgcuguuuua    60
gacugagg                                                             68

<210> SEQ ID NO 1409
<211> LENGTH: 96
<212> TYPE: RNA
<213> ORGANISM: Homo sapiens

<400> SEQUENCE: 1409
accugaguaa ccuuugcuag uccgacucca gccaguacug gucuuagacu ggugaugggu    60
caggguucau auuuuggcau cucucucugg gcaucu                              96
```

```
<210> SEQ ID NO 1410
<211> LENGTH: 96
<212> TYPE: RNA
<213> ORGANISM: Homo sapiens

<400> SEQUENCE: 1410
ggagugaacu cagaugugga gcacuaccuu ugugagcagu gugacccaag gccuguggac    60
aggguaagcu gaaccucuga uaaaacucug aucuau                              96

<210> SEQ ID NO 1411
<211> LENGTH: 95
<212> TYPE: RNA
<213> ORGANISM: Homo sapiens

<400> SEQUENCE: 1411
gauaguaaua agaaagauga gcucauugua auaugagcuu cauuuauaca uuucauauua    60
ccauuagcuc aucuuuuuua uuacuaccuu caaca                               95

<210> SEQ ID NO 1412
<211> LENGTH: 98
<212> TYPE: RNA
<213> ORGANISM: Homo sapiens

<400> SEQUENCE: 1412
agaaugggca aaugaacagu aaauuuggag gccuggggcc ucccugcug cuggagaagu     60 guuugcacgg gugggccuug ucuuugaaag gaggugga                            98

<210> SEQ ID NO 1413
<211> LENGTH: 94
<212> TYPE: RNA
<213> ORGANISM: Homo sapiens

<400> SEQUENCE: 1413
gugugugugu gugugugugg uuauuuuggu auaguagcuc uagacucuau uauaguuucc    60
ugagcugcug uaccaaaaua ccacaaacgg gcug                                94

<210> SEQ ID NO 1414
<211> LENGTH: 96
<212> TYPE: RNA
<213> ORGANISM: Homo sapiens

<400> SEQUENCE: 1414
gcuccaguaa caucuuaaag uaaauaugca ccaaaauuac uuuugguaaa uacaguuuug    60
gugcauauuu acuuuaggau guuacuggag cuccca                              96

<210> SEQ ID NO 1415
<211> LENGTH: 95
<212> TYPE: RNA
<213> ORGANISM: Homo sapiens

<400> SEQUENCE: 1415
uccccucugg cggcugcgca cgggccgugu gagcuauugc gguggcugg ggcagaugac     60 gcgugcgccg gccggccgcc gaggggcuac cguuc                               95

<210> SEQ ID NO 1416
<211> LENGTH: 97
<212> TYPE: RNA
<213> ORGANISM: Homo sapiens

<400> SEQUENCE: 1416
```

-continued cuucauccac cagucuucca ggaacaucaa ggaucuuaaa cuuugccaga gcuacaaagg    60
caaaguuuaa gauccuugaa guuccugggg gaaccau    97

<210> SEQ ID NO 1417
<211> LENGTH: 95
<212> TYPE: RNA
<213> ORGANISM: Homo sapiens

<400> SEQUENCE: 1417
agugaaauug cuaggucaua uggucagucu acuuuuagag uaauugugaa acuguuuuuc    60
aaaguagcug uaccauuugc acucccugug gcaau    95

<210> SEQ ID NO 1418
<211> LENGTH: 79
<212> TYPE: RNA
<213> ORGANISM: Homo sapiens

<400> SEQUENCE: 1418
agcaaagaag uguuugccc ucaggaaau gugugugcu cugauguaau uagguugaca    60
uacguuuccc ugguagcca    79

<210> SEQ ID NO 1419
<211> LENGTH: 94
<212> TYPE: RNA
<213> ORGANISM: Homo sapiens

<400> SEQUENCE: 1419
cgggcagcgg gugccaggca cggugucagc aggcaacaug gccgagaggc cggggccucc    60
gggcggcgcc guguccgcga ccgcguaccc ugac    94

<210> SEQ ID NO 1420
<211> LENGTH: 97
<212> TYPE: RNA
<213> ORGANISM: Homo sapiens

<400> SEQUENCE: 1420
ccaguggcgc aauggauaac gcgucugacu acggaucaga agauucuagg uucgacuccu    60
ggcuggcucg cgaugucugu uuugccacac uugaccc    97

<210> SEQ ID NO 1421
<211> LENGTH: 94
<212> TYPE: RNA
<213> ORGANISM: Homo sapiens

<400> SEQUENCE: 1421
gcuaggcgug guggcgggcg ccugugaucc caacuacuca ggaggcuggg gcagcagaau    60
cgcuugaacc cgggaggcga agguugcagu gagc    94

<210> SEQ ID NO 1422
<211> LENGTH: 98
<212> TYPE: RNA
<213> ORGANISM: Homo sapiens

<400> SEQUENCE: 1422
ggauucuuau aggacaguau guucuuccag gacagaacau ucuuugcuau uuuguacugg    60
aagaacaugc aaaacuaaaa aaaaaaaaag uuauugcu    98

<210> SEQ ID NO 1423
<211> LENGTH: 95
<212> TYPE: RNA

-continued

<213> ORGANISM: Homo sapiens

<400> SEQUENCE: 1423
gauauacacu auauuaugua uaaauguaua cacacuuccu auauguaucc acauauauau    60
aguguauaua uuauacaugu auaggugugu auaug    95

<210> SEQ ID NO 1424
<211> LENGTH: 96
<212> TYPE: RNA
<213> ORGANISM: Homo sapiens

<400> SEQUENCE: 1424
gguauuguua gauuauuuuu gugggacauu aacaacagca ucagaagcaa caucagcuuu    60
aguuaaugaa uccggaaag uuaagugacu uuauuu    96

<210> SEQ ID NO 1425
<211> LENGTH: 97
<212> TYPE: RNA
<213> ORGANISM: Homo sapiens

<400> SEQUENCE: 1425
cuagauaagu uauuaggugg gugcaaaggu aauugcaguu uucccauua uuuuaauugc    60 gaaaacagca auuaccuuug caccaaccug auggagu    97

<210> SEQ ID NO 1426
<211> LENGTH: 96
<212> TYPE: RNA
<213> ORGANISM: Homo sapiens

<400> SEQUENCE: 1426
ccucaguaag accaagcuca gugugccauu uccuugucug uagccauguc uagggcucu    60 ugaguuggcc aucgaguga gggccugcuu auucua    96

<210> SEQ ID NO 1427
<211> LENGTH: 95
<212> TYPE: RNA
<213> ORGANISM: Homo sapiens

<400> SEQUENCE: 1427
gucgaggccg uggcccggaa guggucgggg ccgcugcggg cggaagggcg ccugugcuuc    60
guccgcucgg cgguggccca gccaggcccg cggga    95

<210> SEQ ID NO 1428
<211> LENGTH: 99
<212> TYPE: RNA
<213> ORGANISM: Homo sapiens

<400> SEQUENCE: 1428
uuuagcgguu ucucccugaa gugaugugua acugaucagg aucuacucau gucgucuuug    60
guaaaguuau gucgcuuguc agggugagga gaguuuuug    99

<210> SEQ ID NO 1429
<211> LENGTH: 96
<212> TYPE: RNA
<213> ORGANISM: Homo sapiens

<400> SEQUENCE: 1429
gggaccugcg uggguogggg cgugugagug ugugugugug agugugugc gcuccggguc    60 cacgcucaug cacacaccca cacgcccaca cucagg    96

<210> SEQ ID NO 1430
<211> LENGTH: 94
<212> TYPE: RNA
<213> ORGANISM: Homo sapiens

<400> SEQUENCE: 1430
aauucagccc ugccacuggc uuaugucaug accuuggcu acucaggcug ucugcacaau    60
gagccaguug gacaggagca gugccacuca acuc    94

<210> SEQ ID NO 1431
<211> LENGTH: 98
<212> TYPE: RNA
<213> ORGANISM: Homo sapiens

<400> SEQUENCE: 1431
uacaauccaa cgaggauucu aauuucucca cgucuuuggu aauaagguuu ggcaaagaug    60
uggaaaaauu ggaauccuca uucgauuggu uauaacca    98

<210> SEQ ID NO 1432
<211> LENGTH: 96
<212> TYPE: RNA
<213> ORGANISM: Homo sapiens

<400> SEQUENCE: 1432 uggggagug aagaguagau aaaauauugg uaccugauga aucgaggcc agguucaau    60 acuuuaucug cucuucauuu ccccauaucu acuuac    96

<210> SEQ ID NO 1433
<211> LENGTH: 96
<212> TYPE: RNA
<213> ORGANISM: Homo sapiens

<400> SEQUENCE: 1433
agauaaaucu auagacaaaa uacaaucccg gacaacaaga agcuccuaua gcuccuguag    60
cuucuugugc ucuaggauug uauuuuguuu auauau    96

<210> SEQ ID NO 1434
<211> LENGTH: 98
<212> TYPE: RNA
<213> ORGANISM: Homo sapiens

<400> SEQUENCE: 1434
cauauuaggu uaaugcaaaa guaaucgcgg uuugugccag augacgauuu gaauuaauaa    60
auucauuugg uauaaaccgc gauuauuuuu gcaucaac    98

<210> SEQ ID NO 1435
<211> LENGTH: 97
<212> TYPE: RNA
<213> ORGANISM: Homo sapiens

<400> SEQUENCE: 1435
auaaaauuuc caauuggaac cuaaugauuc aucagacuca gauauuuaag uuaacaguau    60
uugagaauga ugaaucauua gguuccgguc agaaauu    97

<210> SEQ ID NO 1436
<211> LENGTH: 96
<212> TYPE: RNA
<213> ORGANISM: Homo sapiens

<400> SEQUENCE: 1436

```
guuaugugaa gguauucuug uguucucuag aucagugcuu uuagaaaauu ugugugaucu    60
aaagaacaca aagaauaccu acacagaacc accugc                              96

<210> SEQ ID NO 1437
<211> LENGTH: 98
<212> TYPE: RNA
<213> ORGANISM: Homo sapiens

<400> SEQUENCE: 1437
aucugugcuc uuugauuaca guuguucaac caguuacuaa ucuaacuaau uguaacuggu    60
ugaacaacug aacccaaagg gugcaaagua gaaacauu                            98

<210> SEQ ID NO 1438
<211> LENGTH: 75
<212> TYPE: RNA
<213> ORGANISM: Homo sapiens

<400> SEQUENCE: 1438
aacucacaca uuaaccaaag aggaaggucc cauuacugca gggaucuuag caguacuggg    60
accuaccucu uuggu                                                    75

<210> SEQ ID NO 1439
<211> LENGTH: 97
<212> TYPE: RNA
<213> ORGANISM: Homo sapiens

<400> SEQUENCE: 1439
uagggugacc agccauuaug guuugccugg gacugaggaa uuugcuggga uaugucaguu    60
ccaggccaac caggcugguu ggucucccug aagcaac                             97

<210> SEQ ID NO 1440
<211> LENGTH: 94
<212> TYPE: RNA
<213> ORGANISM: Homo sapiens

<400> SEQUENCE: 1440 ugggguqucu gugcuauggc agcccuagca cacagauacg cccagagaaa gccugaacgu    60
ugggcguauc uguaugcuag ggcugcugua acaa                                94

<210> SEQ ID NO 1441
<211> LENGTH: 97
<212> TYPE: RNA
<213> ORGANISM: Homo sapiens

<400> SEQUENCE: 1441 auggguaaa accauuaugc auuguauuuu uaggucccaa uacaugugggg cccuaaaaau    60 acaaugcaua augguuuuc acucuuuauc uucuuau                              97

<210> SEQ ID NO 1442
<211> LENGTH: 96
<212> TYPE: RNA
<213> ORGANISM: Homo sapiens

<400> SEQUENCE: 1442
cuccuaugca cccucuuucc auaggugaug agucacaggg cucagggaau gugucugcac    60
cugugacuca ucaccagugg aaagcccauc ccauau                              96

<210> SEQ ID NO 1443
<211> LENGTH: 83
<212> TYPE: RNA
```

```
<213> ORGANISM: Homo sapiens

<400> SEQUENCE: 1443
agcuuaggua ccaauuuggc cacaaugggu uagaacacua uuccauugug uucuuaccca    60
ccauggccaa aauugggccu aag                                           83

<210> SEQ ID NO 1444
<211> LENGTH: 99
<212> TYPE: RNA
<213> ORGANISM: Homo sapiens

<400> SEQUENCE: 1444
uccagccugu gcccagcagc cccugagaac cacgucugcu cugagcuggg uacugccugu    60
ucagaacaaa ugccgguucc cagacgcugc cagcuggcc                          99

<210> SEQ ID NO 1445
<211> LENGTH: 97
<212> TYPE: RNA
<213> ORGANISM: Homo sapiens

<400> SEQUENCE: 1445
uagccaguca gaaaugagcu uauucauaaa agugcaguau ggugaaguca aucuguaauu    60
uuauguauaa gcuagucucu gauugaaaca ugcagca                            97

<210> SEQ ID NO 1446
<211> LENGTH: 95
<212> TYPE: RNA
<213> ORGANISM: Homo sapiens

<400> SEQUENCE: 1446
ucuuaucaau gagguagacc auggguucuc auuguaauag uguagaaugu ugguuaacug    60
uggacucccu ggcucugucu caaaucuacu gauuc                              95

<210> SEQ ID NO 1447
<211> LENGTH: 97
<212> TYPE: RNA
<213> ORGANISM: Homo sapiens

<400> SEQUENCE: 1447
uauuaugcca ugacauugug ucaauaugcg augaugguu gugauggcac agcgucauca     60
cguggugacg caacaucaug acguaagacg ucacaac                            97

<210> SEQ ID NO 1448
<211> LENGTH: 100
<212> TYPE: RNA
<213> ORGANISM: Homo sapiens

<400> SEQUENCE: 1448
cccccagaau cugucaggca ccagccaggc auugcucagc ccguuccccu cuggggagc     60 aaggaguggu gcugggguug ucucugcugg gguuucuccu                         100

<210> SEQ ID NO 1449
<211> LENGTH: 89
<212> TYPE: RNA
<213> ORGANISM: Homo sapiens

<400> SEQUENCE: 1449
cuaauggaua aggcauuggc cuccuaagcc agggauugug gguucgaguc ccaucugggg    60
uggccuguga cuuuuguccu uuuuccccc                                     89
```

```
<210> SEQ ID NO 1450
<211> LENGTH: 96
<212> TYPE: RNA
<213> ORGANISM: Homo sapiens

<400> SEQUENCE: 1450
acggaagccu gcacgcauuu aacaccagca cgcucaaugu agucuuguaa ggaacagguu    60
gaagugugcc guggugeguc uggaggaagc gccugu                              96

<210> SEQ ID NO 1451
<211> LENGTH: 77
<212> TYPE: RNA
<213> ORGANISM: Homo sapiens

<400> SEQUENCE: 1451
agcacggccu cuccgaagcc ugcccggcuc ucgggaacc ugccucccgc auggcagcug     60
cugcccuucg gaggccg                                                   77

<210> SEQ ID NO 1452
<211> LENGTH: 97
<212> TYPE: RNA
<213> ORGANISM: Homo sapiens

<400> SEQUENCE: 1452
uacuuacucu acgugugugu cacucgauga ccacugugaa gacaguaaaa uguacagugg    60
uucucuugug gcucaagcgu aauguagagu acugguc                             97

<210> SEQ ID NO 1453
<211> LENGTH: 97
<212> TYPE: RNA
<213> ORGANISM: Homo sapiens

<400> SEQUENCE: 1453
gcuugaugau gcugcugaug cuggcgguga ucccgauggu gugagcugga aaugggguge    60 uacgucaucg uugucaucgu caucaucauc auccgag                             97

<210> SEQ ID NO 1454
<211> LENGTH: 95
<212> TYPE: RNA
<213> ORGANISM: Homo sapiens

<400> SEQUENCE: 1454
aaagacaugc uguccacagu guguuugaua agcugacaug ggacagggau ucuuuucacu    60
guugugucag uuuaucaaac ccauacuugg augac                               95

<210> SEQ ID NO 1455
<211> LENGTH: 98
<212> TYPE: RNA
<213> ORGANISM: Homo sapiens

<400> SEQUENCE: 1455
aagucacgug cuguggcucc agcuucauag gaaggcucuu gucugucagg caguggaguu    60
acuuacagac aagagccuug cucaggccag cccugccc                            98

<210> SEQ ID NO 1456
<211> LENGTH: 79
<212> TYPE: RNA
<213> ORGANISM: Homo sapiens

<400> SEQUENCE: 1456
```

```
ugcaugaguu cgucuuggUC uaggauuguu ggaggaguca gaaaaacuac cccagggauc    60
cugaaguccu uugggugga                                                 79

<210> SEQ ID NO 1457
<211> LENGTH: 98
<212> TYPE: RNA
<213> ORGANISM: Homo sapiens

<400> SEQUENCE: 1457
uucucacccc cgccugacac gggcgacagc ugcggcccgc uguuucacu cgggccgagu     60 gcgucuccug ucaggcaagg gagagcagag cccccug                             98

<210> SEQ ID NO 1458
<211> LENGTH: 97
<212> TYPE: RNA
<213> ORGANISM: Homo sapiens

<400> SEQUENCE: 1458
gauugaugcu guugguuugg ugcaaaagua auugcagugc uucccauuua aaaguaaugg    60
cacacacugc aauuacuuuu gcuccaacuu aauacuu                             97

<210> SEQ ID NO 1459
<211> LENGTH: 94
<212> TYPE: RNA
<213> ORGANISM: Homo sapiens

<400> SEQUENCE: 1459
agagcaucgu gcuugaccuu ccacgcucuc guguccacua gcaggcaggu uuucugacac    60
aggcugcgga auucaggaca gugcaucaug gaga                                94

<210> SEQ ID NO 1460
<211> LENGTH: 83
<212> TYPE: RNA
<213> ORGANISM: Homo sapiens

<400> SEQUENCE: 1460
gcccuagcuu gguucuaaau cccauggugc cuucuccuug ggaaaaacag agaaggcacu    60
augagauuua gaaucaaguu agg                                            83

<210> SEQ ID NO 1461
<211> LENGTH: 96
<212> TYPE: RNA
<213> ORGANISM: Homo sapiens

<400> SEQUENCE: 1461
uguauccuug guuuuagua guuuuacuau gaugaggugu gccauccacc ccaucauagu     60
aaacuacuga aaaucaaaga uacaagugcc ugacca                              96

<210> SEQ ID NO 1462
<211> LENGTH: 96
<212> TYPE: RNA
<213> ORGANISM: Homo sapiens

<400> SEQUENCE: 1462
uugccuaaag ucacacaggu uauagaucug gauuggaacc cagggagcca gacugccugg    60
guucaaaucc agaucuauaa cuugugugac uuuggg                              96

<210> SEQ ID NO 1463
<211> LENGTH: 100
<212> TYPE: RNA
```

<213> ORGANISM: Homo sapiens

<400> SEQUENCE: 1463
gggccaaggu gggccagggg uggguguuggg acagcuccgu uuaaaaaggc aucuccaaga    60
gcuuccauca aaggcugccu cuuggugcag cacagguaga    100

<210> SEQ ID NO 1464
<211> LENGTH: 95
<212> TYPE: RNA
<213> ORGANISM: Homo sapiens

<400> SEQUENCE: 1464
ugcucggcug uuccuagggu guuucucuca ucucuggucu auaaugggguu aaauaguaga    60 gaugagggca acacccuagg aacagcagag gaacc    95

<210> SEQ ID NO 1465
<211> LENGTH: 96
<212> TYPE: RNA
<213> ORGANISM: Homo sapiens

<400> SEQUENCE: 1465
ucuauuuguc uuaggugagc uaaaugugug cugggacaca uuugagccaa auguccagc    60 acacauuuag cucacauaag aaaaauggac ucuagu    96

<210> SEQ ID NO 1466
<211> LENGTH: 67
<212> TYPE: RNA
<213> ORGANISM: Homo sapiens

<400> SEQUENCE: 1466
aaaaugguga gagcguugag gggaguucca gacggagaug cgaggacccc ucggggucug    60
acccaca    67

<210> SEQ ID NO 1467
<211> LENGTH: 100
<212> TYPE: RNA
<213> ORGANISM: Homo sapiens

<400> SEQUENCE: 1467
ucccaucugg acccgcugg gcagggcuuc ugagcuccuu agcacuagca ggaggggcuc    60
caggggcccu cccuccaugg cagccaggac aggacucuca    100

<210> SEQ ID NO 1468
<211> LENGTH: 95
<212> TYPE: RNA
<213> ORGANISM: Homo sapiens

<400> SEQUENCE: 1468
ggugagugcg uuccaagug ugaagggacc cuuccuguag ugucuuauau acaauacagu    60
aggaauguuc cuucuuugcc acucauacac cuuua    95

<210> SEQ ID NO 1469
<211> LENGTH: 90
<212> TYPE: RNA
<213> ORGANISM: Homo sapiens

<400> SEQUENCE: 1469
ucuaagaaac gcaguggucu cugagccug caggggcagg ccagcccugc acugaacgcc    60
uguucuugcc agguggcaga agguugcugc    90

```
<210> SEQ ID NO 1470
<211> LENGTH: 96
<212> TYPE: RNA
<213> ORGANISM: Homo sapiens

<400> SEQUENCE: 1470
cucgggaggg gcgggagggg ggcccccggu gcucggaucu cgagggugcu uauuguucgg      60
uccgagccug ggucuccuc uucccccaa cccccc                                 96

<210> SEQ ID NO 1471
<211> LENGTH: 97
<212> TYPE: RNA
<213> ORGANISM: Homo sapiens

<400> SEQUENCE: 1471
uuagguaauu ccuccacuca aaacccuuca gugacuucca ugacaugaaa uaggaaguca      60 uuggagggu ugagcagagg aaugaccugu uuuaaaa                               97

<210> SEQ ID NO 1472
<211> LENGTH: 97
<212> TYPE: RNA
<213> ORGANISM: Homo sapiens

<400> SEQUENCE: 1472
caucauaagg agccuagacu ucccauuuga agguggccau uccuaccac cuucaaaugg      60 uaaguccagg cuccuucuga uucaauaaau gaggagc                              97

<210> SEQ ID NO 1473
<211> LENGTH: 98
<212> TYPE: RNA
<213> ORGANISM: Homo sapiens

<400> SEQUENCE: 1473
cucuuguuca cagccaaacu cuacuugucc uucugagugu aauuacguac augcaguagc      60
ucaggagaca agcagguuua cccuguggau gagucuga                             98

<210> SEQ ID NO 1474
<211> LENGTH: 99
<212> TYPE: RNA
<213> ORGANISM: Homo sapiens

<400> SEQUENCE: 1474
cgcccaccuc agccucccaa aaugcuggga uuacaggcau gagccacugc ggucgaccau      60
gaccuggaca uguuugugcc caguacuguc aguuugcag                            99

<210> SEQ ID NO 1475
<211> LENGTH: 95
<212> TYPE: RNA
<213> ORGANISM: Homo sapiens

<400> SEQUENCE: 1475
auauauaucu auaucuagcu ccguauauau auauauauau auauagauau cuccauauau      60
auggagauag auauagaaau aaaacaagca aagaa                                95

<210> SEQ ID NO 1476
<211> LENGTH: 96
<212> TYPE: RNA
<213> ORGANISM: Homo sapiens

<400> SEQUENCE: 1476
```

```
uagauugagg aaggggcuga gugguaggcg gugcugcugu gcucugauga agacccaugu    60
ggcuagcaac agcgcuuacc uuuugucucu gggucc                              96
```

<210> SEQ ID NO 1477
<211> LENGTH: 96
<212> TYPE: RNA
<213> ORGANISM: Homo sapiens

<400> SEQUENCE: 1477

```
agagaagcug acaaguacu ggcucagca gauugaggag agcaccacag uggucaucac      60
acagucugcu gagguuggag cugcugagau gacacu                              96
```

<210> SEQ ID NO 1478
<211> LENGTH: 98
<212> TYPE: RNA
<213> ORGANISM: Homo sapiens

<400> SEQUENCE: 1478

```
guacacagua gaagcauccc uugcaggggc uguugggug cauccuaagc ugugcuggag     60
cuucccgaug uacucuguag augucuuugc accuucug                            98
```

<210> SEQ ID NO 1479
<211> LENGTH: 97
<212> TYPE: RNA
<213> ORGANISM: Homo sapiens

<400> SEQUENCE: 1479

```
aaugcuguuu caagguagua ccaguaccuu guguucagug gaaccaaggu aaacacaagg    60
uauuggauau accuugagau agcauuacac cuaagug                             97
```

<210> SEQ ID NO 1480
<211> LENGTH: 85
<212> TYPE: RNA
<213> ORGANISM: Homo sapiens

<400> SEQUENCE: 1480

```
aggguagagg gaugaggggg aaaguucuau aguccuguaa uuagaucuca ggacuauaga    60 acuuccccc ucaucccucu gcccu                                           85
```

<210> SEQ ID NO 1481
<211> LENGTH: 94
<212> TYPE: RNA
<213> ORGANISM: Homo sapiens

<400> SEQUENCE: 1481

```
acugauauau uugucuuauu ugagagcuga ggaguauuuu uaugcaaucu gaaugaucuc    60
agcugucuga aaaugucuuc aauuuuaaag gcuu                                94
```

<210> SEQ ID NO 1482
<211> LENGTH: 97
<212> TYPE: RNA
<213> ORGANISM: Homo sapiens

<400> SEQUENCE: 1482

```
uacuuauuac ugguagugag ucucuaagaa aagaggaggu gguuguuuc cuccucuuuu     60 cuuugagacu cacuaccaau aauaagaaau acuacua                             97
```

<210> SEQ ID NO 1483
<211> LENGTH: 95
<212> TYPE: RNA

<213> ORGANISM: Homo sapiens

<400> SEQUENCE: 1483
auagcuguug ugucacuucc ucaugcugac auauuuacua gaggguaaaa uuaauaaccu    60
ucuaguaaga guggcagucg aagggaaggg cucau    95

<210> SEQ ID NO 1484
<211> LENGTH: 97
<212> TYPE: RNA
<213> ORGANISM: Homo sapiens

<400> SEQUENCE: 1484
ucccuuuccc aggggagggg cuggguuuac guugggagaa cuuuuacggu gaaccaggag    60
guucucccaa cguaagccca gccccucccc ucugccu    97

<210> SEQ ID NO 1485
<211> LENGTH: 97
<212> TYPE: RNA
<213> ORGANISM: Homo sapiens

<400> SEQUENCE: 1485
aacuuaacau caugcuaccu cuuuguauca uauuuuguua uucggucac agaaugaccu    60 aguauucugu accagggaag guaguucuua acuauau    97

<210> SEQ ID NO 1486
<211> LENGTH: 75
<212> TYPE: RNA
<213> ORGANISM: Homo sapiens

<400> SEQUENCE: 1486 gugggagcc ugguuagacc uggcccagac cucagcuaca caagcugaug gacugaguca    60
ggggccacac ucucc    75

<210> SEQ ID NO 1487
<211> LENGTH: 94
<212> TYPE: RNA
<213> ORGANISM: Homo sapiens

<400> SEQUENCE: 1487
cgccuccuac cgcagugcuu gacgggaggc ggagcgggga acgaggccgu cggccauuuu    60
gugucugcuu ccugugggac guggugguag ccgu    94

<210> SEQ ID NO 1488
<211> LENGTH: 98
<212> TYPE: RNA
<213> ORGANISM: Homo sapiens

<400> SEQUENCE: 1488
aaccucucuu agccucuguu ucuuuauugc gguagauacu auuaaccuaa aaugagaagg    60
cuaauaguau cuaccacaau aaaauuguug ugaggaua    98

<210> SEQ ID NO 1489
<211> LENGTH: 97
<212> TYPE: RNA
<213> ORGANISM: Homo sapiens

<400> SEQUENCE: 1489
aaacccacac cacugcauuu uggccaucga gggguugggc uuggugucau gcccaagau    60 aaccagcacc ccaacuuugg acagcaugga uuagucu    97

```
<210> SEQ ID NO 1490
<211> LENGTH: 98
<212> TYPE: RNA
<213> ORGANISM: Homo sapiens

<400> SEQUENCE: 1490
cagagaggag cugccacuug ggcacugaaa caauguccau uaggcuuugu uauggaaacu    60
ucuccugauc auuguuuugu guccauugag cuuccaau                            98

<210> SEQ ID NO 1491
<211> LENGTH: 99
<212> TYPE: RNA
<213> ORGANISM: Homo sapiens

<400> SEQUENCE: 1491
uggcggccug ggcgggagcg cgcgggcggg gccggccccg cugccuggaa uuaacccgc    60 ugugcuugcu cgucccgccc gcagcccuag gcggcgucg                          99

<210> SEQ ID NO 1492
<211> LENGTH: 99
<212> TYPE: RNA
<213> ORGANISM: Homo sapiens

<400> SEQUENCE: 1492
uggcuaaggu guuggcucgg gcuccccacu gcaguuaccc uccccucggc guuacugagc    60 acuggggcu uucgggcucu gcgucugcac agauacuuc                           99

<210> SEQ ID NO 1493
<211> LENGTH: 100
<212> TYPE: RNA
<213> ORGANISM: Homo sapiens

<400> SEQUENCE: 1493
gugagcgggc gcggcaggga ucgcgggcgg guggcggccu agggcgcgga gggcggaccg    60
ggaauggcgc gccgugcgcc gccggcguaa cugcggcgcu                         100

<210> SEQ ID NO 1494
<211> LENGTH: 98
<212> TYPE: RNA
<213> ORGANISM: Homo sapiens

<400> SEQUENCE: 1494
uggccgacgg ggcgcgcgcg gccuggaggg gcgggcgga cgcagagccg cguuuagucu    60
aucgcugcgg uugcgagcgc uguagggagc cugugcug                           98

<210> SEQ ID NO 1495
<211> LENGTH: 96
<212> TYPE: RNA
<213> ORGANISM: Homo sapiens

<400> SEQUENCE: 1495
gugacccugg gcaaguuccu gaagaucaga cacaucagau cccuuaucug uaaaaugggc    60
augauccagg aaccugccuc uacgguugcc uugggg                             96

<210> SEQ ID NO 1496
<211> LENGTH: 99
<212> TYPE: RNA
<213> ORGANISM: Homo sapiens

<400> SEQUENCE: 1496
```

```
ugggugaaag gaaggaaaga cauaggauag agucaccucu guccucuguc cucuaccuau    60
agaggugacu guccuauguc uuccuuccu cuuaccccu                            99

<210> SEQ ID NO 1497
<211> LENGTH: 97
<212> TYPE: RNA
<213> ORGANISM: Homo sapiens

<400> SEQUENCE: 1497
aucugaguug ggaggguccc ucuccaaaug ugucuugggg uggggauca agacacauuu    60 ggagagggaa ccucccaacu cggccucugc caucauu                            97

<210> SEQ ID NO 1498
<211> LENGTH: 97
<212> TYPE: RNA
<213> ORGANISM: Homo sapiens

<400> SEQUENCE: 1498
accaagugau auucauuguc uaccugagcu agaauacaag uaguuggcgu cuucagagac    60
acuuguaugc uagcucaggu agauauugaa ugaaaaa                            97

<210> SEQ ID NO 1499
<211> LENGTH: 94
<212> TYPE: RNA
<213> ORGANISM: Homo sapiens

<400> SEQUENCE: 1499
uuuuuuuuua guauuuuucc aucaguguuc auaaggaaug uugcucugua guuucuuau    60 aguguggcuu ucuuagagca aagaugguuc ccua                               94

<210> SEQ ID NO 1500
<211> LENGTH: 94
<212> TYPE: RNA
<213> ORGANISM: Homo sapiens

<400> SEQUENCE: 1500
caguuccuaa caggccucag accaguaccg gucuguggcc uggggguuga ggaccccugc    60
ucuaggcugg uacugcugau gcuuaaaaag agag                               94

<210> SEQ ID NO 1501
<211> LENGTH: 94
<212> TYPE: RNA
<213> ORGANISM: Homo sapiens

<400> SEQUENCE: 1501
gaucaggagu cugccagugg agucagcaca ccugcuuuuc accugugauc ccaggagagg    60
aagcagcugc cucugaggcc ucaggcucag uggc                               94

<210> SEQ ID NO 1502
<211> LENGTH: 96
<212> TYPE: RNA
<213> ORGANISM: Homo sapiens

<400> SEQUENCE: 1502
aggaaguguu ggccuguggc ugcacucacu uccuucagcc ccaggaagcc uuggucgggg    60
gcaggaggga gggucaggca gggcuggggg ccugac                             96

<210> SEQ ID NO 1503
<211> LENGTH: 94
<212> TYPE: RNA
```

<213> ORGANISM: Homo sapiens

<400> SEQUENCE: 1503
aucacagaca ccuccaagug ugcagggcac uggugggggc cggggcaggc ccagcgaaag    60
ugcaggaccu ggcacuuagu cggaagugag ggug                                94

<210> SEQ ID NO 1504
<211> LENGTH: 97
<212> TYPE: RNA
<213> ORGANISM: Homo sapiens

<400> SEQUENCE: 1504
ggccuagcca aauacuguau uuugaucga cauuugguug aaaaauaucu auguauuagu     60
aaaccugugu uguucaagag uccacugugu uuugcug                            97

<210> SEQ ID NO 1505
<211> LENGTH: 96
<212> TYPE: RNA
<213> ORGANISM: Homo sapiens

<400> SEQUENCE: 1505
cagugcuggg gucucaggag gcagcgcucu caggacguca ccaccauggc cugggcucug    60
cuccuccuca cccuccucac ucagggcaca ggugau                             96

<210> SEQ ID NO 1506
<211> LENGTH: 97
<212> TYPE: RNA
<213> ORGANISM: Homo sapiens

<400> SEQUENCE: 1506
aaucuaucac ugcuuuuuag gauaagcuug acuuuuguuc aaauaaaaau gcaaaaggaa    60
aguguauccu aaaaggcaau gacaguuuaa uguguuu                            97

<210> SEQ ID NO 1507
<211> LENGTH: 98
<212> TYPE: RNA
<213> ORGANISM: Homo sapiens

<400> SEQUENCE: 1507
acgaauggcu augcacugca caacccuagg agagggugcc auucacauag acuauaauug    60
aauggcgcca cuagguugu gcagugcaca accuacac                             98

<210> SEQ ID NO 1508
<211> LENGTH: 96
<212> TYPE: RNA
<213> ORGANISM: Homo sapiens

<400> SEQUENCE: 1508
uucauuccuu caguguugaa acaaucucua cugaaccagc uucaaacaag uucacuggag    60
uuuguuucaa uauugcaaga augauaagau ggaagc                             96

<210> SEQ ID NO 1509
<211> LENGTH: 81
<212> TYPE: RNA
<213> ORGANISM: Homo sapiens

<400> SEQUENCE: 1509
ggguaagugg aaagauggug ggccgcagaa caugugcuga guucgugcca uaugucugcu    60
gaccaucacc uuuagaagcc c                                             81

```
<210> SEQ ID NO 1510
<211> LENGTH: 97
<212> TYPE: RNA
<213> ORGANISM: Homo sapiens

<400> SEQUENCE: 1510
aacuaugcaa ggauauuuga ggagagguua uccguguuau guucgcuuca uucaucauga      60
auaauacaug guuaaccucu uuuugaauau cagacuc                              97

<210> SEQ ID NO 1511
<211> LENGTH: 78
<212> TYPE: RNA
<213> ORGANISM: Homo sapiens

<400> SEQUENCE: 1511
cugaaauagg uugccuguga gguguucacu uucuauauga ugaauauuau acagucaacc      60
ucuuuccgau aucgaauc                                                   78

<210> SEQ ID NO 1512
<211> LENGTH: 98
<212> TYPE: RNA
<213> ORGANISM: Homo sapiens

<400> SEQUENCE: 1512
guguaguaga gcuaggagga gaggguccug gagaagcgug gaccgguccg gguggguucc      60
ggcagguucu cacccucucu aggccccauu cuccucug                             98

<210> SEQ ID NO 1513
<211> LENGTH: 100
<212> TYPE: RNA
<213> ORGANISM: Homo sapiens

<400> SEQUENCE: 1513
gcucgguugc cgugguugcg ggcccugccc gcccgccagc ucgcugacag cacgacucag      60
ggcggaggga aguagguccg uuggucgguc gggaacgagg                          100

<210> SEQ ID NO 1514
<211> LENGTH: 97
<212> TYPE: RNA
<213> ORGANISM: Homo sapiens

<400> SEQUENCE: 1514
uaccgacccu cgauuugguu caggaccuuc ccugaaccaa ggaagaguca cagucucuuc      60
cuugguucag ggaggguccc caacaauguc cucaugg                              97

<210> SEQ ID NO 1515
<211> LENGTH: 97
<212> TYPE: RNA
<213> ORGANISM: Homo sapiens

<400> SEQUENCE: 1515
cugcuccuuc ucccauaccc auugcauauc ggaguuguga auucucaaaa caccuccugu      60
gugcauggau uacaggaggg ugagccuugu caucgug                              97

<210> SEQ ID NO 1516
<211> LENGTH: 89
<212> TYPE: RNA
<213> ORGANISM: Homo sapiens

<400> SEQUENCE: 1516
```

```
ggagaggcug ugcugugggg caggcgcagg ccugagcccu gguuucgggc ugccuggguc    60
ucuggccugc gcgugacuuu ggggguggcu                                     89

<210> SEQ ID NO 1517
<211> LENGTH: 95
<212> TYPE: RNA
<213> ORGANISM: Homo sapiens

<400> SEQUENCE: 1517
gcuguugagg cugcgcagcc aggcccugac gguggguggu cugcgggccu ucugaagguc    60
ucccacguug uggcccagca gcgcagucac guugc                               95

<210> SEQ ID NO 1518
<211> LENGTH: 93
<212> TYPE: RNA
<213> ORGANISM: Homo sapiens

<400> SEQUENCE: 1518
ccuuccggcg ucccaggcgg ggcgccgcgg gaccgcccuc gugucugugg cggugggauc    60
ccgcggccgu guuuccugg uggcccggcc aug                                  93

<210> SEQ ID NO 1519
<211> LENGTH: 21
<212> TYPE: DNA
<213> ORGANISM: Homo sapiens

<400> SEQUENCE: 1519
gtgcattgct gttgcattgc a                                              21

<210> SEQ ID NO 1520
<211> LENGTH: 21
<212> TYPE: DNA
<213> ORGANISM: Homo sapiens

<400> SEQUENCE: 1520
tattgcactc gtcccggcct c                                              21

<210> SEQ ID NO 1521
<211> LENGTH: 21
<212> TYPE: DNA
<213> ORGANISM: Homo sapiens

<400> SEQUENCE: 1521
tagtagaccg tatagcgtac g                                              21

<210> SEQ ID NO 1522
<211> LENGTH: 23
<212> TYPE: DNA
<213> ORGANISM: Homo sapiens

<400> SEQUENCE: 1522
atcaacagac attaattggg cgc                                            23

<210> SEQ ID NO 1523
<211> LENGTH: 22
<212> TYPE: DNA
<213> ORGANISM: Homo sapiens

<400> SEQUENCE: 1523
aggcagtgta ttgttagctg gc                                             22

<210> SEQ ID NO 1524
```

```
<211> LENGTH: 22
<212> TYPE: DNA
<213> ORGANISM: Homo sapiens

<400> SEQUENCE: 1524
aagacgggag gaaagaaggg ag                                              22

<210> SEQ ID NO 1525
<211> LENGTH: 22
<212> TYPE: DNA
<213> ORGANISM: Homo sapiens

<400> SEQUENCE: 1525
tcggggatca tcatgtcacg ag                                              22

<210> SEQ ID NO 1526
<211> LENGTH: 22
<212> TYPE: DNA
<213> ORGANISM: Homo sapiens

<400> SEQUENCE: 1526
tcagcaaaca tttattgtgt gc                                              22

<210> SEQ ID NO 1527
<211> LENGTH: 22
<212> TYPE: DNA
<213> ORGANISM: Homo sapiens

<400> SEQUENCE: 1527
caaaactggc aattactttt gc                                              22

<210> SEQ ID NO 1528
<211> LENGTH: 22
<212> TYPE: DNA
<213> ORGANISM: Homo sapiens

<400> SEQUENCE: 1528
caaaactggc aattactttt gc                                              22

<210> SEQ ID NO 1529
<211> LENGTH: 22
<212> TYPE: DNA
<213> ORGANISM: Homo sapiens

<400> SEQUENCE: 1529
caaaactggc aattactttt gc                                              22

<210> SEQ ID NO 1530
<211> LENGTH: 22
<212> TYPE: DNA
<213> ORGANISM: Homo sapiens

<400> SEQUENCE: 1530
caagaacctc agttgctttt gt                                              22

<210> SEQ ID NO 1531
<211> LENGTH: 22
<212> TYPE: DNA
<213> ORGANISM: Homo sapiens

<400> SEQUENCE: 1531
caaaaatctc aattacttttt gc                                             22

<210> SEQ ID NO 1532
```

```
<211> LENGTH: 22
<212> TYPE: DNA
<213> ORGANISM: Homo sapiens

<400> SEQUENCE: 1532
caaaaaccac agtttctttt gc                                      22

<210> SEQ ID NO 1533
<211> LENGTH: 22
<212> TYPE: DNA
<213> ORGANISM: Homo sapiens

<400> SEQUENCE: 1533
caaaaaccac agtttctttt gc                                      22

<210> SEQ ID NO 1534
<211> LENGTH: 21
<212> TYPE: DNA
<213> ORGANISM: Homo sapiens

<400> SEQUENCE: 1534
tgacaactat ggatgagctc t                                       21

<210> SEQ ID NO 1535
<211> LENGTH: 22
<212> TYPE: DNA
<213> ORGANISM: Homo sapiens

<400> SEQUENCE: 1535
gacaactatg gatgagctct ca                                      22

<210> SEQ ID NO 1536
<211> LENGTH: 22
<212> TYPE: DNA
<213> ORGANISM: Homo sapiens

<400> SEQUENCE: 1536
tgtcttactc cctcaggcac at                                      22

<210> SEQ ID NO 1537
<211> LENGTH: 22
<212> TYPE: DNA
<213> ORGANISM: Homo sapiens

<400> SEQUENCE: 1537
tgtcttactc cctcaggcac at                                      22

<210> SEQ ID NO 1538
<211> LENGTH: 21
<212> TYPE: DNA
<213> ORGANISM: Homo sapiens

<400> SEQUENCE: 1538
gcgacccact cttggtttcc a                                       21

<210> SEQ ID NO 1539
<211> LENGTH: 21
<212> TYPE: DNA
<213> ORGANISM: Homo sapiens

<400> SEQUENCE: 1539
gcgacccata cttggtttca g                                       21

<210> SEQ ID NO 1540
```

```
<211> LENGTH: 21
<212> TYPE: DNA
<213> ORGANISM: Homo sapiens

<400> SEQUENCE: 1540
aacaggtgac tggttagaca a                                               21

<210> SEQ ID NO 1541
<211> LENGTH: 21
<212> TYPE: DNA
<213> ORGANISM: Homo sapiens

<400> SEQUENCE: 1541
aaaacggtga gattttgttt t                                               21

<210> SEQ ID NO 1542
<211> LENGTH: 21
<212> TYPE: DNA
<213> ORGANISM: Homo sapiens

<400> SEQUENCE: 1542
gctagtcctg actcagccag t                                               21

<210> SEQ ID NO 1543
<211> LENGTH: 21
<212> TYPE: DNA
<213> ORGANISM: Homo sapiens

<400> SEQUENCE: 1543
agggtaagct gaacctctga t                                               21

<210> SEQ ID NO 1544
<211> LENGTH: 20
<212> TYPE: DNA
<213> ORGANISM: Homo sapiens

<400> SEQUENCE: 1544
gatgagctca ttgtaatatg                                                 20

<210> SEQ ID NO 1545
<211> LENGTH: 23
<212> TYPE: DNA
<213> ORGANISM: Homo sapiens

<400> SEQUENCE: 1545
gtttgcacgg gtgggccttg tct                                             23

<210> SEQ ID NO 1546
<211> LENGTH: 19
<212> TYPE: DNA
<213> ORGANISM: Homo sapiens

<400> SEQUENCE: 1546
tgagctgctg taccaaaat                                                  19

<210> SEQ ID NO 1547
<211> LENGTH: 21
<212> TYPE: DNA
<213> ORGANISM: Homo sapiens

<400> SEQUENCE: 1547
taaagtaaat atgcaccaaa a                                               21

<210> SEQ ID NO 1548
```

```
<211> LENGTH: 20
<212> TYPE: DNA
<213> ORGANISM: Homo sapiens

<400> SEQUENCE: 1548
gcgtgcgccg gccggccgcc                                              20

<210> SEQ ID NO 1549
<211> LENGTH: 22
<212> TYPE: DNA
<213> ORGANISM: Homo sapiens

<400> SEQUENCE: 1549
caaagtttaa gatccttgaa gt                                           22

<210> SEQ ID NO 1550
<211> LENGTH: 20
<212> TYPE: DNA
<213> ORGANISM: Homo sapiens

<400> SEQUENCE: 1550
aaagtagctg taccatttgc                                              20

<210> SEQ ID NO 1551
<211> LENGTH: 19
<212> TYPE: DNA
<213> ORGANISM: Homo sapiens

<400> SEQUENCE: 1551
aggttgacat acgtttccc                                               19

<210> SEQ ID NO 1552
<211> LENGTH: 19
<212> TYPE: DNA
<213> ORGANISM: Homo sapiens

<400> SEQUENCE: 1552
aggcacggtg tcagcaggc                                               19

<210> SEQ ID NO 1553
<211> LENGTH: 22
<212> TYPE: DNA
<213> ORGANISM: Homo sapiens

<400> SEQUENCE: 1553
ggctggctcg cgatgtctgt tt                                           22

<210> SEQ ID NO 1554
<211> LENGTH: 19
<212> TYPE: DNA
<213> ORGANISM: Homo sapiens

<400> SEQUENCE: 1554
gggcgcctgt gatcccaac                                               19

<210> SEQ ID NO 1555
<211> LENGTH: 23
<212> TYPE: DNA
<213> ORGANISM: Homo sapiens

<400> SEQUENCE: 1555
agtatgttct tccaggacag aac                                          23

<210> SEQ ID NO 1556
```

```
<211> LENGTH: 20
<212> TYPE: DNA
<213> ORGANISM: Homo sapiens

<400> SEQUENCE: 1556
atgtataaat gtatacacac                                              20

<210> SEQ ID NO 1557
<211> LENGTH: 21
<212> TYPE: DNA
<213> ORGANISM: Homo sapiens

<400> SEQUENCE: 1557
agttaatgaa tcctggaaag t                                            21

<210> SEQ ID NO 1558
<211> LENGTH: 22
<212> TYPE: DNA
<213> ORGANISM: Homo sapiens

<400> SEQUENCE: 1558
gaaaacagca attacctttg ca                                           22

<210> SEQ ID NO 1559
<211> LENGTH: 21
<212> TYPE: DNA
<213> ORGANISM: Homo sapiens

<400> SEQUENCE: 1559
tgagttggcc atctgagtga g                                            21

<210> SEQ ID NO 1560
<211> LENGTH: 20
<212> TYPE: DNA
<213> ORGANISM: Homo sapiens

<400> SEQUENCE: 1560
gtccgctcgg cggtggccca                                              20

<210> SEQ ID NO 1561
<211> LENGTH: 24
<212> TYPE: DNA
<213> ORGANISM: Homo sapiens

<400> SEQUENCE: 1561
ctgaagtgat gtgtaactga tcag                                         24

<210> SEQ ID NO 1562
<211> LENGTH: 21
<212> TYPE: DNA
<213> ORGANISM: Homo sapiens

<400> SEQUENCE: 1562
cacgctcatg cacacaccca c                                            21

<210> SEQ ID NO 1563
<211> LENGTH: 19
<212> TYPE: DNA
<213> ORGANISM: Homo sapiens

<400> SEQUENCE: 1563
gagccagttg gacaggagc                                               19

<210> SEQ ID NO 1564
```

```
<211> LENGTH: 23
<212> TYPE: DNA
<213> ORGANISM: Homo sapiens

<400> SEQUENCE: 1564
attctaattt ctccacgtct ttg                                               23

<210> SEQ ID NO 1565
<211> LENGTH: 21
<212> TYPE: DNA
<213> ORGANISM: Homo sapiens

<400> SEQUENCE: 1565
tagataaaat attggtacct g                                                 21

<210> SEQ ID NO 1566
<211> LENGTH: 21
<212> TYPE: DNA
<213> ORGANISM: Homo sapiens

<400> SEQUENCE: 1566
cttcttgtgc tctaggattg t                                                 21

<210> SEQ ID NO 1567
<211> LENGTH: 23
<212> TYPE: DNA
<213> ORGANISM: Homo sapiens

<400> SEQUENCE: 1567
attcatttgg tataaaccgc gat                                               23

<210> SEQ ID NO 1568
<211> LENGTH: 22
<212> TYPE: DNA
<213> ORGANISM: Homo sapiens

<400> SEQUENCE: 1568
ttgagaatga tgaatcatta gg                                                22

<210> SEQ ID NO 1569
<211> LENGTH: 21
<212> TYPE: DNA
<213> ORGANISM: Homo sapiens

<400> SEQUENCE: 1569
tcttgtgttc tctagatcag t                                                 21

<210> SEQ ID NO 1570
<211> LENGTH: 23
<212> TYPE: DNA
<213> ORGANISM: Homo sapiens

<400> SEQUENCE: 1570
ttacagttgt tcaaccagtt act                                               23

<210> SEQ ID NO 1571
<211> LENGTH: 21
<212> TYPE: DNA
<213> ORGANISM: Homo sapiens

<400> SEQUENCE: 1571
caaagaggaa ggtcccatta c                                                 21

<210> SEQ ID NO 1572
```

<211> LENGTH: 22
<212> TYPE: DNA
<213> ORGANISM: Homo sapiens

<400> SEQUENCE: 1572
ttatggtttg cctgggactg ag                                              22

<210> SEQ ID NO 1573
<211> LENGTH: 19
<212> TYPE: DNA
<213> ORGANISM: Homo sapiens

<400> SEQUENCE: 1573
tgggcgtatc tgtatgcta                                                  19

<210> SEQ ID NO 1574
<211> LENGTH: 22
<212> TYPE: DNA
<213> ORGANISM: Homo sapiens

<400> SEQUENCE: 1574
tatgcattgt atttttaggt cc                                              22

<210> SEQ ID NO 1575
<211> LENGTH: 21
<212> TYPE: DNA
<213> ORGANISM: Homo sapiens

<400> SEQUENCE: 1575
tttccatagg tgatgagtca c                                               21

<210> SEQ ID NO 1576
<211> LENGTH: 21
<212> TYPE: DNA
<213> ORGANISM: Homo sapiens

<400> SEQUENCE: 1576
ttggccacaa tgggttagaa c                                               21

<210> SEQ ID NO 1577
<211> LENGTH: 24
<212> TYPE: DNA
<213> ORGANISM: Homo sapiens

<400> SEQUENCE: 1577
tcagaacaaa tgccggttcc caga                                            24

<210> SEQ ID NO 1578
<211> LENGTH: 22
<212> TYPE: DNA
<213> ORGANISM: Homo sapiens

<400> SEQUENCE: 1578
gagcttattc ataaaagtgc ag                                              22

<210> SEQ ID NO 1579
<211> LENGTH: 20
<212> TYPE: DNA
<213> ORGANISM: Homo sapiens

<400> SEQUENCE: 1579
agaccatggg ttctcattgt                                                 20

<210> SEQ ID NO 1580

```
<211> LENGTH: 22
<212> TYPE: DNA
<213> ORGANISM: Homo sapiens

<400> SEQUENCE: 1580
ttgtgtcaat atgcgatgat gt                                              22

<210> SEQ ID NO 1581
<211> LENGTH: 25
<212> TYPE: DNA
<213> ORGANISM: Homo sapiens

<400> SEQUENCE: 1581
aggcaccagc caggcattgc tcagc                                           25

<210> SEQ ID NO 1582
<211> LENGTH: 25
<212> TYPE: DNA
<213> ORGANISM: Homo sapiens

<400> SEQUENCE: 1582
cccatctggg gtggcctgtg acttt                                           25

<210> SEQ ID NO 1583
<211> LENGTH: 21
<212> TYPE: DNA
<213> ORGANISM: Homo sapiens

<400> SEQUENCE: 1583
gaagtgtgcc gtggtgtgtc t                                               21

<210> SEQ ID NO 1584
<211> LENGTH: 21
<212> TYPE: DNA
<213> ORGANISM: Homo sapiens

<400> SEQUENCE: 1584
aagcctgccc ggctcctcgg g                                               21

<210> SEQ ID NO 1585
<211> LENGTH: 22
<212> TYPE: DNA
<213> ORGANISM: Homo sapiens

<400> SEQUENCE: 1585
tgtgtcactc gatgaccact gt                                              22

<210> SEQ ID NO 1586
<211> LENGTH: 22
<212> TYPE: DNA
<213> ORGANISM: Homo sapiens

<400> SEQUENCE: 1586
tacgtcatcg ttgtcatcgt ca                                              22

<210> SEQ ID NO 1587
<211> LENGTH: 20
<212> TYPE: DNA
<213> ORGANISM: Homo sapiens

<400> SEQUENCE: 1587
gttgtgtcag tttatcaaac                                                 20

<210> SEQ ID NO 1588
```

```
<211> LENGTH: 23
<212> TYPE: DNA
<213> ORGANISM: Homo sapiens

<400> SEQUENCE: 1588
acttacagac aagagccttg ctc                                           23

<210> SEQ ID NO 1589
<211> LENGTH: 22
<212> TYPE: DNA
<213> ORGANISM: Homo sapiens

<400> SEQUENCE: 1589
tggtctagga ttgttggagg ag                                            22

<210> SEQ ID NO 1590
<211> LENGTH: 23
<212> TYPE: DNA
<213> ORGANISM: Homo sapiens

<400> SEQUENCE: 1590
gacacgggcg acagctgcgg ccc                                           23

<210> SEQ ID NO 1591
<211> LENGTH: 22
<212> TYPE: DNA
<213> ORGANISM: Homo sapiens

<400> SEQUENCE: 1591
cacacactgc aattactttt gc                                            22

<210> SEQ ID NO 1592
<211> LENGTH: 19
<212> TYPE: DNA
<213> ORGANISM: Homo sapiens

<400> SEQUENCE: 1592
aggctgcgga attcaggac                                                19

<210> SEQ ID NO 1593
<211> LENGTH: 23
<212> TYPE: DNA
<213> ORGANISM: Homo sapiens

<400> SEQUENCE: 1593
taaatcccat ggtgccttct cct                                           23

<210> SEQ ID NO 1594
<211> LENGTH: 21
<212> TYPE: DNA
<213> ORGANISM: Homo sapiens

<400> SEQUENCE: 1594
aaactactga aaatcaaaga t                                             21

<210> SEQ ID NO 1595
<211> LENGTH: 21
<212> TYPE: DNA
<213> ORGANISM: Homo sapiens

<400> SEQUENCE: 1595
gttcaaatcc agatctataa c                                             21

<210> SEQ ID NO 1596
```

```
<211> LENGTH: 25
<212> TYPE: DNA
<213> ORGANISM: Homo sapiens

<400> SEQUENCE: 1596
aggggtggtg ttgggacagc tccgt                                        25

<210> SEQ ID NO 1597
<211> LENGTH: 20
<212> TYPE: DNA
<213> ORGANISM: Homo sapiens

<400> SEQUENCE: 1597
agggtgtttc tctcatctct                                              20

<210> SEQ ID NO 1598
<211> LENGTH: 21
<212> TYPE: DNA
<213> ORGANISM: Homo sapiens

<400> SEQUENCE: 1598
tgagctaaat gtgtgctggg a                                            21

<210> SEQ ID NO 1599
<211> LENGTH: 23
<212> TYPE: DNA
<213> ORGANISM: Homo sapiens

<400> SEQUENCE: 1599
gcgaggaccc ctcggggtct gac                                          23

<210> SEQ ID NO 1600
<211> LENGTH: 25
<212> TYPE: DNA
<213> ORGANISM: Homo sapiens

<400> SEQUENCE: 1600
gctgggcagg gcttctgagc tcctt                                        25

<210> SEQ ID NO 1601
<211> LENGTH: 20
<212> TYPE: DNA
<213> ORGANISM: Homo sapiens

<400> SEQUENCE: 1601
aggaatgttc cttctttgcc                                              20

<210> SEQ ID NO 1602
<211> LENGTH: 23
<212> TYPE: DNA
<213> ORGANISM: Homo sapiens

<400> SEQUENCE: 1602
gaacgcctgt tcttgccagg tgg                                          23

<210> SEQ ID NO 1603
<211> LENGTH: 21
<212> TYPE: DNA
<213> ORGANISM: Homo sapiens

<400> SEQUENCE: 1603
tccgagcctg ggtctccctc t                                            21

<210> SEQ ID NO 1604
```

```
<211> LENGTH: 22
<212> TYPE: DNA
<213> ORGANISM: Homo sapiens

<400> SEQUENCE: 1604
actcaaaacc cttcagtgac tt                                              22

<210> SEQ ID NO 1605
<211> LENGTH: 22
<212> TYPE: DNA
<213> ORGANISM: Homo sapiens

<400> SEQUENCE: 1605
agacttccca tttgaaggtg gc                                              22

<210> SEQ ID NO 1606
<211> LENGTH: 23
<212> TYPE: DNA
<213> ORGANISM: Homo sapiens

<400> SEQUENCE: 1606
aaactctact tgtccttctg agt                                             23

<210> SEQ ID NO 1607
<211> LENGTH: 24
<212> TYPE: DNA
<213> ORGANISM: Homo sapiens

<400> SEQUENCE: 1607
gacctggaca tgtttgtgcc cagt                                            24

<210> SEQ ID NO 1608
<211> LENGTH: 20
<212> TYPE: DNA
<213> ORGANISM: Homo sapiens

<400> SEQUENCE: 1608
atggagatag atatagaaat                                                 20

<210> SEQ ID NO 1609
<211> LENGTH: 21
<212> TYPE: DNA
<213> ORGANISM: Homo sapiens

<400> SEQUENCE: 1609
ggctagcaac agcgcttacc t                                               21

<210> SEQ ID NO 1610
<211> LENGTH: 21
<212> TYPE: DNA
<213> ORGANISM: Homo sapiens

<400> SEQUENCE: 1610
acagtctgct gaggttggag c                                               21

<210> SEQ ID NO 1611
<211> LENGTH: 23
<212> TYPE: DNA
<213> ORGANISM: Homo sapiens

<400> SEQUENCE: 1611
atcccttgca ggggctgttg ggt                                             23

<210> SEQ ID NO 1612
```

```
<211> LENGTH: 22
<212> TYPE: DNA
<213> ORGANISM: Homo sapiens

<400> SEQUENCE: 1612
tagtaccagt accttgtgtt ca                                              22

<210> SEQ ID NO 1613
<211> LENGTH: 22
<212> TYPE: DNA
<213> ORGANISM: Homo sapiens

<400> SEQUENCE: 1613 aggggggaaag ttctatagtc ct                                             22

<210> SEQ ID NO 1614
<211> LENGTH: 19
<212> TYPE: DNA
<213> ORGANISM: Homo sapiens

<400> SEQUENCE: 1614
agctgtctga aaatgtctt                                                  19

<210> SEQ ID NO 1615
<211> LENGTH: 22
<212> TYPE: DNA
<213> ORGANISM: Homo sapiens

<400> SEQUENCE: 1615
gtgagtctct aagaaaagag ga                                              22

<210> SEQ ID NO 1616
<211> LENGTH: 20
<212> TYPE: DNA
<213> ORGANISM: Homo sapiens

<400> SEQUENCE: 1616
tctagtaaga gtggcagtcg                                                 20

<210> SEQ ID NO 1617
<211> LENGTH: 22
<212> TYPE: DNA
<213> ORGANISM: Homo sapiens

<400> SEQUENCE: 1617
gttctcccaa cgtaagccca gc                                              22

<210> SEQ ID NO 1618
<211> LENGTH: 22
<212> TYPE: DNA
<213> ORGANISM: Homo sapiens

<400> SEQUENCE: 1618
agtattctgt accagggaag gt                                              22

<210> SEQ ID NO 1619
<211> LENGTH: 21
<212> TYPE: DNA
<213> ORGANISM: Homo sapiens

<400> SEQUENCE: 1619
agacctggcc cagacctcag c                                               21

<210> SEQ ID NO 1620
```

```
<211> LENGTH: 19
<212> TYPE: DNA
<213> ORGANISM: Homo sapiens

<400> SEQUENCE: 1620
gtgtctgctt cctgtggga                                           19

<210> SEQ ID NO 1621
<211> LENGTH: 23
<212> TYPE: DNA
<213> ORGANISM: Homo sapiens

<400> SEQUENCE: 1621
ctaatagtat ctaccacaat aaa                                      23

<210> SEQ ID NO 1622
<211> LENGTH: 22
<212> TYPE: DNA
<213> ORGANISM: Homo sapiens

<400> SEQUENCE: 1622
aaccagcacc ccaactttgg ac                                       22

<210> SEQ ID NO 1623
<211> LENGTH: 23
<212> TYPE: DNA
<213> ORGANISM: Homo sapiens

<400> SEQUENCE: 1623
acttgggcac tgaaacaatg tcc                                      23

<210> SEQ ID NO 1624
<211> LENGTH: 24
<212> TYPE: DNA
<213> ORGANISM: Homo sapiens

<400> SEQUENCE: 1624
tgtgcttgct cgtcccgccc gcag                                     24

<210> SEQ ID NO 1625
<211> LENGTH: 24
<212> TYPE: DNA
<213> ORGANISM: Homo sapiens

<400> SEQUENCE: 1625 actggggct ttcgggctct gcgt                                      24

<210> SEQ ID NO 1626
<211> LENGTH: 25
<212> TYPE: DNA
<213> ORGANISM: Homo sapiens

<400> SEQUENCE: 1626
agggatcgcg ggcgggtggc ggcct                                    25

<210> SEQ ID NO 1627
<211> LENGTH: 23
<212> TYPE: DNA
<213> ORGANISM: Homo sapiens

<400> SEQUENCE: 1627
atcgctgcgg ttgcgagcgc tgt                                      23

<210> SEQ ID NO 1628
```

```
<211> LENGTH: 21
<212> TYPE: DNA
<213> ORGANISM: Homo sapiens

<400> SEQUENCE: 1628
atgatccagg aacctgcctc t                                           21

<210> SEQ ID NO 1629
<211> LENGTH: 24
<212> TYPE: DNA
<213> ORGANISM: Homo sapiens

<400> SEQUENCE: 1629
aaagacatag gatagagtca cctc                                        24

<210> SEQ ID NO 1630
<211> LENGTH: 22
<212> TYPE: DNA
<213> ORGANISM: Homo sapiens

<400> SEQUENCE: 1630
gtccctctcc aaatgtgtct tg                                          22

<210> SEQ ID NO 1631
<211> LENGTH: 22
<212> TYPE: DNA
<213> ORGANISM: Homo sapiens

<400> SEQUENCE: 1631
acttgtatgc tagctcaggt ag                                          22

<210> SEQ ID NO 1632
<211> LENGTH: 19
<212> TYPE: DNA
<213> ORGANISM: Homo sapiens

<400> SEQUENCE: 1632
agtgtggctt tcttagagc                                              19

<210> SEQ ID NO 1633
<211> LENGTH: 19
<212> TYPE: DNA
<213> ORGANISM: Homo sapiens

<400> SEQUENCE: 1633
tctaggctgg tactgctga                                              19

<210> SEQ ID NO 1634
<211> LENGTH: 19
<212> TYPE: DNA
<213> ORGANISM: Homo sapiens

<400> SEQUENCE: 1634
aagcagctgc ctctgaggc                                              19

<210> SEQ ID NO 1635
<211> LENGTH: 21
<212> TYPE: DNA
<213> ORGANISM: Homo sapiens

<400> SEQUENCE: 1635
gtggctgcac tcacttcctt c                                           21

<210> SEQ ID NO 1636
```

```
<211> LENGTH: 19
<212> TYPE: DNA
<213> ORGANISM: Homo sapiens

<400> SEQUENCE: 1636
aagtgtgcag ggcactggt                                              19

<210> SEQ ID NO 1637
<211> LENGTH: 22
<212> TYPE: DNA
<213> ORGANISM: Homo sapiens

<400> SEQUENCE: 1637
aaacctgtgt tgttcaagag tc                                          22

<210> SEQ ID NO 1638
<211> LENGTH: 21
<212> TYPE: DNA
<213> ORGANISM: Homo sapiens

<400> SEQUENCE: 1638
aggaggcagc gctctcagga c                                           21

<210> SEQ ID NO 1639
<211> LENGTH: 22
<212> TYPE: DNA
<213> ORGANISM: Homo sapiens

<400> SEQUENCE: 1639
tttaggataa gcttgacttt tg                                          22

<210> SEQ ID NO 1640
<211> LENGTH: 23
<212> TYPE: DNA
<213> ORGANISM: Homo sapiens

<400> SEQUENCE: 1640
aatggcgcca ctagggttgt gca                                         23

<210> SEQ ID NO 1641
<211> LENGTH: 21
<212> TYPE: DNA
<213> ORGANISM: Homo sapiens

<400> SEQUENCE: 1641
ttgaaacaat ctctactgaa c                                           21

<210> SEQ ID NO 1642
<211> LENGTH: 22
<212> TYPE: DNA
<213> ORGANISM: Homo sapiens

<400> SEQUENCE: 1642
tggtgggccg cagaacatgt gc                                          22

<210> SEQ ID NO 1643
<211> LENGTH: 22
<212> TYPE: DNA
<213> ORGANISM: Homo sapiens

<400> SEQUENCE: 1643
ataatacatg gttaacctct tt                                          22

<210> SEQ ID NO 1644
```

```
<211> LENGTH: 21
<212> TYPE: DNA
<213> ORGANISM: Homo sapiens

<400> SEQUENCE: 1644
aatattatac agtcaacctc t                                              21

<210> SEQ ID NO 1645
<211> LENGTH: 23
<212> TYPE: DNA
<213> ORGANISM: Homo sapiens

<400> SEQUENCE: 1645
ggcaggttct caccctctct agg                                            23

<210> SEQ ID NO 1646
<211> LENGTH: 25
<212> TYPE: DNA
<213> ORGANISM: Homo sapiens

<400> SEQUENCE: 1646
ggcggaggga agtaggtccg ttggt                                          25

<210> SEQ ID NO 1647
<211> LENGTH: 22
<212> TYPE: DNA
<213> ORGANISM: Homo sapiens

<400> SEQUENCE: 1647
cttggttcag ggagggtccc ca                                             22

<210> SEQ ID NO 1648
<211> LENGTH: 22
<212> TYPE: DNA
<213> ORGANISM: Homo sapiens

<400> SEQUENCE: 1648
tacccattgc atatcggagt tg                                             22

<210> SEQ ID NO 1649
<211> LENGTH: 24
<212> TYPE: DNA
<213> ORGANISM: Homo sapiens

<400> SEQUENCE: 1649
tgcctgggtc tctggcctgc gcgt                                           24

<210> SEQ ID NO 1650
<211> LENGTH: 21
<212> TYPE: DNA
<213> ORGANISM: Homo sapiens

<400> SEQUENCE: 1650
tcccacgttg tggcccagca g                                              21

<210> SEQ ID NO 1651
<211> LENGTH: 22
<212> TYPE: DNA
<213> ORGANISM: Homo sapiens

<400> SEQUENCE: 1651
aggcggggcg ccgcgggacc gc                                             22

<210> SEQ ID NO 1652
```

<211> LENGTH: 59
<212> TYPE: DNA
<213> ORGANISM: Homo sapiens

<400> SEQUENCE: 1652
aaaaaaaatc ttcatgatgt gtattgagcg gtacgcccag ttgccaccat gactgagtc    59

<210> SEQ ID NO 1653
<211> LENGTH: 62
<212> TYPE: DNA
<213> ORGANISM: Homo sapiens

<400> SEQUENCE: 1653
aaaaaatgta tcagaaaagt ttgattacct agaaagtgtg tatagaaact gcaaataaac    60
gt    62

<210> SEQ ID NO 1654
<211> LENGTH: 61
<212> TYPE: DNA
<213> ORGANISM: Homo sapiens

<400> SEQUENCE: 1654
aaactatggc tttaaactac cctccagagt gtgcagactg atgggacatc aaatttgcca    60
c    61

<210> SEQ ID NO 1655
<211> LENGTH: 61
<212> TYPE: DNA
<213> ORGANISM: Homo sapiens

<400> SEQUENCE: 1655
aaactgaata gttcaggaga ctttacaaac ctttgtttca actttcttat ctggaaataa    60
t    61

<210> SEQ ID NO 1656
<211> LENGTH: 59
<212> TYPE: DNA
<213> ORGANISM: Homo sapiens

<400> SEQUENCE: 1656
aaagtagctt cctccaaccc gcagcctctc tgcacactaa taaaacatgt ggcttggaa    59

<210> SEQ ID NO 1657
<211> LENGTH: 62
<212> TYPE: DNA
<213> ORGANISM: Homo sapiens

<400> SEQUENCE: 1657
aaatacctgt ttctttggga cattccgtcc tgatgatttt tattttgtt ggttttatt    60 tt    62

<210> SEQ ID NO 1658
<211> LENGTH: 61
<212> TYPE: DNA
<213> ORGANISM: Homo sapiens

<400> SEQUENCE: 1658
aaatgacgac agtagtaaag gctgattcaa aattatggaa aactttctga gggctgggaa    60
a    61

<210> SEQ ID NO 1659

```
<211> LENGTH: 61
<212> TYPE: DNA
<213> ORGANISM: Homo sapiens

<400> SEQUENCE: 1659
aaatttaatt ctgtggggaa aaattattga gccagttgtc agtgttctgt tacatgactg    60
g                                                                   61

<210> SEQ ID NO 1660
<211> LENGTH: 62
<212> TYPE: DNA
<213> ORGANISM: Homo sapiens

<400> SEQUENCE: 1660
aacactatcc atgcattact tactggtaat tacctgctgg tatataattc catgtagcct    60
tt                                                                  62

<210> SEQ ID NO 1661
<211> LENGTH: 62
<212> TYPE: DNA
<213> ORGANISM: Homo sapiens

<400> SEQUENCE: 1661
aacccaggcc agacagagca tctcttttt ttttttttga gacagagtct ctgtcgccca    60
gg                                                                  62

<210> SEQ ID NO 1662
<211> LENGTH: 61
<212> TYPE: DNA
<213> ORGANISM: Homo sapiens

<400> SEQUENCE: 1662
aagaagtaaa ctggatactg tactgatact attcaatgca atgcaattca atgcaatgaa    60
a                                                                   61

<210> SEQ ID NO 1663
<211> LENGTH: 65
<212> TYPE: DNA
<213> ORGANISM: Homo sapiens

<400> SEQUENCE: 1663
aagacgacgt ggcacacatt ccacgtgggt gctgccgcca ccccagtcgg tcgtggcgtg    60
cagct                                                               65

<210> SEQ ID NO 1664
<211> LENGTH: 62
<212> TYPE: DNA
<213> ORGANISM: Homo sapiens

<400> SEQUENCE: 1664
aagaggaggg agagtcagag agagtgtgta tgggtgtgtg tgagtgtgag tgtgtgtgta    60
cg                                                                  62

<210> SEQ ID NO 1665
<211> LENGTH: 61
<212> TYPE: DNA
<213> ORGANISM: Homo sapiens

<400> SEQUENCE: 1665
aagagtttac ttttgcaagt catttggtct tcagtctact actgaggaat agagaggcac    60
```

<210> SEQ ID NO 1666
<211> LENGTH: 62
<212> TYPE: DNA
<213> ORGANISM: Homo sapiens

<400> SEQUENCE: 1666
aagtgagtag ctcacgcagc aacgttttta ataggatttt tagacactga gggtcactcc    60
aa                                                                  62

<210> SEQ ID NO 1667
<211> LENGTH: 60
<212> TYPE: DNA
<213> ORGANISM: Homo sapiens

<400> SEQUENCE: 1667
aatcatgcca ctactcacca gtgttgttca ccaacaccca cccccacaca caccaacatt    60

<210> SEQ ID NO 1668
<211> LENGTH: 62
<212> TYPE: DNA
<213> ORGANISM: Homo sapiens

<400> SEQUENCE: 1668
aatcttgcat ggcattaatt gttccttgct tttatagttg tattttgtac attttggatt    60
tc                                                                  62

<210> SEQ ID NO 1669
<211> LENGTH: 61
<212> TYPE: DNA
<213> ORGANISM: Homo sapiens

<400> SEQUENCE: 1669
aattaacatc gtgggtcact acagggagaa aatccaggtc atgcagttcc tggcccatca    60
a                                                                   61

<210> SEQ ID NO 1670
<211> LENGTH: 61
<212> TYPE: DNA
<213> ORGANISM: Homo sapiens

<400> SEQUENCE: 1670
acaaaaaaaa aattagctgg gtgtggtggc agtcacctgt agtcccagct acttgggagg    60
c                                                                   61

<210> SEQ ID NO 1671
<211> LENGTH: 62
<212> TYPE: DNA
<213> ORGANISM: Homo sapiens

<400> SEQUENCE: 1671
acaagtatcc ttgttgagta ccaagtgcta cagaaaccat aagataaaaa tactttctac    60
ct                                                                  62

<210> SEQ ID NO 1672
<211> LENGTH: 65
<212> TYPE: DNA
<213> ORGANISM: Homo sapiens

<400> SEQUENCE: 1672

```
acacccttgg gcctctgttt gtcccctttc cagtcctcca ccccacccct ggagcccagc    60
ctggg                                                                65
```

<210> SEQ ID NO 1673
<211> LENGTH: 52
<212> TYPE: DNA
<213> ORGANISM: Homo sapiens

<400> SEQUENCE: 1673

```
acataagagg ctgccgtagt taatccaccc caacggccgg aggagccgcc gg            52
```

<210> SEQ ID NO 1674
<211> LENGTH: 62
<212> TYPE: DNA
<213> ORGANISM: Homo sapiens

<400> SEQUENCE: 1674

```
acccacccat atcatcaaca gcctctaaag gctcagaggg aatctgcctt gcagctctac    60
tc                                                                   62
```

<210> SEQ ID NO 1675
<211> LENGTH: 62
<212> TYPE: DNA
<213> ORGANISM: Homo sapiens

<400> SEQUENCE: 1675

```
acctcctttt cttctagctt tgttgtcctc ccaggaacca aaaaccccca gctattttct    60
ga                                                                   62
```

<210> SEQ ID NO 1676
<211> LENGTH: 63
<212> TYPE: DNA
<213> ORGANISM: Homo sapiens

<400> SEQUENCE: 1676

```
acctctttcg ttccttctag aaggtctgga ggacgtagag ttattgaaaa tgcagatggt    60
tct                                                                  63
```

<210> SEQ ID NO 1677
<211> LENGTH: 59
<212> TYPE: DNA
<213> ORGANISM: Homo sapiens

<400> SEQUENCE: 1677

```
acgcactgac tttgatattc caggcacacg gactggctat ttatcaccac ttcttttc      59
```

<210> SEQ ID NO 1678
<211> LENGTH: 61
<212> TYPE: DNA
<213> ORGANISM: Homo sapiens

<400> SEQUENCE: 1678

```
actattacct gggtatttat ccactaatga gtcacaagaa aaggagtgga tttggtaaga    60
a                                                                    61
```

<210> SEQ ID NO 1679
<211> LENGTH: 63
<212> TYPE: DNA
<213> ORGANISM: Homo sapiens

<400> SEQUENCE: 1679
acttaaggtc gggatgcctt tttttccatg taaggaaatg aaaagaccaa aatcttcagg    60
caa                                                                 63

<210> SEQ ID NO 1680
<211> LENGTH: 63
<212> TYPE: DNA
<213> ORGANISM: Homo sapiens

<400> SEQUENCE: 1680 agaaagggc tagagctgcc ttttacaact gtaaccactg taatgagaag gcacaggaga    60
ccc                                                                 63

<210> SEQ ID NO 1681
<211> LENGTH: 61
<212> TYPE: DNA
<213> ORGANISM: Homo sapiens

<400> SEQUENCE: 1681 agaaatatg cagaataact ggtcttgtta agagtgcaat attatatttt tatgtaaaaa    60
t                                                                   61

<210> SEQ ID NO 1682
<211> LENGTH: 64
<212> TYPE: DNA
<213> ORGANISM: Homo sapiens

<400> SEQUENCE: 1682
agaatggagc agcagcagga cagaccccca cgaggccccc cagagaggag gaagatccca    60
cgga                                                                64

<210> SEQ ID NO 1683
<211> LENGTH: 62
<212> TYPE: DNA
<213> ORGANISM: Homo sapiens

<400> SEQUENCE: 1683
agacatcttt cagtttcatg attaaggatt gttgctgttt tatagttact ctgttcatca    60
ca                                                                  62

<210> SEQ ID NO 1684
<211> LENGTH: 61
<212> TYPE: DNA
<213> ORGANISM: Homo sapiens

<400> SEQUENCE: 1684
agagacacta cacttcccgt gcagactcag atgccaactc aaagtgcctt agcccaggtt    60
c                                                                   61

<210> SEQ ID NO 1685
<211> LENGTH: 63
<212> TYPE: DNA
<213> ORGANISM: Homo sapiens

<400> SEQUENCE: 1685
agccacatct actgaggcct catgctgctc ttgctctgta agacacggag cccagaaacc    60
cat                                                                 63

<210> SEQ ID NO 1686
<211> LENGTH: 60
<212> TYPE: DNA

<213> ORGANISM: Homo sapiens

<400> SEQUENCE: 1686
agctttttta aagtaaaaaa aaaaaaagag aggacacaaa accaaatgtt actgctcaac    60

<210> SEQ ID NO 1687
<211> LENGTH: 61
<212> TYPE: DNA
<213> ORGANISM: Homo sapiens

<400> SEQUENCE: 1687
aggaaaatgc cctgtcccta gctcacactc atccacactt aagccctcgt gcacacacac    60
a    61

<210> SEQ ID NO 1688
<211> LENGTH: 64
<212> TYPE: DNA
<213> ORGANISM: Homo sapiens

<400> SEQUENCE: 1688
aggaaactga tgacctgaga ccaagagtct tgttgatgtt ctgacttaga taaaggtttt    60
gatc    64

<210> SEQ ID NO 1689
<211> LENGTH: 60
<212> TYPE: DNA
<213> ORGANISM: Homo sapiens

<400> SEQUENCE: 1689
aggcagcagg cttaggcctt ccctgcaacc ccaacaccca caagtttgtt tctctaggaa    60

<210> SEQ ID NO 1690
<211> LENGTH: 59
<212> TYPE: DNA
<213> ORGANISM: Homo sapiens

<400> SEQUENCE: 1690
aggccctggg cgcagctgaa gcctggacgc agccacacag tggccggggc tgaagccac    59

<210> SEQ ID NO 1691
<211> LENGTH: 59
<212> TYPE: DNA
<213> ORGANISM: Homo sapiens

<400> SEQUENCE: 1691
aggtttcata attggttcta cgacccgtttt gagcctagaa ttattgttct tatataaga    59

<210> SEQ ID NO 1692
<211> LENGTH: 64
<212> TYPE: DNA
<213> ORGANISM: Homo sapiens

<400> SEQUENCE: 1692
agtggccatt tacactgaat gagttgcatt ctgataatgt cttatctctt atacgtagaa    60
taaa    64

<210> SEQ ID NO 1693
<211> LENGTH: 62
<212> TYPE: DNA
<213> ORGANISM: Homo sapiens

<400> SEQUENCE: 1693

```
agtgtgtacc ttttaaaatt attccctctc aacaaaactt tataggcagt cttctgcaga    60
ct                                                                  62

<210> SEQ ID NO 1694
<211> LENGTH: 61
<212> TYPE: DNA
<213> ORGANISM: Homo sapiens

<400> SEQUENCE: 1694
agtttatgat tgaatttta agcaaattac tgtatttgaa actacaactt gatttggttt    60
t                                                                   61

<210> SEQ ID NO 1695
<211> LENGTH: 62
<212> TYPE: DNA
<213> ORGANISM: Homo sapiens

<400> SEQUENCE: 1695
agtttcacat tcaatatggt aggagttgaa acaagggaga aatgctgtgg tttgaagtgg    60
tt                                                                  62

<210> SEQ ID NO 1696
<211> LENGTH: 62
<212> TYPE: DNA
<213> ORGANISM: Homo sapiens

<400> SEQUENCE: 1696
ataagaggag ggagagtcag agagagtgtg tatgggtgtg tgtgagtgtg agtgtgtgtg    60
ta                                                                  62

<210> SEQ ID NO 1697
<211> LENGTH: 65
<212> TYPE: DNA
<213> ORGANISM: Homo sapiens

<400> SEQUENCE: 1697
atagaaagag cctaggagac aaaagggcca gtcccctgc ccagaatgga gcagcagcag     60
gacag                                                               65

<210> SEQ ID NO 1698
<211> LENGTH: 61
<212> TYPE: DNA
<213> ORGANISM: Homo sapiens

<400> SEQUENCE: 1698
atattctaaa aagtcaaaac gttaacaata gttttatct aataaaagca ctgcaagaaa     60
a                                                                   61

<210> SEQ ID NO 1699
<211> LENGTH: 61
<212> TYPE: DNA
<213> ORGANISM: Homo sapiens

<400> SEQUENCE: 1699
atatttcccc ttggacactt ggttagacgc cttccaggtc aggatgcaca tttctggatt    60
g                                                                   61

<210> SEQ ID NO 1700
<211> LENGTH: 61
<212> TYPE: DNA
<213> ORGANISM: Homo sapiens
```

```
<400> SEQUENCE: 1700
atctctatgt ggacagagga tgatttctgc caatatggaa aagcttttt ctcactgtag    60 g                                                                  61

<210> SEQ ID NO 1701
<211> LENGTH: 62
<212> TYPE: DNA
<213> ORGANISM: Homo sapiens

<400> SEQUENCE: 1701
atctgaattt taaacatgc tgtttatgac acaatgacac atttgttgca ccaattaagt    60
gt                                                                 62

<210> SEQ ID NO 1702
<211> LENGTH: 61
<212> TYPE: DNA
<213> ORGANISM: Homo sapiens

<400> SEQUENCE: 1702
atgaaaatga gttgtgaaag ttttgagtag atattacttt atcacttttt gaactaagaa    60
a                                                                   61

<210> SEQ ID NO 1703
<211> LENGTH: 61
<212> TYPE: DNA
<213> ORGANISM: Homo sapiens

<400> SEQUENCE: 1703
atgccagggg tactgaatct gcaaagcaaa tgagcagcca aggaccagca tctgtccgca    60
t                                                                   61

<210> SEQ ID NO 1704
<211> LENGTH: 60
<212> TYPE: DNA
<213> ORGANISM: Homo sapiens

<400> SEQUENCE: 1704
attaaatcaa aattaattca tccaataccc ctttactaga agttttacta gaaaatgtat    60

<210> SEQ ID NO 1705
<211> LENGTH: 62
<212> TYPE: DNA
<213> ORGANISM: Homo sapiens

<400> SEQUENCE: 1705
attattacag ttccacatca aggccgagtg caccgcccac cactgccacg gcctttgacc    60
at                                                                  62

<210> SEQ ID NO 1706
<211> LENGTH: 62
<212> TYPE: DNA
<213> ORGANISM: Homo sapiens

<400> SEQUENCE: 1706 attattttt tctttttaa ctaataaggc gagaagaggg aagttggaga gggaaaagtt    60
ag                                                                  62

<210> SEQ ID NO 1707
<211> LENGTH: 63
```

```
<212> TYPE: DNA
<213> ORGANISM: Homo sapiens

<400> SEQUENCE: 1707
attcaaacca attcacccag aaaaaagacc aataggtgca aaaataaaag gaaaaccagt    60
gaa                                                                 63

<210> SEQ ID NO 1708
<211> LENGTH: 62
<212> TYPE: DNA
<213> ORGANISM: Homo sapiens

<400> SEQUENCE: 1708
attcttgcat ctggccttag aaatgtgaag ttatattctc aagtttattt ttttccaagt    60
gt                                                                  62

<210> SEQ ID NO 1709
<211> LENGTH: 61
<212> TYPE: DNA
<213> ORGANISM: Homo sapiens

<400> SEQUENCE: 1709
attgaggcca aagggctgat cagaattgcc tttataatat atttgatgga tgcctataaa    60
t                                                                   61

<210> SEQ ID NO 1710
<211> LENGTH: 59
<212> TYPE: DNA
<213> ORGANISM: Homo sapiens

<400> SEQUENCE: 1710
atttgactcg ggccttagaa ctttgcatag cagctgctac tagctctttg agataatac     59

<210> SEQ ID NO 1711
<211> LENGTH: 61
<212> TYPE: DNA
<213> ORGANISM: Homo sapiens

<400> SEQUENCE: 1711
atttttctga acacctatgc aggtcttatt tacagtagtt actaagggaa cacacaaaga    60
a                                                                   61

<210> SEQ ID NO 1712
<211> LENGTH: 62
<212> TYPE: DNA
<213> ORGANISM: Homo sapiens

<400> SEQUENCE: 1712
caaagcgatg tcagagggcg gttttgagct ttctataagc tatagctttg tttatttcac    60
cc                                                                  62

<210> SEQ ID NO 1713
<211> LENGTH: 62
<212> TYPE: DNA
<213> ORGANISM: Homo sapiens

<400> SEQUENCE: 1713
caccatggcc ccctcatcat agcaataaca ttcccactgc caggggttct tgagccagcc    60
ag                                                                  62
```

```
<210> SEQ ID NO 1714
<211> LENGTH: 65
<212> TYPE: DNA
<213> ORGANISM: Homo sapiens

<400> SEQUENCE: 1714
cacctgcttc ccagcttcac aataaacggc tgcgtctcct ccgcacacct gtggtgcctg    60
ccacc                                                                65

<210> SEQ ID NO 1715
<211> LENGTH: 61
<212> TYPE: DNA
<213> ORGANISM: Homo sapiens

<400> SEQUENCE: 1715
cacttcgagt tgttggccag ccagttaaag ctgtgggtcg aagagggaa atgttaactg     60 g                                                                    61

<210> SEQ ID NO 1716
<211> LENGTH: 62
<212> TYPE: DNA
<213> ORGANISM: Homo sapiens

<400> SEQUENCE: 1716
cactttggac cttacgatca ggcacaggtc aggggtgaca cagactcatc ctgaacagca    60
tg                                                                   62

<210> SEQ ID NO 1717
<211> LENGTH: 61
<212> TYPE: DNA
<213> ORGANISM: Homo sapiens

<400> SEQUENCE: 1717
cagctggact gcattgaagg cgaggctgcc ccttggatca agcagaaaac aagagaaaga    60
a                                                                    61

<210> SEQ ID NO 1718
<211> LENGTH: 62
<212> TYPE: DNA
<213> ORGANISM: Homo sapiens

<400> SEQUENCE: 1718
cagtgtgtaa gctaaacaaa aactaaaact aagaattctc aaaaaaactt gttcaaaaca    60
gg                                                                   62

<210> SEQ ID NO 1719
<211> LENGTH: 63
<212> TYPE: DNA
<213> ORGANISM: Homo sapiens

<400> SEQUENCE: 1719
catagagttt aacacaagtc ctgtgaattt cttcactgtt gaaaattatt ttaaacaaaa    60
tag                                                                  63

<210> SEQ ID NO 1720
<211> LENGTH: 59
<212> TYPE: DNA
<213> ORGANISM: Homo sapiens

<400> SEQUENCE: 1720
catccagcag gttgggttct agggctgaac caggcgccag gctccagagg acgaaggga     59
```

<210> SEQ ID NO 1721
<211> LENGTH: 65
<212> TYPE: DNA
<213> ORGANISM: Homo sapiens

<400> SEQUENCE: 1721
catcttttgg caggaggagg atgcttcctt ggctctgtgc ccagacccgc ctggtcccca    60
ggtct    65

<210> SEQ ID NO 1722
<211> LENGTH: 63
<212> TYPE: DNA
<213> ORGANISM: Homo sapiens

<400> SEQUENCE: 1722
catgtcttat gtgtgtcctg aaaaaataag agcctgccca agactttggg cctcttgaca    60
gaa    63

<210> SEQ ID NO 1723
<211> LENGTH: 63
<212> TYPE: DNA
<213> ORGANISM: Homo sapiens

<400> SEQUENCE: 1723
catgttcatt gggccctttc acacccaca gtgataaatg aaaaggatag aggtagtttt    60
ttc    63

<210> SEQ ID NO 1724
<211> LENGTH: 61
<212> TYPE: DNA
<213> ORGANISM: Homo sapiens

<400> SEQUENCE: 1724
catttgattg aaaaaaatca acaaaaaata aacaccgttt actcttagac aaggacaagt    60
t    61

<210> SEQ ID NO 1725
<211> LENGTH: 62
<212> TYPE: DNA
<213> ORGANISM: Homo sapiens

<400> SEQUENCE: 1725
ccaagtggag cctgacagcc agaactctgt gtccccgtc taaccacagc tccttttcca    60
ga    62

<210> SEQ ID NO 1726
<211> LENGTH: 62
<212> TYPE: DNA
<213> ORGANISM: Homo sapiens

<400> SEQUENCE: 1726
cccaggagcc taatagggta ggcccaaatc tctgtttgct gaggaggtca ttgccatcca    60
ta    62

<210> SEQ ID NO 1727
<211> LENGTH: 62
<212> TYPE: DNA
<213> ORGANISM: Homo sapiens

<400> SEQUENCE: 1727

```
cccccatctc atgccctgg ctgggacgtg gctcagccag cacttgtcca gctgagcgcc    60
ag                                                                  62

<210> SEQ ID NO 1728
<211> LENGTH: 60
<212> TYPE: DNA
<213> ORGANISM: Homo sapiens

<400> SEQUENCE: 1728
ccccccagtt atgccttcca agaggaactt cagacacaaa agtccactga tgcaaattgg    60

<210> SEQ ID NO 1729
<211> LENGTH: 62
<212> TYPE: DNA
<213> ORGANISM: Homo sapiens

<400> SEQUENCE: 1729
ccctccagca caaacacaag gtcatggcca cactgtgaca cactacacca cacacaacag    60
cc                                                                  62

<210> SEQ ID NO 1730
<211> LENGTH: 63
<212> TYPE: DNA
<213> ORGANISM: Homo sapiens

<400> SEQUENCE: 1730
ccctggttac attactatat gaaggcagtg atttgaaatg aaaattcctt tcctcttgga    60
agc                                                                 63

<210> SEQ ID NO 1731
<211> LENGTH: 61
<212> TYPE: DNA
<213> ORGANISM: Homo sapiens

<400> SEQUENCE: 1731
ccgcctggat gcggatggcc ggagaggacc ggcggctcgg aggaagcccc caccgtgggc    60
a                                                                   61

<210> SEQ ID NO 1732
<211> LENGTH: 63
<212> TYPE: DNA
<213> ORGANISM: Homo sapiens

<400> SEQUENCE: 1732
cctatgtatg tgttatctgg ccatcccaac ccaaactgtt gaagtttgta gtaacttcag    60
tga                                                                 63

<210> SEQ ID NO 1733
<211> LENGTH: 65
<212> TYPE: DNA
<213> ORGANISM: Homo sapiens

<400> SEQUENCE: 1733
cctgctcccg gaaccggacg gcacagggcg ttcttgccca ccccaggggc caggcttgcg    60
gaggg                                                               65

<210> SEQ ID NO 1734
<211> LENGTH: 62
<212> TYPE: DNA
<213> ORGANISM: Homo sapiens
```

<400> SEQUENCE: 1734
cctggatgac agagcgagac tccgcctcaa aaaagaata caaatgctcc aacattattt    60
tt    62

<210> SEQ ID NO 1735
<211> LENGTH: 61
<212> TYPE: DNA
<213> ORGANISM: Homo sapiens

<400> SEQUENCE: 1735
cctggtccag cctcgcctcc cagactctgc acctgctagc acagctgtcc acgtctgtgt    60
g    61

<210> SEQ ID NO 1736
<211> LENGTH: 60
<212> TYPE: DNA
<213> ORGANISM: Homo sapiens

<400> SEQUENCE: 1736
cgaccagagg agccttttta aaacacatgt ttttatacaa aataagaacg aggattttaa    60

<210> SEQ ID NO 1737
<211> LENGTH: 61
<212> TYPE: DNA
<213> ORGANISM: Homo sapiens

<400> SEQUENCE: 1737
ctacttcctg tctgcatgcc caaggcttct gaagcagcca atgtcgatgc aacaacattt    60
g    61

<210> SEQ ID NO 1738
<211> LENGTH: 65
<212> TYPE: DNA
<213> ORGANISM: Homo sapiens

<400> SEQUENCE: 1738
ctcatgttct taccttctat taatagagta cttgagccag atggactaac tggtctcaca    60
ttttc    65

<210> SEQ ID NO 1739
<211> LENGTH: 62
<212> TYPE: DNA
<213> ORGANISM: Homo sapiens

<400> SEQUENCE: 1739
ctcatttggt cagcctagca tgcaaccagt ggtgtgctgg taaaatgttt aacaaccagc    60
tc    62

<210> SEQ ID NO 1740
<211> LENGTH: 61
<212> TYPE: DNA
<213> ORGANISM: Homo sapiens

<400> SEQUENCE: 1740
ctctacctaa aagttggtta aaaatgcaat tggcattaac aaggaaaaat actgaattag    60
t    61

<210> SEQ ID NO 1741
<211> LENGTH: 62

```
<212> TYPE: DNA
<213> ORGANISM: Homo sapiens

<400> SEQUENCE: 1741
ctctggatca ggcagatata aactttctag cgcattttga gagagggctt tcttgggtga      60
gg                                                                    62

<210> SEQ ID NO 1742
<211> LENGTH: 62
<212> TYPE: DNA
<213> ORGANISM: Homo sapiens

<400> SEQUENCE: 1742
ctgagcttgc aatgccgcca agcgcccccc gccagcccgc ccccggttgt ccacctcccg      60
cg                                                                    62

<210> SEQ ID NO 1743
<211> LENGTH: 63
<212> TYPE: DNA
<213> ORGANISM: Homo sapiens

<400> SEQUENCE: 1743
ctgataaaaa atattttagg ataattgcct acagagggat ttattttat gatgctggaa       60 ata                                                                   63

<210> SEQ ID NO 1744
<211> LENGTH: 59
<212> TYPE: DNA
<213> ORGANISM: Homo sapiens

<400> SEQUENCE: 1744
ctggcagagg aagaaggaag gcagacatct ccgcagccac tcctgggcct tttatgtgc       59

<210> SEQ ID NO 1745
<211> LENGTH: 63
<212> TYPE: DNA
<213> ORGANISM: Homo sapiens

<400> SEQUENCE: 1745
ctgtatccat taaagtaact ttttaacta tgagaattag aaaataaggg acaacagggg       60
tta                                                                   63

<210> SEQ ID NO 1746
<211> LENGTH: 61
<212> TYPE: DNA
<213> ORGANISM: Homo sapiens

<400> SEQUENCE: 1746
ctgtattagc tggaaatcat caggaaccca gcttgcctcc atctctctga gatgtgctgg      60
g                                                                     61

<210> SEQ ID NO 1747
<211> LENGTH: 62
<212> TYPE: DNA
<213> ORGANISM: Homo sapiens

<400> SEQUENCE: 1747
ctgtttcttt gggacattcc gtcctgatga ttttatttt tgttggtttt tattttttggg      60 gg                                                                    62
```

<210> SEQ ID NO 1748
<211> LENGTH: 62
<212> TYPE: DNA
<213> ORGANISM: Homo sapiens

<400> SEQUENCE: 1748
cttagaaagt gaggatcctg gatgaattat tttagggaga aagtgtaggt ttagatcagc    60
tg                                                                  62

<210> SEQ ID NO 1749
<211> LENGTH: 63
<212> TYPE: DNA
<213> ORGANISM: Homo sapiens

<400> SEQUENCE: 1749
cttcaactcc tccatggatg gggcgacacg gggagaacat acaaactctg ccttcggtca    60
ttt                                                                 63

<210> SEQ ID NO 1750
<211> LENGTH: 63
<212> TYPE: DNA
<213> ORGANISM: Homo sapiens

<400> SEQUENCE: 1750
cttccaatat aactaggcaa aaagaagtga ggagaaacct gcatgaaagc attcttccct    60
gaa                                                                 63

<210> SEQ ID NO 1751
<211> LENGTH: 61
<212> TYPE: DNA
<213> ORGANISM: Homo sapiens

<400> SEQUENCE: 1751
cttccccagt tataaagagg tcacatagtc gtgtgggtcg aggattctgt gcctccagga    60
c                                                                   61

<210> SEQ ID NO 1752
<211> LENGTH: 64
<212> TYPE: DNA
<213> ORGANISM: Homo sapiens

<400> SEQUENCE: 1752
cttcttctgt tttgccccat ggtcaagtcc ctgttcccca ggcaggtttc agctgattgg    60
cagc                                                                64

<210> SEQ ID NO 1753
<211> LENGTH: 65
<212> TYPE: DNA
<213> ORGANISM: Homo sapiens

<400> SEQUENCE: 1753
ctttggcctc tgtttgtccc ctttccagtc ctccacccca ccctggagc ccagcctggg     60 agcgc                                                               65

<210> SEQ ID NO 1754
<211> LENGTH: 61
<212> TYPE: DNA
<213> ORGANISM: Homo sapiens

<400> SEQUENCE: 1754
gaaaaaccta gaaatttatc tcatggcaga tacatttgaa agtacttcag aagaatttat    60

```
<210> SEQ ID NO 1755
<211> LENGTH: 61
<212> TYPE: DNA
<213> ORGANISM: Homo sapiens

<400> SEQUENCE: 1755
gaaaaccttg gctttagccc tctggaatca gagcttaccc accatagtat attttgatat    60
t                                                                   61

<210> SEQ ID NO 1756
<211> LENGTH: 62
<212> TYPE: DNA
<213> ORGANISM: Homo sapiens

<400> SEQUENCE: 1756
gaaaggagga ccagtcagga tgaggccccg cctttcccc caccctccca tgagactgcc     60
ct                                                                  62

<210> SEQ ID NO 1757
<211> LENGTH: 60
<212> TYPE: DNA
<213> ORGANISM: Homo sapiens

<400> SEQUENCE: 1757
gaactgaaca gaacaagact ttttcctcat acatctccaa attgtttaaa cttactttat    60

<210> SEQ ID NO 1758
<211> LENGTH: 61
<212> TYPE: DNA
<213> ORGANISM: Homo sapiens

<400> SEQUENCE: 1758
gaatgtcacc agtcctgccc aatgccttga caacagactg aattttaaat gttcacaaca    60
t                                                                   61

<210> SEQ ID NO 1759
<211> LENGTH: 62
<212> TYPE: DNA
<213> ORGANISM: Homo sapiens

<400> SEQUENCE: 1759
gaattgcaaa tagtctctat ttgtaattga acttatccta aaacaaatag tttataaatg    60
tg                                                                  62

<210> SEQ ID NO 1760
<211> LENGTH: 62
<212> TYPE: DNA
<213> ORGANISM: Homo sapiens

<400> SEQUENCE: 1760
gaccttactg ggtacacccc tctaaccagt gcttacaggt taatgcatgt taatgaatat    60
tt                                                                  62

<210> SEQ ID NO 1761
<211> LENGTH: 56
<212> TYPE: DNA
<213> ORGANISM: Homo sapiens

<400> SEQUENCE: 1761
```

```
gacgaagcct tccccatgaa accccaccac tggctaaaac tggacacatc ctgcct        56

<210> SEQ ID NO 1762
<211> LENGTH: 64
<212> TYPE: DNA
<213> ORGANISM: Homo sapiens

<400> SEQUENCE: 1762
gacgtagcac agaaaaaccc tttgacacaa accatgtgtt ctgattttttg gttcagaaaa   60 tatt                                                                 64

<210> SEQ ID NO 1763
<211> LENGTH: 62
<212> TYPE: DNA
<213> ORGANISM: Homo sapiens

<400> SEQUENCE: 1763
gagaggacac tcccgttttc ggtgccatca gtgccccgtc tacagctccc ccagctcccc   60
cc                                                                   62

<210> SEQ ID NO 1764
<211> LENGTH: 62
<212> TYPE: DNA
<213> ORGANISM: Homo sapiens

<400> SEQUENCE: 1764 gagattttc ttttaagccc tgctctttct ctgagaacca aaagatgcct tgaatattta    60
tt                                                                   62

<210> SEQ ID NO 1765
<211> LENGTH: 64
<212> TYPE: DNA
<213> ORGANISM: Homo sapiens

<400> SEQUENCE: 1765
gagctgtgac ccatcccagg aggcctgtgc acacatccca ggcatgtccc agacacatcc   60
caca                                                                 64

<210> SEQ ID NO 1766
<211> LENGTH: 62
<212> TYPE: DNA
<213> ORGANISM: Homo sapiens

<400> SEQUENCE: 1766
gagtatttga aagcaggact tcagaacagt gtttgatttt tattttataa atttaagcat   60
tc                                                                   62

<210> SEQ ID NO 1767
<211> LENGTH: 63
<212> TYPE: DNA
<213> ORGANISM: Homo sapiens

<400> SEQUENCE: 1767
gataagaata ggtcattttc tattcaccat cctttactat taagggaaag gaaaagaaca   60
cta                                                                  63

<210> SEQ ID NO 1768
<211> LENGTH: 64
<212> TYPE: DNA
<213> ORGANISM: Homo sapiens
```

```
<400> SEQUENCE: 1768
gatggggttt tcaaagacct ctcacaatat taaatgcact tcaataatca ttgctgtttt    60
atgt                                                                 64

<210> SEQ ID NO 1769
<211> LENGTH: 61
<212> TYPE: DNA
<213> ORGANISM: Homo sapiens

<400> SEQUENCE: 1769
gattgagatt gattcagatt tttgcactgt agatgagcgt atgtctcagt gctgcccaa     60 g                                                                    61

<210> SEQ ID NO 1770
<211> LENGTH: 62
<212> TYPE: DNA
<213> ORGANISM: Homo sapiens

<400> SEQUENCE: 1770
gcaaggcttt aaatgacttt ggagagggtc acaaatccta aaagaagcat tgaagtgagg    60
tg                                                                   62

<210> SEQ ID NO 1771
<211> LENGTH: 64
<212> TYPE: DNA
<213> ORGANISM: Homo sapiens

<400> SEQUENCE: 1771
gcacactgcc tgagggacaa cagacatcag aacaaacccc cagagagaaa cagtcaaaat    60
cagg                                                                 64

<210> SEQ ID NO 1772
<211> LENGTH: 62
<212> TYPE: DNA
<213> ORGANISM: Homo sapiens

<400> SEQUENCE: 1772
gcactcataa aatatttgta caaggagtga gtgggggaga atgagcaca atatgggttc     60 tg                                                                   62

<210> SEQ ID NO 1773
<211> LENGTH: 61
<212> TYPE: DNA
<213> ORGANISM: Homo sapiens

<400> SEQUENCE: 1773
gcagtccttt tactacagct atgaagaaac gcaacaagaa actcaatgca caacaaagga    60
t                                                                    61

<210> SEQ ID NO 1774
<211> LENGTH: 61
<212> TYPE: DNA
<213> ORGANISM: Homo sapiens

<400> SEQUENCE: 1774
gccaatattc cttattaata caaacacaaa aatcattaac aaaaatatta gcaaactgaa    60
t                                                                    61
```

```
<210> SEQ ID NO 1775
<211> LENGTH: 60
<212> TYPE: DNA
<213> ORGANISM: Homo sapiens

<400> SEQUENCE: 1775
gcccagagtc tgaaactcct gactggtcag gtgctactta agaccagctt gggcaattca    60

<210> SEQ ID NO 1776
<211> LENGTH: 59
<212> TYPE: DNA
<213> ORGANISM: Homo sapiens

<400> SEQUENCE: 1776
gcctcccccg caggttatgt cagcagctct gagacagcag tatcacaggc cagatgttg     59

<210> SEQ ID NO 1777
<211> LENGTH: 62
<212> TYPE: DNA
<213> ORGANISM: Homo sapiens

<400> SEQUENCE: 1777
ggaaaaggct gagtccaccg ctgtgcagct taagatcccc gaggtggagc tggtcacgct    60
gg                                                                  62

<210> SEQ ID NO 1778
<211> LENGTH: 59
<212> TYPE: DNA
<213> ORGANISM: Homo sapiens

<400> SEQUENCE: 1778
ggaccagctg accaggcttg tgctcagaga agcagacaaa acaaagattc aaggtttta     59

<210> SEQ ID NO 1779
<211> LENGTH: 60
<212> TYPE: DNA
<213> ORGANISM: Homo sapiens

<400> SEQUENCE: 1779
ggaggagagt gcatggtgca gaggggggctg gggcgcacgg agaagcaggt ccctatattg   60

<210> SEQ ID NO 1780
<211> LENGTH: 65
<212> TYPE: DNA
<213> ORGANISM: Homo sapiens

<400> SEQUENCE: 1780
ggcagctcct ctccttgggc tcctggctgc caggcgttgg tgccacttct taaaggcctg    60
gaacc                                                               65

<210> SEQ ID NO 1781
<211> LENGTH: 62
<212> TYPE: DNA
<213> ORGANISM: Homo sapiens

<400> SEQUENCE: 1781
ggcttgactt gtaagttcaa cctaaaccac aatcctagac catcatggat ttaggagtag    60
at                                                                  62

<210> SEQ ID NO 1782
<211> LENGTH: 64
<212> TYPE: DNA
<213> ORGANISM: Homo sapiens
```

<400> SEQUENCE: 1782
gggcaaagga gttggattgc tgaattacaa tgaaacatgt cttattacta aagaaagtga    60
ttta                                                                 64

<210> SEQ ID NO 1783
<211> LENGTH: 61
<212> TYPE: DNA
<213> ORGANISM: Homo sapiens

<400> SEQUENCE: 1783
gggcagcctt tttttttttt tttttaattg caacaatgca aaagccaaga aagtataagg    60
g                                                                    61

<210> SEQ ID NO 1784
<211> LENGTH: 60
<212> TYPE: DNA
<213> ORGANISM: Homo sapiens

<400> SEQUENCE: 1784
gggggctgct tctcaggagg ccaggccctt ctgagcggaa ccgtcctgga gagagcctgc    60

<210> SEQ ID NO 1785
<211> LENGTH: 60
<212> TYPE: DNA
<213> ORGANISM: Homo sapiens

<400> SEQUENCE: 1785
ggtcattgcc ttcatataac atgcttcgtg ctcatggtca ttgccttcat ataacatgct    60

<210> SEQ ID NO 1786
<211> LENGTH: 63
<212> TYPE: DNA
<213> ORGANISM: Homo sapiens

<400> SEQUENCE: 1786
ggtttctggc cgtgattgga tgtgaagtag aagaggtcct cgatcatggt gttagaattg    60
act                                                                  63

<210> SEQ ID NO 1787
<211> LENGTH: 61
<212> TYPE: DNA
<213> ORGANISM: Homo sapiens

<400> SEQUENCE: 1787
gtaaactgga tactgtactg atactattca atgcaatgca attcaatgca atgaaaacaa    60
a                                                                    61

<210> SEQ ID NO 1788
<211> LENGTH: 61
<212> TYPE: DNA
<213> ORGANISM: Homo sapiens

<400> SEQUENCE: 1788
gtaagatata tgcagcctca cagaagcagc ctctgcctcc actttaccag ctacgttttt    60
a                                                                    61

<210> SEQ ID NO 1789
<211> LENGTH: 62
<212> TYPE: DNA
<213> ORGANISM: Homo sapiens

<400> SEQUENCE: 1789
gtacagtagc ttttcaaact gcagttttat tgctaagttt ttagtatggg tgatactgga    60
gt                                                                    62

<210> SEQ ID NO 1790
<211> LENGTH: 61
<212> TYPE: DNA
<213> ORGANISM: Homo sapiens

<400> SEQUENCE: 1790
gtattactgt gattctctct gtaagctccc catgtggcca aggaccccc tcctaccagg     60
g                                                                     61

<210> SEQ ID NO 1791
<211> LENGTH: 62
<212> TYPE: DNA
<213> ORGANISM: Homo sapiens

<400> SEQUENCE: 1791
gtctttctgg ggtttttctg tttgggtttg gtttggtttt tatttctcct tttgtgttcc    60
aa                                                                    62

<210> SEQ ID NO 1792
<211> LENGTH: 62
<212> TYPE: DNA
<213> ORGANISM: Homo sapiens

<400> SEQUENCE: 1792
gtgcaatggt ataaatttca agctggatat gtctaatggg tatttaaaca ataaatgtgc    60
ag                                                                    62

<210> SEQ ID NO 1793
<211> LENGTH: 62
<212> TYPE: DNA
<213> ORGANISM: Homo sapiens

<400> SEQUENCE: 1793
gtgcctaagc gggggtgaaa gaggacgtgt tacccactgc catgcaccag gactggctgt    60
gt                                                                    62

<210> SEQ ID NO 1794
<211> LENGTH: 62
<212> TYPE: DNA
<213> ORGANISM: Homo sapiens

<400> SEQUENCE: 1794
gtggaggggt ataagaggag ggagagtcag agagagtgtg tatgggtgtg tgtgagtgtg    60
ag                                                                    62

<210> SEQ ID NO 1795
<211> LENGTH: 61
<212> TYPE: DNA
<213> ORGANISM: Homo sapiens

<400> SEQUENCE: 1795
gtgtgtgtat gagagagaga gtgtgtgttt gtgtgtttca aggtcagaac aggttttttt    60
g                                                                     61

```
<210> SEQ ID NO 1796
<211> LENGTH: 62
<212> TYPE: DNA
<213> ORGANISM: Homo sapiens

<400> SEQUENCE: 1796
gttatggtag ggttcttcag atgtaatatt ttactggtac tatttattta taaataggaa      60
tt                                                                    62

<210> SEQ ID NO 1797
<211> LENGTH: 63
<212> TYPE: DNA
<213> ORGANISM: Homo sapiens

<400> SEQUENCE: 1797
gttctaatat atattgtatt tttatttgat agcttgggat ttaaaacatc tctgttgaag      60
gct                                                                   63

<210> SEQ ID NO 1798
<211> LENGTH: 61
<212> TYPE: DNA
<213> ORGANISM: Homo sapiens

<400> SEQUENCE: 1798
gtttgggggc ctttctttaa ctgccttcct ggcttagctc agatggcaga tgagagtgta      60
g                                                                     61

<210> SEQ ID NO 1799
<211> LENGTH: 59
<212> TYPE: DNA
<213> ORGANISM: Homo sapiens

<400> SEQUENCE: 1799
taaaaatggc aaagaagaaa gagccaggac cccgtgccat caaatcctcc ggccttgtg       59

<210> SEQ ID NO 1800
<211> LENGTH: 61
<212> TYPE: DNA
<213> ORGANISM: Homo sapiens

<400> SEQUENCE: 1800
taaacctgca gaacatttta cttaaaagag gaaacacaag atcttcaatg aacgtcatcg      60
g                                                                     61

<210> SEQ ID NO 1801
<211> LENGTH: 61
<212> TYPE: DNA
<213> ORGANISM: Homo sapiens

<400> SEQUENCE: 1801
taaatagtat tcacaaaaaa gattttccta gattttatct attgaatagg tgtcaatatg      60
g                                                                     61

<210> SEQ ID NO 1802
<211> LENGTH: 61
<212> TYPE: DNA
<213> ORGANISM: Homo sapiens

<400> SEQUENCE: 1802
taaattgact gagacttgca aaatacccct gagagttgtc aggggtgtct tctgcctggt      60
c                                                                     61
```

<210> SEQ ID NO 1803
<211> LENGTH: 59
<212> TYPE: DNA
<213> ORGANISM: Homo sapiens

<400> SEQUENCE: 1803
taattagacc cctccccttg tgtcaactcc ggcagctcaa gacccccgag caacatttg    59

<210> SEQ ID NO 1804
<211> LENGTH: 60
<212> TYPE: DNA
<213> ORGANISM: Homo sapiens

<400> SEQUENCE: 1804
taccaaatat aagttggatg cattttarttt tagacacaaa gctttatttt tccacatcat    60

<210> SEQ ID NO 1805
<211> LENGTH: 63
<212> TYPE: DNA
<213> ORGANISM: Homo sapiens

<400> SEQUENCE: 1805
tacgcttgct tgtctttaaa tcttcaatat gaaggactat taattccaag attaaaagtt    60
cat    63

<210> SEQ ID NO 1806
<211> LENGTH: 61
<212> TYPE: DNA
<213> ORGANISM: Homo sapiens

<400> SEQUENCE: 1806
tactgtactg atactattca atgcaatgca attcaatgca atgaaaacaa aattccatta    60
c    61

<210> SEQ ID NO 1807
<211> LENGTH: 63
<212> TYPE: DNA
<213> ORGANISM: Homo sapiens

<400> SEQUENCE: 1807
tagaagcgag ggcaccagca gttgtgggtg gggagcaagg gaagagagaa actcttcagc    60
gaa    63

<210> SEQ ID NO 1808
<211> LENGTH: 59
<212> TYPE: DNA
<213> ORGANISM: Homo sapiens

<400> SEQUENCE: 1808
tagtgtccca gtacaaaaag gctgtaagat agtcaaccac agtagtcacc tatgtctgt    59

<210> SEQ ID NO 1809
<211> LENGTH: 61
<212> TYPE: DNA
<213> ORGANISM: Homo sapiens

<400> SEQUENCE: 1809
tagtttgata gaatcgagag ttaagatgtt tctatttgaa agtggattca accatcagac    60
c    61

```
<210> SEQ ID NO 1810
<211> LENGTH: 62
<212> TYPE: DNA
<213> ORGANISM: Homo sapiens

<400> SEQUENCE: 1810
tcaaagaggc tgaggctggc acaggacatg cggtagccag cacacagggc agtgagggag    60
gg                                                                   62

<210> SEQ ID NO 1811
<211> LENGTH: 65
<212> TYPE: DNA
<213> ORGANISM: Homo sapiens

<400> SEQUENCE: 1811
tcaccaaagc atcagtgatg ttctagaagc atcccagcag atggaggatc ctaatgtatt    60
tgttc                                                                65

<210> SEQ ID NO 1812
<211> LENGTH: 59
<212> TYPE: DNA
<213> ORGANISM: Homo sapiens

<400> SEQUENCE: 1812
tcactgacct ggtggtgggg ctgtgacctg ggcagctcaa gactggtgcc ccttgctga     59

<210> SEQ ID NO 1813
<211> LENGTH: 62
<212> TYPE: DNA
<213> ORGANISM: Homo sapiens

<400> SEQUENCE: 1813 tcactttta aactcacata ggtaggtatc tttatagttg tagactatgg aatgtcagtg    60
tt                                                                   62

<210> SEQ ID NO 1814
<211> LENGTH: 62
<212> TYPE: DNA
<213> ORGANISM: Homo sapiens

<400> SEQUENCE: 1814
tcagaagttt aaatattaag catgacagaa atatgtatt aacactactc aaagcaaaag    60
tg                                                                   62

<210> SEQ ID NO 1815
<211> LENGTH: 62
<212> TYPE: DNA
<213> ORGANISM: Homo sapiens

<400> SEQUENCE: 1815
tcatagaaag gagcaaccaa aatgtcacaa cccaaaactt tacaagcttt gcttcagaat    60
ta                                                                   62

<210> SEQ ID NO 1816
<211> LENGTH: 62
<212> TYPE: DNA
<213> ORGANISM: Homo sapiens

<400> SEQUENCE: 1816
tcctgccaag ccaaatgtgc ttcctgcagc tcacgcccac cagctactga agggacccaa    60
gg                                                                   62
```

<210> SEQ ID NO 1817
<211> LENGTH: 62
<212> TYPE: DNA
<213> ORGANISM: Homo sapiens

<400> SEQUENCE: 1817
tccttgctgc attgtacagt agcttttcaa actgcagttt tattgctaag tttttagtat    60
gg    62

<210> SEQ ID NO 1818
<211> LENGTH: 61
<212> TYPE: DNA
<213> ORGANISM: Homo sapiens

<400> SEQUENCE: 1818
tcggcatagt tcttggcgtt aacatctcag tgtcctcttt agttctcttt gaggattcat    60
g    61

<210> SEQ ID NO 1819
<211> LENGTH: 59
<212> TYPE: DNA
<213> ORGANISM: Homo sapiens

<400> SEQUENCE: 1819
tcgtctggca tctcccacac aagacccaag tagctgctac cttctttggc cccttgctg    59

<210> SEQ ID NO 1820
<211> LENGTH: 62
<212> TYPE: DNA
<213> ORGANISM: Homo sapiens

<400> SEQUENCE: 1820
tctaataaaa agtcacaaag ttatcttctt taacaaactt tactcttatt cttagctgta    60
ta    62

<210> SEQ ID NO 1821
<211> LENGTH: 63
<212> TYPE: DNA
<213> ORGANISM: Homo sapiens

<400> SEQUENCE: 1821
tctcagcaac aacacttatg catccaaaca ctcacaaatg aaacctgaaa gaatcttttc    60
tga    63

<210> SEQ ID NO 1822
<211> LENGTH: 60
<212> TYPE: DNA
<213> ORGANISM: Homo sapiens

<400> SEQUENCE: 1822
tctccttcct tgttacccat gaaaaactgg caacattcca agaatagcat ctgtacaaag    60

<210> SEQ ID NO 1823
<211> LENGTH: 61
<212> TYPE: DNA
<213> ORGANISM: Homo sapiens

<400> SEQUENCE: 1823
tctgcacatc tagcctctgg ccctcctctt cactgcctcc acctgctccc gcttgccatc    60
c    61

<210> SEQ ID NO 1824
<211> LENGTH: 61
<212> TYPE: DNA
<213> ORGANISM: Homo sapiens

<400> SEQUENCE: 1824
tcttggcgtt aacatctcag tgtcctcttt agttctcttt gaggattcat gtcattgagg    60
g                                                                    61

<210> SEQ ID NO 1825
<211> LENGTH: 62
<212> TYPE: DNA
<213> ORGANISM: Homo sapiens

<400> SEQUENCE: 1825
tctttgataa cagggattga ttttaaaatg tacatgtatt aaattacatt tgtaatttaa    60
gg                                                                   62

<210> SEQ ID NO 1826
<211> LENGTH: 62
<212> TYPE: DNA
<213> ORGANISM: Homo sapiens

<400> SEQUENCE: 1826
tgaaagaaaa atgggtaaca aagaaccct taaaacaggt taatttggat tgtaacgttc     60
ag                                                                   62

<210> SEQ ID NO 1827
<211> LENGTH: 61
<212> TYPE: DNA
<213> ORGANISM: Homo sapiens

<400> SEQUENCE: 1827
tgaaagtatt ccaggaacag tgaatggtag aagacacaag aacatttgtt tgtttgtctt    60
c                                                                    61

<210> SEQ ID NO 1828
<211> LENGTH: 63
<212> TYPE: DNA
<213> ORGANISM: Homo sapiens

<400> SEQUENCE: 1828
tgacagtgca gccagccttc agtctgtggc caaaggccca agagcccctg gcaaccaacc    60
cac                                                                  63

<210> SEQ ID NO 1829
<211> LENGTH: 61
<212> TYPE: DNA
<213> ORGANISM: Homo sapiens

<400> SEQUENCE: 1829
tgacataacc aatttgtaat gattttggaa ctgtgtttca aatggactgt tacagactga    60
a                                                                    61

<210> SEQ ID NO 1830
<211> LENGTH: 59
<212> TYPE: DNA
<213> ORGANISM: Homo sapiens

<400> SEQUENCE: 1830

```
tgagccccac gtggagctcg ggacggatag tagacagcaa taactcggtg tgtggccgc      59

<210> SEQ ID NO 1831
<211> LENGTH: 62
<212> TYPE: DNA
<213> ORGANISM: Homo sapiens

<400> SEQUENCE: 1831
tgaggacttg tgtctctgtg cttttaaatg cataaatgca ttataggatc atttgttgga      60
at                                                                    62

<210> SEQ ID NO 1832
<211> LENGTH: 62
<212> TYPE: DNA
<213> ORGANISM: Homo sapiens

<400> SEQUENCE: 1832
tgatgaggca cattcagaac aaatgctttt ttttttttga dacagagtct cgctctgacg      60
cc                                                                    62

<210> SEQ ID NO 1833
<211> LENGTH: 63
<212> TYPE: DNA
<213> ORGANISM: Homo sapiens

<400> SEQUENCE: 1833
tgattgaggg ggaaaagaat gatctttatt aatgacaagg gaaaccatga gtaatgccac      60
aat                                                                   63

<210> SEQ ID NO 1834
<211> LENGTH: 61
<212> TYPE: DNA
<213> ORGANISM: Homo sapiens

<400> SEQUENCE: 1834
tgcagagtgg taaccatgct tacacactaa actataatat aaaggaaatg aagccatgtt      60
a                                                                     61

<210> SEQ ID NO 1835
<211> LENGTH: 60
<212> TYPE: DNA
<213> ORGANISM: Homo sapiens

<400> SEQUENCE: 1835
tgctctcttg aaatcttaaa tatgattatt tgagctcata taaggtggat tggagcagat      60

<210> SEQ ID NO 1836
<211> LENGTH: 60
<212> TYPE: DNA
<213> ORGANISM: Homo sapiens

<400> SEQUENCE: 1836
tgctggtaaa gtattttggt ggcagctgcc atcatggtca ttgccttcat ataacatgct      60

<210> SEQ ID NO 1837
<211> LENGTH: 64
<212> TYPE: DNA
<213> ORGANISM: Homo sapiens

<400> SEQUENCE: 1837
tggaagcata ctgaaagtgt cttggtgggc ctgagccaag cacaggtgtt tgaggactac      60
```

```
agtt                                                              64

<210> SEQ ID NO 1838
<211> LENGTH: 59
<212> TYPE: DNA
<213> ORGANISM: Homo sapiens

<400> SEQUENCE: 1838
tggacgcagc cacacagtgg ccggggctga agccacacag cccagaaggc cagaaaagg   59

<210> SEQ ID NO 1839
<211> LENGTH: 64
<212> TYPE: DNA
<213> ORGANISM: Homo sapiens

<400> SEQUENCE: 1839
tggatggaag tgtctggaaa gggcacgaga gagtcttcca ggtactgatc ctgtttcttg   60
ctct                                                              64

<210> SEQ ID NO 1840
<211> LENGTH: 62
<212> TYPE: DNA
<213> ORGANISM: Homo sapiens

<400> SEQUENCE: 1840
tgggacctcc ccagcccagg aaaaactgga agccttcccc cagcaaggca gaagcttgga   60
gg                                                                62

<210> SEQ ID NO 1841
<211> LENGTH: 62
<212> TYPE: DNA
<213> ORGANISM: Homo sapiens

<400> SEQUENCE: 1841
tggtgtaggg gcttagaggc atgggcttgc tgtgggtttt taattgatca gttttcatgt   60
gg                                                                62

<210> SEQ ID NO 1842
<211> LENGTH: 63
<212> TYPE: DNA
<213> ORGANISM: Homo sapiens

<400> SEQUENCE: 1842
tgtaattgta gcatcaaaat gacaacagca gcagagcagc gaatcttgca cagccccaca   60
gca                                                               63

<210> SEQ ID NO 1843
<211> LENGTH: 63
<212> TYPE: DNA
<213> ORGANISM: Homo sapiens

<400> SEQUENCE: 1843
tgtctctgga gaaaagggct agagctgcct tttacaactg taaccactgt aatgagaagg   60
cac                                                               63

<210> SEQ ID NO 1844
<211> LENGTH: 65
<212> TYPE: DNA
<213> ORGANISM: Homo sapiens

<400> SEQUENCE: 1844
```

```
tgtctgacct acattgggct tttctcagaa ctttgaacga tcccatgcaa agaattccca    60
ccctg                                                                65

<210> SEQ ID NO 1845
<211> LENGTH: 63
<212> TYPE: DNA
<213> ORGANISM: Homo sapiens

<400> SEQUENCE: 1845
tgtgtgtggt gggttgtctg tgtgcatatg tcctgcccgt gtatatgcac ccacaccatg    60
tgc                                                                  63

<210> SEQ ID NO 1846
<211> LENGTH: 59
<212> TYPE: DNA
<213> ORGANISM: Homo sapiens

<400> SEQUENCE: 1846
tgttatttaa cctgagtata gtatttaacg aagcctagaa gcacggctgt gggtggtga     59

<210> SEQ ID NO 1847
<211> LENGTH: 63
<212> TYPE: DNA
<213> ORGANISM: Homo sapiens

<400> SEQUENCE: 1847
tgtttatgca ttcacaaggt gactgggatg tagagaggcg ttagtgggca ggtggccaca    60
gca                                                                  63

<210> SEQ ID NO 1848
<211> LENGTH: 62
<212> TYPE: DNA
<213> ORGANISM: Homo sapiens

<400> SEQUENCE: 1848
ttaaactcct taaacagttt agaaattagc tccaggttct taaactaaca aaataaaac     60 ct                                                                   62

<210> SEQ ID NO 1849
<211> LENGTH: 62
<212> TYPE: DNA
<213> ORGANISM: Homo sapiens

<400> SEQUENCE: 1849
ttaacatttg tttttagtta aaagtatcta cttactgttt tagctctgaa ctcaaaccag    60
aa                                                                   62

<210> SEQ ID NO 1850
<211> LENGTH: 62
<212> TYPE: DNA
<213> ORGANISM: Homo sapiens

<400> SEQUENCE: 1850
ttacagctgg ttctgagccg cttgccttgt gatggtaaga caccaacctt tacattcttc    60
cc                                                                   62

<210> SEQ ID NO 1851
<211> LENGTH: 61
<212> TYPE: DNA
<213> ORGANISM: Homo sapiens
```

<400> SEQUENCE: 1851
ttagtacaga ctgtgacgcc cccagtgtgg cttgcaggct agtggcagcg gaagcatgtg    60
g                                                                   61

<210> SEQ ID NO 1852
<211> LENGTH: 61
<212> TYPE: DNA
<213> ORGANISM: Homo sapiens

<400> SEQUENCE: 1852
ttcaattacc tccccctggg tctgtcccac aacacgtggg aattctggga gatacaattc    60
a                                                                   61

<210> SEQ ID NO 1853
<211> LENGTH: 61
<212> TYPE: DNA
<213> ORGANISM: Homo sapiens

<400> SEQUENCE: 1853
ttcaattacc tcccctgggg tctctcccac aacacgtggg aattctggta gatacaattt    60
c                                                                   61

<210> SEQ ID NO 1854
<211> LENGTH: 63
<212> TYPE: DNA
<213> ORGANISM: Homo sapiens

<400> SEQUENCE: 1854
ttcaggcata aattagagaa atggttctgg atatggtgca aaaatgagtt ttcacctggt    60
atc                                                                 63

<210> SEQ ID NO 1855
<211> LENGTH: 60
<212> TYPE: DNA
<213> ORGANISM: Homo sapiens

<400> SEQUENCE: 1855
ttcaggttca gtattatgta gttgttcgtt ggttatacaa gttcttggtc cctccagaac    60

<210> SEQ ID NO 1856
<211> LENGTH: 62
<212> TYPE: DNA
<213> ORGANISM: Homo sapiens

<400> SEQUENCE: 1856
ttcatatatg aggacttgtg tctctgtgct tttaaatgca taaatgcatt ataggatcat    60
tt                                                                  62

<210> SEQ ID NO 1857
<211> LENGTH: 62
<212> TYPE: DNA
<213> ORGANISM: Homo sapiens

<400> SEQUENCE: 1857
ttgtatacac atttgcatat acccacatgg ggacataagc taatttttt acaggacaca    60
ga                                                                  62

<210> SEQ ID NO 1858
<211> LENGTH: 62

```
<212> TYPE: DNA
<213> ORGANISM: Homo sapiens

<400> SEQUENCE: 1858
ttgtcactga gaagatgttt attttggtca gttgggtttt tatgtattat acttagtcaa    60
at                                                                  62

<210> SEQ ID NO 1859
<211> LENGTH: 62
<212> TYPE: DNA
<213> ORGANISM: Homo sapiens

<400> SEQUENCE: 1859
ttgtgaaata ttaaatgcaa atttacaact gcagatgacg tatgtgcctt gaactgaata    60
tt                                                                  62

<210> SEQ ID NO 1860
<211> LENGTH: 62
<212> TYPE: DNA
<213> ORGANISM: Homo sapiens

<400> SEQUENCE: 1860
ttgtgattct gagcttgcaa tgccgccaag cgccccccgc cagcccgccc ccggttgtcc    60
ac                                                                  62

<210> SEQ ID NO 1861
<211> LENGTH: 62
<212> TYPE: DNA
<213> ORGANISM: Homo sapiens

<400> SEQUENCE: 1861
ttgtgattta gatgtatcca tccttttttct attaagaata caaatgctgg gctgggcaca   60
gt                                                                  62

<210> SEQ ID NO 1862
<211> LENGTH: 61
<212> TYPE: DNA
<213> ORGANISM: Homo sapiens

<400> SEQUENCE: 1862
ttgtttctag ttgggggtaa ctacacacaa tgctgctagc aacagttttg tccatgtctc    60
t                                                                   61

<210> SEQ ID NO 1863
<211> LENGTH: 62
<212> TYPE: DNA
<213> ORGANISM: Homo sapiens

<400> SEQUENCE: 1863
tttattaaat ctgaatttta aaacatgctg tttatgacac aatgacacat ttgttgcacc    60
aa                                                                  62

<210> SEQ ID NO 1864
<211> LENGTH: 62
<212> TYPE: DNA
<213> ORGANISM: Homo sapiens

<400> SEQUENCE: 1864
tttcaacggt ccaaacgccc aaccttcaga aagaggaagt cagatagaaa tagtccctga    60
ga                                                                  62
```

```
<210> SEQ ID NO 1865
<211> LENGTH: 63
<212> TYPE: DNA
<213> ORGANISM: Homo sapiens

<400> SEQUENCE: 1865
tttccaaaca aatctttcta cgcttaaatg atcaaattag aaaaaccaat tcctataatt    60
aat                                                                 63

<210> SEQ ID NO 1866
<211> LENGTH: 62
<212> TYPE: DNA
<213> ORGANISM: Homo sapiens

<400> SEQUENCE: 1866
tttccagtag gaaaagcaat gctttcttgt ctttagactc aaatgcttag ggaacgtttc    60
at                                                                  62

<210> SEQ ID NO 1867
<211> LENGTH: 61
<212> TYPE: DNA
<213> ORGANISM: Homo sapiens

<400> SEQUENCE: 1867
tttccatact cctgagcttt ggggagggag acagtggcca agtagcaggc agaataagat    60
c                                                                   61

<210> SEQ ID NO 1868
<211> LENGTH: 61
<212> TYPE: DNA
<213> ORGANISM: Homo sapiens

<400> SEQUENCE: 1868
tttcccatga gatgaagcac atgtgacgaa tacggactag ataacctcta agaattttcc    60
a                                                                   61

<210> SEQ ID NO 1869
<211> LENGTH: 60
<212> TYPE: DNA
<213> ORGANISM: Homo sapiens

<400> SEQUENCE: 1869
tttctacaag ttcagaatat tttaaacctg atttactaga cctgggaatt ttcaacatgg    60

<210> SEQ ID NO 1870
<211> LENGTH: 63
<212> TYPE: DNA
<213> ORGANISM: Homo sapiens

<400> SEQUENCE: 1870
tttcttgtgc ttgcttcggc agcatatata ctgaaattag aaaaagaaaa cttttctttt    60
tta                                                                 63

<210> SEQ ID NO 1871
<211> LENGTH: 61
<212> TYPE: DNA
<213> ORGANISM: Homo sapiens

<400> SEQUENCE: 1871
tttgggtaga ggatactatt tccagaatag tgtttagctc acctaggggg atatgtttgt    60
```

```
a                                                               61

<210> SEQ ID NO 1872
<211> LENGTH: 62
<212> TYPE: DNA
<213> ORGANISM: Homo sapiens

<400> SEQUENCE: 1872
tttttaacta ataaggcgag aagagggaag ttggagaggg aaaagttagc ccagaaggaa    60
ag                                                               62

<210> SEQ ID NO 1873
<211> LENGTH: 62
<212> TYPE: DNA
<213> ORGANISM: Homo sapiens

<400> SEQUENCE: 1873
ttttttttca ttattctaaa actcttgttg ttagatacaa gatttaatta agatctaagc    60
tc                                                               62

<210> SEQ ID NO 1874
<211> LENGTH: 63
<212> TYPE: DNA
<213> ORGANISM: Homo sapiens

<400> SEQUENCE: 1874
tttttttttt gacgtattat tgacaaatgt attcagcgcc atacacaaga gaatattat    60 tac                                                              63

<210> SEQ ID NO 1875
<211> LENGTH: 40
<212> TYPE: DNA
<213> ORGANISM: Homo sapiens
<220> FEATURE:
<221> NAME/KEY: misc_feature
<222> LOCATION: (1)...(17)
<223> OTHER INFORMATION: ribonucleotides in a RNA/DNA oliogonucleotide

<400> SEQUENCE: 1875
ucucgaggua caucguuaga agcttgaatt cgagcagaaa                          40

<210> SEQ ID NO 1876
<211> LENGTH: 40
<212> TYPE: DNA
<213> ORGANISM: Homo sapiens
<220> FEATURE:
<221> NAME/KEY: misc_feature
<222> LOCATION: (34)...(40)
<223> OTHER INFORMATION: ribonucleotides in a RNA/DNA oliogonucleotide

<400> SEQUENCE: 1876
tttggatttg ctggtgcagt acaactaggc ttacucgagc                          40

<210> SEQ ID NO 1877
<211> LENGTH: 18
<212> TYPE: RNA
<213> ORGANISM: Homo sapiens

<400> SEQUENCE: 1877
acguugcacu cugauacc                                                  18

<210> SEQ ID NO 1878
<211> LENGTH: 26
```

```
<212> TYPE: RNA
<213> ORGANISM: Homo sapiens

<400> SEQUENCE: 1878
ccgguucauc acgucuaaga aucaug                                           26

<210> SEQ ID NO 1879
<211> LENGTH: 23
<212> TYPE: DNA
<213> ORGANISM: Homo sapiens

<400> SEQUENCE: 1879
tttctgctcg aattcaagct tct                                              23

<210> SEQ ID NO 1880
<211> LENGTH: 29
<212> TYPE: DNA
<213> ORGANISM: Homo sapiens

<400> SEQUENCE: 1880
tttttttttg gatttgctgg tgcagtaca                                        29

<210> SEQ ID NO 1881
<211> LENGTH: 29
<212> TYPE: DNA
<213> ORGANISM: Homo sapiens

<400> SEQUENCE: 1881 ttttttttc tgctcgaatt caagcttct                                         29
```